United States Patent
Cai et al.

(10) Patent No.: US 9,969,752 B2
(45) Date of Patent: May 15, 2018

(54) INHIBITORS OF HIF PROLYL HYDROXYLASE

(71) Applicants: MERCK SHARP & DOHME CORP., Rahway, NJ (US); MSD R&D (CHINA) CO., LTD., Shanghai (CN)

(72) Inventors: Jiaqiang Cai, Shanghai (CN); Alejandro Crespo, Edison, NJ (US); Xiaoxing Du, Shanghai (CN); Byron Gabriel Dubois, New York, NY (US); Deodialsingh Guiadeen, Chesterfield, NJ (US); Shankaran Kothandaraman, Plain City, OH (US); Ping Liu, Westfield, NJ (US); Rongqiang Liu, Shanghai (CN); Weiguo Quan, Shanghai (CN); Christopher Sinz, Middletown, NJ (US); Liping Wang, Cranbury, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days. days.

(21) Appl. No.: 15/514,536

(22) PCT Filed: Sep. 23, 2015

(86) PCT No.: PCT/US2015/051571
§ 371 (c)(1),
(2) Date: Mar. 27, 2017

(87) PCT Pub. No.: WO2016/049099
PCT Pub. Date: Mar. 31, 2016

(65) Prior Publication Data
US 2017/0233412 A1 Aug. 17, 2017

(30) Foreign Application Priority Data
Sep. 28, 2014 (WO) ................ PCT/CN2014/087697

(51) Int. Cl.
*C07D 471/06* (2006.01)
*C07D 498/06* (2006.01)
*C07D 513/06* (2006.01)
*C07D 498/16* (2006.01)

(52) U.S. Cl.
CPC ......... *C07D 513/06* (2013.01); *C07D 471/06* (2013.01); *C07D 498/06* (2013.01); *C07D 498/16* (2013.01)

(58) Field of Classification Search
CPC ... C07D 471/06; C07D 498/06; C07D 513/06
See application file for complete search history.

(56) References Cited

U.S. PATENT DOCUMENTS

| 5,583,135 A | 12/1996 | Matsuo et al. |
| 6,624,159 B2 | 9/2003 | Anderson et al. |
| 2002/0103170 A1 | 8/2002 | Turner et al. |
| 2004/0176366 A1 | 9/2004 | Wathen et al. |

FOREIGN PATENT DOCUMENTS

| WO | WO2007103905 A2 | 9/2007 |
| WO | WO2009108496 | 9/2009 |
| WO | WO2016049097 | 3/2016 |
| WO | WO2016049098 | 3/2016 |
| WO | WO2016049099 | 3/2016 |
| WO | WO2016049100 | 3/2016 |

OTHER PUBLICATIONS

Sickle cell anemia [online], retrieved from the internet on Jul. 24, 2017; URL:http://www.mayoclinic.org/diseases-conditions/sickle-cell-anemia/home/ovc-20302367?p=1.*
Rabinowitz, Inhibition of Hypoxia-inducible Factor Prolyl Hydroxylase Domain Oxgen Sensors, Journal of Medicinal Chemistry, 2013, 9369-9402, vol. 56.
Mayo Clinic Staff, Sickle Cell Anemia, Mayo Clinic, 1998, Online Http://www.Mayoclinic.org/Diseaes-Conditions/Sickle-Cell-Anemia/Home/OVC-20302367.
Michael H. Rabinowitz et al., Inhibitors of HIF Prolyl Hydroxylases, Annual Report in Medicinal Chemistry, 2010, 123-139, 45.

* cited by examiner

*Primary Examiner* — Shawquia Jackson
(74) *Attorney, Agent, or Firm* — Matthew A. Leff; Gloria M. Fuentes

(57) ABSTRACT

The present invention concerns compounds of formula I or pharmaceutically acceptable salts thereof, which inhibit HIF prolyl hydroxylase, their use for enhancing endogenous production of erythropoietin, and for treating conditions associated with reduced endogenous production of erythropoietin such as anemia and like conditions, as well as pharmaceutical compositions comprising such a compound and a pharmaceutical carrier.

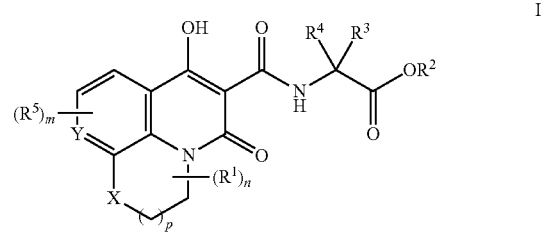

6 Claims, No Drawings

INHIBITORS OF HIF PROLYL HYDROXYLASE

BACKGROUND OF THE INVENTION

The insufficient delivery of oxygen to cells and tissues is associated with anemia, which is defined as a deficiency in the blood's oxygen-carrying capacity, and ischemia, in which restrictions in blood supply are caused by a constriction or blockage of blood vessels. Anemia can be caused by the loss of red blood cells (hemorrhage), excessive red blood cell destruction (hemolysis) or deficiencies in erythropoiesis (production of red blood cells from precursors found in the bone marrow). The symptoms of anemia can include weakness, dizziness, fatigue, pallor, impairment of cognitive function and a general reduction in quality of life. Chronic and/or severe anemia can lead to the exacerbation of myocardial, cerebral or peripheral ischemia and to heart failure. Ischemia is defined as an absolute or relative shortage of oxygen to a tissue or organ and can result from disorders such as atherosclerosis, diabetes, thromboembolisms, hypotension, etc. The heart, brain and kidney are especially sensitive to ischemic stress caused by low blood supply.

The primary pharmacological treatment for anemia is administration of some variant of recombinant human erythropoietin (EPO). For anemias associated with kidney disease, chemotherapy-induced anemia, anemia from HIV-therapy or anemia due to blood loss, recombinant EPO is administered to enhance the supply of the hormone, correct the shortage of red blood cells and increase the blood's oxygen-carrying capacity. EPO replacement is not always sufficient to stimulate optimal erythropoiesis (e.g., in patients with iron processing deficiencies) and has associated risks.

Hypoxia-inducible factor (HIF) has been identified as a primary regulator of the cellular response to low oxygen. HIF is a heterodimeric gene transcription factor consisting of a highly regulated α-subunit (HIF-α) and a constitutively expressed β-subunit (HIF-β, also known as ARNT, or aryl hydrocarbon receptor nuclear transporter). HIF target genes are reported to be associated with various aspects of erythropoiesis (e.g., erythropoietin (EPO) and EPO receptor), glycolysis and angiogenesis (e.g., vascular endothelial growth factor (VEGF)). Genes for proteins involved in iron absorption, transport and utilization as well as heme synthesis are also targets of HIF.

Under normal oxygenation, HIF-α is a substrate in a reaction with molecular oxygen, which is catalyzed by a family of iron(II)-, 2-ketoglutarate- and ascorbate-dependent dioxygenase enzymes called PHD-1 (EGLN2), or egg laying abnormal 9 homolog 2, PHD2 (EGLN1), and PHD3 (EGLN3). Proline residues of HIF-α are hydroxylated (e.g., Pro-402 and Pro-564 of HIF-1α) and the resulting product is a target of the tumor suppressor protein von-Hippel Lindau, a component of an E3 ubiquitin ligase multiprotein complex involved in protein ubiquitination. Under low oxygenation, the HIF-α hydroxylation reaction is less efficient and HIF-α is available to dimerize with HIF-β. HIF dimers are translocated to the cell nucleus where they bind to a hypoxia-responsive enhancer element of HIF target genes.

Cellular levels of HIF are known to increase under conditions of hypoxia and after exposure to hypoxia mimetic agents. The latter includes, but is not limited to, specific metal ions (e.g., cobalt, nickel, manganese), iron chelators (e.g., desferrioxamine) and analogs of 2-ketoglurate (e.g., N-oxalyl glycine). The compounds of the present invention inhibit the HIF prolyl hydroxylases (PHD-1, PHD-2, PHD-3) and can also serve to modulate HIF levels. These compounds therefore have utility for the treatment and/or prevention of disorders or conditions where HIF modulation is desirable, such as anemia and ischemia. As an alternative to recombinant erythropoietin therapy, the compounds of the present invention provide a simpler and broader method for the management of anemia.

SUMMARY OF THE INVENTION

The present invention concerns compounds of formula I or pharmaceutically acceptable salts thereof,

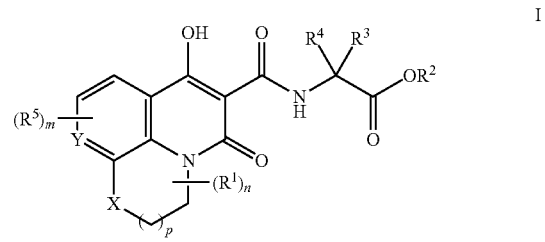

which inhibit HIF prolyl hydroxylase, their use for enhancing endogenous production of erythropoietin, and for treating conditions associated with reduced endogenous production of erythropoietin such as anemia and like conditions, as well as pharmaceutical compositions comprising such a compound and a pharmaceutical carrier.

DETAILED DESCRIPTION OF THE INVENTION

The present invention provides a compound of formula I or a pharmaceutically acceptable salt thereof:

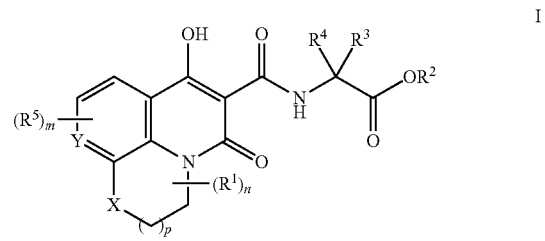

wherein:
Y is CH or N;
X is O, $CH_2$, S, S(O), $S(O)_2$, NH or N-Me;
m is 0, 1, 2 or 3;
n is 0, 1 or 2;
p is 0 or 1;
$R^1$ is independently selected from aryl, heterocyclyl, -Me-aryl, and -Me-heterocyclyl, said aryl and heterocyclyl are optionally substituted with 1, 2, or 3 substituents independently selected from: halogen, $CF_3$, phenyl, CN, $S(O)_2R^b$, and heterocyclyl, wherein said phenyl and heterocyclyl are optionally substituted with 1, 2, or 3 substituents independently selected from: $CF_3$, halogen, $C(O)N(R^b)_2$, $N(R^b)_2$, $C_{1-4}$ alkyl, $O(C_{1-4})$alkyl, and CN;
$R^2$ is hydrogen or methyl;
$R^3$ and R4 are each independently selected from hydrogen, hydroxyl, and $C_{1-4}$alkyl, said alkyl optionally substituted with OH;

R⁵ is independently selected from OH, halogen, CF₃, OCF₃, CN, $C_{1-4}$ alkyl, $O(C_{1-4})$alkyl, $S(O)_2R^b$, $C_{3-6}$ cycloalkyl, phenyl, and heterocyclyl, said cycloalkyl and heterocyclyl are optionally substituted with 1, 2, or 3 substituents independently selected from: OH, $C_{1-4}$ alkyl, $O(C_{1-4})$ alkyl, $S(O)_2R^b$, $C(O)N(R^b)_2$, and $N(R^b)_2$; and $R^b$ is independently hydrogen or $C_{1-4}$ alkyl.

Another embodiment of the present invention provides a compound of formula II or a pharmaceutically acceptable salt thereof:

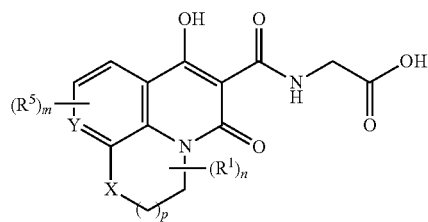

II wherein:
Y is CH or N;
X is O, CH₂, S, S(O), S(O)₂, NH or N-Me;
m is 0, 1 or 2;
n is 0 or 1;
p is 0 or 1;
R¹ is independently selected from phenyl, -Me-phenyl, thiazolyl, -Me-thiazolyl, pyridinyl and oxazolyl, all of which are optionally substituted with 1 or 2 substituents independently selected from: Br, F, Cl, CF₃, phenyl, CN, $S(O)_2R^b$, pyrazolyl, and pyridinyl, wherein said phenyl, pyrazolyl and pyridinyl are optionally substituted with 1 or 2 substituents independently selected from: CF₃, Cl, $C(O)N(R^b)_2$, $N(R^b)_2$, $C_{1-4}$ alkyl, $O(C_{1-4})$alkyl, and CN;
R5 is independently selected from OH, Br, F, Cl, CF₃, OCF₃, CN, $C_{1-4}$ alkyl, $O(C_{1-4})$alkyl, $S(O)_2R^b$, cyclopropyl, phenyl, isoxazolyl, pyrazolyl, pyrimidinyl and pyridinyl, said cyclopropy, phenyl, isoxazolyl, pyrazolyl, pyrimidinyl and pyridinyl are optionally substituted with 1 or 2 substituents independently selected from: OH, $C_{1-4}$ alkyl, $O(C_{1-4})$alkyl, $S(O)_2R^b$, $C(O)N(R^b)_2$, and $N(R^b)_2$; and
$R^b$ is independently hydrogen or $C_{1-4}$ alkyl.

Illustrative but nonlimiting examples of compounds of the invention are the following:

2-(7-Hydroxy-5-oxo-3-(4-(trifluoromethyl)phenyl)-3,5-dihydro-2H-[1,4]oxazino[2,3,4-ij]quinoline-6-carboxamido)acetic acid;

2-(7-Hydroxy-5-oxo-3-(4-(trifluoromethyl)phenyl)-3,5-dihydro-2H-[1,4]oxazino[2,3,4-ij]quinoline-6-carboxamido)acetic acid;

2-(7-Hydroxy-5-oxo-3-(4-(trifluoromethyl)benzyl)-3,5-dihydro-2H-[1,4]oxazino[2,3,4-ij]quinoline-6-carboxamido)acetic acid;

2-(9-Cyano-7-hydroxy-5-oxo-3-(4-(trifluoromethyl)benzyl)-3,5-dihydro-2H-[1,4]oxazino[2,3,4-ij]quinoline-6-carboxamido)acetic acid;

2-(9-Bromo-7-hydroxy-5-oxo-3-(4-(trifluoromethyl)benzyl)-3,5-dihydro-2H-[1,4]oxazino[2,3,4-ij]quinoline-6-carboxamido)acetic acid;

2-(7-Hydroxy-9-(methylsulfonyl)-5-oxo-3-(4-(trifluoromethyl)benzyl)-3,5-dihydro-2H-[1,4]oxazino[2,3,4-ij]quinoline-6-carboxamido)acetic acid;

2-(7-hydroxy-9-methyl-5-oxo-3-(4-(trifluoromethyl)benzyl)-3,5-dihydro-2H-[1,4]oxazino[2,3,4-ij]quinoline-6-carboxamido)acetic acid;

2-(9-(1,2-Dihydroxypropan-2-yl)-7-hydroxy-5-oxo-3-(4-(trifluoromethyl)benzyl)-3,5-dihydro-2H-[1,4]oxazino[2,3,4-ij]quinoline-6-carboxamido)acetic acid;

2-(1-Hydroxy-3-oxo-6-(4-(trifluoromethyl)phenyl)-3,5,6,7-tetrahydropyrido[3,2,1-ij]quinoline-2-carboxamido)acetic acid;

2-(7-Hydroxy-5-oxo-2-(4-(trifluoromethyl)phenyl)-3,5-dihydro-2H-[1,4]oxazino[2,3,4-ij]quinoline-6-carboxamido)acetic acid;

2-(8-Bromo-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(7-Hydroxy-8-(methylsulfonyl)-5-oxo-2-(4-(trifluoromethyl)phenyl)-3,5-dihydro-2H-[1,4]oxazino[2,3,4-ij]quinoline-6-carboxamido)acetic acid;

2-(8-Cyano-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(9-Cyano-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(9-Bromo-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(7-Hydroxy-9-(methylsulfonyl)-5-oxo-2-(4-(trifluoromethyl)phenyl)-3,5-dihydro-2H-[1,4]oxazino[2,3,4-ij]quinoline-6-carboxamido)acetic acid;

2-(7-Hydroxy-9-methyl-5-oxo-2-(4-(trifluoromethyl)phenyl)-3,5-dihydro-2H-[1,4]oxazino[2,3,4-ij]quinoline-6-carboxamido)acetic acid;

2-(10-Cyano-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(10-Bromo-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(7-Hydroxy-10-(methylsulfonyl)-5-oxo-2-(4-(trifluoromethyl)phenyl)-3,5-dihydro-2H-[1,4]oxazino[2,3,4-ij]quinoline-6-carboxamido)acetic acid;

2-(7-Hydroxy-10-methyl-5-oxo-2-(4-(trifluoromethyl)phenyl)-3,5-dihydro-2H-[1,4]oxazino[2,3,4-ij]quinoline-6-carboxamido)acetic acid;

2-(8-bromo-7-hydroxy-5-oxo-3-(4-(trifluoromethyl)benzyl)-3,5-dihydro-2H-[1,4]oxazino[2,3,4-ij]quinoline-6-carboxamido)acetic acid;

2-(10-Bromo-7-hydroxy-5-oxo-3-(4-(trifluoromethyl)benzyl)-3,5-dihydro-2H-[1,4]oxazino[2,3,4-ij]quinoline-6-carboxamido)acetic acid;

2-(7-Hydroxy-8-(methylsulfonyl)-5-oxo-3-(4-(trifluoromethyl)benzyl)-3,5-dihydro-2H-[1,4]oxazino[2,3,4-ij]quinoline-6-carboxamido)acetic acid;

2-(8-Cyano-7-hydroxy-5-oxo-3-(4-(trifluoromethyl)benzyl)-3,5-dihydro-2H-[1,4]oxazino[2,3,4-ij]quinoline-6-carboxamido)acetic acid;

2-(7-Hydroxy-8-methyl-5-oxo-3-(4-(trifluoromethyl)benzyl)-3,5-dihydro-2H-[1,4]oxazino[2,3,4-ij]quinoline-6-carboxamido)acetic acid;

2-(7-Hydroxy-10-(methylsulfonyl)-5-oxo-3-(4-(trifluoromethyl)benzyl)-3,5-dihydro-2H-[1,4]oxazino[2,3,4-ij]quinoline-6-carboxamido)acetic acid;

2-(10-Cyano-7-hydroxy-5-oxo-3-(4-(trifluoromethyl)benzyl)-3,5-dihydro-2H-[1,4]oxazino[2,3,4-ij]quinoline-6-carboxamido)acetic acid;

2-(7-Hydroxy-10-methyl-5-oxo-3-(4-(trifluoromethyl)benzyl)-3,5-dihydro-2H-[1,4]oxazino[2,3,4-ij]quinoline-6-carboxamido)acetic acid;

2-(9-acetyl-7-hydroxy-5-oxo-3-(4-(trifluoromethyl)benzyl)-3,5-dihydro-2H-[1,4]oxazino[2,3,4-ij]quinoline-6-carboxamido)acetic acid;

2-(7-Hydroxy-9-(1-hydroxyethyl)-5-oxo-3-(4-(trifluoromethyl)benzyl)-3,5-dihydro-2H-[1,4]oxazino[2,3,4-ij]quinoline-6-carboxamido)acetic acid;

2-(7-Hydroxy-9-(2-hydroxypropan-2-yl)-5-oxo-3-(4-(trifluoromethyl)benzyl)-3,5-dihydro-2H-[1,4]oxazino[2,3,4-ij]quinoline-6-carboxamido)acetic acid;

2-(10-cyano-7-hydroxy-5-oxo-3,5-dihydro-2H-[1,4]oxazino[2,3,4-ij]quinoline-6-carboxamido)acetic acid;

2-(7-Hydroxy-10-(methylsulfonyl)-5-oxo-3,5-dihydro-2H-[1,4]oxazino[2,3,4-ij]quinoline-6-carboxamido)acetic acid;

2-(7-Hydroxy-10-methyl-5-oxo-3,5-dihydro-2H-[1,4]oxazino[2,3,4-ij]quinoline-6-carboxamido)acetic acid;

2-(7-hydroxy-5-oxo-10-phenyl-3,5-dihydro-2H-[1,4]oxazino[2,3,4-ij]quinoline-6-carboxamido)acetic acid;

2-(9-Cyano-7-hydroxy-5-oxo-3,5-dihydro-2H-[1,4]oxazino[2,3,4-ij]quinoline-6-carboxamido)acetic acid;

2-(7-hydroxy-9-(methylsulfonyl)-5-oxo-3,5-dihydro-2H-[1,4]oxazino[2,3,4-ij]quinoline-6-carboxamido)acetic acid;

2-(7-Hydroxy-9-methyl-5-oxo-3,5-dihydro-2H-[1,4]oxazino[2,3,4-ij]quinoline-6-carboxamido)acetic acid;

2-(8-Cyano-1-hydroxy-3-oxo-3,5,6,7-tetrahydropyrido[3,2,1-ij]quinoline-2-carboxamido)acetic acid;

2-(1-Hydroxy-8-(methylsulfonyl)-3-oxo-3,5,6,7-tetrahydropyrido[3,2,1-ij]quinoline-2-carboxamido)acetic acid;

2-(1-Hydroxy-8-methyl-3-oxo-3,5,6,7-tetrahydropyrido[3,2,1-ij]quinoline-2-carboxamido)acetic acid;

2-(9-Bromo-1-hydroxy-3-oxo-3,5,6,7-tetrahydropyrido[3,2,1-ij]quinoline-2-carboxamido)acetic acid;

2-(9-Cyano-1-hydroxy-3-oxo-3,5,6,7-tetrahydropyrido[3,2,1-ij]quinoline-2-carboxamido)acetic acid;

2-(1-Hydroxy-9-(methylsulfonyl)-3-oxo-3,5,6,7-tetrahydropyrido[3,2,1-ij]quinoline-2-carboxamido)acetic acid;

2-(1-Hydroxy-3-oxo-6-(thiazol-5-yl)-3,5,6,7-tetrahydropyrido[3,2,1-ij]quinoline-2-carboxamido)acetic acid 2-(7-Hydroxy-5-oxo-2-(4-(trifluoromethyl)phenyl)-3,5-dihydro-2H-[1,4]oxazino[2,3,4-ij][1,7]naphthyridine-6-carboxamido)acetic acid;

2-(9-Cyano-2-(4-cyanophenyl)-7-hydroxy-5-oxo-3,5-dihydro-2H-[1,4]oxazino[2,3,4-ij]quinoline-6-carboxamido)acetic acid;

2-(9-Bromo-2-(4-bromophenyl)-7-hydroxy-5-oxo-3,5-dihydro-2H-[1,4]oxazino[2,3,4-ij]quinoline-6-carboxamido)acetic acid;

2-(8-Cyano-2-(4-cyanophenyl)-7-hydroxy-5-oxo-3,5-dihydro-2H-[1,4]oxazino[2,3,4-ij]quinoline-6-carboxamido)acetic acid;

2-(8-Bromo-2-(4-bromophenyl)-7-hydroxy-5-oxo-3,5-dihydro-2H-[1,4]oxazino[2,3,4-ij]quinoline-6-carboxamido)acetic acid;

2-(10-Cyano-2-(4-cyanophenyl)-7-hydroxy-5-oxo-3,5-dihydro-2H-[1,4]oxazino[2,3,4-ij]quinoline-6-carboxamido)acetic acid;

2-(10-Bromo-2-(4-bromophenyl)-7-hydroxy-5-oxo-3,5-dihydro-2H-[1,4]oxazino[2,3,4-ij]quinoline-6-carboxamido)acetic acid;

2-(7-Hydroxy-5-oxo-2-(4-(trifluoromethyl)phenyl)-3,5-dihydro-2H-[1,4]thiazino[2,3,4-ij]quinoline-6-carboxamido)acetic acid;

2-(7-Hydroxy-1-oxido-5-oxo-2-(4-(trifluoromethyl)phenyl)-3,5-dihydro-2H-[1,4]thiazino[2,3,4-ij]quinoline-6-carboxamido)acetic acid;

2-(7-Hydroxy-1,1-dioxido-5-oxo-2-(4-(trifluoromethyl)phenyl)-3,5-dihydro-2H-[1,4]thiazino[2,3,4-ij]quinoline-6-carboxamido)acetic acid;

2-(7-hydroxy-1-oxido-5-oxo-2-(4-(trifluoromethyl)phenyl)-3,5-dihydro-2H-[1,4]thiazino[2,3,4-ij]quinoline-6-carboxamido)acetic acid;

2(9-Cyano-1-hydroxy-3-oxo-6-(4-(trifluoromethyl)phenyl)-3,5,6,7-tetrahydropyrido[3,2,1-ij]quinoline-2-carboxamido)acetic acid;

2-(7-Hydroxy-8-methyl-5-oxo-2-(4-(trifluoromethyl)phenyl)-3,5-dihydro-2H-[1,4]oxazino[2,3,4-ij]quinoline-6-carboxamido)acetic acid;

2-(7-Hydroxy-5-oxo-2-(4-(trifluoromethyl)phenyl)-1,2,3,5-tetrahydropyrido[1,2,3-de]quinoxaline-6-carboxamido)acetic acid;

2-(7-Hydroxy-1-methyl-5-oxo-2-(4-(trifluoromethyl)phenyl)-1,2,3,5-tetrahydropyrido[1,2,3-de]quinoxaline-6-carboxamido)acetic acid;

2-(9-Fluoro-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(10-Fluoro-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(8-Fluoro-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(8-fluoro-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(8-Chloro-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(8-chloro-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(10-Chloro-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(10-chloro-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(9-Chloro-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(9-chloro-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(7-Hydroxy-2-(4-(methylsulfonyl)phenyl)-5-oxo-10-(trifluoromethyl)-3,5-dihydro-2H-[1,4]oxazino[2,3,4-ij]quinoline-6-carboxamido)acetic acid;

2-(2-(4-cyanophenyl)-7-hydroxy-5-oxo-10-(trifluoromethyl)-3,5-dihydro-2H-[1,4]oxazino[2,3,4-ij]quinoline-6-carboxamido)acetic acid;

2-(2-(4-cyanophenyl)-7-hydroxy-10-(trifluoromethyl)-3,5-dihydro-2H-[1,4]oxazino[2,3,4-ij]quinoline-6-carboxamido)acetic acid;

2-(7-hydroxy-8-methoxy-5-oxo-2-(4-(trifluoromethyl)phenyl)-3,5-dihydro-2H-[1,4]oxazino[2,3,4-ij]quinoline-6-carboxamido)acetic acid;

2-(7,8-dihydroxy-5-oxo-2-(4-(trifluoromethyl)phenyl)-3,5-dihydro-2H-[1,4]oxazino[2,3,4-ij]quinoline-6-carboxamido)acetic acid;

2-(7-Hydroxy-9-methoxy-5-oxo-2-(4-(trifluoromethyl)phenyl)-3,5-dihydro-2H-[1,4]oxazino[2,3,4-ij]quinoline-6-carboxamido)acetic acid;

2-(7,9-Dihydroxy-5-oxo-2-(4-(trifluoromethyl)phenyl)-3,5-dihydro-2H-[1,4]oxazino[2,3,4-ij]quinoline-6-carboxamido)acetic acid;

2-(1-Hydroxy-3-oxo-6-(6-(trifluoromethyl)pyridin-3-yl)-3,5,6,7-tetrahydropyrido[3,2,1-ij]quinoline-2-carboxamido)acetic acid;

2-(9-cyano-1-hydroxy-3-oxo-6-(6-(trifluoromethyl)pyridin-3-yl)-3,5,6,7-tetrahydropyrido[3,2,1-ij]quinoline-2-carboxamido)acetic acid;

2-(1-hydroxy-9-(methylsulfonyl)-3-oxo-6-(6-(trifluoromethyl)pyridin-3-yl)-3,5,6,7-tetrahydropyrido[3,2,1-ij]quinoline-2-carboxamido)acetic acid;

2-(7-Hydroxy-5-oxo-8-(trifluoromethoxy)-2-(4-(trifluoromethyl)phenyl)-3,5-dihydro-2H-[1,4]oxazino[2,3,4-ij]quinoline-6-carboxamido)acetic acid;

2-(7-hydroxy-5-oxo-8-(trifluoromethoxy)-2-(4-(trifluoromethyl)phenyl)-3,5-dihydro-2H-[1,4]oxazino[2,3,4-ij]quinoline-6-carboxamido)acetic acid;

2-(2-(4-Cyanophenyl)-7-hydroxy-5-oxo-8-(trifluoromethoxy)-3,5-dihydro-2H-[1,4]oxazino[2,3,4-ij]quinoline-6-carboxamido)acetic acid;

2-(2-(4-cyanophenyl)-7-hydroxy-5-oxo-8-(trifluoromethoxy)-3,5-dihydro-2H-[1,4]oxazino[2,3,4-ij]quinoline-6-carboxamido)acetic acid;

2-(9-Cyano-7-hydroxy-5-oxo-2-(4-(trifluoromethyl)phenyl)-3,5-dihydro-2H-[1,4]thiazino[2,3,4-ij]quinoline-6-carboxamido)acetic acid;

2-(9-Cyano-7-hydroxy-1-oxido-5-oxo-2-(4-(trifluoromethyl)phenyl)-3,5-dihydro-2H-[1,4]thiazino[2,3,4-ij]quinoline-6-carboxamido)acetic acid;

2-(9-Cyano-7-hydroxy-5-oxo-3-(4-(trifluoromethyl)phenyl)-1,2,3,5-tetrahydropyrido[1,2,3-de]quinoxaline-6-carboxamido)acetic acid;

2-(9-Cyano-7-hydroxy-5-oxo-2-(4-(trifluoromethyl)phenyl)-1,2,3,5-tetrahydropyrido[1,2,3-de]quinoxaline-6-carboxamido)acetic acid;

2-(8-Cyano-7-hydroxy-5-oxo-2-(4-(trifluoromethyl)phenyl)-1,2,3,5-tetrahydropyrido[1,2,3-de]quinoxaline-6-carboxamido)acetic acid;

2-(9-Cyano-7-hydroxy-1-methyl-5-oxo-3-(4-(trifluoromethyl)phenyl)-1,2,3,5-tetrahydropyrido[1,2,3-de]quinoxaline-6-carboxamido)acetic acid;

2-(9-Cyano-7-hydroxy-1-methyl-5-oxo-2-(4-(trifluoromethyl)phenyl)-1,2,3,5-tetrahydropyrido[1,2,3-de]quinoxaline-6-carboxamido)acetic acid;

2-(8-Cyano-7-hydroxy-5-oxo-2-(4-(trifluoromethyl)phenyl)-3,5-dihydro-2H-[1,4]thiazino[2,3,4-ij]quinoline-6-carboxamido)acetic acid;

2-(8-Fluoro-7-hydroxy-5-oxo-3-(4-(trifluoromethyl)phenyl)-3,5-dihydro-2H-[1,4]thiazino[2,3,4-ij]quinoline-6-carboxamido)acetic acid;

2-(8-Cyano-7-hydroxy-5-oxo-3-(4-(trifluoromethyl)phenyl)-3,5-dihydro-2H-[1,4]thiazino[2,3,4-ij]quinoline-6-carboxamido)acetic acid;

2-(7-Hydroxy-5-oxo-3-(4-(trifluoromethyl)phenyl)-3,5-dihydro-2H-[1,4]thiazino[2,3,4-ij]quinoline-6-carboxamido)acetic acid;

2-(7-hydroxy-1,1-dioxido-5-oxo-3-(4-(trifluoromethyl)phenyl)-3,5-dihydro-2H-[1,4]thiazino[2,3,4-ij]quinoline-6-carboxamido)acetic acid;

2-(9-Cyano-7-hydroxy-5-oxo-3-(4-(trifluoromethyl)phenyl)-3,5-dihydro-2H-[1,4]thiazino[2,3,4-ij]quinoline-6-carboxamido)acetic acid;

2-(7-Hydroxy-5-oxo-2-(6-(trifluoromethyl)pyridin-3-yl)-3,5-dihydro-2H-[1,4]thiazino[2,3,4-ij]quinoline-6-carboxamido)acetic acid;

2-(7-Hydroxy-1,1-dioxido-5-oxo-2-(6-(trifluoromethyl)pyridin-3-yl)-3,5-dihydro-2H-[1,4]thiazino[2,3,4-ij]quinoline-6-carboxamido)acetic acid;

2-(7-Hydroxy-5-oxo-3-(thiazol-5-yl)-3,5-dihydro-2H-[1,4]thiazino[2,3,4-ij]quinoline-6-carboxamido)acetic acid;

2-(7-Hydroxy-5-oxo-3-(4-(trifluoromethyl)phenyl)-1,2,3,5-tetrahydropyrido[1,2,3-de]quinoxaline-6-carboxamido)acetic acid;

2-(7-Hydroxy-1-methyl-5-oxo-3-(4-(trifluoromethyl)phenyl)-1,2,3,5-tetrahydropyrido[1,2,3-de]quinoxaline-6-carboxamido)acetic acid;

2-(7-Hydroxy-5-oxo-2-(4-(trifluoromethyl)phenyl)-1,2,3,5-tetrahydropyrido[1,2,3-de]quinoxaline-6-carboxamido)acetic acid;

2-(10-Cyano-7-hydroxy-5-oxo-2-(thiazol-5-yl)-1,2,3,5-tetrahydropyrido[1,2,3-de]quinoxaline-6-carboxamido)acetic acid;

2-(7-Hydroxy-5-oxo-2-(thiazol-5-yl)-1,2,3,5-tetrahydropyrido[1,2,3-de]quinoxaline-6-carboxamido)acetic acid;

2-(7-Hydroxy-5-oxo-3-(thiazol-5-yl)-1,2,3,5-tetrahydropyrido[1,2,3-de]quinoxaline-6-carboxamido)acetic acid;

2-(7-Hydroxy-1-methyl-5-oxo-2-(thiazol-5-yl)-1,2,3,5-tetrahydropyrido[1,2,3-de]quinoxaline-6-carboxamido)acetic acid;

2-(7-Hydroxy-1-methyl-5-oxo-3-(thiazol-5-yl)-1,2,3,5-tetrahydropyrido[1,2,3-de]quinoxaline-6-carboxamido)acetic acid;

2-(10-Cyano-7-hydroxy-5-oxo-2-(4-(trifluoromethyl)phenyl)-1,2,3,5-tetrahydropyrido[1,2,3-de]quinoxaline-6-carboxamido)acetic acid;

2-(10-Fluoro-7-hydroxy-5-oxo-3-(4-(trifluoromethyl)phenyl)-1,2,3,5-tetrahydropyrido[1,2,3-de]quinoxaline-6-carboxamido)acetic acid;

2-(10-Fluoro-7-hydroxy-5-oxo-2-(4-(trifluoromethyl)phenyl)-1,2,3,5-tetrahydropyrido[1,2,3-de]quinoxaline-6-carboxamido)acetic acid;

2-(10-Fluoro-7-hydroxy-1-methyl-5-oxo-3-(4-(trifluoromethyl)phenyl)-1,2,3,5-tetrahydropyrido[1,2,3-de]quinoxaline-6-carboxamido)acetic acid;

2-(9-Fluoro-7-hydroxy-5-oxo-3-(4-(trifluoromethyl)phenyl)-1,2,3,5-tetrahydropyrido[1,2,3-de]quinoxaline-6-carboxamido)acetic acid;

2-(8-Fluoro-7-hydroxy-5-oxo-2-(4-(trifluoromethyl)phenyl)-1,2,3,5-tetrahydropyrido[1,2,3-de]quinoxaline-6-carboxamido)acetic acid;

2-(9-Fluoro-7-hydroxy-5-oxo-2-(4-(trifluoromethyl)phenyl)-1,2,3,5-tetrahydropyrido[1,2,3-de]quinoxaline-6-carboxamido)acetic acid;

2-(8-Fluoro-7-hydroxy-5-oxo-3-(4-(trifluoromethyl)phenyl)-1,2,3,5-tetrahydropyrido[1,2,3-de]quinoxaline-6-carboxamido)acetic acid;

2-(9-Fluoro-7-hydroxy-1-methyl-5-oxo-3-(4-(trifluoromethyl)phenyl)-1,2,3,5-tetrahydropyrido[1,2,3-de]quinoxaline-6-carboxamido)acetic acid;

2-(9-Fluoro-7-hydroxy-1-methyl-5-oxo-2-(4-(trifluoromethyl)phenyl)-1,2,3,5-tetrahydropyrido[1,2,3-de]quinoxaline-6-carboxamido)acetic acid;

2-(7-Hydroxy-5-oxo-9-(trifluoromethoxy)-2-(4-(trifluoromethyl)phenyl)-3,5-dihydro-2H-[1,4]oxazino[2,3,4-ij]quinoline-6-carboxamido)acetic acid;

2-(2-(4-Cyanophenyl)-7-hydroxy-5-oxo-9-(trifluoromethoxy)-3,5-dihydro-2H-[1,4]oxazino[2,3,4-ij]quinoline-6-carboxamido)acetic acid;

2-(7-Hydroxy-5-oxo-2-(6-(trifluoromethyl)pyridin-3-yl)-1,2,3,5-tetrahydropyrido[1,2,3-de]quinoxaline-6-carboxamido)acetic acid;

2-(7-Hydroxy-5-oxo-3-(6-(trifluoromethyl)pyridin-3-yl)-1,2,3,5-tetrahydropyrido[1,2,3-de]quinoxaline-6-carboxamido)acetic acid;

2-(7-Hydroxy-1-methyl-5-oxo-3-(6-(trifluoromethyl)pyridin-3-yl)-1,2,3,5-tetrahydropyrido[1,2,3-de]quinoxaline-6-carboxamido)acetic acid;

2-(6-Hydroxy-4-oxo-2-phenyl-2,4-dihydro-1H-pyrrolo[3,2,1-ij]quinoline-5-carboxamido)acetic acid;

2-(1-Hydroxy-3-oxo-5-phenyl-3,5,6,7-tetrahydropyrido[3,2,1-ij]quinoline-2-carboxamido)acetic acid;

2-(5-(4-Chlorobenzyl)-1-hydroxy-3-oxo-3,5,6,7-tetrahydropyrido[3,2,1-ij]quinoline-2-carboxamido)acetic acid;

2-(7-Hydroxy-5-oxo-3,5-dihydro-2H-[1,4]oxazino[2,3,4-ij]quinoline-6-carboxamido)acetic acid;

2-(3-(4-Bromophenyl)-7-hydroxy-5-oxo-3,5-dihydro-2H-[1,4]oxazino[2,3,4-ij]quinoline-6-carboxamido)acetic acid;

N-[(7-Hydroxy-10-{4-[(methylsulfonyl)amino]phenyl}-5-oxo-3-[4-(trifluoromethyl)phenyl]-2,3-dihydro-5H-[1,4]oxazino[2,3,4-ij]quinolin-6-yl)carbonyl]glycine;

N-({7-hydroxy-10-(5-methoxypyridin-3-yl)-5-oxo-3-[4-(trifluoromethyl)phenyl]-2,3-dihydro-5H-[1,4]oxazino[2,3,4-ij]quinolin-6-yl}carbonyl)glycine;

N-({7-hydroxy-5-oxo-10-pyridin-2-yl-3-[4-(trifluoromethyl)phenyl]-2,3-dihydro-5H-[1,4]oxazino[2,3,4-ij]quinolin-6-yl}carbonyl)glycine;

N-({7-hydroxy-10-(2-methoxypyrimidin-5-yl)-5-oxo-3-[4-(trifluoromethyl)phenyl]-2,3-dihydro-5H-[1,4]oxazino[2,3,4-ij]quinolin-6-yl}carbonyl)glycine;

N-({10-(3-carbamoylphenyl)-7-hydroxy-5-oxo-3-[4-(trifluoromethyl)phenyl]-2,3-dihydro-5H-[1,4]oxazino[2,3,4-ij]quinolin-6-yl}carbonyl)glycine;

2-(7-hydroxy-5-oxo-10-(1H-pyrazol-5-yl)-3-(4-(trifluoromethyl)phenyl)-3,5-dihydro-2H-[1,4]oxazino[2,3,4-ij]quinoline-6-carboxamido)acetic acid;

N-{[3-(4'-Carbamoylbiphenyl-4-yl)-7-hydroxy-5-oxo-2,3-dihydro-5H-[1,4]oxazino[2,3,4-ij]quinolin-6-yl]carbonyl}glycine;

N-{[3-(3'-chlorobiphenyl-4-yl)-7-hydroxy-5-oxo-2,3-dihydro-5H-[1,4]oxazino[2,3,4-ij]quinolin-6-yl]carbonyl}glycine;

N-[(7-hydroxy-5-oxo-3-{4-[6-(trifluoromethyl)pyridin-3-yl]phenyl}-2,3-dihydro-5H-[1,4]oxazino[2,3,4-ij]quinolin-6-yl)carbonyl]glycine;

N-{[7-hydroxy-3-(4'-methylbiphenyl-4-yl)-5-oxo-2,3-dihydro-5H-[1,4]oxazino[2,3,4-ij]quinolin-6-yl]carbonyl}glycine;

N-{[7-hydroxy-3-(4'-methoxybiphenyl-4-yl)-5-oxo-2,3-dihydro-5H-[1,4]oxazino[2,3,4-ij]quinolin-6-yl]carbonyl}glycine;

N-{[3-(4'-cyanobiphenyl-4-yl)-7-hydroxy-5-oxo-2,3-dihydro-5H-[1,4]oxazino[2,3,4-ij]quinolin-6-yl]carbonyl}glycine;

N-({7-hydroxy-3-[4-(2-methoxypyridin-3-yl)phenyl]-5-oxo-2,3-dihydro-5H-[1,4]oxazino[2,3,4-ij]quinolin-6-yl}carbonyl)glycine;

N-{[7-hydroxy-5-oxo-3-(4-pyridin-4-ylphenyl)-2,3-dihydro-5H-[1,4]oxazino[2,3,4-ij]quinolin-6-yl]carbonyl}glycine;

N-({3-[4-(6-aminopyridin-3-yl)phenyl]-7-hydroxy-5-oxo-2,3-dihydro-5H-[1,4]oxazino[2,3,4-ij]quinolin-6-yl}carbonyl)glycine;

N-{[3-(3'-cyanobiphenyl-4-yl)-7-hydroxy-5-oxo-2,3-dihydro-5H-[1,4]oxazino[2,3,4-ij]quinolin-6-yl]carbonyl}glycine;

N-{[7-hydroxy-5-oxo-3-(4-pyridin-3-ylphenyl)-2,3-dihydro-5H-[1,4]oxazino[2,3,4-ij]quinolin-6-yl]carbonyl}glycine;

2-(3-(4-(1H-pyrazol-5-yl)phenyl)-7-hydroxy-5-oxo-3,5-dihydro-2H-[1,4]oxazino[2,3,4-ij]quinoline-6-carboxamido)acetic acid;

N-[(7-Hydroxy-5-oxo-10-pyridin-3-yl-2,3-dihydro-5H-[1,4]oxazino[2,3,4-ij]quinolin-6-yl)carbonyl]glycine;

N-{[7-hydroxy-10-(6-methoxypyridin-3-yl)-5-oxo-2,3-dihydro-5H-[1,4]oxazino[2,3,4-ij]quinolin-6-yl]carbonyl}glycine;

N-{[10(3,5-dimethylisoxazol-4-yl)-7-hydroxy-5-oxo-2,3-dihydro-5H-[1,4]oxazino[2,3,4-ij]quinolin-6-yl]carbonyl}glycine;

N-{[10-(6-aminopyridin-3-yl)-7-hydroxy-5-oxo-2,3-dihydro-5H-[1,4]oxazino[2,3,4-ij]quinolin-6-yl]carbonyl}glycine;

2-(7-Hydroxy-5-oxo-3-(4-chlorophenyl)-3,5-dihydro-2H-[1,4]oxazino[2,3,4-ij]quinoline-6-carboxamido)acetic acid;

2-(9-fluoro-7-hydroxy-5-oxo-3-(4-(trifluoromethyl)phenyl)-3,5-dihydro-2H-[1,4]oxazino[2,3,4-ij]quinoline-6-carboxamido)acetic acid;

2-(9-bromo-7-hydroxy-5-oxo-3-(4-(trifluoromethyl)phenyl)-3,5-dihydro-2H-[1,4]oxazino[2,3,4-ij]quinoline-6-carboxamido)acetic acid;

2-(7-hydroxy-5-oxo-3-(6-(trifluoromethyl)pyridin-3-yl)-3,5-dihydro-2H-[1,4]oxazino[2,3,4-ij]quinoline-6-carboxamido)acetic acid;

2-(10-bromo-7-hydroxy-5-oxo-3-(4-(trifluoromethyl)phenyl)-3,5-dihydro-2H-[1,4]oxazino[2,3,4-ij]quinoline-6-carboxamido)acetic acid;

2-(8-fluoro-7-hydroxy-5-oxo-3-(4-(trifluoromethyl)phenyl)-3,5-dihydro-2H-[1,4]oxazino[2,3,4-ij]quinoline-6-carboxamido)acetic acid;

2-(7-hydroxy-3-(4-methoxyphenyl)-5-oxo-3,5-dihydro-2H-[1,4]oxazino[2,3,4-ij]quinoline-6-carboxamido)acetic acid;

2-(10-fluoro-7-hydroxy-5-oxo-3-(4-(trifluoromethyl)phenyl)-3,5-dihydro-2H-[1,4]oxazino[2,3,4-ij]quinoline-6-carboxamido)acetic acid;

2-(10-chloro-7-hydroxy-5-oxo-3-(4-(trifluoromethyl)phenyl)-3,5-dihydro-2H-[1,4]oxazino[2,3,4-ij]quinoline-6-carboxamido)acetic acid;

2-(9-chloro-7-hydroxy-5-oxo-3-(4-(trifluoromethyl)phenyl)-3,5-dihydro-2H-[1,4]oxazino[2,3,4-ij]quinoline-6-carboxamido)acetic acid;

droxy-5-oxo-3-(3-(trifluoromethyl)phenyl)-3,5-dihydro-2H-[1,4]oxazino[2,3,4-ij]quinoline-6-carboxamido)acetic acid;

2-(7-hydroxy-5-oxo-3-(thiazol-2-yl)-3,5-dihydro-2H-[1,4]oxazino[2,3,4-ij]quinoline-6-carboxamido)acetic acid;

2-(8-bromo-7-hydroxy-5-oxo-3-(4-(trifluoromethyl)phenyl)-3,5-dihydro-2H-[1,4]oxazino[2,3,4-ij]quinoline-6-carboxamido)acetic acid;

2-(10-bromo-7-hydroxy-5-oxo-3-(thiazol-4-yl)-3,5-dihydro-2H-[1,4]oxazino[2,3,4-ij]quinoline-6-carboxamido)acetic acid;

2-(7-hydroxy-5-oxo-3-(2-(trifluoromethyl)thiazol-5-yl)-3,5-dihydro-2H-[1,4]oxazino[2,3,4-ij]quinoline-6-carboxamido)acetic acid;

2-(8-fluoro-7-hydroxy-5-oxo-3-(thiazol-5-yl)-3,5-dihydro-2H-[1,4]oxazino[2,3,4-ij]quinoline-6-carboxamido)acetic acid;

2-(7-hydroxy-3-(oxazol-5-yl)-5-oxo-3,5-dihydro-2H-[1,4]oxazino[2,3,4-ij]quinoline-6-carboxamido)acetic acid;

2-(10-fluoro-7-hydroxy-5-oxo-3-(thiazol-5-yl)-3,5-dihydro-2H-[1,4]oxazino[2,3,4-ij]quinoline-6-carboxamido)acetic acid;
2-(8,10-difluoro-7-hydroxy-5-oxo-3-(thiazol-5-yl)-3,5-dihydro-2H-[1,4]oxazino[2,3,4-ij]quinoline-6-carboxamido)acetic acid;
2-(8-bromo-7-hydroxy-5-oxo-3-(thiazol-5-yl)-3,5-dihydro-2H-[1,4]oxazino[2,3,4-ij]quinoline-6-carboxamido)acetic acid;
2-(10-bromo-7-hydroxy-5-oxo-3-(thiazol-5-yl)-3,5-dihydro-2H-[1,4]oxazino[2,3,4-ij]quinoline-6-carboxamido)acetic acid;
ammonium 2-(9-cyano-7-hydroxy-5-oxo-3-(4-(trifluoromethyl)phenyl)-3,5-dihydro-2H-[1,4]oxazino[2,3,4-ij]quinoline-6-carboxamido)acetate;
ammonium 2-(8-cyano-7-hydroxy-5-oxo-3-(4-(trifluoromethyl)phenyl)-3,5-dihydro-2H-[1,4]oxazino[2,3,4-ij]quinoline-6-carboxamido)acetate;
ammonium 2-(3-(4-cyanophenyl)-7-hydroxy-5-oxo-3,5-dihydro-2H-[1,4]oxazino[2,3,4-ij]quinoline-6-carboxamido)acetate;
ammonium 2-(10-cyano-7-hydroxy-5-oxo-3-(thiazol-5-yl)-3,5-dihydro-2H-[1,4]oxazino[2,3,4-ij]quinoline-6-carboxamido)acetate;
ammonium 2-(7-hydroxy-9-(methylsulfonyl)-5-oxo-3-(4-(trifluoromethyl)phenyl)-3,5-dihydro-2H-[1,4]oxazino[2,3,4-ij]quinoline-6-carboxamido)acetate;
2-(7-Hydroxy-5-oxo-9-(1H-pyrazol-5-yl)-3-(4-(trifluoromethyl)phenyl)-3,5-dihydro-2H-[1,4]oxazino[2,3,4-ij]quinoline-6-carboxamido)acetic acid;
2-(7-Hydroxy-10-methyl-5-oxo-3-(thiazol-4-yl)-3,5-dihydro-2H-[1,4]oxazino[2,3,4-ij]quinoline-6-carboxamido)acetic acid; and
2-(10-Cyclopropyl-7-hydroxy-5-oxo-3-(thiazol-4-yl)-3,5-dihydro-2H-[1,4]oxazino[2,3,4-ij]quinoline-6-carboxamido)acetic acid;
or a pharmaceutically acceptable salt thereof.

As used herein, the term "alkyl" means both branched- and straight-chain saturated aliphatic hydrocarbon groups having the specified number of carbon atoms. For example, $C_1$-$C_4$ alkyl includes, but is not limited to, methyl (Me), ethyl (Et), n-propyl (Pr), n-butyl (Bu), n-pentyl, n-hexyl, and the isomers thereof such as isopropyl (i-Pr), isobutyl (i-Bu), secbutyl (s-Bu), tert-butyl (t-Bu) and the like.

The term "cycloalkyl" means a monocyclic saturated carbocyclic ring, having the specified number of carbon atoms, e.g., 3, 4, 5 or 6 carbon atoms. Non-limiting examples of $C_3$-$C_6$ cycloalkyl include cyclopropyl, cyclobutyl, cyclopentyl and cyclohexyl.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and polycarbocyclic ring systems, wherein the individual carbocyclic rings in the polyring systems are fused or attached to each other via a single bond. Suitable aryl groups include phenyl, naphthyl, and biphenylenyl.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

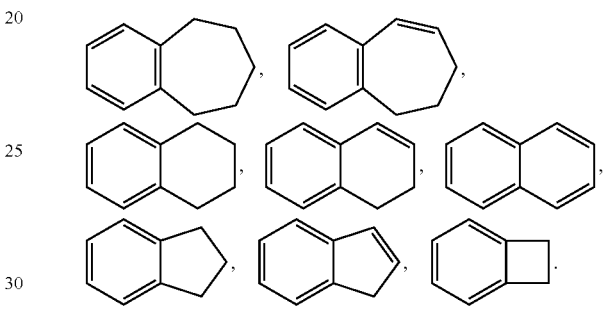

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Non limiting examples of heterocyclylic moieties include, but are not limited to, the following: azepanyl, azabenzimidazole, benzoimidazolyl, benzofuryl, benzofurazanyl, benzopyrazolyl, benzothiazolyl, benzothienyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazolinyl, isooxazolinyl, oxetanyl, pyranyl, pyrazinyl, pyrazolidinyl, pyrazolyl, pyridazinyl, pyridopyridinyl, pyridazinyl, pyridinyl, pyrimidyl, pyrrolyl, quinazolinyl, quinolyl, quinoxalinyl, quinoxalinyl, tetrahydropyranyl, tetrahydroisoquinolinyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuryl, tetrahydrothienyl, tetrahydroquinolinyl, 2,3-dihydrobenzofuryl, 2,3-dihydrobenzo-1,4-dioxinyl, imidazo(2,1-b)(1,3)thiazole, and benzo-1,3-dioxolyl.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuryl, 2,3-dihydrobenzo-1,4-dioxinyl (i.e., 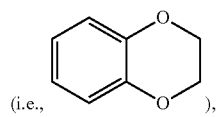 ), imidazo(2,1-b)(1,3)thiazole, (i.e., 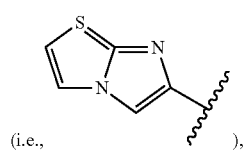 ), and benzo-1,3-dioxolyl (i.e., 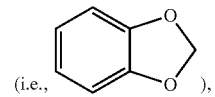 ), In certain contexts herein,

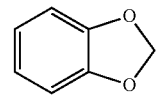

is alternatively referred to as phenyl having as a substituent methylenedioxy attached to two adjacent carbon atoms.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

When any variable (e.g., $R^b$, etc.) occurs more than one time in any substituent or in formula I, its definition in each occurrence is independent of its definition at every other occurrence. Also, combinations of substituents and/or variables are permissible only if such combinations result in stable compounds.

In choosing compounds of the present invention, one of ordinary skill in the art will recognize that the various substituents, i.e. $R^1$, $R^2$, $R^3$, etc., are to be chosen in conformity with well-known principles of chemical structure connectivity.

Lines drawn into the ring systems from substituents indicate that the indicated bond can be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups can be on the same carbon or on different carbons, so long as a stable structure results. The phrase "optionally substituted with one or more substituents" should be taken to be equivalent to the phrase "optionally substituted with at least one substituent" and in such cases one embodiment will have from zero to three substituents.

In another embodiment of the invention, X is O.
In another embodiment of the invention, X is $CH_2$.
In another embodiment of the invention, X is S.

In another embodiment of the invention, X is S(O).
In another embodiment of the invention, X is S(O)$_2$.
In another embodiment of the invention, X is NH.
In another embodiment of the invention, X is N-Me.
In another embodiment of the invention, Y is CH.
In another embodiment of the invention, Y is N.
In another embodiment of the invention, R$^1$ is phenyl optionally substituted with F, Br, Cl, CF$_3$, and CN.
In another embodiment of the invention, R$^1$ is phenyl substituted with CF$_3$.
In another embodiment of the invention, R$^2$ is hydrogen.
In another embodiment of the invention, R$^3$ is hydrogen.
In another embodiment of the invention, R$^4$ is hydrogen.
In another embodiment of the invention, R$^5$ is absent, F, Br, Cl, CF$_3$, or CN.
In another embodiment of the invention, m is 0, 1 or 2.
In another embodiment of the invention, m is 0 or 1.
In another embodiment of the invention, m is 1.
In another embodiment of the invention, m is 0.
In another embodiment of the invention, n is 0 or 1.
In another embodiment of the invention, n is 1.
In another embodiment of the invention, n is 0.
In another embodiment of the invention, p is 0.
In another embodiment of the invention, p is 1.
In another embodiment of the invention, R$^b$ is independently hydrogen or methyl.

Optical Isomers—Diastereomers—Geometric Isomers—Tautomers

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts and solvates thereof. Unless specifically mentioned otherwise, reference to one isomer applies to any of the possible isomers. Whenever the isomeric composition is unspecified, all possible isomers are included. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —CH$_2$C(O)— groups (keto forms) may undergo tautomerism to form hydroxy-CH=C(OH)— groups (enol forms). Both keto and enol forms, individually as well as mixtures thereof, are included within the scope of the present invention.

Salts

Pharmaceutically acceptable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydro-scopicity and solubility. The term "pharmaceutically acceptable salts" refers to salts prepared from pharmaceutically acceptable non-toxic bases or acids. When the compound of the present invention is acidic, its corresponding salt can be conveniently prepared from inorganic bases or organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from organic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylamino-ethanol, ethanolamine, ethylenediamine, N-ethylmorpholine, N-ethylpiperidine, glucamine, glucosamine, histidine, hydrabamine, isopropylamine, dicyclohexylamine, lysine, methyl-glucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from inorganic or organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methane-sulfonic, mucic, nitric, pamoic, pantothenic, phosphoric, succinic, sulfuric, tartaric, p-toluene-sulfonic acid and the like. Preferred are citric, hydrobromic, hydrochloric, maleic, phosphoric, sulfuric, and tartaric acids.

Solvates

The present invention includes within its scope solvates of compounds of Formula I. As used herein, the term "solvate" refers to a complex of variable stoichiometry formed by a solute (i.e., a compound of Formula I) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrate includes, but is not limited to, hemi-, mono, sesqui-, di- and trihydrates.

Prodrugs

The present invention includes within its scope the use of prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of formula I or with a compound which may not be a compound of formula I, but which converts to a compound of formula I in vivo after administration to the patient. Conventional procedures for the selection and preparation of suitable prodrug derivatives are described, for example, in "Design of Prodrugs," ed. H. Bundgaard, Elsevier, 1985.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

Compounds of the present invention are inhibitors of hypoxia-inducible factor (HIF) prolyl hydroxylases, and as such are useful in the treatment and prevention of diseases and conditions in which HIF modulation is desirable, such as anemia and ischemia. Compounds of the invention can be used in a selective and controlled manner to induce hypoxia-inducible factor stabilization and to rapidly and reversibly stimulate erythropoietin production and secretion. Accordingly, another aspect of the present invention provides a method of treating or preventing a disease or condition in a mammal, the treatment or prevention of which is effected or facilitated by HIF prolyl hydroxylase inhibition, which comprises administering an amount of a compound of Formula I that is effective for inhibiting HIF prolyl hydroxylase. This aspect of the present invention further includes the use of a compound of Formula I in the manufacture of a medicament for the treatment or prevention of a disease or condition modulated by HIF prolyl hydroxylase.

In one embodiment is a method of enhancing endogenous production of erythropoietin in a mammal which comprises administering to said mammal an amount of a compound of Formula I that is effective for enhancing endogenous production of erythropoietin.

Another embodiment is a method of treating anemia in a mammal which comprises administering to said mammal a therapeutically effective amount of a compound of Formula I. "Anemia" includes, but is not limited to, chronic kidney disease anemia, chemotherapy-induced anemia (e.g., anemia resulting from antiviral drug regimens for infectious diseases, such as HIV and hepatitis C virus), anemia of chronic disease, anemia associated with cancer conditions, anemia resulting from radiation treatment for cancer, anemias of chronic immune disorders such as rheumatoid arthritis, inflammatory bowel disease, and lupus, and anemias due to menstruation or of senescence or in other individuals with iron processing deficiencies such as those who are iron-replete but unable to utilize iron properly.

Another embodiment is a method of treating ischemic diseases in a mammal, which comprises administering to said mammal a therapeutically effective amount of a compound of Formula I.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.1-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., anemia.

Pharmaceutical Composition

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or a pharmaceutically acceptable salt or solvate thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term co administration is understood to include the administration of the two agents concomitantly or sequentially, or alternatively as a fixed dose combination of the two active components.

Compounds of the invention can be administered as the sole active ingredient or in combination with a second active ingredient, including other active ingredients known to be useful for improving the level of erythropoietin in a patient. Abbreviations Used in the Description of the Preparation of the Compounds of the Present Invention:

~ Approximately
AcOH Acetic acid
$Ag_2O$ Silver oxide
AIBN 2,2'-azobis(2-methylpropionitrile)
Aq Aqueous
Bn Benzyl
BnBr Benzylbromide
BnCl Benzylchloride
BnOH Benzylalcohol
$Boc_2O$ or di-tert-butyl dicarbonate
$BOC_2O$
Brine Saturated aqueous sodium chloride solution
BuLi n-butyl lithium
CDI Carbonyl diimidazole
DBU 1,8-diazabicyclo[5.4.0]undec-7-ene
DCC N,N'-dicyclohexylcarbodiimide
DEAD diethylazodicarboxylate
DCM Dichloromethane
DIPEA N,N-diisopropylethylaime
DMAP 4-N,N-dimethylaminopyridine
DMF N,N-dimethylformamide
DMSO Dimethyl sulfoxide
DPPA Diphenyl phosphoryl azide EDC or EDCI 1-(3-dimethylaminopropyl)-3-ethylcarboiimide hydrogenchloride salt
EtOAc or EA Ethyl acetate
Et (et) Ethyl
EtOH Ethanol
Et$_2$O or ether Diethyl ether
Et$_3$N triethylamine
g Gram
h or hr Hour
HATU O-(7-Azabenzotriazol-1-yl)-N,N,N',N'-tetramethyluronium hexafluorophosphate
HCl Hydrochloric acid
HOBt 1-hydroxybenzatriazole
HPLC High-performance liquid chromatography
i-propanol Isopropyl alcohol
i-PrOH or IPA Isopropyl alcohol
K$_2$CO$_3$ Potassium carbonate
KOH Potassium hydroxide
LiOH Lithium hydroxide
Mg Milligrams
mL Milliliters
mmol Millimole
MeCN Acetonitrile
MeOH Methanol
min Minutes
ms or MS Mass spectrum
μg Microgram(s)
μL Microliters
NaOEt Sodium ethoxide
NaOMe Sodium methoxide
Na$_2$SO$_4$ Sodium sulfate
NBS N-bromosuccinimide
NHAc Acetamido
NHCbz Benzyloxycarboxamido
NaOH Sodium hydroxide
NaN$_3$ Sodium azide
NH$_4$OH ammonium hydroxide
NMP N-methylpyrrolidone
Pd/C Palladium on carbon
Pd(OH)$_2$ Palladium hydroxide
Pd(PPh$_3$)$_4$ Palladium tetrakis(triphenylphosphine)
PhLi Phenyl lithium
PG Protecting group
Ph Phenyl group
PMB Para-methoxybenzyl
PPTS Pyridinium Para-toluenesulfonate
PPh$_3$ Triphenyphosphine
R$_f$ Retention time
RT or rt Room temperature
SOCl$_2$ Thionyl chloride
TEA Triethylamine
TFA Trifluoroacetic acid
THF Tetrahydrofuran
TBTU O-(Benzotriazol-1-yl)-N,N,N',N'-tetramethyluronium tetrafluoroborate
TMS Trimethylsilyl
TMSBr Trimethylsilyl bromide
TMSCN Trimethylsilyl cyanide
TMSCHN$_2$ (trimethylsilyl)diazomethane
TsCl Para-toluenesulfonyl chloride The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound in place of multiple substituents which are allowed under the definitions of Formula I defined previously.

GENERAL EXPERIMENTAL COMMENTS

Reactions sensitive to moisture or air were performed under nitrogen using anhydrous solvents and reagents. The progress of reactions was determined by either analytical thin layer chromatography (TLC) performed with E. Merck precoated TLC plates, silica gel 60F-254, layer thickness 0.25 mm or liquid chromatography-mass spectrum (LC-MS). Mass analysis was performed on a Waters Micromass® ZQ™ with electrospray ionization in positive ion detection mode. High performance liquid chromatography (HPLC) was conducted on an Agilent 1100 series HPLC on Waters C18 XTerra 3.5 μm 3.0×50 mm column with gradient 10:90-100 v/v CH$_3$CN/H$_2$O+v 0.05% TFA over 3.75 min then hold at 100 CH$_3$CN+v 0.05% TFA for 1.75 min; flow rate 1.0 mL/min, UV wavelength 254 nm). Concentration of solutions was carried out on a rotary evaporator under reduced pressure. Flash chromatography was performed using a Biotage Flash Chromatography apparatus (Dyax Corp.) on silica gel (32-63 mM, 60 Å pore size) in pre-packed cartridges. $^1$H-NMR spectra were obtained on a 400 or 500 MHz VARIAN Spectrometer in CDCl$_3$ or CD$_3$OD or other solvents as indicated and chemical shifts are reported as δ using the solvent peak as reference and coupling constants are reported in hertz (Hz).

Schemes 1-4 outline the general synthetic sequence for compounds of Formula I. In Scheme 1, condensation of substituted aniline 1 with bromoketone 2 provided imine 3. Imine 3 was reduced to cyclic aniline 4, which upon reacting with triethyl methanetricarboxylate afforded the tricyclic compound 5. Amide formation with glycine 6 gave ester 7. The corresponding carboxylic acids of general Formula Ia were obtained after hydrolysis of the ester.

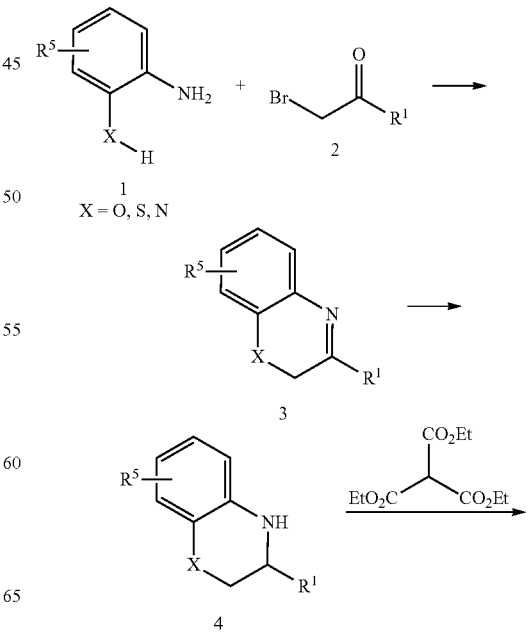

Scheme 1

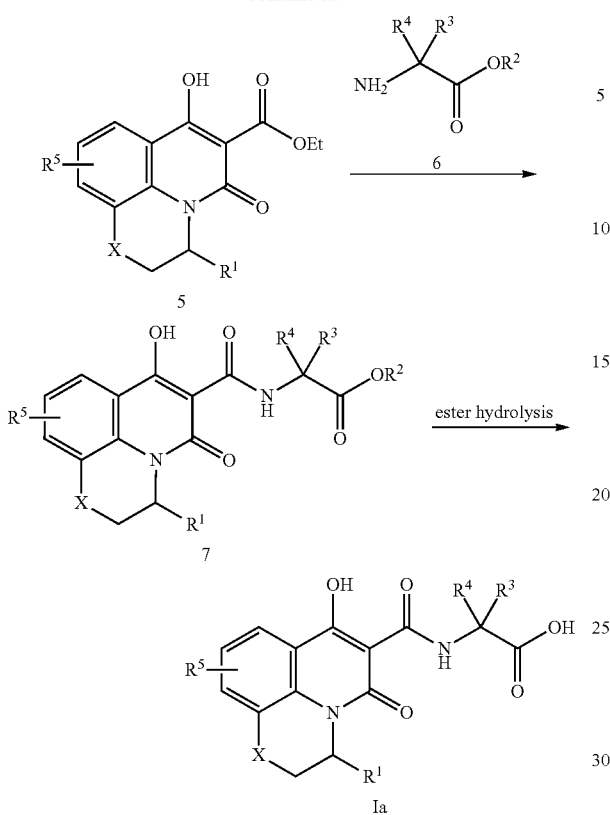

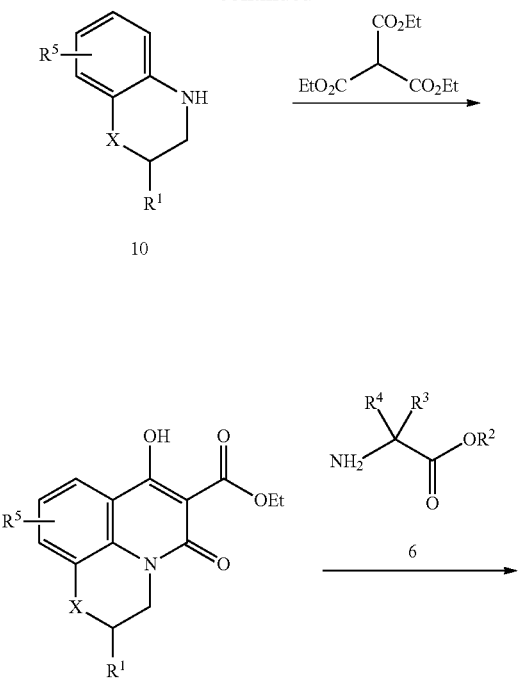

Scheme 2 illustrates the general synthesis of the regioisomeric tricyclics. Condensation of substituted aniline 1 with bromoester 8 provided cyclic amide 9. Amide 9 was reduced to cyclic aniline 10, which upon reacting with triethyl methanetricarboxylate afforded the tricycic compound 11. Amide formation with glycine 6 gave ester 12. The corresponding carboxylic acids of general Formula Ib were obtained by hydrolysis of the ester.

Scheme 2

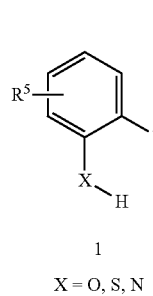

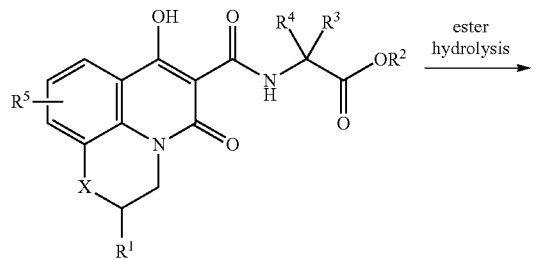

In Scheme 3, the synthesis of compounds of general Formula Ic is illustrated. The coupling between organometallic reagent 13 and LG-$R^1$ (LG=leaving group) provided quinoline derivative 14 which was reduced to cyclic aniline 15. The remaining synthesis is similar to those described in Schemes 1 and 2.

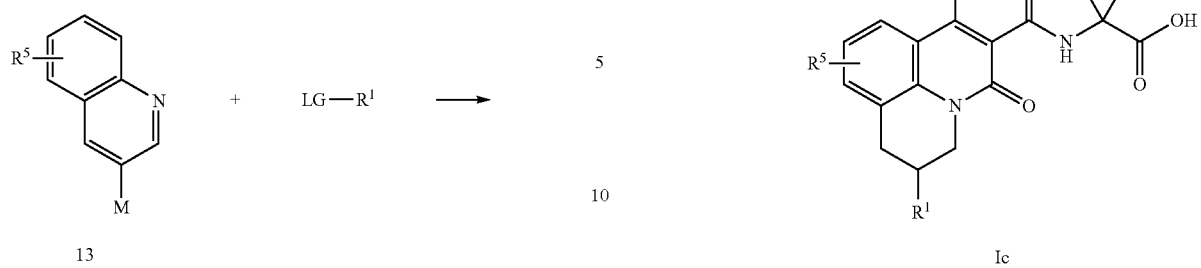

For nitrogen containing heteroaromatic analogs, where in Formula Id, one or two of A, B or C are nitrogen, the synthesis is shown in Scheme 4. The condensation of aniline 18 and bromoamide 8 afforded cyclic amide 19. Carbonylation followed by alkylation with ethyl 3-chloro-3-oxo-propanoate provided compound 21. In the presence of a base, 21 cyclized to give tricyclic intermediate 22. Then amide formation with glycine 6 and subsequent hydrolysis completed the synthesis.

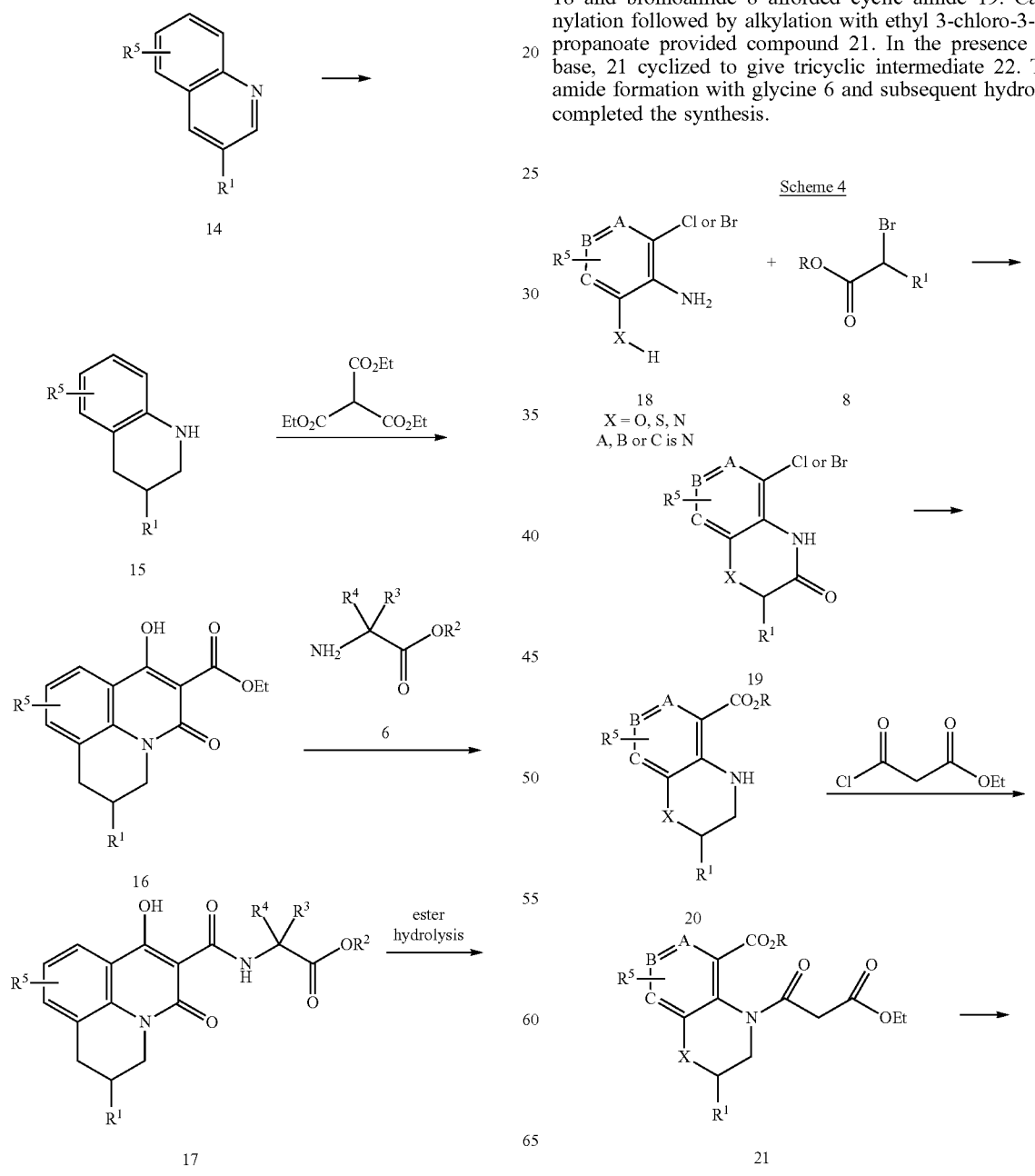

-continued

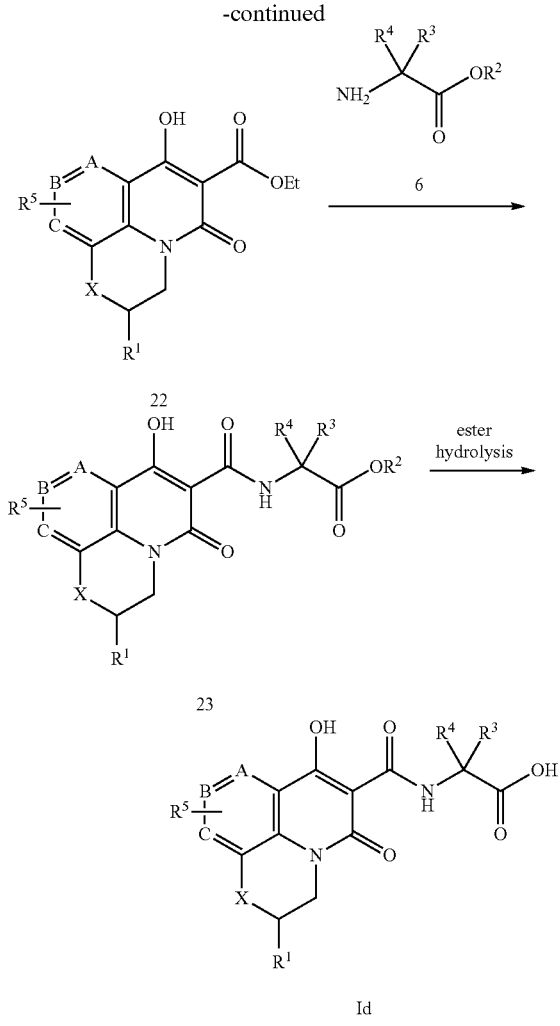

Starting materials useful for the preparation of the compounds in the present invention are known in the art or may be prepared using chemical methodologies known to those skilled in the art.

Intermediate 1 tert-Butyl 2-(10-bromo-7-hydroxy-5-oxo-3-(4-(trifluoromethyl)phenyl)-3,5-dihydro-2H-[1,4]oxazino[2,3,4-ij]quinoline-6-carboxamido)acetate

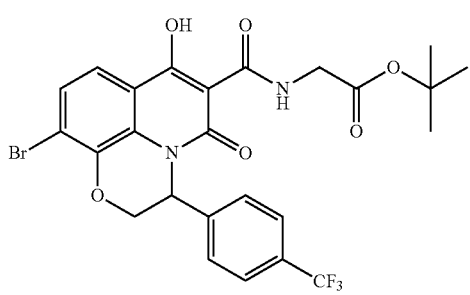 [SMILES: CC(C)(C)OC(=O)CNC(=O)c1c(O)c2ccc(Br)c3c2n(c1=O)C(c1ccc(C(F)(F)F)cc1)CO3]

Step A: 8-bromo-2-(4-(trifluoromethyl)phenyl)-2H-benzo[b][1,4]oxazine

Into a 3-L 3-necked round-bottom flask were placed a solution of 2-amino-6-bromophenol (56.3 g, 299.43 mmol, 1.00 equiv) in dichloromethane (600 mL), Bu$_4$NSO$_4$H (5 g, 1.05 equiv), aq K$_2$CO$_3$ (207 mL, 1.00 equiv, 20%). This was followed by the addition of a solution of 2-bromo-1-[4-(trifluoromethyl)phenyl]ethan-1-one (80 g, 299.58 mmol, 1.00 equiv) in dichloromethane (200 mL) dropwise with stirring at room temperature. The resulting solution was stirred overnight at room temperature. Then it was diluted with 500 mL of water and extracted with 3×500 mL of dichloromethane. The organic layers were combined, dried and concentrated under vacuum. The crude product was re-crystallized from EA/Hexane (1:10) to give 8-bromo-3-[4-(trifluoromethyl)phenyl]-2H-1,4-benzoxazine as a solid.

Step B: 8-bromo-2-(4-(trifluoromethyl)phenyl)-3,4-dihydro-2H-benzo[b][1,4]oxazine Into a 3-L 3-necked round-bottom flask was placed a solution of 8-bromo-3-[4-(trifluoromethyl)phenyl]-2H-1,4-benzoxazine (68 g, 190.94 mmol, 1.00 equiv) in methanol (1700 mL). This was followed by the addition of sodium borohydride (36 g, 977.60 mmol, 5.00 equiv) in several batches at 0° C. The resulting solution was stirred overnight at room temperature. The resulting mixture was concentrated under vacuum. The residue was dissolved with H$_2$O (500 mL) and DCM (500 mL). The aq layer was extracted with 2×5 00 mL of dichloromethane. The organic layers were combined, dried and concentrated under vacuum. The residue was applied onto a silica gel column and eluted with ethyl acetate/petroleum ether (1:10) to privide 8-bromo-3-[4-(trifluoromethyl)phenyl]-3,4-dihydro-2H-1,4-benzoxazine as an oil.

Step C: ethyl 10-bromo-7-hydroxy-5-oxo-3-(4-(trifluoromethyl)phenyl)-3,5-dihydro-2H-[1,4]oxazino[2,3,4-ij]quinoline-6-carboxylate Into a 500-mL 3-necked round-bottom flask was placed 8-bromo-3-[4-(trifluoromethyl)phenyl]-3,4-dihydro-2H-1,4-benzoxazine (51.5 g, 143.79 mmol, 1.00 equiv), triethyl methanetricarboxylate (130 g, 559.79 mmol, 4.00 equiv). The resulting solution was stirred for 2 days at 200° C. Then it was cooled and applied onto a silica gel column and eluted with ethyl acetate/petroleum ether (1:2) to privide ethyl 10-bromo-7-hydroxy-5-oxo-3-(4-(trifluoromethyl)phenyl)-3,5-dihydro-2H-[1,4]oxazino[2,3,4-ij]quinoline-6-carboxylate as a solid.

Step D: tert-butyl 2-(10-bromo-7-hydroxy-5-oxo-3-(4-(trifluoromethyl)phenyl)-3,5-dihydro-2H-[1,4]oxazino[2,3,4-ij]quinoline-6-carboxamido)acetate Into a 1-L 3-necked round-bottom flask were placed a solution of Step C product (50 g, 100.35 mmol, 1.00 equiv) in toluene (500 mL), tert-butyl 2-aminoacetate hydrochloride (25.2 g, 150.33 mmol, 1.50 equiv), DIEA (32.3 g, 250.39 mmol, 2.50 equiv). The resulting solution was heated to reflux for 2 h. The resulting mixture was cooled and concentrated under vacuum. The residue was applied onto a silica gel column and eluted with ethyl acetate/petroleum ether (1:3) to afford Intermediate 1 as a solid.

¹H NMR (CDCl₃, 300 MHz) δ 10.31 (1H, s), 7.75 (1H, d), 7.25 (2H, d), 7.47 (1H, d),7.20 (2H, d), 6.09 (1H, s), 4.76 (1H, dd), 4.40 (1H, dd), 4.12 (1H, dd), 4.39 (1H, dd), 1.47 (9H, s).

Intermediate 2 tert-Butyl 2-(9-bromo-7-hydroxy-5-oxo-3-(4-(trifluoromethyl)phenyl)-3,5-dihydro-2H-[1,4]oxazino[2,3,4-ij]quinoline-6-carboxamido)acetate

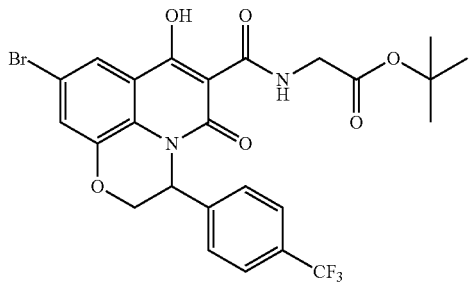 [SMILES: CC(C)(C)OC(=O)CNC(=O)c1c(O)c2cc(Br)cc3c2n(c1=O)C(c1ccc(C(F)(F)F)cc1)CO3]

Intermediate 2 was synthesized following procedures described for Intermediate 1 but replacing 2-amino-6-bromophenol with 2-amino-5-bromophenol in Step A. LC/MS (m/z): 583 (M+H)⁺.

Intermediate 3 tert-Butyl 2-(8-bromo-7-hydroxy-5-oxo-3-(4-(trifluoromethyl)phenyl)-3,5-dihydro-2H-[1,4]oxazino[2,3,4-ij]quinoline-6-carboxamido)acetate

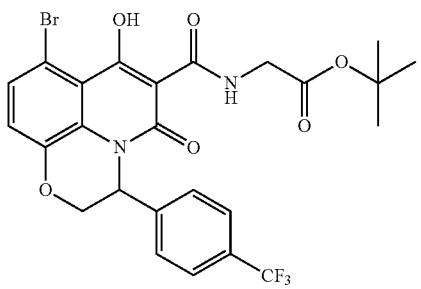 [SMILES: CC(C)(C)OC(=O)CNC(=O)c1c(O)c2c(Br)ccc3c2n(c1=O)C(c1ccc(C(F)(F)F)cc1)CO3]

Intermediate 3 was synthesized following procedures described for Intermediate 1 but replacing 2-amino-6-bromophenol with 2-amino-4-bromophenol in Step A. LC/MS (m/z): 583 (M+H)⁺.

Intermediate 4 tert-Butyl 2-(3-(4-bromophenyl)-7-hydroxy-5-oxo-3,5-dihydro-2H-[1,4]oxazino[2,3,4-ij]quinoline-6-carboxamido)acetate

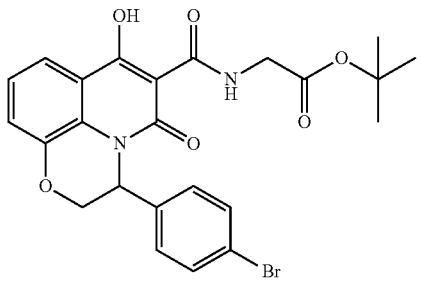 [SMILES: CC(C)(C)OC(=O)CNC(=O)c1c(O)c2cccc3c2n(c1=O)C(c1ccc(Br)cc1)CO3]

Step A: 3-(4-(trifluoromethyl)phenyl)-3,4-dihydro-2H-benzo[b][1,4]oxazine

A suspension of 3-(4-bromophenyl)-2H-benzo[b][1,4]oxazine (300 mg, 1.041 mmol) in DCM (6.0 ml) was treated with sodium cyanoborohydride (327 mg, 5.21 mmol) and the mixture stirred at rt overnight. TLC showed incomplete conversion. The mixture was then treated with MeOH and after 24 h the reaction was complete. The reaction was quenched with water and diluted with DCM. The layers were separated and the organic layer was dried (MgSO₄) and concentrated in vacuo to afford an oil. Purification on the CombiFlash Companion eluting with 0 to 10% EtOAc/hexane afforded the desired product as a racemic mixture. ¹H NMR (500 MHz, (CDCl3) δ 7.53 (d, J=8.3 Hz, 2H), 7.30 (d, J=8.3 Hz, 2H), 6.84 (m, 2H), 6.73 (m, 2H), 4.51 (m, 1H), 4.27 (m, 1H), 3.97 (m, 2H).

Step B: ethyl 3-(4-bromophenyl)-7-hydroxy-5-oxo-3,5-dihydro-2H-[1,4]oxazino[2,3,4-ij]quinoline-6-carboxylate A neat mixture of Step A product (275 mg, 0.948 mmol) and triethyl methanetricarboxylate (880 mg, 3.79 mmol) was heated at 200° C. for a total of 2 h. The mixture was cooled to rt and triturated and filtered from ether/hexane to afford the desired product (racemic). ¹H NMR (500 MHz, (CDCl3) δ 7.84 (d, J=8.0 Hz, 1H), 7.42 (d, J=8.4 Hz, 2H), 7.28 (d, 1H), 7.24 (t, J=7.8 Hz, 1H), 7.04 (d, J=8.5 Hz, 2H), 5.98 (s,1H), 4.61(d, J=11.4 Hz, 1H), 4.62-4.44 (m, 3H), 4.34 (d, J=11.4 Hz, 1H), 1.46 (t, J=7.1, Hz, 3H).

Step C: tert-Butyl 2-(3-(4-bromophenyl)-7-hydroxy-5-oxo-3,5-dihydro-2H-[1,4]oxazino[2,3,4-ij]quinoline-6-carboxamido)acetate A suspension of Step B product (0.235g, 0.546 mmol) and tert-butyl 2-aminoacetate (0.092 ml, 0.655 mmol) in DME (3.0 ml) was stirred at 80° C. for 8 h. The solvent was evaporated and trituration with ether/hexane followed by filtration afforded Intermediate 2. ¹H NMR (500 MHz, (CDCl3) δ 10.47(t, 1H), 7.89 (m, 1H), 7.44 (d, J=8.5 Hz, 2H), 7.28-7.25 (m, 2H), 7.02 (d, J=8.2 Hz, 2H), 5.99 (s,1H), 4.62 (d, J=11.4 Hz, 1H), 4.37 (d, J=11.7, Hz, 1H), 4.22-4.17 (dd, 1H), 4.04-3.98 (dd, 1H), 3.51 (q, J=6.8 Hz, 1H), 1.50 (s, 9H).

Intermediate 5 tert-Butyl 2-(10-bromo-7-hydroxy-5-oxo-3,5-dihydro-2H-[1,4]oxazino[2,3,4-ij]quinoline-6-carboxamido)acetate

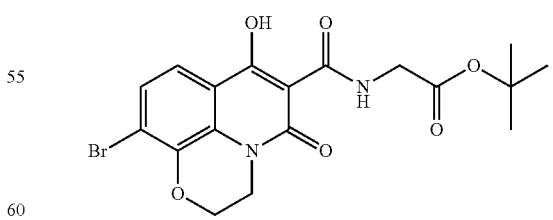

Step A: 8-bromo-3,4-dihydro-2H-benzo[b][1,4]oxazine

A suspension of 2-amino-6-bromophenol (1 g, 5.32 mmol), 1,2-dibromoethane (1.199 g, 6.38 mmol) and K₂CO₃

(2.205 g, 15.96 mmol) in DMF (10 mL) was heated at 125° C. for 16 h. LCMS showed that the reaction completed. The mixture was cooled to room temperature. The resulting mixture was diluted with aqueous NaCl (50 mL) and extracted with EtOAc (50 mL*3). The combined organic layers were washed with aqueous NaCl (50 mL*3), dried over $Na_2SO_4$, filtered and evaporate to give 8-bromo-3,4-dihydro-2H-benzo[b][1,4]oxazine as an oil. $^1$H NMR (CDCl$_3$, 400 MHz): δ 6.89 (d, J=8.0 Hz, 1H), 6.63 (t, J=8.0 Hz, 1H), 6.53 (d, J=8.0 Hz, 1H), 4.36 (t, J=4.0 Hz, 2H), 3.85 (brs, 1H), 3.44-3.46 (m, 2H).

Step B: ethyl 10-bromo-7-hydroxy-5-oxo-3,5-dihydro-2H-[1,4]oxazino[2,3,4-ij]quinoline-6-carboxylate A mixture of 8-bromo-3,4-dihydro-2H-benzo[b][1,4]oxazine (1.2 g, 5.61 mmol) and triethyl methanetricarboxylate (5.21 g, 22.42 mmol) was heated to 250° C. and stirred for 0.5 h. The resulting mixture was cooled to room temperature, and was then recrystallised with petroleum ether (50 mL) to give ethyl 10-bromo-7-hydroxy-5-oxo-3,5-dihydro-2H-[1,4]oxazino[2,3,4-ij]quinoline-6-carboxylate as a solid. $^1$H NMR (CDCl$_3$, 400 MHz): δ 14.28 (s, 1H), 7.63 (d, J=8.8 Hz, 1H), 7.39 (d, J=8.8 Hz, 1H), 4.52 (q, J=7.2 Hz, 14.4 Hz, 2H), 4.46 (t, J=5.2 Hz, 2H), 4.25 (t, J=5.2 Hz, 2H), 1.49 (t, J=7.2 Hz, 3H).

Step C: tert-butyl 2-(10-bromo-7-hydroxy-5-oxo-3,5-dihydro-2H-[1,4]oxazino[2,3,4-ij]quinoline-6-carboxamido)acetate A solution of ethyl 10-bromo-7-hydroxy-5-oxo-3,5-dihydro-2H-[1,4]oxazino[2,3,4-ij]quinoline-6-carboxylate (1.77 g, 5.00 mmol), tert-butyl 2-aminoacetate HCl salt (1.005 g, 6.00 mmol) and DIPEA (2.008 mL, 11.50 mmol) in toluene (50 mL) was heated to 120° C. and stirred for 2 h. TLC (petroleum ether: EtOAc=5:1) showed that the reaction completed. The resulting mixture was concentrated in vacuo to give the crude which was recrystallised from DCM (20 mL) and petroleum ether (5 mL) to give Intermediate 3 as a solid. $^1$H NMR (CDCl$_3$, 400 MHz): δ 10.55 (t, J=5.2 Hz, 1H), 7.65 (d, J=8.8 Hz, 1H), 7.42 (d, J=8.8 Hz, 1H), 4.48 (t, J=5.2 Hz, 2H), 4.29 (t, J=5.2 Hz, 2H), 4.14 (d, J=5.2 Hz, 2H), 1.51 (s, 9H).

Intermediate 6 tert-Butyl 2-(10-bromo-7-hydroxy-5-oxo-3-(thiazol-5-yl)-3,5-dihydro-2H-[1,4]oxazino[2,3,4-ij]quinoline-6-carboxamido)acetate

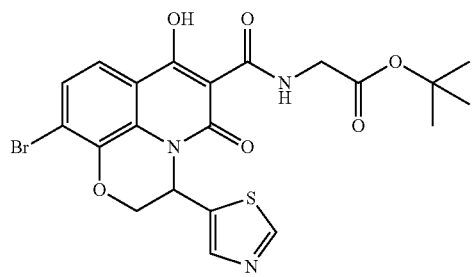 [SMILES: CC(C)(C)OC(=O)CNC(=O)c1c(O)c2ccc(Br)c3c2n(c1=O)C(c1cncs1)CO3]

Intermediate 6 was synthesized following procedures described for Intermediate 1 but replacing 2-bromo-1-[4-(trifluoromethyl)phenyl]ethan-1-one with 2-bromo-1-(thiazol-5-yl)ethanone in Step A. LC/MS (m/z): 522 (M+H)$^+$.

Intermediate 7 tert-Butyl 2-(10-bromo-7-hydroxy-5-oxo-3-(thiazol-4-yl)-3,5-dihydro-2H-[1,4]oxazino[2,3,4-ij]quinoline-6-carboxamido)acetate

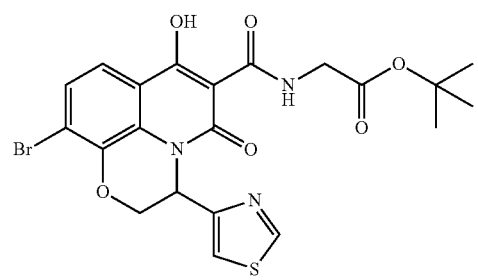 [SMILES: CC(C)(C)OC(=O)CNC(=O)c1c(O)c2ccc(Br)c3c2n(c1=O)C(c1cscn1)CO3]

Intermediate 7 was synthesized following procedures described for Intermediate 1 but replacing 2-bromo-1-[4-(trifluoromethyl)phenyl]ethan-1-one with 2-bromo-1-(thiazol-4-yl)ethanone in Step A. LC/MS (m/z): 522 (M+H)$^+$.

Examples 1, 1a, 1b 2-(7-Hydroxy-5-oxo-3-(4-(trifluoromethyl)phenyl)-3,5-dihydro-2H-[1,4]oxazino[2,3,4-ij]quinoline-6-carboxamido)acetic acid Example 1

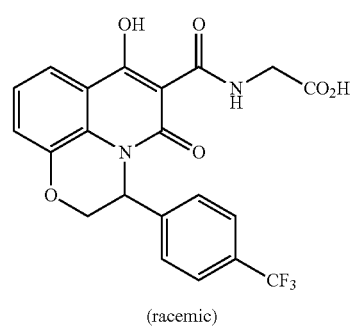

(racemic)

Example 1a

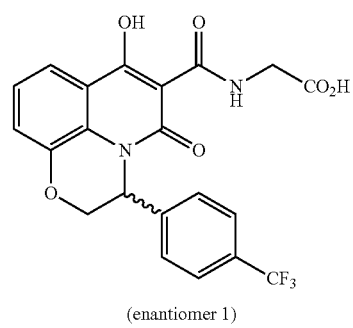

(enantiomer 1)

-continued

Example 1b

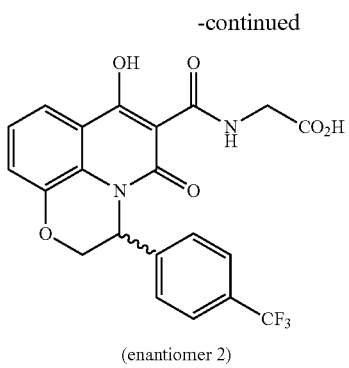

(enantiomer 2)

Step A: 3-(4-(trifluoromethyl)phenyl)-2H-benzo[b][1,4]oxazine

To a solution of 2-aminophenol (33.7 g, 309.2 mmol) in DCM (1000 mL) were added 20% aq $K_2CO_3$ (1000 mL) and n-Bu$_4$NHSO$_4$ (200 mg). Then 2-bromo-1-(4-(trifluoromethyl)phenyl)ethanone (82.2 g, 309.2 mmol) in DCM (500 mL) was added dropwise to the above reaction mixture. The resulting mixture was stirred at room temperature for 20 h. TLC (petroleum ether: EtOAc=10:1) showed that the reaction completed. The reaction mixture was extracted with DCM (500 mL*3). The combined organic layers were washed with brine (500 mL*3), dried over Na$_2$SO$_4$, filtered and concentrated in vacuo to give 3-(4-(trifluoromethyl)phenyl)-2H-benzo[b][1,4]oxazine as a solid. $^1$H NMR (CDCl$_3$, 400 MHz) δ 8.04 (d, J=8.0 Hz, 2H), 7.74 (d, J=8.0 Hz, 2H), 7.46 (dd, J=1.6 Hz, 8.0 Hz, 1H), 7.20 (td, J=1.6 Hz, 8.0 Hz, 1H), 7.06 (td, J=1.2 Hz, 8.0 Hz, 1H), 6.94 (dd, J=1.2 Hz, 8.0 Hz, 1H), 5.09 (s, 2H).

Step B: 3-(4-(trifluoromethyl)phenyl)-3,4-dihydro-2H-benzo[b][1,4]oxazine

To a solution of 3-(4-(trifluoromethyl)phenyl)-2H-benzo[b][1,4]oxazine (80 g, 288.8 mmol) in DCM (1500 mL) and MeOH (500 mL) were added AcOH (5 mL) and NaBH$_3$CN (90.7 g, 1444 mmol). The resulting solution was stirred at room temperature for 3 h. TLC (petroleum ether: EtOAc=10:1) showed that the reaction completed. The resulting mixture was diluted with water (1000 mL) and extracted with DCM (500 mL*3). The combined organic layers were washed with brine (500 mL*3), dried over Na$_2$SO$_4$, filtered and concentrated in vacuo to give a crude compound which was purified by Combi-Flash (EtOAc in petroleum ether: 0-5%) to give 3-(4-(trifluoromethyl)phenyl)-3,4-dihydro-2H-benzo[b][1,4]oxazine as a solid. $^1$H NMR (CDCl$_3$, 400 MHz): δ 7.66 (d, J=8.0 Hz, 2H), 7.55 (d, J=8.0 Hz, 2H), 6.83-6.88 (m, 2H), 6.70-6.76 (m, 2H), 4.62 (dd, J=4.0 Hz, 8.0 Hz, 1H), 4.30 (dd, J=4.0 Hz, 10 Hz, 1H), 4.00-4.05 (m, 2H).

Step C: ethyl 7-hydroxy-5-oxo-3-(4-(trifluoromethyl)phenyl)-3,5-dihydro-2H-[1,4]oxazino[2,3,4-ij]quinoline-6-carboxylate 3-(4-(Trifluoromethyl)phenyl)-3,4-dihydro-2H-benzo[b][1,4]oxazine (30 g, 107.4 mmol) was mixed with triethyl methanetricarboxylate (99.9 g, 429.6 mmol). Then the mixture was stirred at 260° C. for 2 h under nitrogen. After cooling to room temperature, the mixture was purified by Combi-Flash (EtOAc in petroleum ether: 0-10%) to give ethyl 7-hydroxy-5-oxo-3-(4-(trifluoromethyl)phenyl)-3,5-dihydro-2H-[1,4]oxazino[2,3,4-ij]quinoline-6-carboxylate as a solid. $^1$H NMR (CDCl$_3$, 400 MHz): δ 14.43 (s, 1H), 7.88 (d, J=5.6 Hz, 1H), 7.55 (d, J=8.0 Hz, 2H), 7.22-7.29 (m, 4H), 6.05 (s, 1H), 4.63 (d, J=10.8 Hz, 1H), 4.35-4.57 (m, 3H), 1.45 (t, J=7.2 Hz, 3H).

Step D: tert-butyl 2-(7-hydroxy-5-oxo-3-(4-(trifluoromethyl)phenyl)-3,5-dihydro-2H-[1,4]oxazino[2,3,4-ij]quinoline-6-carboxamido)acetate To a solution of ethyl 7-hydroxy-5-oxo-3-(4-(trifluoromethyl)phenyl)-3,5-dihydro-2H-[1,4]oxazino[2,3,4-ij]quinoline-6-carboxylate (15 g, 35.7 mmol) and tert-butyl 2-aminoacetate hydrochloride (7.2 g, 42.9 mmol) in toluene (120 mL) was added DIPEA (10.62 g, 82.2 mmol). The resulting mixture was stirred at 120° C. for 2 hours under nitrogen. TLC (petroleum ether: EtOAc=5:1) showed that the reaction completed. To the mixture was added aq NaCl (200 mL), and it was extracted with EtOAc (150 mL*3). The combined organic layers were dried over anhydrous Na$_2$SO$_4$, filtered and concentrated under reduced pressure. The residue was purified by Combi-Flash (DCM in petroleum ether: 0-70%) to afford tert-butyl 2-(7-hydroxy-5-oxo-3-(4-(trifluoromethyl)phenyl)-3,5-dihydro-2H-[1,4]oxazino[2,3,4-ij]quinoline-6-carboxamido)acetate as a solid. $^1$H NMR (CDCl$_3$, 400 MHz): δ 10.42 (t, J=4.0 Hz, 1H), 7.86-7.91 (m, 1H), 7.56 (d, J=8.0 Hz, 2H), 7.22-7.28 (m, 4H), 6.07 (s, 1H), 4.64 (d, J=12 Hz, 1H), 4.39 (dd, J=4.0 Hz, 12 Hz, 1H), 4.17 (dd, J=4.0 Hz, 20.0 Hz, 1H), 3.99 (dd, J=4.0 Hz, 20.0 Hz, 1H), 1.47 (s, 9H).

Step E: 2-(7-hydroxy-5-oxo-3-(4-(trifluoromethyl)phenyl)-3,5-dihydro-2H-[1,4]oxazino[2,3,4-ij]quinoline-6-carboxamido)acetic acid (Example 1—racemic; Example 1a—enantiomer 1/peak 1; Example 1 b—enantomer 2/peak 2)

To a solution of tert-butyl 2-(7-hydroxy-5-oxo-3-(4-(trifluoromethyl)phenyl)-3,5-dihydro-2H-[1,4]oxazino[2,3,4-ij]quinoline-6-carboxamido)acetate (10 g, 19.8 mmol) in DCM (80 mL) was added TFA (15.3 mL, 198 mmol). The resulting mixture was stirred at 50° C. for 3 hours. LCMS showed that the reaction completed. The resulting mixture was concentrated in vacuo to give crude product which was recrystallized with EtOAc (100 mL) to afford 2-(7-hydroxy-5-oxo-3-(4-(trifluoromethyl)phenyl)-3,5-dihydro-2H-[1,4]oxazino[2,3,4-ij]quinoline-6-carboxamido)acetic acid as a solid (Example 1—racemic). $^1$H NMR (DMSO-d$_6$, 400 MHz): δ 12.94 (brs, 1H), 10.29 (t, J=5.6 Hz, 1H), 7.78 (dd, J=2.0 Hz, 7.2 Hz, 1H), 7.68 (d, J=8.0 Hz, 2H), 7.27-7.34 (m, 4H), 6.13 (s, 1H), 4.75 (d, J=12 Hz, 1H), 4.48 (dd, J=2.4 Hz, 11.6 Hz, 1H), 4.03-4.14 (m, 2H). LC/MS (m/z): 449 (M+H)$^+$. Human HIF-PHD2 IC$_{50}$: 15.77 nM.

The racemate was resolved by SFC (Instrument: Thar SFC 80; Column: OJ 250 mm*30mm, 20 um; Mobile phase: A: Supercritical CO$_2$, B: EtOH (0.1% NH$_3$.H$_2$O), A:B=60:40 at 80 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford:

Example 1a (enantiomer 1/peak 1, RT:1.478 min, Chiralcel OJ-H 250×4.6 mm I.D., 5 um Mobile phase: methanol (0.05% DEA) in CO2 from 5% to 40% Flow rate: 2.35 mL/min Wavelength: 220 nm) as a white solid. Human HIF-PHD2 IC$_{50}$: 33.69 nM.

Example 1b (enantiomer 2/peak 2, RT: 1.697 min) as a white solid. Human HIF-PHD2 IC$_{50}$: 13.06 nM.

Examples 2, 2a and 2b 2-(7-Hydroxy-5-oxo-3-(4-(trifluoromethyl)phenyl)-3,5-dihydro-2H-[1,4]oxazino[2,3,4-ij]quinoline-6-carboxamido)acetic acid Example 2

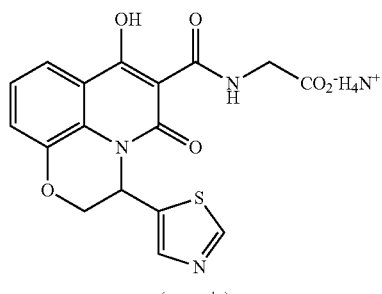

(racemic)

Example 2a

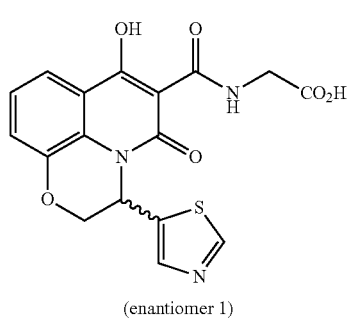

(enantiomer 1)

Example 2b

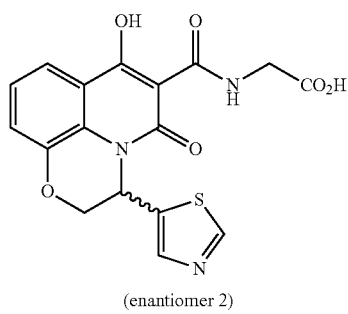

(enantiomer 2)

Step A: 3-(thiazol-5-yl)-2H-benzo[b][1,4]oxazine

To a solution of 2-aminophenol (1.15 g, 10.54 mmol) in DCM (100 mL) were added K$_2$CO$_3$ (20% aqueous solution, 14.56 g, 21.08 mmol) and n-Bu$_4$NHSO$_4$ (179 mg, 0.527 mmol). Then 2-bromo-1-(thiazol-5-yl)ethanone hydrobromide (3.02 g, 10.54 mmol) was added to the above reaction mixture over 5 min. The resulting mixture was stirred at room temperature overnight. The reaction mixture was extracted with DCM (50 mL*3). The combined organic layers were washed with brine (50 mL*3), dried over Na$_2$SO$_4$, filtered and concentrated. The residue was purified by silica chromatography (EtOAc in hexanes: 10-60%) to give 3-(thiazol-5-yl)-2H-benzo[b][1,4]oxazine as a solid. LC/MS (m/z): 217 (M+H)$^+$.

Step B: 3-(thiazol-5-yl)-3,4-dihydro-2H-benzo[b][1,4]oxazine

To a solution of Step A product (0.65 g, 3.01 mmol) in DCM (15 mL) and MeOH (5 mL) were added AcOH (0.05 mL) and NaBH$_3$CN (0.91 g, 14 mmol). The resulting solution was stirred at room temperature overnight. The resulting mixture was diluted with water (10 mL) and extracted with DCM (10 mL*3). The combined organic layers were washed with brine (20 mL*3), dried over Na$_2$SO$_4$, filtered and concentrated in vacuo to give a crude compound which was purified by silica chromatography (EtOAc in hexanes: 10-60%) to give 3-(thiazol-5-yl)-3,4-dihydro-2H-benzo[b][1,4]oxazine. LC/MS (m/z): 219 (M+H)$^+$.

Step C: ethyl 7-hydroxy-5-oxo-3-(thiazol-5-yl)-3,5-dihydro-2H-[1,4]oxazino[2,3,4-ij]quinoline-6-carboxylate 3-(Thiazol-5-yl)-3,4-dihydro-2H-benzo[b][1,4]oxazine (1 g, 4.58 mmol) was mixed with triethyl methanetricarboxylate (4.26 g, 18.33 mmol). Then the mixture was stirred at 190° C. for 2.5 h under nitrogen. After cooling to room temperature, the mixture was purified by silica chromatography (EtOAc in hexanes: 20-100%) to give ethyl 7-hydroxy-5-oxo-3-(thiazol-5-yl)-3,5-dihydro-2H-[1,4]oxazino[2,3,4-ij]quinoline-6-carboxylate. LC/MS (m/z): 359 (M+H)$^+$.

Step D: tert-butyl 2-(7-hydroxy-5-oxo-3-(thiazol-5-yl)-3,5-dihydro-2H-[1,4]oxazino[2,3,4-ij]quinoline-6-carboxamido)acetate To a solution of ethyl 7-hydroxy-5-oxo-3-(thiazol-5-yl)-3,5-dihydro-2H-[1,4]oxazino[2,3,4-ij]quinoline-6-carboxylate (2 g, 5.58 mmol) and tert-butyl 2-aminoacetate (1.464 g, 11.16 mmol) in toluene (6 mL) was added DIPEA (1.95 mL, 11.16 mmol). The resulting mixture was stirred at 120° C. for 2 hours under nitrogen. To the mixture was added aq NaCl (20 mL), and it was extracted with EtOAc (20 mL*3). The combined organic layers were dried over anhydrous Na$_2$SO$_4$, filtered and concentrated under reduced pressure. The residue was purified by silica chromatography (EtOAc in hexanes: 10-80%) to give tert-butyl 2-(7-hydroxy-5-oxo-3-(thiazol-5-yl)-3,5-dihydro-2H-[1,4]oxazino[2,3,4-ij]quinoline-6-carboxamido)acetate as a solid. LC/MS (m/z): 444 (M+H)$^+$.

Step E: Ammonium 2-(7-hydroxy-5-oxo-3-(thiazol-5-yl)-3,5-dihydro-2H-[1,4]oxazino[2,3,4-ij]quinoline-6-carboxamido)acetate (Example 2—racemic)

To a solution of tert-butyl 2-(7-hydroxy-5-oxo-3-(thiazol-5-yl)-3,5-dihydro-2H-[1,4]oxazino[2,3,4-ij]quinoline-6-carboxamido)acetate (0.31 g, 0.699 mmol) in DCM (1 mL) was added TFA (0.54 mL, 6.99 mmol). The resulting mixture was stirred at 50° C. for 2 hours. LCMS showed that the reaction completed and the resulting mixture was concentrated in vacuo. Acetonitrile (2 mL) was added and the solution was concentrated to dryness. This was repeated three times to remove all the remaining TFA. To the residue was added acetonitrile and water. The solution was freezed and lyophilized overnight. Then 2N NH$_3$ in methanol (2 mL) was added and the mixture was stirred at rt for 2 h. The solution was concentrated and lyophlized with acetonitrile and water overnight to give ammonium 2-(7-hydroxy-5- oxo-3-(thiazol-5-yl)-3,5-dihydro-2H-[1,4]oxazino[2,3,4-ij]quinoline-6-carboxamido)acetate as a solid. (Example 2—racemic). $^1$H NMR (DMSO-$d_6$, 500 MHz): δ 10.31 (t, 1H), 8.95 (s, 1H), 7.92 (s, 1H), 7.72 (d, 1H), 7.41 (d, 2H), 7.28 (d, 1H), 6.41 (s, 1H), 4.58 (d, 1H), 4.47 (dd, 1H), 3.99 (m, 2H). LC/MS (m/z): 388 (M+PH)$^+$. Human HIF-PHD2 IC$_{50}$: 7.19 nM.

Step F: 2-(7-hydroxy-5-oxo-3-(thiazol-5-yl)-3,5-dihydro-2H-[1,4]oxazino[2,3,4-ij]quinoline-6-carboxamido)acetic acid (Example 2a—from enantiomer 1 and Example 2b—from enantiomer 2)

The racemic $^t$butyl ester from Step D was resolved by SFC [OJ, 30×250mm, 50% MeOH (0.2% TFA)/CO2, 70 mL/min, 100 bar, 35 C, 240 nM]) to afford: enantiomer 1/peak 1: tert-butyl 2-(7-hydroxy-5-oxo-3-(thiazol-5-yl)-3,5-dihydro-2H-[1,4]oxazino[2,3,4-ij]quinoline-6-carboxamido)acetate; and enantiomer 2/peak 2: tert-butyl 2-(7-hydroxy-5-oxo-3-(thiazol-5-yl)-3,5-dihydro-2H-[1,4]oxazino[2,3,4-ij]quinoline-6-carboxamido)acetate.

To a solution of eantiomer 1/peak 1 (0.85 g, 1.917 mmol) in DCM (8 mL) was added TFA (1.48 mL, 19.2 mmol). The resulting mixture was stirred at rt for 8 hours. LCMS showed that the reaction completed and the resulting mixture was concentrated in vacuo. The residue was lyophilized with acetonitrile and water overnight to give 2-(7-hydroxy-5-oxo-3-(thiazol-5-yl)-3,5-dihydro-2H-[1,4]oxazino[2,3,4-ij]quinoline-6-carboxamido)acetic acid (Example 2a—from enantiomer 1). $^1$H NMR (DMSO-$d_6$, 500 MHz): δ 10.33 (t, 1H), 8.95 (s, 1H), 7.85 (s, $^1$H), 7.64 (d, 1H), 7.41 (d, 2H), 7.28 (d, 1H), 6.41 (s, 1H), 4.78 (d, 1H), 4.43 (dd, 1H), 4.07 (m, 2H). LC/MS (m/z): 388 (M+PH)$^+$. Human HIF-PHD2 IC$_{50}$: 14.84 nM.

Example 2b—from enantiomer 2 was made similarly. $^1$H NMR (DMSO-$d_6$, 500 MHz): δ 10.33 (t, 1H), 8.95 (s, 1H), 7.85 (s, 1H), 7.64 (d, 1H), 7.41 (d, 2H), 7.28 (d, 1H), 6.41 (s, 1H), 4.78 (d, 1H), 4.43 (dd, 1H), 4.07 (m, 2H). LC/MS (m/z): 388 (M+PH)$^+$. Human HIF-PHD2 IC$_{50}$: 4.18 nM.

Example 3

2-(7-Hydroxy-5-oxo-3-(4-(trifluoromethyl)benzyl)-3,5-dihydro-2H-[1,4]oxazino[2,3,4-ij]quinoline-6-carboxamido)acetic acid

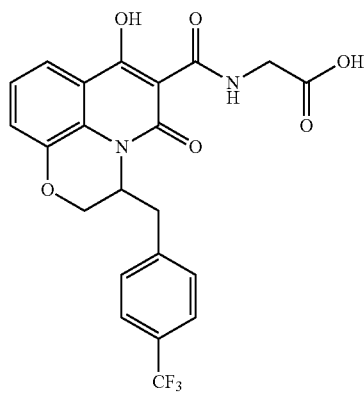

Step A: 2-(4-(trifluoromethyl)phenyl)acetyl chloride

A solution of 2-(4-(trifluoromethyl)phenyl)acetic acid (50 g, 244 mmol) in thionyl chloride (160 mL) was refluxed for 2 h. The resulting mixture was concentrated in vacuo to give 2-(4-(trifluoromethyl)phenyl)acetyl chloride as an oil, which was used in the next step directly.

Step B: 1-bromo-3-(4-(trifluoromethyl)phenyl)propan-2-one

To a solution of 2-(4-(trifluoromethyl)phenyl)acetyl chloride (50 g, 224 mmol) in dry THF (400 mL) and Acetonitrile (400 mL) was added pre-cooled trimethylsilyl diazomethane (248 mL, 494 mmol) dropwise. After stirring at 0° C. for 3 h, aq HBr (254 mL, 2246 mmol) was added dropwise to the mixture at 0° C. After the addition, the mixture was allowed to warm up to room temperature and stirred for 16 h. The resulting mixture was diluted with water and extracted with EtOAc (400 mL*3). The combined extracts were washed with water (200 mL*2), saturated aqueous NaHCO$_3$ (200 mL*2) and water (200 mL*2), then dried over Na$_2$SO$_4$ and concentrated in vacuo. The residue was purified by Combi-Flash (EtOAc in petroleum ether: 0~30%) to give 1-bromo-3-(4-(trifluoromethyl)phenyl)propan-2-one as a solid. $^1$H NMR (CDCl$_3$, 400 MHz): δ 7.63 (d, J=8.0 Hz, 2H), 7.36 (d, J=8.0 Hz, 2H), 4.05 (s, 2H), 3.94 (s, 2H).

Step C: 3-(4-(trifluoromethyl)benzyl)-2H-benzo[b][1,4]oxazine

To a solution of 2-aminophenol (1 g, 9.16 mmol) in DCM (40 mL) were added K$_2$CO$_3$ (40 mL, 9.16 mmol) and tetrabutylammonium hydrogen sulfate (0.031 g, 0.092 mmol), then 1-bromo-3-(4-(trifluoromethyl)phenyl)propan-2-one (2.58 g, 9.16 mmol) in DCM (20 mL) was added dropwise to above mixture. The mixture was stirred at room temperature for 20 h. The reaction mixture was extracted with DCM (50 mL*3). The combined organic layers were washed with brine (50 mL*3), dried over Na$_2$SO$_4$, filtered and concentrated in vacuo to give crude which was purified by Combi-Flash (EtOAc in petroleum ether: 0-10%) to give 3-(4-(trifluoromethyl)benzyl)-2H-benzo[b][1,4]oxazine as an oil, which was used in the next step directly.

Step D: 3-(4-(trifluoromethyl)benzyl)-3,4-dihydro-2H-benzo[b][1,4]oxazine

To a solution of 3-(4-(trifluoromethyl)benzyl)-2H-benzo[b][1,4]oxazine (770 mg, 2.64 mmol) in DCM (10 mL) and MeOH (5 mL) were added AcOH (0.5 mL, 8.73 mmol) and sodium cyanoborohydride (831 mg, 13.22 mmol). The resulting mixture was stirred at room temperature for 16 h. The mixture was diluted with water (50 mL) and extracted with ethyl acacate (3*50 mL). The combined organic fractions were washed with aqueous ammonium chloride (saturated, 3*50 mL), dried over Na$_2$SO$_4$, filtered and the solvent evaporated under reduced pressure. The residue was purified by silica gel column chromatography (EtOAc in petroleum ether: 0-15%) to give 3-(4-(trifluoromethyl)benzyl)-3,4-dihydro-2H-benzo[b][1,4]oxazine as an oil. $^1$H NMR (CDCl$_3$, 400 MHz): δ 7.62 (d, J=8.0 Hz, 2H), 7.36 (d, J=8.0 Hz, 2H), 6.76-6.83 (m, 2H), 6.68 (td, J=1.2 Hz, 8.0 Hz, 1H), 6.55 (dd, J=1.2 Hz, 8.0 Hz, 1H), 4.25 (d, J=4.0 Hz, 12.0 Hz, 1H), 4.01 (q, J=6.0 Hz, 11.2 Hz, 1H), 3.63-3.72 (m, 2H), 2.94 (dd, J=5.2 Hz, 13.2 Hz, 1H), 2.82 (dd, J=9.2 Hz, 13.6 Hz, 1H).

Step E: ethyl 7-hydroxy-5-oxo-3-(4-(trifluoromethyl)benzyl)-3,5-dihydro-2H-[1,4]oxazino[2,3,4-ij]quinoline-6-carboxylate The mixture of 3-(4-(trifluoromethyl)benzyl)-3,4-dihydro-2H-benzo[b][1,4]oxazine (280 mg, 0.955 mmol) and triethyl methanetricarboxylate (887 mg, 3.82 mmol) was heated to 260° C. for 1 h. Upon cooling, the mixture was purified by silica gel column chromatography (EtOAc in petroleum ether: 0-15%) to give ethyl 7-hydroxy-5-oxo-3-(4-(trifluoromethyl)benzyl)-3,5-dihydro-2H-[1,4]oxazino[2,3,4-ij]quinoline-6-carboxylate as a solid. $^1$H NMR (CDCl$_3$, 400 MHz): δ 14.35 (s, 1H), 7.88 (dd, J=1.2 Hz, 8.0 Hz, 1H), 7.63 (d, J=8.0 Hz, 2H), 7.55 (d, J=8.0 Hz, 2H), 7.26-7.28 (m, 1H), 7.20 (t, J=8.0 Hz, 1 Hz), 5.56 (d, J=11.2 Hz, 1H), 4.49-4.66 (m, 2H), 4.26 (d, J=12.0 Hz, 1H), 3.90 (td, J=2.0 Hz, 12.0 Hz, 1H), 3.22 (dd, J=3.2 Hz, 12.0 Hz, 1H), 2.89 (t, J=12.0 Hz, 1H), 1.52 (t, J=6.8 Hz, 3H).

Step F: tert-butyl 2-(7-hydroxy-5-oxo-3-(4-(trifluoromethyl)benzyl)-3,5-dihydro-2H-[1,4]oxazino[2,3,4-ij]quinoline-6-carboxamido)acetate The solution of ethyl 7-hydroxy-5-oxo-3-(4-(trifluoromethyl)benzyl)-3,5-dihydro-2H-[1,4]oxazino[2,3,4-ij]quinoline-6-carboxylate (284 mg, 0.655 mmol), tert-butyl 2-aminoacetate HCl salt (132 mg, 0.786 mmol) and DIPEA (0.263 mL, 1.507 mmol) in Toluene (3 mL) was heated and stirred at 120° C. for 2 h. The resulting mixture was concentrated in vacuo and the residue was purified by silica gel column chromatography (EtOAc in petroleum ether: 0-10%) to give tert-butyl 2-(7-hydroxy-5-oxo-3-(4-(trifluoromethyl)benzyl)-3,5-dihydro-2H-[1,4]oxazino[2,3,4-ij]quinoline-6-carboxamido)acetate as a solid. $^1$H NMR (CDCl$_3$, 400 MHz): δ 10.63 (t, J=4.4 Hz, 1H), 7.83 (dd, J=1.6 Hz, 8.0 Hz, 1H), 7.63 (d, J=8.0 Hz, 2H), 7.53 (d, J=8.0 Hz, 2H), 7.26-7.29 (m, 1H), 7.23 (t, J=8.0 Hz, 1H), 5.08 (d, J=12.0 Hz, 1H), 4.29 (d, J=12.0 Hz, 1H), 4.14-4.24 (m, 2H), 3.94 (d, J=12.0 Hz, 1H), 3.17 (dd, J=3.0 Hz, 12.0 Hz, 1H), 2.95 (d, J=12.8 Hz, 1H), 1.54 (s, 9H).

Step G: 2-(7-hydroxy-5-oxo-3-(4-(trifluoromethyl)benzyl)-3,5-dihydro-2H-[1,4]oxazino[2,3,4-ij]quinoline-6-carboxamido)acetic acid To a solution of tert-butyl 2-(7-hydroxy-5-oxo-3-(4-(trifluoromethyl)benzyl)-3,5-dihydro-2H-[1,4]oxazino[2,3,4-ij]quinoline-6-carboxamido)acetate (200 mg, 0.386 mmol) in DCM (5 mL) was added 2,2,2-trifluoroacetic acid (440 mg, 3.86 mmol). The resulting mixture was heated to 60° C. and stirred at 60° C. for 8 h. The resulting mixture was concentrated in vacuo and the residue was re-crystallized from EtOAc (5 mL) and petroleum ether (10 mL) to give 2-(7-hydroxy-5-oxo-3-(4-(trifluoromethyl)benzyl)-3,5-dihydro-2H-[1,4]oxazino[2,3,4-ij]quinoline-6-carboxamido)acetic acid as a solid. $^1$H NMR (DMSO-d$_6$, 400 MHz): δ 12.93 (brs, 1H), 10.44 (t, J=5.6 Hz, 1H), 7.71 (d, J=8.0 Hz, 3H), 7.50 (d, J=8.0 Hz, 2H), 7.36 (d, J=6.8 Hz, 1H), 7.29 (t, J=8.0 Hz, 1H), 5.08 (d, J=6.0 Hz, 1H), 4.28 (d, J=11.2 Hz, 1H), 4.02-4.19 (m, 3H), 2.95-3.05 (m, 2H). LC/MS (m/z): 463 (M+H)$^+$. Human HIF-PHD2 IC$_{50}$: 21.05 nM.

Example 4

2-(9-Cyano-7-hydroxy-5-oxo-3-(4-(trifluoromethyl)benzyl)-3,5-dihydro-2H-[1,4]oxazino[2,3,4-ij]quinoline-6-carboxamido)acetic acid

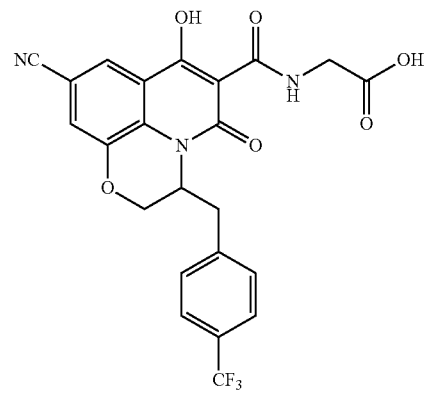 [SMILES: N#Cc1cc2c3c(c1)c(O)c(C(=O)NCC(=O)O)c(=O)n3C(Cc1ccc(C(F)(F)F)cc1)CO2]

Step A: 7-bromo-3-(4-(trifluoromethyl)benzyl)-2H-benzo[b][1,4]oxazine

To a solution of 2-amino-5-bromophenol (2 g, 10.64 mmol) in DCM (40 mL) were added aq. K$_2$CO$_3$ (40 mL, 10.64 mmol) and tetrabutylammonium hydrogen sulfate (0.036 g, 0.106 mmol), then 1-bromo-3-(4-(trifluoromethyl)phenyl)propan-2-one (2.99 g, 10.64 mmol) in DCM (20 mL) was added dropwise to above solution. The resulting mixture was stirred at room temperature for 20 h, then extracted with DCM (50 mL*3). The combined organic layers were washed with brine (50 mL*3), dried over Na$_2$SO$_4$, filtered and concentrated in vacuo to give 7-bromo-3-(4-(trifluoromethyl)benzyl)-2H-benzo[b][1,4]oxazine as an oil, which was used in the next step directly.

Step B: 7-bromo-3-(4-(trifluoromethyl)benzyl)-3,4-dihydro-2H-benzo[b][1,4]oxazine To a solution of 7-bromo-3-(4-(trifluoromethyl)benzyl)-2H-benzo[b][1,4]oxazine (3.6 g, 9.73 mmol) in DCM (10 mL) and MeOH (5 mL) were added AcOH (1 mL, 17.47 mmol) and sodium cyanoborohydride (3.06 g, 48.6 mmol). The resulting mixture was stirred at room temperature for 2 h. The mixture was diluted with water (50 mL), extracted with ethyl acetate (3*50 mL). The combined organic fractions were washed with aqueous ammonium chloride (saturated, 3*50 mL), dried (Na$_2$SO$_4$), filtered and the solvent was evaporated under reduced pressure. The residue was purified by silica gel column chromatography (EtOAc in petroleum ether: 0-15%) to give 7-bromo-3-(4-(trifluoromethyl)benzyl)-3,4-dihydro-2H-benzo[b][1,4]oxazine as an oil. $^1$H NMR (CDCl$_3$, 400 MHz): δ 7.62 (d, J=8.0 Hz, 2H), 7.35 (d, J=8.0 Hz, 2H), 6.95 (d, J=2.0 Hz, 1H), 6.87 (dd, J=2.4 Hz, 8.0 Hz, 1H), 6.41 (d, J=8.0 Hz, 1H), 4.23 (dd, J=4.0 Hz, 12.0 Hz, 1H), 3.98 (q, J=6.0 Hz, 10.4 Hz, 1H), 3.60-3.72 (m, 2H), 2.93 (dd, J=4.0 Hz, 12.0 Hz, 1H), 2.80 (dd, J=8.8 Hz, 9.6 Hz, 1H).

Step C: ethyl 9-bromo-7-hydroxy-5-oxo-3-(4-(trifluoromethyl)benzyl)-3,5-dihydro-2H-[1,4]oxazino[2,3,4-ij]quinoline-6-carboxylate The mixture of 7-bromo-3-(4-(trifluoromethyl)benzyl)-3,4-dihydro-2H-benzo[b][1,4]oxazine (1.6 g, 4.30 mmol) and triethyl methanetricarboxylate (3.99 g, 17.20 mmol) was heated at 260° C. for 1 h. The mixture was purified by silica gel column chromatography (EtOAc in petroleum ether: 0-15%) to give ethyl 9-bromo-7-hydroxy-5-oxo-3-(4-(trifluoromethyl)benzyl)-3,5-dihydro-2H-[1,4]oxazino[2,3,4-ij]quinoline-6-carboxylate as a solid. $^1$H NMR (CDCl$_3$, 400 MHz): δ 14.35 (s, 1H), 7.93 (d, J=2.0 Hz, 1H), 7.63 (d, J=8.0 Hz, 2H), 7.53 (d, J=8.0 Hz, 2H), 7.40 (d, J=2.0 Hz, 1H), 5.05 (d, J=11.2 Hz, 1H), 4.49-4.65 (m, 2H), 4.27 (d, J=12.0 Hz, 1H), 3.90 (d, J=11.2 Hz, 1H), 3.20 (dd, J=2.8 Hz, 12.8 Hz, 1H), 2.85 (t, J=12.0 Hz, 1H), 1.52 (t, J=8.0 Hz, 3H).

Step D: 2-(9-bromo-7-hydroxy-5-oxo-3-(4-(trifluoromethyl)benzyl)-3,5-dihydro-2H-[1,4]oxazino[2,3,4-ij]quinoline-6-carboxamido)acetate To a solution of ethyl 9-bromo-7-hydroxy-5-oxo-3-(4-(trifluoromethyl)benzyl)-3,5-dihydro-2H-[1,4]oxazino[2,3,4-ij]quinoline-6-carboxylate (1.1 g, 2.147 mmol), tert-butyl 2-aminoacetate HCl salt (0.432 g, 2.58 mmol) and DIPEA (0.863 mL, 4.94 mmol) in Toluene (15 mL) was heated to 120° C. and stirred at 120° C. for 2 h. TLC (petroleum ether: EtOAc=5:1) showed that the reaction was completed. The resulting mixture was concentrated in vacuo and the residue was purified by Combi-Flash (EtOAc in petroleum ether: 0-15%) to give tert-butyl 2-(9-bromo-7-hydroxy-5-oxo-3-(4-(trifluoromethyl)benzyl)-3,5-dihydro-2H-[1,4]oxazino[2,3,4-ij]quinoline-6-carboxamido)acetate as a solid. $^1$H NMR (CDCl$_3$, 400 MHz): δ 10.56 (t, J=5.2 Hz, 1H), 7.95 (d, J=2.4 Hz, 1H), 7.64 (d, J=8.0 Hz, 2H), 7.50 (d, J=8.0 Hz, 2H), 7.40 (d, J=2.4 Hz, 1H), 5.06 (d, J=10.8 Hz, 1H), 4.30 (d, J=12.0 Hz, 1H), 4.10-4.23 (m, 2H), 3.93 (d, J=11.2 Hz, 1H), 3.16 (dd, J=4.0 Hz, 13.2 Hz, 1H), 2.90 (dd, J=11.2 Hz, 12.8 Hz, 1H), 1.54 (s, 9H).

Step E: tert-butyl 2-(9-cyano-7-hydroxy-5-oxo-3-(4-(trifluoromethyl)benzyl)-3,5-dihydro-2H-[1,4]oxazino[2,3,4-ij]quinoline-6-carboxamido)acetate To a solution of tert-butyl 2-(9-bromo-7-hydroxy-5-oxo-3-(4-(trifluoromethyl)benzyl)-3,5-dihydro-2H-[1,4]oxazino[2,3,4-ij]quinoline-6-carboxamido)acetate (150 mg, 0.251 mmol) in DMA (2 mL) were added zinc cyanide (59 mg, 0.502 mmol), Pd$_2$(dba)$_3$ (0.023 g, 0.025 mmol), DPPF (14 mg, 0.025 mmol) and zinc dust (33 mg, 0.502 mmol). The reaction solution was heated to 130° C. by microwave for 30 min. The mixture was cooled, water (10 mL) was added and the mixture was extracted with ethyl acacate (3*20 mL). The combined organic fractions were washed with water (3*30 mL), dried over Na$_2$SO$_4$, filtered and the solvent was evaporated under reduced pressure. The residue was purified by silica gel column chromatography (EtOAc in petroleum ether: 0-60%) to give tert-butyl 2-(9-cyano-7-hydroxy-5-oxo-3-(4-(trifluoromethyl)benzyl)-3,5-dihydro-2H-[1,4]oxazino[2,3,4-ij]quinoline-6-carboxamido)acetate as a solid. $^1$H NMR (CDCl$_3$, 400 MHz): δ 10.41 (t, J=4.8 Hz, 1H), 8.16 (d, J=1.6 Hz, 1H), 7.65 (d, J=8.0 Hz, 2H), 7.51 (d, J=8.0 Hz, 2H), 7.45 (d, J=1.6 Hz, 1H), 5.09 (d, J=10.0 Hz, 1H), 4.36 (d, J=12.0 Hz, 1H), 4.11-4.24 (m, 2H), 3.95 (d, J=12.8 Hz, 1H), 3.17 (dd, J=3.2 Hz, 12.8 Hz, 1H), 2.87-2.95 (s, 1H), 1.54 (s, 9H).

Step F: 2-(9-cyano-7-hydroxy-5-oxo-3-(4-(trifluoromethyl)benzyl)-3,5-dihydro-2H-[1,4]oxazino[2,3,4-ij]quinoline-6-carboxamido)acetic acid To a solution of tert-butyl 2-(9-cyano-7-hydroxy-5-oxo-3-(4-(trifluoromethyl)benzyl)-3,5-dihydro-2H-[1,4]oxazino[2,3,4-ij]quinoline-6-carboxamido)acetate (150 mg, 0.276 mmol) in DCM (5 mL) was added 2,2,2-trifluoroacetic acid (315 mg, 2.76 mmol). The resulting mixture was heated for 3 h. The reaction mixture was concentrated in vacuo and the residue was re-crystallised from EtOAc (5 mL) and petroleum ether (20 mL) to give 2-(9-cyano-7-hydroxy-5-oxo-3-(4-(trifluoromethyl)benzyl)-3,5-dihydro-2H-[1,4]oxazino[2,3,4-ij]quinoline-6-carboxamido)acetic acid as a solid. $^1$H NMR (DMSO-d$_6$, 400 MHz): δ 12.99 (brs, 1H), 10.28 (t, J=5.2 Hz, 1H), 8.09 (s, 1H), 7.79 (s, 1H), 7.69 (d, J=8.0 Hz, 2H), 7.48 (d, J=8.0 Hz, 2H), 5.11 (d, J=6.0 Hz, 1H), 4.37 (d, J=12.0 Hz, 1H), 4.10-4.21 (m, 3H), 2.94-3.07 (m, 2H). LC/MS (m/z): 488 (M+H)$^+$. Human HIF-PHD2 IC$_{50}$: 3.0 nM.

Example 5

2-(9-Bromo-7-hydroxy-5-oxo-3-(4-(trifluoromethyl)benzyl)-3,5-dihydro-2H-[1,4]oxazino[2,3,4-ij]quinoline-6-carboxamido)acetic acid

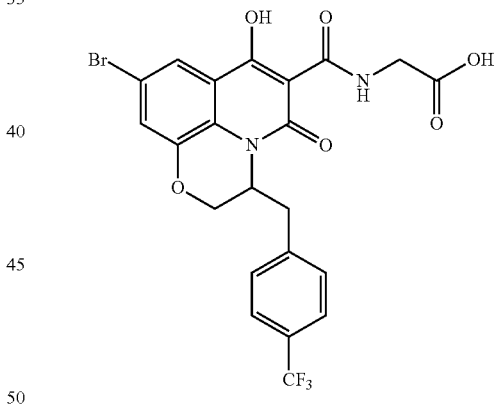

To a solution of Step D product of Example 4 (100 mg, 0.167 mmol) in DCM (1 mL) was added 2,2,2-trifluoroacetic acid (191 mg, 1.674 mmol). The resulting mixture was heated at 60° C. for 3 h. The resulting mixture was concentrated in vacuo and the residue was re-crystallised from EtOAc (1 mL) and petroleum ether (15 mL) to give 2-(9-bromo-7-hydroxy-5-oxo-3-(4-(trifluoromethyl)benzyl)-3,5-dihydro-2H-[1,4]oxazino[2,3,4-ij]quinoline-6-carboxamido)acetic acid as a solid. $^1$H NMR (DMSO-d$_6$, 400 MHz): δ 12.95 (brs, 1H), 10.36 (t, J=5.6 Hz, 1H), 7.77 (d, J=2.0 Hz, 1H), 7.69 (d, J=8.0 Hz, 2H), 7.56 (d, J=2.0 Hz, 1H), 7.48 (d, J=8.0 Hz, 2H), 5.08 (d, J=8.0 Hz, 1H), 4.33 (d, J=12.0 Hz, 1H), 4.02-4.20 (m, 3H), 2.94-3.05 (m, 2H). LC/MS (m/z): 541 (M+H)$^+$. Human HIF-PHD2 IC$_{50}$: 18 nM.

Example 6

2-(7-Hydroxy-9-(methylsulfonyl)-5-oxo-3-(4-(trifluoromethyl)benzyl)-3,5-dihydro-2H-[1,4]oxazino[2,3,4-ij]quinoline-6-carboxamido)acetic acid

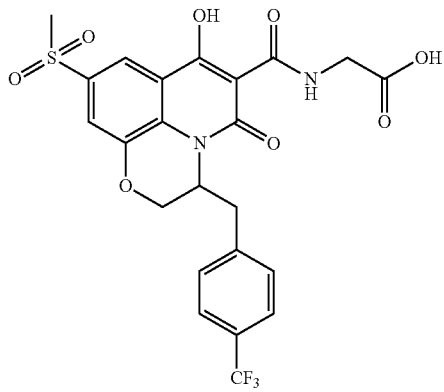 [SMILES: CS(=O)(=O)c1cc2c3c(c1)c(O)c(C(=O)NCC(=O)O)c(=O)n3C(Cc1ccc(C(F)(F)F)cc1)CO2]

Step A: tert-butyl 2-(7-hydroxy-9-(methylsulfonyl)-5-oxo-3-(4-(trifluoromethyl)benzyl)-3,5-dihydro-2H-[1,4]oxazino[2,3,4-ij]quinoline-6-carboxamido)acetate A solution of Step D product of Example 4 (200 mg, 0.335 mmol), sodium methanesulfinate (41 mg, 0.402 mmol), NaOH (2.68 mg, 0.067 mmol), L-proline (7.71 mg, 0.067 mmol) and copper(I) iodide (6.38 mg, 0.033 mmol) in DMSO (2 mL) was heated to 120° C. under $N_2$ for 60 h. The mixture was cooled, water (5 mL) was added and the mixture was extracted with ethyl acetate (3*4 mL). The solvent was evaporated under reduced pressure. The residue was purified by silica gel column chromatography eluting with EtOAc in petroleum ether: 0-20% to give tert-butyl 2-(7-hydroxy-9-(methylsulfonyl)-5-oxo-3-(4-(trifluoromethyl)benzyl)-3,5-dihydro-2H-[1,4]oxazino[2,3,4-ij]quinoline-6-carboxamido)acetate as a solid. $^1$H NMR (CDCl$_3$, 400 MHz): δ 10.42 (t, J=4.8 Hz, 1H), 8.43 (d, J=1.6 Hz, 1H), 7.76 (d, J=1.6 Hz, 1H), 7.65 (d, J=8.0 Hz, 2H), 7.51 (d, J=8.0 Hz, 2H), 5.13 (d, J=10.0 Hz, 1H), 4.39 (d, J=12.0 Hz, 1H), 4.13-4.24 (m, 2H), 3.98 (d, J=12.0 Hz, 1H), 3.18 (dd, J=4.0 Hz, 9.2 Hz, 1H), 3.13 (s, 3H), 2.92 (t, J=11.2 Hz, 1H), 1.54 (s, 9H).

Step B: 2-(7-hydroxy-9-(methylsulfonyl)-5-oxo-3-(4-(trifluoromethyl)benzyl)-3,5-dihydro-2H-[1,4]oxazino[2,3,4-ij]quinoline-6-carboxamido)acetic acid To a solution of tert-butyl 2-(7-hydroxy-9-(methylsulfonyl)-5-oxo-3-(4-(trifluoromethyl)benzyl)-3,5-dihydro-2H-[1,4]oxazino[2,3,4-ij]quinoline-6-carboxamido)acetate (60 mg, 0.101 mmol) in DCM (1 mL) was added 2,2,2-trifluoroacetic acid (115 mg, 1.006 mmol). The resulting mixture was heated at 60° C. for 3 h. The reaction mixture was concentrated in vacuo and the residue was re-crystallised from EtOAc (1 mL) and petroleum ether (15 mL) to give 2-(7-hydroxy-9-(methylsulfonyl)-5-oxo-3-(4-(trifluoromethyl)benzyl)-3,5-dihydro-2H-[1,4]oxazino[2,3,4-ij]quinoline-6-carboxamido)acetic acid as a solid. $^1$H NMR (DMSO-d$_6$, 400 MHz): δ 12.97 (brs, 1H), 10.30 (t, J=5.2 Hz, 1H), 8.15 (s, 1H), 7.79 (s, 1H), 7.71 (d, J=8.0 Hz, 2H), 7.50 (d, J=8.0 Hz, 2H), 5.13 (d, J=6.0 Hz, 1H), 4.38 (d, J=12.0 Hz, 1H), 4.10-4.22 (m, 3H), 3.31 (s, 3H), 2.96-3.07 (m, 2H). LC/MS (m/z): 541 (M+H)$^+$. Human HIF-PHD2 IC$_{50}$: 1.7 nM.

Example 7

2-(7-hydroxy-9-methyl-5-oxo-3-(4-(trifluoromethyl)benzyl)-3,5-dihydro-2H-[1,4]oxazino[2,3,4-ij]quinoline-6-carboxamido)acetic acid

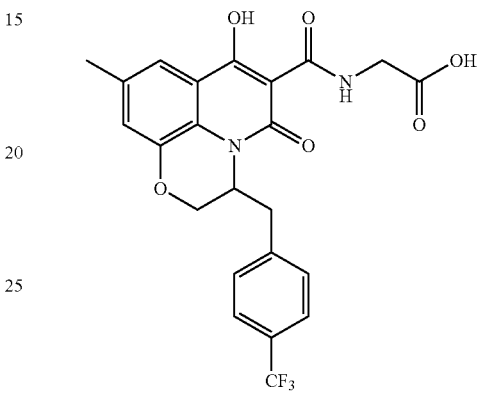

Step A: tert-butyl 2-(7-hydroxy-9-methyl-5-oxo-3-(4-(trifluoromethyl)benzyl)-3,5-dihydro-2H-[1,4]oxazino[2,3,4-ij]quinoline-6-carboxamido)acetate A suspension of Step D product of Example 4 (200 mg, 0.335 mmol), 2,4,6-trimethyl-1,3,5,2,4,6-trioxatriborinane (42 mg, 0.335 mmol), Pd(Ph$_3$P)$_4$ (38.7 mg, 0.033 mmol) and K$_2$CO$_3$ (139 mg, 1.004 mmol) in DMF (1 mL) was heated at 120° C. for 45 min. The resulting mixture was concentrated in vacuo and the residue was purified by silica gel column chromatography (EtOAc in petroleum ether: 0-15%) to give tert-butyl 2-(7-hydroxy-9-methyl-5-oxo-3-(4-(trifluoromethyl)benzyl)-3,5-dihydro-2H-[1,4]oxazino[2,3,4-ij]quinoline-6-carboxamido)acetate as a solid. $^1$H NMR (CDCl$_3$, 400 MHz): δ 10.67 (t, J=5.6 Hz, 1H), 7.63 (d, J=8.0 Hz, 2H), 7.62 (s, 1H), 7.52 (d, J=8.0 Hz, 2H), 7.10 (s, 1H), 5.06 (d, J=10.8 Hz, 1H), 4.27 (d, J=12.0 Hz, 1H), 4.15-4.23 (m, 2H), 3.91 (d, J=11.2 Hz, 1H), 3.16 (dd, J=4.0 Hz, 12.8 Hz, 1H), 2.92 (t, J=12.0 Hz, 1H), 2.44 (s, 3h), 1.53 (s, 9H).

Step B: 2-(7-hydroxy-9-methyl-5-oxo-3-(4-(trifluoromethyl)benzyl)-3,5-dihydro-2H-[1,4]oxazino[2,3,4-ij]quinoline-6-carboxamido)acetic acid To a solution of tert-butyl 2-(7-hydroxy-9-methyl-5-oxo-3-(4-(trifluoromethyl)benzyl)-3,5-dihydro-2H-[1,4]oxazino[2,3,4-ij]quinoline-6-carboxamido)acetate (100 mg, 0.188 mmol) in DCM (1 mL) was added 2,2,2-trifluoroacetic acid (214 mg, 1.878 mmol). The resulting mixture was heated at 60° C. for 3 h. The reaction mixture was concentrated in vacuo and the residue was re-crystallised from EtOAc (1 mL) and petroleum ether (15 mL) to give 2-(7-hydroxy-9-methyl-5-oxo-3-(4-(trifluoromethyl)benzyl)-3,5-dihydro-2H-[1,4]oxazino[2,3,4-ij]quinoline-6-carboxamido)acetic acid as a solid. $^1$H NMR (DMSO-d$_6$, 400 MHz): δ 10.46 (t, J=5.6 Hz, 1H), 7.71 (d, J=8.0 Hz, 2H), 7.49 (d, J=8.0 Hz, 2H), 7.49 (d, J=8.0 Hz, 1H), 7.21 (d, J=1.2 Hz, 1H), 5.05 (d, J=2.4 Hz, 1H), 4.26 (d, J=12.0 Hz, 1H), 4.09-4.20 (m, 2H), 4.06 (d, J=12.0 Hz, 1H), 2.92-3.03 (m, 2H), 2.38 (s, 3H). LC/MS (m/z): 477 (M+H)+. Human HIF-PHD2 IC$_{50}$: 37 nM.

Example 8

2-(9-(1,2-Dihydroxypropan-2-yl)-7-hydroxy-5-oxo-3-(4-(trifluoromethyl)benzyl)-3,5-dihydro-2H-[1,4]oxazino[2,3,4-ij]quinoline-6-carboxamido)acetic acid

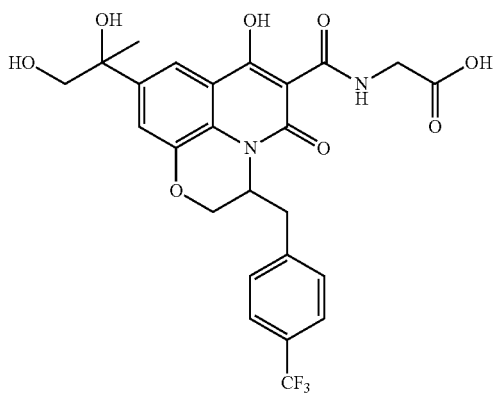 [SMILES: CC(O)(CO)c1cc2c3c(c1)c(O)c(C(=O)NCC(=O)O)c(=O)n3C(Cc1ccc(C(F)(F)F)cc1)CO2]

Step A: tert-butyl 2-(7-hydroxy-5-oxo-9-(prop-1-en-2-yl)-3-(4-(trifluoromethyl)benzyl)-3,5-dihydro-2H-[1,4]oxazino[2,3,4-ij]quinoline-6-carboxamido)acetate A solution of Step D product of Example 4 (500 mg, 0.837 mmol), potassium trifluoro(prop-1-en-2-yl)borate (186 mg, 1.255 mmol), PdCl$_2$(dppf)-CH$_2$Cl$_2$ adduct (13.67 mg, 0.017 mmol) and Et$_3$N (0.117 mL, 0.837 mmol) in 2-propanol (3 mL) was heated at 100° C. by microwave for 45 min. The resulting mixture was concentrated in vacuo and the residue was purified by silica gel column chromatography (EtOAc in petroleum ether: 0-15%) to give tert-butyl 2-(7-hydroxy-5-oxo-9-(prop-1-en-2-yl)-3-(4-(trifluoromethyl)benzyl)-3,5-dihydro-2H-[1,4]oxazino[2,3,4-ij]quinoline-6-carboxamido)acetate as a solid. $^1$H NMR (CDCl$_3$, 400 MHz): δ 10.64 (t, J=4.8 Hz, 1H), 7.89 (d, J=2.0 Hz, 1H), 7.64 (d, J=8.0 Hz, 2H), 7.52 (d, J=8.0 Hz, 2H), 7.43 (d, J=2.0 Hz, 1H), 5.47 (s, 1H), 5.18 (s, 1H), 5.07 (d, J=10.4 Hz, 1H), 4.29 (d, J=12.0 Hz, 1H), 4.11-4.24 (m, 2H), 3.94 (d, J=12.0 Hz, 1H), 3.17 (dd, J=4.0 Hz, 12.8 Hz, 1H), 2.94 (t, J=12.0 Hz, 1H), 2.22 (s, 3H), 1.54 (s, 9H).

Step B: tert-butyl 2-(7-hydroxy-9-(2-methyloxiran-2-yl)-5-oxo-3-(4-(trifluoromethyl)benzyl)-3,5-dihydro-2H-[1,4]oxazino[2,3,4-ij]quinoline-6-carboxamido)acetate To a solution of tert-butyl 2-(7-hydroxy-5-oxo-9-(prop-1-en-2-yl)-3-(4-(trifluoromethyl)benzyl)-3,5-dihydro-2H-[1,4]oxazino[2,3,4-ij]quinoline-6-carboxamido)acetate (100 mg, 0.179 mmol) in DCM (5 mL) was added mCPBA (46.3 mg, 0.269 mmol). The reaction was stirred at 15° C. for 5 h. The resulting mixture was diluted with aqueous NaHCO$_3$ (15 mL) and extracted with DCM (10 mL*3). The combined organic layers were washed with aqueous NaHCO$_3$ (15 mL*3), dried over Na$_2$SO$_4$, filtered and concentrated in vacuo to give tert-butyl 2-(7-hydroxy-9-(2-methyloxiran-2-yl)-5-oxo-3-(4-(trifluoromethyl)benzyl)-3,5-dihydro-2H-[1,4]oxazino[2,3,4-ij]quinoline-6-carboxamido)acetate which was used directly in the next step.

Step C: tert-butyl 2-(9-(1,2-dihydroxypropan-2-yl)-7-hydroxy-5-oxo-3-(4-(trifluoromethyl)benzyl)-3,5-dihydro-2H-[1,4]oxazino[2,3,4-ij]quinoline-6-carboxamido)acetate To a solution of tert-butyl 2-(7-hydroxy-9-(2-methyloxiran-2-yl)-5-oxo-3-(4-(trifluoromethyl)benzyl)-3,5-dihydro-2H-[1,4]oxazino[2,3,4-ij]quinoline-6-carboxamido)acetate (80 mg, 0.139 mmol) in BuOH (3 mL) was added MeOH (0.141 mL, 3.48 mmol) and NaBH$_4$ (26.3 mg, 0.696 mmol). The reaction was stirred at room temperature for 1 h. The resulting mixture was heated at 80° C. for 1 h. The reaction mixture was concentrated in vacuo and the residue was purified by silica gel column chromatography (EtOAc in petroleum ether: 0-30%) to give tert-butyl 2-(9-(1,2-dihydroxypropan-2-yl)-7-hydroxy-5-oxo-3-(4-(trifluoromethyl)benzyl)-3,5-dihydro-2H-[1,4]oxazino[2,3,4-ij]quinoline-6-carboxamido)acetate as a solid. $^1$H NMR (CDCl$_3$, 400 MHz): δ 10.64 (t, J=5.6 Hz, 1H), 7.87 (d, J=2.0 Hz, 1H), 7.63 (d, J=8.0 Hz, 2H), 7.52 (d, J=8.0 Hz, 2H), 7.44 (d, J=2.0 Hz, 1H), 5.07 (d, J=10.0 Hz, 1H), 4.30 (d, J=12.0 Hz, 1H), 4.11-4.24 (m, 2H), 3.87-3.95 (m, 2H), 3.73 (d, J=10.8 Hz, 1H), 3.17 (dd, J=3.2 Hz, 12 Hz, 1H), 2.93 (t, J=12.0 Hz, 1H), 2.68 (brs, 1H), 1.60 (s, 3H), 1.54 (s, 9H).

Step D: 2-(9-(1,2-dihydroxypropan-2-yl)-7-hydroxy-5-oxo-3-(4-(trifluoromethyl)benzyl)-3,5-dihydro-2H-[1,4]oxazino[2,3,4-ij]quinoline-6-carboxamido)acetic acid To a solution of tert-butyl 2-(9-(1,2-dihydroxypropan-2-yl)-7-hydroxy-5-oxo-3-(4-(trifluoromethyl)benzyl)-3,5-dihydro-2H-[1,4]oxazino[2,3,4-ij]quinoline-6-carboxamido)acetate (40 mg, 0.067 mmol) in DCM (1 mL) was added 2,2,2-trifluoroacetic acid (76.4 mg, 0.67 mmol). The resulting mixture was heated at 60° C. for 3 h. LCMS showed that the reaction was completed. The reaction mixture was concentrated in vacuo and the residue was then taken into MeOH (2 mL) and refluxed for 2 h. The resulting mixture was concentrated in vacuo to give a crude material which was purified by HPLC (Column: Grace 150*21.5*5 um C18; Mobile phase: From 38% MeCN in water (0.225% FA) to 68% MeCN in water (0.225% FA); Wavelength: 220 nm) to give 2-(9-(1,2-dihydroxypropan-2-yl)-7-hydroxy-5-oxo-3-(4-(trifluoromethyl)benzyl)-3,5-dihydro-2H-[1,4]oxazino[2,3,4-ij]quinoline-6-carboxamido)acetic acid as a solid. $^1$H NMR (DMSO-d$_6$, 400 MHz): δ 10.47 (t, J=5.6 Hz, 1H), 7.81 (s, 1H), 7.72 (dd, J=3.2 Hz, 8.0 Hz, 2H), 7.52 (d, J=8.0 Hz, 2H), 7.42 (dd, J=2.0 Hz, 4.8 Hz, 1H), 5.16 (s, 1H), 5.04 (d, J=6.4 Hz, 1H), 4.26 (dd, J=4.0 Hz, 12.0 Hz, 1H), 4.29 (d, J=11.2 Hz, 1H), 4.04-4.12 (m, 3H), 3.42-3.45 (m, 1H), 2.95-3.05 (m, 2H), 2.54 (s, 1H), 1.42 (d, J=3.2 Hz, 3H). LC/MS (m/z): 537 (M+H)+. Human HIF-PHD2 IC$_{50}$: 30 nM.

Example 9

2-(1-Hydroxy-3-oxo-6-(4-(trifluoromethyl)phenyl)-3,5,6,7-tetrahydropyrido[3,2,1-ij]quinoline-2-carboxamido)acetic acid

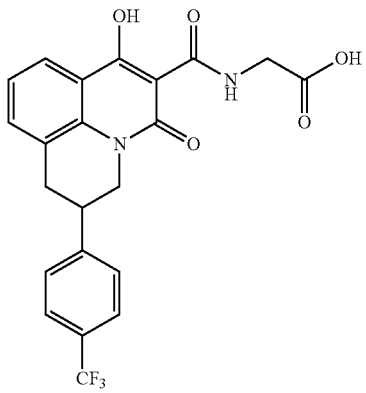

Step A: 3-(4-(trifluoromethyl)phenyl)quinoline

A 100 mL round bottom flask was charged with 3-bromoquinoline (3 g, 14.4 mmol), (4-(trifluoromethyl)phenyl) boronic acid (2.74 g, 14.4 mmol), Pd(Ph$_3$P)$_4$ (832 mg, 0.72 mmol), K$_2$CO$_3$ (5.97 g, 43.2 mmol) and DMF (70 mL). The flask was purged with N$_2$ and heated at 80° C. for 16 hr. The reaction was poured into water and extracted with EtOAc (50 mL*3). The combined organic layers were washed with brine and then dried over Na$_2$SO$_4$, filtered and evaporated to dryness. The residue was purified by silica gel column chromatography (80 g column, EtOAc in Petroleum ether from 0% to 10%) to give 3-(4-(trifluoromethyl)phenyl)quinolone as a solid. $^1$H NMR (CD$_3$OD, 400 MHz): δ 9.17 (d, J=2.2 Hz, 1H), 8.65 (d, J=1.8 Hz, 1H), 8.10-8.02 (m, 2H), 8.00 (d, J=8.2 Hz, 2H), 7.83 (d, J=7.9 Hz, 2H), 7.81-7.77 (m, 1H), 7.69-7.62 (m, 1H).

Step B: 3-(4-(trifluoromethyl)phenyl)-1,2,3,4-tetrahydroquinoline

To a solution of 3-(4-(trifluoromethyl)phenyl)quinoline (500 mg, 1.83 mmol) in EtOH (10 mL) was added Pd/C (80 mg) under Ar. The suspension was degassed under vacuum and purged with H$_2$ for 5 times. The mixture was stirred under H$_2$ at 50° C. for 20 hr. The reaction mixture was filtered and the filtrate was evaporated to dryness. The residue was purified via silica gel column chromatography (20 g column, EtOAc in Petroleum ether from 0% to 4%) to give 3-(4-(trifluoromethyl)phenyl)-1,2,3,4-tetrahydroquinoline as a solid. $^1$H NMR (CDCl$_3$, 400 MHz): δ 7.58 (d, J=8.2 Hz, 2H), 7.35 (d, J=7.9 Hz, 2H), 7.07-6.96 (m, 2H), 6.66 (t, J=7.3 Hz, 1H), 6.55 (d, J=7.9 Hz, 1H), 4.02 (brs, 1H), 3.52-3.43 (m, 1H), 3.35 (t, J=10.6 Hz, 1H), 3.27-3.16 (m, 1H), 3.01 (d, J=7.9 Hz, 2H).

Step C: Ethyl 1-hydroxy-3-oxo-6-(4-(trifluoromethyl)phenyl)-3,5,6,7-tetrahydropyrido[3,2,1-ij]quinoline-2-carboxylate A thumb flask was charged with 3-(4-(trifluoromethyl)phenyl)-1,2,3,4-tetrahydroquinoline (157 mg, 0.566 mmol) and triethyl methanetricarboxylate (526 mg, 2.26 mmol). The flask was purged with N$_2$. The mixture was heated to 260° C. and stirred for 30 min. LCMS and TLC (Petroleum ether: EtOAc=4:1) showed the starting material was consumed completely and the desired compound formed. The resulting mixture was evaporated to dryness, and the residue was purified via silica gel column chromatography (20 g column, EtOAc in Petroleum ether from 0% to 19%) to give ethyl 1-hydroxy-3-oxo-6-(4-(trifluoromethyl)phenyl)-3,5,6,7-tetrahydropyrido[3,2,1-ij]quinoline-2-carboxylate as a solid. $^1$H NMR (CDCl$_3$, 400 MHz): δ 14.18 (s, 1H), 8.05 (d, J=8.2 Hz, 1H), 7.62 (d, J=7.9 Hz, 2H), 7.47 (d, J=7.1 Hz, 1H), 7.39 (d, J=7.9 Hz, 2H), 7.18 (t, J=7.6 Hz, 1H), 4.91 (dd, J=14.2, 2.8 Hz, 1H), 4.49 (q, J=7.1 Hz, 2H), 3.66 (dd, J=13.8, 10.3 Hz, 1H), 3.33-3.24 (m, 1H), 3.23-3.17 (m, 2H), 1.47 (t, J=7.1 Hz, 3H).

Step D: Tert-butyl 2-(1-hydroxy-3-oxo-6-(4-(trifluoromethyl)phenyl)-3,5,6,7-tetrahydropyrido[3,2,1-ij]quinoline-2-carboxamido)acetate A 10 mL vial was charged with ethyl 1-hydroxy-3-oxo-6-(4-(trifluoromethyl)phenyl)-3,5,6,7-tetrahydropyrido[3,2,1-ij]quinoline-2-carboxylate (240 mg, 0.575 mmol), tert-butyl 2-aminoacetate (151 mg, 1.15 mmol), DIPEA (297 mg, 2.3 mmol) and toluene (3 mL). The mixture was heated to 110° C. and stirred for 3 hr. LCMS showed the starting material was consumed completely and the desired compound was formed. The reaction mixture was poured into water and acidified to pH~1, then extracted with EtOAc (20 mL*3). The combined organic layers were dried over Na$_2$SO$_4$, filtered and evaporated to dryness. The residue was purified via silica gel column chromatography (12 g column, EtOAc in Petroleum ether from 0% to 16%) to give tert-butyl 2-(1-hydroxy-3-oxo-6-(4-(trifluoromethyl)phenyl)-3,5,6,7-tetrahydropyrido[3,2,1-ij]quinoline-2-carboxamido) acetate as a solid. $^1$H NMR (CDCl$_3$, 400 MHz): δ 10.72 (brs, 1H), 8.09 (d, J=7.5 Hz, 1H), 7.65 (d, J=8.0 Hz, 2H), 7.49 (d, J=7.5 Hz, 1H), 7.43 (d, J=8.5 Hz, 2H), 7.25-7.21 (m, 1H), 5.02-4.88 (m, 1H), 4.22-4.04 (m, 2H), 3.71 (dd, J=13.8, 10.3 Hz, 1H), 3.37-3.27 (m, 1H), 3.25 (d, J=7.5 Hz, 2H), 1.50 (s, 9H).

Step E: 2-(1-hydroxy-3-oxo-6-(4-(trifluoromethyl)phenyl)-3,5,6,7-tetrahydropyrido[3,2,1-ij]quinoline-2-carboxamido)acetic acid A 100 mL round bottom flask was charged with tert-butyl 2-(1-hydroxy-3-oxo-6-(4-(trifluoromethyl)phenyl)-3,5,6,7-tetrahydropyrido[3,2,1-ij]quinoline-2-carboxamido)acetate (220 mg, 0.438 mmol), TFA (0.3 mL) and DCM (5 mL). The mixture was stirred at 40° C. for 1 hr. LCMS and TLC (Petroleum ether: EtOAc=3:1) showed the starting material was consumed and the desired compound formed. The solvent was evaporated and the residue was re-dissolved in DCM (10 mL) and evaporated to dryness again. The workup repeated for three times to remove TFA completely. Then the residue was washed with EtOAc (20 mL) and dried under vacuo to give 2-(1-hydroxy-3-oxo-6-(4-(trifluoromethyl) phenyl)-3,5,6,7-tetrahydropyrido[3,2,1-ij]quinoline-2-carboxamido)acetic acid as a solid. $^1$H NMR (DMSO-d$_6$, 400 MHz): δ 12.86 (brs, 1H), 10.51 (t, J=5.5 Hz, 1H), 7.95 (d, J=7.7 Hz, 1H), 7.73 (d, J=8.2 Hz, 2H), 7.62 (d, J=7.9 Hz, 2H), 7.62 (d, J=7.9 Hz, 1H), 7.29 (t, J=7.7 Hz, 1H), 4.63 (d, J=11.5 Hz, 1H), 4.11 (d, J=5.7 Hz, 2H), 3.90-3.77 (m, 1H), 3.41 (m, 1H), 3.25 (d, J=7.6 Hz, 2H). LC/MS (m/z): 447 (M+H)⁺. Human HIF-PHD2 IC$_{50}$: 7.2 nM.

Example 10

2-(7-Hydroxy-5-oxo-2-(4-(trifluoromethyl)phenyl)-3,5-dihydro-2H-[1,4]oxazino[2,3,4-ij]quinoline-6-carboxamido)acetic acid

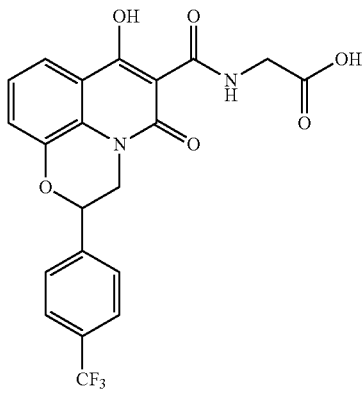 [SMILES: O=C(O)CNC(=O)c1c(O)c2cccc3c2n(c1=O)CC(c1ccc(C(F)(F)F)cc1)O3]

Step A: 2-bromo-2-(4-(trifluoromethyl)phenyl)acetyl chloride

To a slurry of 2-(4-(trifluoromethyl)phenyl)acetic acid (5 g, 24.5 mmol) in CCl$_4$ (2.5 mL) was added SOCl$_2$ (7 mL, 96.2 mmol). The mixture was heated at 65° C. for 45 min, then diluted with CCl$_4$ (12 mL). NBS (5.3 g, 29.8 mmol) was added followed by 1 drop of 48% HBr. The temperature was increased to 85° C. for an additional 2 hr. The reaction mixture was cooled to room temperature and diluted with hexane (125 mL). The solids were filtered off and the filtrate was evaporated in vacuo. The residue was dissolved in hexane (15 mL), filtered again and the filtrate was concentrated in vacuo to give 2-bromo-2-(4-(trifluoromethyl)phenyl)acetyl chloride as an oil. ¹H NMR (CDCl$_3$, 400 MHz, CDCl$_3$): δ 7.71 (d, J=8.0 Hz, 2H), 7.63 (d, J=8.0 Hz, 2H), 5.70 (s, 1 H).

Step B: 2-(4-(trifluoromethyl)phenyl)-2H-benzo[b][1,4]oxazin-3(4H)-one

A 250 mL round bottom flask was charged with 2-bromo-2-(4-(trifluoromethyl)phenyl)acetyl chloride (4.4 g, 0.0146 mmol), 2-aminophenol (2.07 g, 0.019 mmol), K$_2$CO$_3$ (10 g, 0.073 mmol) and DMF (80 mL). The mixture was stirred at room temperature for 20 hr. The reaction mixture was poured into water and extracted with EtOAc (50 mL*3). The combined organic layers were evaporated to dryness. The residue was purified via silica gel column chromatography (80 g column, EtOAc in Petroleum ether from 0% to 20%) to give 2-(4-(trifluoromethyl)phenyl)-2H-benzo[b][1,4]oxazin-3(4H)-one as a solid. ¹H NMR (CDCl$_3$, 400 MHz): δ 8.17 (brs, 1H), 7.68-7.56 (m, 4H), 7.10 (d, J=8.0 Hz, 1H), 7.07-6.95 (m, 2H), 6.81 (dd, J=7.5, 1.5 Hz, 1H), 5.75 (s, 1H).

Step C: 2-(4-(trifluoromethyl)phenyl)-3,4-dihydro-2H-benzo[b][1,4]oxazine

A 100 mL three neck flask was charged with 2-(4-(trifluoromethyl)phenyl)-2H-benzo[b][1,4]oxazin-3(4H)-one (1700 mg, 5.80 mmol) and THF (30 mL). The flask was purged with N$_2$ and cooled to 0° C. Then BH$_3$-Me$_2$S (4 mL) was added slowly. After addition, the mixture was warmed to 40° C. and stirred for 3 hr. LCMS and TLC (Petroleum ether: EtOAc=4:1) showed the starting material was consumed and the desired compound was formed. The reaction mixture was cooled to 0° C. and 1 M HCl (10 mL) was added slowly. Then the mixture was basified to pH 12 with NaOH solution and extracted with EtOAc (50 mL*3). The organic layers were dried over Na$_2$SO$_4$, filtered and evaporated to dryness to give 2-(4-(trifluoromethyl)phenyl)-3,4-dihydro-2H-benzo[b][1,4]oxazine as a solid. ¹H NMR (CDCl$_3$, 400 MHz): δ 7.59 (d, J=8.2 Hz, 2H), 7.48 (d, J=8.2 Hz, 2H), 6.85 (dd, J=7.9, 0.9 Hz, 1H), 6.76 (d, J=8.0 Hz, 1H), 6.66 (d, J=8.0 Hz, 1H), 6.61 (d, J=7.7 Hz, 1H), 5.10 (dd, J=8.3, 1.6 Hz, 1H), 3.48 (dd, J=11.9, 2.4 Hz, 1H), 3.28 (dd, J=11.8, 8.5 Hz, 1H).

Step D: ethyl 7-hydroxy-5-oxo-2-(4-(trifluoromethyl)phenyl)-3,5-dihydro-2H-[1,4]oxazino[2,3,4-ij]quinoline-6-carboxylate A thumb flask was charged with 2-(4-(trifluoromethyl)phenyl)-3,4-dihydro-2H-benzo[b][1,4]oxazine (200 mg, 0.716 mmol) and triethyl methanetricarboxylate (665 mg, 2.865 mmol). The flask was purged with N$_2$ and heated to 240° C. for 15 min. LCMS and TLC (Petroleum ether: EtOAc=3:1) showed the starting material was consumed and the desired compound formed. The mixture was purified via silica gel column chromatography (20 g column, EtOAc in Petroleum ether from 0% to 20%) to give ethyl 7-hydroxy-5-oxo-2-(4-(trifluoromethyl)phenyl)-3,5-dihydro-2H-[1,4]oxazino[2,3,4-ij]quinoline-6-carboxylate as a solid. ¹H NMR (CDCl$_3$, 400 MHz): δ 14.30 (s, 1H), 7.81 (d, J=7.9 Hz, 1H), 7.73 (d, J=7.9 Hz, 2H), 7.62 (d, J=7.9 Hz, 2H), 7.33 (d, J=7.9 Hz, 1H), 7.21 (t, J=7.9 Hz, 1H), 5.19 (t, J=7.9 Hz, 1H), 4.97 (dd, J=14.1, 2.6 Hz, 1H), 4.59-4.44 (m, 2H), 3.66 (dd, J=14.2, 9.6 Hz, 1H), 1.49 (t, J=7.2 Hz, 3H).

Step E: tert-butyl 2-(7-hydroxy-5-oxo-2-(4-(trifluoromethyl)phenyl)-3,5-dihydro-2H-[1,4]oxazino[2,3,4-ij]quinoline-6-carboxamido)acetate A 10 mL vial was charged with ethyl 7-hydroxy-5-oxo-2-(4-(trifluoromethyl)phenyl)-3,5-dihydro-2H-[1,4]oxazino[2,3,4-ij]quinoline-6-carboxylate (335 mg, 0.787 mmol), tert-butyl 2-aminoacetate (264 mg, 1.574 mmol), DIPEA (406 mg, 3.148 mmol) and toluene (4 mL). The mixture was heated to 110° C. and stirred for 3 hr. LCMS showed the starting material was consumed and the desired compound formed. The reaction mixture was poured into water and acidified to pH~1, then extracted with EtOAc (20 mL*3). The combined organic layers were dried over Na$_2$SO$_4$, filtered and evaporated to dryness. The residue was purified via silica gel column chromatography (20 g column, EtOAc in Petroleum Ether from 0% to 8%) to give tert-butyl 2-(7-hydroxy-5-oxo-2-(4-(trifluoromethyl)phenyl)-3,5-dihydro-2H-[1,4]oxazino[2,3,4-ij]quinoline-6-carboxamido)acetate as a solid. ¹H NMR (CDCl$_3$, 400 MHz): δ 10.59 (brs, 1H), 7.83 (d, J=7.0 Hz, 1H), 7.76-7.70 (d, J=8.0 Hz, 2H), 7.64 (d, J=8.0 Hz, 2H), 7.33 (d, J=8.0 Hz, 1H), 7.23 (d, J=8.0 Hz, 1H), 5.21 (dd, J=9.5, 2.0 Hz, 1H), 4.99 (dd, J=14.0, 2.5 Hz, 1H), 4.07-4.22 (m, 2 H), 3.69 (dd, J=14.0, 10.0 Hz, 1H), 1.51 (s, 9H).

Step F: 2-(7-hydroxy-5-oxo-2-(4-(trifluoromethyl)phenyl)-3,5-dihydro-2H-[1,4]oxazino[2,3,4-ij]quinoline-6-carboxamido)acetic acid A 100 mL round bottom flask was charged with tert-butyl 2-(7-hydroxy-5-oxo-2-(4-(trifluoromethyl)phenyl)-3,5-dihydro-2H-[1,4]oxazino[2,3,4-ij]quinoline-6-carboxamido)acetate (320 mg, 0.634 mmol), TFA(0.4 mL) and DCM (10 mL). The mixture was stirred at 40° C. for 1 hr. LCMS and TLC (Petroleum ether: EtOAc=3:1) showed the starting material was consumed and the desired compound was formed. The solvent was then evaporated and the residue was washed with EtOAc (20 mL) and dried under vacuo to give 2-(7-hydroxy-5-oxo-2-(4-(trifluoromethyl)phenyl)-3,5-dihydro-2H-[1,4]oxazino[2,3,4-ij]quinoline-6-carboxamido)acetic acid as a solid. $^1$H NMR (DMSO-$d_6$, 400 MHz): δ 10.41 (t, J=5.5 Hz, 1H), 7.87-7.80 (m, 2H), 7.80-7.73 (m, 2H), 7.69 (d, J=7.9 Hz, 1H), 7.42 (d, J=7.9 Hz, 1H), 7.32-7.25 (m, 1H), 5.50 (d, J=7.3 Hz, 1H), 4.73 (dd, J=13.7, 2.4 Hz, 1H), 4.12 (d, J=5.5 Hz, 2H), 3.85 (dd, J=13.7, 9.5 Hz, 1H). LC/MS (m/z): 449 (M+H)$^+$. Human HIF-PHD2 IC$_{50}$: 6.4 nM.

Example 11

2-(8-Bromo-7-hydroxy-5-oxo-2-(4-(trifluoromethyl)phenyl)-3,5-dihydro-2H-[1,4]oxazino[2,3,4-ij]quinoline-6-carboxamido)acetic acid

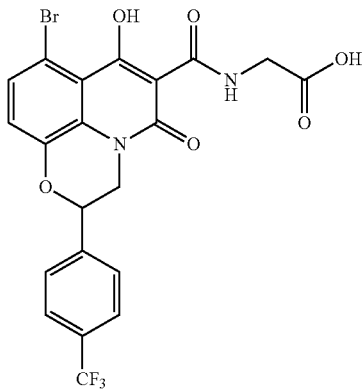

Step A: 6-bromo-2-(4-(trifluoromethyl)phenyl)-2H-benzo[b][1,4]oxazin-3(4H)-one

A 250 mL round bottom flask was charged with 2-bromo-2-(4-(trifluoromethyl)phenyl)acetyl chloride (6.0 g, 19.9 mmol), 2-amino-4-bromophenol (3.74 g, 19.9 mmol), K$_2$CO$_3$ (13.7 g, 99.5 mmol) and DMF (100 mL). The mixture was stirred at room temperature for 20 hr. TLC (Petroleum ether: EtOAc=3:1) showed the desired compound was formed. The reaction mixture was poured into water and extracted with EtOAc (50 mL*3). The combined organic layers were evaporated to dryness. The residue was purified via silica gel column chromatography (80 g column, EtOAc in Petroleum ether from 0% to 15%) to give 6-bromo-2-(4-(trifluoromethyl)phenyl)-2H-benzo[b][1,4]oxazin-3(4H)-one as a solid. $^1$H NMR (CDCl$_3$, 400 MHz): δ 8.05 (brs, 1H), 7.64 (d, J=8.0 Hz, 2H), 7.58 (d, J=8.0 Hz, 2H), 7.13 (dd, J=8.8, 2.3 Hz, 1H), 6.99-6.94 (m, 2H), 5.74 (s, 1H).

Step B: 6-bromo-2-(4-(trifluoromethyl)phenyl)-3,4-dihydro-2H-benzo[b][1,4]oxazine A 250 mL three neck flask was charged with 6-bromo-2-(4-(trifluoromethyl)phenyl)-2H-benzo[b][1,4]oxazin-3 (4H)-one (2.3 g, 6.18 mmol) and THF (60 mL). The flask was purged with N$_2$ and cooled to 0° C. Then BH$_3$-Me$_2$S (10 mL) was added slowly. After addition, the mixture was warmed to 40° C. and stirred for 3 hr. TLC (Petroleum: EtOAc=3:1) showed the starting material was consumed and the desired compound was formed. The reaction mixture was cooled to 0° C. and 1 M HCl (10 mL) was added slowly. Then the mixture was basified to pH 12 with NaOH solution and extracted with EtOAc (50 mL*3). The organic layers were dried over Na$_2$SO$_4$, filtered and evaporated to dryness to give 6-bromo-2-(4-(trifluoromethyl)phenyl)-3,4-dihydro-2H-benzo[b][1,4]oxazine as a solid. $^1$H NMR (CDCl$_3$, 400 MHz): δ 7.67 (d, J=8.2 Hz, 2H), 7.54 (d, J=8.2 Hz, 2H), 6.84-6.74 (m, 3H), 5.13 (dd, J=8.4, 2.0 Hz, 1H), 4.00 (brs, 1H), 3.56 (d, J=11.9 Hz, 1H), 3.34 (d, J=11.9, 8.9 Hz, 1H).

Step C: ethyl 8-bromo-7-hydroxy-5-oxo-2-(4-(trifluoromethyl)phenyl)-3,5-dihydro-2H-[1,4]oxazino[2,3,4-ij]quinoline-6-carboxylate A 100 mL round bottom flask was charged with 6-bromo-2-(4-(trifluoromethyl)phenyl)-3,4-dihydro-2H-benzo[b][1,4]oxazine (2.91 g, 8.13 mmol) and triethyl methanetricarboxylate (7.55 g, 32.5 mmol). The flask was purged with N$_2$ and heated at 250° C. for 3hr. TLC (Petroleum ether: EtOAc=3:1) showed the starting material was consumed and the desired compound formed. The reaction mixture was purified via silica gel column chromatography (20 g column, EtOAc in Petroleum ether from 0% to 90%) to give ethyl 8-bromo-7-hydroxy-5-oxo-2-(4-(trifluoromethyl)phenyl)-3,5-dihydro-2H-[1,4]oxazino[2,3,4-ij]quinoline-6-carboxylate as a solid. $^1$H NMR (CDCl$_3$, 400 MHz): δ 7.70 (d, J=8.2 Hz, 2H), 7.58 (d, J=8.2 Hz, 2H), 7.47 (d, J=8.6 Hz, 1H), 7.12 (d, J=8.6 Hz, 1H), 5.20-5.11 (m, 1H), 5.04-4.91 (m, 1H), 4.59-4.45 (m, 2H), 3.70-3.57 (m, 1H), 1.47 (t, J=7.2 Hz, 3H).

Step D: tert-butyl 2-(8-bromo-7-hydroxy-5-oxo-2-(4-(trifluoromethyl)phenyl)-3,5-dihydro-2H-[1,4]oxazino[2,3,4-ij]quinoline-6-carboxamido)acetate A 30 mL vial was charged with ethyl 8-bromo-7-hydroxy-5-oxo-2-(4-(trifluoromethyl)phenyl)-3,5-dihydro-2H-[1,4]oxazino[2,3,4-ij]quinoline-6-carboxylate (900 mg, 1.81 mmol), tert-butyl 2-aminoacetate (839 mg, 3.61 mmol), DIPEA (934 mg, 7.42 mmol) and toluene (9 mL). The mixture was heated to 115° C. and stirred for 3 hr. LCMS showed the starting material was consumed and the desired compound formed. The reaction mixture was poured into water, and then extracted with EtOAc (20 mL*3). The combined organic layers were dried over Na$_2$SO$_4$, filtered and evaporated to dryness. The residue was purified via silica gel column chromatography (EtOAc in Petroleum Ether from 0% to 20%) to give tert-butyl 2-(8-bromo-7-hydroxy-5-oxo-2-(4-(trifluoromethyl)phenyl)-3,5-dihydro-2H-[1,4]oxazino[2,3,4-ij]quinoline-6-carboxamido)acetate as a solid. $^1$H NMR (CDCl$_3$, 400 MHz): δ 10.67 (brs, 1H), 7.72 (d, J=8.2 Hz, 2H), 7.60 (d, J=8.2 Hz, 2H), 7.49 (d, J=8.6 Hz, 1H), 7.13 (d, J=8.6 Hz, 1H), 5.23-5.12 (m, 1H), 5.07-4.93 (m, 1H), 4.21-4.04 (m, 2H), 3.73-3.61 (m, 1H), 1.49 (s, 9H).

Step E: 2-(8-bromo-7-hydroxy-5-oxo-2-(4-(trifluoromethyl)phenyl)-3,5-dihydro-2H-[1,4]oxazino[2,3,4-ij]quinoline-6-carboxamido)acetic acid A 100 mL round bottom flask was charged with tert-butyl 2-(8-bromo-7-hydroxy-5-oxo-2-(4-(trifluoromethyl)phenyl)-3,5-dihydro-2H-[1,4]oxazino[2,3,4-ij]quinoline-6-carboxamido)acetate (100 mg, 0.17 mmol), TFA(4 mL) and DCM (4 mL). The mixture was stirred at 40° C. for 1 hr. LCMS showed the starting material was consumed and the desired compound was formed. The solvent was evaporated and the residue was purified via prep-HPLC (Column: ASB C18 150*25 mm; Mobile phase: 57-87% MeCN in water (0.1% HCl); Wavelength: 220 nm) to give 2-(8-bromo-7-hydroxy-5-oxo-2-(4-(trifluoromethyl)phenyl)-3,5-dihydro-2H-[1,4]oxazino[2,3,4-ij]quinoline-6-carboxamido)acetic acid as a solid. $^{1}$H NMR (DMSO-d$_{6}$, 400 MHz): δ 10.53 (brs, 1H), 7.83 (d, J=8.0 Hz, 2H), 7.75 (d, J=8.0 Hz, 2H), 7.53 (d, J=8.4 Hz, 1H), 7.30 (d, J=8.8 Hz, 1H), 5.48 (d, J=7.1 Hz, 1H), 4.77 (d, J=11.5 Hz, 1H), 4.13 (d, J=5.7 Hz, 2H), 3.84 (dd, J=13.7, 9.3 Hz, 1H). LC/MS (m/z): 529 (M+H)$^{+}$. Human HIF-PHD2 IC$_{50}$: 2.6 nM.

Example 12

2-(7-Hydroxy-8-(methylsulfonyl)-5-oxo-2-(4-(trifluoromethyl)phenyl)-3,5-dihydro-2H-[1,4]oxazino[2,3,4-ij]quinoline-6-carboxamido)acetic acid

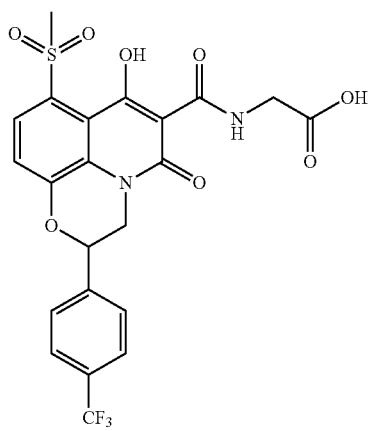 [SMILES: CS(=O)(=O)c1ccc2c3c1c(O)c(C(=O)NCC(=O)O)c(=O)n3CC(c1ccc(C(F)(F)F)cc1)O2]

Step A: tert-butyl 2-(7-hydroxy-8-(methylsulfonyl)-5-oxo-2-(4-(trifluoromethyl)phenyl)-3,5-dihydro-2H-[1,4]oxazino[2,3,4-ij]quinoline-6-carboxamido)acetate A thumb flask was charged with Step D product of Example 11 (150 mg, 0.257 mmol), CH$_{3}$SO$_{2}$Na (31 mg, 0.308 mmol), L-proline (6 mg, 0.051 mmol), NaOH (2 mg, 0.051 mmol), CuI (5 mg, 0.0257 mmol) and DMSO (2 mL). The flask was purged with N$_{2}$ and heated at 120° C. for 3 hr. LCMS showed the starting material was consumed and the desired compound was formed. The mixture was purified via prep-HPLC (Column: ASB C18 150*25 mm; Mobile phase: 55-85% MeCN in water (0.1% HCl); Wavelength: 220 nm) to give tert-butyl 2-(7-hydroxy-8-(methylsulfonyl)-5-oxo-2-(4-(trifluoromethyl)phenyl)-3,5-dihydro-2H-[1,4]oxazino[2,3,4-ij]quinoline-6-carboxamido)acetate as a solid. LC/MS (m/z): 583 (M+H)$^{+}$.

Step B: 2-(7-hydroxy-8-(methylsulfonyl)-5-oxo-2-(4-(trifluoromethyl)phenyl)-3,5-dihydro-2H-[1,4]oxazino[2,3,4-ij]quinoline-6-carboxamido)acetic acid A 100 mL round bottom flask was charged with tert-butyl 2-(7-hydroxy-8-(methylsulfonyl)-5-oxo-2-(4-(trifluoromethyl)phenyl)-3,5-dihydro-2H-[1,4]oxazino[2,3,4-ij]quinoline-6-carboxamido)acetate (40 mg, 0.069 mmol), TFA(4 mL) and DCM (4 mL). The mixture was stirred at 30° C. for 4 hr. LCMS showed the starting material was consumed and the desired compound was formed. The solvent was evaporated to give 2-(8-bromo-7-hydroxy-5-oxo-2-(4-(trifluoromethyl)phenyl)-3,5-dihydro-2H-[1,4]oxazino[2,3,4-ij]quinoline-6-carboxamido)acetic acid as a solid. $^{1}$H NMR (DMSO-d$_{6}$, 400 MHz): δ 8.08 (d, J=8.4 Hz, 1H), 7.84 (d, J=8.0 Hz, 2H), 7.76 (d, J=8.0 Hz, 2H), 7.56 (d, J=8.4 Hz, 1H), 5.60 (d, J=6.8 Hz, 1H), 4.82 (d, J=15.2 Hz, 1H), 4.16 (d, J=4.8 Hz, 2H), 3.92 (dd, J=12.5, 10.7 Hz, 1H), 3.51 (s, 3H). LC/MS (m/z): 527 (M+H)$^{+}$. Human HIF-PHD2 IC$_{50}$: 19 nM.

Example 13

2-(8-Cyano-7-hydroxy-5-oxo-2-(4-(trifluoromethyl)phenyl)-3,5-dihydro-2H-[1,4]oxazino[2,3,4-ij]quinoline-6-carboxamido)acetic acid

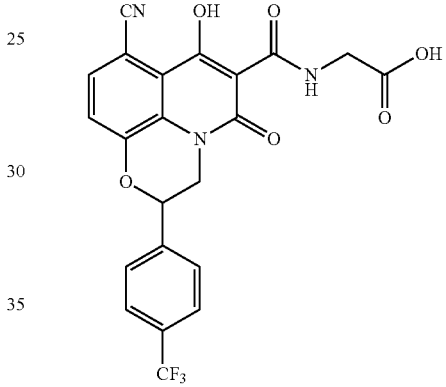

Step A: tert-butyl 2-(8-cyano-7-hydroxy-5-oxo-2-(4-(trifluoromethyl)phenyl)-3,5-dihydro-2H-[1,4]oxazino[2,3,4-ij]quinoline-6-carboxamido)acetate A microwave tube was charged with Step D product of Example 11 (50 mg, 0.0857 mmol), Zn(CN)$_{2}$ (26 mg, 0.223 mmol), Zn (15 mg, 0.223 mmol), Pd$_{2}$(dba)$_{3}$ (10.2 mg, 0.0111 mmol), dppf (6.2 mg, 0.0111 mmol) and DMA (1.5 mL). The tube was purged with N$_{2}$ and heated at 80° C. for 30 min. LCMS showed the starting material was consumed and the desired compound was formed. The mixture was purified via prep-HPLC (Column: ASB C18 150*25 mm; Mobile phase: 58-88% MeCN in water (0.1% HCl); Wavelength: 220 nm) to give tert-butyl 2-(8-cyano-7-hydroxy-5-oxo-2-(4-(trifluoromethyl)phenyl)-3,5-dihydro-2H-[1,4]oxazino[2,3,4-ij]quinoline-6-carboxamido)acetate as a solid.

Step B: 2-(8-cyano-7-hydroxy-5-oxo-2-(4-(trifluoromethyl)phenyl)-3,5-dihydro-2H-[1,4]oxazino[2,3,4-ij]quinoline-6-carboxamido)acetic acid A 100 mL round bottom flask was charged with tert-butyl 2-(8-cyano-7-hydroxy-5-oxo-2-(4-(trifluoromethyl)phenyl)-3,5-dihydro-2H-[1,4]oxazino[2,3,4-ij]quinoline-6-carboxamido)acetate (10 mg, 0.0189 mmol), TFA(4 mL) and DCM (4 mL). The mixture was stirred at 30° C. for 1 hr. LCMS showed the starting material was consumed and the desired compound was formed. The solvent was evaporated and the residue was purified via prep-HPLC (Column: ASB C18 150*25 mm; Mobile phase: 45-75% MeCN in water (0.1% HCl); Wavelength: 220 nm) to give 2-(8-cyano-7-hydroxy-5-oxo-2-(4-(trifluoromethyl)phenyl)-3,5-dihydro-2H-[1,4]oxazino[2,3,4-ij]quinoline-6-carboxamido)acetic acid as a solid. $^1$H NMR (DMSO-d$_6$, 400 MHz): δ 10.41 (brs, 1H), 7.84 (d, J=8.0 Hz, 2H), 7.79 (d, J=8.2 Hz, 1H), 7.76 (d, J=8.0 Hz, 2H), 7.52 (d, J=8.2 Hz, 1H), 5.59 (d, J=8.4 Hz, 1H), 4.79 (d, J=13.0 Hz, 1H), 4.14 (d, J=5.5 Hz, 2H), 3.87 (dd, J=13.2, 9.7 Hz, 1H). LC/MS (m/z): 474 (M+H)$^+$. Human HIF-PHD2 IC$_{50}$: 1.0 nM.

Example 14

2-(9-Cyano-7-hydroxy-5-oxo-2-(4-(trifluoromethyl)phenyl)-3,5-dihydro-2H-[1,4]oxazino[2,3,4-ij]quinoline-6-carboxamido)acetic acid (peak 1)

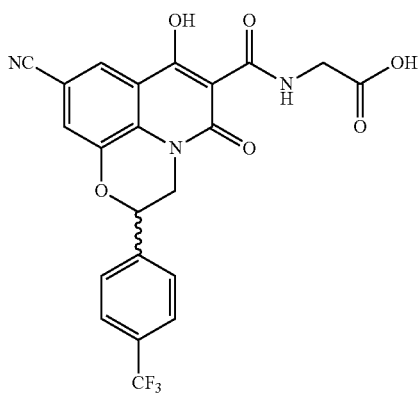 [SMILES: N#Cc1cc2c3c(c1)c(O)c(C(=O)NCC(=O)O)c(=O)n3CC(c1ccc(C(F)(F)F)cc1)O2]

Example 15

2-(9-Cyano-7-hydroxy-5-oxo-2-(4-(trifluoromethyl)phenyl)-3,5-dihydro-2H-[1,4]oxazino[2,3,4-ij]quinoline-6-carboxamido)acetic acid (peak 2)

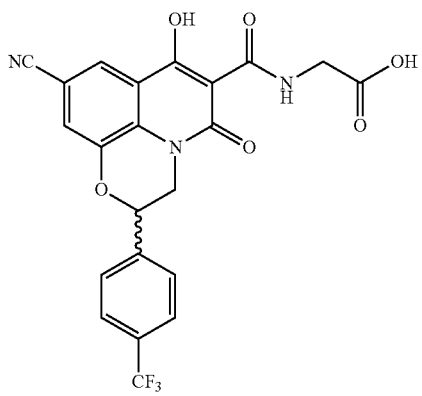 [SMILES: N#Cc1cc2c3c(c1)c(O)c(C(=O)NCC(=O)O)c(=O)n3CC(c1ccc(C(F)(F)F)cc1)O2]

Step A: 7-bromo-2-(4-(trifluoromethyl)phenyl)-2H-benzo[b][1,4]oxazin-3(4H)-one

To a solution of 2-amino-5-bromophenol (2.5 g, 13.34 mmol) in DMF (50 mL) was added K$_2$CO$_3$ (4.61 g, 33.4 mmol). The reaction mixture was cooled by ice-water bath, and 2-bromo-2-(4-(trifluoromethyl)phenyl)acetyl chloride (5.0 g, 16.7 mmol) was added dropwise. The reaction was stirred at room temperature for 20 h. TLC (petroleum ether: EtOAc=5:1) showed that the reaction was complete. The resulting mixture was quenched and diluted by H$_2$O (40 mL), extracted with DCM (30 mL*3). The combined organic layers were washed by brine (100 mL*3), dried over Na$_2$SO$_4$, filtered and concentrated in vacuo and the residue was purified by column chromatography (EtOAc in petroleum ether: 0-20%) to give 7-bromo-2-(4-(trifluoromethyl)phenyl)-2H-benzo[b][1,4]oxazin-3(4H)-one as a solid. $^1$H NMR (CDCl$_3$, 400 MHz): δ 8.62 (s, 1H), 7.58 (d, J=8.0 Hz, 2H), 7.64 (d, J=8.0 Hz, 2H), 7.25 (d, J=7.2 Hz, 1H), 7.11(dd, J=2.0, 8.4 Hz, 1H), 6.69(d, J=8.4Hz, 1H), 5.75 (s, 1H).

Step B: 7-bromo-2-(4-(trifluoromethyl)phenyl)-3,4-dihydro-2H-benzo[b][1,4]oxazine To the cooled solution of 7-bromo-2-(4-(trifluoromethyl)phenyl)-2H-benzo[b][1,4]oxazin-3(4H)-one (2.0 g, 5.6 mmol) in THF (30 mL) was slowly added BH$_3$-Me$_2$S (4.37g, 56.0 mmol), then the reaction mixture was stirred at room temperature overnight. MeOH was added slowly to quench the reaction, and the solvent was evaporated to give the crude product, which was directly used in the next step. $^1$H NMR (CDCl$_3$, 400 MHz): 7.67 (d, J=8.0 Hz, 2 H), 7.53 (d, J=8.0 Hz, 2 H), 7.07 (d, J=1.6 Hz, 1 H), 6.93 (dd, J=8.0, 2.0 Hz, 1 H), 6.55 (d, J=8.0 Hz, 1 H), 5.15 (d, J=8.8 Hz, 1 H), 3.56 (dd, J=12.0, 2.4 Hz, 1 H), 3.32 (dd, J=12.0, 8.0 Hz, 1 H).

Step C: ethyl 9-bromo-7-hydroxy-5-oxo-2-(4-(trifluoromethyl)phenyl)-3,5-dihydro-2H-[1,4]oxazino[2,3,4-ij]quinoline-6-carboxylate To a thumb flask was charged with 7-bromo-2-(4-(trifluoromethyl)phenyl)-3,4-dihydro-2H-benzo[b][1,4]oxazine (2.0 g, 5.6 mmol) and triethyl methanetricarboxylate(5.2 g, 22.4 mmol). The reaction mixture was heated to 250° C. for 1.5 hours. After cooling to rt, the mixture was purified by silica gel column chromatography (EtOAc: petroleum ether=0-20%) to give ethyl 9-bromo-7-hydroxy-5-oxo-2-(4-(trifluoromethyl)phenyl)-3,5-dihydro-2H-[1,4]oxazino[2,3,4-ij]quinoline-6-carboxylate as a solid. $^1$H NMR (CDCl$_3$, 400 MHz): 14.30 (s, 1 H), 7.93 (s, 1 H), 7.72 (d, J=8.0 Hz, 2 H), 7.59 (d, J=8.0 Hz, 2 H), 7.45 (s, 1 H), 5.19 (d, J=9.03 Hz, 1 H), 4.92 (dd, J=14.31, 2.26 Hz, 1 H), 4.40-4.58 (m, 2 H), 3.67 (dd, J=14.0, 9.2 Hz, 1 H), 1.48 (t, J=6.8 Hz, 3 H).

Step D: 2-(9-bromo-7-hydroxy-5-oxo-2-(4-(trifluoromethyl)phenyl)-3,5-dihydro-2H-[1,4]oxazino[2,3,4-ij]quinoline-6-carboxamido)acetate To a mixture of ethyl 9-bromo-7-hydroxy-5-oxo-2-(4-(trifluoromethyl)phenyl)-3,5-dihydro-2H-[1,4]oxazino[2,3,4-ij]quinoline-6-carboxylate(2.2 g, 4.43 mmol), tert-butyl 2-aminoacetate(1.1 g, 4.74 mmol) in toluene (40 mL), DIPEA (2.2 g, 17.05 mmol) was added. The reaction mixture was then heated to 120° C. for 2 h. Then the solvent was evaporated and the residue was purified by silica gel column chromatography (EtOAc in petroleum ether: 0-20%) to give tert-butyl 2-(9-bromo-7-hydroxy-5-oxo-2-(4-(trifluoromethyl)phenyl)-3,5-dihydro-2H-[1,4]oxazino[2,3,4-ij]quinoline-6-carboxamido)acetate as a solid. $^1$H NMR (CDCl$_3$, 400 MHz) δ: 7.96 (d, J=2.0 Hz, 1 H), 7.74 (d, J=8.0 Hz, 2 H), 7.61 (d, J=8.0 Hz, 2 H), 7.46 (d, J=2.0 Hz, 1H), 5.22 (d, J=7.2 Hz, 1 H), 4.96 (dd, J=14.4, 2.8 Hz, 1 H), 4.09-4.19 (m, 2 H), 3.70 (dd, J=14.0, 9.60 Hz, 1 H), 1.51 (s, 9 H).

Step E: tert-butyl 2-(9-cyano-7-hydroxy-5-oxo-2-(4-(trifluoromethyl)phenyl)-3,5-dihydro-2H-[1,4]oxazino[2,3,4-ij]quinoline-6-carboxamido)acetate A mixture of tert-butyl 2-(9-bromo-7-hydroxy-5-oxo-2-(4-(trifluoromethyl)phenyl)-3,5-dihydro-2H-[1,4]oxazino[2,3,4-ij]quinoline-6-carboxamido)acetate (200 mg, 0.344 mmol), Zn(CN)$_2$ (80.78 mg, 0.688 mmol), Zn dust (44.98 mg, 0.688 mmol), Pd$_2$(dba)$_3$ (31.5 mg, 0.0344 mmol), dppf (19.1 mg, 0.0344 mmol) in DMA (2 mL) was heated to 130° C. by microwave for 30 mins. TLC (petroleum ether: EtOAc=5:1) showed that the starting material was consumed.

Then the mixture was diluted with EtOAc (30 mL), washed with brine. The organic layer was evaporated to give the crude product, which was further purified by silica gel column chromatography (ethyl acetate in petroleum ether: 0-20%) to give tert-butyl 2-(9-cyano-7-hydroxy-5-oxo-2-(4-(trifluoromethyl)phenyl)-3,5-dihydro-2H-[1,4]oxazino[2,3,4-ij]quinoline-6-carboxamido)acetate as a solid. $^1$H NMR (CDCl$_3$, 400 MHz): δ 10.4 (s, 1 H), 8.4 (s, 1 H), 7.9 (d, J=8.8 Hz, 2 H), 7.61 (d, J=8.0 Hz, 2 H), 7.51 (s, 1 H), 5.23 (d, J=9.6 Hz, 1H), 4.98 (dd, J=14.0, 2.4 Hz, 1 H), 4.04-4.23 (m, 2 H), 3.73 (dd, J=14.4, 10.0 Hz, 1 H), 1.51 (s, 9 H).

Step F: 2-(9-cyano-7-hydroxy-5-oxo-2-(4-(trifluoromethyl)phenyl)-3,5-dihydro-2H-[1,4]oxazino[2,3,4-ij]quinoline-6-carboxamido)acetic acid (peak 1) and 2-(9-cyano-7-hydroxy-5-oxo-2-(4-(trifluoromethyl)phenyl)-3,5-dihydro-2H-[1,4]oxazino[2,3,4-ij]quinoline-6-carboxamido)acetic acid (peak 2)

To a solution of tert-butyl 2-(9-cyano-7-hydroxy-5-oxo-2-(4-(trifluoromethyl)phenyl)-3,5-dihydro-2H-[1,4]oxazino[2,3,4-ij]quinoline-6-carboxamido) acetate (80 mg, 0.152 mmol) in DCM (2 mL) was added TFA (345.45 mg, 3.03 mmol). The resulting mixture was heated to 50° C. and stirred for 6 hours. LCMS showed that the reaction was complete. The resulting mixture was concentrated in vacuo to give the crude product, which was re-crystallized from EtOAc (5 mL) to afford 2-(9-cyano-7-hydroxy-5-oxo-2-(4-(trifluoromethyl)phenyl)-3,5-dihydro-2H-[1,4]oxazino[2,3,4-ij]quinoline-6-carboxamido) acetic acid as a solid. The racemate was resolved by SFC (Instrument: Thar SFC 80; Column: OJ 250 mm*30mm, 20 um; Mobile phase: A: Supercritical CO$_2$ , B: EtOH (0.1% NH$_3$.H$_2$O), A:B=60:40 at 80 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford:

Example 14 (peak 1, RT: 4.223 min, Chiralcel OJ-H 250×4.6 mm I.D., 5 um Mobile phase: methanol (0.05% DEA) in CO$_2$ from 5% to 40% Flow rate: 2.35mL/min Wavelength: 220 nm) as a solid $^1$H NMR (DMSO-d$_6$, 400 MHz) δ: 10.25 (d, J=5.2 Hz, 1H), 8.10 (d, J=1.6 Hz, 1H), 7.88 (d, J=1.6 Hz, 1H), 7.85 (d, J=8.0 Hz, 2H), 7.77 (d, J=8.4 Hz, 2H), δ 5.54 (d, J=7.2 Hz, 1H), 4.75 (dd, J=2.8 Hz, 13.6 Hz, 1H),4.13 (d, J=5.6 Hz, 2H), 3.88 (dd, J=9.2 Hz, 13.6 Hz, 1H). LC/MS (m/z): 474 (M+H)$^+$. Human HIF-PHD2 IC$_{50}$: 0.9 nM.

Example 15 (peak 2, RT: 4.682 min) as a solid (Human HIF-PHD2 IC$_{50}$: 1.3 nM).

Example 16

2-(9-Bromo-7-hydroxy-5-oxo-2-(4-(trifluoromethyl)phenyl)-3,5-dihydro-2H-[1,4]oxazino[2,3,4-ij]quinoline-6-carboxamido)acetic acid

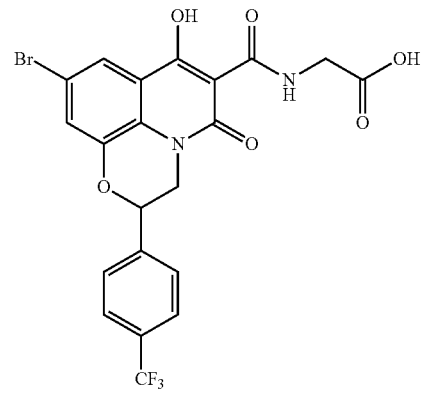

Step A: 2-(9-bromo-7-hydroxy-5-oxo-2-(4-(trifluoromethyl)phenyl)-3,5-dihydro-2H-[1,4]oxazino[2,3,4-ij]quinoline-6-carboxamido)acetic acid To a solution of Step D product of Example 14/15 (50 mg, 0.086 mmol) in DCM (2 mL) was added TFA (195.8 mg, 1.72 mmol). The resulting mixture was heated to 50° C. for 6 hours. LCMS showed that the reaction was complete. The resulting mixture was concentrated in vacuo to give the crude product, which was re-crystallized from EtOAc (5 mL) to afford 2-(9-bromo-7-hydroxy-5-oxo-2-(4-(trifluoromethyl)phenyl)-3,5-dihydro-2H-[1,4]oxazino[2,3,4-ij]quinoline-6-carboxamido) acetic acid as a solid. $^1$H NMR (DMSO-d$_6$, 400 MHz) δ 10.34 (d, J=5.6 Hz, 1H), 7.84 (d, J=8.4 Hz, 2H), 7.76 (s, 1H), 7.75 (d, J=7.6 Hz, 2H), 7.66 (s, 1H), 5.54 (d, J=8.4 Hz, 1H), 4.72 (d, J=11.2 Hz, 1H), 4.12 (d, J=5.6 Hz, 2H), 3.88(dd, J=9.2 Hz, 14.0 Hz, 1H). LC/MS (m/z): 527 (M+H)$^+$. Human HIF-PHD2 IC$_{50}$: 4.4 nM.

Example 17

2-(7-Hydroxy-9-(methylsulfonyl)-5-oxo-2-(4-(trifluoromethyl)phenyl)-3,5-dihydro-2H-[1,4]oxazino[2,3,4-ij]quinoline-6-carboxamido)acetic acid (peak 1)

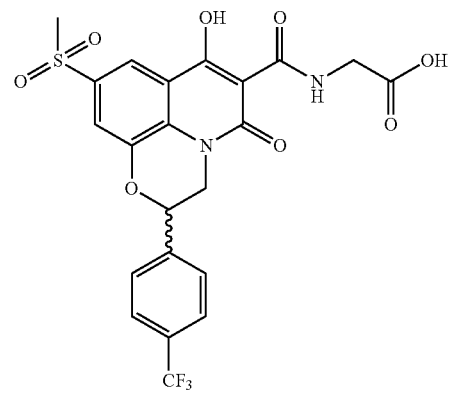 [SMILES: CS(=O)(=O)c1cc2c3c(c1)c(O)c(C(=O)NCC(=O)O)c(=O)n3CC(c1ccc(C(F)(F)F)cc1)O2]

Example 18

2-(7-Hydroxy-9-(methylsulfonyl)-5-oxo-2-(4-(trifluoromethyl)phenyl)-3,5-dihydro-2H-[1,4]oxazino[2,3,4-ij]quinoline-6-carboxamido)acetic acid (peak 2)

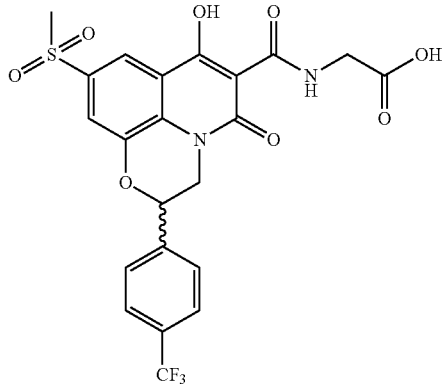 [SMILES: CS(=O)(=O)c1cc2c3c(c1)c(O)c(C(=O)NCC(=O)O)c(=O)n3CC(c1ccc(C(F)(F)F)cc1)O2]

Step A: tert-butyl 2-(7-hydroxy-9-(methylsulfonyl)-5-oxo-2-(4-(trifluoromethyl)phenyl)-3,5-dihydro-2H-[1,4]oxazino[2,3,4-ij]quinoline-6-carboxamido)acetate To a solution of Step D product of Example 14/15 (100 mg, 0.172 mmol) in DMSO (1 mL) were added L-proline (4.0 mg, 0.035 mmol), MeSO$_2$Na (21.11 mg, 0.207 mmol), NaOH(1.38 mg, 0.034 mmol), CuI (3.27 mg, 0.017 mmol), then the reaction mixture was heated at 120° C. for 2 days. Upon cooling, the solvent was evaporated to give the crude product, which was further purified by pre-HPLC (Instrument: DB, Column: ASB C18 150*25 mm Mobile phase A: water (0.025% HCl, V/V), Mobile phase B: acetonitrile 90%) to give tert-butyl 2-(7-hydroxy-9-(methylsulfonyl)-5-oxo-2-(4-(trifluoromethyl)phenyl)-3,5-dihydro-2H-[1,4]oxazino[2,3,4-ij]quinoline-6-carboxamido)acetate as a solid.

Step B: 2-(7-hydroxy-9-(methylsulfonyl)-5-oxo-2-(4-(trifluoromethyl)phenyl)-3,5-dihydro-2H-[1,4]oxazino[2,3,4-ij]quinoline-6-carboxamido)acetic acid (peak 1) and 2-(7-hydroxy-9-(methylsulfonyl)-5-oxo-2-(4-(trifluoromethyl)phenyl)-3,5-dihydro-2H-[1,4]oxazino[2,3,4-ij]quinoline-6-carboxamido)acetic acid (peak 2)

To a solution of tert-butyl 2-(7-hydroxy-9-(methylsulfonyl)-5-oxo-2-(4-(trifluoromethyl)phenyl)-3,5-dihydro-2H-[1,4]oxazino[2,3,4-ij]quinoline-6-carboxamido)acetate (20 mg, 0.0344 mmol) in DCM (2 mL) was added TFA (78.32 mg, 0.69 mmol). The resulting mixture was heated at 50° C. for 6 hours. LCMS showed that the reaction was complete. The resulting mixture was concentrated in vacuo to give crude product which was re-crystallized from EtOAc (5 mL) to afford 2-(7-hydroxy-9-(methylsulfonyl)-5-oxo-2-(4-(trifluoromethyl)phenyl)-3,5-dihydro-2H-[1,4]oxazino[2,3,4-ij]quinoline-6-carboxamido)acetic acid as a white solid. This racemic material was resolved by SFC (Instrument: Thar MG; Column: Chiralpak AS-H 150*4.6 mm I.D., 5 um Mobile phase: ethanol (0.05% DEA) in CO$_2$ from 5% to 40%, Flow rate: 3 mL/min; Wavelength: 254 nm;) to afford:

Example 17 (peak 1, RT: 5.171 min, Chiralcel OJ-H 250×4.6 mm I.D., 5 um Mobile phase: methanol (0.05% DEA) in CO2 from 5% to 40% Flow rate: 2.35mL/min Wavelength: 220 nm) as a solid. $^1$H NMR (DMSO-d$_6$, 400 MHz) δ 8.17 (s, 1H), 7.87 (d, J=8.0 Hz, 2H), 7.87 (d, J=8.0 Hz, 1H), 7.80 (d, J=8.0 Hz, 2H), 5.58 (d, J=9.2 Hz, 1H), 4.81 (d, J=12.4 Hz, 1H), 4.15 (s, 2H), 3.89 (q, J=9.6, 13.2Hz, 1H), 2.31(s, 3H). LC/MS (m/z): 527 (M+H)$^+$. Human HIF-PHD2 IC$_{50}$: 0.9 nM.

Example 18 (peak 2, RT: 6.371 min) as a solid (Human HIF-PHD2 IC$_{50}$: 1.3 nM).

Example 19

2-(7-Hydroxy-9-methyl-5-oxo-2-(4-(trifluoromethyl)phenyl)-3,5-dihydro-2H-[1,4]oxazino[2,3,4-ij]quinoline-6-carboxamido)acetic acid

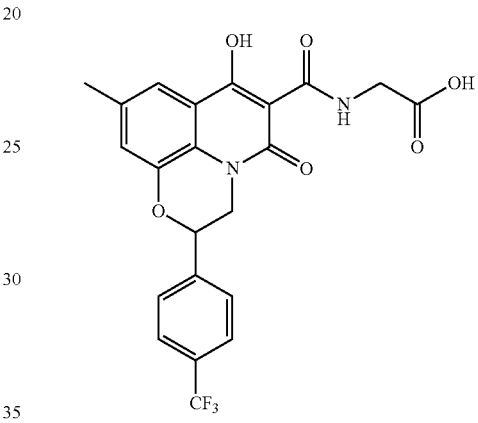

Step A: tert-butyl 2-(7-hydroxy-9-methyl-5-oxo-2-(4-(trifluoromethyl)phenyl)-3,5-dihydro-2H-[1,4]oxazino[2,3,4-ij]quinoline-6-carboxamido)acetate To a solution of Step D product of Example 14/15 (200 mg, 0.344 mmol) in DMF (2 mL) were added 2,4,6-trimethyl-1,3,5,2,4,6-trioxatriborinane(51.7 mg, 0.0412 mmol), Pd(PPh$_3$)$_4$ (39.8 mg, 0.0344 mmol), K$_2$CO$_3$ (142.42 mg, 1.032 mmol), then the reaction mixture was heated to 120° C. for 1 hr. LCMS showed that the reaction was complete. The resulting mixture was concentrated in vacuo to give crude product, which was further purified by silica gel column chromatography (ethyl acetate in petroleum ether: 0-20%) to give tert-butyl 2-(7-hydroxy-9-methyl-5-oxo-2-(4-(trifluoromethyl)phenyl)-3,5-dihydro-2H-[1,4]oxazino[2,3,4-ij]quinoline-6-carboxamido)acetate as a solid. $^1$H NMR (CDCl$_3$, 400 MHz) δ: 7.73 (d, J=8.4 Hz, 2H), 7.63 (s, 1H), 7.62 (d, J=8.4 Hz, 2H), 7.17 (d, J=1.6 Hz, 1H), 5.19 (d, J=7.2 Hz, 1H). 4.96 (dd, J=2.4, 14.0 Hz, 1H), 4.09-4.20 (m, 2H), 3.68 (q, J=10.0, 14.4 Hz, 1H), 2.39 (s, 3H), 1.50 (s, 9 H).

Step B: 2-(7-hydroxy-9-methyl-5-oxo-2-(4-(trifluoromethyl)phenyl)-3,5-dihydro-2H-[1,4]oxazino[2,3,4-ij]quinoline-6-carboxamido)acetic acid To a solution of tert-butyl 2-(7-hydroxy-9-methyl-5-oxo-2-(4-(trifluoromethyl)phenyl)-3,5-dihydro-2H-[1,4]oxazino[2,3,4-ij]quinoline-6-carboxamido)acetate (80 mg, 0.154 mmol) in DCM (2 mL) was added TFA (352.12 mg, 3.1 mmol). The resulting mixture was heated to 50° C. for 6 hours. LCMS showed that the reaction was complete. The resulting mixture was concentrated in vacuo to give crude product, which was re-crystallized with EtOAc (5 mL) to afford 2-(7-hydroxy-9-methyl-5-oxo-2-(4-(trifluoromethyl)phenyl)-3,5-dihydro-2H-[1,4]oxazino[2,3,4-ij]quinoline-6-carboxamido)acetic acid as a solid. $^1$H NMR (DMSO-$d_6$, 400 MHz): δ 10.47 (s, 1H), 7.78 (d, J=8.0 Hz, 2H), 7.85 (d, J=7.2 Hz, 2H), 7.52 (s, 1H), 7.31 (s, 1H), 5.51 (d, J=8.0 Hz, 1H). 4.73 (d, J=12.4 Hz, 1H), 4.14 (d, J=5.6 Hz, 2H), 3.89 (dd, J=9.6, 13.2Hz, 1H), 2.39 (s, 3H). LC/MS (m/z): 463 (M+H)[+]. Human HIF-PHD2 $IC_{50}$: 5.6 nM.

Example 20

2-(10-Cyano-7-hydroxy-5-oxo-2-(4-(trifluoromethyl)phenyl)-3,5-dihydro-2H-[1,4]oxazino[2,3,4-ij]quinoline-6-carboxamido)acetic acid (peak 1)

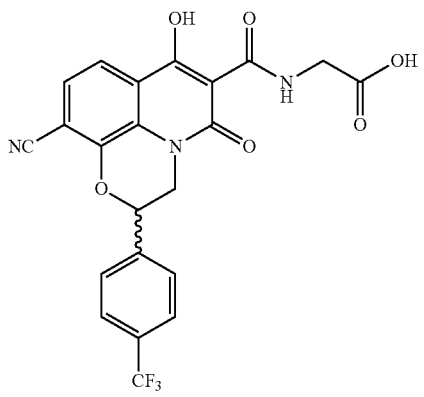 [SMILES: N#Cc1ccc2c(O)c(C(=O)NCC(=O)O)c(=O)n3c2c1OC(c1ccc(C(F)(F)F)cc1)C3]

Example 21

2-(10-Cyano-7-hydroxy-5-oxo-2-(4-(trifluoromethyl)phenyl)-3,5-dihydro-2H-[1,4]oxazino[2,3,4-ij]quinoline-6-carboxamido)acetic acid (peak 2)

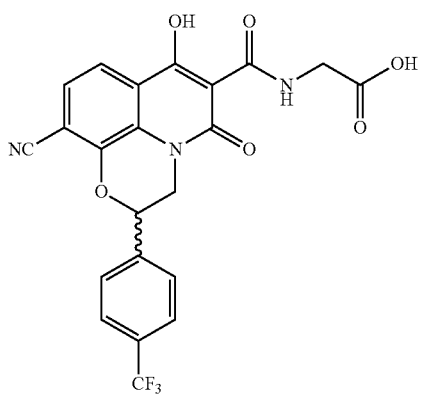 [SMILES: N#Cc1ccc2c(O)c(C(=O)NCC(=O)O)c(=O)n3c2c1OC(c1ccc(C(F)(F)F)cc1)C3]

Step A: 8-bromo-2-(4-(trifluoromethyl)phenyl)-2H-benzo[b][1,4]oxazin-3(4H)-one

To a solution of 2-amino-6-bromophenol (2.5 g, 13.34 mmol) in DMF (50 mL) was added $K_2CO_3$ (4.61 g, 33.4 mmol). The reaction mixture was cooled by ice-water bath, and 2-bromo-2-(4-(trifluoromethyl)phenyl)acetyl chloride (5.0 g, 16.7 mmol) was added dropwise. The reaction mixture was stirred at room temperature for 20 h. TLC (petroleum ether: EtOAc=5:1) showed that the reaction was complete. The resulting mixture was diluted with $H_2O$ (40 mL) and extracted with DCM (30 mL*3). The combined organic layers were washed with brine (100 mL*3), dried over $Na_2SO_4$, filtered and concentrated in vacuo to give the crude product, which was further purified by silica gel column chromatography (EtOAc in petroleum ether: 0-20%) to give 8-bromo-2-(4-(trifluoromethyl)phenyl)-2H-benzo[b][1,4]oxazin-3(4H)-one as a solid.$^1$H NMR (CDCl$_3$, 400 MHz): δ 8.31 (s, 1H), 7.62-7.67 (m, 4H), 7.24 (d, J=0.4 Hz, 1H), 6.86 (t, J=8.0Hz, 1H), 6.73(d, J=7.2Hz, 1H), 5.91 (s, 1H).

Step B: 8-bromo-2-(4-(trifluoromethyl)phenyl)-3,4-dihydro-2H-benzo[b][1,4]oxazine To a solution of 8-bromo-2-(4-(trifluoromethyl)phenyl)-2H-benzo[b][1,4]oxazin-3(4H)-one (2.0 g, 5.6 mmol) in THF (30 mL) was slowly added $BH_3\text{-}Me_2S$ (4.37g, 56.0 mmol) with ice-bath cooling, then the reaction mixture was stirred at room temperature overnight. LCMS showed that the reaction was complete. MeOH was added to quench the reaction. The solvent was evaporated to give the crude product, which was directly used in the next step.$^1$H NMR (CDCl$_3$, 400 MHz): δ 7.65-7.68 (m, 2 H), 7.58 (d, J=8.4 Hz, 2 H), 6.95 (d, J=6.8 Hz, 1 H), 6.65-6.71 (m, 1 H), 6.59 (dd, J=8.0, 1.6 Hz, 1 H), 5.26 (dd, J=7.6, 2.0 Hz, 1 H), 3.61 (dd, J=12.0, 2.4 Hz, 1 H), 3.34 (dd, J=12.0, 8.4 Hz, 1 H).

Step C: ethyl 10-bromo-7-hydroxy-5-oxo-2-(4-(trifluoromethyl)phenyl)-3,5-dihydro-2H-[1,4]oxazino[2,3,4-ij]quinoline-6-carboxylate A thumb flask was charged with 8-bromo-2-(4-(trifluoromethyl)phenyl)-3,4-dihydro-2H-benzo[b][1,4]oxazine (2.0 g, 5.6 mmol) and triethyl methanetricarboxylate(5.2 g, 22.4 mmol), and the reaction mixture was heated to 250° C. for 1.5 hours. LCMS showed that the reaction was complete. After cooled to rt, the mixture was purified by silica gel column chromatography (EtOAc in petroleum ether: 0-20%) to give ethyl 10-bromo-7-hydroxy-5-oxo-2-(4-(trifluoromethyl)phenyl)-3,5-dihydro-2H-[1,4]oxazino[2,3,4-ij]quinoline-6-carboxylate as a solid. $^1$H NMR (CDCl$_3$, 400 MHz): 14.31 (s, 1 H), 7.62-7.74 (m, 5 H), 7.42 (d, J=8.4 Hz, 1 H), 5.31 (d, J=7.2 Hz, 1 H), 4.91-4.97 (m, 1 H), 4.48-4.54 (m, 2 H), 3.78-3.84 (m, 1 H), 1.47 (t, J=7.2 Hz, 3 H).

Step D: tert-butyl 2-(10-bromo-7-hydroxy-5-oxo-2-(4-(trifluoromethyl)phenyl)-3,5-dihydro-2H-[1,4]oxazino[2,3,4-ij]quinoline-6-carboxamido)acetate A mixture of ethyl 10-bromo-7-hydroxy-5-oxo-2-(4-(trifluoromethyl)phenyl)-3,5-dihydro-2H-[1,4]oxazino[2,3,4-ij]quinoline-6-carboxylate(2.2 g, 4.43 mmol), tert-butyl 2-aminoacetate(1.1 g, 4.74 mmol) in toluene (40 mL) with DIPEA (2.2 g, 17.05 mmol) was heated to 120° C. for 2 h. TLC (petroleum ether: EtOAc=2:1) showed that the starting material was consumed. Then the solvent was evaporated to give the crude product, which was further purified by silica gel column chromatography (EtOAc in petroleum ether: 0-20%) to give tert-butyl 2-(10-bromo-7-hydroxy-5-oxo-2-(4-(trifluoromethyl)phenyl)-3,5-dihydro-2H-[1,4]oxazino[2,3,4-ij]quinoline-6-carboxamido)acetate as a solid. $^1$H NMR (CDCl$_3$, 400 MHz): δ 10.49 (s, 1 H), 7.64-7.74 (m, 5 H), 7.45 (d, J=8.40 Hz, 1 H), 5.30-5.33 (m, 1 H), 4.97 (dd, J=14.4, 2.8 Hz, 1 H), 4.07-4.19 (m, 2 H), 3.82 (dd, J=14.0, 4.8 Hz, 1 H), 1.50 (s, 9 H).

Step E: tert-butyl 2-(10-cyano-7-hydroxy-5-oxo-2-(4-(trifluoromethyl)phenyl)-3,5-dihydro-2H-[1,4]oxazino[2,3,4-ij]quinoline-6-carboxamido)acetate A mixture of tert-butyl 2-(10-bromo-7-hydroxy-5-oxo-2-(4-(trifluoromethyl)phenyl)-3,5-dihydro-2H-[1,4]oxazino[2,3,4-ij]quinoline-6-carboxamido)acetate (200 mg, 0.344 mmol), Zn(CN)$_2$ (80.78 mg, 0.688 mmol), Zn dust (44.98 mg, 0.688 mmol), Pd$_2$(dba)$_3$ (31.5 mg, 0.0344 mmol), dppf (19.1 mg, 0.0344 mmol) in DMA (2mL) was heated to 130° C. by microwave for 30 mins. TLC (petroleum ether: EtOAc=5:1) showed that the starting material was consumed; EtOAc was added to dilute the reaction mixture. The mixture was washed by brine, and the organic layer was evaporated to give the crude product, which was further purified by silica gel column chromatography (ethyl acetate in petroleum ether: 0-20%) to give tert-butyl 2-(10-cyano-7-hydroxy-5-oxo-2-(4-(trifluoromethyl)phenyl)-3,5-dihydro-2H-[1,4]oxazino[2,3,4-ij]quinoline-6-carboxamido) acetate as a solid. $^1$H NMR (CDCl$_3$, 400 MHz): δ 10.45 (s, 1 H), 7.86 (d, J=8.4 Hz, 1 H), 7.75 (d, J=8.0 Hz, 2 H), 7.65 (d, J=8.8 Hz, 2 H), 7.45 (d, J=8.0Hz, 1 H), 5.39 (d, J=6.8 Hz, 1 H), 5.01 (dd, J=14.8, 2.8 Hz, 1 H), 4.08-4.21 (m, 2 H), 3.83 (dd, J=14.0, 9.2 Hz, 1 H), 1.51(s, 9H).

Step F: 2-(10-cyano-7-hydroxy-5-oxo-2-(4-(trifluoromethyl)phenyl)-3,5-dihydro-2H-[1,4]oxazino[2,3,4-ij]quinoline-6-carboxamido)acetic acid (peak 1) and 2-(10-cyano-7-hydroxy-5-oxo-2-(4-(trifluoromethyl)phenyl)-3,5-dihydro-2H-[1,4]oxazino[2,3,4-ij]quinoline-6-carboxamido)acetic acid (peak 2)

To a solution of tert-butyl 2-(10-cyano-7-hydroxy-5-oxo-2-(4-(trifluoromethyl)phenyl)-3,5-dihydro-2H-[1,4]oxazino[2,3,4-ij]quinoline -6-carboxamido) acetate (80 mg, 0.152 mmol) in DCM (2 mL) was added TFA (345.45 mg, 3.03 mmol). The resulting mixture was heated to 50° C. for 6 hours. LCMS showed that the reaction was complete. The resulting mixture was concentrated in vacuo to give crude product, which was re-crystallized from EtOAc (5 mL) to afford 2-(10-cyano-7-hydroxy-5-oxo-2-(4-(trifluoromethyl)phenyl)-3,5-dihydro-2H-[1,4]oxazino [2,3,4-ij]quinoline-6-carboxamido) acetic acid as a solid. This racemic material was resolved by SFC (Instrument: Thar SFC 80; Column: OJ 250 mm*30mm, 20 um; Mobile phase: A: Supercritical CO$_2$, B: EtOH (0.1% NH$_3$.H$_2$O), A:B=60:40 at 80 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford:

Example 20 (peak 1, RT: 4.544 min, Chiralcel OJ-H 250×4.6 mm I.D., 5 um Mobile phase: methanol (0.05% DEA) in CO$_2$ from 5% to 40% Flow rate: 2.35mL/min Wavelength: 220 nm), a solid. $^1$H NMR (DMSO-d$_6$, 400 MHz) δ 10.32 (d, J=5.6 Hz, 1H), 7.88 (d, J=8.4 Hz, 2H), 7.75-7.81 (m, 3H), 7.64-7.67 (d, J=8.4 Hz, 1H), δ 5.72 (d, J=6.8 Hz, 1H), 4.82 (d, J=11.2 Hz, 1H), 4.13 (d, J=5.2 Hz, 2H), 3.89 (dd, J=9.6, 13.2Hz, 1H). LC/MS (m/z): 474 (M+H)$^+$. Human HIF-PHD2 IC$_{50}$: 0.5 nM.

Example 21 (peak 2, RT: 5.049 min), a solid. Human HIF-PHD2 IC$_{50}$: 0.6 nM.

Example 22

2-(10-Bromo-7-hydroxy-5-oxo-2-(4-(trifluoromethyl)phenyl)-3,5-dihydro-2H-[1,4]oxazino[2,3,4-ij]quinoline-6-carboxamido)acetic acid

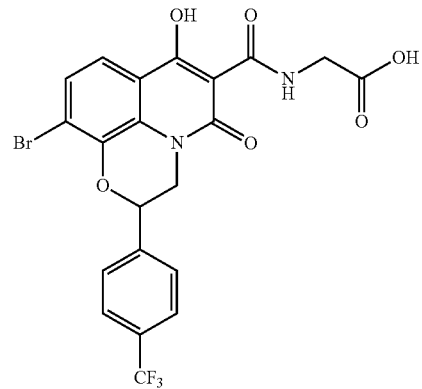

To a solution of Step D product of Example 20/21 (50 mg, 0.086 mmol) in DCM (2 mL) was added TFA (195.8 mg, 1.72 mmol). The resulting mixture was heated to 50° C. for 6 hours. LCMS showed that the reaction was complete. The resulting mixture was concentrated in vacuo to give the crude product which was re-crystallized from EtOAc (5 mL) to afford 2-(10-bromo-7-hydroxy-5-oxo-2-(4-(trifluoromethyl)phenyl)-3,5-dihydro-2H-[1,4]oxazino[2,3,4-ij]quinoline-6-carboxamido) acetic acid as a solid. $^1$H NMR (DMSO-d$_6$, 400 MHz,) δ 10.34 (t, J=5.6 Hz, 1H), 7.86 (d, J=8.4 Hz, 2H), 7.77 (d, J=8.0 Hz, 2H), 7.55-7.63 (m, 2H), 5.63 (d, J=6.8 Hz, 1H), 4.75-4.80 (m, 1H), 4.12 (d, J=6.0 Hz, 2H), 3.98 (dd, J=9.2, 13.6Hz, 1H). LC/MS (m/z): 527 (M+H)$^+$. Human HIF-PHD2 IC$_{50}$: 2.3 nM.

Example 23

2-(7-Hydroxy-10-(methylsulfonyl)-5-oxo-2-(4-(trifluoromethyl)phenyl)-3,5-dihydro-2H-[1,4]oxazino[2,3,4-ij]quinoline-6-carboxamido)acetic acid (peak 1)

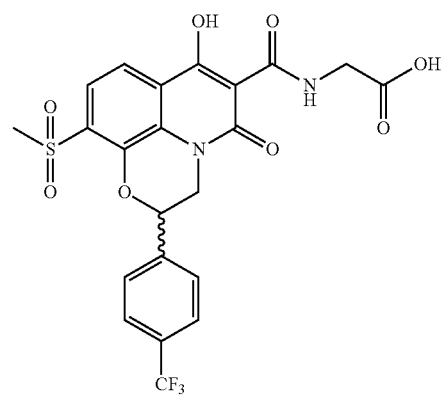 [SMILES: CS(=O)(=O)c1ccc2c(O)c(C(=O)NCC(=O)O)c(=O)n3c2c1OC(c1ccc(C(F)(F)F)cc1)C3]

Example 24

2-(7-Hydroxy-10-(methylsulfonyl)-5-oxo-2-(4-(trifluoromethyl)phenyl)-3,5-dihydro-2H-[1,4]oxazino[2,3,4-ij]quinoline-6-carboxamido)acetic acid (peak 2)

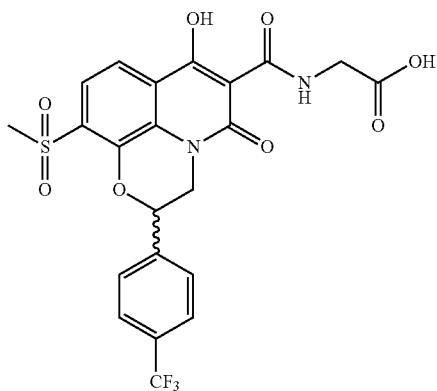 [SMILES: CS(=O)(=O)c1ccc2c(O)c(C(=O)NCC(=O)O)c(=O)n3c2c1OC(c1ccc(C(F)(F)F)cc1)C3]

Step A: tert-butyl 2-(7-hydroxy-10-(methylsulfonyl)-5-oxo-2-(4-(trifluoromethyl)phenyl)-3,5-dihydro-2H-[1,4]oxazino[2,3,4-ij]quinoline-6-carboxamido)acetate To a solution of Step D product of Example 20/21 (100 mg, 0.172 mmol) in DMSO (1 mL) were added L-proline (4.0 mg, 0.035 mmol), MeSO$_2$Na (21.11 mg, 0.207 mmol), NaOH (1.38 mg, 0.034 mmol), CuI (3.27 mg, 0.017 mmol), then the reaction mixture was heated to 120° C. for 2 days. The solvent was evaporated to give the crude product, which was further purified by pre-HPLC (Instrument: DB, Column: ASB C18 150*25 mmMobile phase A: water (0.025% HCl, V/V), Mobile phase B: acetonitrile 90%) to give tert-butyl 2-(7-hydroxy-10-(methylsulfonyl)-5-oxo-2-(4-(trifluoromethyl)phenyl)-3,5-dihydro-2H-[1,4]oxazino[2,3,4-ij]quinoline-6-carboxamido)acetate as a solid.

Step B: 2-(7-hydroxy-10-(methylsulfonyl)-5-oxo-2-(4-(trifluoromethyl)phenyl)-3,5-dihydro-2H-[1,4]oxazino[2,3,4-ij]quinoline-6-carboxamido)acetic acid (peak 1) and 2-(7-hydroxy-10-(methylsulfonyl)-5-oxo-2-(4-(trifluoromethyl)phenyl)-3,5-dihydro-2H-[1,4]oxazino[2,3,4-ij]quinoline-6-carboxamido)acetic acid (peak 2)

To a solution of Step A product (20 mg, 0.0344 mmol) in DCM (2 mL) was added TFA (78.32 mg, 0.69 mmol). The resulting mixture was heated to 50° C. and stirred for 6 hours. LCMS showed that the reaction was complete. The resulting mixture was concentrated in vacuo to give the crude product, which was re-crystallized from EtOAc (5 mL) to afford 2-(7-hydroxy-10-(methylsulfonyl)-5-oxo-2-(4-(trifluoromethyl)phenyl)-3,5-dihydro-2H-[1,4]oxazino[2,3,4-ij]quinoline-6-carboxamido)acetic acid as a solid. This racemic material was resolved by SFC (Instrument: Thar SFC 80; Column: OJ 250 mm*30mm, 20 um; Mobile phase: A: Supercritical CO$_2$ , B: EtOH (0.1% NH$_3$.H$_2$O), A:B=60:40 at 80 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford:

Example 23 (peak 1,RT: 3.02 min, Chiralcel OJ-H 250× 4.6 mm I.D., 5 um Mobile phase: methanol (0.05% DEA) in CO2 from 5% to 40% Flow rate: 2.35mL/min Wavelength: 220 nm) as a solid. $^1$H NMR (DMSO-d$_6$, 400 MHz): δ 10.35 (t, J=5.2 Hz, 1H), 7.81-7.89 (m, 5H), 7.71 (d, J=8.4 Hz, 1H), 5.75 (d, J=7.6 Hz, 1H), 4.87 (d, J=11.2 Hz, 1H), 4.13 (d, J=5.6 Hz, 2H), 3.90 (dd, J=9.6, 4.4 Hz, 1H), 3.31 (s, 3H). LC/MS (m/z): 527 (M+H)$^+$. Human HIF-PHD2 IC$_{50}$: 1.6 nM.

Example 24 (peak 2, RT: 9.94 min) as a solid. Human HIF-PHD2 IC$_{50}$: 1.3 nM.

Example 25

2-(7-Hydroxy-10-methyl-5-oxo-2-(4-(trifluoromethyl)phenyl)-3,5-dihydro-2H-[1,4]oxazino[2,3,4-ij]quinoline-6-carboxamido)acetic acid

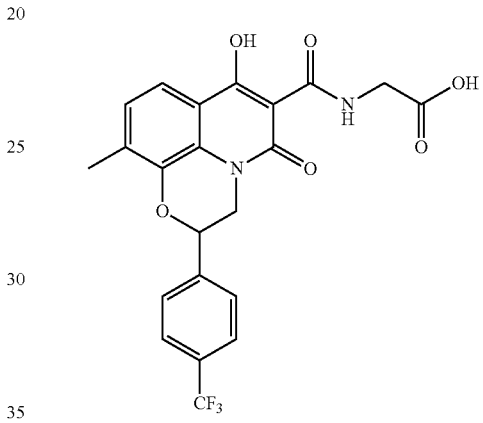

Step A: tert-butyl 2-(7-hydroxy-10-methyl-5-oxo-2-(4-(trifluoromethyl)phenyl)-3,5-dihydro-2H-[1,4]oxazino[2,3,4-ij]quinoline-6-carboxamido)acetate To a solution of Step D product of Example 20/21 (200 mg, 0.344 mmol) in DMF (2 mL) were added 2,4,6-trimethyl-1,3,5,2,4,6-trioxatriborinane (51.7 mg, 0.0412 mmol), Pd(PPh$_3$)$_4$ (39.8 mg, 0.0344 mmol), and K$_2$CO$_3$ (142.42 mg, 1.032 mmol), then the reaction mixture was heated to 120° C. for 1 h. LCMS showed that the reaction was complete. The resulting mixture was concentrated in vacuo to give crude product, which was further purified by column-chromatography (ethyl acetate in petroleum ether: 0-20%) give tert-butyl 2-(7-hydroxy-10-methyl-5-oxo-2-(4-(trifluoromethyl)phenyl)-3,5-dihydro-2H-[1,4]oxazino[2,3,4-ij]quinoline-6-carboxamido)acetate as a solid. $^1$H NMR (CDCl$_3$, 400 MHz): δ 10.58 (s, 1 H), 7.71 (d, J=8.4 Hz, 2 H), 7.71 (d, J=7.6 Hz, 1 H), 7.62 (d, J=8.4 Hz, 2 H), 7.11 (d, J=8.4 Hz, 1 H), 5.19 (d, J=7.6 Hz, 1 H), 4.98 (dd, J=14.4, 2.8 Hz, 1 H), 4.07-4.19 (m, 2 H), 3.66 (dd, J=14.0, 9.60 Hz, 1 H), 2.41(s, 3H), 1.49 (s, 9 H).

Step B: 2-(7-hydroxy-10-methyl-5-oxo-2-(4-(trifluoromethyl)phenyl)-3,5-dihydro-2H-[1,4]oxazino[2,3,4-ij]quinoline-6-carboxamido)acetic acid To a solution of tert-butyl 2-(7-hydroxy-10-methyl-5-oxo-2-(4-(trifluoromethyl)phenyl)-3,5-dihydro-2H-[1,4]oxazino[2,3,4-ij]quinoline-6-carboxamido)acetate (80 mg, 0.154 mmol) in DCM (2 mL) was added TFA (352.12 mg, 3.1 mmol). The resulting mixture was heated to 50° C. and stirred for 6 hours. LCMS showed that the reaction was complete. The resulting mixture was concentrated in vacuo to give the crude product, which was re-crystallized with EtOAc (5 mL) to afford 2-(7-hydroxy-10-methyl-5-oxo-2-(4-(trifluoromethyl)phenyl)-3,5-dihydro-2H-[1,4]oxazino[2,3,4-ij]quinoline-6-carboxamido)acetic acid as a solid. $^1$H NMR (DMSO-$d_6$, 400 MHz) δ 10.43 (t, J=4.8 Hz, 1H), 7.79-7.88 (m, 4H), 7.63 (d, J=8.0 Hz, 1H), 7.24 (d, J=8.4 Hz, 1H), 5.53 (d, J=8.8 Hz, 1H). 4.77 (d, J=11.2 Hz, 1H), 4.14 (d, J=4.8 Hz, 2H), 3.90 (q, J=8.8, 13.6 Hz, 1H), 2.37(s, 3H). LC/MS (m/z): 463 (M+H)$^+$. Human HIF-PHD2 IC$_{50}$: 5.4 nM.

Example 26

2-(8-bromo-7-hydroxy-5-oxo-3-(4-(trifluoromethyl)benzyl)-3,5-dihydro-2H-[1,4]oxazino[2,3,4-ij]quinoline-6-carboxamido)acetic acid

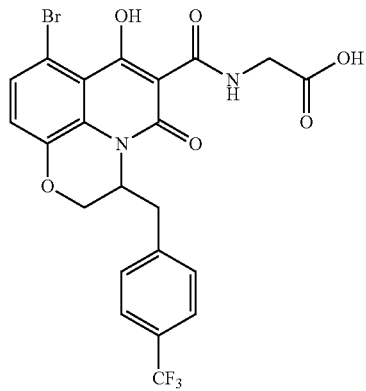 [SMILES: O=C(O)CNC(=O)c1c(O)c2c(Br)ccc3c2n(c1=O)C(Cc1ccc(C(F)(F)F)cc1)CO3]

Step A: 6-bromo-3-(4-(trifluoromethyl)benzyl)-2H-benzo[b][1,4]oxazine

To a solution of 2-amino-4-bromophenol (5 g, 26.6 mmol) in DCM (120 ml) were added aqueous $K_2CO_3$ (120 mL, 26.6 mmol) and tetrabutylammonium hydrogen sulfate (0.090 g, 0.266 mmol). 1-Bromo-3-(4-(trifluoromethyl)phenyl)propan-2-one (7.47 g, 26.6 mmol) in DCM (20 mL) was added dropwise to the reaction mixture. The mixture was stirred at room temperature for 20 h. LCMS showed that the reaction was complete. The resulting mixture was extracted with DCM (50 mL*3). The combined organic layers were washed with brine (50 mL*3), dried over $Na_2SO_4$, filtered and concentrated in vacuo to give 8-bromo-3-(4-(trifluoromethyl)benzyl)-2H-benzo[b][1,4]oxazine as an oil, which was used directly in the next step.

Step B: 6-bromo-3-(4-(trifluoromethy)benzyl)-3,4-dihydro-2H-benzo[b][1,4]oxazine To a solution of 6-bromo-3-(4-(trifluoromethyl)benzyl)-2H-benzo[b][1,4]oxazine (10.3 g, 27.8 mmol) in DCM (40 mL) and MeOH (20 mL) were added AcOH (2 mL, 34.9 mmol) and sodium cyanoborohydride (2.62 g, 41.7 mmol). The resulting mixture was stirred at room temperature for 2 h. The mixture was then diluted with ethyl acetate (200 mL), washed with sodium bicarbonate (5%, 200 mL), water, and brine, dried over sodium sulfate, and filtered. The solvent was removed under reduced pressure. The residue was purified by column chromatography on silica gel Isolute Flash Si; 100 g prepacked (EtOAc in petroleum ether: 0-15%) to give 6-bromo-3-(4-(trifluoromethyl)benzyl)-3,4-dihydro-2H-benzo[b][1,4]oxazine as a solid. $^1$H NMR (CDCl$_3$, 400 MHz): δ 7.63 (d, J=8.0 Hz, 2H), 7.35 (d, J=8.0 Hz, 2H), 6.75 (dd, J=2.0 Hz, 8.4 Hz, 1H), 6.66-6.68 (m, 2H), 4.22 (dd, J=2.8 Hz, 10.4 Hz, 1H), 3.98 (q, J=6.0 Hz, 10.8 Hz, 1H), 3.73 (s, 1H), 3.61-3.67 (m, 1H), 2.93 (dd, J=5.2 Hz, 13.2 Hz, 1H), 2.80 (dd, J=9.2 Hz, 13.6 Hz, 1H).

Step C: ethyl 8-bromo-7-hydroxy-5-oxo-3-(4-(trifluoromethyl)benzyl)-3,5-dihydro-2H-[1,4]oxazino[2,3,4-ij]quinoline-6-carboxylate A mixture of 6-bromo-3-(4-(trifluoromethyl)benzyl)-3,4-dihydro-2H-benzo[b][1,4]oxazine (6.4 g, 17.20 mmol) and triethyl methanetricarboxylate (15.97 g, 68.8 mmol) was heated at 240° C. for 5 h. The resulting mixture was purified by silica gel column chromatography (EtOAc in pretroleum ether: 0-30%) to give ethyl 8-bromo-7-hydroxy-5-oxo-3-(4-(trifluoromethyl)benzyl)-3,5-dihydro-2H-[1,4]oxazino[2,3,4-ij]quinoline-6-carboxylate as a solid. $^1$H NMR (CDCl$_3$, 400 MHz): δ 15.25 (s, 1H), 7.62 (d, J=8.0 Hz, 2H), 7.53 (d, J=8.0 Hz, 2H), 7.48 (d, J=8.4 Hz, 1H), 7.08 (d, J=8.4 Hz, 1H), 5.15 (d, J=10.8 Hz, 1H), 4.53-4.66 (m, 2H), 4.24 (d, J=11.2 Hz, 1H), 3.85 (d, J=11.6 Hz, 1H), 3.15 (dd, J=2.8 Hz, 12.8 Hz, 1H), 2.85 (t, J=12.0 Hz, 1H), 1.52 (t, J=7.2 Hz, 3H).

Step D: tert-butyl 2-(8-bromo-7-hydroxy-5-oxo-3-(4-(trifluoromethyl)benzyl)-3,5-dihydro-2H-[1,4]oxazino[2,3,4-ij]quinoline-6-carboxamido)acetate A solution of ethyl 8-bromo-7-hydroxy-5-oxo-3-(4-(trifluoromethyl)benzyl)-3,5-dihydro-2H-[1,4]oxazino[2,3,4-ij]quinoline-6-carboxylate (2.8 g, 5.47 mmol), tert-butyl 2-aminoacetate HCl salt (1.100 g, 6.56 mmol) and DIPEA (2.196 mL, 12.57 mmol) in Toluene (50 ml) was heated at 120° C. for 2 h. The resulting mixture was concentrated in vacuo to give the crude which was purified by silica gel column chromatography (DCM in petroleum ether: 0-50%) to give tert-butyl 2-(8-bromo-7-hydroxy-5-oxo-3-(4-(trifluoromethyl)benzyl)-3,5-dihydro-2H-[1,4]oxazino[2,3,4-ij]quinoline-6-carboxamido)acetate as a solid. $^1$H NMR (CDCl$_3$, 400 MHz): δ 10.72 (t, J=5.2 Hz, 1H), 7.63 (d, J=8.0 Hz, 2H), 7.51 (d, J=4.0 Hz, 8.0 Hz, 3H), 7.08 (d, J=8.4 Hz, 1H), 5.17 (d, J=8.0 Hz, 1H), 4.27 (d, J=12.0 Hz, 1H), 4.10-4.24 (m, 2H), 3.88 (d, J=12.0 Hz, 1H), 3.13 (dd, J=4.0 Hz, 13.6 Hz, 1H), 2.90 (t, J=12.0 Hz, 1H), 1.54 (s, 9H).

Step E: 2-(8-bromo-7-hydroxy-5-oxo-3-(4-(trifluoromethyl)benzyl)-3,5-dihydro-2H-[1,4]oxazino[2,3,4-ij]quinoline-6-carboxamido)acetic acid To a solution of tert-butyl 2-(8-bromo-7-hydroxy-5-oxo-3-(4-(trifluoromethyl)benzyl)-3,5-dihydro-2H-[1,4]oxazino[2,3,4-ij]quinoline-6-carboxamido)acetate (100 mg, 0.167 mmol) in DCM (1 mL) was added 2,2,2-trifluoroacetic acid (191 mg, 1.674 mmol). The reaction was heated at 60° C. for 3 h. The resulting mixture was concentrated in vacuo to give the crude which was re-crystallised from EtOAc (1 mL) and petroleum ether (10 mL) to give 2-(8-bromo-7-hydroxy-5-oxo-3-(4-(trifluoromethyl)benzyl)-3,5-dihydro-2H-[1,4]oxazino[2,3,4-ij]quinoline-6-carboxamido)acetic acid as a solid. $^1$H NMR (DMSO-$d_6$, 400 MHz): δ 10.56 (t, J=5.6 Hz, 1H), 7.71 (d, J=8.0 Hz, 2H), 7.54 (d, J=8.0 Hz, 1H), 7.49 (d, J=8.0 Hz, 2H), 7.23 (d, J=8.0 Hz, 1H), 5.15 (brs, 1H), 4.27

(d, J=12.0 Hz, 1H), 4.09-4.21 (m, 2H), 4.05 (d, J=12.0 Hz, 1H), 2.92-3.01 (m, 2H). LC/MS (m/z): 541 (M+H)+. Human HIF-PHD2 IC$_{50}$: 8.1 nM.

Example 27

2-(10-Bromo-7-hydroxy-5-oxo-3-(4-(trifluoromethyl)benzyl)-3,5-dihydro-2H-[1,4]oxazino[2,3,4-ij]quinoline-6-carboxamido)acetic acid

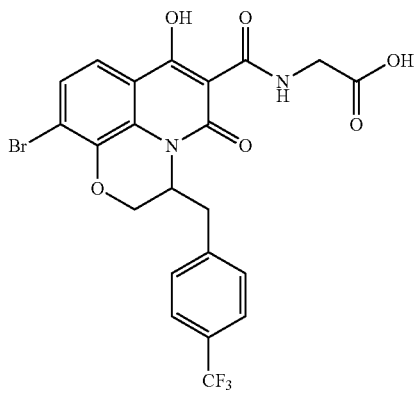 [SMILES: O=C(O)CNC(=O)c1c(O)c2ccc(Br)c3c2n(c1=O)C(Cc1ccc(C(F)(F)F)cc1)CO3]

Step A: 8-bromo-3-(4-(trifluoromethyl)benzyl)-2H-benzo[b][1,4]oxazine

To a solution of 2-amino-6-bromophenol (5 g, 26.6 mmol) in DCM (120 mL) were added aqueous K$_2$CO$_3$ (120 mL, 26.6 mmol) and tetrabutylammonium hydrogen sulfate (0.090 g, 0.266 mmol), then 1-bromo-3-(4-(trifluoromethyl)phenyl)propan-2-one (7.47 g, 26.6 mmol) in DCM (20 mL) was added dropwise to the reaction mixture. The reaction was stirred at room temperature for 20 h. LCMS showed that the reaction completed. The resulting mixture was extracted with DCM (50 mL*3). The combined organic layers were washed with brine (50 mL*3), dried over Na$_2$SO$_4$, filtered and concentrated in vacuo to give 8-bromo-3-(4-(trifluoromethyl)benzyl)-2H-benzo[b][1,4]oxazine as an oil, which was used directly in the next step.

Step B: 8-bromo-3-(4-(trifluoromethyl)benzyl)-3,4-dihydro-2H-benzo[b][1,4]oxazine To a solution of 8-bromo-3-(4-(trifluoromethyl)benzyl)-2H-benzo[b][1,4]oxazine (10.3 g, 27.8 mmol) in DCM (40 mL) and MeOH (20 mL) were added AcOH (2 mL, 34.9 mmol) and sodium cyanoborohydride (2.62 g, 41.7 mmol). The resulting mixture was stirred at room temperature for 2 h. The mixture was then diluted with ethyl acetate (200 mL), washed with sodium bicarbonate (5%, 200 mL), water, and brine, dried over sodium sulfate, and filtered. The solvent was removed under reduced pressure. The residue was purified by silica gel column chromatography (EtOAc in petroleum ether: 0-15%) to give 8-bromo-3-(4-(trifluoromethyl)benzyl)-3,4-dihydro-2H-benzo[b][1,4]oxazine as a solid. $^1$H NMR (CDCl$_3$, 400 MHz): δ 7.63 (d, J=8.0 Hz, 2H), 7.35 (d, J=8.0 Hz, 2H), 6.91 (dd, J=1.2 Hz, 8.0 Hz, 1H), 6.64 (t, J=8.0 Hz, 1H), 6.47 (dd, J=1.2 Hz, 8.0 Hz, 1H), 4.36 (dd, J=2.8 Hz, 10.8 Hz, 1H), 4.10 (q, J=6.0 Hz, 10.8 Hz, 1H), 3.75 (s, 1H), 3.65-3.70 (m, 1H), 2.95 (dd, J=5.2 Hz, 13.6 Hz, 1H), 2.82 (dd, J=9.2 Hz, 13.2 Hz, 1H).

Step C: ethyl 10-bromo-7-hydroxy-5-oxo-3-(4-(trifluoromethyl)benzyl)-3,5-dihydro-2H-[1,4]oxazino[2,3,4-ij]quinoline-6-carboxylate A mixture of 8-bromo-3-(4-(trifluoromethyl)benzyl)-3,4-dihydro-2H-benzo[b][1,4]oxazine (6.4 g, 17.20 mmol) and triethyl methanetricarboxylate (15.97 g, 68.8 mmol) was heated at 240° C. for 5 h. The resulting mixture was purified by silica gel column chromatography (EtOAc in pretroleum ether: 0-30%) to give ethyl 10-bromo-7-hydroxy-5-oxo-3-(4-(trifluoromethyl)benzyl)-3,5-dihydro-2H-[1,4]oxazino[2,3,4-ij]quinoline-6-carboxylate as a solid. $^1$H NMR (CDCl$_3$, 400 MHz): δ 14.38 (s, 1H), 7.69 (d, J=8.0 Hz, 1H), 7.63 (d, J=8.0 Hz, 2H), 7.56 (d, J=8.0 Hz, 2H), 7.43 (d, J=8.0 Hz, 1H), 5.10 (d, J=10.8 Hz, 1H), 4.49-4.66 (m, 2H), 4.42 (d, J=12.0 Hz, 1H), 3.95 (d, J=12.0 Hz, 1H), 3.20 (dd, J=2.8 Hz, 12.8 Hz, 1H), 2.90 (t, J=12.0 Hz, 1H), 1.52 (t, J=7.6 Hz, 3H).

Step D: tert-butyl 2-(10-bromo-7-hydroxy-5-oxo-3-(4-(trifluoromethyl)benzyl)-3,5-dihydro-2H-[1,4]oxazino[2,3,4-ij]quinoline-6-carboxamido)acetate A solution of ethyl 10-bromo-7-hydroxy-5-oxo-3-(4-(trifluoromethyl)benzyl)-3,5-dihydro-2H-[1,4]oxazino[2,3,4-ij]quinoline-6-carboxylate (2.8 g, 5.47 mmol), tert-butyl 2-aminoacetate HCl salt (1.100 g, 6.56 mmol) and DIPEA (2.196 mL, 12.57 mmol) in toluene (50 mL) was heated at 120° C. for 2 h. The resulting mixture was concentrated in vacuo to give the crude which was purified by silica gel column chromatography (DCM in petroleum ether: 0-50%) to give tert-butyl 2-(10-bromo-7-hydroxy-5-oxo-3-(4-(trifluoromethyl)benzyl)-3,5-dihydro-2H-[1,4]oxazino[2,3,4-ij]quinoline-6-carboxamido)acetate as a solid. $^1$H NMR (CDCl$_3$, 400 MHz): δ 10.52 (t, J=5.2 Hz, 1H), 7.70 (d, J=8.0 Hz, 1H), 7.64 (d, J=8.0 Hz, 2H), 7.53 (d, J=8.0 Hz, 2H), 7.46 (d, J=8.0 Hz, 1H), 5.12 (d, J=11.6 Hz, 1H), 4.45 (d, J=12.0 Hz, 1H), 4.10-4.23 (m, 2H), 3.99 (d, J=11.6 Hz, 1H), 3.16 (dd, J=3.6 Hz, 12.8 Hz, 1H), 2.95 (t, J=11.2 Hz, 1H), 1.54 (s, 9H).

Step E: 2-(10-bromo-7-hydroxy-5-oxo-3-(4-(trifluoromethyl)benzyl)-3,5-dihydro-2H-[1,4]oxazino[2,3,4-ij]quinoline-6-carboxamido)acetic acid To a solution of tert-butyl 2-(10-bromo-7-hydroxy-5-oxo-3-(4-(trifluoromethyl)benzyl)-3,5-dihydro-2H-[1,4]oxazino[2,3,4-ij]quinoline-6-carboxamido)acetate (100 mg, 0.167 mmol) in DCM (1 mL) was added 2,2,2-trifluoroacetic acid (191 mg, 1.674 mmol). The resulting mixture was heated at 60° C. for 3 h. TLC (petroleum ether: EtOAc=2:1) showed that the reaction completed. The resulting mixture was concentrated in vacuo to give the crude which was re-crystallised from EtOAc (1 mL) and petroleum ether (10 mL) to give 2-(10-bromo-7-hydroxy-5-oxo-3-(4-(trifluoromethyl)benzyl)-3,5-dihydro-2H-[1,4]oxazino[2,3,4-ij]quinoline-6-carboxamido)acetic acid as a solid. $^1$H NMR (DMSO-d$_6$, 400 MHz): δ 12.96 (brs, 1H), 10.35 (t, J=5.6 Hz, 1H), 7.68 (d, J=8.0 Hz, 1H), 7.60 (d, J=8.0 Hz, 1H), 7.54 (d, J=8.0 Hz, 1H), 7.47 (d, J=8.0 Hz, 2H), 5.12 (brs, 1H), 4.46 (d, J=12.0 Hz, 1H), 4.08-4.19 (m, 3H), 2.96-3.07 (m, 2H). LC/MS (m/z): 541 (M+H)+. Human HIF-PHD2 IC$_{50}$: 5.7 nM.

Example 28

2-(7-Hydroxy-8-(methylsulfonyl)-5-oxo-3-(4-(trifluoromethyl)benzyl)-3,5-dihydro-2H-[1,4]oxazino[2,3,4-ij]quinoline-6-carboxamido)acetic acid

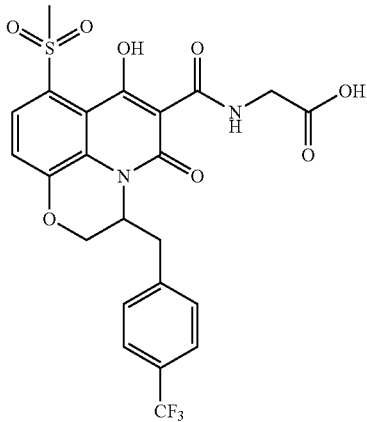 [SMILES: CS(=O)(=O)c1ccc2c3c1c(O)c(C(=O)NCC(=O)O)c(=O)n3C(Cc1ccc(C(F)(F)F)cc1)CO2]

Step A: tert-butyl 2-(7-hydroxy-8-(methylsulfonyl)-5-oxo-3-(4-(trifluoromethyl)benzyl)-3,5-dihydro-2H-[1,4]oxazino[2,3,4-ij]quinoline-6-carboxamido)acetate A suspension of Step D product of Example 26 (200 mg, 0.335 mmol), sodium methanesulfinate (41.0 mg, 0.402 mmol), NaOH (2.68 mg, 0.067 mmol), L-proline (7.71 mg, 0.067 mmol) and copper(I) iodide (6.38 mg, 0.033 mmol) in DMSO (2 mL) was stirred at 120° C. under $N_2$ for 60 h. The mixture was cooled, water (5 mL) was added and the mixture was extracted with ethyl acacate (3*4 mL). The solvent was evaporated under reduced pressure. The residue was purified by column chromatography on silica gel Isolute Flash Si; 5 g prepacked, eluting with (EtOAc in DCM: 0-20%) to give crude tert-butyl 2-(7-hydroxy-8-(methylsulfonyl)-5-oxo-3-(4-(trifluoromethyl)benzyl)-3,5-dihydro-2H-[1,4]oxazino[2,3,4-ij]quinoline-6-carboxamido)acetate as a solid. $^1$H NMR (CDCl$_3$, 400 MHz): δ: 10.70 (s, 1H), 8.30 (d, J=8.0 Hz, 1H), 7.65 (d, J=8.0 Hz, 2H), 7.52 (d, J=8.0 Hz, 2H), 7.36 (d, J=8.0 Hz, 1H), 5.22 (d, J=10.4 Hz, 1H), 4.35 (d, J=12.0 Hz, 1H), 4.12-4.26 (m, 2H), 3.97 (d, J=12.0 Hz, 1H), 3.57 (s, 3H), 3.13 (dd, J=3.2 Hz, 13.2 Hz, 1H), 2.88 (t, J=12.0 Hz, 1H), 1.54 (s, 9 H).

Step B: 2-(7-hydroxy-8-(methylsulfonyl)-5-oxo-3-(4-(trifluoromethyl)benzyl)-3,5-dihydro-2H-[1,4]oxazino[2,3,4-ij]quinoline-6-carboxamido)acetic acid To a solution of tert-butyl 2-(7-hydroxy-8-(methylsulfonyl)-5-oxo-3-(4-(trifluoromethyl)benzyl)-3,5-dihydro-2H-[1,4]oxazino[2,3,4-ij]quinoline-6-carboxamido)acetate (80 mg, 0.134 mmol) in DCM (1 mL) was added 2,2,2-trifluoroacetic acid (153 mg, 1.341 mmol). The resulting mixture was heated at 50° C. for 3 h. The resulting mixture was concentrated in vacuo to give the crude which was washed with EtOAc (1 mL) and petroleum ether (10 mL) to give 2-(7-hydroxy-8-(methylsulfonyl)-5-oxo-3-(4-(trifluoromethyl)benzyl)-3,5-dihydro-2H-[1,4]oxazino[2,3,4-ij]quinoline-6-carboxamido)acetic acid as a solid. $^1$H NMR (DMSO-d$_6$, 400 MHz): δ 13.04 (brs, 1H), 10.55 (s, 1H), 8.10 (d, J=8.0 Hz, 1H), 7.71 (d, J=8.0 Hz, 2H), 7.51 (d, J=8.0 Hz, 2H), 7.51 (d, J=8.0 Hz, 1H), 5.21 (brs, 1H), 4.36 (d, J=12.0 Hz, 1H), 4.15-4.24 (m, 3H), 3.54 (s, 3H), 2.94-3.04 (m, 2H). LC/MS (m/z): 541 (M+H)$^+$. Human HIF-PHD2 IC$_{50}$: 42 nM.

Example 29

2-(8-Cyano-7-hydroxy-5-oxo-3-(4-(trifluoromethyl)benzyl)-3,5-dihydro-2H-[1,4]oxazino[2,3,4-ij]quinoline-6-carboxamido)acetic acid

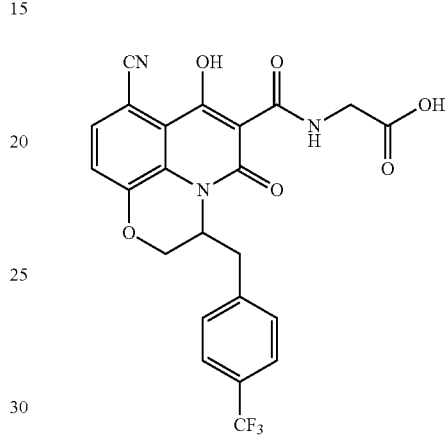

Step A: tert-butyl 2-(8-cyano-7-hydroxy-5-oxo-3-(4-(trifluoromethyl)benzyl)-3,5-dihydro-2H-[1,4]oxazino[2,3,4-ij]quinoline-6-carboxamido)acetate To a solution of Step D product of Example 26 (150 mg, 0.251 mmol) in DMA (2 mL) were added zinc cyanide (59.0 mg, 0.502 mmol), Pd$_2$(dba)$_3$ (22.99 mg, 0.025 mmol), dppf (13.92 mg, 0.025 mmol) and zinc dust (32.8 mg, 0.502 mmol). The reaction solution was heated at 130° C. by a microwave for 30 min. TLC (petroleum ether: EtOAc=2:1) showed that the reaction completed. The mixture was cooled, water (10 mL) was added and the mixture was extracted with ethyl acacate (3*20 mL). The combined organic fractions were washed with water (3*30 mL), dried (Na$_2$SO$_4$), filtered and the solvent was evaporated under reduced pressure. The residue was purified by silica gel column chromatography (EtOAc in petroleum ether: 0-60%) to give tert-butyl 2-(8-cyano-7-hydroxy-5-oxo-3-(4-(trifluoromethyl)benzyl)-3,5-dihydro-2H-[1,4]oxazino[2,3,4-ij]quinoline-6-carboxamido)acetate as a solid. $^1$H NMR (CDCl$_3$, 400 MHz): δ: 10.55 (s, 1H), 7.64 (d, J=8.0 Hz, 1H), 7.64 (d, J=8.0 Hz, 2H), 7.50 (d, J=8.0 Hz, 2H), 7.30 (d, J=8.0 Hz, 1H), 5.22 (dd, J=3.2 Hz, 12.8 Hz, 1H), 4.37 (d, J=12.0 Hz, 1H), 4.12-4.25 (m, 2H), 3.99 (d, J=12.0 Hz, 1H), 3.13 (dd, J=3.6 Hz, 14.0 Hz, 1H), 2.88 (t, J=12.0 Hz, 1H), 1.54 (s, 9 H).

Step B: 2-(8-cyano-7-hydroxy-5-oxo-3-(4-(trifluoromethyl)benzyl)-3,5-dihydro-2H-[1,4]oxazino[2,3,4-ij]quinoline-6-carboxamido)acetic acid To a solution of tert-butyl 2-(8-cyano-7-hydroxy-5-oxo-3-(4-(trifluoromethyl)benzyl)-3,5-dihydro-2H-[1,4]oxazino[2,3,4-ij]quinoline-6-carboxamido)acetate (65 mg, 0.120 mmol) in DCM (1 mL) was added 2,2,2-trifluoroacetic acid (136 mg, 1.196 mmol). The resulting mixture was heated at 60° C. for 3 h. TLC (pretroleum ether: EtOAc=2:1) showed that the reaction completed. The resulting mixture was concentrated in vacuo to give the crude which was re-crystallised from EtOAc (1 mL) and petroleum ether (10 mL) to give 2-(8-cyano-7-hydroxy-5-oxo-3-(4-(trifluoromethyl)benzyl)-3,5-dihydro-2H-[1,4]oxazino[2,3,4-ij]quinoline-6-carboxamido)acetic acid as a solid. $^1$H NMR (DMSO-d$_6$, 400 MHz): δ 10.44 (s, 1H), 7.79 (d, J=8.0 Hz, 1H), 7.69 (d, J=8.0 Hz, 2H), 7.47 (d, J=8.0 Hz, 2H), 7.44 (d, J=8.0 Hz, 1H), 5.15 (brs, 1H), 4.39 (d, J=12.0 Hz, 1H), 4.12-4.23 (m, 3H), 2.94-3.05 (m, 2H). LC/MS (m/z): 488 (M+H)$^+$. Human HIF-PHD2 IC$_{50}$: 1.3 nM.

Example 30

2-(7-Hydroxy-8-methyl-5-oxo-3-(4-(trifluoromethyl)benzyl)-3,5-dihydro-2H-[1,4]oxazino[2,3,4-ij]quinoline-6-carboxamido)acetic acid

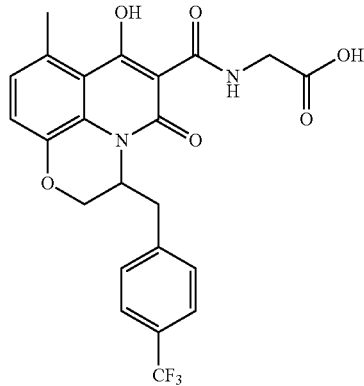 [SMILES: Cc1ccc2c3c1c(O)c(C(=O)NCC(=O)O)c(=O)n3C(Cc1ccc(C(F)(F)F)cc1)CO2]

Step A: tert-butyl 2-(7-hydroxy-8-methyl-5-oxo-3-(4-(trifluoromethyl)benzyl)-3,5-dihydro-2H-[1,4]oxazino[2,3,4-ij]quinoline-6-carboxamido)acetate A solution of Step D product of Example 26 (200 mg, 0.335 mmol), 2,4,6-trimethyl-1,3,5,2,4,6-trioxatriborinane (42.0 mg, 0.335 mmol), Pd(Ph$_3$P)$_4$ (38.7 mg, 0.033 mmol) and K$_2$CO$_3$ (139 mg, 1.004 mmol) in DMF (1 mL) was heated at 120° C. by MW for 1 h. TLC (petroleum ether: EtOAc=5:1) showed that the reaction completed. To the reaction was added brine (10 mL) and the mixture was extracted with DCM (10 mL*3). The organic layers were concentrated in vacuo to give the crude which was purified by silica gel column chromatography (EtOAc in petroleum ether: 0-15%) to give tert-butyl 2-(7-hydroxy-8-methyl-5-oxo-3-(4-(trifluoromethyl)benzyl)-3,5-dihydro-2H-[1,4]oxazino[2,3,4-ij]quinoline-6-carboxamido)acetate as a solid. $^1$H NMR (CDCl$_3$, 400 MHz): δ 10.79 (s, 1H), 7.63 (d, J=8.0 Hz, 2H), 7.52 (d, J=8.0 Hz, 2H), 7.14 (d, J=8.0 Hz, 1H), 6.98 (d, J=8.0 Hz, 1H), 5.14 (d, J=10.8 Hz, 1H), 4.10-4.28 (m, 3H), 3.86 (d, J=12.0 Hz, 1H), 3.13 (dd, J=3.2 Hz, 13.2 Hz, 1H), 2.88 (t, J=12.0 Hz, 1H), 2.80 (s, 3H), 1.54 (s, 9 H).

Step B: 2-(7-hydroxy-8-methyl-5-oxo-3-(4-(trifluoromethyl)benzyl)-3,5-dihydro-2H-[1,4]oxazino[2,3,4-ij]quinoline-6-carboxamido)acetic acid To a solution of tert-butyl 2-(7-hydroxy-8-methyl-5-oxo-3-(4-(trifluoromethyl)benzyl)-3,5-dihydro-2H-[1,4]oxazino[2,3,4-ij]quinoline-6-carboxamido)acetate (124 mg, 0.233 mmol) in DCM (1 mL) was added 2,2,2-trifluoroacetic acid (266 mg, 2.329 mmol). The resulting mixture was heated at 40° C. for 3 h. TLC (petroleum ether: EtOAc=5:1) showed that the reaction completed. The resulting mixture was concentrated in vacuo to give the crude which was re-crystallised from EtOAc (1 mL) and petroleum ether (15 mL) to give 2-(7-hydroxy-8-methyl-5-oxo-3-(4-(trifluoromethyl)benzyl)-3,5-dihydro-2H-[1,4]oxazino[2,3,4-ij]quinoline-6-carboxamido)acetic acid as a solid. $^1$H NMR (DMSO-d$_6$, 400 MHz): δ 10.59 (t, J=5.6 Hz, 1H), 7.72 (d, J=8.0 Hz, 2H), 7.51 (d, J=8.0 Hz, 2H), 7.24 (d, J=8.0 Hz, 1H), 7.06 (d, J=8.0 Hz, 1H), 5.10 (d, J=4.0 Hz, 1H), 4.22 (d, J=12.0 Hz, 1H), 4.08-4.19 (m, 2H), 4.00 (d, J=12.0 Hz, 1H), 2.91-3.02 (m, 2H), 2.72 (s, 3H). LC/MS (m/z): 477 (M+H)$^+$. Human HIF-PHD2 IC$_{50}$: 39 nM.

Example 31

2-(7-Hydroxy-10-(methylsulfonyl)-5-oxo-3-(4-(trifluoromethyl)benzyl)-3,5-dihydro-2H-[1,4]oxazino[2,3,4-ij]quinoline-6-carboxamido)acetic acid

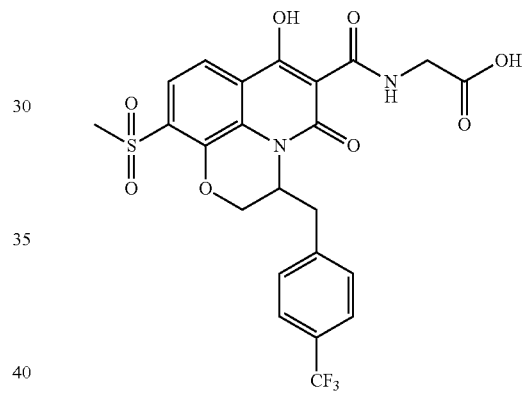

Step A: tert-butyl 2-(7-hydroxy-10-(methylsulfonyl)-5-oxo-3-(4-(trifluoromethyl)benzyl)-3,5-dihydro-2H-[1,4]oxazino[2,3,4-ij]quinoline-6-carboxamido)acetate A suspension of Step D product of Example 27 (200 mg, 0.335 mmol), sodium methanesulfinate (41.0 mg, 0.402 mmol), NaOH (2.68 mg, 0.067 mmol), L-proline (7.71 mg, 0.067 mmol) and CuI (6.38 mg, 0.033 mmol) in DMSO (2 mL) was heated at 120° C. under N$_2$ for 60 h. The mixture was cooled and quenched with water (5 mL) and extracted with ethyl acetate (3*4 mL). The solvent was evaporated under reduced pressure. The residue was purified by column chromatography on silica gel Isolute Flash Si; 5 g pre-packed, eluting with (EtOAc in petroleum ether: 0-30%) to give tert-butyl 2-(7-hydroxy-10-(methylsulfonyl)-5-oxo-3-(4-(trifluoromethyl)benzyl)-3,5-dihydro-2H-[1,4]oxazino[2,3,4-ij]quinoline-6-carboxamido)acetate as a solid. $^1$H NMR (CDCl$_3$, 400 MHz): δ 10.49 (t, J=5.2 Hz, 1H), 7.96 (d, J=8.0 Hz, 1H), 7.85 (d, J=8.0 Hz, 1H), 7.63 (d, J=8.0 Hz, 2H), 7.48 (d, J=8.0 Hz, 2H), 5.18 (d, J=10.4 Hz, 1H), 4.57 (d, J=12.0 Hz, 1H), 4.10-4.24 (m, 3H), 3.29 (s, 3H), 3.20 (dd, J=4.0 Hz, 16.0 Hz, 1H), 2.97 (t, J=12.0 Hz, 1H), 1.54 (s, 9H).

Step B: 2-(7-hydroxy-10-(methylsulfonyl)-5-oxo-3-(4-(trifluoromethyl)benzyl)-3,5-dihydro-2H-[1,4]oxazino[2,3,4-ij]quinoline-6-carboxamido)acetic acid To a solution of tert-butyl 2-(7-hydroxy-10-(methylsulfonyl)-5-oxo-3-(4-(trifluoromethyl)benzyl)-3,5-dihydro-2H-[1,4]oxazino[2,3,4-ij]quinoline-6-carboxamido)acetate (70 mg, 0.117 mmol) in DCM (1 mL) was added 2,2,2-trifluoroacetic acid (134 mg, 1.173 mmol). The resulting mixture was heated at 60° C. for 3h. LCMS showed that the reaction completed. The resulting mixture was concentrated in vacuo to give the crude which was re-crystallised from EtOAc (1 mL) and petroleum ether (15 mL) to give 2-(7-hydroxy-10-(methylsulfonyl)-5-oxo-3-(4-(trifluoromethyl)benzyl)-3,5-dihydro-2H-[1,4]oxazino[2,3,4-ij]quinoline-6-carboxamido)acetic acid as a solid. $^1$H NMR (DMSO-$d_6$, 400 MHz): δ 13.00 (brs, 1H), 10.37 (t, J=5.6 Hz, 1H), 7.85 (d, J=8.0 Hz, 1H), 7.69 (d, J=8.0 Hz, 2H), 7.68 (d, J=8.0 Hz, 1H), 7.47 (d, J=8.0 Hz, 2H), 5.17 (t, J=5.6 Hz, 1H), 4.57 (d, J=12.0 Hz, 1H), 4.29 (d, J=12.0 Hz, 1H), 4.12-4.22 (m, 2H), 3.34 (s, 3H), 3.02-3.10 (m, 2H). LC/MS (m/z): 541 (M+H)$^+$. Human HIF-PHD2 IC$_{50}$: 1.0 nM.

Example 32

2-(10-Cyano-7-hydroxy-5-oxo-3-(4-(trifluoromethyl)benzyl)-3,5-dihydro-2H-[1,4]oxazino[2,3,4-ij]quinoline-6-carboxamido)acetic acid

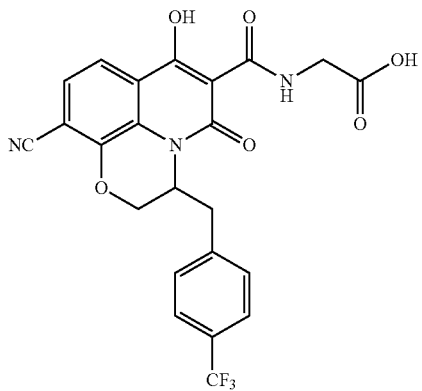 [SMILES: N#Cc1ccc2c(O)c(C(=O)NCC(=O)O)c(=O)n3c2c1OCC3Cc1ccc(C(F)(F)F)cc1]

Step A: tert-butyl 2-(10-cyano-7-hydroxy-5-oxo-3-(4-(trifluoromethyl)benzyl)-3,5-dihydro-2H-[1,4]oxazino[2,3,4-ij]quinoline-6-carboxamido)acetate To a solution of Step D product of Example 27 (150 mg, 0.251 mmol) in DMA (2 mL) were added zinc cyanide (59.0 mg, 0.502 mmol), Pd$_2$(dba)$_3$ (22.99 mg, 0.025 mmol), DPPF (13.92 mg, 0.025 mmol) and Zinc dust (32.8 mg, 0.502 mmol). The reaction solution was heated at 130° C. by microwave for 30 min. TLC (petroleum ether: EtOAc=2:1) showed that the reaction completed. The mixture was cooled and quenched with water (10 mL). Then the mixture was extracted with ethyl acetate (3*20 mL). The combined organic fractions were washed with water (3*30 mL), dried over Na$_2$SO$_4$, filtered and the solvent was evaporated under reduced pressure. The residue was purified by silica gel column chromatography (EtOAc in petroleum ether: 0-60%) to give tert-butyl 2-(10-cyano-7-hydroxy-5-oxo-3-(4-(trifluoromethyl)benzyl)-3,5-dihydro-2H-[1,4]oxazino[2,3,4-ij]quinoline-6-carboxamido)acetate as a solid. $^1$H NMR (CDCl$_3$, 400 MHz): δ 10.49 (t, J=5.2 Hz, 1H), 7.86 (d, J=8.0 Hz, 1H), 7.65 (d, J=8.0 Hz, 2H), 7.53 (d, J=8.0 Hz, 2H), 7.44 (d, J=8.0 Hz, 1H), 5.13 (d, J=10.8 Hz, 1H), 4.51 (d, J=12.0 Hz, 1H), 4.11-4.24 (m, 2H), 4.06 (d, J=12.0 Hz, 1H), 3.16 (dd, J=2.8 Hz, 12.8 Hz, 1H), 2.92 (t, J=12.0 Hz, 1H), 1.54 (s, 9H).

Step B: 2-(10-cyano-7-hydroxy-5-oxo-3-(4-(trifluoromethyl)benzyl)-3,5-dihydro-2H-[1,4]oxazino[2,3,4-ij]quinoline-6-carboxamido)acetic acid To a solution of tert-butyl 2-(10-cyano-7-hydroxy-5-oxo-3-(4-(trifluoromethyl)benzyl)-3,5-dihydro-2H-[1,4]oxazino[2,3,4-ij]quinoline-6-carboxamido)acetate (70 mg, 0.129 mmol) in DCM (1 mL) was added 2,2,2-trifluoroacetic acid (147 mg, 1.288 mmol). The resulting mixture was heated at 60° C. for 3 h. TLC (pretroleum ether: EtOAc=2:1) showed that the reaction completed. The resulting mixture was concentrated in vacuo to give the crude which was re-crystallised from EtOAc (1 mL) and petroleum ether (15 mL) to give 2-(10-cyano-7-hydroxy-5-oxo-3-(4-(trifluoromethyl)benzyl)-3,5-dihydro-2H-[1,4]oxazino[2,3,4-ij]quinoline-6-carboxamido)acetic acid as a solid. $^1$H NMR (DMSO-$d_6$, 400 MHz): δ 10.34 (t, J=5.6 Hz, 1H), 7.74 (d, J=8.0 Hz, 1H), 7.66 (d, J=8.0 Hz, 2H), 7.61 (d, J=8.0 Hz, 1H), 7.47 (d, J=8.0 Hz, 2H), 5.17 (t, J=6.4 Hz, 1H), 4.56 (d, J=12.0 Hz, 1H), 4.31 (dd, J=2.0 Hz, 11.6 Hz, 1H) 4.10-4.21 (m, 2H), 3.01-3.08 (m, 2H). LC/MS (m/z): 488 (M+H)$^+$. Human HIF-PHD2 IC$_{50}$: 1.3 nM.

Example 33

2-(7-Hydroxy-10-methyl-5-oxo-3-(4-(trifluoromethyl)benzyl)-3,5-dihydro-2H-[1,4]oxazino[2,3,4-ij]quinoline-6-carboxamido)acetic acid

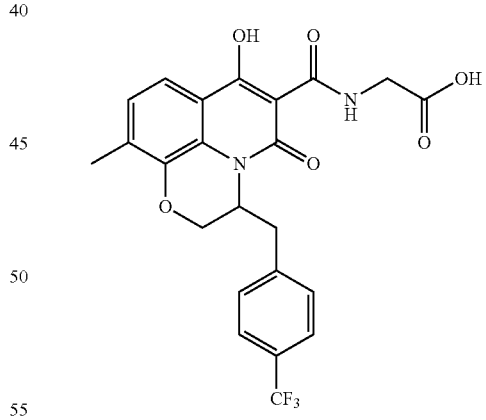

Step A: tert-butyl 2-(7-hydroxy-10-methyl-5-oxo-3-(4-(trifluoromethyl)benzyl)-3,5-dihydro-2H-[1,4]oxazino[2,3,4-ij]quinoline-6-carboxamido)acetate A suspension of Step D product of Example 27 (200 mg, 0.335 mmol), 2,4,6-trimethyl-1,3,5,2,4,6-trioxatriborinane (42.0 mg, 0.335 mmol), Pd(Ph$_3$P)$_4$ (38.7 mg, 0.033 mmol) and K$_2$CO$_3$ (139 mg, 1.004 mmol) in DMF (1 mL) was heated at 120° C. by microwave for 1 h. TLC (petroleum ether: EtOAc=5:1) showed that the reaction completed. The resulting mixture was quenched with aq NaCl (10 mL) and extracted with DCM (10 mL*3). The organic layers were concentrated in vacuo to give the crude which was purified by silica gel column chromatography (EtOAc in petroleum ether: 0-15%) to give tert-butyl 2-(7-hydroxy-10-methyl-5-oxo-3-(4-(trifluoromethyl)benzyl)-3,5-dihydro-2H-[1,4]oxazino[2,3,4-ij]quinoline-6-carboxamido)acetate as a solid. $^1$H NMR (CDCl$_3$, 400 MHz): δ 10.63 (t, J=5.6 Hz, 1H), 7.72 (d, J=8.0 Hz, 1H), 7.63 (d, J=8.0 Hz, 2H), 7.53 (d, J=8.0 Hz, 2H), 7.11 (d, J=8.0 Hz, 1H), 5.08 (d, J=10.8 Hz, 1H), 4.34 (d, J=12.0 Hz, 1H), 4.10-4.23 (m, 2H), 3.91 (d, J=11.2 Hz, 1H), 3.15 (dd, J=3.2 Hz, 12.8 Hz, 1H), 2.95 (t, J=12.0 Hz, 1H), 2.41 (s, 3H), 1.54 (s, 9 H).

Step B: 2-(7-hydroxy-10-methyl-5-oxo-3-(4-(trifluoromethyl)benzyl)-3,5-dihydro-2H-[1,4]oxazino[2,3,4-ij]quinoline-6-carboxamido)acetic acid To a solution of tert-butyl 2-(7-hydroxy-10-methyl-5-oxo-3-(4-(trifluoromethyl)benzyl)-3,5-dihydro-2H-[1,4]oxazino[2,3,4-ij]quinoline-6-carboxamido)acetate (114 mg, 0.214 mmol) in DCM (1 mL) was added 2,2,2-trifluoroacetic acid (244 mg, 2.141 mmol). The resulting mixture was heated at 40° C. for 3 h. TLC (petroleum ether: EtOAc=5:1) showed that the reaction completed. The resulting mixture was concentrated in vacuo to give the crude which was re-crystallised from EtOAc (1 mL) and petroleum ether (15 mL) to give 2-(7-hydroxy-10-methyl-5-oxo-3-(4-(trifluoromethyl)benzyl)-3,5-dihydro-2H-[1,4]oxazino[2,3,4-ij]quinoline-6-carboxamido)acetic acid as a solid. $^1$H NMR (DMSO-d$_6$, 400 MHz): δ 12.94 (s, 1H), 10.42 (t, J=5.6 Hz, 1H), 7.69 (d, J=8.0 Hz, 2H), 7.60 (d, J=8.0 Hz, 1H), 7.49 (d, J=8.0 Hz, 2H), 7.19 (d, J=8.0 Hz, 1H), 5.08 (d, J=6.4 Hz, 1H), 4.36 (d, J=12.0 Hz, 1H), 4.08-4.19 (m, 2H), 4.06 (d, J=12.0 Hz, 1H), 2.98-3.05 (m, 2H), 2.32 (s, 3H). LC/MS (m/z): 477 (M+H)$^+$. Human HIF-PHD2 IC$_{50}$: 17 nM.

Example 34

2-(9-acetyl-7-hydroxy-5-oxo-3-(4-(trifluoromethyl)benzyl)-3,5-dihydro-2H-[1,4]oxazino[2,3,4-ij]quinoline-6-carboxamido)acetic acid

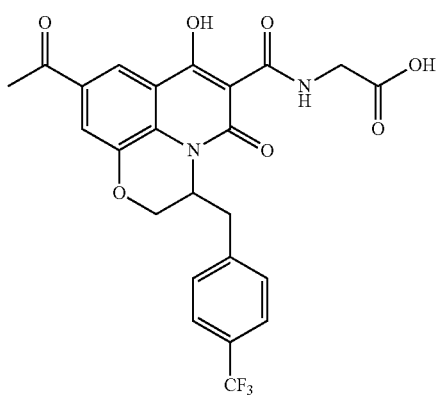 [SMILES: CC(=O)c1cc2c3c(c1)c(O)c(C(=O)NCC(=O)O)c(=O)n3C(Cc1ccc(C(F)(F)F)cc1)CO2]

Step A: tert-butyl 2-(9-acetyl-7-hydroxy-5-oxo-3-(4-(trifluoromethyl)benzyl)-3,5-dihydro-2H-[1,4]oxazino[2,3,4-ij]quinoline-6-carboxamido)acetate To a solution of Step A product of Example 8 (800 mg, 1.432 mmol) in THF (5 mL) and Water (5.00 mL) were added potassium osmate dihydrate (52.8 mg, 0.143 mmol) and sodium periodate (919 mg, 4.30 mmol). The resulting mixture was stirred at room temperature for 16 h. TLC (petroleum ether: EtOAc=3:1) showed that the reaction completed. The resulting mixture was extracted with EtOAc (5 mL*3), dried over Na$_2$SO$_4$, filtered and evaporated in vacuo to give the crude which was recrystallised from EtOAc (2 mL) and petroleum ether (15 mL) to give tert-butyl 2-(9-acetyl-7-hydroxy-5-oxo-3-(4-(trifluoromethyl)benzyl)-3,5-dihydro-2H-[1,4]oxazino[2,3,4-ij]quinoline-6-carboxamido)acetate as a solid. $^1$H NMR (CDCl$_3$, 400 MHz): δ 10.50 (t, J=4.8 Hz, 1H), 8.41 (d, J=2.0 Hz, 1H), 7.87 (s, 1H), 7.64 (d, J=8.0 Hz, 2H), 7.52 (d, J=8.0 Hz, 2H), 5.09 (d, J=10.0 Hz, 1H), 4.34 (d, J=12.0 Hz, 1H), 4.12-4.24 (m, 2H), 3.94 (d, J=12.0 Hz, 1H), 3.17 (dd, J=3.6 Hz, 12.8 Hz, 1H), 2.92 (t, J=12.0 Hz, 1H), 2.69 (s, 3H), 1.54 (s, 9H).

Step B: 2-(9-acetyl-7-hydroxy-5-oxo-3-(4-(trifluoromethyl)benzyl)-3,5-dihydro-2H-[1,4]oxazino[2,3,4-ij]quinoline-6-carboxamido)acetic acid To a solution of tert-butyl 2-(9-acetyl-7-hydroxy-5-oxo-3-(4-(trifluoromethyl)benzyl)-3,5-dihydro-2H-[1,4]oxazino[2,3,4-ij]quinoline-6-carboxamido)acetate (50 mg, 0.089 mmol) in DCM (1 mL) was added 2,2,2-trifluoroacetic acid (102 mg, 0.892 mmol). The resulting mixture was heated at 60° C. for 3 h. TLC (pretroleum ether: EtOAc=2:1) showed that the reaction completed. The resulting mixture was concentrated in vacuo to give the crude which was re-crystallised from EtOAc (1 mL) and petroleum ether (15 mL) to give 2-(9-acetyl-7-hydroxy-5-oxo-3-(4-(trifluoromethyl)benzyl)-3,5-dihydro-2H-[1,4]oxazino[2,3,4-ij]quinoline-6-carboxamido)acetic acid as a solid. $^1$H NMR (DMSO-d$_6$, 400 MHz): δ 10.33 (d, J=5.6 Hz, 1H), 8.26 (d, J=1.6 Hz, 1H), 7.78 (d, J=1.6 Hz, 1H), 7.70 (d, J=8.0 Hz, 2H), 7.50 (d, J=8.0 Hz, 2H), 5.11 (d, J=6.4 Hz, 1H), 4.35 (d, J=12.0 Hz, 1H), 4.09-4.21 (m, 3H), 2.96-3.08 (m, 2H), 2.64 (s, 3H). LC/MS (m/z): 505 (M+H)$^+$. Human HIF-PHD2 IC$_{50}$: 3.2 nM.

Example 35

2-(7-Hydroxy-9-(1-hydroxyethyl)-5-oxo-3-(4-(trifluoromethyl)benzyl)-3,5-dihydro-2H-[1,4]oxazino[2,3,4-ij]quinoline-6-carboxamido)acetic acid

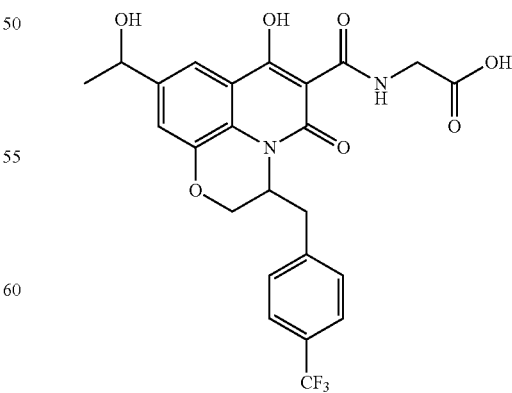

To a solution of Example 34 product (50 mg, 0.099 mmol) in THF (5 mL) was added NaBH$_4$ (3.75 mg, 0.099 mmol).

The reaction was stirred at room temperature for 3 h. TLC (petroleum ether: EtOAc=2:1) showed that the reaction was completed. The resulting mixture was quenched with aqueous 1 M HCl to pH=4 and extracted with DCM (10 mL*3). The combined organic layers were washed with aqueous NaCl (10 mL*3), dried over $Na_2SO_4$, filtered and concentrated in vacuo to give the crude which was purified prep-HPLC to give 2-(7-hydroxy-9-(1-hydroxyethyl)-5-oxo-3-(4-(trifluoromethyl)benzyl)-3,5-dihydro-2H-[1,4]oxazino[2,3,4-ij]quinoline-6-carboxamido)acetic acid as a solid. $^1$H NMR (DMSO-$d_6$, 400 MHz): δ 12.94 (s, 1H), 10.46 (t, J=4.8 Hz, 1H), 7.71 (d, J=8.0 Hz, 2H), 7.68 (d, J=1.6 Hz, 1H), 7.52 (d, J=8.0 Hz, 2H), 7.32 (d, J=1.6 Hz, 1H), 5.35 (d, J=2.8 Hz, 1H), 5.06 (d, J=4.0 Hz, 1H), 4.80 (brs, 1H), 4.27 (d, J=12.0 Hz, 1H), 4.14 (t, J=5.6 Hz, 2H), 4.07 (d, J=12.0 Hz, 1H), 2.96-3.05 (m, 2H), 1.35 (d, J=6.8 Hz, 3H). LC/MS (m/z): 507 (M+H)$^+$. Human HIF-PHD2 $IC_{50}$: 12 nM.

Example 36

2-(7-Hydroxy-9-(2-hydroxypropan-2-yl)-5-oxo-3-(4-(trifluoromethyl)benzyl)-3,5-dihydro-2H-[1,4]oxazino[2,3,4-ij]quinoline-6-carboxamido)acetic acid

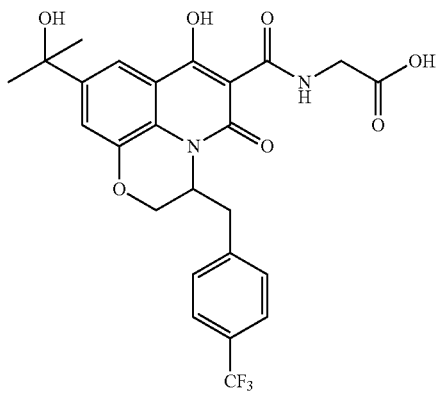 [SMILES: CC(C)(O)c1cc2c3c(c1)c(O)c(C(=O)NCC(=O)O)c(=O)n3C(Cc1ccc(C(F)(F)F)cc1)CO2]

Step A: 2-(7-hydroxy-9-(2-hydroxypropan-2-yl)-5-oxo-3-(4-(trifluoromethyl)benzyl)-3,5-dihydro-2H-[1,4]oxazino[2,3,4-ij]quinoline-6-carboxamido)acetic acid To a solution of Example 34 product (100 mg, 0.178 mmol) in THF (5 mL) was added methylmagnesium bromide (1.274 mL, 1.784 mmol) at −50° C. Then the resulting mixture was stirred at −50° C. for 1 h. TLC (petroleum ether: EtOAc=2:1) showed that the reaction completed. The resulting mixture was warmed to room temperature and quenched by aqueous 1 M HCl to pH=4. The mixture was extracted with EtOAc (5 mL*3). The combined organic layers were washed with aqueous NaCl (10 mL*3), dried over $Na_2SO_4$, filtered and evaporated to give the crude which was purified prep-HPLC (Column: Gemini 150*21.5mm*5 um; Mobile phase: From 50% MeCN in water (0.225% FA) to 80% MeCN in water (0.225% FA); Wavelength: 220 nm) to give 2-(7-hydroxy-9-(2-hydroxypropan-2-yl)-5-oxo-3-(4-(trifluoromethyl)benzyl)-3,5-dihydro-2H-[1,4]oxazino[2,3,4-ij]quinoline-6-carboxamido)acetic acid as a solid. $^1$H NMR (DMSO-$d_6$, 400 MHz): δ 12.94 (s, 1H), 10.47 (t, J=5.6 Hz, 1H), 7.81 (d, J=1.6 Hz, 1H), 7.71 (d, J=8.0 Hz, 2H), 7.50 (d, J=8.0 Hz, 2H), 7.42 (d, J=1.6 Hz, 1H), 5.25 (s, 1H), 5.05 (d, J=6.4 Hz, 1H), 4.27 (d, J=12.0 Hz, 1H), 4.15 (t, J=5.6 Hz, 2H), 4.07 (d, J=12.0 Hz, 1H), 2.94-3.05 (m, 2H), 1.46 (s, 6H). LC/MS (m/z): 521 (M+H)$^+$. Human HIF-PHD2 $IC_{50}$: 17 nM.

Example 37

2-(10-cyano-7-hydroxy-5-oxo-3,5-dihydro-2H-[1,4]oxazino[2,3,4-ij]quinoline-6-carboxamido)acetic acid

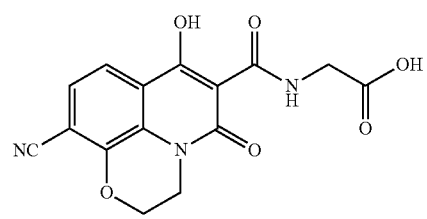 [SMILES: N#Cc1ccc2c(O)c(C(=O)NCC(=O)O)c(=O)n3c2c1OCC3]

Step A: tert-butyl 2-(10-cyano-7-hydroxy-5-oxo-3,5-dihydro-2H-[1,4]oxazino[2,3,4-ij]quinoline-6-carboxamido)acetate To a solution of Intermediate 3 (150 mg, 0.341 mmol) in DMA (2 mL) were added zinc cyanide (80 mg, 0.683 mmol), $Pd_2(dba)_3$ (31.3 mg, 0.034 mmol), DPPF (18.93 mg, 0.034 mmol) and Zinc dust (44.7 mg, 0.683 mmol). The reaction solution was heated at 130° C. by microwave for 30 min. TLC (petroleum ether: EtOAc=5:1) showed that the reaction completed. The mixture was cooled and quenched with water (10 mL). Then the mixture was extracted with ethyl acacate (3*20 mL). The combined organic fractions were washed with water (3*10 mL), dried ($Na_2SO_4$), filtered and the solvent was evaporated under reduced pressure. The residue was purified by silica gel column chromatography (EtOAc in petroleum ether: 0-60%) to give tert-butyl 2-(10-cyano-7-hydroxy-5-oxo-3,5-dihydro-2H-[1,4]oxazino[2,3,4-ij]quinoline-6-carboxamido)acetate as a solid. $^1$H NMR (CDCl$_3$, 400 MHz): δ 10.50 (s, 1H), 7.81 (d, J=8.0 Hz, 1H), 7.39 (d, J=8.0 Hz, 1H), 4.55 (t, J=5.2 Hz, 2H), 4.31 (t, J=5.2 Hz, 2H), 4.14 (d, J=5.2 Hz, 2H), 1.52 (s, 9H).

Step B: 2-(10-cyano-7-hydroxy-5-oxo-3,5-dihydro-2H-[1,4]oxazino[2,3,4-ij]quinoline-6-carboxamido) acetic acid To a solution of tert-butyl 2-(10-cyano-7-hydroxy-5-oxo-3,5-dihydro-2H-[1,4]oxazino[2,3,4-ij]quinoline-6-carboxamido)acetate (108 mg, 0.280 mmol) in DCM (1 mL) was added 2,2,2-trifluoroacetic acid (320 mg, 2.80 mmol). The resulting mixture was heated to 50° C. and stirred for 3 h. TLC (petroleum ether: EtOAc=2:1) showed that the reaction completed. The resulting mixture was concentrated in vacuo to give the crude which was re-crystallised from EtOAc (1 mL) and petroleum ether (15 mL) to give 2-(10-cyano-7-hydroxy-5-oxo-3,5-dihydro-2H-[1,4]oxazino[2,3,4-ij]quinoline-6-carboxamido)acetic acid as a solid. $^1$H NMR (DMSO-$d_6$, 400 MHz): δ 10.40 (t, J=5.2 Hz, 1H), 7.70 (d, J=8.0 Hz, 1H), 7.59 (d, J=8.0 Hz, 1H), 4.60 (t, J=4.4 Hz, 2H), 4.21 (t, J=4.4 Hz, 2H), 4.15 (d, J=5.6 Hz, 2H). LC/MS (m/z): 330 (M+H)$^+$. Human HIF-PHD2 $IC_{50}$: 1.5 nM.

Example 38

2-(7-Hydroxy-10-(methylsulfonyl)-5-oxo-3,5-dihydro-2H-[1,4]oxazino[2,3,4-ij]quinoline-6-carboxamido)acetic acid

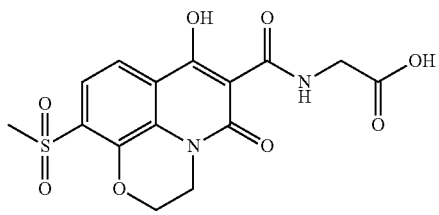 [SMILES: CS(=O)(=O)c1ccc2c(O)c(C(=O)NCC(=O)O)c(=O)n3c2c1OCC3]

Step A: tert-butyl 2-(7-hydroxy-10-(methylsulfonyl)-5-oxo-3,5-dihydro-2H-[1,4]oxazino[2,3,4-ij]quinoline-6-carboxamido)acetate A suspension of Intermediate 3 (200 mg, 0.455 mmol), sodium methanesulfinate (55.8 mg, 0.546 mmol), NaOH (3.64 mg, 0.091 mmol), L-proline (10.48 mg, 0.091 mmol) and copper(I) iodide (8.67 mg, 0.046 mmol) in DMSO (2 mL) was heated to 120° C. under $N_2$ and stirred at 120° C. for 60 h. The mixture was cooled and quenched with water (5 mL). Then the mixture was extracted with ethyl acacate (3*4 mL). The solvent was evaporated under reduced pressure. The residue was purified by silica gel column chromatography eluting with EtOAc in petroleum ether (0-30%) to give tert-butyl 2-(7-hydroxy-10-(methylsulfonyl)-5-oxo-3,5-dihydro-2H-[1,4]oxazino[2,3,4-ij]quinoline-6-carboxamido)acetate as a solid. $^1$H NMR (CDCl$_3$, 400 MHz): δ 10.50 (t, J=5.2 Hz, 1H), 7.92 (d, J=8.8 Hz, 1H), 7.82 (d, J=8.8 Hz, 1H), 4.60 (t, J=5.2 Hz, 2H), 4.35 (t, J=5.2 Hz, 2H), 4.15 (d, J=5.2 Hz, 2H), 3.30 (s, 3H), 1.52 (s, 9H).

Step B: 2-(7-hydroxy-10-(methylsulfonyl)-5-oxo-3,5-dihydro-2H-[1,4]oxazino[2,3,4-ij]quinoline-6-carboxamido)acetic acid To a solution of tert-butyl 2-(7-hydroxy-10-(methylsulfonyl)-5-oxo-3,5-dihydro-2H-[1,4]oxazino[2,3,4-ij]quinoline-6-carboxamido)acetate (60 mg, 0.137 mmol) in DCM (1 mL) was added 2,2,2-trifluoroacetic acid (156 mg, 1.368 mmol). The resulting mixture was heated to 50° C. and stirred for 3 h. TLC (petroleum ether: EtOAc=2:1) showed that the reaction completed. The resulting mixture was concentrated in vacuo to give the crude which was re-crystallised from EtOAc (1 mL) and petroleum ether (15 mL) to give 2-(7-hydroxy-10-(methylsulfonyl)-5-oxo-3,5-dihydro-2H-[1,4]oxazino[2,3,4-ij]quinoline-6-carboxamido)acetic acid as a solid. $^1$H NMR (DMSO-d$_6$, 400 MHz): δ 12.98 (brs, 1H), 10.42 (t, J=5.6 Hz, 1H), 7.81 (d, J=8.0 Hz, 1H), 7.68 (d, J=8.0 Hz, 1H), 4.62 (t, J=4.8 Hz, 2H), 4.22 (t, J=4.8 Hz, 2H), 4.16 (d, J=5.6 Hz, 2H), 3.36 (s, 3H). LC/MS (m/z): 383 (M+H)$^+$. Human HIF-PHD2 IC$_{50}$: 1.6 nM.

Example 39

2-(7-Hydroxy-10-methyl-5-oxo-3,5-dihydro-2H-[1,4]oxazino[2,3,4-ij]quinoline-6-carboxamido)acetic acid

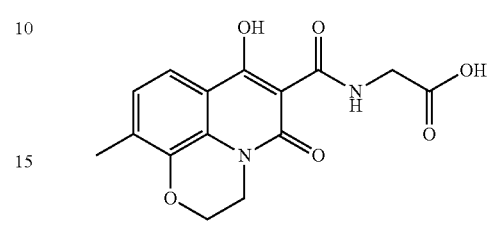

Step A: tert-butyl 2-(7-hydroxy-10-methyl-5-oxo-3,5-dihydro-2H-[1,4]oxazino[2,3,4-ij]quinoline-6-carboxamido)acetate A solution of Intermediate 3 (150 mg, 0.341 mmol), 2,4,6-trimethyl-1,3,5,2,4,6-trioxatriborinane (42.9 mg, 0.341 mmol), Pd(Ph$_3$P)$_4$ (39.5 mg, 0.034 mmol) and K$_2$CO$_3$ (142 mg, 1.024 mmol) in DMF (1 mL) was heated to 120° C. by microwave for 45 min. The resulting mixture was concentrated in vacuo to give the crude which was purified by silica gel column chromatography (EtOAc in petroleum ether: 0-15%) to give tert-butyl 2-(7-hydroxy-10-methyl-5-oxo-3,5-dihydro-2H-[1,4]oxazino[2,3,4-ij]quinoline-6-carboxamido)acetate as a solid. $^1$H NMR (CDCl$_3$, 400 MHz): δ 10.65 (t, J=5.2 Hz, 1H), 7.68 (d, J=8.8 Hz, 1H), 7.08 (d, J=8.8 Hz, 1H), 4.39 (t, J=5.2 Hz, 2H), 4.25 (t, J=5.2 Hz, 2H), 4.14 (d, J=5.2 Hz, 2H), 2.36 (s, 3H), 1.51 (s, 9H).

Step B: 2-(7-hydroxy-10-methyl-5-oxo-3,5-dihydro-2H-[1,4]oxazino[2,3,4-ij]quinoline-6-carboxamido)acetic acid To a solution of tert-butyl 2-(7-hydroxy-10-methyl-5-oxo-3,5-dihydro-2H-[1,4]oxazino[2,3,4-ij]quinoline-6-carboxamido)acetate (30 mg, 0.080 mmol) in DCM (1 mL) was added 2,2,2-trifluoroacetic acid (91 mg, 0.801 mmol). The resulting mixture was heated to 50° C. and stirred for 3 h. TLC (petroleum ether: EtOAc=5:1) showed that the reaction completed. The resulting mixture was concentrated in vacuo to give the crude which was re-crystallised from EtOAc (1 mL) and petroleum ether (15 mL) to give 2-(7-hydroxy-10-methyl-5-oxo-3,5-dihydro-2H-[1,4]oxazino[2,3,4-ij]quinoline-6-carboxamido)acetic acid as a solid. $^1$H NMR (DMSO-d$_6$, 400 MHz): δ 12.92 (brs, 1H), 10.47 (t, J=4.8 Hz, 1H), 7.56 (d, J=8.0 Hz, 1H), 7.17 (d, J=8.0 Hz, 1H), 4.42 (t, J=4.8 Hz, 2H), 4.14 (t, J=4.8 Hz, 2H), 4.13 (d, J=5.6 Hz, 2H), 2.08 (s, 3H). LC/MS (m/z): 319 (M+H)$^+$. Human HIF-PHD2 IC$_{50}$: 12 nM.

Following the same procedure of Example 39, compound of Example 40 in Table 1 was synthesized using phenylboronic acid.

TABLE 1

| Example Name | structure | MS m/z (m + 1)+ and human HIF-PHD2 IC50 |
|---|---|---|
| Example 40 | 2-(7-hydroxy-5-oxo-10-phenyl-3,5-dihydro-2H-[1,4]oxazino[2,3,4-ij]quinoline-6-carboxamido)acetic acid | (M + 1)+ 381<br>IC50: 1.6 nM |

Example 41

2-(9-Cyano-7-hydroxy-5-oxo-3,5-dihydro-2H-[1,4]oxazino[2,3,4-ij]quinoline-6-carboxamido)acetic acid

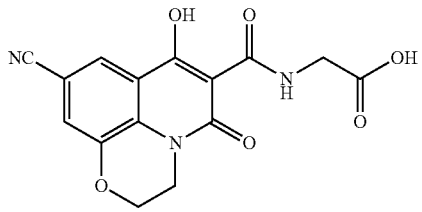 [SMILES: N#Cc1cc2c3c(c1)c(O)c(C(=O)NCC(=O)O)c(=O)n3CCO2]

Step A: 7-bromo-3,4-dihydro-2H-benzo[b][1,4]oxazine

A solution of 2-amino-5-bromophenol (1 g, 5.32 mmol), 1,2-dibromoethane (1.199 g, 6.38 mmol) and K$_2$CO$_3$ (2.205 g, 15.96 mmol) in DMF (10 mL) was heated to 125° C. and stirred at 125° C. for 16 h. LCMS showed that the reaction completed. The mixture was cooled to room temperature. The reaction mixture was diluted with aqueous NaCl (50 mL) and extracted with EtOAc (50 mL*3). The combined organic layers were washed with aqueous NaCl (50 mL*3), dried over Na$_2$SO$_4$, filtered and evaporated to give the crude which was purified by silica gel column chromatography (EtOAc in petroleum ether: 0-25%) to give 7-bromo-3,4-dihydro-2H-benzo[b][1,4]oxazine as an oil. $^1$H NMR (CDCl$_3$, 400 MHz): δ 6.92 (d, J=2.0 Hz, 1H), 6.86 (dd, J=2.0 Hz, 8.4 Hz, 1H), 6.46 (d, J=8.4 Hz, 1H), 4.24 (t, J=4.8 Hz, 2H), 3.76 (brs, 1H), 3.41 (t, J=4.8 Hz, 2H).

Step B: ethyl 9-bromo-7-hydroxy-5-oxo-3,5-dihydro-2H-[1,4]oxazino[2,3,4-ij]quinoline-6-carboxylate A mixture of 7-bromo-3,4-dihydro-2H-benzo[b][1,4]oxazine (760 mg, 3.55 mmol) and triethyl methanetricarboxylate (3298 mg, 14.20 mmol) was heated to 250° C. and stirred for 0.5 h. The resulting mixture was cooled to room temperature. The product was recrystallised from petroleum ether (50 mL) to give ethyl 9-bromo-7-hydroxy-5-oxo-3,5-dihydro-2H-[1,4]oxazino[2,3,4-ij]quinoline-6-carboxylate as a solid. $^1$H NMR (CDCl$_3$, 400 MHz): δ 14.25 (s, 1H), 7.88 (d, J=1.6 Hz, 1H), 7.33 (d, J=1.6 Hz, 1H), 4.52 (q, J=6.8 Hz, 14.0 Hz, 2H), 4.36 (t, J=5.2 Hz, 2H), 4.21 (t, J=5.2 Hz, 2H), 1.49 (t, J=6.8 Hz, 3H).

Step C: tert-butyl 2-(9-bromo-7-hydroxy-5-oxo-3,5-dihydro-2H-[1,4]oxazino[2,3,4-ij]quinoline-6-carboxamido)acetate A solution of ethyl 9-bromo-7-hydroxy-5-oxo-3,5-dihydro-2H-[1,4]oxazino[2,3,4-ij]quinoline-6-carboxylate (1g, 2.82 mmol), tert-butyl 2-aminoacetate HCl salt (0.568 g, 3.39 mmol) and DIPEA (1.134 mL, 6.49 mmol) in toluene (20 mL) was heated to 120° C. and stirred for 2 h. TLC (petroleum ether: EtOAc=5:1) showed that the reaction was comple. The resulting mixture was concentrated in vacuo to give the crude which was recrystallised from DCM (10 mL) and petroleum ether (15 mL) to give tert-butyl 2-(9-bromo-7-hydroxy-5-oxo-3,5-dihydro-2H-[1,4]oxazino[2,3,4-ij]quinoline-6-carboxamido)acetate as a solid. $^1$H NMR (CDCl$_3$, 400 MHz): δ 10.58 (t, J=5.2 Hz, 1H), 7.90 (d, J=1.6 Hz, 1H), 7.34 (d, J=1.6 Hz, 1H), 4.38 (t, J=5.2 Hz, 2H), 4.24 (t, J=5.2 Hz, 2H), 4.14 (d, J=5.2 Hz, 2H), 1.51 (s, 9H).

Step D: tert-butyl 2-(9-cyano-7-hydroxy-5-oxo-3,5-dihydro-2H-[1,4]oxazino[2,3,4-ij]quinoline-6-carboxamido)acetate To a solution of tert-butyl 2-(9-bromo-7-hydroxy-5-oxo-3,5-dihydro-2H-[1,4]oxazino[2,3,4-ij]quinoline-6-carboxamido)acetate (150 mg, 0.341 mmol) in DMA (2 mL) were added zinc cyanide (80 mg, 0.683 mmol), Pd$_2$(dba)$_3$ (31.3 mg, 0.034 mmol), DPPF (18.93 mg, 0.034 mmol) and Zinc dust (44.7 mg, 0.683 mmol). The reaction solution was heated to 130° C. by microwave for 30 min. TLC (petroleum ether: EtOAc=5:1) showed that the reaction was complete. The mixture was cooled and quenched with water (10 mL). Then the mixture was extracted with ethyl acacate (3*20 mL). The combined organic fractions were washed with water (3*30 mL), dried over Na$_2$SO$_4$, filtered and evaporated under reduced pressure. The residue was purified by silica gel column chromatography (EtOAc in petroleum ether: 0-60%) to give tert-butyl 2-(9-cyano-7-hydroxy-5-oxo-3,5-dihydro-2H-[1,4]oxazino[2,3,4-ij]quinoline-6-carboxamido)acetate as a solid. $^1$H NMR (CDCl$_3$, 400 MHz): δ 10.42 (t, J=5.2 Hz, 1H), 8.11 (d, J=1.6 Hz, 1H), 7.39 (d, J=1.6 Hz, 1H), 4.42 (t, J=5.2 Hz, 2H), 4.27 (t, J=5.2 Hz, 2H), 4.14 (d, J=5.2 Hz, 2H), 1.51 (s, 9H).

Step E: 2-(9-cyano-7-hydroxy-5-oxo-3,5-dihydro-2H-[1,4]oxazino[2,3,4-ij]quinoline-6-carboxamido)acetic acid To a solution of tert-butyl 2-(9-cyano-7-hydroxy-5-oxo-3,5-dihydro-2H-[1,4]oxazino[2,3,4-ij]quinoline-6-carboxamido)acetate (120 mg, 0.311 mmol) in DCM (1 mL) was added 2,2,2-trifluoroacetic acid (355 mg, 3.11 mmol). The resulting mixture was heated to 50° C. and stirred for 3 h. TLC (pretroleum ether: EtOAc=2:1) showed that the reaction was complete. The resulting mixture was concentrated in vacuo to give the crude which was re-crystallised from EtOAc (1 mL) and petroleum ether (15 mL) to give 2-(9-cyano-7-hydroxy-5-oxo-3,5-dihydro-2H-[1,4]oxazino[2,3,4-ij]quinoline-6-carboxamido)acetic acid as a solid. $^1$H NMR (DMSO-$d_6$, 400 MHz): δ 12.98 (brs, 1H), 10.32 (t, J=5.6 Hz, 1H), 8.04 (d, J=1.6 Hz, 1H), 7.74 (d, J=1.6 Hz, 1H), 4.45 (t, J=4.8 Hz, 2H), 4.16 (t, J=4.8 Hz, 2H), 4.15 (d, J=6.4 Hz, 2H). LC/MS (m/z): 330 (M+H)$^+$. Human HIF-PHD2 $IC_{50}$: 1.8 nM.

Example 42

2-(7-hydroxy-9-(methylsulfonyl)-5-oxo-3,5-dihydro-2H-[1,4]oxazino[2,3,4-ij]quinoline-6-carboxamido)acetic acid

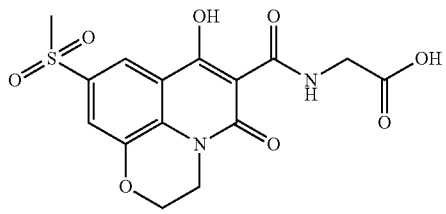 [SMILES: CS(=O)(=O)c1cc2c3c(c1)c(O)c(C(=O)NCC(=O)O)c(=O)n3CCO2]

Step A: tert-butyl 2-(7-hydroxy-9-(methylsulfonyl)-5-oxo-3,5-dihydro-2H-[1,4]oxazino[2,3,4-ij]quinoline-6-carboxamido)acetate A solution of Step C product of Example 41 (200 mg, 0.455 mmol), sodium methanesulfinate (55.8 mg, 0.546 mmol), NaOH (3.64 mg, 0.091 mmol), L-proline (10.48 mg, 0.091 mmol) and copper(I) iodide (8.67 mg, 0.046 mmol) in DMSO (2 mL) was stirred under $N_2$ at 120° C. for 60 h. The mixture was cooled and quenched with water (5 mL). Then the mixture was extracted with ethyl acacate (3*4 mL). The solvent was evaporated under reduced pressure, and the residue was purified by column chromatography on silica gel Isolute Flash Si; 5 g prepacked, eluting with (EtOAc in petroleum ether: 0-30%) to give tert-butyl 2-(7-hydroxy-9-(methylsulfonyl)-5-oxo-3,5-dihydro-2H-[1,4]oxazino[2,3,4-ij]quinoline-6-carboxamido)acetate as a solid. $^1$H NMR (CDCl$_3$, 400 MHz): δ 10.44 (t, J=5.2 Hz, 1H), 8.38 (d, J=1.6 Hz, 1H), 7.71 (d, J=1.6 Hz, 1H), 4.44 (t, J=4.4 Hz, 2H), 4.29 (t, J=4.4 Hz, 2H), 4.15 (d, J=5.6 Hz, 2H), 3.11 (s, 3H), 1.52 (s, 9H).

Step B: 2-(7-hydroxy-9-(methylsulfonyl)-5-oxo-3,5-dihydro-2H-[1,4]oxazino[2,3,4-ij]quinoline-6-carboxamido)acetic acid To a solution of tert-butyl 2-(7-hydroxy-9-(methylsulfonyl)-5-oxo-3,5-dihydro-2H-[1,4]oxazino[2,3,4-ij]quinoline-6-carboxamido)acetate (50 mg, 0.114 mmol) in DCM (1 mL) was added 2,2,2-trifluoroacetic acid (130 mg, 1.140 mmol). The resulting mixture was heated to 50° C. and stirred for 3 h. TLC (pretroleum ether: EtOAc=2:1) showed that the reaction was complete. The resulting mixture was concentrated in vacuo to give the crude which was re-crystallised from EtOAc (1 mL) and petroleum ether (15 mL) to give 2-(7-hydroxy-9-(methylsulfonyl)-5-oxo-3,5-dihydro-2H-[1,4]oxazino[2,3,4-ij]quinoline-6-carboxamido)acetic acid as a solid. $^1$H NMR (DMSO-$d_6$, 400 MHz): δ 13.01 (brs, 1H), 10.35 (t, J=5.6 Hz, 1H), 8.11 (d, J=1.6 Hz, 1H), 7.74 (d, J=1.6 Hz, 1H), 4.49 (t, J=4.8 Hz, 2H), 4.18 (t, J=4.8 Hz, 2H), 4.16 (d, J=6.4 Hz, 2H), 3.30 (s, 3H). LC/MS (m/z): 383 (M+H)$^+$. Human HIF-PHD2 $IC_{50}$: 1.8 nM.

Example 43

2-(7-hydroxy-9-methyl-5-oxo-3,5-dihydro-2H-[1,4]oxazino[2,3,4-ij]quinoline-6-carboxamido)acetic acid

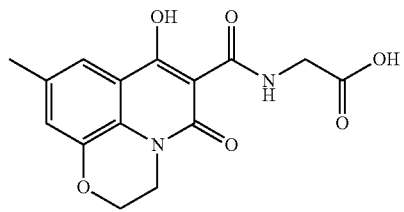 [SMILES: Cc1cc2c3c(c1)c(O)c(C(=O)NCC(=O)O)c(=O)n3CCO2]

Step A: tert-butyl 2-(7-hydroxy-9-methyl-5-oxo-3,5-dihydro-2H-[1,4]oxazino[2,3,4-ij]quinoline-6-carboxamido)acetate A solution of Step C product of Example 41 (150 mg, 0.341 mmol), 2,4,6-trimethyl-1,3,5,2,4,6-trioxatriborinane (86 mg, 0.683 mmol), Pd(Ph$_3$P)$_4$ (39.5 mg, 0.034 mmol) and K$_2$CO$_3$ (142 mg, 1.024 mmol) in DMF (1 mL) was heated to 130° C. by microwave for 45 min. To the reaction mixture was added aq NaCl (10 mL) and the mixture was extracted with DCM (10 mL*3). The organic layers were concentrated in vacuo, and the residue was purified by Combi-Flash (EtOAc in petroleum ether: 0-15%) to give tert-butyl 2-(7-hydroxy-9-methyl-5-oxo-3,5-dihydro-2H-[1,4]oxazino[2,3,4-ij]quinoline-6-carboxamido)acetate as a solid. $^1$H NMR (CDCl$_3$, 400 MHz): δ 10.70 (t, J=5.2 Hz, 1H), 7.57 (s, 1H), 7.05 (s, 1H), 4.36 (t, J=4.4 Hz, 2H), 4.24 (t, J=4.4 Hz, 2H), 4.14 (d, J=5.6 Hz, 2H), 2.41 (s, 3H), 1.51 (s, 9H).

Step B: 2-(7-hydroxy-9-methyl-5-oxo-3,5-dihydro-2H-[1,4]oxazino[2,3,4-ij]quinoline-6-carboxamido)acetic acid To a solution of tert-butyl 2-(7-hydroxy-9-methyl-5-oxo-3,5-dihydro-2H-[1,4]oxazino[2,3,4-ij]quinoline-6-carboxamido)acetate (30 mg, 0.080 mmol) in DCM (1 mL) was added 2,2,2-trifluoroacetic acid (91 mg, 0.801 mmol). The resulting mixture was heated to 50° C. and stirred for 3 h. TLC (petroleum ether: EtOAc=5:1) showed that the reaction was completed. The resulting mixture was concentrated in vacuo to give the crude which was re-crystallised from EtOAc (1 mL) and petroleum ether (15 mL) to give 2-(7-hydroxy-9-methyl-5-oxo-3,5-dihydro-2H-[1,4]oxazino[2,3,4-ij]quinoline-6-carboxamido)acetic acid as a solid. $^1$H NMR (DMSO-$d_6$, 400 MHz): δ 10.51 (t, J=5.6 Hz, 1H), 7.45 (s, 1H), 7.16 (s, 1H), 4.38 (t, J=4.4 Hz, 2H), 4.13 (d, J=5.6 Hz, 2H), 4.13 (t, J=4.4 Hz, 2H), 2.36 (s, 3H). LC/MS (m/z): 319 (M+H)$^+$. Human HIF-PHD2 $IC_{50}$: 24 nM.

Example 44

2-(8-Cyano-1-hydroxy-3-oxo-3,5,6,7-tetrahydropyrido[3,2,1-ij]quinoline-2-carboxamido)acetic acid

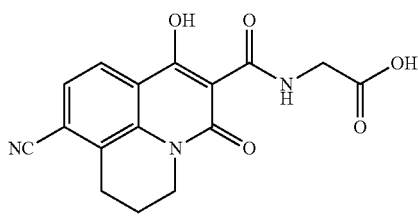 [SMILES: N#Cc1ccc2c(O)c(C(=O)NCC(=O)O)c(=O)n3c2c1CCC3]

Step A: ethyl 8-bromo-1-hydroxy-3-oxo-3,5,6,7-tetrahydropyrido[3,2,1-ij]quinoline-2-carboxylate A mixture of 5-bromo-1,2,3,4-tetrahydroquinoline (211 mg, 1 mmol) and triethyl methanetricarboxylate (928 mg, 4 mmol) was stirred at 250° C. for 0.5 h. The resulting mixture was cooled to room temperature and recrystallization from petroleum ether (50 mL) gave ethyl 8-bromo-1-hydroxy-3-oxo-3,5,6,7-tetrahydropyrido[3,2,1-ij]quinoline-2-carboxylate as a solid. $^1$H NMR (CDCl$_3$, 400 MHz): δ 14.14 (s, 1H), 7.88 (d, J=8.0 Hz, 1H), 7.42 (d, J=8.0 Hz, 1H), 4.51 (q, J=7.2 Hz, 14.8 Hz, 2H), 4.14 (t, J=5.6 Hz, 2H), 3.00 (t, J=5.6 Hz, 2H), 2.06-2.12 (m, 2H), 1.49 (t, J=7.2 Hz, 3H).

Step B: tert-butyl 2-(8-bromo-1-hydroxy-3-oxo-3,5,6,7-tetrahydropyrido[3,2,1-ij]quinoline-2-carboxamido)acetate A solution of ethyl 8-bromo-1-hydroxy-3-oxo-3,5,6,7-tetrahydropyrido[3,2,1-ij]quinoline-2-carboxylate (351 mg, 1.0 mmol), tert-butyl 2-aminoacetate HCl salt (200 mg, 1.2 mmol) and DIPEA (297 mg, 2.3 mmol) in toluene (10 mL) was stirred at 120° C. for 2 h. TLC (petroleum ether: EtOAc=5:1) showed that the reaction was complete. The resulting mixture was concentrated in vacuo to give the crude which was crystallised from DCM (4 mL) and petroleum ether (1 mL) to give tert-butyl 2-(8-bromo-1-hydroxy-3-oxo-3,5,6,7-tetrahydropyrido[3,2,1-ij]quinoline-2-carboxamido)acetate as a solid. $^1$H NMR (CDCl$_3$, 400 MHz): δ 10.70 (s, 1H), 7.89 (d, J=8.0 Hz, 1H), 7.45 (d, J=8.0 Hz, 1H), 4.17 (t, J=6.0 Hz, 2H), 4.13 (d, J=5.2 Hz, 2H), 3.01 (t, J=6.0 Hz, 2H), 2.05-2.18 (m, 2H), 1.51 (s, 9H).

Step C: tert-butyl 2-(8-cyano-1-hydroxy-3-oxo-3,5,6,7-tetrahydropyrido[3,2,1-ij]quinoline-2-carboxamido)acetate To a solution of tert-butyl 2-(8-bromo-1-hydroxy-3-oxo-3,5,6,7-tetrahydropyrido[3,2,1-ij]quinoline-2-carboxamido)acetate (436 mg, 1.0 mmol) in DMA (2 mL) were added zinc cyanide (234 mg, 2.0 mmol), Pd$_2$(dba)$_3$ (91.5 mg, 0.1 mmol), dppf (13.92 mg, 0.1 mmol) and zinc dust (130 mg, 2 mmol). The reaction solution was heated to 130° C. by microwave for 30 min. TLC (petroleum ether: EtOAc=2:1) showed that the reaction was complete. The mixture was cooled, water (10 mL) was added and the mixture was extracted with ethyl acacate (3*20 mL). The combined organic fractions were washed with water (3*30 mL), dried (Na$_2$SO$_4$), filtered and the solvent was evaporated under reduced pressure. The residue was purified by silica gel column chromatography (EtOAc in petroleum ether: 0-60%) to give tert-butyl 2-(8-cyano-1-hydroxy-3-oxo-3,5,6,7-tetrahydropyrido[3,2,1-ij]quinoline-2-carboxamido)acetate as a solid. $^1$H NMR (CDCl$_3$, 400 MHz): δ 10.66 (s, 1H), 8.13 (d, J=8.0 Hz, 1H), 7.47 (d, J=8.0 Hz, 1H), 4.21 (t, J=6.0 Hz, 2H), 4.14 (d, J=5.2 Hz, 2H), 3.22 (t, J=6.0 Hz, 2H), 2.15-2.22 (m, 2H), 1.52 (s, 9H).

Step D: 2-(8-cyano-1-hydroxy-3-oxo-3,5,6,7-tetrahydropyrido[3,2,1-ij]quinoline-2-carboxamido)acetic acid To a solution of tert-butyl 2-(8-cyano-1-hydroxy-3-oxo-3,5,6,7-tetrahydropyrido[3,2,1-ij]quinoline-2-carboxamido)acetate (383 mg, 1.0 mmol) in DCM (1 mL) was added 2,2,2-trifluoroacetic acid (1140 mg, 10 mmol). The resulting mixture was stirred at 60° C. for 3 h. TLC (petroleum ether: EtOAc=2:1) showed that the reaction was complete. The resulting mixture was concentrated in vacuo to give the crude which was re-crystallised from EtOAc (1 mL) and petroleum ether (10 mL) to give 2-(8-cyano-1-hydroxy-3-oxo-3,5,6,7-tetrahydropyrido[3,2,1-ij]quinoline-2-carboxamido)acetic acid as a solid. $^1$H NMR (DMSO-d$_6$, 400 MHz): δ 10.49 (t, J=5.6 Hz, 1H), 8.04 (d, J=8.0 Hz, 1H), 7.67 (d, J=8.0 Hz, 1H), 4.14 (d, J=8.0 Hz, 2H), 4.09 (t, J=6.4 Hz, 2H), 3.12 (t, J=6.4 Hz, 2H), 2.06-2.12 (m, 2H). LC/MS (m/z): 328 (M+H)$^+$. Human HIF-PHD2 IC$_{50}$: 0.9 nM.

Example 45

2-(1-Hydroxy-8-(methylsulfonyl)-3-oxo-3,5,6,7-tetrahydropyrido[3,2,1-ij]quinoline-2-carboxamido)acetic acid

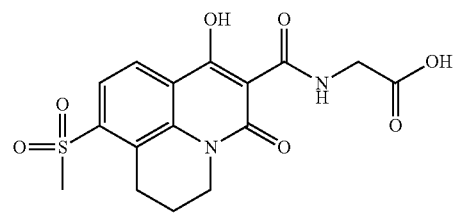 [SMILES: CS(=O)(=O)c1ccc2c(O)c(C(=O)NCC(=O)O)c(=O)n3c2c1CCC3]

Step A: tert-butyl 2-(1-hydroxy-8-(methylsulfonyl)-3-oxo-3,5,6,7-tetrahydropyrido[3,2,1-ij]quinoline-2-carboxamido)acetate A suspension of Step B product of Example 44 (436 mg, 1.0 mmol), sodium methanesulfinate (122.4 mg, 1.2 mmol), NaOH (8 mg, 0.2 mmol), L-proline (23 mg, 0.2 mmol) and copper(I) iodide (19 mg, 0.1 mmol) in DMSO (2 mL) was stirred at 120° C. under N$_2$ for 60 h. The mixture was cooled, water (5 mL) was added and the mixture was extracted with ethyl acacate (3*4 mL). The solvent was evaporated under reduced pressure. The residue was purified by column chromatography on silica gel Isolute Flash Si; 5 g prepacked, eluting with (EtOAc in DCM: 0-20%) to give tert-butyl 2-(1-hydroxy-8-(methylsulfonyl)-3-oxo-3,5,6,7-tetrahydropyrido[3,2,1-ij]quinoline-2-carboxamido)acetate as a solid. $^1$H NMR (CDCl$_3$, 400 MHz): δ 10.67 (s, 1H), 8.26 (d, J=8.0 Hz, 1H), 7.94 (d, J=8.0 Hz, 1H), 4.21 (t, J=6.0 Hz, 2H), 4.14 (d, J=5.2 Hz, 2H), 3.47 (t, J=6.0 Hz, 2H), 3.17 (s, 3H), 2.14-2.20 (m, 2H), 1.52 (s, 9H).

Step B: 2-(1-hydroxy-8-(methylsulfonyl)-3-oxo-3,5,6,7-tetrahydropyrido[3,2,1-ij]quinoline-2-carboxamido)acetic acid To a solution of tert-butyl 2-(1-hydroxy-8-(methylsulfonyl)-3-oxo-3,5,6,7-tetrahydropyrido[3,2,1-ij]quinoline-2-carboxamido)acetate (436 mg, 1.0 mmol) in DCM (1 mL) was added 2,2,2-trifluoroacetic acid (1140 mg, 10 mmol). The resulting mixture was heated to 60° C. and stirred for 3 h. TLC (petroleum ether: EtOAc=2:1) showed that the reaction was completed. The resulting mixture was concentrated in vacuo to give the crude which was re-crystallised with EtOAc (1 mL) and petroleum ether (10 mL) to give 2-(1-hydroxy-8-(methylsulfonyl)-3-oxo-3,5,6,7-tetrahydropyrido[3,2,1-ij]quinoline-2-carboxamido)acetic acid as a solid. $^1$H NMR (DMSO-$d_6$, 400 MHz): δ 10.51 (t, J=5.6 Hz, 1H), 8.16 (d, J=8.0 Hz, 1H), 7.85 (d, J=8.0 Hz, 1H), 4.15 (d, J=6.4 Hz, 2H), 4.09 (t, J=5.6 Hz, 2H), 3.38 (t, J=5.6 Hz, 2H), 3.34 (s, 3H), 2.04-2.10 (m, 2H). LC/MS (m/z): 381 (M+H)$^+$. Human HIF-PHD2 IC$_{50}$: 1.1 nM.

Example 46

2-(1-Hydroxy-8-methyl-3-oxo-3,5,6,7-tetrahydropyrido[3,2,1-ij]quinoline-2-carboxamido)acetic acid

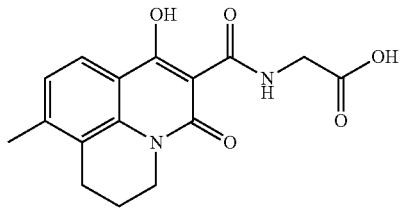 [SMILES: Cc1ccc2c(O)c(C(=O)NCC(=O)O)c(=O)n3c2c1CCC3]

Step A: tert-butyl 2-(1-hydroxy-8-methyl-3-oxo-3,5,6,7-tetrahydropyrido[3,2,1-ij]quinoline-2-carboxamido)acetate A solution of Step B product of Example 44 (436 mg, 1.0 mmol), 2,4,6-trimethyl-1,3,5,2,4,6-trioxatriborinane (126 mg, 1.0 mmol), Pd(Ph$_3$P)$_4$ (115.5 mg, 0.1 mmol) and K$_2$CO$_3$ (444 mg, 3.0 mmol) in DMF (3 mL) was heated at 120° C. by microwave for 1 h. TLC (petroleum ether: EtOAc=5:1) showed that the reaction was complete. Brine (10 mL) was added and the mixture was extracted with DCM (10 mL*3). The organic layers were concentrated in vacuo to give the crude which was purified by silica gel column chromatography (EtOAc in petroleum ether: 0-15%) to give tert-butyl 2-(1-hydroxy-8-methyl-3-oxo-3,5,6,7-tetrahydropyrido[3,2,1-ij]quinoline-2-carboxamido)acetate as a solid. $^1$H NMR (CDCl$_3$, 400 MHz): δ 10.81 (s, 1H), 7.95 (d, J=8.0 Hz, 1H), 7.10 (d, J=8.0 Hz, 1H), 4.18 (t, J=6.0 Hz, 2H), 4.14 (d, J=5.2 Hz, 2H), 2.85 (t, J=6.0 Hz, 2H), 2.40 (s, 3H), 2.08-2.14 (m, 2H), 1.51 (s, 9H).

Step B: 2-(1-hydroxy-8-methyl-3-oxo-3,5,6,7-tetrahydropyrido[3,2,1-ij]quinoline-2-carboxamido)acetic acid To a solution of tert-butyl 2-(1-hydroxy-8-methyl-3-oxo-3,5,6,7-tetrahydropyrido[3,2,1-ij]quinoline-2-carboxamido)acetate (372 mg, 1.0 mmol) in DCM (1 mL) was added 2,2,2-trifluoroacetic acid (1140 mg, 10 mmol). The resulting mixture was heated to 60° C. and stirred for 3 h. TLC (petroleum ether: EtOAc=2:1) showed that the reaction was complete. The resulting mixture was concentrated in vacuo to give the crude which was re-crystallised with EtOAc (1 mL) and petroleum ether (10 mL) to give 2-(1-hydroxy-8-methyl-3-oxo-3,5,6,7-tetrahydropyrido[3,2,1-ij]quinoline-2-carboxamido)acetic acid as a solid. $^1$H NMR (DMSO-$d_6$, 400 MHz): δ 10.57 (t, J=5.6 Hz, 1H), 7.82 (d, J=8.0 Hz, 1H), 7.18 (d, J=8.0 Hz, 1H), 4.12 (d, J=5.6 Hz, 2H), 4.06 (t, J=5.6 Hz, 2H), 2.82 (t, J=5.6 Hz, 2H), 2.37 (s, 3H), 2.00-2.05 (m, 2H). LC/MS (m/z): 317 (M+H)$^+$. Human HIF-PHD2 IC$_{50}$: 18 nM.

Example 47

2-(9-Bromo-1-hydroxy-3-oxo-3,5,6,7-tetrahydropyrido[3,2,1-ij]quinoline-2-carboxamido)acetic acid

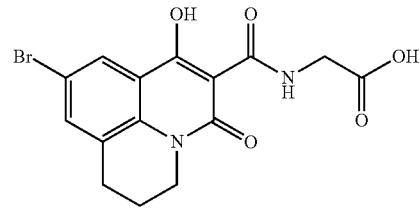 [SMILES: O=C(O)CNC(=O)c1c(O)c2cc(Br)cc3c2n(c1=O)CCC3]

Step A: ethyl 9-bromo-1-hydroxy-3-oxo-3,5,6,7-tetrahydropyrido[3,2,1-ij]quinoline-2-carboxylate A mixture of 6-bromo-1,2,3,4-tetrahydroquinoline (211 mg, 1 mmol) and triethyl methanetricarboxylate (928 mg, 4 mmol) was stirred at 250° C. for 0.5 h. The resulting mixture was cooled to room temperature then recrystallised from petroleum ether (50 mL) to give ethyl 9-bromo-1-hydroxy-3-oxo-3,5,6,7-tetrahydropyrido[3,2,1-ij]quinoline-2-carboxylate as a solid. $^1$H NMR (CDCl$_3$, 400 MHz) δ 14.11 (s, 1H), 8.11 (s, 1H), 7.51 (s, 1H), 4.49 (q, J=6.8 Hz, 2H), 4.11 (t, J=6.0 Hz, 2H), 2.95-2.91 (m, 2H), 2.06 (t, J=6.0 Hz, 2H), 1.48 (t, J=7.2 Hz, 3H).

Step B: tert-butyl 2-(9-bromo-1-hydroxy-3-oxo-3,5,6,7-tetrahydropyrido[3,2,1-ij]quinoline-2-carboxamido)acetate To a solution of ethyl 9-bromo-1-hydroxy-3-oxo-3,5,6,7-tetrahydropyrido[3,2,1-ij]quinoline-2-carboxylate (500 mg, 1.42 mmol) in toluene (10 mL) was added tert-butyl 2-aminoacetate hydrochloride (495 mg, 2.13 mmol) and DIPEA (732 mg, 5.68 mmol). The mixture was refluxed for 3 h. The residue was concentrated in vacuum to remove the solvent, then diluted with DCM (20 mL), washed with water (10 mL), 0.5 M aq HCl solution (10 mL) and brine (10 mL). The organic layer was dried over Na$_2$SO$_4$, concentrated in vacuum to give the tert-butyl 2-(9-bromo-1-hydroxy-3-oxo-3,5,6,7-tetrahydropyrido[3,2,1-ij]quinoline-2-carboxamido)acetate as a solid, which was used for next step without further purification. $^1$H NMR (CDCl$_3$, 400 MHz) δ 10.56 (s, 1H), 8.14 (s, 1H), 7.51 (s, 1H), 4.16-4.11 (m, 4H), 2.95 (t, J=6.0 Hz, 2H), 2.09 (t, J=6.0 Hz, 2H), 1.50 (s, 9H).

Step C: 2-(9-bromo-1-hydroxy-3-oxo-3,5,6,7-tetrahydropyrido[3,2,1-ij]quinoline-2-carboxamido)acetic acid To a solution of tert-butyl 2-(9-bromo-1-hydroxy-3-oxo-3,5,6,7-tetrahydropyrido[3,2,1-ij]quinoline-2-carboxamido)

acetate (50 mg, 0.11 mmol) in DCM (2 mL) was added TFA (0.5 mL). The mixture was stirred at room temperature for 5 h when LC-MS showed the reaction was complete. The mixture was concentrated in vacuum to give the crude, which was washed with a mixed solvent of petroleum ether and EtOAc (3:1, 10 mL) to give the 2-(9-bromo-1-hydroxy-3-oxo-3,5,6,7-tetrahydropyrido[3,2,1-ij]quinoline-2-carboxamido)acetic acid as a solid. $^1$H NMR (DMSO-d$_6$, 400 MHz): δ 10.53 (brs, 1H), 7.96 (s, 1H), 7.75 (s, 1H), 4.11-4.13 (m, 2H), 4.04-4.06 (m, 2H), 2.95-2.97 (m, 2H), 1.95-2.01 (m, 2H). LC/MS (m/z): 383 (M+H)$^+$. Human HIF-PHD2 IC$_{50}$: 99 nM.

Example 48

2-(9-Cyano-1-hydroxy-3-oxo-3,5,6,7-tetrahydropyrido[3,2,1-ij]quinoline-2-carboxamido)acetic acid

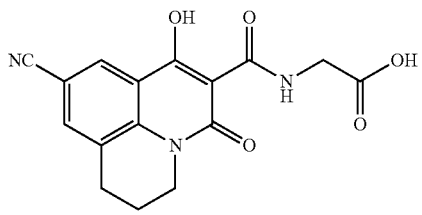

Step A: tert-butyl 2-(9-cyano-1-hydroxy-3-oxo-3,5,6,7-tetrahydropyrido[3,2,1-ij]quinoline-2-carboxamido)acetate To a solution of Step B product of Example 47 (200 mg, 0.46 mmol) in DMA (4 mL) were added zinc cyanide (140 mg, 1.196 mmol), Pd$_2$(dba)$_3$ (54 mg, 0.0598 mmol), DPPF (33.2 mg, 0.00598 mmol) and zinc (78.2 mg, 1.196 mmol). The reaction solution was heated at 120° C. by microwave for 30 mins. TLC (petroleum ether: EtOAc=5:1) showed that the reaction was complete. The mixture was cooled, water (10 mL) was added and the mixture was extracted with EtOAc (3*10 mL). The combined organic fractions were washed with water (3*10 mL), dried over Na$_2$SO$_4$, filtered and the solvent was evaporated under reduced pressure. The residue was purified by silica gel column chromatography (EtOAc in petroleum ether: 0-40%) to give tert-butyl 2-(9-cyano-1-hydroxy-3-oxo-3,5,6,7-tetrahydropyrido[3,2,1-ij]quinoline-2-carboxamido)acetate as a solid. $^1$H NMR (CDCl$_3$, 400 MHz) δ 10.51 (t, J=4.8 Hz, 1H), 8.35 (s, 1H), 7.61 (s, 1H), 4.17 (t, J=6.0 Hz, 2H), 4.12 (d, J=5.2 Hz, 2H), 3.0 (t, J=6.0 Hz, 2H), 2.12 (t, J=6.0 Hz, 2H), 1.50 (s, 9H).

Step B: 2-(9-cyano-1-hydroxy-3-oxo-3,5,6,7-tetrahydropyrido[3,2,1-ij]quinoline-2-carboxamido)acetic acid To a solution of tert-butyl 2-(9-cyano-1-hydroxy-3-oxo-3,5,6,7-tetrahydropyrido[3,2,1-ij]quinoline-2-carboxamido)acetate (383 mg, 1.0 mmol) in DCM (1 mL) was added 2,2,2-trifluoroacetic acid (1140 mg, 10 mmol). The resulting mixture was heated at 60° C. for 3 h. TLC (pretroleum ether: EtOAc=2:1) showed that the reaction was complete. The resulting mixture was concentrated in vacuo to give the crude which was re-crystallised with EtOAc (1 mL) and petroleum ether (10 mL) to give 2-(9-cyano-1-hydroxy-3-oxo-3,5,6,7-tetrahydropyrido[3,2,1-ij]quinoline-2-carbox-amido)acetic acid as a solid. $^1$H NMR (DMSO-d$_6$, 400 MHz) δ 12.97 (brs, 1H), 10.41 (t, J=4.8 Hz, 1H), 8.27 (s, 1H), 7.96 (s, 1H), 4.14 (d, J=5.6 Hz, 2H), 4.06 (t, J=5.6 Hz, 2H), 2.98-2.96 (m, 2H), 2.03-2.01 (m, 2H). LC/MS (m/z): 328 (M+H)$^+$. Human HIF-PHD2 IC$_{50}$: 2.6 nM.

Example 49

2-(1-Hydroxy-9-(methylsulfonyl)-3-oxo-3,5,6,7-tetrahydropyrido[3,2,1-ij]quinoline-2-carboxamido)acetic acid

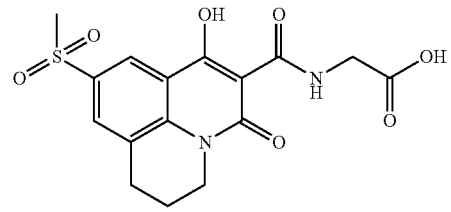 [SMILES: CS(=O)(=O)c1cc2c3c(c1)c(O)c(C(=O)NCC(=O)O)c(=O)n3CCC2]

Step A: tert-butyl 2-(1-hydroxy-9-(methylsulfonyl)-3-oxo-3,5,6,7-tetrahydropyrido[3,2,1-ij]quinoline-2-carboxamido)acetate A solution of Step B product of Example 47 (436 mg, 1.0 mmol), sodium methanesulfinate (122 mg, 1.2 mmol), NaOH (8 mg, 0.2 mmol), L-proline (23 mg, 0.2 mmol) and copper(I) iodide (19 mg, 0.1 mmol) in DMSO (2 mL) was stirred at 120° C. under N$_2$ for 60 h. The mixture was cooled, water (5 mL) was added and the mixture was extracted with ethyl acacate (3*4 mL). The solvent was evaporated under reduced pressure. The residue was purified by column chromatography on silica gel Isolute Flash Si; 5 g prepacked, eluting with (EtOAc in DCM: 0-20%) to give tert-butyl 2-(1-hydroxy-9-(methylsulfonyl)-3-oxo-3,5,6,7-tetrahydropyrido[3,2,1-ij]quinoline-2-carboxamido)acetate as a solid. $^1$H NMR (CDCl$_3$, 400 MHz): δ 10.54 (t, J=5.2 Hz, 1H), 8.60 (s, 1H), 7.89 (s, 1H), 4.17 (t, J=6.0 Hz, 2H), 4.11 (d, J=5.2 Hz, 2H), 3.08 (s, 3H), 3.03 (t, J=6.0 Hz, 2H), 2.15-2.09 (m, 2H), 1.49 (s, 9H).

Step B: 2-(1-hydroxy-9-(methylsulfonyl)-3-oxo-3,5,6,7-tetrahydropyrido[3,2,1-ij]quinoline-2-carboxamido)acetic acid To a solution of tert-butyl 2-(1-hydroxy-9-(methylsulfonyl)-3-oxo-3,5,6,7-tetrahydropyrido[3,2,1-ij]quinoline-2-carboxamido)acetate (436 mg, 1.0 mmol) in DCM (1 mL) was added 2,2,2-trifluoroacetic acid (1140 mg, 10 mmol). The resulting mixture was heated at 60° C. for 3 h. TLC (petroleum ether: EtOAc=2:1) showed that the reaction was complete. The resulting mixture was concentrated in vacuo to give the crude which was re-crystallised with EtOAc (1 mL) and petroleum ether (10 mL) to give 2-(1-hydroxy-9-(methylsulfonyl)-3-oxo-3,5,6,7-tetrahydropyrido[3,2,1-ij]quinoline-2-carboxamido)acetic acid as a solid. $^1$H NMR (DMSO-d$_6$, 400 MHz) δ 10.44 (t, J=5.2 Hz, 1H), 8.37 (s, 1H), 8.06 (s, 1H), 4.15 (d, J=5.2 Hz, 2H), 4.09 (t, J=4.8 Hz, 2H), 3.27 (s, 3H), 3.05-3.04 (m, 2H), 2.01-2.0 (m, 2H). LC/MS (m/z): 381 (M+H)$^+$. Human HIF-PHD2 IC$_{50}$: 1.4 nM.

Example 50, 50a and 50b 2-(1-Hydroxy-3-oxo-6-(thiazol-5-yl)-3,5,6,7-tetrahydropyrido[3,2,1-ij]quinoline-2-carboxamido)acetic acid

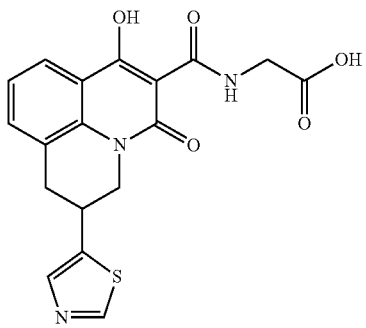

Example 50
(racemic)

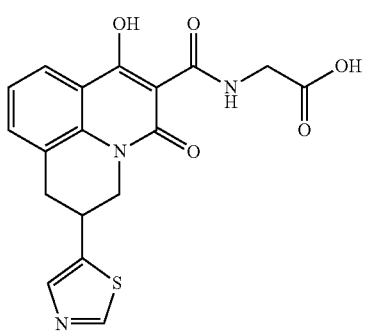

Example 50a
(enantiomer 1)

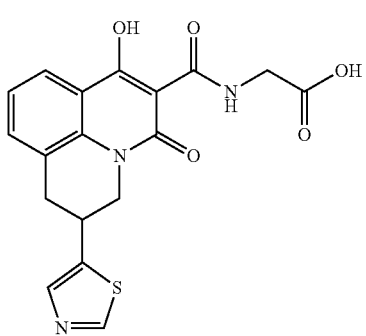

Example 50b
(enantiomer 2)

Step A: 5-(quinolin-3-yl)thiazole

To a solution of 5-bromothiazole (3 g, 18.29 mmol), quinolin-3-ylboronic acid (4.75 g, 27.4 mmol), Pd(Ph$_3$P)$_4$ (2.114 g, 1.829 mmol) and K$_2$CO$_3$ (7.58 g, 54.9 mmol) in DMF (50 mL) was heated to 120° C. and stirred for 16 h. TLC (petroleum ether: EtOAc=5:1) showed that the reaction was complete. To the resulting mixture was added a.q NaCl (100 mL) and extracted with DCM (100 mL*3). The organic layers were concentrated in vacuo to give crude which was purified by silica gel column chromatography (EtOAc in petroleum ether: 0-15%) to give 5-(quinolin-3-yl)thiazole as a solid. $^1$H NMR (CDCl$_3$, 400 MHz): δ 9.17 (d, J=2.0 Hz, 1H), 8.89 (s, 1H), 8.31 (d, J=2.0 Hz, 1H), 8.28 (s, 1H), 8.14 (d, J=8.8 Hz, 1H), 7.88 (d, J=8.0 Hz, 1H), 7.76 (td, J=0.8 Hz, 8.0 Hz, 1H), 7.47 (td, J=2.4 Hz, 8.0 Hz, 1H).

Step B: 5-(1,2,3,4-tetrahydroquinolin-3-yl)thiazole

To a solution of 5-(quinolin-3-yl)thiazole (1 g, 4.71 mmol) in Ethanol (20 mL) was PtO$_2$ (0.535 g, 2.355 mmol). The resulting mixture was heated to 110° C. under H$_2$ (2 MPa) and stirred at 110° C. for 16 h. The new point was detected by TLC (DCM) and the starting material was not consumed complete. The resulting mixture was filtered and concentrated in vacuo to give crude which was purified by silica gel column chromatography (EtOAc in DCM: 0-10%) to give 5-(1,2,3,4-tetrahydroquinolin-3-yl)thiazole as an oil. $^1$H NMR (CDCl$_3$, 400 MHz): δ 8.71 (s, 1H), 7.74 (s, 1H), 7.04 (t, J=7.6 Hz, 1H), 6.99 (d, J=7.6 Hz, 1H), 6.67 (td, J=1.2 Hz, 7.6 Hz, 1H), 6.56 (d, J=7.6 Hz, 1H), 4.02 (brs, 1H), 3.59-3.65 (m, 2H), 3.35 (dd, J=7.2 Hz, 11.2 Hz, 1H), 3.20 (dd, J=4.0 Hz, 10.8 Hz, 1H), 2.97 (dd, J=5.2 Hz, 16.0 Hz, 1H).

Step C: ethyl 1-hydroxy-3-oxo-6-(thiazol-5-yl)-3,5,6,7-tetrahydropyrido[3,2,1-ij]quinoline-2-carboxylate A mixture of 5-(1,2,3,4-tetrahydroquinolin-3-yl)thiazole (170 mg, 0.786 mmol) and triethyl methanetricarboxylate (730 mg, 3.14 mmol) was heated to 250° C. and stirred at 250° C. for 10 min. The resulting mixture was cooled to room temperature then purified by silica gel column chromatography (EtOAc in DCM: 0-10%) to give ethyl 1-hydroxy-3-oxo-6-(thiazol-5-yl)-3,5,6,7-tetrahydropyrido[3,2,1-ij]quinoline-2-carboxylate as a solid. $^1$H NMR (CDCl$_3$, 400 MHz): δ 14.22 (s, 1H), 8.73 (s, 1H), 8.08 (d, J=8.0 Hz, 1H), 7.76 (s, 1H), 7.48 (d, J=8.0 Hz, 1H), 7.21 (t, J=8.0 Hz, 1H), 4.81 (dd, J=2.0 Hz, 13.6 Hz, 1H), 4.51 (dd, J=7.2 Hz, 14.0 Hz, 2H), 3.94 (dd, J=9.6 Hz, 14.0 Hz, 1H), 3.68-3.74 (m, 1H), 4.41 (dd, J=3.2 Hz, 16.0 Hz, 1H), 3.21 (dd, J=10.0 Hz, 16.0 Hz, 1H), 1.49 (t, J=6.8 Hz, 3H).

Step D: tert-butyl 2-(1-hydroxy-3-oxo-6-(thiazol-5-yl)-3,5,6,7-tetrahydropyrido[3,2,1-ij]quinoline-2-carboxamido)acetate To a solution of ethyl 1-hydroxy-3-oxo-6-(thiazol-5-yl)-3,5,6,7-tetrahydropyrido[3,2,1-ij]quinoline-2-carboxylate (110 mg, 0.309 mmol), tert-butyl 2-aminoacetate. HCl (62.1 mg, 0.370 mmol) and DIPEA (124 μL, 0.710 mmol) in Toluene (5 mL) was heated to 120° C. and stirred at 120° C. for 2 h. TLC (petroleum ether: EtOAc=2:1) showed that the reaction was complete. The resulting mixture was concentrated in vacuo to give crude then purified by silica gel column chromatography (EtOAc in DCM: 0-10%) to give tert-butyl 2-(1-hydroxy-3-oxo-6-(thiazol-5-yl)-3,5,6,7-tetrahydropyrido[3,2,1-ij]quinoline-2-carboxamido)acetate as a solid. $^1$H NMR (CDCl$_3$, 400 MHz): δ 10.71 (t, J=5.6 Hz, 1H), 8.75 (s, 1H), 8.10 (d, J=8.0 Hz, 1H), 7.78 (s, 1H), 7.49 (d, J=8.0 Hz, 1H), 7.25 (t, J=8.0 Hz, 1H), 4.84 (d, J=12.0 Hz, 1H), 4.08-4.20 (m, 2H), 3.96 (t, J=12.4 Hz, 1H), 3.70-3.77 (m, 1H), 3.43 (dd, J=3.2 Hz, 16 Hz, 1H), 3.23 (dd, J=10.4 Hz, 16 Hz, 1H), 1.51 (s, 9H).

Step E: 2-(1-hydroxy-3-oxo-6-(thiazol-5-yl)-3,5,6,7-tetrahydropyrido[3,2,1-ij]quinoline-2-carboxamido) acetic acid To a solution of tert-butyl 2-(1-hydroxy-3-oxo-6-(thiazol-5-yl)-3,5,6,7-tetrahydropyrido[3,2,1-ij]quinoline-2-carboxamido)acetate (120 mg, 0.272 mmol) in DCM (1 mL) was added 2,2,2-trifluoroacetic acid (310 mg, 2.72 mmol). The resulting mixture was heated to 50° C. and stirred at 50° C. for 3 h. TLC (petroleum ether: EtOAc=5:1) showed that the reaction was complete. The resulting mixture was concentrated in vacuo to give cude then re-crystallised from EtOAc (5 mL) and petroleum ether (5 mL) to give Example 50 compound, 2-(1-hydroxy-3-oxo-6-(thiazol-5-yl)-3,5,6,7-tetrahydropyrido[3,2,1-ij]quinoline-2-carboxamido)acetic acid (racemic) as a solid. $^1$H NMR (DMSO-d$_6$, 400 MHz): δ 10.52 (t, J=5.6 Hz, 1H), 8.96 (s, 1H), 7.96 (d, J=8.0 Hz, 1H), 7.81 (s, 1H), 7.65 (d, J=8.0 Hz, 1H), 7.31 (t, J=8.0 Hz, 1H), 4.50 (dd, J=3.2 Hz, 11.6 Hz, 1H), 4.10-4.15 (m, 3H), 3.86-3.92 (m, 1H), 3.44-3.48 (m, 1H), 3.20-3.27 (m, 1H). LC/MS (m/z): 386 (M+H)$^+$. Human HIF-PHD2 IC$_{50}$: 7.3 nM.

The racemate was resolved by SFC [OJ, 30×250mm, 50% MeOH (0.2% TFA)/CO2, 70 mL/min, 100 bar, 35 C, 240 nM] to afford:

Example 50a (enantiomer 1/faster eluting enatiomer) as a solid. Human HIF-PHD2 IC$_{50}$: 6.7 nM.

Example 50b (enantiomer 2/slower eluting enantiomer) as a solid. Human HIF-PHD2 IC$_{50}$: 8.3 nM.

Example 51

2-(7-Hydroxy-5-oxo-2-(4-(trifluoromethyl)phenyl)-3,5-dihydro-2H-[1,4]oxazino[2,3,4-ij][1,7]naphthyridine-6-carboxamido)acetic acid

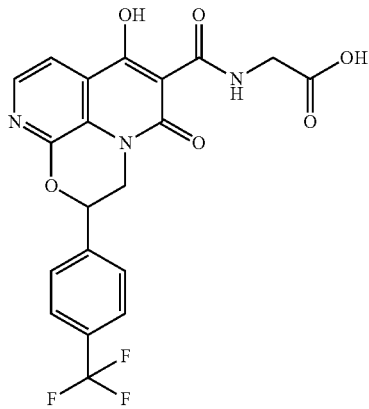 [SMILES: O=C(O)CNC(=O)c1c(O)c2ccnc3c2n(c1=O)CC(c1ccc(C(F)(F)F)cc1)O3]

Step A: 4-chloro-3-nitropyridin-2-ol

A solution of 2,4-dichloro-3-nitropyridine (10 g, 51.8 mmol) and cesium acetate (19.89 g, 104 mmol) in DMF (200 mL) was stirred at 80° C. for 18 h. The reaction mixture was cooled to room temperature and the reaction was quenched by adding water. The organic layer was extracted with EtOAc (200 mL*3), and the combined organic layers were washed with water and saturated aq NaCl, dried over anhydrous sodium sulfate, filtered and concentrated in vacuo to give 4-chloro-3-nitropyridin-2-ol as a solid. $^1$H NMR (DMSO-d$_6$, 400 MHz): δ 8.22 (d, J=5.6 Hz, 1H), 7.92 (s, 1H), 7.06 (d, J=5.6 Hz, 1H).

Step B: 3-amino-4-chloropyridin-2-ol

To a solution of 4-chloro-3-nitropyridin-2-ol (10 g, 40.1 mmol) in EtOH (150 mL) was added tin(ii) chloride dihydrate (45.2 g, 201 mmol). The reaction was heated at 80° C. for 2 h. The reaction mixture was cooled to room temperature and the ethanol was evaporated under reduced pressure. The reaction mixture was neutralized with saturated aqueous NaHCO$_3$. The sample was filtered and extracted with EtOAc (200 mL*3). The EtOAc extracts were washed with saturated NaHCO$_3$. The organic extracts were dried over Na$_2$SO$_4$, filtered and concentrated to give 3-amino-4-chloropyridin-2-ol as a solid. $^1$H NMR (DMSO-d$_6$, 400 MHz): δ 10.84 (brs, 1H), 7.43 (d, J=5.6 Hz, 1H), 6.67 (d, J=5.6 Hz, 1H), 4.71 (brs, 2H).

Step C: 8-chloro-3-(4-(trifluoromethyl)phenyl)-1H-pyrido[2,3-b][1,4]oxazin-2(3H)-one To a solution of 3-amino-4-chloropyridin-2-ol (4 g, 27.7 mmol) in DMF (120 mL) was added 2-bromo-2-(4-(trifluoromethyl)phenyl)acetyl chloride (12.51 g, 41.5 mmol) dropwise at room temperature and the mixture was stirred for 45 min. K$_2$CO$_3$ (9.56 g, 69.2 mmol) was added to above mixture portion wise at room temperature, and the reaction mixture was heated stirred at 100° C. for 18 hours. The resulting mixture was cooled to room temperature and water was added, and then the mixture was extracted with EtOAc (100 mL*3). The combined organic layers were washed with water and brine, dried over anhydrous sodium sulfate, filtered and evaporated in vacuo. The residue was purified by Combi-Flash (EtOAc in petroleum: 0-20%) to give 8-chloro-3-(4-(trifluoromethyl)phenyl)-1H-pyrido[2,3-b][1,4]oxazin-2(3H)-one as a solid. $^1$H NMR (CDCl$_3$, 400 MHz): δ 8.05 (d, J=5.6 Hz, 1H), 7.90 (brs, 1H), 7.68 (d, J=8.0 Hz, 2H), 7.57 (d, J=8.0 Hz, 2H), 7.01 (d, J=5.6 Hz, 1H), 5.88 (s, 1H).

Step D: 8-chloro-3-(4-(trifluoromethyl)phenyl)-2,3-dihydro-1H-pyrido[2,3-b][1,4]oxazine To a solution of 8-chloro-3-(4-(trifluoromethyl)phenyl)-1H-pyrido[2,3-b][1,4]oxazin-2(3H)-one (3 g, 9.13 mmol) in THF (80 mL) was added BH$_3$-DMS (8.67 mL, 91 mmol) dropwise at room temperature under nitrogen atmosphere. The reaction mixture was stirred at room temperature for 16 h, then quenched by addition of MeOH. The reaction mixture was evaporated in vacuo to give 8-chloro-3-(4-(trifluoromethyl)phenyl)-2,3-dihydro-1H-pyrido[2,3-b][1,4]oxazine as an oil. $^1$H NMR (CDCl$_3$, 400 MHz): δ 7.72 (d, J=5.2 Hz, 1H), 7.70 (d, J=8.0 Hz, 2H), 7.54 (d, J=8.0 Hz, 2H), 6.82 (d, J=5.2 Hz, 1H), 5.23 (dd, J=2.0 Hz, 8.4 Hz, 1H), 4.41 (brs, 1H), 3.72 (td, J=5.2 Hz, 12.4 Hz, 1H), 3.41 (dd, J=9.6 Hz, 12.4 Hz, 1H).

Step E: ethyl 3-(4-(trifluoromethyl)phenyl)-2,3-dihydro-1H-pyrido[2,3-b][1,4]oxazine-8-carboxylate A suspension of 8-chloro-3-(4-(trifluoromethyl)phenyl)-2,3-dihydro-1H-pyrido[2,3-b][1,4]oxazine (3.17 g, 9.07 mmol), PdCl$_2$(dppf) (0.663 g, 0.907 mmol) and sodium acetate (1.487 g, 18.13 mmol) in Ethanol (30 mL) was heated to 120° C. under CO (3 MPa) and stirred at 120° C. for 16 h. LCMS showed that the reaction was completed. The reaction mixture was evaporated in vacuo to give the crude which was purified by silica gel column chromatography (EtOAc in petroleum ether: 0-40%) to give ethyl 3-(4-(trifluoromethyl)phenyl)-2,3-dihydro-1H-pyrido[2,3-b][1,4]oxazine-8-carboxylate as a solid. $^1$H NMR (CDCl$_3$, 400 MHz): δ 7.99 (d, J=4.8 Hz, 1H), 7.70 (d, J=8.0 Hz, 2H), 7.62 (s, 1H), 7.55 (d, J=8.0 Hz, 2H), 6.95 (d, J=4.8 Hz, 1H), 5.20 (dd, J=2.0 Hz, 8.4 Hz, 1H), 4.47 (q, J=6.8 Hz, 16.4 Hz, 2H), 3.76 (td, J=3.2 Hz, 12.0 Hz, 1H), 3.47 (dd, J=8.4 Hz, 12.0 Hz, 1H), 1.47 (t, J=6.8 Hz, 3H).

Step F: ethyl 1-(3-ethoxy-3-oxopropanoyl)-3-(4-(trifluoromethyl)phenyl)-2,3-dihydro-1H-pyrido[2,3-b][1,4]oxazine-8-carboxylate To a solution of ethyl 3-(4-(trifluoromethyl)phenyl)-2,3-dihydro-1H-pyrido[2,3-b][1,4]oxazine-8-carboxylate (500 mg, 1.419 mmol) in acetonitrile (3 mL) was added ethyl 3-chloro-3-oxopropanoate (321 mg, 2.129 mmol). The resulting mixture was stirred at 70° C. for 1 h. The reaction mixture was evaporated in vacuo. The residue was purified by silica gel column chromatography (EtOAc in petroleum ether: 0-40%) to give ethyl 1-(3-ethoxy-3-oxopropanoyl)-3-(4-(trifluoromethyl)phenyl)-2,3-dihydro-1H-pyrido[2,3-b][1,4]oxazine-8-carboxylate as a solid.

Step G: ethyl 7-hydroxy-5-oxo-2-(4-(trifluoromethyl)phenyl)-3,5-dihydro-2H-[1,4]oxazino[2,3,4-ij][1,7]naphthyridine-6-carboxylate To a solution of ethyl 1-(3-ethoxy-3-oxopropanoyl)-3-(4-(trifluoromethyl)phenyl)-2,3-dihydro-1H-pyrido[2,3-b][1,4]oxazine-8-carboxylate (500 mg, 1.072 mmol) and EtOH (0.063 mL, 1.072 mmol) in toluene (3 mL) was added NaH (64.3 mg, 1.608 mmol) at room temperature. The reaction was stirred at room temperature for 1 h. LCMS showed that the reaction was completed. The resulting mixture was poured into 0.5 M HCl (5 mL) and extracted with EtOAc (10 mL*3). The combined organic layers were washed brine (10 mL*3), dried over Na$_2$SO$_4$, filtered and evaporated in vacuo to give ethyl 7-hydroxy-5-oxo-2-(4-(trifluoromethyl)phenyl)-3,5-dihydro-2H-[1,4]oxazino[2,3,4-ij][1,7]naphthyridine-6-carboxylate as a solid. $^1$H NMR (CDCl$_3$, 400 MHz): δ 8.55 (d, J=5.2 Hz, 1H), 7.75 (d, J=8.0 Hz, 2H), 7.61 (d, J=8.0 Hz, 2H), 7.22 (d, J=5.2 Hz, 1H), 5.31 (dd, J=2.4 Hz, 9.6 Hz, 1H), 4.98 (dd, J=2.4 Hz, 16.0 Hz, 1H), 4.51-4.59 (m, 2H), 3.72 (dd, J=9.6 Hz, 14.8 Hz, 1H), 1.50 (t, J=7.2 Hz, 3H).

Step H: tert-butyl 2-(7-hydroxy-5-oxo-2-(4-(trifluoromethyl)phenyl)-3,5-dihydro-2H-[1,4]oxazino[2,3,4-ij][1,7]naphthyridine-6-carboxamido)acetate A solution of ethyl 7-hydroxy-5-oxo-2-(4-(trifluoromethyl)phenyl)-3,5-dihydro-2H-[1,4]oxazino[2,3,4-ij][1,7]naphthyridine-6-carboxylate (580 mg, 1.173 mmol), tert-butyl 2-aminoacetate HCl salt (236 mg, 1.407 mmol) and DIPEA (471 µL, 2.70 mmol) in toluene (5 mL) was stirred at 120° C. for 2 h. LCMS showed that the reaction was complete. The resulting mixture was concentrated in vacuo and the residue was purified by silica gel column chromatography (EtOAc in DCM: 0-10%) to give tert-butyl 2-(7-hydroxy-5-oxo-2-(4-(trifluoromethyl)phenyl)-3,5-dihydro-2H-[1,4]oxazino[2,3,4-ij][1,7]naphthyridine-6-carboxamido)acetate as a solid. $^1$H NMR (CDCl$_3$, 400 MHz): δ 10.50 (t, J=6.0 Hz, 1H), 8.59 (d, J=5.6 Hz, 1H), 7.76 (d, J=8.0 Hz, 2H), 7.63 (d, J=8.0 Hz, 2H), 7.22 (d, J=5.6 Hz, 1H), 5.33 (dd, J=2.0 Hz, 9.6 Hz, 1H), 5.02 (dd, J=2.0 Hz, 14.0 Hz, 1H), 4.10-4.22 (m, 2H), 3.76 (dd, J=9.6 Hz, 14.0 Hz, 1H), 1.52 (s, 9H).

Step I: 2-(7-hydroxy-5-oxo-2-(4-(trifluoromethyl)phenyl)-3,5-dihydro-2H-[1,4]oxazino[2,3,4-ij][1,7]naphthyridine-6-carboxamido)acetic acid To a solution of tert-butyl 2-(7-hydroxy-5-oxo-2-(4-(trifluoromethyl)phenyl)-3,5-dihydro-2H-[1,4]oxazino[2,3,4-ij][1,7]naphthyridine-6-carboxamido)acetate (400 mg, 0.791 mmol) in DCM (1 mL) was added 2,2,2-trifluoroacetic acid (902 mg, 7.91 mmol). The resulting mixture was stirred at 40° C. for 2 h. LCMS showed that the reaction was complete. The resulting mixture was concentrated in vacuo to give the crude which was re-crystallised from MeOH (5 mL) to give 2-(7-hydroxy-5-oxo-2-(4-(trifluoromethyl)phenyl)-3,5-dihydro-2H-[1,4]oxazino[2,3,4-ij][1,7]naphthyridine-6-carboxamido)acetic acid as a solid. $^1$H NMR (DMSO-d$_6$, 400 MHz): δ 10.43 (t, J=6.0 Hz, 1H), 8.51 (d, J=5.2 Hz, 1H), 7.87 (d, J=8.4 Hz, 2H), 7.79 (d, J=8.4 Hz, 2H), 7.42 (d, J=5.2 Hz, 1H), 5.67 (dd, J=2.0 Hz, 9.6 Hz, 1H), 4.80 (dd, J=2.8 Hz, 10.0 Hz, 1H), 4.16 (d, J=5.6 Hz, 2H), 3.92 (dd, J=9.6 Hz, 11.2 Hz, 1H). LC/MS (m/z): 450 (M+H)$^+$. Human HIF-PHD2 IC$_{50}$: 13 nM.

Example 52

2-(9-Cyano-2-(4-cyanophenyl)-7-hydroxy-5-oxo-3,5-dihydro-2H-[1,4]oxazino[2,3,4-ij]quinoline-6-carboxamido)acetic acid

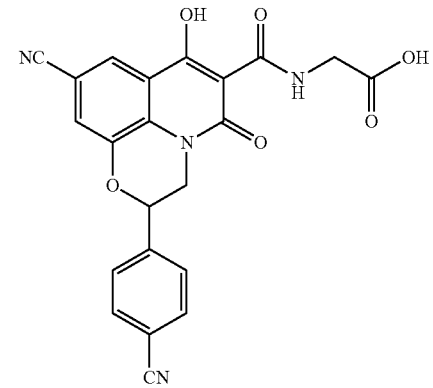 [SMILES: N#Cc1ccc(C2Cn3c(=O)c(C(=O)NCC(=O)O)c(O)c4cc(C#N)cc(c43)O2)cc1]

Step A: 2-bromo-2-(4-bromophenyl)acetyl chloride

A solution of 2-(4-bromophenyl)acetic acid (25 g, 0.12 mol) in dry CCl$_4$ (30 mL) and SOCl$_2$ (57 g, 35 ml, 0.48 mol) was heated at 65° C. until the acid was converted to the acid chloride. NBS (24.92 g, 0.14 mol) in anhydrous CCl$_4$ (40 mL) and concentrated HBr (8 drops) were added to the acid chloride. The temperature was raised to 85° C. and stirred for 3-4 h. The precipitated succinimide was filtered off, washed with CCl$_4$ and discarded. The filtrate was concentrated in vacuo to give 2-bromo-2-(4-bromophenyl)acetyl chloride as an oil. $^1$H NMR (CDCl$_3$, 400 MHz): δ 7.57 (d, J=8.4 Hz, 2H), 7.37 (d, J=8.4 Hz, 2H), 5.63 (s, 1H).

Step B: 7-bromo-2-(4-bromophenyl)-2H-benzo[b][1,4]oxazin-3(4H)-one

A solution of 2-amino-5-bromophenol (3.71 g, 12 mmol), 2-bromo-2-(4-bromophenyl)acetyl chloride (1.87 g, 10 mmol) and K$_2$CO$_3$ (2.76 g, 20 mmol) in DMF (15 mL) was stirred at room temperature for 5 h. TLC (petroleum ether:EtOAc=5:1) showed that the starting material was consumed. Water (150 mL) was added. This mixture was extracted with EtOAc (30 mL*3), washed by brine, dried over Na$_2$SO$_4$. A solution of the crude product in DCM (20 mL) was stirred at room temperature for 30 min. The precipitation was collected to give 7-bromo-2-(4-bromophenyl)-2H-benzo[b][1,4]oxazin-3(4H)-one as a solid. $^1$H NMR (CDCl$_3$, 400 MHz): δ 8.55 (d, J=20.4 Hz, 1H), 7.51 (d, J=8.0 Hz, 2H), 7.31 (d, J=8.0 Hz, 2H), 7.21 (s, 1H), 7.10 (d, J=8.0 Hz, 1H), 6.68 (d, J=8.8 Hz, 1H), 5.65 (s, 1H).

Step C: 7-bromo-2-(4-bromophenyl)-3,4-dihydro-2H-benzo[b][1,4]oxazine

To a solution of 7-bromo-2-(4-bromophenyl)-2H-benzo[b][1,4]oxazin-3(4H)-one (1.78 g, 4.67 mmol) in THF (25 mL) was added BH$_3$-Me$_2$S (5 mL, 50 mmol) at room temperature. The resulting solution was stirred at room temperature overnight. TLC (petroleum ether: EtOAc=5:1) showed that the starting material was consumed. Water (150 mL) was added. This mixture was extracted with EtOAc (30 mL*3), washed by brine, dried over Na$_2$SO$_4$. The organic layer was concentrated to give 7-bromo-2-(4-bromophenyl)-3,4-dihydro-2H-benzo[b][1,4]oxazine as a solid. $^1$H NMR (CDCl$_3$, 400 MHz): δ 7.54 (d, J=8.4 Hz, 2H), 7.28 (d, J=8.0 Hz, 2H), 7.05 (d, J=2.4 Hz, 1H), 6.92 (dd, J=2.0 Hz, 8.4 Hz, 1H), 6.54 (d, J=8.4 Hz, 1H), 5.05 (dd, J=2.4 Hz, 8.4 Hz, 1H), 3.51 (dd, J=2.4 Hz, 12.0 Hz, 1H), 3.30 (dd, J=8.4 Hz, 12.0 Hz, 1H).

Step D: ethyl 9-bromo-2-(4-bromophenyl)-7-hydroxy-5-oxo-3,5-dihydro-2H-[1,4]oxazino[2,3,4-ij]quinoline-6-carboxylate A mixture 7-bromo-2-(4-bromophenyl)-3,4-dihydro-2H-benzo[b][1,4]oxazine (1.71 g, 4.67 mmol) and triethyl methanetricarboxylate (4.34 g, 18.7 mmol) was stirred at 260° C. under N$_2$ atmosphere for 2 h. TLC (petroleum ether: EtOAc=2:1) showed that the starting material was consumed. This crude product was purified via column chromatography (SiO$_2$, EtOAc in petroleum ether: 0-60%) to give ethyl 9-bromo-2-(4-bromophenyl)-7-hydroxy-5-oxo-3,5-dihydro-2H-[1,4]oxazino[2,3,4-ij]quinoline-6-carboxylate as a solid. $^1$H NMR (CDCl$_3$, 400 MHz): δ 14.29 (s, 1H), 7.91 (d, J=2.0 Hz, 1H), 7.59 (d, J=8.0 Hz, 2H), 7.42 (d, J=2.0 Hz, 1H), 7.33 (d, J=8.4 Hz, 2H), 5.08 (d, J=2.4 Hz, 1H), 4.87 (dd, J=2.4 Hz, 14.4 Hz, 1H), 4.50-4.56 (m, 2H), 3.64 (dd, J=9.2 Hz, 14.0 Hz, 1H), 1.40 (t, J=7.2 Hz, 3H).

Step E: tert-butyl 2-(9-bromo-2-(4-bromophenyl)-7-hydroxy-5-oxo-3,5-dihydro-2H-[1,4]oxazino[2,3,4-ij]quinoline-6-carboxamido)acetate A solution of ethyl 9-bromo-2-(4-bromophenyl)-7-hydroxy-5-oxo-3,5-dihydro-2H-[1,4]oxazino[2,3,4-ij]quinoline-6-carboxylate (1 g, 1.97 mmol), tert-butyl 2-aminoacetate hydrochloride (395 mg, 2.36 mmol) and DIPEA (762 mg, 5.91 mmol) in toluene (20 mL) was refluxed for 3 h. TLC (petroleum ether: EtOAc=2:1) showed that the starting material was consumed. The solvent was removed under reduced pressure. DCM (10 mL) was added and the mixture was stirred for 20 min. Then, the solid was filtered and washed with DCM (2 mL*2) to give tert-butyl 2-(9-bromo-2-(4-bromophenyl)-7-hydroxy-5-oxo-3,5-dihydro-2H-[1,4]oxazino[2,3,4-ij]quinoline-6-carboxamido)acetate as a solid. $^1$H NMR (CDCl$_3$ 400 MHz): δ 10.54 (brs, 1H), 7.94 (d, J=2.4 Hz, 1H), 7.60 (d, J=8.4 Hz, 2H), 7.43 (d, J=2.4 Hz, 1H), 7.34 (d, J=8.4 Hz, 2H), 5.10 (dd, J=2.4 Hz, 9.6 Hz, 1H), 4.90 (dd, J=2.4 Hz, 14.4 Hz, 1H), 4.15-4.12 (m, 2H), 3.66 (dd, J=9.6 Hz, 14 Hz, 1H), 1.51 (s, 9H).

Step F: tert-butyl 2-(9-cyano-2-(4-cyanophenyl)-7-hydroxy-5-oxo-3,5-dihydro-2H-[1,4]oxazino[2,3,4-ij]quinoline-6-carboxamido)acetate To a solution of tert-butyl 2-(9-bromo-2-(4-bromophenyl)-7-hydroxy-5-oxo-3,5-dihydro-2H-[1,4]oxazino[2,3,4-ij]quinoline-6-carboxamido)acetate (592 mg, 1.0 mmol) in DMA (4 ml) were added zinc cyanide (468 mg, 4.0 mmol), Pd$_2$(dba)$_3$ (183 mg, 0.2 mmol), dppf (28 mg, 0.2 mmol) and zinc (260 mg, 4 mmol). The reaction solution was heated at 120° C. by microwave for 30 mins. TLC showed that the reaction was complete. The mixture was cooled, water (10 mL) was added and the mixture was extracted with EtOAc (3*10 mL). The combined organic fractions were washed with water (3*10 mL), dried over Na$_2$SO$_4$, filtered and the solvent was evaporated under reduced pressure. The residue was purified by silica gel column chromatography (EtOAc in petroleum ether: 0-40%) to give tert-butyl 2-(9-cyano-2-(4-cyanophenyl)-7-hydroxy-5-oxo-3,5-dihydro-2H-[1,4]oxazino[2,3,4-ij]quinoline-6-carboxamido)acetate as solid. $^1$H NMR (CDCl$_3$, 400 MHz): δ 10.35 (brs, 1H), 8.16 (d, J=1.6 Hz, 1H), 7.79 (d, J=8.8 Hz, 2H), 7.62 (d, J=8.0 Hz, 2H), 7.51 (d, J=1.2 Hz, 1H), 5.23 (d, J=9.6 Hz, 1H), 4.97 (dd, J=2.4 Hz, 14 Hz, 1H), 4.09-4.17 (m, 2H), 3.71 (dd, J=9.6 Hz, 14.4 Hz, 1H), 1.52 (s, 9H).

Step G: 2-(9-cyano-2-(4-cyanophenyl)-7-hydroxy-5-oxo-3,5-dihydro-2H-[1,4]oxazino[2,3,4-ij]quinoline-6-carboxamido)acetic acid To a solution of tert-butyl 2-(9-cyano-2-(4-cyanophenyl)-7-hydroxy-5-oxo-3,5-dihydro-2H-[1,4]oxazino[2,3,4-ij]quinoline-6-carboxamido)acetate (486 mg, 1.0 mmol) in DCM (1 mL) was added 2,2,2-trifluoroacetic acid (1140 mg, 10 mmol). The resulting mixture was heated to 60° C. and stirred for 3 h. TLC (pretroleum ether: EtOAc=2:1) showed that the reaction was complete. The resulting mixture was concentrated in vacuo to give the crude which was re-crystallised from EtOAc (1 mL) and petroleum ether (10 mL) to give 2-(9-cyano-2-(4-cyanophenyl)-7-hydroxy-5-oxo-3,5-dihydro-2H-[1,4]oxazino[2,3,4-ij]quinoline-6-carboxamido)acetic acid as a solid. $^1$H NMR (DMSO-d$_6$, 400 MHz): δ 10.28 (brs, 1H), 8.13 (s, 1H), 7.98 (d, J=8.8 Hz, 2H), 7.91 (s, 1H), 7.76 (d, J=8.4 Hz, 2H), 5.55 (d, J=6.8 Hz, 1H), 4.76 (d, J=11.6 Hz, 1H), 4.15 (d, J=5.6 Hz, 2H), 3.87 (dd, J=9.0 Hz, 13.6 Hz, 1H). LC/MS (m/z): 431 (M+H)$^+$. Human HIF-PHD2 IC$_{50}$: 0.5 nM.

Example 53

2-(9-Bromo-2-(4-bromophenyl)-7-hydroxy-5-oxo-3,5-dihydro-2H-[1,4]oxazino[2,3,4-ij]quinoline-6-carboxamido)acetic acid

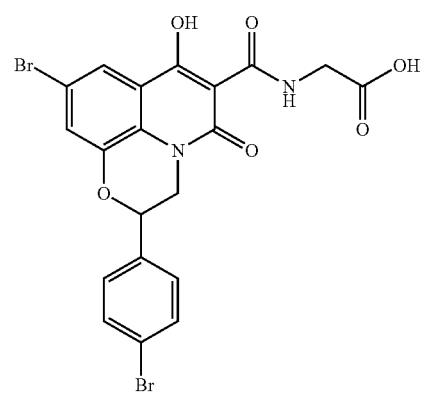 [SMILES: O=C(O)CNC(=O)c1c(O)c2cc(Br)cc3c2n(c1=O)CC(c1ccc(Br)cc1)O3]

To a solution of Step E product of Example 52 (592 mg, 1.0 mmol) in DCM (1 mL) was added 2,2,2-trifluoroacetic acid (1140 mg, 10 mmol). The resulting mixture was heated to 60° C. and stirred for 3 h. TLC (pretroleum ether: EtOAc=2:1) showed that the reaction was complete. The resulting mixture was concentrated in vacuo to give the crude which was re-crystallised from EtOAc (1 mL) and petroleum ether (10 mL) to give 2-(9-bromo-2-(4-bromophenyl)-7-hydroxy-5-oxo-3,5-dihydro-2H-[1,4]oxazino[2,3,4-ij]quinoline-6-carboxamido)acetic acid as a solid. $^1$H NMR (DMSO-$d_6$, 400 MHz): δ 10.39 (brs, 1H), 7.77 (s, 1H), 7.68 (d, J=8.8 Hz, 2H), 7.66 (s, 1H), 7.50 (d, J=8.4 Hz, 2H), 5.43 (d, J=8.0 Hz, 1H), 4.68 (d, J=12 Hz, 1H), 4.14 (d, J=5.2 Hz, 2H), 3.87 (dd, J=9.6 Hz, 13.6 Hz, 1H). LC/MS (m/z): 539 (M+H)$^+$. Human HIF-PHD2 IC$_{50}$: 3.5 nM.

Example 54

2-(8-Cyano-2-(4-cyanophenyl)-7-hydroxy-5-oxo-3,5-dihydro-2H-[1,4]oxazino[2,3,4-ij]quinoline-6-carboxamido)acetic acid

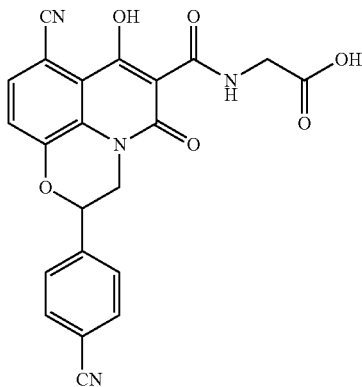 [SMILES: N#Cc1ccc(C2Cn3c(=O)c(C(=O)NCC(=O)O)c(O)c4c(C#N)ccc(c43)O2)cc1]

Step A: 6-bromo-2-(4-bromophenyl)-2H-benzo[b][1,4]oxazin-3(4H)-one

A solution of 2-amino-4-bromophenol (0.37 g, 1.2 mmol), 2-bromo-2-(4-bromophenyl)acetyl chloride (0.19 g, 1.0 mmol) and K$_2$CO$_3$ (0.28 g, 2.0 mmol) in DMF (15 mL) was stirred at room temperature for 5 h. TLC showed that the starting material was consumed. Water (150 mL) was added. This mixture was extracted with EtOAc (30 mL*3), and the organic layers were washed by brine, dried over Na$_2$SO$_4$. A solution of the crude product in DCM (20 mL) was stirred at room temperature for 30 min. The soild precipitate was collected to give 6-bromo-2-(4-bromophenyl)-2H-benzo[b][1,4]oxazin-3(4H)-one as a solid.

Step B: 6-bromo-2-(4-bromophenyl)-3,4-dihydro-2H-benzo[b][1,4]oxazine

To a solution of 6-bromo-2-(4-bromophenyl)-2H-benzo[b][1,4]oxazin-3(4H)-one (381m g, 1.0 mmol) in THF (25 mL) was added BH$_3$-Me$_2$S (1 mL, 10.7 mmol) at room temperature. The resulting solution was stirred at room temperature overnight. TLC showed that the starting material was consumed. Water (150 mL) was added. This mixture was extracted with EtOAc (30 mL*3), washed with brine, dried over Na$_2$SO$_4$. The crude product was triturated with DCM (10 mL*2) to give 6-bromo-2-(4-bromophenyl)-3,4-dihydro-2H-benzo[b][1,4]oxazine as a solid. $^1$H NMR (CDCl$_3$, 400 MHz): δ 7.51 (d, J=8.4 Hz, 2H), 7.25 (d, J=8.4 Hz, 2H), 6.72-6.77 (m, 3H), 5.00 (d, J=8.4 Hz, 1H), 3.48 (dd, J=2.0 Hz, 12 Hz, 1H), 3.30(dd, J=8.4 Hz, 12 Hz, 1H).

Step C: ethyl 8-bromo-2-(4-bromophenyl)-7-hydroxy-5-oxo-3,5-dihydro-2H-[1,4]oxazino[2,3,4-ij]quinoline-6-carboxylate A mixture of 6-bromo-2-(4-bromophenyl)-3,4-dihydro-2H-benzo[b][1,4]oxazine (4.34 g, 18.7 mmol) and triethyl methanetricarboxylate (4.34 g, 18.7 mmol) was stirred at 260° C. under N$_2$ atmosphere for 2 h. TLC (petroleum ether: EtOAc=2:1) showed that the starting material was consumed. This crude product was purified via column chromatography (SiO$_2$, EtOAc in petroleum ether: 0-60%) to give ethyl 8-bromo-2-(4-bromophenyl)-7-hydroxy-5-oxo-3,5-dihydro-2H-[1,4]oxazino[2,3,4-ij]quinoline-6-carboxylate as a solid. $^1$H NMR (CDCl$_3$, 400 MHz): δ 15.19 (s, 1H), 7.58 (d, J=8.0 Hz, 1H), 7.47 (d, J=8.4 Hz, 2H), 7.33 (d, J=8.4 Hz, 2H), 7.11 (d, J=8.4 Hz, 1H), 5.04 (d, J=9.6 Hz, 1H), 4.96 (d, J=14 Hz, 1H), 4.42-4.54 (m, 2H), 3.80 (dd, J=9.6 Hz, 14 Hz, 1H), 1.48 (t, J=7.2 Hz, 3H).

Step D: tert-butyl 2-(8-bromo-2-(4-bromophenyl)-7-hydroxy-5-oxo-3,5-dihydro-2H-[1,4]oxazino[2,3,4-ij]quinoline-6-carboxamido)acetate A solution of ethyl 8-bromo-2-(4-bromophenyl)-7-hydroxy-5-oxo-3,5-dihydro-2H-[1,4]oxazino[2,3,4-ij]quinoline-6-carboxylate (1 g, 1.97 mmol), tert-butyl 2-aminoacetate hydrochloride (395 mg, 2.36 mmol) and DIPEA (762 mg, 5.91 mmol) in toluene (20 mL) was refluxed for 3 h. TLC (petroleum ether: EtOAc=2:1) showed that the starting material was consumed. The solvent was removed under reduced pressure. DCM (10 mL) was added and the mixture was stirred for 20 min. Then, the solid was filtrated and washed by DCM (2 mL*2) to give tert-butyl 2-(8-bromo-2-(4-bromophenyl)-7-hydroxy-5-oxo-3,5-dihydro-2H-[1,4]oxazino[2,3,4-ij]quinoline-6-carboxamido)acetate as a solid. $^1$H NMR (CDCl$_3$, 400 MHz): δ 10.70 (brs, 1H), 7.58 (d, J=8.0 Hz, 2H), 7.48 (d, J=8.8 Hz, 1H), 7.34 (d, J=8.0 Hz, 2H), 7.10 (d, J=8.4 Hz, 1H), 5.05 (d, J=9.2 Hz, 1H), 4.98 (d, J=14 Hz, 1H), 4.11-4.15 (m, 2H), 3.62-3.68 (m, 1H), 1.51 (s, 9H).

Step E: tert-butyl 2-(8-cyano-2-(4-cyanophenyl)-7-hydroxy-5-oxo-3,5-dihydro-2H-[1,4]oxazino[2,3,4-ij]quinoline-6-carboxamido)acetate To a solution of tert-butyl 2-(8-bromo-2-(4-bromophenyl)-7-hydroxy-5-oxo-3,5-dihydro-2H-[1,4]oxazino[2,3,4-ij]quinoline-6-carboxamido)acetate (592 mg, 1.0 mmol) in DMA (4 ml) were added zinc cyanide (468 mg, 4.0 mmol), Pd$_2$(dba)$_3$ (183 mg, 0.2 mmol), dppf (28 mg, 0.2 mmol) and zinc (260 mg, 4 mmol). The reaction solution was heated at 120° C. by microwave for 30 mins. TLC (petroleum ether: EtOAc=2:1) showed that the reaction was complete. The mixture was cooled, water (10 mL) was added and the mixture was extracted with EtOAc (3*10 mL). The combined organic fractions were washed with water (3*10 mL), dried over Na$_2$SO$_4$, filtered and the solvent was evaporated under reduced pressure. The residue was purified by silica gel column chromatography (EtOAc in petroleum ether: 0-40%) to give tert-butyl 2-(8-cyano-2-(4-cyanophenyl)-7-hydroxy-5-oxo-3,5-dihydro-2H-[1,4]oxazino[2,3,4-ij]quinoline-6-carboxamido)acetate as solid. ¹H NMR (CDCl₃, 400 MHz): δ 10.48 (brs, 1H), 7.79 (d, J=8.0 Hz, 2H), 7.61-7.66 (m, 3H), 7.36 (d, J=8.0 Hz, 1H), 5.28 (d, J=8.8 Hz, 1H), 5.04 (d, J=14 Hz, 1H), 4.10-4.22 (m, 2H), 3.69 (dd, J=8.8 Hz, 14 Hz, 1H), 1.52 (s, 9H).

Step F: 2-(8-cyano-2-(4-cyanophenyl)-7-hydroxy-5-oxo-3,5-dihydro-2H-[1,4]oxazino[2,3,4-ij]quinoline-6-carboxamido)acetic acid To a solution of tert-butyl 2-(8-cyano-2-(4-cyanophenyl)-7-hydroxy-5-oxo-3,5-dihydro-2H-[1,4]oxazino[2,3,4-ij]quinoline-6-carboxamido)acetate (486 mg, 1.0 mmol) in DCM (1 mL) was added 2,2,2-trifluoroacetic acid (1140 mg, 10 mmol). The resulting mixture was heated to 60° C. and stirred for 3 h. TLC (pretroleum ether: EtOAc=2:1) showed that the reaction was complete. The resulting mixture was concentrated in vacuo to give the crude which was re-crystallised from EtOAc (1 mL) and petroleum ether (10 mL) to give 2-(8-cyano-2-(4-cyanophenyl)-7-hydroxy-5-oxo-3,5-dihydro-2H-[1,4]oxazino[2,3,4-ij]quinoline-6-carboxamido)acetic acid as a solid. ¹H NMR (DMSO-d₆, 400 MHz): δ 13.02 (brs, 1H), 10.44 (brs, 1H), 7.97 (d, J=8.0 Hz, 2H), 7.82 (d, J=8.0 Hz, 1H), 7.76 (d, J=8.0 Hz, 2H), 7.55 (d, J=8.4 Hz, 1H), 5.61 (d, J=8.4 Hz, 1H), 4.80 (d, J=13.6 Hz, 1H), 4.17 (d, J=4.8 Hz, 2H), 3.89 (dd, J=8.8 Hz, 13.6 Hz, 1H). LC/MS (m/z): 431 (M+H)⁺. Human HIF-PHD2 IC₅₀: 1.1 nM.

Example 55

2-(8-Bromo-2-(4-bromophenyl)-7-hydroxy-5-oxo-3,5-dihydro-2H-[1,4]oxazino[2,3,4-ij]quinoline-6-carboxamido)acetic acid

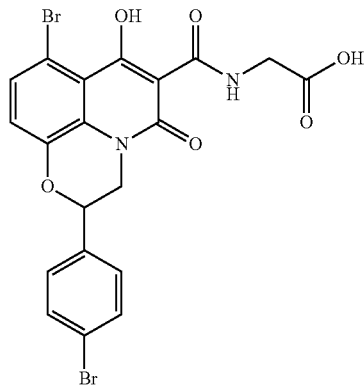 [SMILES: O=C(O)CNC(=O)c1c(O)c2c(Br)ccc3c2n(c1=O)CC(c1ccc(Br)cc1)O3]

To a solution of Step D product of Example 54 (592 mg, 1.0 mmol) in DCM (1 mL) was added 2,2,2-trifluoroacetic acid (1140 mg, 10 mmol). The resulting mixture was heated to 60° C. and stirred for 3 h. TLC (pretroleum ether: EtOAc=2:1) showed that the reaction was complete. The resulting mixture was concentrated in vacuo to give the crude which was re-crystallised from EtOAc (1 mL) and petroleum ether (10 mL) to give 2-(8-bromo-2-(4-bromophenyl)-7-hydroxy-5-oxo-3,5-dihydro-2H-[1,4]oxazino[2,3,4-ij]quinoline-6-carboxamido)acetic acid as a solid. ¹H NMR (DMSO-d₆, 400 MHz): δ 10.57 (brs, 1H), 7.68 (d, J=8.0 Hz, 2H), 7.54 (d, J=8.0 Hz, 1H), 7.49 (d, J=8.0 Hz, 2H), 7.29 (d, J=8.0 Hz, 1H), 5.36 (d, J=7.2 Hz, 1H), 4.74 (dd, J=1.6 Hz, 13.2 Hz, 1H), 4.14 (d, J=5.6 Hz, 2H), 3.84 (q, J=9.6 Hz, 14.0 Hz, 1H). LC/MS (m/z): 536 (M+H)⁺. Human HIF-PHD2 IC₅₀: 2.5 nM.

Example 56

2-(10-Cyano-2-(4-cyanophenyl)-7-hydroxy-5-oxo-3,5-dihydro-2H-[1,4]oxazino[2,3,4-ij]quinoline-6-carboxamido)acetic acid

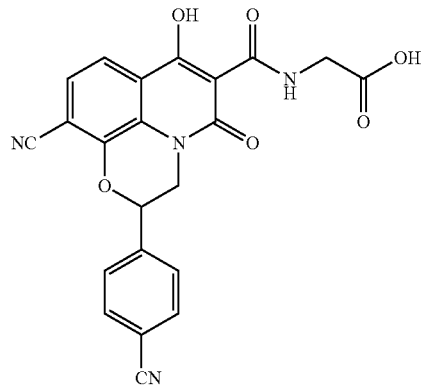 [SMILES: N#Cc1ccc(C2Cn3c(=O)c(C(=O)NCC(=O)O)c(O)c4ccc(C#N)c(c43)O2)cc1]

Step A: 8-bromo-2-(4-bromophenyl)-2H-benzo[b][1,4]oxazin-3(4H)-one

A suspension of 2-amino-6-bromophenol (0.37 g, 1.2 mmol), 2-bromo-2-(4-bromophenyl)acetyl chloride (0.19 g, 1.0 mmol) and K₂CO₃ (0.28 g, 2.0 mmol) in DMF (15 mL) was stirred at room temperature for 5 h. TLC (petroleum ether: EtOAc=5:1) showed that the starting material was consumed. Water (150 mL) was added. This mixture was extracted with EtOAc (30 mL*3), washed by brine, dried over Na₂SO₄. A solution of the crude product in DCM (20 mL) was stirred at room temperature for 30 min. The soild precipitate was collected to give 8-bromo-2-(4-bromophenyl)-2H-benzo[b][1,4]oxazin-3(4H)-one as a solid. ¹H NMR (CDCl₃, 400 MHz): δ 8.07 (s, 1H), 7.50 (d, J=8.4 Hz, 2H), 7.381 (d, J=8.4 Hz, 2H), 7.23 (d, J=8.0 Hz, 1H), 6.85 (t, J=8.0 Hz, 1H), 6.72 (d, J=7.6 Hz, 1H), 5.82 (s, 1H).

Step B: 8-bromo-2-(4-bromophenyl)-3,4-dihydro-2H-benzo[b][1,4]oxazine

To a solution of 8-bromo-2-(4-bromophenyl)-2H-benzo[b][1,4]oxazin-3(4H)-one (381 mg, 1.0 mmol) in THF (25 mL) was added BH₃-Me₂S (1 mL, 10.7 mmol) at room temperature. The resulting solution was stirred at room temperature overnight. TLC (petroleum ether: EtOAc=5:1) showed that the starting material was consumed. Water (150 mL) was added. This mixture was extracted with EtOAc (30 mL*3), and the organic layers were washed by brine, dried over Na₂SO₄. The crude product was trituaged with DCM (10 mL*2) to give 8-bromo-2-(4-bromophenyl)-3,4-dihydro-2H-benzo[b][1,4]oxazine as a solid. ¹H NMR (CDCl₃, 400 MHz): δ 7.54 (d, J=8.4 Hz, 2H), 7.33 (d, J=8.4 Hz, 2H), 6.96 (dd, J=1.2 Hz, 8.0 Hz, 1H), 6.68 (t, J=8.0 Hz, 1H), 6.60 (d, J=1.2 Hz, 1H), 5.17 (dd, J=2.0 Hz, 8.0 Hz, 1H), 3.57 (dd, J=2.4 Hz, 12 Hz, 1H), 3.31(dd, J=8.0 Hz, 12 Hz, 1H).

Step C: ethyl 10-bromo-2-(4-bromophenyl)-7-hydroxy-5-oxo-3,5-dihydro-2H-[1,4]oxazino[2,3,4-ij]quinoline-6-carboxylate A mixture of 8-bromo-2-(4-bromophenyl)-3,4-dihydro-2H-benzo[b][1,4]oxazine (367 mg, 1.0 mmol) and triethyl methanetricarboxylate (928 mg, 4.0 mmol) was stirred at 260° C. under $N_2$ atmosphere for 2 h. TLC (petroleum ether: EtOAc=2:1) showed that the starting material was consumed. This crude product was purified via column chromatography ($SiO_2$, EtOAc in petroleum ether: 0-60%) to give ethyl 10-bromo-2-(4-bromophenyl)-7-hydroxy-5-oxo-3,5-dihydro-2H-[1,4]oxazino[2,3,4-ij]quinoline-6-carboxylate as a solid. $^1$H NMR ($CDCl_3$, 400 MHz): δ 14.31 (s, 1H), 7.65 (d, J=8.8 Hz, 1H), 7.58 (d, J=8.4 Hz, 2H), 7.41 (d, J=8.4 Hz, 1H), 7.38 (d, J=8.0 Hz, 2H), 5.22 (d, J=6.8 Hz, 1H), 4.88 (dd, J=2.4 Hz, 14.4 Hz, 1H), 4.49-4.55 (m, 2H), 3.80 (dd, J=8.4 Hz, 14 Hz, 1H), 1.48 (t, J=6.8 Hz, 3H).

Step D: tert-butyl 2-(10-bromo-2-(4-bromophenyl)-7-hydroxy-5-oxo-3,5-dihydro-2H-[1,4]oxazino[2,3,4-ij]quinoline-6-carboxamido)acetate A solution of ethyl 10-bromo-2-(4-bromophenyl)-7-hydroxy-5-oxo-3,5-dihydro-2H-[1,4]oxazino[2,3,4-ij]quinoline-6-carboxylate (1 g, 1.97 mmol), tert-butyl 2-aminoacetate hydrochloride (395 mg, 2.36 mmol) and DIPEA (762 mg, 5.91 mmol) in toluene (20 mL) was refluxed for 3 h. TLC (petroleum ether: EtOAc=5:1) showed that the starting material was consumed. The solvent was removed under reduced pressure. DCM (10 mL) was added and the mixture was stirred for 20 min. Then, the solid was filtrated and washed by DCM (2 mL*2) to give tert-butyl 2-(10-bromo-2-(4-bromophenyl)-7-hydroxy-5-oxo-3,5-dihydro-2H-[1,4]oxazino[2,3,4-ij]quinoline-6-carboxamido)acetate as a solid. $^1$H NMR ($CDCl_3$, 400 MHz): δ 10.51 (t, J=5.6 Hz, 1H), 7.67 (d, J=8.4 Hz, 1H), 7.59 (d, J=8.4 Hz, 2H), 7.45 (d, J=8.4 Hz, 1H), 7.40 (d, J=8.4 Hz, 2H), 5.22 (dd, J=2.4 Hz, 8.8 Hz, 1H), 4.92 (dd, J=2.8 Hz, 14 Hz, 1H), 4.11-4.15 (m, 2H), 3.80 (dd, J=9.6 Hz, 14 Hz, 1H), 1.51 (s, 9H).

Step E: tert-butyl 2-(10-cyano-2-(4-cyanophenyl)-7-hydroxy-5-oxo-3,5-dihydro-2H-[1,4]oxazino[2,3,4-ij]quinoline-6-carboxamido)acetate To a solution of tert-butyl 2-(10-bromo-2-(4-bromophenyl)-7-hydroxy-5-oxo-3,5-dihydro-2H-[1,4]oxazino[2,3,4-ij]quinoline-6-carboxamido)acetate (592 mg, 1.0 mmol) in DMA (4 mL) were added zinc cyanide (468 mg, 4.0 mmol), $Pd_2(dba)_3$ (183 mg, 0.2 mmol), dppf (28 mg, 0.2 mmol) and zinc (260 mg, 4 mmol). The reaction solution was heated at 120° C. by microwave for 30 mins. TLC (petroleum ether: EtOAc=5:1) showed that the reaction was complete. The mixture was cooled, water (10 mL) was added and the mixture was extracted with EtOAc (3*10 mL). The combined organic fractions were washed with water (3*10 mL), dried over $Na_2SO_4$, filtered and the solvent was evaporated under reduced pressure. The residue was purified by CombiFlash (EtOAc in petroleum ether: 0-40%) to give tert-butyl 2-(10-cyano-2-(4-cyanophenyl)-7-hydroxy-5-oxo-3,5-dihydro-2H-[1,4]oxazino[2,3,4-ij]quinoline-6-carboxamido)acetate as solid. $^1$H NMR ($CDCl_3$, 400 MHz): δ 10.43 (brs, 1H), 7.88 (d, J=8.4 Hz, 1H), 7.79 (d, J=8.4 Hz, 2H), 7.66 (d, J=8.4 Hz, 2H), 7.46 (d, J=8.4 Hz, 1H), 5.39 (d, J=7.2 Hz, 1H), 5.01 (d, J=14.4 Hz, 1H), 4.10-4.21 (m, 2H), 3.80 (dd, J=8.8 Hz, 14 Hz, 1H), 1.52 (s, 9H).

Step F: 2-(10-cyano-2-(4-cyanophenyl)-7-hydroxy-5-oxo-3,5-dihydro-2H-[1,4]oxazino[2,3,4-ij]quinoline-6-carboxamido)acetic acid To a solution of tert-butyl 2-(10-cyano-2-(4-cyanophenyl)-7-hydroxy-5-oxo-3,5-dihydro-2H-[1,4]oxazino[2,3,4-ij]quinoline-6-carboxamido)acetate (486 mg, 1.0 mmol) in DCM (1 mL) was added 2,2,2-trifluoroacetic acid (1140 mg, 10 mmol). The resulting mixture was heated to 60° C. and stirred for 3 h. TLC (pretroleum ether: EtOAc=2:1) showed that the reaction was completed. The resulting mixture was concentrated in vacuo to give the crude which was re-crystallised with EtOAc (1 mL) and petroleum ether (10 mL) to give 2-(10-cyano-2-(4-cyanophenyl)-7-hydroxy-5-oxo-3,5-dihydro-2H-[1,4]oxazino[2,3,4-ij]quinoline-6-carboxamido)acetic acid as a solid. $^1$H NMR (DMSO-$d_6$, 400 MHz): δ 10.35 (brs, 1H), 8.01 (d, J=8.0 Hz, 2H), 7.78 (d, J=8.0 Hz, 2H), 7.78 (d, J=8.0 Hz, 1H), 7.67 (d, J=8.4 Hz, 1H), 5.73 (d, J=8.0 Hz, 1H), 4.83 (d, J=11.6 Hz, 1H), 4.15 (d, J=5.6 Hz, 2H), 3.93 (dd, J=8.8 Hz, 13.6 Hz, 1H). LC/MS (m/z): 431 (M+H)$^+$. Human HIF-PHD2 $IC_{50}$: 0.6 nM.

Example 57

2-(10-Bromo-2-(4-bromophenyl)-7-hydroxy-5-oxo-3,5-dihydro-2H-[1,4]oxazino[2,3,4-ij]quinoline-6-carboxamido)acetic acid

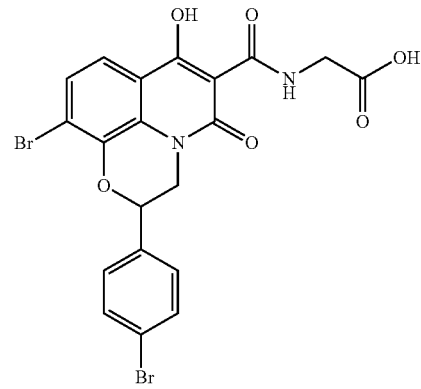 [SMILES: O=C(O)CNC(=O)c1c(O)c2ccc(Br)c3c2n(c1=O)CC(c1ccc(Br)cc1)O3]

To a solution of Step D product of Example 56 (582 mg, 1.0 mmol) in DCM (1 mL) was added 2,2,2-trifluoroacetic acid (1140 mg, 10 mmol). The resulting mixture was heated to 60° C. and stirred for 3 h. TLC (pretroleum ether: EtOAc=2:1) showed that the reaction was complete. The resulting mixture was concentrated in vacuo to give the crude which was re-crystallised from EtOAc (1 mL) and petroleum ether (10 mL) to give 2-(10-bromo-2-(4-bromophenyl)-7-hydroxy-5-oxo-3,5-dihydro-2H-[1,4]oxazino[2,3,4-ij]quinoline-6-carboxamido)acetic acid as a solid. $^1$H NMR ($CDCl_3$, 400 MHz): δ 10.51 (t, J=5.6 Hz, 1H), 7.67 (d, J=8.4 Hz, 1H), 7.59 (d, J=8.4 Hz, 2H), 7.45 (d, J=8.4 Hz, 1H), 7.40 (d, J=8.4 Hz, 2H), 5.22 (dd, J=2.4 Hz, 8.8 Hz, 1H), 4.92 (dd, J=2.8 Hz, 14 Hz, 1H), 4.11-4.15 (m, 2H), 3.80 (dd, J=9.6 Hz, 14 Hz, 1H), 1.51 (s, 9H). LC/MS (m/z): 537 (M+H)$^+$. Human HIF-PHD2 $IC_{50}$: 2.7 nM.

Example 58

2-(7-Hydroxy-5-oxo-2-(4-(trifluoromethyl)phenyl)-3,5-dihydro-2H-[1,4]thiazino[2,3,4-ij]quinoline-6-carboxamido)acetic acid

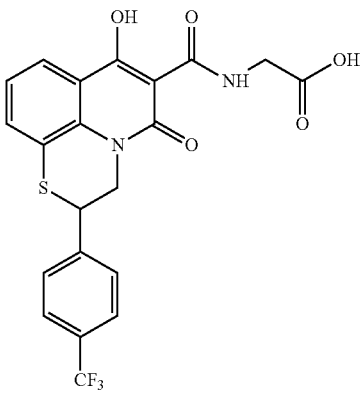 [SMILES: O=C(O)CNC(=O)c1c(O)c2cccc3c2n(c1=O)CC(c1ccc(C(F)(F)F)cc1)S3]

Step A: Ethyl 2-(4-(trifluoromethyl)phenyl)acetate

A 100 mL round bottom flask was charged with 2-(4-(trifluoromethyl)phenyl)acetic acid (10 g, 0.049 mol) and SOCl$_2$ (50 mL). The mixture was refluxed for 2 hr, then SOCl$_2$ was evaporated and to the residue was added to EtOH (50 mL). The mixture was then refluxed for 1 hr. The reaction mixture was evaporated to dryness and dissolved with EtOAc (20 mL). The organic layer was washed with water, dried over Na$_2$SO$_4$, filtered and evaporated to dryness to give ethyl 2-(4-(trifluoromethyl)phenyl)acetate as a solid. $^1$H NMR (CDCl$_3$, 400 MHz): δ 7.59 (d, J=8.0 Hz, 2H), 7.41 (d, J=8.0 Hz, 2H), 4.22-4.11 (m, 2H), 3.68 (s, 2H), 1.26 (t, J=8.0 Hz, 3H).

Step B: Ethyl 2-bromo-2-(4-(trifluoromethyl)phenyl)acetate

To a solution of ethyl 2-(4-(trifluoromethyl)phenyl)acetate (5 g, 21.5 mmol) in CCl$_4$ (100 mL) was added NBS (11.5 g, 64.6 mmol). The resulting mixture was heated to reflux and stirred for 16 hr. The reaction mixture was then filtered and the filtrate was evaporated to dryness. The residue was purified via CombiFlash (80 g column, DCM in Petroleum ether from 0% to 30%) to give ethyl 2-bromo-2-(4-(trifluoromethyl)phenyl)acetate as an oil. $^1$H NMR (CDCl$_3$, 400 MHz): δ 7.68 (d, J=8.0 Hz, 2H), 7.63 (d, J=8.0 Hz, 2H), 5.35 (s, 1H), 4.33-4.18 (m, 2H), 1.30 (t, J=7.0 Hz, 3H).

Step C: 2-(4-(trifluoromethyl)phenyl)-2H-benzo[b][1,4]thiazin-3(4H)-one

A 250 mL round bottom flask was charged with ethyl 2-bromo-2-(4-(trifluoromethyl)phenyl)acetate (5.0 g, 16.1 mmol), 2-aminobenzenethiol (2.41 g, 19.3 mmol), DIPEA (6.2 g, 48.2 mmol) and toluene (80 mL). The reaction was stirred at 120° C. for 18 hr. The mixture was poured into water and extracted with EtOAc (50 mL*3). The combined organic layers were evaporated to dryness. The residue was recrystallized from EtOAc to give 2-(4-(trifluoromethyl)phenyl)-2H-benzo[b][1,4]thiazin-3(4H)-one as a solid. $^1$H NMR (CDCl$_3$, 400 MHz): δ 8.87 (brs, 1H), 7.58 (d, J=8.0 Hz, 2H), 7.52 (d, J=8.0 Hz, 2H), 7.34 (d, J=7.7 Hz, 1H), 7.20 (t, J=8.0 Hz, 1H), 7.05 (t, J=8.0 Hz, 1H), 6.89 (d, J=7.9 Hz, 1H), 4.75 (s, 1H).

Step D: 2-(4-(trifluoromethyl)phenyl)-3,4-dihydro-2H-benzo[b][1,4]thiazine

A 250 mL three neck flask was charged with 2-(4-(trifluoromethyl)phenyl)-2H-benzo[b][1,4]thiazin-3(4H)-one (4.1 g, 13.24 mmol) and THF (80 mL). The flask was purged with N$_2$ and BH$_3$-Me$_2$S (13.8 mL) was added slowly. After addition, the mixture was stirred at room temperature for 18 hr. TLC (Petroleum ether: EtOAc=4:1) showed the starting material was consumed. Then the reaction mixture was cooled to 0° C. and 1M HCl (20 mL) was added slowly. Then the mixture was basified to pH 12 with NaOH solution and extracted with EtOAc (50 mL*3). The organic layers were dried over Na$_2$SO$_4$, filtered and evaporated to dryness to give 2-(4-(trifluoromethyl)phenyl)-3,4-dihydro-2H-benzo[b][1,4]thiazine as a solid. $^1$H NMR (CDCl$_3$, 400 MHz): δ 7.62 (d, J=8.2 Hz, 2H), 7.50 (d, J=8.2 Hz, 2H), 7.06 (d, J=7.7 Hz, 1H), 7.01-6.92 (m, 1H), 6.74-6.66 (m, 1H), 6.58 (dd, J=7.9, 0.9 Hz, 1H), 4.42 (dd, J=8.4, 2.9 Hz, 1H), 4.18 (brs, 1H), 3.79 (dt, J=12.1, 3.5 Hz, 1H), 3.68-3.57 (m, 1H).

Step E: Ethyl 7-hydroxy-5-oxo-2-(4-(trifluoromethyl)phenyl)-3,5-dihydro-2H-[1,4]thiazino[2,3,4-ij]quinoline-6-carboxylate A 100 mL round bottom flask was charged with 2-(4-(trifluoromethyl)phenyl)-3,4-dihydro-2H-benzo[b][1,4]thiazine (300 mg, 1.02 mmol) and triethyl methanetricarboxylate (943 mg, 4.06 mmol). The flask was purged with N$_2$ and heated at 260° C. for 3 hr. TLC (Petroleum ether: EtOAc=4:1) showed the starting material was consumed and a new spot was formed. The reaction mixture was diluted with petroleum ether and filtered to give ethyl 7-hydroxy-5-oxo-2-(4-(trifluoromethyl)phenyl)-3,5-dihydro-2H-[1,4]thiazino[2,3,4-ij]quinoline-6-carboxylate as a solid. $^1$H NMR (CDCl$_3$, 400 MHz): δ 14.27 (s, 1H), 8.02 (d, J=8.0 Hz, 1H), 7.65 (d, J=8.0 Hz, 2H), 7.56 (d, J=8.0 Hz, 1H), 7.52 (d, J=8.5 Hz, 2H), 7.19 (t, J=7.8 Hz, 1H), 5.29 (dd, J=14.0, 2.5 Hz, 1H), 4.46-4.55 (m, 2H), 4.42 (d, J=7.0 Hz, 1H), 4.20-4.10 (m, 1H), 1.48 (t, J=7.0 Hz, 3H).

Step F: tert-butyl 2-(7-hydroxy-5-oxo-2-(4-(trifluoromethyl)phenyl)-3,5-dihydro-2H-[1,4]thiazino[2,3,4-ij]quinoline-6-carboxamido)acetate A 30 mL vial was charged with ethyl 7-hydroxy-5-oxo-2-(4-(trifluoromethyl)phenyl)-3,5-dihydro-2H-[1,4]thiazino[2,3,4-ij]quinoline-6-carboxylate (250 mg, 0.574 mmol), tert-butyl 2-aminoacetate (200 mg, 0.861 mmol), DIPEA (296 mg, 2.296 mmol) and toluene (5 mL). The mixture was heated to 115° C. and stirred for 3 hr. TLC (Petroleum ether: EtOAc=4:1) showed the starting material was consumed and a new spot was formed. The reaction mixture was poured into water, and extracted with EtOAc (20 mL*3). The combined organic layers were dried over Na$_2$SO$_4$, filtered and evaporated to dryness. The residue was purified via combi flash (20 g column, DCM in Petroleum Ether from 0% to 90%) to give tert-butyl 2-(7-hydroxy-5-oxo-2-(4-(trifluoromethyl)phenyl)-3,5-dihydro-2H-[1,4]thiazino[2,3,4-ij]quinoline-6-carboxamido)acetate as a solid. $^1$H NMR (CDCl$_3$, 400 MHz): δ 10.61 (brs, 1H), 8.05 (dd, J=7.9, 1.3

Hz, 1H), 7.67 (d, J=8.2 Hz, 2H), 7.55 (t, J=8.2 Hz, 3H), 7.23 (t, J=7.7 Hz, 1H), 5.32 (dd, J=14.0, 2.5 Hz, 1H), 4.44 (dd, J=9.5, 2.4 Hz, 1H), 4.25-4.16 (m, 1H), 4.13 (dd, J=10.5, 5.2 Hz, 2H), 1.50 (s, 9H).

Step G: 2-(7-hydroxy-5-oxo-2-(4-(trifluoromethyl)phenyl)-3,5-dihydro-2H-[1,4]thiazino[2,3,4-ij]quinoline-6-carboxamido)acetic acid A 100 mL round bottom flask was charged with tert-butyl 2-(7-hydroxy-5-oxo-2-(4-(trifluoromethyl)phenyl)-3,5-dihydro-2H-[1,4]thiazino[2,3,4-ij]quinoline-6-carboxamido)acetate (190 mg, 0.365 mmol), TFA (8 mL) and DCM (8 mL). The mixture was stirred at 40° C. for 2 hr. TLC (Petroleum ether: EtOAc=4:1) showed the starting material was consumed and the desired compound was formed. The solvent was then evaporated to give 2-(7-hydroxy-5-oxo-2-(4-(trifluoromethyl)phenyl)-3,5-dihydro-2H-[1,4]thiazino[2,3,4-ij]quinoline-6-carboxamido)acetic acid as a solid. $^1$H NMR (DMSO-$d_6$, 400 MHz): δ 10.36 (t, J=5.5 Hz, 1H), 7.90 (dd, J=7.9, 1.1 Hz, 1H), 7.75 (d, J=8.2 Hz, 2H), 7.70 (dd, J=7.6, 1.2 Hz, 1H), 7.64 (d, J=8.2 Hz, 2H), 7.28 (t, J=7.8 Hz, 1H), 4.94-4.82 (m, 2H), 4.47 (dd, J=14.2, 8.9 Hz, 1H), 4.09 (d, J=5.7 Hz, 2H). LC/MS (m/z): 465 (M+H)$^+$. Human HIF-PHD2 IC$_{50}$: 6.5 nM.

Example 59

2-(7-Hydroxy-1-oxido-5-oxo-2-(4-(trifluoromethyl)phenyl)-3,5-dihydro-2H-[1,4]thiazino[2,3,4-ij]quinoline-6-carboxamido)acetic acid

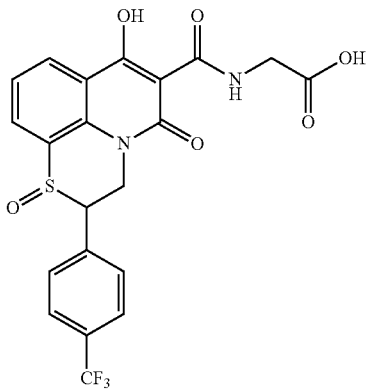 [SMILES: O=C(O)CNC(=O)c1c(O)c2cccc3c2n(c1=O)CC(c1ccc(C(F)(F)F)cc1)S3=O]

Step A: tert-butyl 2-(7-hydroxy-1-oxido-5-oxo-2-(4-(trifluoromethyl)phenyl)-3,5-dihydro-2H-[1,4]thiazino[2,3,4-ij]quinoline-6-carboxamido)acetate To a suspension of Step F product of Example 58 (100 mg, 0.192 mmol) in MeCN (5 mL) was added H$_2$O$_2$ (0.5 mL). The mixture was stirred at 80° C. for 20 hr. LCMS showed the desired compound was formed. Then the mixture was evaporated to give crude product tert-butyl 2-(7-hydroxy-1-oxido-5-oxo-2-(4-(trifluoromethyl)phenyl)-3,5-dihydro-2H-[1,4]thiazino[2,3,4-ij]quinoline-6-carboxamido)acetate as a solid and the residue was used directly in the next step.

Step B: 2-(7-hydroxy-1-oxido-5-oxo-2-(4-(trifluoromethyl)phenyl)-3,5-dihydro-2H-[1,4]thiazino[2,3,4-ij]quinoline-6-carboxamido)acetic acid A 100 mL round bottom flask was charged with tert-butyl 2-(7-hydroxy-1-oxido-5-oxo-2-(4-(trifluoromethyl)phenyl)-3,5-dihydro-2H-[1,4]thiazino[2,3,4-ij]quinoline-6-carboxamido)acetate (1.0 mmol), TFA (8 mL) and DCM (8 mL). The mixture was stirred at 40° C. for 2 hr. TLC (Petroleum ether: EtOAc=4:1) showed the starting material was consumed.

The solvent was then evaporated to give 2-(7-hydroxy-1-oxido-5-oxo-2-(4-(trifluoromethyl)phenyl)-3,5-dihydro-2H-[1,4]thiazino[2,3,4-ij]quinoline-6-carboxamido)acetic acid as a solid. $^1$H NMR (DMSO-$d_6$, 400 MHz) δ 10.36 (t, J=5.3 Hz, 1H), 8.43 (d, J=8.0 Hz, 1H), 8.34 (d, J=7.0 Hz, 1H), 7.87 (d, J=8.0 Hz, 2H), 7.73 (d, J=8.0 Hz, 2H), 7.57 (t, J=7.8 Hz, 1H), 5.20 (d, J=12.0 Hz, 1H), 4.90 (d, J=12.0 Hz, 1H), 4.44 (t, J=13.3 Hz, 1H), 4.17 (d, J=5.5 Hz, 2H). LC/MS (m/z): 481 (M+H)$^+$. Human HIF-PHD2 IC$_{50}$: 1.0 nM.

Example 60

2-(7-Hydroxy-1,1-dioxido-5-oxo-2-(4-(trifluoromethyl)phenyl)-3,5-dihydro-2H-[1,4]thiazino[2,3,4-ij]quinoline-6-carboxamido)acetic acid

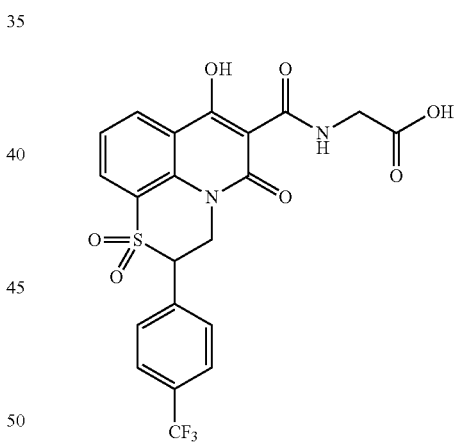

A 10 mL vial was charged with Example 58 product (30 mg, 0.063 mmol), H$_2$O$_2$ (1.5 mL), MeCN (1.5 mL), H$_2$O (1 mL) and TFA (0.5 mL). The mixture was heated at 80° C. for 0.5 hr. LCMS showed the desired compound was formed. Then water (20 mL) was added and the mixture was freeze-dried to give 2-(7-hydroxy-1,1-dioxido-5-oxo-2-(4-(trifluoromethyl)phenyl)-3,5-dihydro-2H-[1,4]thiazino[2,3,4-ij]quinoline-6-carboxamido)acetic acid as a solid. $^1$H NMR (DMSO-$d_6$, 400 MHz) δ 10.25 (brs, 1H), 8.46 (d, J=8.0 Hz, 1H), 8.38 (d, J=7.0 Hz, 1H), 7.91 (d, J=8.0 Hz, 2H), 7.78 (d, J=8.0 Hz, 2H), 7.63 (t, J=7.8 Hz, 1H), 5.58 (d, J=9.5 Hz, 1H), 5.40 (d, J=12.6 Hz, 1H), 4.67 (t, J=12.0 Hz, 1H), 4.16 (d, J=5.5 Hz, 2H). LC/MS (m/z): 497 (M+H)$^+$. Human HIF-PHD2 IC$_{50}$: 0.8 nM.

From the reaction of Example 60, the product of Example 61 in Table 2 was also isolated.

TABLE 2

| Example | Name | Structure | MS m/z (m + 1)+ and human HIF-PHD2 IC$_{50}$) |
|---|---|---|---|
| Example 61 | 2-(7-hydroxy-1-oxido-5-oxo-2-(4-(trifluoromethyl)phenyl)-3,5-dihydro-2H-[1,4]thiazino[2,3,4-ij]quinoline-6-carboxamido)acetic acid | 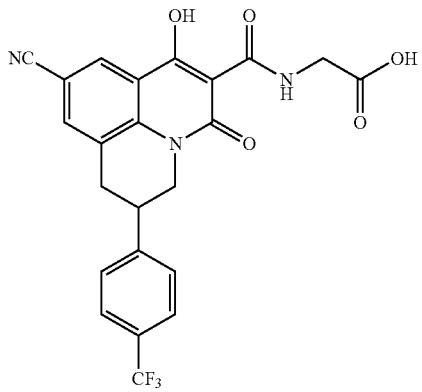 | (M + 1)+ 481 IC$_{50}$: 1.0 nM |

Example 62

2-(9-Cyano-1-hydroxy-3-oxo-6-(4-(trifluoromethyl)phenyl)-3,5,6,7-tetrahydropyrido[3,2,1-ij]quinoline-2-carboxamido)acetic acid

Step A: 6-bromo-3-(4-(trifluoromethyl)phenyl)-1,2,3,4-tetrahydroquinoline

To a solution of 3-(4-(trifluoromethyl)phenyl)-1,2,3,4-tetrahydroquinoline (325 mg, 1.172 mmol) in DCM (6 mL) was added a solution of NBS (209 mg, 1.172 mmol) in DCM (6 mL) dropwise in 30 min at room temperature. The mixture was stirred at room temperature for 3 hr. TLC (Petroleum ether: EtOAc=10:1) showed the starting material was consumed. Then the reaction mixture was evaporated to dryness and the residue was purified via silica gel column chromatography (20 column, EtOAc in petroleum ether from 0% to 4%) to give 6-bromo-3-(4-(trifluoromethyl)phenyl)-1,2,3,4-tetrahydroquinoline as a solid. $^1$H NMR (CDCl$_3$, 400 MHz): δ 7.60 (d, J=8.2 Hz, 2H), 7.35 (d, J=8.2 Hz, 2H), 7.15-7.08 (m, 2H), 6.44 (d, J=8.2 Hz, 1H), 3.49 (dd, J=11.3, 3.3 Hz, 1H), 3.34 (t, J=10.6 Hz, 1H), 3.25-3.15 (m, 1H), 2.98 (d, J=7.9 Hz, 2H).

Step B: Ethyl 9-bromo-1-hydroxy-3-oxo-6-(4-(trifluoromethyl)phenyl)-3,5,6,7-tetrahydropyrido[3,2,1-ij]quinoline-2-carboxylate A 100 mL round bottom flask was charged with 6-bromo-3-(4-(trifluoromethyl)phenyl)-1,2,3,4-tetrahydroquinoline (450 mg, 1.26 mmol) and triethyl methanetricarboxylate (1.17 g, 5.05 mmol). The flask was purged with N$_2$ and the mixture was stirred at 260° C. for 30 min. TLC (Petroleum ether: EtOAc=4:1) showed the starting material was consumed. The reaction mixture was diluted with petroleum ether and filtered to give ethyl 9-bromo-1-hydroxy-3-oxo-6-(4-(trifluoromethyl)phenyl)-3,5,6,7-tetrahydropyrido[3,2,1-ij]quinoline-2-carboxylate as a solid. $^1$H NMR (CDCl$_3$, 400 MHz): δ 14.20 (s, 1H), 8.19 (d, J=1.8 Hz, 1H), 7.64 (d, J=8.2 Hz, 2H), 7.59 (s, 1H), 7.40 (d, J=7.9 Hz, 2H), 4.92-4.84 (m, 1H), 4.52 (q, J=7.1 Hz, 2H), 3.69 (dd, J=13.8, 10.3 Hz, 1H), 3.34-3.25 (m, 1H), 3.22 (d, J=7.7 Hz, 2H), 1.48 (t, J=7.2 Hz, 3H).

Step C: tert-butyl 2-(9-bromo-1-hydroxy-3-oxo-6-(4-(trifluoromethyl)phenyl)-3,5,6,7-tetrahydropyrido[3,2,1-ij]quinoline-2-carboxamido)acetate A 30 mL vial was charged with ethyl 9-bromo-1-hydroxy-3-oxo-6-(4-(trifluoromethyl)phenyl)-3,5,6,7-tetrahydropyrido[3,2,1-ij]quinoline-2-carboxylate (450 mg, 0.907 mmol), tert-butyl 2-aminoacetate (316 mg, 1.36 mmol), DIPEA (468 mg, 3.628 mmol) and toluene (10 mL). The mixture was heated to 115° C. and stirred for 4 hr. TLC (Petroleum ether: EtOAc=2:1) showed the starting material was consumed. The reaction mixture was poured into water, extracted with EtOAc (20 mL*3). The combined organic layers were dried over Na$_2$SO$_4$, filtered and evaporated to give tert-butyl 2-(9-bromo-1-hydroxy-3-oxo-6-(4-(trifluoromethyl)phenyl)-3,5,6,7-tetrahydropyrido[3,2,1-ij]quinoline-2-carboxamido)acetate as a solid. $^1$H NMR (CDCl$_3$, 400 MHz): δ 10.66 (t, J=5.0 Hz, 1H), 8.21 (d, J=2.2 Hz, 1H), 7.66 (d, J=7.9 Hz, 2H), 7.59 (d, J=2.0 Hz, 1H), 7.41 (d, J=7.9 Hz, 2H), 4.95-4.86 (m, 1H), 4.13 (d, J=5.6 Hz, 2H), 3.71 (dd, J=13.6, 10.5 Hz, 1H), 3.37-3.27 (m, 1H), 3.23 (d, J=8.4 Hz, 2H), 1.51 (s, 9H).

Step D: tert-butyl 2-(9-cyano-1-hydroxy-3-oxo-6-(4-(trifluoromethyl)phenyl)-3,5,6,7-tetrahydropyrido[3,2,1-ij]quinoline-2-carboxamido)acetate A microwave tube was charged with tert-butyl 2-(9-bromo-1-hydroxy-3-oxo-6-(4-(trifluoromethyl)phenyl)-3,5,6,7-tetrahydropyrido[3,2,1-ij]quinoline-2-carboxamido)acetate (100 mg, 0.172 mmol), Zn(CN)$_2$ (53 mg, 0.447 mmol), Zn (29 mg, 0.447 mmol), Pd$_2$(dba)$_3$ (20 mg, 0.0224 mmol), dppf (12 mg, 0.0224 mmol) and DMA (2 mL). The tube was purged with N$_2$ and the reaction was heated by microwave at 120° C. for 30 min. LCMS showed the starting material was consumed and the desired compound was formed. The mixture was purified via prep-HPLC (Column: ASB C18 150*25 mm; Mobile phase: 63-93% MeCN in water (0.1% HCl; Wavelength: 220 nm) to give tert-butyl 2-(9-cyano-1-hydroxy-3-oxo-6-(4-(trifluoromethyl)phenyl)-3,5,6,7-tetrahydropyrido[3,2,1-ij]quinoline-2-carboxamido)acetate as a solid, which was used in the next step directly.

Step E: 2-(9-cyano-1-hydroxy-3-oxo-6-(4-(trifluoromethyl)phenyl)-3,5,6,7-tetrahydropyrido[3,2,1-ij]quinoline-2-carboxamido)acetic acid A 100 mL round bottom flask was charged with tert-butyl 2-(9-cyano-1-hydroxy-3-oxo-6-(4-(trifluoromethyl)phenyl)-3,5,6,7-tetrahydropyrido[3,2,1-ij]quinoline-2-carboxamido)acetate (527 mg, 1.0 mmol), TFA (8 mL) and DCM (8 mL). The mixture was stirred at 40° C. for 2 hr. LCMS showed the starting material was consumed. The solvent was then evaporated to give 2-(9-cyano-1-hydroxy-3-oxo-6-(4-(trifluoromethyl)phenyl)-3,5,6,7-tetrahydropyrido[3,2,1-ij]quinoline-2-carboxamido)acetic acid as a solid. $^1$H NMR (DMSO-d$_6$, 400 MHz): δ 10.36 (brs, 1H), 8.38 (s, 1H), 8.07 (s, 1H), 7.77 (d, J=8.0 Hz, 2H), 7.64 (d, J=7.5 Hz, 2H), 4.64 (d, J=12.6 Hz, 1H), 4.15 (d, J=5.0 Hz, 2H), 3.87 (t, J=11.8 Hz, 1H), 3.10-3.45 (m, 3H). LC/MS (m/z): 472 (M+H)$^+$. Human HIF-PHD2 IC$_{50}$: 1.9 nM.

Example 63

2-(7-Hydroxy-8-methyl-5-oxo-2-(4-(trifluoromethyl)phenyl)-3,5-dihydro-2H-[1,4]oxazino[2,3,4-ij]quinoline-6-carboxamido)acetic acid

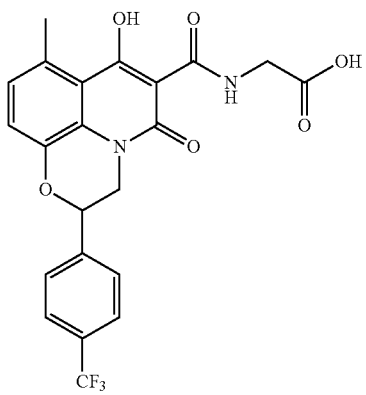

Step A: tert-butyl 2-(7-hydroxy-8-methyl-5-oxo-2-(4-(trifluoromethyl)phenyl)-3,5-dihydro-2H-[1,4]oxazino[2,3,4-ij]quinoline-6-carboxamido)acetate A 10 mL vial was charged Step D product of Example 11 (100 mg, 0.171 mol), 2,4,6-trimethyl-1,3,5,2,4,6-trioxatriborinane (32 mg, 0.257 mmol), Pd catlyst (9 mg, 0.0171 mmol), KOAc (50 mg, 0.513 mmol) and DMA (1.5 mL). The vial was purged with N$_2$, and the mixture was stirred at 85° C. for 16 hr. LCMS showed the starting material was consumed and the desired compound was formed. The reaction mixture was evaporated to dryness and the residue was purified via prep-HPLC (Column: ASB C18 150*25 mm; Mobile phase: 70-100% MeCN in water (0.1% HCl); Wavelength: 220 nm) to give tert-butyl 2-(7-hydroxy-8-methyl-5-oxo-2-(4-(trifluoromethyl)phenyl)-3,5-dihydro-2H-[1,4]oxazino[2,3,4-ij]quinoline-6-carboxamido)acetate as a solid. $^1$H NMR (DMSO-d$_6$, 400 MHz): δ 10.57 (t, J=5.5 Hz, 1H), 7.85 (d, J=8.0 Hz, 2H), 7.78 (d, J=8.0 Hz, 2H), 7.33 (d, J=8.0 Hz, 1H), 7.08 (d, J=8.0 Hz, 1H), 5.47 (d, J=7.0 Hz, 1H), 4.76 (dd, J=13.8, 2.3 Hz, 1H), 4.11 (d, J=5.5 Hz, 2H), 3.88 (dd, J=13.8, 9.3 Hz, 1H), 2.73 (s, 3H), 1.44 (s, 9H).

Step B: 2-(7-hydroxy-8-methyl-5-oxo-2-(4-(trifluoromethyl)phenyl)-3,5-dihydro-2H-[1,4]oxazino[2,3,4-ij]quinoline-6-carboxamido)acetic acid A 100 mL round bottom flask was charged with tert-butyl 2-(7-hydroxy-8-methyl-5-oxo-2-(4-(trifluoromethyl)phenyl)-3,5-dihydro-2H-[1,4]oxazino[2,3,4-ij]quinoline-6-carboxamido)acetate (519 mg, 1.0 mmol), TFA (8 mL) and DCM (8 mL). The mixture was stirred at 40° C. for 2 hr. LCMS showed the starting material was consumed and the desired compound was formed. The solvent was then evaporated to give 2-(7-hydroxy-8-methyl-5-oxo-2-(4-(trifluoromethyl)phenyl)-3,5-dihydro-2H-[1,4]oxazino[2,3,4-ij]quinoline-6-carboxamido)acetic acid as a solid. $^1$H NMR (DMSO-d$_6$, 400 MHz) δ 10.60 (brs, 1H), 7.85 (d, J=8.0 Hz, 2H), 7.78 (d, J=8.0 Hz, 2H), 7.32 (d, J=8.0 Hz, 1H), 7.08 (d, J=8.0 Hz, 1H), 5.46 (d, J=8.5 Hz, 1H), 4.77 (d, J=12.6 Hz, 1H), 4.14 (d, J=5.5 Hz, 2H), 3.87 (dd, J=13.3, 9.3 Hz, 1H), 2.73 (s, 3H). LC/MS (m/z): 463 (M+H)$^+$. Human HIF-PHD2 IC$_{50}$: 13 nM.

Example 64

2-(7-Hydroxy-5-oxo-2-(4-(trifluoromethyl)phenyl)-1,2,3,5-tetrahydropyrido[1,2,3-de]quinoxaline-6-carboxamido)acetic acid (TFA salt)

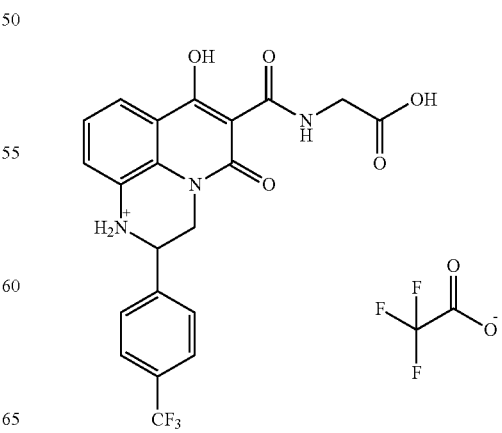

Step A: 3-(4-(trifluoromethyl)phenyl)-3,4-dihydroquinoxalin-2(1H)-one

A 30 mL vial was charged with ethyl 2-bromo-2-(4-(trifluoromethyl)phenyl)acetate (311 g, 1 mmol), 2-aminobenzenethiol (108 mg, 1 mmol), DIPEA (387 mg, 3 mmol) and toluene (5 mL). The mixture was stirred at 120° C. for 1.5 hr. LCMS and TLC (DCM: EtOAc=20:1) showed the desired compound was formed. The reaction mixture was poured into water and extracted with EtOAc (50 mL*3). The combined organic layers were evaporated to give 3-(4-(trifluoromethyl)phenyl)-3,4-dihydroquinoxalin-2(1H)-one as a solid. $^1$H NMR (CDCl$_3$, 400 MHz): δ 8.62 (brs, 1H), 7.53 (d, J=8.0Hz, 2H), 7.49 (d, J=8.0Hz, 2H), 6.88 (t, J=8.0Hz, 1H), 6.72 (t, J=8.0Hz, 1H), 6.70-6.64 (m, 2H), 5.08 (s, 1H), 4.23 (brs, 1H).

Step B: 2-(4-(trifluoromethyl)phenyl)-1,2,3,4-tetrahydroquinoxaline

A 100 mL three neck flask was charged with 3-(4-(trifluoromethyl)phenyl)-3,4-dihydroquinoxalin-2(1H)-one (280 mg, 0.958 mmol) and THF (10 mL). The flask was purged with N$_2$ and BH$_3$-Me$_2$S (1 mL) was added slowly. After addition, the mixture was stirred at room temperature for 18 hr. TLC (Petroleum ether: DCM=1:1) showed the starting material was consumed. Then the reaction mixture was cooled to 0° C. and 1M HCl (20 mL) was added slowly. Then the mixture was basified to pH 12 with NaOH solution and extracted with EtOAc (50 mL*3). The organic layers were dried over Na$_2$SO$_4$, filtered and evaporated to dryness to give 2-(4-(trifluoromethyl)phenyl)-1,2,3,4-tetrahydroquinoxaline as a solid. $^1$H NMR (CDCl$_3$, 400 MHz): δ 7.63 (d, J=8.0 Hz, 2H), 7.52 (d, J=8.0 Hz, 2H), 6.70-6.66(m, 2H), 6.64-6.59 (m, 2H), 4.59 (dd, J=7.7, 2.9 Hz, 1H), 3.50 (dd, J=11.0, 3.1 Hz, 1H), 3.32 (dd, J=11.0, 7.7 Hz, 1H).

Step C: Ethyl 7-hydroxy-5-oxo-2-(4-(trifluoromethyl)phenyl)-1,2,3,5-tetrahydropyrido[1,2,3-de]quinoxaline-6-carboxylate A thumb flask was charged with 2-(4-(trifluoromethyl)phenyl)-1,2,3,4-tetrahydroquinoxaline (470 mg, 1.69 mmol) and triethyl methanetricarboxylate (1177 mg, 5.07 mmol). The flask was purged with N$_2$ and heated at 220° C. for 10 min. TLC (Petroleum ether: EtOAc=4:1) showed the starting material was consumed. The reaction mixture was purified via silica gel column chromatography (EtOAc in Petroleum ether from 0% to 30%) to give ethyl 7-hydroxy-5-oxo-2-(4-(trifluoromethyl)phenyl)-1,2,3,5-tetrahydropyrido[1,2,3-de]quinoxaline-6-carboxylate as a solid. $^1$H NMR (CDCl$_3$, 400 MHz): δ 14.21 (s, 1H), 7.68 (d, J=8.0 Hz, 2H), 7.63 (d, J=8.0 Hz, 1H), 7.56 (d, J=8.0 Hz, 2H), 7.11 (t, J=7.8 Hz, 1H), 6.99 (d, J=8.0 Hz, 1H), 4.91 (dd, J=13.6, 3.0 Hz, 1H), 4.57-4.44 (m, 3H), 4.40 (brs, 1H), 3.56 (dd, J=13.3, 9.8 Hz, 1H), 1.47 (t, J=7.3 Hz, 3H).

Step D: tert-butyl 2-(7-hydroxy-5-oxo-2-(4-(trifluoromethyl)phenyl)-1,2,3,5-tetrahydropyrido[1,2,3-de]quinoxaline-6-carboxamido)acetate A 30 mL vial was charged with ethyl 7-hydroxy-5-oxo-2-(4-(trifluoromethyl)phenyl)-1,2,3,5-tetrahydropyrido[1,2,3-de]quinoxaline-6-carboxylate (150 mg, 0.359 mmol), tert-butyl 2-aminoacetate (125 mg, 0.538 mmol), DIPEA (185 mg, 1.436 mmol) and toluene (8 mL). The mixture was heated to 115° C. and stirred for 1 hr. TLC (DCM) showed the starting material was consumed and a new spot was formed. The reaction mixture was poured into water, extracted with EtOAc (20 mL*3). The combined organic layers were dried over Na$_2$SO$_4$, filtered and evaporated to give tert-butyl 2-(7-hydroxy-5-oxo-2-(4-(trifluoromethyl)phenyl)-1,2,3,5-tetrahydropyrido[1,2,3-de]quinoxaline-6-carboxamido)acetate as a solid. $^1$H NMR (DMSO-d$_6$, 400 MHz): δ 10.51 (t, J=5.6 Hz, 1H), 7.80 (d, J=8.0 Hz, 2H), 7.71 (d, J=8.0 Hz, 2H), 7.38 (d, J=7.5 Hz, 1H), 7.21-7.10 (m, 2H), 7.05 (s, 1H), 4.71 (d, J=6.0 Hz, 1H), 4.55 (d, J=11.5 Hz, 1H), 4.09 (d, J=5.5 Hz, 2H), 3.84 (dd, J=13.0, 8.5 Hz, 1H), 1.43 (s, 9H).

Step E: 2-(7-hydroxy-5-oxo-2-(4-(trifluoromethyl)phenyl)-1,2,3,5-tetrahydropyrido[1,2,3-de]quinoxaline-6-carboxamido)acetic acid A 100 mL round bottom flask was charged with tert-butyl 2-(7-hydroxy-5-oxo-2-(4-(trifluoromethyl)phenyl)-1,2,3,5-tetrahydropyrido[1,2,3-de]quinoxaline-6-carboxamido)acetate (165 mg, 0.328 mmol), TFA (5 mL) and DCM (10 mL). The mixture was stirred at 40° C. for 1 hr. LCMS showed the starting material was consumed. The solvent was then evaporated to give 2-(7-hydroxy-5-oxo-2-(4-(trifluoromethyl)phenyl)-1,2,3,5-tetrahydropyrido[1,2,3-de]quinoxaline-6-carboxamido)acetic acid (TFA salt) as a solid. $^1$H NMR (DMSO-d$_6$, 400 MHz) δ 10.48 (brs, 1H), 7.76 (d, J=8.2 Hz, 2H), 7.67 (d, J=8.2 Hz, 2H), 7.34 (d, J=7.3 Hz, 1H), 7.18-7.05 (m, 2H), 7.01 (brs, 1H), 4.67 (d, J=5.7 Hz, 1H), 4.51 (d, J=12.8 Hz, 1H), 4.02 (d, J=5.1 Hz, 2H), 3.80 (dd, J=12.7, 8.3 Hz, 1H). LC/MS (m/z): 448 (M+H)$^+$. Human HIF-PHD2 IC$_{50}$: 4.5 nM.

Example 65

2-(7-Hydroxy-1-methyl-5-oxo-2-(4-(trifluoromethyl)phenyl)-1,2,3,5-tetrahydropyrido[1,2,3-de]quinoxaline-6-carboxamido)acetic acid

Step A: ethyl 7-hydroxy-1-methyl-5-oxo-2-(4-(trifluoromethyl)phenyl)-1,2,3,5-tetrahydropyrido[1,2,3-de]quinoxaline-6-carboxylate A 30 mL vial was charged with Example 64 Step C product (100 mg ,0.239 mmol), paraformaldehyde (150 mg, 1.67 mmol), formic acid (0.5 mL) and toluene (5 mL). The mixture was heated at 100° C. for 5 hr. LCMS showed the desired compound was formed. The reaction mixture was purified via prep-HPLC (Column: ASB C18 150*25 mm; Mobile phase: 56-86% MeCN in water (0.1% HCl); Wavelength: 220 nm) to give ethyl 7-hydroxy-1-methyl-5-oxo-2-(4-(trifluoromethyl)phenyl)-1,2,3,5-tetrahydropyrido[1,2,3-de]quinoxaline-6-carboxylate as an oil. $^1$H NMR (DMSO-$d_6$, 400 MHz): δ 14.20 (s, 1H), 8.11 (s, 1H), 7.59 (d, J=7.5 Hz, 1H), 7.54 (d, J=8.0 Hz, 2H), 7.18-7.25 (m, 2H), 6.95 (d, J=8.0 Hz, 1H), 4.67-4.58 (m, 2H), 4.52-4.40 (m, 2H), 4.25 (dd, J=15.1, 5.5 Hz, 1H), 2.94 (s, 3H), 1.45 (t, J=7.3 Hz, 3H).

Step B: tert-butyl 2-(7-hydroxy-1-methyl-5-oxo-2-(4-(trifluoromethyl)phenyl)-1,2,3,5-tetrahydropyrido[1,2,3-de]quinoxaline-6-carboxamido)acetate A 30 mL vial was charged with ethyl 7-hydroxy-1-methyl-5-oxo-2-(4-(trifluoromethyl)phenyl)-1,2,3,5-tetrahydropyrido[1,2,3-de]quinoxaline-6-carboxylate (432 mg, 1.0 mmol), tert-butyl 2-aminoacetate (249 mg, 1.50 mmol), DIPEA (616 mg, 4.0 mmol) and toluene (8 mL). The mixture was heated to 115° C. and stirred for 1 hr. TLC (DCM) showed the starting material was consumed and a new spot was formed. The reaction mixture was poured into water, extracted with EtOAc (20 mL*3). The combined organic layers were dried over Na$_2$SO$_4$, filtered and evaporated to give tert-butyl 2-(7-hydroxy-1-methyl-5-oxo-2-(4-(trifluoromethyl)phenyl)-1,2,3,5-tetrahydropyrido[1,2,3-de]quinoxaline-6-carboxamido)acetate as a solid. $^1$H NMR (DMSO-$d_6$, 400 MHz): δ 10.54 (t, J=4.8 Hz, 1H), 7.62 (d, J=7.9 Hz, 1H), 7.57 (d, J=7.9 Hz, 2H), 7.26-7.23 (m, 3H), 6.97 (d, J=7.7 Hz, 1H), 4.66-4.57 (m, 2H), 4.37-4.28 (m, 1H), 4.10 (dd, J=5.1, 1.1 Hz, 2H), 2.95 (s, 3H), 1.49 (s, 9H).

Step C: 2-(7-hydroxy-1-methyl-5-oxo-2-(4-(trifluoromethyl)phenyl)-1,2,3,5-tetrahydropyrido[1,2,3-de]quinoxaline-6-carboxamido)acetic acid A 100 mL round bottom flask was charged with tert-butyl 2-(7-hydroxy-1-methyl-5-oxo-2-(4-(trifluoromethyl)phenyl)-1,2,3,5-tetrahydropyrido[1,2,3-de]quinoxaline-6-carboxamido)acetate (165 mg, 0.328 mmol), TFA (5 mL) and DCM (10 mL). The mixture was stirred at 40° C. for 1 hr. LCMS showed the starting material was consumed and the desired compound was formed. The solvent was then evaporated and the residue was purified by prep-HPLC (Column: ASB C18 150*25 mm; Mobile phase: 50-80-15% MeCN in water (0.1% HCl); Wavelength: 220 nm) to give the title product 2-(7-hydroxy-1-methyl-5-oxo-2-(4-(trifluoromethyl)phenyl)-1,2,3,5-tetrahydropyrido[1,2,3-de]quinoxaline-6-carboxamido)acetic acid as a solid. $^1$H NMR (CD$_3$OD, 400 MHz) δ 7.49 (d, J=7.9 Hz, 2H), 7.38 (d, J=7.72 Hz, 1H), 7.24 (d, J=7.7 Hz, 2H), 7.14 (t, J=7.6 Hz, 1H), 6.94 (d, J=7.5 Hz, 1H), 4.70 (brs, 1H), 4.53 (d, J=13.2 Hz, 1H), 4.16-4.02 (m, 1H), 3.98 (s, 2H), 2.86 (brs, 3H). LC/MS (m/z): 462 (M+H)$^+$. Human HIF-PHD2 IC$_{50}$: 34 nM.

Example 66

2-(9-Fluoro-7-hydroxy-5-oxo-2-(4-(trifluoromethyl)phenyl)-3,5-dihydro-2H-[1,4]oxazino[2,3,4-ij]quinoline-6-carboxamido)acetic acid

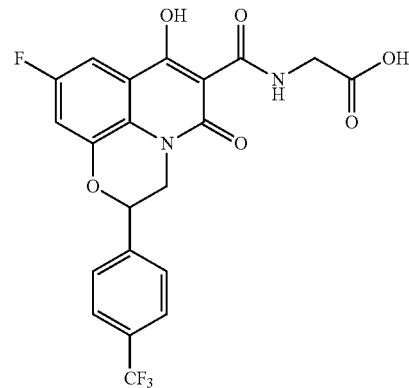

Step A: 7-fluoro-2-(4-(trifluoromethyl)phenyl)-2H-benzo[b][1,4]oxazin-3(4H)-one To a solution of 2-amino-5-fluorophenol (1 g, 7.87 mmol) and DIPEA (4 g, 31.48 mmol) in DCM (15 mL) was added 2-bromo-2-(4-(trifluoromethyl)phenyl)acetyl chloride (2.37 g, 7.87 mmol) slowly at room temperature. The mixture was stirred at room temperature for 20 hr. TLC (Petroleum ether: EtOAc=3:1) showed the starting material was consumed. The reaction mixture was poured into water and extracted with EtOAc (50 mL*3). The combined organic layers were evaporated to give 7-fluoro-2-(4-(trifluoromethyl)phenyl)-2H-benzo[b][1,4]oxazin-3(4H)-one as a solid. $^1$H NMR (CDCl$_3$, 400 MHz): δ 8.70 (brs, 1H), 7.65 (d, J=8.0 Hz, 2H), 7.60 (d, J=8.0 Hz, 2H), 6.84 (dd, J=9.0, 2.4 Hz, 1H), 6.80-6.75 (m, 1H), 6.74-6.68 (m, 1H), 5.75 (s, 1H).

Step B: 7-fluoro-2-(4-(trifluoromethyl)phenyl)-3,4-dihydro-2H-benzo[b][1,4]oxazine A 250 mL three neck flask was charged with 7-fluoro-2-(4-(trifluoromethyl)phenyl)-2H-benzo[b][1,4]oxazin-3(4H)-one (1.54 g, 4.95 mmol) and THF (20 mL). The flask was purged with N$_2$, then BH$_3$-Me$_2$S (3 mL) was added slowly. After addition, the mixture was stirred at room temperature for 20 hr. TLC (Petroleum ether: EtOAc=3:1) showed the starting material was consumed. Then 1 M HCl (10 mL) was added to the reaction mixture slowly at room temperature. After quenching, the mixture was basified to pH 12 with NaOH solution and then extracted with EtOAc (50 mL*3). The organic layers were dried over Na$_2$SO$_4$, filtered and evaporated to give 7-fluoro-2-(4-(trifluoromethyl)phenyl)-3,4-dihydro-2H-benzo[b][1,4]oxazine as an oil. $^1$H NMR (CDCl$_3$, 400 MHz): δ 7.66 (d, J=7.5 Hz, 2H), 7.52 (d, J=7.5 Hz, 2H), 6.67 (d, J=9.3 Hz, 1H), 6.62-6.52 (m, 2H), 5.16 (d, J=7.3 Hz, 1H), 3.78 (brs, 1H), 3.52 (d, J=11.5 Hz, 1H), 3.29 (dd, J=11.4, 8.7 Hz, 1H).

Step C: Ethyl 9-fluoro-7-hydroxy-5-oxo-2-(4-(trifluoromethyl)phenyl)-3,5-dihydro-2H-[1,4]oxazino[2,3,4-ij]quinoline-6-carboxylate A 100 mL round bottom flask was charged with 7-fluoro-2-(4-(trifluoromethyl)phenyl)-3,4-dihydro-2H-benzo[b][1, 4]oxazine (1.3 g, 4.37 mmol) and triethyl methanetricarboxylate (4 g, 17.5 mmol). The flask was purged with $N_2$ and heated at 220° C. for 0.5 hr. TLC (Petroleum ether: EtOAc=3:1) showed the starting material was consumed. The reaction mixture was diluted with petroleum ether (20 mL) and filtered, and the cake was collected as ethyl 9-fluoro-7-hydroxy-5-oxo-2-(4-(trifluoromethyl)phenyl)-3,5-dihydro-2H-[1,4]oxazino[2,3,4-ij]quinoline-6-carboxylate as a solid. $^1$H NMR (CDCl$_3$, 400 MHz): δ 14.30 (brs, 1H), 7.73 (d, J=7.94 Hz, 2H), 7.60 (d, J=8.2 Hz, 2H), 7.49 (dd, J=8.5, 2.3 Hz, 1H), 7.11 (dd, J=8.8, 2.4 Hz, 1H), 5.22 (d, J=8.4 Hz, 1H), 4.95 (dd, J=14.2, 2.1 Hz, 1H), 4.59-4.47 (m, 2H), 3.67 (dd, J=14.2, 9.6 Hz, 1H), 1.49 (t, J=7.2 Hz, 3H).

Step D: tert-butyl 2-(9-fluoro-7-hydroxy-5-oxo-2-(4-(trifluoromethyl)phenyl)-3,5-dihydro-2H-[1,4]oxazino[2,3,4-ij]quinoline-6-carboxamido)acetate A 30 mL vial was charged with ethyl 9-fluoro-7-hydroxy-5-oxo-2-(4-(trifluoromethyl)phenyl)-3,5-dihydro-2H-[1,4]oxazino[2,3,4-ij]quinoline-6-carboxylate (1130 mg, 2.58 mmol), tert-butyl 2-aminoacetate (900 mg, 3.88 mmol), DIPEA (1330 mg, 10.32 mmol) and toluene (15 mL). The mixture was heated to 115° C. and stirred for 1 hr. LCMS showed the starting material was consumed. The reaction mixture was poured into water and extracted with EtOAc (20 mL*3). The combined organic layers were dried over Na$_2$SO$_4$, filtered and evaporated to give tert-butyl 2-(9-fluoro-7-hydroxy-5-oxo-2-(4-(trifluoromethyl)phenyl)-3,5-dihydro-2H-[1,4]oxazino[2,3,4-ij]quinoline-6-carboxamido)acetate as a solid. $^1$H NMR (CDCl$_3$, 400 MHz): δ 10.58 (t, J=4.8 Hz, 1H), 7.74 (d, J=8.2 Hz, 2H), 7.62 (d, J=7.9 Hz, 2H), 7.50 (dd, J=8.5, 2.8 Hz, 1H), 7.11 (dd, J=8.9, 2.8 Hz, 1H), 5.24 (dd, J=9.5, 2.2 Hz, 1H), 4.98 (dd, J=14.3, 2.7 Hz, 1H), 4.23-4.06 (m, 2H), 3.70 (dd, J=14.1, 9.7 Hz, 1H), 1.51 (s, 9H).

Step E: 2-(9-fluoro-7-hydroxy-5-oxo-2-(4-(trifluoromethyl)phenyl)-3,5-dihydro-2H-[1,4]oxazino[2,3,4-ij]quinoline-6-carboxamido)acetic acid A 100 mL round bottom flask was charged with tert-butyl 2-(9-fluoro-7-hydroxy-5-oxo-2-(4-(trifluoromethyl)phenyl)-3,5-dihydro-2H-[1,4]oxazino[2,3,4-ij]quinoline-6-carboxamido)acetate (1120 mg, 2.14 mmol), TFA (10 mL) and DCM (15 mL). The mixture was stirred at 40° C. for 1 hr. LCMS showed the starting material was consumed. The solvent was evaporated and the residue was washed with petroleum ether to give 2-(9-fluoro-7-hydroxy-5-oxo-2-(4-(trifluoromethyl)phenyl)-3,5-dihydro-2H-[1,4]oxazino[2,3,4-ij]quinoline-6-carboxamido)acetic acid as a solid. $^1$H NMR (DMSO-d$_6$, 400 MHz) δ 10.44 (t, J=5.3 Hz, 1H), 7.87 (d, J=12.0 Hz, 2H), 7.79 (d, J=12.0 Hz, 2H), 7.47 (dd, J=9.3, 2.3 Hz, 1H), 7.43 (dd, J=8.5, 2.5 Hz, 1H), 5.58 (d, J=8.0 Hz, 1H), 4.76 (d, J=11.5 Hz, 1H), 4.15 (d, J=5.5 Hz, 2H), 3.89 (dd, J=13.8, 9.3 Hz, 1H). LC/MS (m/z): 467 (M+H)$^+$. Human HIF-PHD2 IC$_{50}$: 5.0 nM.

Example 67

2-(10-Fluoro-7-hydroxy-5-oxo-2-(4-(trifluoromethyl)phenyl)-3,5-dihydro-2H-[1,4]oxazino[2,3,4-ij]quinoline-6-carboxamido)acetic acid

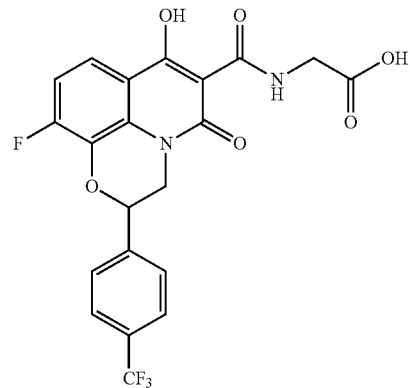

Step A: 8-fluoro-2-(4-(trifluoromethyl)phenyl)-2H-benzo[b][1,4]oxazin-3(4H)-one

To a solution of 2-amino-6-fluorophenol (1 g, 7.87 mmol) and DIPEA (4 g, 31.48 mmol) in DCM (15 mL) was added 2-bromo-2-(4-(trifluoromethyl)phenyl)acetyl chloride (2.37 g, 7.87 mmol) slowly at room temperature. The reaction was stirred at room temperature for 20 hr. The mixture was poured into water and extracted with EtOAc (50 mL*3). The combined organic layers were evaporated to give 8-fluoro-2-(4-(trifluoromethyl)phenyl)-2H-benzo[b][1,4]oxazin-3 (4H)-one as a solid. $^1$H NMR (CDCl$_3$, 400 MHz): δ 8.71 (brs, 1H), 7.64 (s, 4H), 6.96-6.82 (m, 2H), 6.61 (d, J=7.9 Hz, 1H), 5.84 (s, 1H).

Step B: 8-fluoro-2-(4-(trifluoromethyl)phenyl)-3,4-dihydro-2H-benzo[b][1,4]oxazine A 250 mL three neck flask was charged with 8-fluoro-2-(4-(trifluoromethyl)phenyl)-2H-benzo[b][1,4]oxazin-3 (4H)-one (858 mg, 2.76 mmol) and THF (20 mL). The flask was purged with $N_2$, then BH$_3$-Me$_2$S (2 mL) was added slowly. After addition, the mixture was stirred at room temperature for 20 hr. TLC (Petroleum ether: EtOAc=3:1) showed the starting material was consumed. Then 1 M HCl (10 mL) was added to the reaction mixture slowly at room temperature. After quenching, the mixture was basified to pH 12 with NaOH solution and then extracted with EtOAc (50 mL*3). The organic layers were dried over Na$_2$SO$_4$, filtered and evaporated to dryness to give 8-fluoro-2-(4-(trifluoromethyl)phenyl)-3,4-dihydro-2H-benzo[b][1,4]oxazine as an oil. $^1$H NMR (CDCl$_3$, 400 MHz): δ 7.67 (d, J=8.2 Hz, 2H), 7.57 (d, J=8.2 Hz, 2H), 6.74 (td, J=8.1, 5.5 Hz, 1H), 6.59-6.52 (m, 1H), 6.45 (d, J=7.9 Hz, 1H), 5.19 (dd, J=8.2, 1.7 Hz, 1H), 4.07 (brs, 1H), 3.60 (dd, J=12.1, 2.2 Hz, 1H), 3.38 (dd, J=12.1, 8.4 Hz, 1H).

Step C: Ethyl 10-fluoro-7-hydroxy-5-oxo-2-(4-(trifluoromethyl)phenyl)-3,5-dihydro-2H-[1,4]oxazino[2,3,4-ij]quinoline-6-carboxylate A 100 mL round bottom flask was charged with 8-fluoro-2-(4-(trifluoromethyl)phenyl)-3,4-dihydro-2H-benzo[b][1, 4]oxazine (800 mg, 2.69 mmol) and triethyl methanetricarboxylate (2.5 g, 10.77 mmol). The flask was purged with $N_2$ and the reaction was heated at 220° C. for 0.5 hr. TLC (Petroleum ether: EtOAc=3:1) showed the starting material was consumed. The reaction mixture was diluted with petroleum ether (20 mL) and filtered. The cake was collected which was ethyl 10-fluoro-7-hydroxy-5-oxo-2-(4-(trifluoromethyl)phenyl)-3,5-dihydro-2H-[1,4]oxazino[2,3,4-ij]quinoline-6-carboxylate as a solid. $^1$H NMR (CDCl$_3$, 400 MHz): δ 14.38 (s, 1H), 7.79 (dd, J=9.0, 5.3 Hz, 1H), 7.73 (d, J=8.2 Hz, 2H), 7.63 (d, J=8.2 Hz, 2H), 7.07 (t, J=9.37 Hz, 1H), 5.29-5.21 (m, 1H), 4.96 (dd, J=14.3, 2.6 Hz, 1H), 4.59-4.45 (m, 2H), 3.74 (dd, J=14.3, 9.3 Hz, 1H), 1.49 (t, J=7.1 Hz, 3H).

Step D: tert-butyl 2-(10-fluoro-7-hydroxy-5-oxo-2-(4-(trifluoromethyl)phenyl)-3,5-dihydro-2H-[1,4]oxazino[2,3,4-ij]quinoline-6-carboxamido)acetate A 30 mL vial was charged with ethyl 10-fluoro-7-hydroxy-5-oxo-2-(4-(trifluoromethyl)phenyl)-3,5-dihydro-2H-[1,4]oxazino[2,3,4-ij]quinoline-6-carboxylate (608 mg, 1.39 mmol), tert-butyl 2-aminoacetate (484 mg, 2.08 mmol), DIPEA (717 mg, 5.56 mmol) and toluene (15 mL). The mixture was heated to 115° C. and stirred for 1 hr. LCMS showed the starting material was consumed and the desired compound formed. The reaction mixture was poured into water and extracted with EtOAc (20 mL*3). The combined organic layers were dried over Na$_2$SO$_4$, filtered and evaporated to give tert-butyl 2-(10-fluoro-7-hydroxy-5-oxo-2-(4-(trifluoromethyl)phenyl)-3,5-dihydro-2H-[1,4]oxazino[2,3,4-ij]quinoline-6-carboxamido)acetate as a solid. $^1$H NMR (CDCl$_3$, 400 MHz): δ 10.46 (t, J=5.2 Hz, 1H), 7.79 (dd, J=9.0, 5.3 Hz, 1H), 7.72 (d, J=8.0 Hz, 2H), 7.63 (d, J=8.0 Hz, 2H), 7.09 (t, J=9.4 Hz, 1H), 5.24 (d, J=7.5 Hz, 1H), 4.97 (dd, J=14.2, 2.5 Hz, 1H), 4.21-4.04 (m, 2H), 3.74 (dd, J=14.2, 9.4 Hz, 1H), 1.50 (s, 9H).

Step E: 2-(10-fluoro-7-hydroxy-5-oxo-2-(4-(trifluoromethyl)phenyl)-3,5-dihydro-2H-[1,4]oxazino[2,3,4-ij]quinoline-6-carboxamido)acetic acid A 100 mL round bottom flask was charged with tert-butyl 2-(10-fluoro-7-hydroxy-5-oxo-2-(4-(trifluoromethyl)phenyl)-3,5-dihydro-2H-[1,4]oxazino[2,3,4-ij]quinoline-6-carboxamido)acetate (619 mg, 1.18 mmol), TFA (10 mL) and DCM (15 mL). The mixture was stirred at 40° C. for 1 hr. LCMS showed the starting material was consumed and the desired compound was formed. The solvent was then evaporated and the residue was washed with petroleum ether to give 2-(10-fluoro-7-hydroxy-5-oxo-2-(4-(trifluoromethyl)phenyl)-3,5-dihydro-2H-[1,4]oxazino[2,3,4-ij]quinoline-6-carboxamido)acetic acid as a solid. $^1$H NMR (DMSO-d$_6$, 400 MHz) δ 10.35 (brs, 1H), 7.88 (d, J=8.0 Hz, 2H), 7.80 (d, J=8.0 Hz, 2H), 7.74 (dd, J=8.8, 5.3 Hz, 1H), 7.35 (t, J=9.5 Hz, 1H), 5.60 (d, J=8.0 Hz, 1H), 4.80 (d, J=13.0 Hz, 1H), 4.15 (d, J=5.5 Hz, 2H), 3.93 (dd, J=13.8, 9.8 Hz, 1H). LC/MS (m/z): 467 (M+H)$^+$. Human HIF-PHD2 IC$_{50}$: 4.3 nM.

Example 68

2-(8-Fluoro-7-hydroxy-5-oxo-2-(4-(trifluoromethyl)phenyl)-3,5-dihydro-2H-[1,4]oxazino[2,3,4-ij]quinoline-6-carboxamido)acetic acid

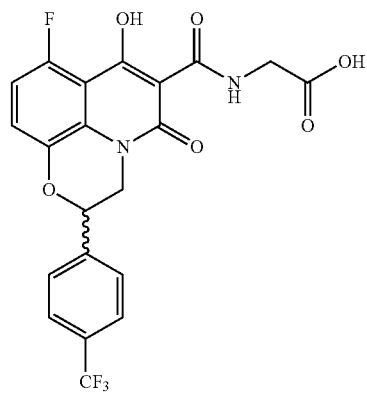 [SMILES: O=C(O)CNC(=O)c1c(O)c2c(Cl)ccc3c2n(c1=O)CC(c1ccc(C(F)(F)F)cc1)O3]

Step A: 6-fluoro-2-(4-(trifluoromethyl)phenyl)-2H-benzo[b][1,4]oxazin-3(4H)-one

To a solution of 2-amino-4-fluorophenol (127 mg, 1.0 mmol) and DIPEA (636 mg, 4.0 mmol) in DCM (15 mL) was added 2-bromo-2-(4-(trifluoromethyl)phenyl)acetyl chloride (300 mg, 1.0 mmol) slowly at room temperature. The reaction was stirred at room temperature for 20 hr. The mixture was poured into water and extracted with EtOAc (50 mL*3). The combined organic layers were evaporated to give 6-fluoro-2-(4-(trifluoromethyl)phenyl)-2H-benzo[b][1,4]oxazin-3(4H)-one as solid, which was used in the next step without any purification.

Step B: 6-fluoro-2-(4-(trifluoromethyl)phenyl)-3,4-dihydro-2H-benzo[b][1,4]oxazine A 250 mL three neck flask was charged with 6-fluoro-2-(4-(trifluoromethyl)phenyl)-2H-benzo[b][1,4]oxazin-3(4H)-one (622 mg, 2 mmol) and THF (20 mL). The flask was purged with N$_2$, then BH$_3$-Me$_2$S (3 mL) was added slowly. After addition, the mixture was stirred at room temperature for 20 hr. TLC (Petroleum ether: EtOAc=3:1) showed the starting material was consumed. Then 1 M HCl (10 mL) was added to the reaction mixture slowly at room temperature. After quenching, the mixture was basified to pH 12 with NaOH solution and then extracted with EtOAc (50 mL*3). The organic layers were dried over Na$_2$SO$_4$, filtered and evaporated to give 6-fluoro-2-(4-(trifluoromethyl)phenyl)-3,4-dihydro-2H-benzo[b][1,4]oxazine as a solid. $^1$H NMR (CDCl$_3$, 400 MHz) δ 7.68 (d, J=8.0 Hz, 2H), 7.54 (d, J=8.0 Hz, 2H), 6.85-6.81 (m, 1H), 6.42-6.37 (m, 2H), 5.10 (d, J=7.2 Hz, 1H), 4.02 (brs, 1H), 3.56-3.52 (m, 1H), 3.37-3.31 (m, 1H).

Step C: ethyl 8-fluoro-7-hydroxy-5-oxo-2-(4-(trifluoromethyl)phenyl)-3,5-dihydro-2H-[1,4]oxazino[2,3,4-ij]quinoline-6-carboxylate A 100 mL round bottom flask was charged with 6-fluoro-2-(4-(trifluoromethyl)phenyl)-3,4-dihydro-2H-benzo[b][1,4]oxazine (297 mg, 1.0 mmol) and triethyl methanetricarboxylate (928 mg, 4.0 mmol). The flask was purged with $N_2$ and the mixture was heated at 220° C. for 0.5 hr. TLC (Petroleum ether: EtOAc=3:1) showed the starting material was consumed. The reaction mixture was diluted with petroleum ether (20 mL) and filtered, and the cake was collected which was ethyl 8-fluoro-7-hydroxy-5-oxo-2-(4-(trifluoromethyl)phenyl)-3,5-dihydro-2H-[1,4]oxazino[2,3,4-ij]quinoline-6-carboxylate as a solid. $^1$H NMR (CDCl$_3$, 400 MHz) δ 14.74 (s, 1H), 7.69 (d, J=8.4 Hz, 2H), 7.57 (d, J=8.0 Hz, 2H), 7.25-7.22 (m, 1H), 6.88-6.86 (m, 1H), 5.10 (d, J=7.2 Hz, 1H), 4.95-4.91 (m, 1H), 4.49 (q, J=4.8 Hz, 2H), 3.62-3.56 (m, 1H), 1.46 (t, J=7.2 Hz, 3H).

Step D: tert-butyl 2-(8-fluoro-7-hydroxy-5-oxo-2-(4-(trifluoromethyl)phenyl)-3,5-dihydro-2H-[1,4]oxazino[2,3,4-ij]quinoline-6-carboxamido)acetate (peak 1) and tert-butyl 2-(8-fluoro-7-hydroxy-5-oxo-2-(4-(trifluoromethyl)phenyl)-3,5-dihydro-2H-[1,4]oxazino[2,3,4-ij]quinoline-6-carboxamido)acetate (peak 2)

A 30 mL vial was charged with ethyl 10-fluoro-7-hydroxy-5-oxo-2-(4-(trifluoromethyl)phenyl)-3,5-dihydro-2H-[1,4]oxazino[2,3,4-ij]quinoline-6-carboxylate (608 mg, 1.39 mmol), tert-butyl 2-aminoacetate (484 mg, 2.08 mmol), DIPEA (717 mg, 5.56 mmol) and toluene (15 mL). The mixture was heated to 115° C. and stirred for 1 hr. LCMS showed the starting material was consumed. The reaction mixture was poured into water and extracted with EtOAc (20 mL*3). The combined organic layers were dried over Na$_2$SO$_4$, filtered and evaporated to give tert-butyl 2-(10-fluoro-7-hydroxy-5-oxo-2-(4-(trifluoromethyl)phenyl)-3,5-dihydro-2H-[1,4]oxazino[2,3,4-ij]quinoline-6-carboxamido)acetate (619 mg, 85.3%) as a solid. The racemate was resolved by SFC (Instrument: Thar SFC 80; Column: OJ 250 mm*30 mm, 20 um; Mobile phase: A: Supercritical CO$_2$, B: EtOH (0.1% NH$_3$.H$_2$O), A:B=60:40 at 80 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford peak 1 (Chiralcel OJ-H 250×4.6 mm I.D., 5 um Mobile phase: methanol (0.05% DEA) in CO$_2$ from 5% to 40% Flow rate: 2.35mL/min Wavelength: 220 nm RT:5.909 min) as a solid and peak 2(Chiralcel OJ-H 250×4.6 mm I.D., 5 um Mobile phase: methanol (0.05% DEA) in CO$_2$ from 5% to 40%; Flow rate: 2.35 mL/min; Wavelength: 220 nm; RT: 9.239 min) as a solid. $^1$H NMR (CDCl$_3$, 400 MHz) δ 10.57 (t, J=3.6 Hz 1H), 7.72 (d, J=8.4 Hz, 2H), 7.61 (d, J=8.0 Hz, 2H), 7.25-7.23 (m, 1H), 6.92-6.87 (m, 1H), 5.14 (d, J=8.4 Hz, 1H), 4.99-4.95 (m, 1H), 4.14-4.11 (m, 2H), 3.66-3.60 (m, 1H), 1.50 (s, 9H).

Step E: 2-(8-fluoro-7-hydroxy-5-oxo-2-(4-(trifluoromethyl)phenyl)-3,5-dihydro-2H-[1,4]oxazino[2,3,4-ij]quinoline-6-carboxamido)acetic acid A 100 mL round bottom flask was charged with tert-butyl 2-(8-fluoro-7-hydroxy-5-oxo-2-(4-(trifluoromethyl)phenyl)-3,5-dihydro-2H-[1,4]oxazino[2,3,4-ij]quinoline-6-carboxamido)acetate (peak 1) (522 mg, 1.2 mmol), TFA (10 mL) and DCM (15 mL). The mixture was stirred at 40° C. for 1 hr. LCMS showed the starting material was consumed. The solvent was then evaporated and the residue was washed with petroleum ether to give 2-(8-fluoro-7-hydroxy-5-oxo-2-(4-(trifluoromethyl)phenyl)-3,5-dihydro-2H-[1,4]oxazino[2,3,4-ij]quinoline-6-carboxamido)acetic acid as a solid (Chiralcel OJ-H 250×4.6 mm I.D., 5 um Mobile phase: methanol (0.05% DEA) in CO$_2$ from 5% to 40% Flow rate: 2.35 mL/min Wavelength: 220 nm; RT: 7.112 min). $^1$H NMR (CDCl$_3$, 1 drop TFA 400 MHz) δ 10.29 (brs, 1H), 7.75 (d, J=8.0 Hz, 2H), 7.63 (d, J=8.0 Hz, 2H), 7.38 (dd, J=4.0 Hz, 1H), 7.04 (t, J=9.6 Hz,1H), 5.20 (d, J=8.8 Hz, 1H), 4.87 (d, J=13.6 Hz, 1H), 4.51-4.31 (m, 2H), 3.77-3.71 (m, 1H). LC/MS (m/z): 467 (M+H)$^+$. Human HIF-PHD2 IC$_{50}$: 4.9 nM.

Similarly, from the enantiomer corresponding to peak 2 of Example 68 step D, Example 69 in Table 3 was synthesized (Chiralcel OJ-H 250×4.6 mm I.D., 5 um Mobile phase: methanol (0.05% DEA) in CO2 from 5% to 40% Flow rate: 2.35mL/min Wavelength: 220 nm RT: 10.24 min).

TABLE 3

| Example | Name | structure | MS m/z (m + 1)$^+$ and human HIF-PHD2 IC$_{50}$ |
|---------|------|-----------|---------------------------------------------------|
| Example 69 | 2-(8-fluoro-7-hydroxy-5-oxo-2-(4-(trifluoromethyl)phenyl)-3,5-dihydro-2H-[1,4]oxazino[2,3,4-ij]quinoline-6-carboxamido)acetic acid | 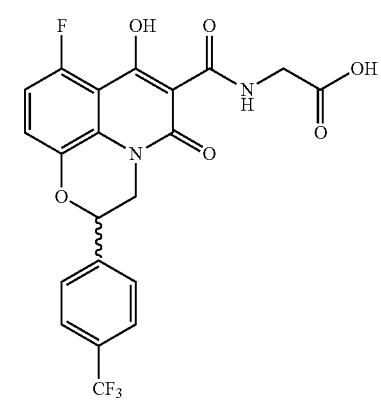 | (M + 1)$^+$ 467 IC$_{50}$ 3.3 nM |

Example 70

2-(8-Chloro-7-hydroxy-5-oxo-2-(4-(trifluoromethyl)phenyl)-3,5-dihydro-2H-[1,4]oxazino[2,3,4-ij]quinoline-6-carboxamido)acetic acid

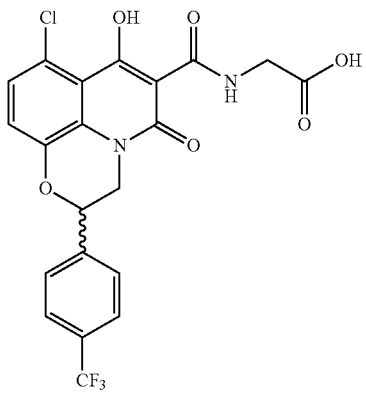 [SMILES: O=C(O)CNC(=O)c1c(O)c2c(Cl)ccc3c2n(c1=O)CC(c1ccc(C(F)(F)F)cc1)O3]

Step A: 6-chloro-2-(4-(trifluoromethyl)phenyl)-2H-benzo[b][1,4]oxazin-3(4H)-one To a solution of 2-amino-4-chlorophenol (2 g, 13.9 mmol) and DIPEA (7.2 g, 55.6 mmol) in DCM (30 mL) was added 2-bromo-2-(4-(trifluoromethyl)phenyl)acetyl chloride (4.2 g, 13.9 mmol) slowly at room temperature. The reaction was stirred at room temperature for 1 hr. The mixture was poured into water and extracted with EtOAc (50 mL*3). The combined organic layers were evaporated to give 6-chloro-2-(4-(trifluoromethyl)phenyl)-2H-benzo[b][1,4]oxazin-3 (4H)-one as a solid. $^1$H NMR (CDCl$_3$, 400 MHz): δ 8.79 (brs, 1H), 7.64 (d, J=8.0 Hz, 2H), 7.58 (d, J=8.0 Hz, 2H), 7.03-6.96 (m, 2H), 6.83 (d, J=1.0 Hz, 1H), 5.73 (s, 1H).

Step B: 6-chloro-2-(4-(trifluoromethyl)phenyl)-3,4-dihydro-2H-benzo[b][1,4]oxazine A 250 mL three neck flask was charged with 6-chloro-2-(4-(trifluoromethyl)phenyl)-2H-benzo[b][1,4]oxazin-3 (4H)-one (4.5 g, 13.7 mmol) and THF (30 mL). The flask was purged with N$_2$, then BH$_3$-Me$_2$S (5 mL) was added slowly. After addition, the mixture was stirred at room temperature for 20 hr. TLC (Petroleum ether: EtOAc=3:1) showed the starting material was consumed. Then 1M HCl (10 mL) was added to the reaction mixture slowly at room temperature. After quenching, the mixture was basified to pH 12 with NaOH solution and extracted with EtOAc (50 mL*3). The organic layers were dried over Na$_2$SO$_4$, filtered and evaporated to dryness to give 6-chloro-2-(4-(trifluoromethyl)phenyl)-3,4-dihydro-2H-benzo[b][1,4]oxazine as a solid. $^1$H NMR (DMSO-d$_6$, 400 MHz): δ 7.74 (d, J=8.2 Hz, 2H), 7.63 (d, J=8.2 Hz, 2H), 6.76 (d, J=8.4 Hz, 1H), 6.62 (d, J=2.4 Hz, 1H), 6.48 (dd, J=8.5, 2.3 Hz, 1H), 6.34 (brs, 1H), 5.12 (d, J=6.2 Hz, 1H), 3.57-3.48 (m, 1H), 3.19 (dd, J=11.8, 8.5 Hz, 1H).

Step C: Ethyl 8-chloro-7-hydroxy-5-oxo-2-(4-(trifluoromethyl)phenyl)-3,5-dihydro-2H-[1,4]oxazino[2,3,4-ij]quinoline-6-carboxylate A 100 mL round bottom flask was charged with 6-chloro-2-(4-(trifluoromethyl)phenyl)-3,4-dihydro-2H-benzo[b][1,4]oxazine (1 g, 3.19 mmol) and triethyl methanetricarboxylate (2.96 g, 12.75 mmol). The flask was purged with N$_2$ and the reaction was heated at 250° C. for 1.5 hr. TLC (Petroleum ether: EtOAc=3:1) showed the starting material was consumed. The reaction mixture was diluted with EtOAc (20 mL) and purified via silica gel column chromatography (40 g column, EtOAc in Petroleum ether from 0% to 30%) to give ethyl 8-chloro-7-hydroxy-5-oxo-2-(4-(trifluoromethyl)phenyl)-3,5-dihydro-2H-[1,4]oxazino[2,3,4-ij]quinoline-6-carboxylate as a solid. $^1$H NMR (CDCl$_3$, 400 MHz): δ 15.16 (s, 1H), 7.72 (d, J=8.0 Hz, 2H), 7.60 (d, J=8.5 Hz, 2H), 7.23 (s, 2H), 5.15 (d, J=9.5 Hz, 1H), 5.01 (d, J=14.0 Hz, 1H), 4.60-4.46 (m, 2H), 3.64 (dd, J=14.3, 9.3 Hz, 1H), 1.49 (t, J=7.3 Hz, 3H).

Step D: tert-butyl 2-(8-chloro-7-hydroxy-5-oxo-2-(4-(trifluoromethyl)phenyl)-3,5-dihydro-2H-[1,4]oxazino[2,3,4-ij]quinoline-6-carboxamido)acetate (peak 1) and tert-butyl 2-(8-chloro-7-hydroxy-5-oxo-2-(4-(trifluoromethyl)phenyl)-3,5-dihydro-2H-[1,4]oxazino[2,3,4-ij]quinoline-6-carboxamido)acetate (peak 2)

A 30 mL vial was charged with ethyl 8-chloro-7-hydroxy-5-oxo-2-(4-(trifluoromethyl)phenyl)-3,5-dihydro-2H-[1,4]oxazino[2,3,4-ij]quinoline-6-carboxylate (400 mg, 0.883 mmol), tert-butyl 2-aminoacetate (221 mg, 1.32 mmol), DIPEA (456 mg, 3.53 mmol) and toluene (5 mL). The mixture was heated to 115° C. and stirred for 1 hr. LCMS showed the starting material was consumed and the desired compound was formed. The reaction mixture was poured into water and extracted with EtOAc (20 mL*3). The combined organic layers were dried over Na$_2$SO$_4$, filtered and evaporated to dryness. The residue was resolved by Chiral SFC (Instrument: Thar SFC 80; Column: OJ 250 mm*30 mm, 20 um; Mobile phase: A: Supercritical CO$_2$, B: MeOH (0.1%NH$_3$.H$_2$O), A:B=55: 45 at 80 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford peak 1 (Chiralcel OJ-3 50*4.6 mm I.D., 3 um Mobile phase: methanol (0.05% DEA) in CO$_2$ from 5% to 40% Flow rate: 4 mL/min Wavelength: 220 nm; RT: 1.137 min) as a solid and peak 2 (Chiralcel OJ-3 50*4.6 mm I.D., 3 um Mobile phase: methanol (0.05% DEA) in CO$_2$ from 5% to 40%; Flow rate: 4mL/min Wavelength: 220 nm; RT: 1.803 min) as a solid.

Step E: 2-(8-chloro-7-hydroxy-5-oxo-2-(4-(trifluoromethyl)phenyl)-3,5-dihydro-2H-[1,4]oxazino[2,3,4-ij]quinoline-6-carboxamido)acetic acid A 100 mL round bottom flask was charged with tert-butyl 2-(8-chloro-7-hydroxy-5-oxo-2-(4-(trifluoromethyl)phenyl)-3,5-dihydro-2H-[1,4]oxazino[2,3,4-ij]quinoline-6-carboxamido)acetate (peak 1) (150 mg, 0.278 mmol), TFA (5 mL) and DCM (10 mL). The mixture was stirred at 40° C. for 1 hr. LCMS showed the starting material was consumed and the desired compound was formed. The solvent was then evaporated and the residue was purified by washing with petroleum ether and EtOAc to give 2-(8-chloro-7-hydroxy-5-oxo-2-(4-(trifluoromethyl)phenyl)-3,5-dihydro-2H-[1,4]oxazino[2,3,4-ij]quinoline-6-carboxamido)acetic acid as a solid (Chiralcel OJ-3 50*4.6 mm I.D., 3 um Mobile phase: methanol (0.05% DEA) in CO$_2$ from 5% to 40% Flow rate: 4 mL/min Wavelength: 254 nm, retain time: 1.322min). $^1$H NMR (DMSO-d$_6$, 400 MHz) δ 10.55 (t, J=5.3 Hz, 1H), 7.85 (d, J=8.0 Hz, 2H), 7.78 (d, J=8.0 Hz, 2H), 7.40 (d, J=8.0 Hz, 1H), 7.33 (d, J=8.0 Hz, 1H), 5.49 (d, J=7.5 Hz, 1H), 4.79 (dd, J=16.0, 2.0 Hz, 1 H), 4.15 (d, J=5.5 Hz, 2H), 3.84 (dd, J=13.8, 9.3 Hz, 1H). LC/MS (m/z): 483 (M+H)+. Human HIF-PHD2 IC$_{50}$: 1.8 nM.

Similarly, from the enantiomer corresponding to peak 2 of Example 70 step D, Example 71 in Table 4 was synthesized (Chiralcel OJ-3 50*4.6 mm I.D., 3 um Mobile phase: methanol (0.05% DEA) in CO2 from 5% to 40% Flow rate: 4mL/min Wavelength: 254 nm, retention time: 1.787min).

2-bromo-2-(4-(trifluoromethyl)phenyl)acetyl chloride (4.2 g, 13.9 mmol) slowly at room temperature. The reaction was stirred at room temperature for 1 hr. The mixture was poured into water and extracted with EtOAc (50 mL*3). The combined organic layers were evaporated to give 8-chloro-2-(4-(trifluoromethyl)phenyl)-2H-benzo[b][1,4]oxazin-3 (4H)-one as a solid. $^1$H NMR (CDCl$_3$, 400 MHz): δ 9.16 (brs, 1H), 7.40-7.75 (m, 4H), 7.10 (d, J=8.2 Hz, 1H), 6.91 (t, J=7.9 Hz, 1H), 6.73 (d, J=7.9 Hz, 1H), 5.90 (s, 1H).

TABLE 4

| Example Name | structure | MS m/z (M + 1)+ and human HIF-PHD2 IC$_{50}$ |
|---|---|---|
| Example 71 | 2-(8-chloro-7-hydroxy-5-oxo-2-(4-(trifluoromethyl)phenyl)-3,5-dihydro-2H-[1,4]oxazino[2,3,4-ij]quinoline-6-carboxamido)acetic acid | (M + 1)+ 483 IC$_{50}$ 5.1 nM |

Example 72

2-(10-Chloro-7-hydroxy-5-oxo-2-(4-(trifluoromethyl)phenyl)-3,5-dihydro-2H-[1,4]oxazino[2,3,4-ij] quinoline-6-carboxamido)acetic acid

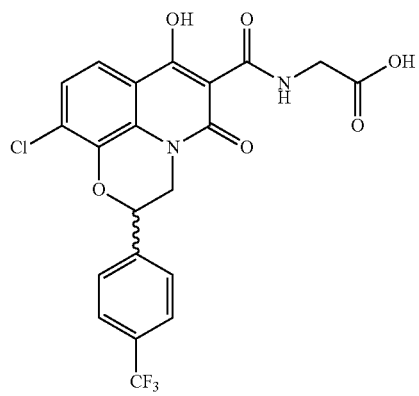 [SMILES: O=C(O)CNC(=O)c1c(O)c2ccc(Cl)c3c2n(c1=O)CC(c1ccc(C(F)(F)F)cc1)O3]

Step A: 8-chloro-2-(4-(trifluoromethyl)phenyl)-2H-benzo[b][1,4]oxazin-3(4H)-one

To a solution of 2-amino-6-chlorophenol (2 g, 13.9 mmol) and DIPEA (7.2 g, 55.6 mmol) in DCM (30 mL) was added Step B: 8-chloro-2-(4-(trifluoromethyl)phenyl)-3,4-dihydro-2H-benzo[b][1,4]oxazine A 250 mL three neck flask was charged with 8-chloro-2-(4-(trifluoromethyl)phenyl)-2H-benzo[b][1,4]oxazin-3 (4H)-one (4.55 g, 13.9 mmol) and THF (30 mL). The flask was purged with N$_2$, then BH$_3$-Me$_2$S (5 mL) was added slowly. After addition, the mixture was stirred at room temperature for 20 hr. TLC (Petroleum: EtOAc=3:1) showed the starting material was consumed. Then 1M HCl (10 mL) was added to the reaction mixture slowly at room temperature to quench the reaction. The mixture was basified to pH 12 with NaOH solution and extracted with EtOAc (50 mL*3). The organic layers were dried over Na$_2$SO$_4$, filtered and evaporated to dryness to give 8-chloro-2-(4-(trifluoromethyl)phenyl)-3,4-dihydro-2H-benzo[b][1,4]oxazine as an oil. $^1$H NMR (DMSO-d$_6$, 400 MHz): δ 7.77 (d, J=8.2 Hz, 2H), 7.65 (d, J=7.9 Hz, 2H), 6.71-6.66 (m, 1H), 6.63-6.58 (m, 1H), 6.58-6.54 (m, 1H), 6.34 (brs, 1H), 5.23 (d, J=5.7 Hz, 1H), 3.57 (dt, J=12.3, 3.0 Hz, 1H), 3.24 (dd, J=11.8, 8.3 Hz, 1H).

Step C: Ethyl 10-chloro-7-hydroxy-5-oxo-2-(4-(trifluoromethyl)phenyl)-3,5-dihydro-2H-[1,4]oxazino [2,3,4-ij]quinoline-6-carboxylate A 100 mL round bottom flask was charged with 8-chloro-2-(4-(trifluoromethyl)phenyl)-3,4-dihydro-2H-benzo[b][1, 4]oxazine (1 g, 3.19 mmol) and triethyl methanetricarboxylate (2.96 g, 12.75 mmol). The flask was purged with N$_2$ and heated at 250° C. for 1.5 hr. TLC (Petroleum ether: EtOAc=3:1) showed the starting material was consumed. The reaction mixture was diluted with EtOAc (20 mL) and purified via combi flash (40 g column, EtOAc in Petroleum ether from 0% to 28%) to give ethyl 10-chloro-7-hydroxy- 5-oxo-2-(4-(trifluoromethyl)phenyl)-3,5-dihydro-2H-[1,4] oxazino[2,3,4-ij]quinoline-6-carboxylate as a solid. $^1$H NMR (CDCl$_3$, 400 MHz): δ 14.32 (s, 1H), 7.73 (d, J=8.0 Hz, 1H), 7.72 (d, J=8.0 Hz, 2H), 7.64 (d, J=8.0 Hz, 2H), 7.27 (d, J=8.0 Hz, 1H), 5.31 (d, J=8.0 Hz, 1H), 4.93 (dd, J=14.3, 2.3 Hz, 1H), 4.57-4.46 (m, 2H), 3.80 (dd, J=14.6, 9.0 Hz, 1H), 1.48 (t, J=7.0 Hz, 3H).

Step D: tert-butyl 2-(10-chloro-7-hydroxy-5-oxo-2-(4-(trifluoromethyl)phenyl)-3,5-dihydro-2H-[1,4]oxazino[2,3,4-ij]quinoline-6-carboxamido)acetate (peak 1) and tert-butyl 2-(10-chloro-7-hydroxy-5-oxo-2-(4-(trifluoromethyl)phenyl)-3,5-dihydro-2H-[1,4]oxazino[2,3,4-ij]quinoline-6-carboxamido)acetate (peak 2)

A 30 mL vial was charged with ethyl 10-chloro-7-hydroxy-5-oxo-2-(4-(trifluoromethyl)phenyl)-3,5-dihydro-2H-[1,4]oxazino[2,3,4-ij]quinoline-6-carboxylate (390 mg, 0.861 mmol), tert-butyl 2-aminoacetate (215 mg, 1.29 mmol), DIPEA (444 mg, 3.44 mmol) and toluene (5 mL). The mixture was heated to 115° C. and stirred for 1 hr. LCMS showed the starting material was consumed. The reaction mixture was poured into water and extracted with EtOAc (20 mL*3). The combined organic layers were dried over Na$_2$SO$_4$, filtered and evaporated to dryness. The residue was resolved by Chiral SFC (Instrument: Thar SFC 80; Column: AD 250 mm*30 mm, 20 um; Mobile phase: A: Supercritical CO$_2$ , B: EtOH (0.1%NH$_3$.H$_2$O), A:B=45: 55 at 80ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford peak 1 (Chiralcel OJ-3 50*4.6 mm I.D., 3 um Mobile phase: methanol (0.05% DEA) in CO$_2$ from 5% to 40% Flow rate: 4mL/min Wavelength: 220 nm. RT: 1.015 min) as a solid and peak 2 (Column: Chiralpak AD-3 50*4.6 mm I.D., 3 um Mobile phase: 40% ethanol (0.05% DEA) in CO$_2$ Flow rate: 4mL/min Wavelength: 220 nm; RT: 1.831 min) as a solid.

Step E: 2-(10-chloro-7-hydroxy-5-oxo-2-(4-(trifluoromethyl)phenyl)-3,5-dihydro-2H-[1,4]oxazino[2,3,4-ij]quinoline-6-carboxamido)acetic acid A 100 mL round bottom flask was charged with tert-butyl 2-(10-chloro-7-hydroxy-5-oxo-2-(4-(trifluoromethyl)phenyl)-3,5-dihydro-2H-[1,4]oxazino[2,3,4-ij]quinoline-6-carboxamido)acetate (peak 1) (70 mg, 0.13 mmol), TFA (5 mL) and DCM (10 mL). The mixture was stirred at 40° C. for 1 hr. LCMS showed the starting material was consumed. The solvent was then evaporated and the residue was purified via prep-HPLC (Column: ASB C18 150*25 mm; Mobile phase: 56-86% MeCN in water (0.1% HCl); Wavelength: 220 nm) to give 2-(10-chloro-7-hydroxy-5-oxo-2-(4-(trifluoromethyl)phenyl)-3,5-dihydro-2H-[1,4]oxazino[2,3,4-ij]quinoline-6-carboxamido)acetic acid as a solid (Chiralcel OJ-3 50*4.6 mm I.D., 3 um Mobile phase: methanol (0.05% DEA) in CO2 from 5% to 40% Flow rate: 4mL/min Wavelength: 220 nm; RT: 1.204min). $^1$H NMR (DMSO-d$_6$, 400 MHz) δ 10.36 (brs, 1H), 7.79-7.85 (m, 4H), 7.71 (d, J=8.5 Hz, 1H), 7.42 (d, J=8.5 Hz, 1H), 5.65 (d, J=7.5 Hz, 1H), 4.81 (d, J=13.6 Hz, 1H), 4.16 (d, J=5.0 Hz, 2H), 4.00 (dd, J=13.6, 9.0 Hz, 1H). LC/MS (m/z): 483 (M+H)$^+$. Human HIF-PHD2 IC$_{50}$: 2.6 nM.

Similarly, from the enantiomer corresponding to peak 2 of Example 72 step D, Example 73 in Table 5 was synthesized (Chiralcel OJ-3 50*4.6 mm I.D., 3 um Mobile phase: methanol (0.05% DEA) in CO$_2$ from 5% to 40%; Flow rate: 4mL/min; Wavelength: 220 nm; retention time: 1.75 min).

TABLE 5

| Example | Name | structure | MS m/z (M + 1)$^+$ and human HIF-PHD2 IC$_{50}$ |
|---|---|---|---|
| Example 73 | 2-(10-chloro-7-hydroxy-5-oxo-2-(4-(trifluoromethyl)phenyl)-3,5-dihydro-2H-[1,4]oxazino[2,3,4-ij]quinoline-6-carboxamido)acetic acid Wavelength: 220 nm, retain time: 1.754 min) | 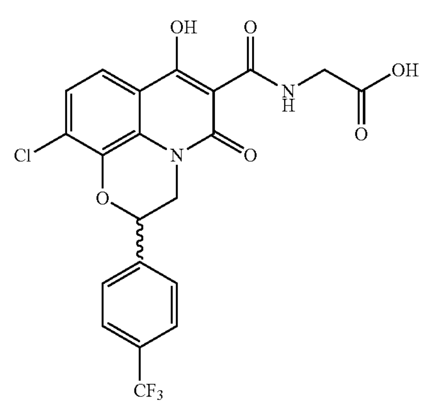 [SMILES: O=C(O)CNC(=O)c1c(O)c2ccc(Cl)c3c2n(c1=O)CC(c1ccc(C(F)(F)F)cc1)O3] | (M + 1)$^+$ 483 IC$_{50}$ 2.8 nM |

Example 74

2-(9-Chloro-7-hydroxy-5-oxo-2-(4-(trifluoromethyl)phenyl)-3,5-dihydro-2H-[1,4]oxazino[2,3,4-ij]quinoline-6-carboxamido)acetic acid

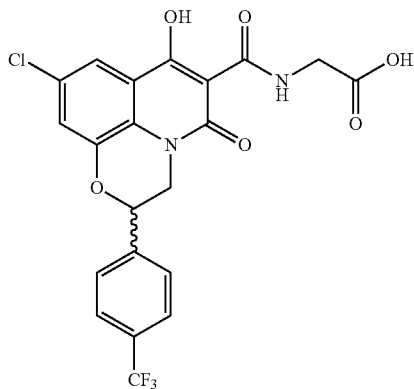 [SMILES: O=C(O)CNC(=O)c1c(O)c2cc(Cl)cc3c2n(c1=O)CC(c1ccc(C(F)(F)F)cc1)O3]

Step A: 7-chloro-2-(4-(trifluoromethyl)phenyl)-2H-benzo[b][1,4]oxazin-3(4H)-one To a mixture of 2-amino-5-chlorophenol (5.0 g, 35.0 mmol), $K_2CO_3$ (9.7 g, 70 mmol) in DMF (50 mL) was added 2-bromo-2-(4-(trifluoromethyl)phenyl)acetyl chloride (12.6 g, 42.0 mmol) dropwise over 20 mins. The reaction mixture was stirred at room temperature for 16 h. TLC (Petroleum ether: EtOAc=3:1) showed the starting material was consumed. The reaction mixture was poured into water and extracted with EtOAc (100 mL*3). The combined organic layers were dried, filtered and concentrated to give the crude product which was further purified via combi flash (80 g column, EtOAc in Petroleum ether from 0% to 15%) to give 7-chloro-2-(4-(trifluoromethyl)phenyl)-2H-benzo[b][1,4]oxazin-3(4H)-one as a solid. $^1H$ NMR (CDCl$_3$, 400 MHz): δ 7.64 (d, J=8.0 Hz, 2 H), 7.58 (d, J=8.0 Hz, 2 H), 7.10 (s, 1 H), 6.97 (d, J=8.0 Hz, 1 H), 6.71 (d, J=8.0 Hz, 1 H), 5.74 (s, 1 H).

Step B: 7-chloro-2-(4-(trifluoromethyl)phenyl)-3,4-dihydro-2H-benzo[b][1,4]oxazine To a solution of 7-chloro-2-(4-(trifluoromethyl)phenyl)-2H-benzo[b][1,4]oxazin-3(4H)-one (5.2 g, 16.0 mmol) in THF (50 mL) was purged with $N_2$ and the reaction mixture was cooled to 0° C. $BH_3$-$Me_2S$ (6.1 g, 80 mmol) was added dropwise over 20 mins. After addition, the mixture was warmed to room temperature and stirred for 3 h. TLC (petroleum ether: EtOAc=3:1) showed the starting material was consumed. The reaction mixture was cooled to 0° C., and MeOH (50 mL) was added slowly to quench the reaction. Then the reaction mixture was concentrated in vacuo to remove the solvent, and the crude product was purified by silica gel column chromatography (80 g column, EtOAc in Petroleum ether from 0% to 15%) to give 7-chloro-2-(4-(trifluoromethyl)phenyl)-3,4-dihydro-2H-benzo[b][1,4]oxazine as an oil. $^1H$ NMR (CDCl$_3$, 400 MHz): δ 7.57 (s, 4 H), 7.04 (d, J=8.0 Hz, 2 H), 6.78 (d, J=8.0 Hz, 1H), 6.69 (t, J=8.0 Hz, 1 H), 6.39 (br. s., 1 H), 4.78 (t, J=6.0 Hz,1 H), 3.64 (dd, J=12.0, 6.0 Hz, 1 H), 3.43 (dd, J=16.0, 4.0 Hz, 1 H).

Step C: ethyl 9-chloro-7-hydroxy-5-oxo-2-(4-(trifluoromethyl)phenyl)-3,5-dihydro-2H-[1,4]oxazino[2,3,4-ij]quinoline-6-carboxylate A 50 mL round bottom flask was charged with 7-chloro-2-(4-(trifluoromethyl)phenyl)-3,4-dihydro-2H-benzo[b][1,4]oxazine (2.0 g, 6.4 mmol) and triethyl methanetricarboxylate (5.94 g, 25.6 mmol). The flask was purged with $N_2$ and heated to 250° C. for 1 hr. TLC (Petroleum ether: EtOAc=3:1) showed the starting material was consumed. The reaction mixture was diluted with petroleum ether (30 mL) and stirred for 20 mins. The mixture was filtered and the filter cake was dried in vacuo to give ethyl 9-chloro-7-hydroxy-5-oxo-2-(4-(trifluoromethyl)phenyl)-3,5-dihydro-2H-[1,4]oxazino[2,3,4-ij]quinoline-6-carboxylate as a solid. $^1H$ NMR (CDCl$_3$, 400 MHz): δ 14.29 (s, 1 H), 7.76 (s, 1 H), 7.71 (d, J=8.0 Hz, 2 H), 7.57 (d, J=8.0 Hz, 2 H), 7.29 (d, J=1.6 Hz, 1 H), 5.19 (d, J=7.6 Hz, 1 H), 4.90 (dd, J=14.0, 2.4 Hz, 1 H), 4.50 (dd, J=6.4, 12.0 Hz, 2 H), 3.67 (q, J=8.0 Hz, 1 H), 1.47 (t, J=7.2 Hz, 3 H).

Step D: tert-butyl 2-(9-chloro-7-hydroxy-5-oxo-2-(4-(trifluoromethyl)phenyl)-3,5-dihydro-2H-[1,4]oxazino[2,3,4-ij]quinoline-6-carboxamido)acetate (peak 1) and tert-butyl 2-(9-chloro-7-hydroxy-5-oxo-2-(4-(trifluoromethyl)phenyl)-3,5-dihydro-2H-[1,4]oxazino[2,3,4-ij]quinoline-6-carboxamido)acetate (peak 2)

A 30 mL vial was charged with ethyl 9-chloro-7-hydroxy-5-oxo-2-(4-(trifluoromethyl)phenyl)-3,5-dihydro-2H-[1,4]oxazino[2,3,4-ij]quinoline-6-carboxylate (1.3 g, 2.87 mmol), tert-butyl 2-aminoacetate (799 mg, 3.44 mmol), DIPEA (934 mg, 7.42 mmol) and toluene (15 mL). The mixture was heated to 120° C. and stirred for 3 h. TLC (petroleum ether: EtOAc=5:1) showed that the starting material was consumed. The solvent was evaporated and the residue was purified via Combi-Flash (20 g column, EtOAc in Petroleum Ether from 0% to 20%) to give 2-(9-chloro-7-hydroxy-5-oxo-2-(4-(trifluoromethyl)phenyl)-3,5-dihydro-2H-[1,4]oxazino[2,3,4-ij]quinoline-6-carboxamido)acetate (1.0 g, 64.9%) as a solid. The racemate was resolved by Chiral SFC (Instrument: Thar SFC 80; Column: OJ 250mm*30mm, 20 um; Mobile phase: A: Supercritical $CO_2$, B: EtOH (0.1% $NH_3.H_2O$), A:B=65:35 at 80 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to give tert-butyl 2-(9-chloro-7-hydroxy-5-oxo-2-(4-(trifluoromethyl)phenyl)-3,5-dihydro-2H-[1,4]oxazino[2,3,4-ij]quinoline-6-carboxamido)acetate (peak 1) (Column: Chiralcel OJ-3 50*4.6 mm I.D., 3 um Mobile phase: methanol (0.05% DEA) in $CO_2$ from 5% to 40%, Flow rate: 4mL/min, Wavelength: 220 nm RT:1.092 min) as a solid, and tert-butyl 2-(9-chloro-7-hydroxy-5-oxo-2-(4-(trifluoromethyl)phenyl)-3,5-dihydro-2H-[1,4]oxazino[2,3,4-ij]quinoline-6-carboxamido)acetate (peak 2) (Column: Chiralcel OJ-3 50*4.6 mm I.D., 3 um Mobile phase: methanol (0.05% DEA) in $CO_2$ from 5% to 40%, Flow rate: 4 mL/min, Wavelength: 220 nm; RT: 1.422 min) as a solid. $^1H$ NMR (CDCl$_3$, 400 MHz): δ 10.52 (br.s., 1 H), 7.80 (d, J=2.0 Hz, 1 H), 7.73 (d, J=8.0 Hz, 2 H), 7.61 (d, J=8.0 Hz, 2 H), 7.31 (d, J=2.0 Hz, 1 H), 5.21 (d, J=8.0 Hz, 1 H), 4.95 (dd, J=12.0, 4.0 Hz, 1 H), 4.07-4.19 (m, 2 H), 3.70 (dd, J=12.0, 8.0 Hz, 1 H), 1.50 (s, 9 H).

Step E: 2-(9-chloro-7-hydroxy-5-oxo-2-(4-(trifluoromethyl)phenyl)-3,5-dihydro-2H-[1,4]oxazino[2,3,4-ij]quinoline-6-carboxamido)acetic acid (peak 1)

A 50 mL round bottom flask was charged with tert-butyl 2-(9-chloro-7-hydroxy-5-oxo-2-(4-(trifluoromethyl)phenyl)-3,5-dihydro-2H-[1,4]oxazino[2,3,4-ij]quinoline-6-carboxamido)acetate (peak 1) (150 mg, 0.31 mmol) in the mixed solvent of TFA(2 mL) and DCM (10 mL). The mixture was stirred at room temperature for 1 hr. LCMS showed the starting material was consumed. The solvent was evaporated and the mixture was recrystallized by EtOAc (10 mL). The suspension was filtered, and the filter cake was dried to give 2-(9-chloro-7-hydroxy-5-oxo-2-(4-(trifluoromethyl)phenyl)-3,5-dihydro-2H-[1,4]oxazino[2,3,4-ij]quinoline-6-carboxamido)acetic acid (Column: Chiralcel OJ-3 50*4.6 mm I.D., 3 um Mobile phase: methanol (0.05% DEA) in $CO_2$ from 5% to 40%, Flow rate: 4mL/min, Wavelength: 220 nm; RT: 1.237 min). $^1$H NMR (DMSO-d6, 400 MHz): δ 10.40 (s, 1H), 7.87 (d, J=8.0 Hz, 2H), 7.79(d, J=8.4 Hz, 2H), 7.66 (s, 1H), 7.59 (s, 1H), 5.58 (d, J=8.0 Hz, 1H), 4.75 (d, J=12.4 Hz, 1H),4.15 (d, J=5.6 Hz, 2H), 3.91 (dd, J=9.6,13.6 Hz, 1H). LC/MS (m/z): 483 (M+H)$^+$. Human HIF-PHD2 $IC_{50}$: 10 nM.

Similarly, from the enantiomer corresponding to peak 2 of Example 74 step D, Example 75 in Table 6 was synthesized (Column: Chiralcel OJ-3 50*4.6 mm I.D., 3 um Mobile phase: methanol (0.05% DEA) in CO2 from 5% to 40%, Flow rate: 4mL/min, Wavelength: 220 nm; RT: 1.551 min).

Example 76

2-(7-Hydroxy-2-(4-(methylsulfonyl)phenyl)-5-oxo-10-(trifluoromethyl)-3,5-dihydro-2H-[1,4]oxazino[2,3,4-ij]quinoline-6-carboxamido)acetic acid

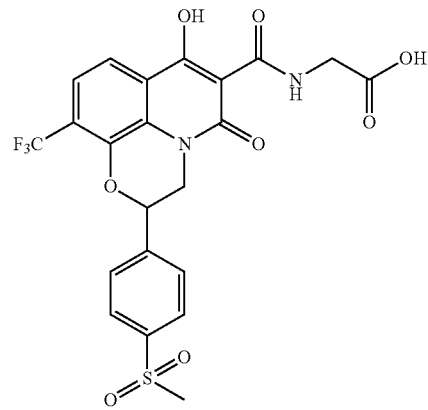

Step A: 2-amino-6-(trifluoromethyl) phenol

A 30 ml hydrogen bottle was charged with 2-nitro-6-(trifluoromethyl)phenol (1.3 g, 6.3 mmol) in MeOH, and wet Pd/C(130 mg, purity:10%) was added under $N_2$ protection.

TABLE 6

| Example | Name | structure | MS m/z (M + 1)$^+$ and human HIF-PHD2 $IC_{50}$ |
|---|---|---|---|
| Example 75 | 2-(9-chloro-7-hydroxy-5-oxo-2-(4-(trifluoromethyl)phenyl)-3,5-dihydro-2H-[1,4]oxazino[2,3,4-ij]quinoline-6-carboxamido)acetic acid | 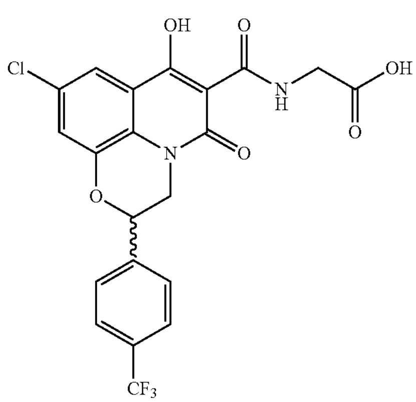 [SMILES: O=C(O)CNC(=O)c1c(O)c2cc(Cl)cc3c2n(c1=O)CC(c1ccc(C(F)(F)F)cc1)O3] | (M + 1)$^+$ 483 $IC_{50}$ 12 nM |

The reaction mixture was degassed and charged by H$_2$ (30 psi), then the reaction mixture was stirred at room temperature for 3 h. TLC (petroleum ether: EtOAc=2:1) showed that the starting material was consumed. The solvent was evaporated to give the desired product, which was directly used in the next step. $^1$H NMR (CDCl$_3$, 400 MHz): δ 6.91 (d, J=8.4 Hz, 2 H), 6.83 (t, J=8.0 Hz, 1 H).

Step B: 2-(4-bromophenyl)-8-(trifluoromethyl)-2H-benzo[b][1,4]oxazin-3(4H)-one

To a solution of 2-amino-6-(trifluoromethyl) phenol (5.13 g, 29 mmol) in DMF (100 mL) was added K$_2$CO$_3$ (16 g, 116 mmol). The mixture was cooled by ice-water bath, to which 2-bromo-2-(4-bromophenyl)acetyl chloride (10.8 g, 35 mmol) was added dropwisely. Then the reaction was stirred at room temperature for 3 h. TLC (petroleum ether: EtOAc=5:1) showed that the reaction was complete. The resulting mixture was quenched and diluted by H$_2$O (400 mL), extracted with DCM (300 mL*3). The combined organic layers were washed by brine (300 mL*3), dried over Na$_2$SO$_4$, filtered and concentrated in vacuo. The residue was purified by column chromatography (EtOAc in petroleum ether: 0-20%) to give 2-(4-bromophenyl)-8-(trifluoromethyl)-2H-benzo[b][1,4]oxazin-3(4H)-one as a solid, which was used for next step without any purification. $^1$H NMR (CDCl$_3$, 400 MHz): δ 8.41 (br.s, 1 H), 7.48 (d, J=8.4 Hz, 2H), 7.33 (d, J=8.4 Hz, 2H), 7.26(d, J=7.6 Hz, 1H), 7.04 (t, J=8.0 Hz, 1H), 6.97 (d, J=7.6 Hz, 1H), 5.78 (s, 1H).

Step C: 2-(4-bromophenyl)-8-(trifluoromethyl)-3,4-dihydro-2H-benzo[b][1,4]oxazine To the solution of 2-(4-bromophenyl)-8-(trifluoromethyl)-2H-benzo[b][1,4]oxazin-3(4H)-one (3.44 g, 9.3 mmol) in THF(50 mL) was added BH$_3$-Me$_2$S(10 mL, 0.18 mol) dropwise, then the reaction mixture was stirred at room temperature overnight. TLC (petroleum ether: EtOAc=5:1) showed that the starting material was consumed. MeOH was added to quench the reaction, and the solvent was then evaporated in vacuo. The residue was purified by column chromatography (EtOAc in Petroleum ether: 0-20%) to get 2-(4-bromophenyl)-8-(trifluoromethyl)-3,4-dihydro-2H-benzo[b][1,4]oxazine as a solid. $^1$H NMR (CDCl$_3$, 400 MHz): δ 7.54 (d, J=8.4 Hz, 2H), 7.31 (t, J=8.0 Hz, 2H), 6.99 (d, J=7.6 Hz, 1H), 6.79-6.87 (m, 2H), 5.19 (dd, J=8.0, 2.0 Hz, 1H), 4.05 (br.s., 1H), 3.61 (dd, J=12.0, 2.0 Hz, 1H), 3.33 (dd, J=12.0, 8.4 Hz, 1H).

Step D: ethyl 2-(4-bromophenyl)-7-hydroxy-5-oxo-10-(trifluoromethyl)-3,5-dihydro-2H-[1,4]oxazino[2,3,4-ij]quinoline-6-carboxylate 2-(4-bromophenyl)-8-(trifluoromethyl)-3,4-dihydro-2H-benzo[b][1,4]oxazine (578 mg, 1.62 mmol) and triethyl methanetricarboxylate (1.5 g, 6.48 mmol) was added into a 50 mL bottom flask. The mixture was stirred at 250° C. for 30 min. TLC (petroleum ether: EtOAc=1:1) showed the reaction was complete. The reaction mixture was purified by Combi-Flash (DCM in EtOAc: 0%-12%) to give ethyl 2-(4-bromophenyl)-7-hydroxy-5-oxo-10-(trifluoromethyl)-3,5-dihydro-2H-[1,4]oxazino[2,3,4-ij]quinoline-6-carboxylate as a solid. $^1$H NMR (DMSO-d$_6$, 400 MHz): δ 7.78 (d, J=8.8 Hz, 1H) 7.70 (d, J=8.4 Hz, 2H) 7.52 (d, J=8.4 Hz, 1H) 7.48 (d, J=8.0 Hz, 2H) 5.52 (d, J=6.4 Hz, 1H) 4.69 (dd, J=14.0, 2.8 Hz, 1H), 4.32 (q, J=7.2 Hz, 2H), 3.82 (dd, J=14.0, 9.6 Hz, H), 1.29 (t, J=7.2 Hz, 3H).

Step E: tert-butyl 2-(2-(4-bromophenyl)-7-hydroxy-5-oxo-10-(trifluoromethyl)-3,5-dihydro-2H-[1,4]oxazino[2,3,4-ij]quinoline-6-carboxamido)acetate To a suspension of ethyl 2-(4-bromophenyl)-7-hydroxy-5-oxo-10-(trifluoromethyl)-3,5-dihydro-2H-[1,4]oxazino[2,3,4-ij]quinoline-6-carboxylate (413 mg, 0.83 mmol) and tert-butyl 2-aminoacetate hydrochloride (168 mg, 1.0 mmol) in toluene (10 mL) was added DIPEA (246 mg, 1.91 mmol). Then the mixture was refluxed for 2 h. LCMS showed the reaction was complete. The solvent was removed and the residue was purified by Combi-Flash (DCM in EtOAc: 0%-12%) to give tert-butyl 2-(2-(4-bromophenyl)-7-hydroxy-5-oxo-10-(trifluoromethyl)-3,5-dihydro-2H-[1,4]oxazino[2,3,4-ij]quinoline-6-carboxamido)acetate as a solid. $^1$H NMR (CDCl$_3$, 400 MHz): δ 10.50 (br.s., 1H), 7.84 (d, J=8.4 Hz, 1H), 7.58 (d, J=8.4 Hz, 2H), 7.47 (d, J=8.8 Hz, 1H), 7.36 (d, J=8.4 Hz, 2H), 5.25 (dd, J=9.2, 2.0 Hz, 1H), 4.94 (dd, J=2.8, 14.4 Hz, 1H), 4.11-4.15 (m, 2H), 3.79 (dd, J=14.4, 9.6 Hz, 1H), 1.50 (s, 9H).

Step F: tert-butyl 2-(7-hydroxy-2-(4-(methylsulfonyl)phenyl)-10-(trifluoromethyl)-3,5-dihydro-2H-[1,4]oxazino[2,3,4-ij]quinoline-6-carboxamido)acetate tert-butyl 2-(2-(4-bromophenyl)-7-hydroxy-10-(trifluoromethyl)-3,5-dihydro-2H-[1,4]oxazino[2,3,4-ij]quinoline-6-carboxamido)acetate (300 mg, 0.527 mmol) and sodium methanesulfinate (64.5 mg, 0.632 mmol) were dissolved in DMSO (13 mL), then pyrrolidine-2-carboxylic acid (12.13 mg, 0.105 mmol), copper(I) iodide (100 mg, 0.527 mmol) and sodium hydroxide (4.21 mg, 0.105 mmol) were added to the mixture. The reaction was stirred at 120° C. for 1 day. The mixture was diluted by EtOAc and washed by brine, then the organic layer was concentrated to give the crude product which was purifired by column-chromatography (EtOAc in Petroleum ether=0-20%) to give the tert-butyl 2-(7-hydroxy-2-(4-(methylsulfonyl)phenyl)-10-(trifluoromethyl)-3,5-dihydro-2H-[1,4]oxazino[2,3,4-ij]quinoline-6-carboxamido)acetate as a solid.

Step G: 2-(7-hydroxy-2-(4-(methylsulfonyl)phenyl)-10-(trifluoromethyl)-3,5-dihydro-2H-[1,4]oxazino[2,3,4-ij]quinoline-6-carboxamido)acetic acid To a solution of tert-butyl 2-(7-hydroxy-2-(4-(methylsulfonyl)phenyl)-10-(trifluoromethyl)-3,5-dihydro-2H-[1,4]oxazino[2,3,4-ij]quinoline-6-carboxamido)acetate (120 mg, 0.211 mmol) in DCM (5 mL) was added TFA (1 mL). The reaction solution was stirred at room temperature for 3 h. TLC (Petroleum ether: EtOAc=2:1) showed that the reaction was completed. The solvent was evaporated under reduced pressure. The residue was purified by recrystallation (EtOAc) to give 2-(7-hydroxy-2-(4-(methylsulfonyl)phenyl)-10-(trifluoromethyl)-3,5-dihydro-2H-[1,4]oxazino[2,3,4-ij]quinoline-6-carboxamido)acetic acid as a solid. $^1$H NMR (CDCl$_3$, 400 MHz): δ 10.37 (t, J=5.6 Hz, 1H), 8.06 (d, J=8.4 Hz, 2H), 7.84 (d, J=6.4 Hz, 1H), 7.82 (d, J=8.0 Hz, 2H), 7.61 (d, J=8.8 Hz, 1H), 5.72 (d, J=7.2 Hz, 1H), 4.86 (d, J=12.0 Hz, 1H), 4.16 (d, J=5.6 Hz, 2H), 3.94 (dd, J=13.2, 8.8 Hz, 1H), 3.27 (s, 3H). LC/MS (m/z): 513 (M+H)$^+$. Human HIF-PHD2 IC$_{50}$: 1.4 nM.

Example 77

2-(2-(4-cyanophenyl)-7-hydroxy-5-oxo-10-(trifluoromethyl)-3,5-dihydro-2H-[1,4]oxazino[2,3,4-ij]quinoline-6-carboxamido)acetic acid

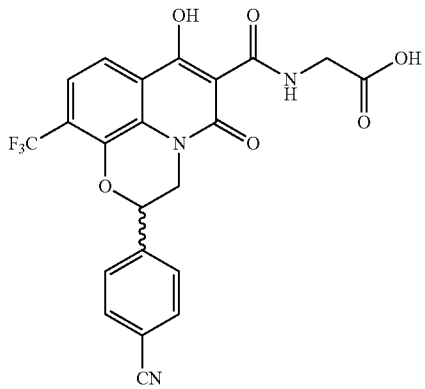 [SMILES: N#Cc1ccc(C2Cn3c(=O)c(C(=O)NCC(=O)O)c(O)c4ccc(C(F)(F)F)c(c43)O2)cc1]

Step A: tert-butyl 2-(2-(4-cyanophenyl)-7-hydroxy-5-oxo-10-(trifluoromethyl)-3,5-dihydro-2H-[1,4]oxazino[2,3,4-ij]quinoline-6-carboxamido)acetate (peak 1) and tert-butyl 2-(2-(4-cyanophenyl)-7-hydroxy-5-oxo-10-(trifluoromethyl)-3,5-dihydro-2H-[1,4]oxazino[2,3,4-ij]quinoline-6-carboxamido)acetate (peak 2)

To a solution of Example 76 Step E product (180 mg, 0.316 mmol) in DMA (8 mL) were added dicyanozinc (74.2 mg, 0.732 mmol), $Pd_2(dba)_3$ (28.9 mg, 0.0316 mmol), dppf (17.5 mg, 0.0316 mmol) and zinc (41.34 mg, 0.732 mmol). The reaction mixture was heated at 120° C. by microwave for 30 min. TLC (petroleum ether: EtOAc=3:1) showed that the reaction was complete. The reaction mixture was cooled, water (10 mL) was added and the mixture was extracted with EtOAc (3*20 mL). The combined organic fractions were washed with water (3*20 mL), dried over $Na_2SO_4$, filtered and the solvent was evaporated under reduced pressure. The crude residue was purified by silica gel column chromatography (EtOAc in petroleum ether: 0-60%) to give tert-butyl 2-(2-(4-cyanophenyl)-7-hydroxy-10-(trifluoromethyl)-3,5-dihydro-2H-[1,4]oxazino[2,3,4-ij]quinoline-6-carboxamido)acetate as a solid. The racemate was resolved by Chiral SFC (Instrument: Thar SFC 80; Column: OJ 250mm*30mm, 20 um; Mobile phase: A: Supercritical $CO_2$, B: MeOH (0.1% $NH_3.H_2O$), A:B=65:40 at 80 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to give peak 1 (Column: Chiralcel OJ-3 50*4.6 mm I.D., 3 um Mobile phase: methanol (0.05% DEA) in $CO_2$ from 5% to 40%, Flow rate: 4mL/min, Wavelength: 220 nm, RT: 1.069 min) as a solid, and peak 2 (Column: Chiralcel OJ-3 50*4.6 mm I.D., 3 um Mobile phase: methanol (0.05% DEA) in $CO_2$ from 5% to 40%, Flow rate: 4mL/min Wavelength: 220 nm; RT: 1.523 min) as a white solid. $^1H$ NMR ($CDCl_3$, 400 MHz): δ 10.48 (br.s, 1H), 7.89 (d, J=8.8 Hz, 1H), 7.78 (d, J=8.0 Hz, 2H), 7.64 (d, J=8.8 Hz, 2H), 7.51 (d, J=8.4 Hz, 1H), 5.36 (d, J=7.2 Hz, 1H), 5.02 (dd, J=11.6, 2.4 Hz, 1H), 4.13-4.17 (m, 2 H), 3.80 (dd, J=14.0, 9.6 Hz, 1H), 1.52(s, 9H).

Step B: 2-(2-(4-cyanophenyl)-7-hydroxy-5-oxo-10-(trifluoromethyl)-3,5-dihydro-2H-[1,4]oxazino[2,3,4-ij]quinoline-6-carboxamido)acetic acid To a solution of tert-butyl 2-(2-(4-cyanophenyl)-7-hydroxy-5-oxo-10-(trifluoromethyl)-3,5-dihydro-2H-[1,4]oxazino[2,3,4-ij]quinoline-6-carboxamido)acetate (peak 1) (50 mg, 0.088 mmol) in DCM (5 mL) was added TFA (1 mL). The reaction solution was stirred at room temperature for 3 h. TLC (petroleum ether: EtOAc=2:1) showed that the reaction was complete. The solvent was evaporated under reduced pressure. The residue was purified by recrystallization (EtOAc) to give 2-(2-(4-cyanophenyl)-7-hydroxy-10-(trifluoromethyl)-3,5-dihydro-2H-[1,4]oxazino[2,3,4-ij]quinoline-6-carboxamido)acetic acid (Column: Chiralcel OJ-3 50*4.6 mm I.D., 3 um Mobile phase: methanol (0.05% DEA) in CO2 from 5% to 40%, Flow rate: 4mL/min, Wavelength: 254 nm; RT: 1.206 min) as a solid. $^1H$ NMR ($DMSO-d_6$, 400 MHz): δ 10.38 (br.s, 1H), 7.99 (d, J=8.4 Hz, 2H), 7.84 (d, J=8.4 Hz, 1H), 7.75 (d, J=7.6 Hz, 2H), 7.62 (d, J=8.4 Hz, 1H), 5.72 (d, J=10.0 Hz, 1H), 4.86 (d, J=12.8 Hz, 1H), 4.14 (s, 2H), 3.93 (s, 1H). LC/MS (m/z): 474 $(M+H)^+$. Human HIF-PHD2 $IC_{50}$: 2.0 nM.

Similarly, from the enantiomer corresponding to peak 2 of Example 77 Step A, Example 78 in Table 7 was synthesized (Column: Chiralcel OJ-3 50*4.6 mm I.D., 3 um Mobile phase: methanol (0.05% DEA) in CO2 from 5% to 40%, Flow rate: 4mL/min, Wavelength: 254 nm, RT: 1.471 min).

TABLE 7

| Example | Name | Structure | MS m/z $(M + 1)^+$ and human HIF-PHD2 $IC_{50}$) |
|---|---|---|---|
| Example 78 | 2-(2-(4-cyanophenyl)-7-hydroxy-10-(trifluoromethyl)-3,5-dihydro-2H-[1,4]oxazino[2,3,4-ij]quinoline-6-carboxamido)acetic acid | 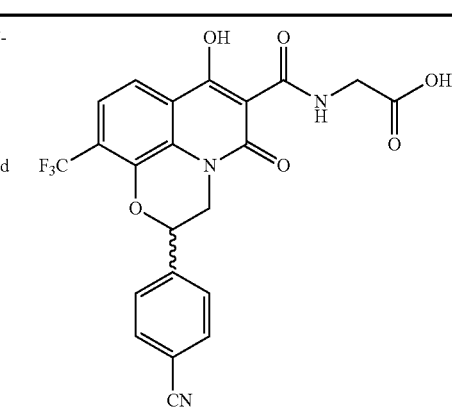 | $(M + 1)^+$ 474 $IC_{50}$ 7.9 nM |

Example 79

2-(7-hydroxy-8-methoxy-5-oxo-2-(4-(trifluoromethyl)phenyl)-3,5-dihydro-2H-[1,4]oxazino[2,3,4-ij]quinoline-6-carboxamido)acetic acid

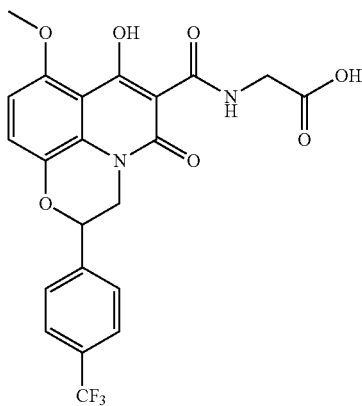 [SMILES: COc1ccc2c3c1c(O)c(C(=O)NCC(=O)O)c(=O)n3CC(c1ccc(C(F)(F)F)cc1)O2]

Step A: 2-amino-4-methoxyphenol

To the solution of 4-methoxy-2-nitrophenol(10 g, 59.16 mmol) in MeOH was added Pd/C(1.0 g, 10%). The mixture was charged by $H_2$ (30 psi) and stirred at room temperature for 4 h. TLC (petroleum ether: EtOAc=2:1) showed that the starting material was consumed. Then the reaction mixture was filtered and the filtrate was concentrated to give 2-amino-4-methoxyphenol as a solid. $^1$H NMR (CDCl$_3$, 400 MHz) δ 6.64 (s, 1H), 6.33 (s, 1H), 6.19 (s, 1H), 3.71(s, 3H).

Step B: 6-methoxy-2-(4-(trifluoromethyl)phenyl)-2H-benzo[b][1,4]oxazin-3(4H)-one To a solution of 2-amino-4-methoxyphenol (4.0 g, 29 mmol) in DMF (50 mL) was added K$_2$CO$_3$ (15.99 g, 166 mmol). The mixture was cooled by ice-water bath, to which was added 2-bromo-2-(4-(trifluoromethyl)phenyl)acetyl chloride (10.35 g, 35 mmol). The reaction was stirred at room temperature for 3 h. TLC (petroleum ether: EtOAc=5:1) showed that the reaction was complete. The resulting mixture was quenched and diluted by H$_2$O (40 mL), and extracted with DCM (30 mL*3). The combined organic layers were washed by brine (100 mL*3), dried over Na$_2$SO$_4$, filtered and concentrated in vacuo. The residue was purified by column chromatography (EtOAc: petroleum ether=0-20%) to give 7-methoxy-2-(4-(trifluoromethyl)phenyl)-2H-benzo[b][1,4]oxazin-3(4H)-one as a solid. $^1$H NMR (CDCl$_3$, 400 MHz,) δ 7.56-7.61 (m, 4H), 6.97(d, J=8.8 Hz, 1H), 6.52(dd, J=2.8, 8.8 Hz, 1H), 6.35(d, J=2.4Hz, 1H), 5.80 (s, 1H), 3.73 (s, 3H).

Step C: 6-methoxy-2-(4-(trifluoromethyl)phenyl)-3,4-dihydro-2H-benzo[b][1,4]oxazine To the solution of 6-methoxy-2-(4-(trifluoromethyl)phenyl)-2H-benzo[b][1,4]oxazin-3(4H)-one (3.0 g, 9.3 mmol) in THF(50 mL) was added BH$_3$-Me$_2$S(13.68 g, 0.18 mol) dropwise, then the reaction mixture was stirred at room temperature for overnight. TLC (petroleum ether: EtOAc=5:1) showed that the starting material was consumed. MeOH was added to quench the reaction and the solvent was evaporated. The residue was purified by column chromatography (EtOAc in Petroleum ether: 0-20%) to give 6-methoxy-2-(4-(trifluoromethyl)phenyl)-3,4-dihydro-2H-benzo[b][1,4]oxazine as an oil. $^1$H NMR (CDCl$_3$, 400 MHz) δ 7.66 (d, J=8.0 Hz, 2H), 7.54(d, J=8.4 Hz, 2H), 6.84(d, J=8.8 Hz, 1H), 6.25-6.31(m, 2H), 5.10 (dd, J=2.0, 8.4 Hz, 1H), 3.75 (s, 3H), 3.53(dd, J=2.4, 12.0 Hz, 1H), 3.36(dd, J=3.2, 12.0 Hz, 1H).

Step D: ethyl 7-hydroxy-8-methoxy-5-oxo-2-(4-(trifluoromethyl)phenyl)-3,5-dihydro-2H-[1,4]oxazino[2,3,4-ij]quinoline-6-carboxylate 6-Methoxy-2-(4-(trifluoromethyl)phenyl)-3,4-dihydro-2H-benzo[b][1,4]oxazine (500 mg, 1.62 mmol) and triethyl methanetricarboxylate (1.5 g, 6.48 mmol) was added into a 50 mL bottom flask. The mixture was stirred for 30 min at 250° C. TLC (petroleum ether: EtOAc=1:1) showed the reaction was complete. The reaction mixture was purified by Combi-Flash (DCM in EtOAc: 0%-12%) to give ethyl 7-hydroxy-8-methoxy-5-oxo-2-(4-(trifluoromethyl)phenyl)-3,5-dihydro-2H-[1,4]oxazino[2,3,4-ij]quinoline-6-carboxylate as a solid. $^1$H NMR (CDCl$_3$, 400 MHz) δ 7.71 (d, J=8.3 Hz, 2H), 7.59 (d, J=8.4 Hz, 2H), 7.28-7.25 (m, 1H), 6.68 (d, J=8.8 Hz, 1H), 5.08 (dd, J=9.5, 2.5 Hz, 1H), 4.98 (dd, J=14.1, 2.8 Hz, 1H), 4.50-4.48 (m, 2H), 3.99 (s, 3H), 3.6 (dd, J=14.3, 9.5 Hz, 1H), 1.46 (t, J=7.0 Hz, 3H).

Step E: tert-butyl 2-(7-hydroxy-8-methoxy-5-oxo-2-(4-(trifluoromethyl)phenyl)-3,5-dihydro-2H-[1,4]oxazino[2,3,4-ij]quinoline-6-carboxamido)acetate To a suspension of ethyl 7-hydroxy-8-methoxy-5-oxo-2-(4-(trifluoromethyl)phenyl)-3,5-dihydro-2H-[1,4]oxazino[2,3,4-ij]quinoline-6-carboxylate (0.4 g, 0.89 mmol) and tert-butyl 2-aminoacetate hydrochloride (248 mg, 1.07 mmol) in toluene (10 mL) was added DIPEA (265 mg, 2.05 mmol). Then the mixture was refluxed for 2 h. LCMS showed the reaction was complete. The solvent was removed and the residue was purified by silica gel column chromatography (DCM in EtOAc: 0%-12%) to give 2-(7-hydroxy-8-methoxy-5-oxo-2-(4-(trifluoromethyl)phenyl)-3,5-dihydro-2H-[1,4]oxazino[2,3,4-ij]quinoline-6-carboxamido)acetate as a solid. $^1$H NMR (CDCl$_3$, 400 MHz) δ 10.72 (t, J=4.9 Hz, 1H), 7.72 (d, J=8.0 Hz, 2H), 7.62 (d, J=8.3 Hz, 2H), 7.27-7.26 (m, 1H), 6.70 (d, J=8.8 Hz, 1H), 5.11-5.10 (m, 1H), 5.02-4.98 (m, 1H), 4.15-4.11 (m, 2H), 3.97 (s, 3H), 3.63 (dd, J=14.1, 9.8 Hz, 1H), 1.50 (s, 9H).

Step F: 2-(7-hydroxy-8-methoxy-5-oxo-2-(4-(trifluoromethyl)phenyl)-3,5-dihydro-2H-[1,4]oxazino[2,3,4-ij]quinoline-6-carboxamido)acetic acid To a solution of 2-(7-hydroxy-8-methoxy-5-oxo-2-(4-(trifluoromethyl)phenyl)-3,5-dihydro-2H-[1,4]oxazino[2,3,4-ij]quinoline-6-carboxamido)acetate (0.1 g, 0.19 mmol) in DCM (1 mL) was added TFA (1 mL) and the reaction was stirred at 30° C.-40° C. for 4 h. LCMS showed the reaction was complete. The solvent was removed and to the residue was added EtOAc (2 mL). After stirring at room temperature for 1 h, the mixture was filtered to give 2-(7-hydroxy-8-methoxy-5-oxo-2-(4-(trifluoromethyl)phenyl)-3,5-dihydro-2H-[1,4]oxazino[2,3,4-ij]quinoline-6-carboxamido)acetic acid as a solid. $^1$H NMR (DMSO-d$_6$, 400 MHz) δ 12.92 (brs, 1H), 10.51 (brs, 1H), 7.81-7.71 (m, 4H), 7.33 (d, J=8.8 Hz, 1H), 6.78 (d, J=9.0 Hz, 1H), 5.34 (d, J=8.2 Hz, 1H), 4.70 (d, J=12.8 Hz, 1H), 4.08 (d, J=4.9 Hz, 2H), 3.80-3.74 (m, 4H). LC/MS (m/z): 479 (M+H)+. Human HIF-PHD2 $IC_{50}$: 4.0 nM.

Example 80

2-(7,8-dihydroxy-5-oxo-2-(4-(trifluoromethyl)phenyl)-3,5-dihydro-2H-[1,4]oxazino[2,3,4-ij]quinoline-6-carboxamido)acetic acid

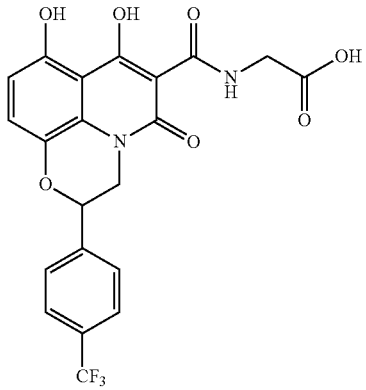

To a suspension of Example 79 Step E product (0.1 g, 0.19 mmol) in AcOH (2 mL) was added HBr/AcOH (2 mL). The mixture was refluxed for 4 h. LCMS showed the reaction was complete. The solvent was removed and the residue was purified by prep.HPLC (Column: Gemini 150*21.5mm*5 um; Mobile phase A: water (0.225% FA, V/V), Mobile phase B: acetonitrile) to give 2-(7,8-dihydroxy-5-oxo-2-(4-(trifluoromethyl)phenyl)-3,5-dihydro-2H-[1,4]oxazino[2,3,4-ij]quinoline-6-carboxamido)acetic acid as a solid. 1H NMR (DMSO-$d_6$, 400 MHz) δ 10.61 (brs, 1H), 7.85-7.83 (m, 2H), 7.78-7.76 (m, 2H), 7.31 (d, J=8.5 Hz, 1H), 6.64 (d, J=9.0 Hz, 1H), 5.40 (d, J=9.5 Hz, 1H), 4.67 (d, J=13.6 Hz, 1H), 4.20 (d, J=5.3 Hz, 2H), 3.85 (brs, 1H). LC/MS (m/z): 465 (M+H)+. Human HIF-PHD2 $IC_{50}$: 12 nM.

Example 81

2-(7-Hydroxy-9-methoxy-5-oxo-2-(4-(trifluoromethyl)phenyl)-3,5-dihydro-2H-[1,4]oxazino[2,3,4-ij]quinoline-6-carboxamido)acetic acid

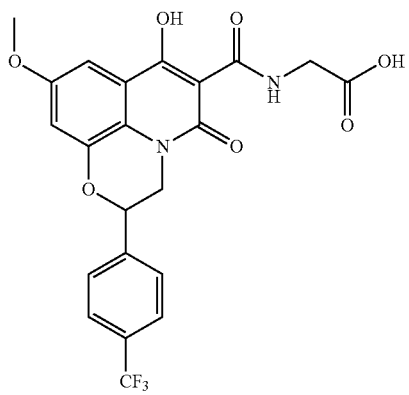 [SMILES: COc1cc2c3c(c1)c(O)c(C(=O)NCC(=O)O)c(=O)n3CC(c1ccc(C(F)(F)F)cc1)O2]

Starting with 5-methoxy-2-nitrophenol, the title compound was synthesized following similar procedures described in Example 79. 1H NMR (DMSO-$d_6$, 400 MHz) δ 12.96 (brs, 1H), 10.52 (t, J=5.6 Hz, 1H), 7.87-7.77 (m, 4H), 7.12 (s, 2H), 5.54 (dd, J=9.3, 2.0 Hz, 1H), 4.73 (dd, J=13.8, 2.8 Hz, 1H), 4.14 (d, J=6.0 Hz, 2H), 3.91-3.83 (m, 4H). LC/MS (m/z): 479 (M+H)+. Human HIF-PHD2 $IC_{50}$: 2.9 nM.

Example 82

2-(7,9-Dihydroxy-5-oxo-2-(4-(trifluoromethyl)phenyl)-3,5-dihydro-2H-[1,4]oxazino[2,3,4-ij]quinoline-6-carboxamido)acetic acid

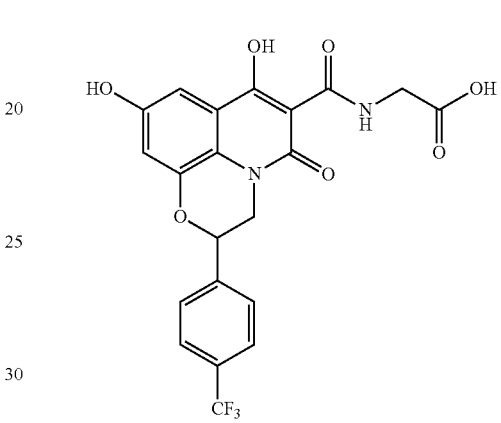

The title compound was synthesized following procedures described in Example 80 and using the methoxy intermediate from Example 81. 1H NMR (DMSO-$d_6$, 400 MHz) δ 10.50 (t, J=5.4 Hz, 1H), 9.92 (brs, 1H), 7.83-7.81 (m, 2H), 7.75-7.73 (m, 2H), 7.01 (d, J=2.4 Hz, 1H), 6.88 (d, J=2.4 Hz, 1H), 5.48 (d, J=7.5 Hz, 1H), 4.67 (d, J=11.7 Hz, 1H), 4.10 (d, J=5.5 Hz, 2H), 3.83 (dd, J=13.7, 9.3 Hz, 1H). LC/MS (m/z): 479 (M+H)+. Human HIF-PHD2 $IC_{50}$: 2.7 nM.

Example 83

2-(1-Hydroxy-3-oxo-6-(6-(trifluoromethyl)pyridin-3-yl)-3,5,6,7-tetrahydropyrido[3,2,1-ij]quinoline-2-carboxamido)acetic acid

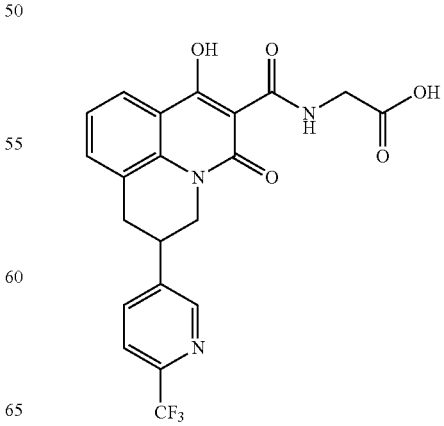

Step A: 3-(6-(trifluoromethyl)pyridin-3-yl)quinoline

To a solution of quinolin-3-ylboronic acid (1.53 g, 8.85 mmol) in dioxane (30 mL) were added 5-bromo-2-(trifluoromethyl)pyridine (2.0 g, 8.85 mmol), Pd(Ph$_3$P)$_4$ (0.51 g, 0.44 mmol) and K$_2$CO$_3$ (3.67 g, 26.55 mmol). Then water (10 mL) was added and the mixture was stirred at 80° C.-100° C. overnight. TLC (petroleum ether: EtOAc=1:1) showed the reaction was complete. The mixture was poured into water (100 mL) and extracted with EtOAc (30 mL*3). The combined organic layers were dried and concentrated. The residue was purified by Combi-Flash (EtOAc in Petroleum ether: 0%-15%) to give 3-(6-(trifluoromethyl)pyridin-3-yl)quinoline as a solid. $^1$H NMR (CDCl$_3$, 400 MHz) δ 9.17 (d, J=2.5 Hz, 1H), 9.09 (d, J=2.0 Hz, 1H), 8.38 (d, J=2.3 Hz, 1H), 8.23-8.15 (m, 2H), 7.95 (dd, J=8.0, 1.3 Hz, 1H), 7.89-7.78 (m, 2H), 7.70-7.61 (m, 1H).

Step B: 3-(6-(trifluoromethyl)pyridin-3-yl)-1,2,3,4-tetrahydroquinoline

To a suspension of 3-(6-(trifluoromethyl)pyridin-3-yl)quinoline (0.6 g, 2.19 mmol) in EtOH (20 mL) was added PtO$_2$ (50 mg, 0.22 mmol) under N$_2$. Then the mixture was stirred at 100° C.-110° C. under H$_2$ (2.0 MPa) for 16 h in a 100 mL of autoclave. LCMS showed the reaction was complete. The reaction mixture was filtered and the filtration was concentrated. The residue was purified by Combi-Flash (EtOAc in DCM: 0%-3%) to give 3-(6-(trifluoromethyl)pyridin-3-yl)-1,2,3,4-tetrahydroquinoline as a solid. $^1$H NMR (CDCl$_3$, 400 MHz) δ 8.64 (s, 1H), 7.71-7.69 (m, 1H), 7.64-7.62 (m, 1H), 7.05-7.00 (m, 2H), 6.67 (t, J=7.3 Hz, 1H), 6.56 (d, J=7.9 Hz, 1H), 4.04 (brs, 1H), 3.58-3.47 (m, 1H), 3.41-3.23 (m, 2H), 3.13-2.93 (m, 2H).

Step C: ethyl 1-hydroxy-3-oxo-6-(6-(trifluoromethyl)pyridin-3-yl)-3,5,6,7-tetrahydropyrido[3,2,1-ij]quinoline-2-carboxylate 3-(6-(trifluoromethyl)pyridin-3-yl)-1,2,3,4-tetrahydroquinoline (250 mg, 0.9 mmol) and triethyl methanetricarboxylate (0.84 g, 3.6 mmol) was added into a 50 mL flask. The mixture was stirred for 30 min at 250° C. TLC (petroleum ether: EtOAc=2:1) showed the reaction was complete. The reaction mixture was purified by silica gel column chromatography (EtOAc in DCM: 0%-12%) to give ethyl 1-hydroxy-3-oxo-6-(6-(trifluoromethyl)pyridin-3-yl)-3,5,6,7-tetrahydropyrido[3,2,1-ij]quinoline-2-carboxylate as a solid. $^1$H NMR (CDCl$_3$, 400 MHz) δ 14.22 (s, 1H), 8.68 (d, J=1.8 Hz, 1H), 8.08 (dd, J=8.0, 1.5 Hz, 1H), 7.79-7.74 (m, 1H), 7.71-7.67 (m, 1H), 7.51-7.47 (m, 1H), 7.21 (d, J=8.0, 7.3 Hz, 1H), 4.90-4.82 (m, 1H), 4.5 (qd, J=7.1 Hz, 0.8 Hz, 2H), 3.82 (dd, J=13.8, 10.3 Hz, 1H), 3.45-3.36 (m, 1H), 3.30-3.23 (m, 2H), 1.48 (t, J=7.2 Hz, 3H).

Step D: tert-butyl 2-(1-hydroxy-3-oxo-6-(6-(trifluoromethyl)pyridin-3-yl)-3,5,6,7-tetrahydropyrido[3,2,1-ij]quinoline-2-carboxamido)acetate To a suspension of ethyl 1-hydroxy-3-oxo-6-(6-(trifluoromethyl)pyridin-3-yl)-3,5,6,7-tetrahydropyrido[3,2,1-ij]quinoline-2-carboxylate (0.21 g, 0.5 mmol) and tert-butyl 2-aminoacetate hydrochloride (140 mg, 0.6 mmol) in toluene (10 mL) was added DIPEA (148 mg, 1.15 mmol). Then the mixture was refluxed for 2 h. LCMS showed the reaction was complete. The solvent was removed and the residue was purified by silica gel column chromatography (EtOAc in DCM: 0%-12%) to give tert-butyl 2-(1-hydroxy-3-oxo-6-(6-(trifluoromethyl)pyridin-3-yl)-3,5,6,7-tetrahydropyrido[3,2,1-ij]quinoline-2-carboxamido)acetate as a solid. $^1$H NMR (CDCl$_3$, 400 MHz) δ 10.58 (t, J=4.7 Hz, 1H), 8.63 (s, 1H), 8.02 (d, J=7.9 Hz, 1H), 7.74-7.68 (m, 1H), 7.66-7.62 (m, 1H), 7.42 (d, J=7.3 Hz, 1H), 7.21-7.13 (m, 1H), 4.82 (dd, J=13.7, 3.3 Hz, 1H), 4.14-3.97 (m, 2H), 3.75 (dd, J=13.7, 10.6 Hz, 1H), 3.36-3.34 (m, 1H), 3.25-3.14 (m, 2H), 1.43 (s, 9H).

Step E: 2-(1-hydroxy-3-oxo-6-(6-(trifluoromethyl)pyridin-3-yl)-3,5,6,7-tetrahydropyrido[3,2,1-ij]quinoline-2-carboxamido)acetic acid To a solution of tert-butyl 2-(1-hydroxy-3-oxo-6-(6-(trifluoromethyl)pyridin-3-yl)-3,5,6,7-tetrahydropyrido[3,2,1-ij]quinoline-2-carboxamido)acetate (0.2 g, 0.4 mmol) in DCM (2 mL) was added TFA (2 mL). The mixture was stirred at 40° C. for 2 h. LCMS showed the reaction was complete. The solvent was removed and to the residue was added EtOAc (2 mL). The mixture was stirred for 30 min at room temperature. The mixture was filtered to give 2-(1-hydroxy-3-oxo-6-(6-(trifluoromethyl)pyridin-3-yl)-3,5,6,7-tetrahydropyrido[3,2,1-ij]quinoline-2-carboxamido)acetic acid as a solid. $^1$H NMR (DMSO-d$_6$, 400 MHz) δ 10.52 (brs, 1H), 8.84 (s, 1H), 8.11 (d, J=7.5 Hz, 1H), 7.98 (d, J=7.8 Hz, 1H), 7.92 (d, J=8.0 Hz, 1H), 7.65 (d, J=7.3 Hz, 1H), 7.31 (t, J=7.7 Hz, 1H), 4.69 (d, J=11.3 Hz, 1H), 4.14 (d, J=5.5 Hz, 2H), 3.96-3.86 (m, 1H), 3.58-3.47 (m, 1H), 3.44-3.33 (m, 1H), 3.30-3.22 (m, 1H). LC/MS (m/z): 448 (M+H)$^+$. Human HIF-PHD2 IC$_{50}$: 5.0 nM.

Example 84

2-(9-cyano-1-hydroxy-3-oxo-6-(6-(trifluoromethyl)pyridin-3-yl)-3,5,6,7-tetrahydropyrido[3,2,1-ij]quinoline-2-carboxamido)acetic acid

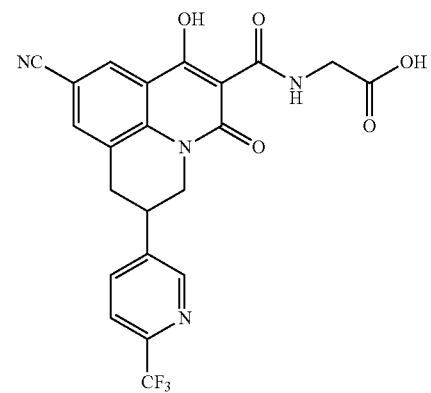

Step A: 6-bromo-3-(6-(trifluoromethyl)pyridin-3-yl)-1,2,3,4-tetrahydroquinoline To a solution of Example 83 Step B product (0.67 g, 2.16 mmol) in DCM (20 mL) was added a suspension of NBS (0.38 g, 2.16 mmol) in DCM (5 mL) slowly. After addition, the mixture was stirred at room temperature for 1 h. LCMS showed the reaction was complete. The solvent was removed and the residue was purified by Combi-Flash (EtOAc in Petroleum ether: 0%-15%) to give 6-bromo-3-

(6-(trifluoromethyl)pyridin-3-yl)-1,2,3,4-tetrahydroquinoline as an oil. $^1$H NMR (CDCl$_3$, 400 MHz) δ 8.62 (s, 1H), 7.69-7.62 (m, 2H), 7.09 (d, J=2.0 Hz, 2H), 6.42 (d, J=8.0 Hz, 1H), 4.05 (brs, 1H), 3.53-3.50 (m, 1H), 3.37-3.27 (m, 2H), 3.03-2.96 (m, 2H).

Step B: ethyl 9-bromo-1-hydroxy-3-oxo-6-(6-(trifluoromethyl)pyridin-3-yl)-3,5,6,7-tetrahydropyrido[3,2,1-ij]quinoline-2-carboxylate 6-Bromo-3-(6-(trifluoromethyl)pyridin-3-yl)-1,2,3,4-tetrahydroquinoline (0.77 g, 2.16 mmol) and triethyl methanetricarboxylate (2.0 g, 8.64 mmol) was added into a 50 mL flask. Then the mixture was stirred for 30 min at 250° C. TLC (petroleum ether: EtOAc=3:1) showed the reaction was complete. The reaction mixture was purified by CombiFlash (EtOAc in DCM: 0%-12%) to give ethyl 9-bromo-1-hydroxy-3-oxo-6-(6-(trifluoromethyl)pyridin-3-yl)-3,5,6,7-tetrahydropyrido[3,2,1-ij]quinoline-2-carboxylate as a solid. $^1$H NMR (CDCl$_3$, 400 MHz) δ 14.23 (s, 1H), 8.68 (s, 1H), 8.20 (d, J=2.0 Hz, 1H), 7.77-7.70 (m, 2H), 7.59 (d, J=2.0 Hz, 1H), 4.82 (dd, J=13.7, 3.4 Hz, 1H), 4.51 (q, J=7.0 Hz, 2H), 3.82 (dd, J=13.9, 10.2 Hz, 1H), 3.45-3.35 (m, 1H), 3.27-3.25 (m, 2H), 1.48 (t, J=7.2 Hz, 3H).

Step C: tert-butyl 2-(9-bromo-1-hydroxy-3-oxo-6-(6-(trifluoromethyl)pyridin-3-yl)-3,5,6,7-tetrahydropyrido[3,2,1-ij]quinoline-2-carboxamido)acetate To a suspension of ethyl 9-bromo-1-hydroxy-3-oxo-6-(6-(trifluoromethyl)pyridin-3-yl)-3,5,6,7-tetrahydropyrido[3,2,1-ij]quinoline-2-carboxylate (0.46 g, 0.93 mmol) and tert-butyl 2-aminoacetate hydrochloride (0.33 g, 1.40 mmol) in toluene (10 mL) was added DIPEA (0.48 g, 3.72 mmol). Then the mixture was refluxed for 2 h. LCMS showed the reaction was complete. The solvent was removed and the residue was purified by silica gel column chromatography (EtOAc in DCM: 0%42%) to give tert-butyl 2-(9-bromo-1-hydroxy-3-oxo-6-(6-(trifluoromethyl)pyridin-3-yl)-3,5,6,7-tetrahydropyrido[3,2,1-ij]quinoline-2-carboxamido)acetate as a solid. $^1$H NMR (CDCl$_3$, 400 MHz) δ 10.57 (t, J=4.8 Hz, 1H), 8.70 (s, 1H), 8.21 (d, J=2.3 Hz, 1H), 7.79-7.75 (m, 1H), 7.73-7.69 (m, 1H), 7.59 (d, J=2.3 Hz, 1H), 4.86 (dd, J=13.8, 3.5 Hz, 1H), 4.19-4.06 (m, 2H), 3.83 (dd, J=13.8, 10.5 Hz, 1H), 3.48-3.35 (m, 1H), 3.32-3.23 (m, 2H), 1.50 (s, 9H).

Step D: tert-butyl 2-(9-cyano-1-hydroxy-3-oxo-6-(6-(trifluoromethyl)pyridin-3-yl)-3,5,6,7-tetrahydropyrido[3,2,1-ij]quinoline-2-carboxamido)acetate To a solution of tert-butyl 2-(9-bromo-1-hydroxy-3-oxo-6-(6-(trifluoromethyl)pyridin-3-yl)-3,5,6,7-tetrahydropyrido[3,2,1-ij]quinoline-2-carboxamido)acetate (0.2 g, 0.34 mmol) in DMA (3.0 mL) were added Zn(CN)$_2$ (0.10 g, 0.88 mmol), Zn (0.058 g, 0.88 mmol), Pd$_2$(dba)$_3$ (46 mg, 0.05 mmol) and dppf (28 mg, 0.05 mmol). Then the mixture was heated by microwave at 120° C. for 30 min. LCMS showed the reaction was complete. The reaction mixture was poured into water (30 mL) and extracted with EtOAc (15 mL*3). The combined organic layers were dried and concentrated. The residue was purified by silica gel column chromatography (EtOAc in DCM: 0%-5%) to give tert-butyl 2-(9-cyano-1-hydroxy-3-oxo-6-(6-(trifluoromethyl)pyridin-3-yl)-3,5,6,7-tetrahydropyrido[3,2,1-ij]quinoline-2-carboxamido)acetate as a solid. $^1$H NMR (CDCl$_3$, 400 MHz) δ 10.41 (t, J=5.0 Hz, 1H), 8.71 (s, 1H), 8.41 (s, 1H), 7.81-7.76 (m, 1H), 7.75-7.71 (m, 1H), 7.69 (s, 1H), 4.90 (dd, J=13.8, 3.0 Hz, 1H), 4.20-4.10 (m, 2H), 3.82 (dd, J=13.8, 10.5 Hz, 1H), 3.49-3.37 (m, 1H), 3.35-3.24 (m, 2H), 1.49 (s, 9H).

Step E: 2-(9-cyano-1-hydroxy-3-oxo-6-(6-(trifluoromethyl)pyridin-3-yl)-3,5,6,7-tetrahydropyrido[3,2,1-ij]quinoline-2-carboxamido)acetic acid To a solution of tert-butyl 2-(9-cyano-1-hydroxy-3-oxo-6-(6-(trifluoromethyl)pyridin-3-yl)-3,5,6,7-tetrahydropyrido[3,2,1-ij]quinoline-2-carboxamido)acetate (0.13 g, 0.25 mmol) in DCM (3 mL) was added TFA (1 mL) and the reaction was stirred at 30° C.-40° C. for 2 h. LCMS showed the reaction was complete. The solvent was removed and to the residue was added EtOAc (1 mL). The mixture was stirred for 30 min at room temperature. The mixture was filtered to give 2-(9-cyano-1-hydroxy-3-oxo-6-(6-(trifluoromethyl)pyridin-3-yl)-3,5,6,7-tetrahydropyrido[3,2,1-ij]quinoline-2-carboxamido)acetic acid as a solid. $^1$H NMR (DMSO-d$_6$, 400 MHz) δ 10.35 (brs, 1H), 8.82 (s, 1H), 8.34 (d, J=1.3 Hz, 1H), 8.09 (d, J=7.3 Hz, 1H), 8.01 (s, 1H), 7.89 (d, J=8.3 Hz, 1H), 4.68 (d, J=13.1 Hz, 1H), 4.14 (d, J=5.8 Hz, 2H), 3.92-3.89 (m, 1H), 3.52-3.49 (m, 1H), 3.37-3.31 (m, 2H). LC/MS (m/z): 473 (M+H)$^+$. Human HIF-PHD2 IC$_{50}$: 0.9 nM.

Example 85

2-(1-hydroxy-9-(methylsulfonyl)-3-oxo-6-(6-(trifluoromethyl)pyridin-3-yl)-3,5,6,7-tetrahydropyrido[3,2,1-ij]quinoline-2-carboxamido)acetic acid

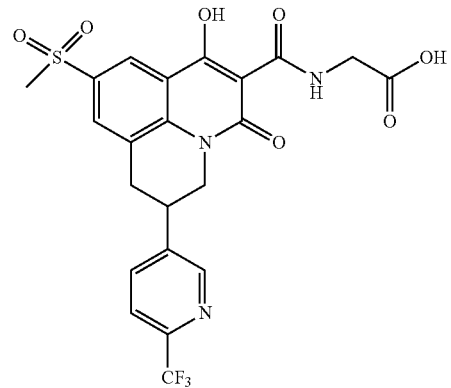 [SMILES: CS(=O)(=O)c1cc2c3c(c1)c(O)c(C(=O)NCC(=O)O)c(=O)n3CC(c1ccc(C(F)(F)F)nc1)C2]

Step A: 2-(1-hydroxy-9-(methylsulfonyl)-3-oxo-6-(6-(trifluoromethyl)pyridin-3-yl)-3,5,6,7-tetrahydropyrido[3,2,1-ij]quinoline-2-carboxamido)acetic acid To a solution of Example 84 Step C product (0.13 g, 0.22 mmol) in DMSO (2.5 mL) were added MeSO$_2$Na (34 mg, 0.33 mmol), pyrrolidine-2-carboxylic acid (5 mg, 0.044 mmol), NaOH (1.8 mg, 0.44 mmol) and CuI (4.2 mg, 0.022 mmol). The mixture was stirred at 120° C. for 3 days. The desired product was detected by LCMS. The reaction mixture was filtered and purified by prep. HPLC (Column: Gemini 150*21.5mm*5 um; Mobile phase A: water (0.225% FA, V/V), Mobile phase B: acetonitrile) to give 2-(1-hydroxy-9-(methylsulfonyl)-3-oxo-6-(6-(trifluoromethyl)pyridin-3-yl)-3,5,6,7-tetrahydropyrido[3,2,1-ij]quinoline-2-carboxamido)acetic acid as a solid. $^1$H NMR (DMSO-d$_6$, 400 MHz) δ 10.46 (brs, 1H), 8.78 (s, 1H), 8.52

(s, 1H), 8.05 (s, 1H), 7.98 (d, J=7.8 Hz, 1H), 7.82 (d, J=8.0 Hz, 1H), 4.81 (d, J=11.3 Hz, 1H), 4.24-4.19 (m, 2H), 3.97-3.89 (m, 1H), 3.53 (dd, J=10.5 Hz, 1H), 3.45-3.36 (m, 2H), 3.15 (s, 3H). LC/MS (m/z): 526 (M+H)$^+$. Human HIF-PHD2 IC$_{50}$: 0.9 nM.

Example 86

2-(7-Hydroxy-5-oxo-8-(trifluoromethoxy)-2-(4-(trifluoromethyl)phenyl)-3,5-dihydro-2H-[1,4]oxazino[2,3,4-ij]quinoline-6-carboxamido)acetic acid

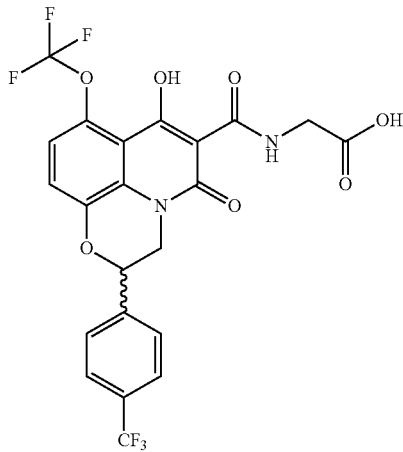 [SMILES: O=C(O)CNC(=O)c1c(O)c2c(OC(F)(F)F)ccc3c2n(c1=O)CC(c1ccc(C(F)(F)F)cc1)O3]

Step A: 2-nitro-4-(trifluoromethoxy)phenol

To a solution of 4-(trifluoromethoxy)phenol (1 g, 5.6 mmol) in AcOH (8 mL) was added HNO$_3$ (1 mL) dropwise at 10-15° C. The mixture was stirred at this temperature for 1.5 h. TLC showed the reaction was completed. The mixture was poured in icewater (15 mL), and extracted with EtOAc (10 mL*3). The combined organic layers were dried over Na$_2$SO$_4$, filtered and concentrated in vacuum. The residue was purified by column chromatography on SiO$_2$ (EtOAc in petroleum ether: 0~30%) to give 2-nitro-4-(trifluoromethoxy)phenol as an oil. $^1$H NMR (CD$_3$OD, 400 MHz) δ 7.99 (s, 1H), 7.59-7.56 (m, 1H), 7.25 (d, J=8.8 Hz, 1H).

Step B: 2-amino-4-(trifluoromethoxy)phenol

To a solution of 2-nitro-4-(trifluoromethoxy)phenol (1 g, 4.4 mmol) in EtOAc (10 mL) was added Pd/C (200 mg, 5% wt). The mixture was stirred under H$_2$ balloon at room temperature for 2 h. The mixture was filtered through the celite and the filtrate was concentrated in vacuum to give the 2-amino-4-(trifluoromethoxy)phenol as a solid. $^1$H NMR (CDCl$_3$, 400 MHz) δ 6.66 (d, J=8.4 Hz, 1H), 6.61 (s, 1H), 7.52-7.49 (m, 1H), 4.15 (brs, 2H).

Step C: 6-(trifluoromethoxy)-2-(4-(trifluoromethyl)phenyl)-2H-benzo[b][1,4]oxazin-3(4H)-one To a solution of 2-amino-4-(trifluoromethoxy)phenol (5.6 g, 29 mmol) in DMF (100 mL) was added K$_2$CO$_3$ (16 g, 116 mmol), and the mixture was cooled by ice-water bath. To this mixture 2-bromo-2-(4-(trifluoromethyl)phenyl)acetyl chloride (10.5 g, 35 mmol) was added dropwise. The reaction was stirred at room temperature for 3 h. TLC (petroleum ether: EtOAc=51) showed that the reaction was complete. The resulting mixture was quenched and diluted by H$_2$O (400 mL) and extracted with DCM (300 mL*3). The combined organic layers were washed by brine (300 mL*3), dried over Na$_2$SO$_4$, filtered and concentrated in vacuo. The residue was purified by column chromatography (EtOAc in petroleum ether: 0-20%) to give 6-(trifluoromethoxy)-2-(4-(trifluoromethyl)phenyl)-2H-benzo[b][1,4]oxazin-3(4H)-one as a solid. $^1$H NMR (CDCl$_3$, 400 MHz) δ 9.15 (brs, 1H), 7.65 (d, J=8.4 Hz, 2H), 7.59 (d, J=8.0 Hz, 2H), 7.07 (d, J=8.4 Hz, 1H), 6.89 (d, J=8.4 Hz, 1H), 6.73 (s, 1H), 5.75 (s, 1H).

Step D: 6-(trifluoromethoxy)-2-(4-(trifluoromethyl)phenyl)-3,4-dihydro-2H-benzo[b][1,4]oxazine To a solution of 6-(trifluoromethoxy)-2-(4-(trifluoromethyl)phenyl)-2H-benzo[b][1,4]oxazin-3(4H)-one (3.5 g, 9.3 mmol) in THF(50 mL) was added BH$_3$-Me$_2$S(10 mL, 0.18 mol) dropwise, then the reaction mixture was stirred at room temperature overnight. TLC (petroleum ether: EtOAc=5:1) showed that the starting material was consumed. MeOH was added to quench the reaction. The solvent was evaporated to give the crude product which was purified by column chromatography (EtOAc in Petroleum ether: 0-20%) to get 6-(trifluoromethoxy)-2-(4-(trifluoromethyl)phenyl)-3,4-dihydro-2H-benzo[b][1,4]oxazine as a solid. $^1$H NMR (CDCl$_3$, 400 MHz) δ 7.58 (d, J=5.6 Hz, 2H), 7.45 (d, J=6.0 Hz, 2H), 6.80 (d, J=4.8 Hz, 1H), 6.49-6.45 (m, 2H), 5.05 (d, J=8.4 Hz, 1H), 4.04-3.98 (m, 1H), 3.47 (d, J=12.0 Hz, 1H), 3.29-3.24 (m, 1H).

Step E: ethyl 7-hydroxy-5-oxo-8-(trifluoromethoxy)-2-(4-(trifluoromethyl)phenyl)-3,5-dihydro-2H-[1,4]oxazino[2,3,4-ij]quinoline-6-carboxylate 6-(Trifluoromethoxy)-2-(4-(trifluoromethyl)phenyl)-3,4-dihydro-2H-benzo[b][1,4]oxazine (588 mg, 1.62 mmol) and triethyl methanetricarboxylate (1.5 g, 6.48 mmol) was added into a 50 mL flask. The mixture was stirred for 30 min at 250° C. TLC (petroleum ether: EtOAc=1:1) showed the reaction was complete. The reaction mixture was purified by Combi-Flash (DCM in EtOAc: 0%-12%) to give ethyl 7-hydroxy-5-oxo-8-(trifluoromethoxy)-2-(4-(trifluoromethyl)phenyl)-3,5-dihydro-2H-[1,4]oxazino[2,3,4-ij]quinoline-6-carboxylate as a solid. $^1$H NMR (CDCl$_3$, 400 MHz) δ 14.84 (s, 1H), 7.72 (d, J=8.0 Hz, 2H), 7.60 (d, J=8.0 Hz, 2H), 7.30 (d, J=8.8 Hz, 1H), 7.09 (d, J=4.8 Hz, 1H), 5.16 (d, J=9.2 Hz, 1H), 5.0 (d, J=16.8 Hz, 1H), 4.53 (q, J=4.8 Hz, 2H), 3.64-3.58 (m, 1H), 1.30(t, J=7.2 Hz, 3H).

Step F: tert-butyl 2-(7-hydroxy-5-oxo-8-(trifluoromethoxy)-2-(4-(trifluoromethyl)phenyl)-3,5-dihydro-2H-[1,4]oxazino[2,3,4-ij]quinoline-6-carboxamido)acetate (peak 1) and tert-butyl 2-(7-hydroxy-5-oxo-8-(trifluoromethoxy)-2-(4-(trifluoromethyl)phenyl)-3,5-dihydro-2H-[1,4]oxazino[2,3,4-ij]quinoline-6-carboxamido)acetate (peak 2)

To a suspension of ethyl 7-hydroxy-5-oxo-8-(trifluoromethoxy)-2-(4-(trifluoromethyl)phenyl)-3,5-dihydro-2H-[1,4]oxazino[2,3,4-ij]quinoline-6-carboxylate (417 mg, 0.83 mmol) and tert-butyl 2-aminoacetate hydrochloride (168 mg, 1.0 mmol) in toluene (10 mL) was added DIPEA (246 mg, 1.91 mmol). The mixture was refluxed for 2 h. LCMS showed the reaction was complete. The solvent was removed and the residue was purified by combi flash (DCM in EtOAc: 0%-12%) to give a solid. The racemate was resolved by Chrial-SFC (Instrument: Thar SFC MG2; Column: OJ 250 mm*30mm, 5 um; Mobile phase: A: Supercritical $CO_2$, B: EtOH(0.1% $NH_3.H_2O$), A:B=75:25 at 60 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to give peak 1 (Column:

1H), 4.91 (d, J=14.0 Hz, 1H), 4.15 (s, 2H), 3.70 (dd, J=10.0 Hz, 10.0 Hz, 1H). LC/MS (m/z): 533 (M+H)$^+$. Human HIF-PHD2 $IC_{50}$: 14 nM.

Similarly, from the enantiomer corresponding to peak 2 of Example 86 Step F, Example 87 in Table 8 was synthesized (Column: Chiralcel OJ-H 250×4.6 mm I.D., 5 um Mobile phase: ethanol(0.05% DEA) in $CO_2$ from 5% to 40% Flow rate: 2.35 mL/min Wavelength: 220 nm; RT: 7.463 min).

TABLE 8

| Example Name | structure | MS m/z (M + 1)$^+$ and human HIF-PHD2 $IC_{50}$ |
|---|---|---|
| Example 87 | 2-(7-hydroxy-5-oxo-8-(trifluoromethoxy)-2-(4-(trifluoromethyl)phenyl)-3,5-dihydro-2H-[1,4]oxazino[2,3,4-ij]quinoline-6-carboxamido)acetic acid | (M + 1)$^+$ 533 $IC_{50}$ 17 nM |

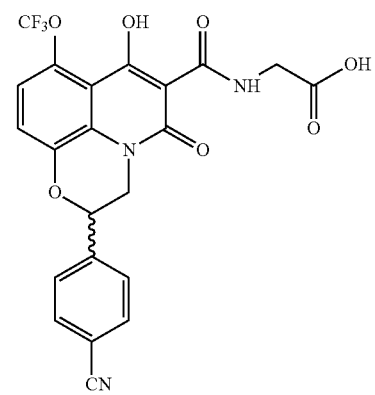

Chiralcel OJ-H 250×4.6 mm I.D., 5 um Mobile phase: ethanol (0.05% DEA) in $CO_2$ from 5% to 40% Flow rate: 2.35mL/min Wavelength: 220 nm; RT: 4.554 min) as a solid and peak 2 (Column: Chiralcel OJ-H 250×4.6 mm I.D., 5 um Mobile phase: ethanol(0.05% DEA) in $CO_2$ from 5% to 40% Flow rate: 2.35 mL/min Wavelength: 220 nm; RT: 6.586 min) as a solid. $^1$H NMR (CDCl$_3$, 400 MHz) δ 10.59 (t, J=3.6 Hz 1H), 7.72 (d, J=8.0 Hz, 2H), 7.61 (d, J=8.0 Hz, 2H), 7.28 (d, J=8.8 Hz, 1H), 7.10 (d, J=8.8 Hz, 1H), 5.16 (d, J=7.6 Hz, 1H), 5.02 (dd, J=2.4 Hz, 2.8 Hz, 1H), 4.13-4.09 (m, 2H), 3.65-3.59 (m, 1H), 1.48 (s, 9H).

Step G: 2-(7-hydroxy-5-oxo-8-(trifluoromethoxy)-2-(4-(trifluoromethyl)phenyl)-3,5-dihydro-2H-[1,4] oxazino[2,3,4-ij]quinoline-6-carboxamido)acetic acid To a suspension of ert-butyl 2-(7-hydroxy-5-oxo-8-(trifluoromethoxy)-2-(4-(trifluoromethyl)phenyl)-3,5-dihydro-2H-[1,4]oxazino[2,3,4-ij]quinoline-6-carboxamido)acetate (peak 1) (112 mg, 0.19 mmol) in DCM (1 mL) was added TFA (1 mL) and the reaction was stirred at 30° C.-40° C. for 4 h. LCMS showed the reaction was complete. The solvent was removed and to the residue was added EtOAc (2 mL). The mixture was stirred for 1 h at room temperature. The mixture was filtered to give 2-(7-hydroxy-5-oxo-8-(trifluoromethoxy)-2-(4-(trifluoromethyl)phenyl)-3,5-dihydro-2H-[1,4]oxazino[2,3,4-ij]quinoline-6-carboxamido)acetic acid (Column: Chiralcel OJ-H 250×4.6 mm I.D., 5 um Mobile phase: ethanol (0.05% DEA) in $CO_2$ from 5% to 40% Flow rate: 2.35mL/min Wavelength: 220 nm; RT: 5.688 min) as a solid. $^1$H NMR (CD$_3$OD, 400 MHz) 7.78-7.73 (m, 4H), 7.38 (d, J=8.8 Hz, 1H), 7.16 (d, J=8.8 Hz, 1H), 5.35 (d, J=8.8 Hz, Example 88

2-(2-(4-Cyanophenyl)-7-hydroxy-5-oxo-8-(trifluoromethoxy)-3,5-dihydro-2H-[1,4]oxazino[2,3,4-ij] quinoline-6-carboxamido)acetic acid Step A: 2-(4-bromophenyl)-6-(trifluoromethoxy)-2H-benzo[b][1,4]oxazin-3(4H)-one To a solution of 2-amino-4-(trifluoromethoxy)phenol (5.6 g, 29 mmol) in DMF (100 mL) was added K$_2$CO$_3$ (16 g, 116 mmol), and the mixture was cooled by ice-water bath. To this mixture was added 2-bromo-2-(4-bromophenyl)acetyl chloride (10.8 g, 35 mmol) dropwise. The reaction was stirred at room temperature for 3 h. TLC (petroleum ether: EtOAc=5:1) showed that the reaction was complete. The resulting mixture was quenched and diluted by H₂O (400 mL), and extracted with DCM (300 mL*3). The combined organic layers were washed by brine (300 mL*3), dried over Na₂SO₄, filtered and concentrated in vacuo. The residue was purified by column chromatography (EtOAc in petroleum ether: 0-20%) to give 2-(4-bromophenyl)-6-(trifluoromethoxy)-2H-benzo[b][1,4]oxazin-3(4H)-one a solid.

Step B: 6-(trifluoromethoxy)-2-(4-(trifluoromethyl) phenyl)-3,4-dihydro-2H-benzo[b][1,4]oxazine To the solution of 2-(4-bromophenyl)-6-(trifluoromethoxy)-2H-benzo[b][1,4]oxazin-3(4H)-one (3.6 g, 9.3 mmol) in THF(50 mL) was added BH₃-Me₂S(10 mL, 0.18 mol) dropwise, then the reaction mixture was stirred at room temperature overnight. TLC (petroleum ether: EtOAc=5:1) showed that the starting material was consumed. MeOH was added to quench the reaction. The solvent was evaporated and the residue was purified by column chromatography (EtOAc in Petroleum ether: 0-20%) to give 6-(trifluoromethoxy)-2-(4-(trifluoromethyl)phenyl)-3,4-dihydro-2H-benzo[b][1,4]oxazine as a solid. ¹H NMR (CDCl₃, 400 MHz) δ 7.53 (d, J=8.4 Hz, 2H), 7.27 (d, J=8.4 Hz, 2H), 6.85 (d, J=8.8 Hz, 1H), 6.52-6.55 (m, 2H), 5.01 (dd, J=2.4 Hz, 2.0 Hz, 1H), 4.08 (brs, 1H), 3.50 (dd, J=2.4 Hz, 2.4 Hz, 1H), 3.33-3.30 (m, 1H).

Step C: ethyl 2-(4-bromophenyl)-7-hydroxy-5-oxo-8-(trifluoromethoxy)-3,5-dihydro-2H-[1,4]oxazino[2,3,4-ij]quinoline-6-carboxylate 6-(trifluoromethoxy)-2-(4-(trifluoromethyl)phenyl)-3,4-dihydro-2H-benzo[b][1,4]oxazine (604 mg, 1.62 mmol) and triethyl methanetricarboxylate (1.5 g, 6.48 mmol) was added into a 50 mL flask. The mixture was stirred for 30 min at 250° C. TLC (petroleum ether: EtOAc=1:1) showed the reaction was complete. The reaction mixture was purified by Combi-Flash (DCM in EtOAc: 0%-12%) to give ethyl 2-(4-bromophenyl)-7-hydroxy-5-oxo-8-(trifluoromethoxy)-3,5-dihydro-2H-[1,4]oxazino[2,3,4-ij]quinoline-6-carboxylate as a solid. ¹H NMR (CDCl₃, 400 MHz) δ 14.83 (s, 1H), 7.59 (d, J=8.4 Hz, 2H), 7.33 (d, J=8.0 Hz, 2H), 7.28 (d, J=8.8 Hz, 1H), 7.09 (d, J=9.2 Hz, 1H), 5.04 (d, J=9.2 Hz, 1H), 4.94 (d, J=16.8 Hz, 1H), 4.52 (q, J=3.2 Hz, 2H), 3.62-3.58 (m, 1H), 1.28 (t, J=6.8 Hz, 3H).

Step D: tert-butyl 2-(2-(4-bromophenyl)-7-hydroxy-5-oxo-8-(trifluoromethoxy)-3,5-dihydro-2H-[1,4] oxazino[2,3,4-ij]quinoline-6-carboxamido)acetate To a suspension of ethyl 2-(4-bromophenyl)-7-hydroxy-5-oxo-8-(trifluoromethoxy)-3,5-dihydro-2H-[1,4]oxazino [2,3,4-ij]quinoline-6-carboxylate (426 mg, 0.83 mmol) and tert-butyl 2-aminoacetate hydrochloride (168 mg, 1.0 mmol) in toluene (10 mL) was added DIPEA (246 mg, 1.91 mmol). Then the mixture was refluxed for 2 h. LCMS showed the reaction was complete. The solvent was removed and the residue was purified by Combi-Flash (DCM in EtOAc: 0%-12%) to give tert-butyl 2-(2-(4-bromophenyl)-7-hydroxy-5-oxo-8-(trifluoromethoxy)-3,5-dihydro-2H-[1,4]oxazino[2,3,4-ij]quinoline-6-carboxamido)acetate as a solid. ¹H NMR (CDCl₃, 400 MHz) δ 10.62 (t, J=3.6 Hz, 1H), 7.60 (d, J=8.0 Hz, 2H), 7.35 (d, J=8.4 Hz, 2H), 7.28 (d, J=8.4 Hz, 1H), 7.10 (d, J=8.4 Hz, 1H), 5.07 (d, J=7.6 Hz, 1H), 4.96 (d, J=14.4 Hz, 1H), 4.15-4.11 (m, 2H), 3.65-3.59 (m, 1H), 1.49 (s, 9H).

Step E: tert-butyl 2-(2-(4-cyanophenyl)-7-hydroxy-5-oxo-8-(trifluoromethoxy)-3,5-dihydro-2H-[1,4] oxazino[2,3,4-ij]quinoline-6-carboxamido)acetate (peak 1) and tert-butyl 2-(2-(4-cyanophenyl)-7-hydroxy-5-oxo-8-(trifluoromethoxy)-3,5-dihydro-2H-[1,4]oxazino[2,3,4-ij]quinoline-6-carboxamido)acetate (peak 2)

To a solution of tert-butyl 2-(2-(4-bromophenyl)-7-hydroxy-5-oxo-8-(trifluoromethoxy)-3,5-dihydro-2H-[1,4]oxazino[2,3,4-ij]quinoline-6-carboxamido)acetate (598 mg, 1.0 mmol) in DMA (4 mL) were added dicyanozinc (234 mg, 2.0 mmol), Pd₂(dba)₃ (91.5 mg, 0.1 mmol), dppf (13.92 mg, 0.1 mmol) and zinc (130 mg, 2 mmol). The reaction solution was heated by microwave at120° C. for 30 mins. TLC (petroleum ether: EtOAc=5:1) showed that the reaction was completed. The mixture was cooled, water (10 mL) was added and the mixture was extracted with EtOAc (3*10 mL). The combined organic fractions were washed with water (3*10 mL), dried over Na₂SO₄, filtered and the solvent was evaporated under reduced pressure. The residue was purified by Combi-Flash (EtOAc in petroleum ether: 0-40%) to give a solid, which was resolved by Chiral-SFC (Instrument: Thar SFC 80; Column: OJ 250 mm*30mm, 20 um; Mobile phase: A: Supercritical CO₂ , B: EtOH(0.1% NH₃.H₂O), A:B=55:45 at 80 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to give peak 1 (Chiralcel OJ-H 250×4.6 mm I.D., 5 um Mobile phase: methanol (0.05% DEA) in CO2 from 5% to 40% Flow rate: 2.35 mL/min Wavelength: 220 nm; RT: 6.810 min) as a solid, and Peak 2 (Chiralcel OJ-H 250×4.6 mm I.D., 5 um Mobile phase: methanol (0.05% DEA) in CO₂ from 5% to 40%; Flow rate: 2.35 mL/min Wavelength: 220 nm; RT: 9.685 min) as a solid. ¹H NMR (CDCl₃, 400 MHz) δ 10.57 (t, J=3.6 Hz, 1H), 7.76 (d, J=8.4 Hz, 2H), 7.60 (d, J=8.4 Hz, 2H), 7.29 (d, J=8.8 Hz, 1H), 7.11 (d, J=8.4 Hz, 1H), 5.16 (d, J=8.4 Hz, 1H), 5.02 (d, J=16.8 Hz, 1H), 4.14-4.10 (m, 2H), 3.64-3.58 (m, 1H), 1.49 (s, 9H).

Step F: 2-(2-(4-cyanophenyl)-7-hydroxy-5-oxo-8-(trifluoromethoxy)-3,5-dihydro-2H-[1,4]oxazino[2,3,4-ij]quinoline-6-carboxamido)acetic acid (peak 1)

To a suspension of tert-butyl 2-(2-(4-cyanophenyl)-7-hydroxy-5-oxo-8-(trifluoromethoxy)-3,5-dihydro-2H-[1,4] oxazino[2,3,4-ij]quinoline-6-carboxamido)acetate (peak 1) (104 mg, 0.19 mmol) in DCM (1 mL) was added TFA (1 mL) and the reaction was stirred at 30° C.-40° C. for 4 h. LCMS showed the reaction was complete. The solvent was removed and to the residue was added EtOAc (2 mL). The mixture was stirred for 1 h at room temperature. The mixture was filtered to give 2-(2-(4-cyanophenyl)-7-hydroxy-5-oxo-8-(trifluoromethoxy)-3,5-dihydro-2H-[1,4]oxazino[2,3,4-ij] quinoline-6-carboxamido)acetic acid (Chiralcel OJ-H 250× 4.6 mm I.D., 5 um Mobile phase: methanol (0.05% DEA) in CO₂ from 5% to 40% Flow rate: 2.35 mL/min; Wavelength: 220 nm; RT: 7.644 min) as a solid. ¹H NMR (CDCl₃, 1 drop of TFA, 400 MHz) δ 10.46 (brs, 1H), 7.82 (d, J=8.0 Hz, 2H), 7.66 (d, J=8.0 Hz, 2H), 7.26-7.21 (m, 2H), 5.23 (d, J=8.4 Hz, 1H), 4.95 (d, J=16.4 Hz, 1H), 4.38-4.35 (m, 2H), 3.68 (dd, J=10.0 Hz, 10.0Hz, 1H). LC/MS (m/z): 490 (M+H)⁺. Human HIF-PHD2 IC₅₀: 8.5 nM.

Similarly, from the enantiomer corresponding to peak 2 of Example 88 Step E, Example 89 in Table 9 was synthesized (Chiralcel OJ-H 250×4.6 mm I.D., 5 um; Mobile phase:

TABLE 9

| Example Name | structure | MS m/z (M + 1)+ and human HIF-PHD2 IC$_{50}$ |
|---|---|---|
| Example 89 | 2-(2-(4-cyanophenyl)-7-hydroxy-5-oxo-8-(trifluoromethoxy)-3,5-dihydro-2H-[1,4]oxazino[2,3,4-ij]quinoline-6-carboxamido)acetic acid | (M + 1)+ 490 IC$_{50}$ 34 nM |

Example 90

2-(9-Cyano-7-hydroxy-5-oxo-2-(4-(trifluoromethyl)phenyl)-3,5-dihydro-2H-[1,4]thiazino[2,3,4-ij]quinoline-6-carboxamido)acetic acid

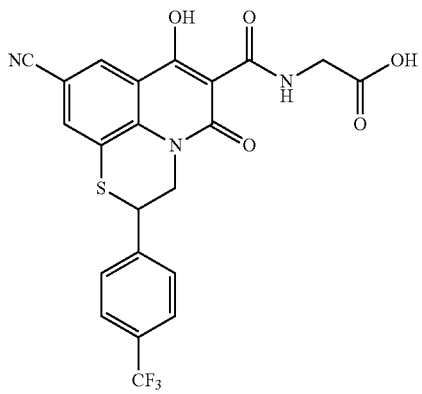

Step A: 2-(4-(trifluoromethyl)phenyl)-2H-benzo[b][1,4]thiazin-3(4H)-one

A 250 mL round bottom flask was charged with ethyl 2-bromo-2-(4-(trifluoromethyl)phenyl)acetate (5.0 g, 16.1 mmol), 2-aminobenzenethiol (2.41 g, 19.3 mmol), DIPEA (6.2 g, 48.2 mmol) and toluene (80 mL). The mixture was stirred at 120° C. for 18 hr. The reaction mixture was poured into water and extracted with EtOAc (50 mL*3). The combined organic layers were evaporated to dryness. The residue was recrystallized from EtOAc to give 2-(4-(trifluoromethyl)phenyl)-2H-benzo[b][1,4]thiazin-3(4H)-one as a solid. $^1$H NMR (CDCl$_3$, 400 MHz): δ 8.87 (brs, 1H), 7.58 (d, J=8.0 Hz, 2H), 7.52 (d, J=8.0 Hz, 2H), 7.34 (d, J=7.7 Hz, 1H), 7.20 (t, J=8.0 Hz, 1H), 7.05 (t, J=8.0 Hz, 1H), 6.89 (d, J=7.9 Hz, 1H), 4.75 (s, 1H).

Step B: 2-(4-(trifluoromethyl)phenyl)-3,4-dihydro-2H-benzo[b][1,4]thiazine

A 250 mL three neck flask was charged with 2-(4-(trifluoromethyl)phenyl)-2H-benzo[b][1,4]thiazin-3(4H)-one (4.1 g, 13.24 mmol) and THF (80 mL). The flask was purged with N$_2$ and BH$_3$-Me$_2$S (13.8 mL) was added slowly. After addition, the mixture was stirred at room temperature for 18 hr. TLC (Petroleum ether: EtOAc=4:1) showed the starting material was consumed. The reaction mixture was cooled to 0° C. and 1M HCl (20 mL) was added slowly. Then the mixture was basified to pH 12 with NaOH solution and extracted with EtOAc (50 mL*3). The organic layers were dried over Na$_2$SO$_4$, filtered and evaporated to dryness to give 2-(4-(trifluoromethyl)phenyl)-3,4-dihydro-2H-benzo[b][1,4]thiazine as a solid. $^1$H NMR (CDCl$_3$, 400 MHz): δ 7.62 (d, J=8.2 Hz, 2H), 7.50 (d, J=8.2 Hz, 2H), 7.06 (d, J=7.7 Hz, 1H), 7.01-6.92 (m, 1 H), 6.74-6.66 (m, 1H), 6.58 (dd, J=7.9, 0.9 Hz, 1H), 4.42 (dd, J=8.4, 2.9 Hz, 1H), 4.18 (brs, 1H), 3.79 (dt, J=12.1, 3.5 Hz, 1H), 3.68-3.57 (m, 1H).

Step C: 7-bromo-2-(4-(trifluoromethyl)phenyl)-3,4-dihydro-2H-benzo[b][1,4]thiazine To a solution of 2-(4-(trifluoromethyl)phenyl)-3,4-dihydro-2H-benzo[b][1,4]thiazine (1000 mg, 3.39 mmol) in DMF (10 mL) was added NBS (603 mg, 3.39 mmol). The resulting mixture was stirred at room temperature for 16 hr. The reaction mixture was diluted with EtOAc (100 mL) and washed with brine (300 mL*2). The organic layer was then dried over Na$_2$SO$_4$, filtered and evaporated to give the crude product. The crude product was purified via silica gel column chromatography (EtOAc in petroleum ether from 0% to 10%) to give 7-bromo-2-(4-(trifluoromethyl)phenyl)-3,4-dihydro-2H-benzo[b][1,4]thiazine as a solid. $^1$H NMR (CDCl$_3$, 400 MHz): δ 7.62 (d, J=8.3 Hz, 2H), 7.48 (d, J=8.1 Hz, 2H), 7.18 (d, J=2.2 Hz, 1H), 7.03 (dd, J=8.6, 2.2 Hz, 1H), 6.45 (d, J=8.6 Hz, 1H), 4.38 (dd, J=8.2, 2.8 Hz, 1H), 4.20 (brs, 1H), 3.78 (dd, J=12.2, 2.9 Hz, 1H), 3.60 (dd, J=12.1, 8.2 Hz, 1H).

Step D: Ethyl 9-bromo-7-hydroxy-5-oxo-2-(4-(trifluoromethyl)phenyl)-3,5-dihydro-2H-[1,4]thiazino[2,3,4-ij]quinoline-6-carboxylate A 100 mL flask was charged with 7-bromo-2-(4-(trifluoromethyl)phenyl)-3,4-dihydro-2H-benzo[b][1,4]thiazine (980 mg, 2.62 mmol) and triethyl methanetricarboxylate (2433 mg, 10.48 mmol). The mixture was stirred at 240° C. for 40 min with the protection of $N_2$. LCMS showed the starting material was consumed and the desired compound was formed. The reaction mixture was washed with petroleum ether, then the solid was collected as ethyl 9-bromo-7-hydroxy-5-oxo-2-(4-(trifluoromethyl)phenyl)-3,5-dihydro-2H-[1,4]thiazino[2,3,4-ij]quinoline-6-carboxylate as a solid. $^1$H NMR (CDCl$_3$, 400 MHz): δ 14.27 (s, 1H), 8.11 (d, J=2.2 Hz, 1H), 7.69-7.63 (m, 3H), 7.51 (d, J=8.1 Hz, 2H), 5.24 (dd, J=14.2, 2.5 Hz, 1H), 4.51 (dtt, J=10.6, 7.1, 3.6 Hz, 2H), 4.42 (dd, J=9.3, 2.2 Hz, 1H), 4.17 (dd, J=14.3, 9.4 Hz, 1H), 1.48 (t, J=7.1 Hz, 3H).

Step E: tert-butyl 2-(9-bromo-7-hydroxy-5-oxo-2-(4-(trifluoromethyl)phenyl)-3,5-dihydro-2H [1,4]thiazino[2,3,4-ij]quinoline-6-carboxamido)acetate A 10 mL vial was charged with ethyl 9-bromo-7-hydroxy-5-oxo-2-(4-(trifluoromethyl)phenyl)-3,5-dihydro-2H-[1,4]thiazino[2,3,4-ij]quinoline-6-carboxylate (560 mg, 1.089 mmol), tert-butyl 2-aminoacetate hydrochloride (274 mg, 1.633 mmol), DIPEA (0.761 mL, 4.36 mmol) and toluene (5 mL). The mixture was heated to 115° C. and stirred for 3 hr. LCMS showed the starting material was consumed and the desired compound was formed. The reaction mixture was poured into water and acidified to pH=3 by 1M HCl, then extracted with EtOAc (30 mL*3). The combined organic layers were dried over Na$_2$SO$_4$, filtered and evaporated to dryness to give tert-butyl 2-(9-bromo-7-hydroxy-5-oxo-2-(4-(trifluoromethyl)phenyl)-3,5-dihydro-2H-[1,4]thiazino[2,3,4-ij]quinoline-6-carboxamido)acetate as a solid. $^1$H NMR (CDCl$_3$, 400 MHz): δ 10.52 (brs, 1H), 8.13 (d, J=2.0 Hz, 1H), 7.69-7.64 (m, 3H), 7.52 (d, J=8.03 Hz, 2 H), 5.26 (dd, J=14.1, 2.5 Hz, 1H), 4.43 (dd, J=9.3, 2.3 Hz, 1H), 4.26-4.16 (m, 1H), 4.12 (dd, J=9.8, 5.3 Hz, 2H), 1.50 (s, 9H).

Step F: tert-butyl 2-(9-cyano-7-hydroxy-5-oxo-2-(4-(trifluoromethyl)phenyl)-3,5-dihydro-2H-[1,4]thiazino[2,3,4-ij]quinoline-6-carboxamido)acetate A microwave tube was charged with zinc cyanide (280 mg, 2.386 mmol), tert-butyl 2-(9-bromo-7-hydroxy-5-oxo-2-(4-(trifluoromethyl)phenyl)-3,5-dihydro-2H-[1,4]thiazino[2,3,4-ij]quinoline-6-carboxamido)acetate (550 mg, 0.918 mmol), Pd$_2$(dba)$_3$ (109 mg, 0.119 mmol), DPPF (66.1 mg, 0.119 mmol), zinc (156 mg, 2.386 mmol) and DMA (10 mL). The tube was purged with $N_2$ and the reaction was heated by microwave at 120° C. for 30 min. LCMS showed the starting material was consumed and the desired compound was formed. The reaction mixture was diluted with EtOAc (20 mL) and filtered, and the filtrate was washed with brine (30 mL*3).

The organic layer was evaporated to dryness and the residue was purified via Combi-Flash (EtOAc in petroleum ether from 0% to 10%) to give tert-butyl 2-(9-cyano-7-hydroxy-5-oxo-2-(4-(trifluoromethyl)phenyl)-3,5-dihydro-2H-[1,4]thiazino[2,3,4-ij]quinoline-6-carboxamido)acetate as a solid. $^1$H NMR (CDCl$_3$, 400 MHz): δ 10.38 (t, J=4.7 Hz, 1H), 8.33 (d, J=1.8 Hz, 1H), 7.75 (d, J=1.8 Hz, 1H), 7.69 (d, J=8.2 Hz, 2H), 7.53 (d, J=7.9 Hz, 2H), 5.30 (dd, J=14.1, 2.4 Hz, 1H), 4.46 (dd, J=9.5, 2.2 Hz, 1H), 4.26-4.17 (m, 1H), 4.16-4.11 (m, 2H), 1.51 (s, 9H).

Step G: 2-(9-cyano-7-hydroxy-5-oxo-2-(4-(trifluoromethyl)phenyl)-3,5-dihydro-2H-[1,4]thiazino[2,3,4-ij]quinoline-6-carboxamido)acetic acid To a suspension of tert-butyl 2-(9-cyano-7-hydroxy-5-oxo-2-(4-(trifluoromethyl)phenyl)-3,5-dihydro-2H-[1,4]thiazino[2,3,4-ij]quinoline-6-carboxamido)acetate (100 mg, 0.183 mmol) in DCM (5 mL) was added TFA (2 mL, 26.0 mmol). The mixture was stirred at room temperature for 2 hr. Then the solvent was removed under vacuo, and the residue was purified via prep-HPLC (Column: ASB C18 150*25 mm; Mobile phase: 51-81% MeCN in water (0.1% HCl); Wavelength: 220 nm) to give 2-(9-cyano-7-hydroxy-5-oxo-2-(4-(trifluoromethyl)phenyl)-3,5-dihydro-2H-[1,4]thiazino[2,3,4-ij]quinoline-6-carboxamido)acetic acid as a solid. $^1$H NMR (DMSO-d$_6$, 400 MHz) δ 10.22 (brs, 1H), 8.27 (d, J=1.5 Hz, 1H), 8.20 (s, 1H), 7.77 (d, J=8.2 Hz, 2H), 7.65 (d, J=7.9 Hz, 2H), 4.94 (d, J=8.2 Hz, 1H), 4.87 (d, J=14.3 Hz, 1H), 4.50 (dd, J=14.2, 8.3 Hz, 1H), 4.11 (d, J=5.7 Hz, 2H). LC/MS (m/z): 490 (M+H)$^+$. Human HIF-PHD2 IC$_{50}$ 1.5 nM.

Example 91

2-(9-Cyano-7-hydroxy-1-oxido-5-oxo-2-(4-(trifluoromethyl)phenyl)-3,5-dihydro-2H-[1,4]thiazino[2,3,4-ij]quinoline-6-carboxamido)acetic acid

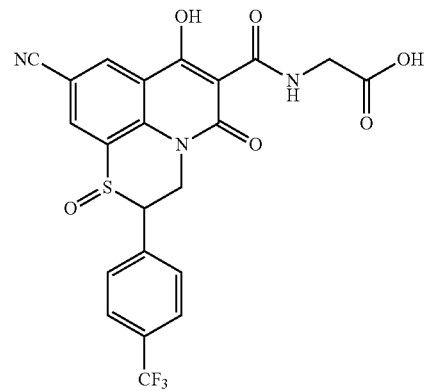 [SMILES: N#Cc1cc2c3c(c1)c(O)c(C(=O)NCC(=O)O)c(=O)n3CC(c1ccc(C(F)(F)F)cc1)S2=O]

Step A: tert-butyl 2-(9-cyano-7-hydroxy-1-oxido-5-oxo-2-(4-(trifluoromethyl)phenyl)-3,5-dihydro-2H-[1,4]thiazino[2,3,4-ij]quinoline-6-carboxamido)acetate To a suspension of Example 90 Step F product (100 mg, 0.183 mmol) in MeCN (5 mL) was added H$_2$O$_2$ (0.481 mL, 5.50 mmol). The mixture was stirred at 80° C. for 20 hr. Then the solvent was removed and the residue tert-butyl 2-(9-cyano-7-hydroxy-1-oxido-5-oxo-2-(4-(trifluoromethyl)phenyl)-3,5-dihydro-2H-[1,4]thiazino[2,3,4-ij]quinoline-6-carboxamido)acetate was used in the next step directly.

Step B: 2-(9-cyano-7-hydroxy-1-oxido-5-oxo-2-(4-(trifluoromethyl)phenyl)-3,5-dihydro-2H-[1,4]thiazino[2,3,4-ij]quinoline-6-carboxamido)acetic acid To a solution of tert-butyl 2-(9-cyano-7-hydroxy-1-oxido-5-oxo-2-(4-(trifluoromethyl)phenyl)-3,5-dihydro-2H-[1,4]

thiazino[2,3,4-ij]quinoline-6-carboxamido)acetate (100 mg) in DCM (5 mL) was added TFA (2 mL, 26.0 mmol), and the resulting mixture was stirred at room temperature for 1 hr. The mixture was evaporated to dryness and the residue was purified by prep-HPLC (Column: ASB C18 150*25 mm; Mobile phase: 36-66% MeCN in water (0.1% HCl); Wavelength: 220 nm) to give 2-(9-cyano-7-hydroxy-1-oxido-5-oxo-2-(4-(trifluoromethyl)phenyl)-3,5-dihydro-2H-[1,4]thiazino[2,3,4-ij]quinoline-6-carboxamido)acetic acid as a solid. $^1$H NMR (400 MHz, DMSO-d6) δ 10.17 (brs, 1H), 8.85 (s, 1H), 8.75 (d, J=1.7 Hz, 1H), 7.83 (d, J=8.1 Hz, 2H), 7.68 (d, J=8.1 Hz, 2H), 5.14 (d, J=12.2 Hz, 1H), 4.87 (d, J=14.3 Hz, 1H), 4.42 (t, J=13.6 Hz, 1H), 4.13 (d, J=5.4 Hz, 2H). LC/MS (m/z): 506 (M+H)$^+$. Human HIF-PHD2 IC$_{50}$ 0.8392 nM.

Example 92

2-(9-Cyano-7-hydroxy-5-oxo-3-(4-(trifluoromethyl)phenyl)-1,2,3,5-tetrahydropyrido[1,2,3-de]quinoxaline-6-carboxamido)acetic acid

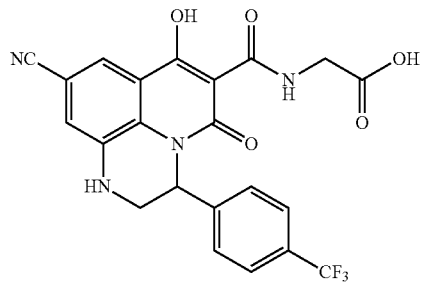 [SMILES: N#Cc1cc2c3c(c1)c(O)c(C(=O)NCC(=O)O)c(=O)n3C(c1ccc(C(F)(F)F)cc1)CN2]

Example 93

2-(9-Cyano-7-hydroxy-5-oxo-2-(4-(trifluoromethyl)phenyl)-1,2,3,5-tetrahydropyrido[1,2,3-de]quinoxaline-6-carboxamido)acetic acid

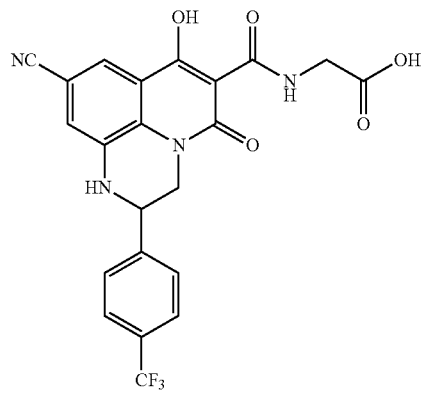 [SMILES: N#Cc1cc2c3c(c1)c(O)c(C(=O)NCC(=O)O)c(=O)n3CC(c1ccc(C(F)(F)F)cc1)N2]

Example 94

2-(8-Cyano-7-hydroxy-5-oxo-2-(4-(trifluoromethyl)phenyl)-1,2,3,5-tetrahydropyrido[1,2,3-de]quinoxaline-6-carboxamido)acetic acid

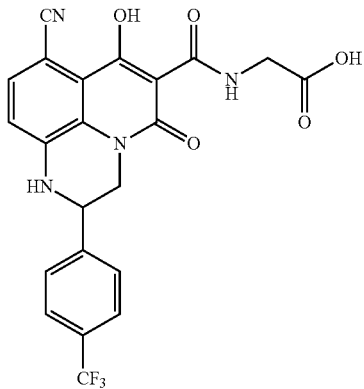

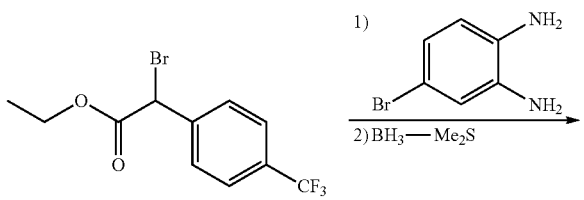

-continued

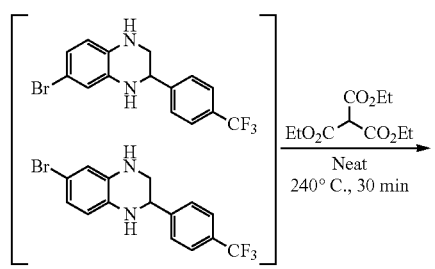

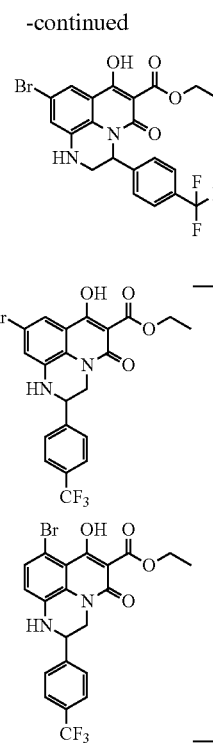

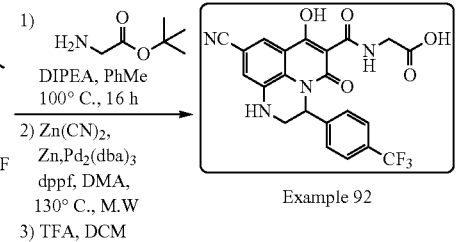

Example 92

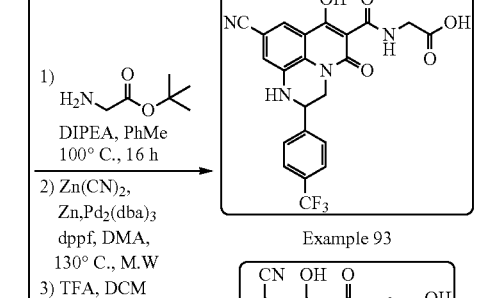

Example 93

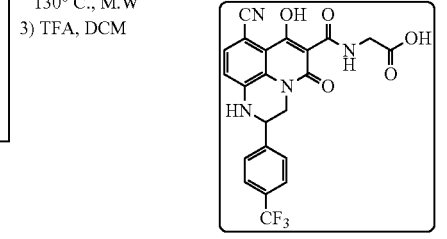

Example 94

Step A: 6-bromo-2-(4-(trifluoromethyl)phenyl)-1,2,3,4-tetrahydroquinoxaline and 7-bromo-2-(4-(trifluoromethyl)phenyl)-1,2,3,4-tetrahydroquinoxaline A 30 mL vial was charged with 4-bromobenzene-1,2-diamine (2 g, 10.69 mmol), ethyl 2-bromo-2-(4-(trifluoromethyl)phenyl)acetate (3.33 g, 10.69 mmol), DIPEA (7.47 mL, 42.8 mmol) and toluene (20 mL). The mixture was heated to 120° C. and stirred for 16 hr. The mixture was diluted with EtOAc (100 mL) and washed with 5% HCl then brine. The organic layer was evaporated to dryness. The crude product was purified via silica gel column chromatography (EtOAc in petroleum ether from 0% to 30%) to give a mixture of 7-bromo-3-(4-(trifluoromethyl)phenyl)-3,4-dihydroquinoxalin-2(1H)-one and 6-bromo-3-(4-(trifluoromethyl)phenyl)-3,4-dihydroquinoxalin-2(1H)-one.

To a solution of 7-bromo-3-(4-(trifluoromethyl)phenyl)-3,4-dihydroquinoxalin-2(1H)-one (0.75 g, 2.021 mmol) and 6-bromo-3-(4-(trifluoromethyl)phenyl)-3,4-dihydroquinoxalin-2(1H)-one (0.75 g, 2.021 mmol) in THF (20 mL) was added BH$_3$-DMS (0.959 mL, 10.10 mmol) slowly at room temperature. The resulting mixture was stirred at room temperature for 16 hr. LCMS showed the starting material was consumed. The reaction mixture was then poured into a solution of 1 M HCl slowly with stirring. After stirring for 5 min, the solution was basified to pH=12 with 10% NaOH solution. Then the mixture was extracted with EtOAc (30 mL*3). The combined organic layers were dried over Na$_2$SO$_4$, filtered and evaporated. The residue was separated by silica gel column chromatography (EtOAc in petroleum ether from 0% to 20%) to give a mixture of 6-bromo-2-(4-(trifluoromethyl)phenyl)-1,2,3,4-tetrahydroquinoxaline and 7-bromo-2-(4-(trifluoromethyl)phenyl)-1,2,3,4-tetrahydroquinoxaline.

Step B: ethyl 8-bromo-7-hydroxy-5-oxo-2-(4-(trifluoromethyl)phenyl)-1,2,3,5 tetrahydropyrido[1,2,3-de]quinoxaline-6-carboxylate, ethyl 9-bromo-7-hydroxy-5-oxo-2-(4-(trifluoromethyl)phenyl)-1,2,3,5-tetrahydropyrido[1,2,3-de]quinoxaline-6-carboxylate and ethyl 9-bromo-7-hydroxy-5-oxo-3-(4-(trifluoromethyl)phenyl)-1,2,3,5-tetrahydropyrido[1,2,3-de]quinoxaline-6-carboxylate A 100 mL flask was charged with a mixture of the product obtained in the last step (7-bromo-2-(4-(trifluoromethyl)phenyl)-1,2,3,4-tetrahydroquinoxaline (450 mg, 1.260 mmol) and 6-bromo-2-(4-(trifluoromethyl)phenyl)-1,2,3,4-tetrahydroquinoxaline (450 mg, 1.260 mmol)) and triethyl methanetricarboxylate (1170 mg, 5.04 mmol). The mixture was stirred at 240° C. for 30 min with the protection of N$_2$. LCMS showed the starting material was consumed. The reaction mixture was then purified via silica gel column chromatography (EtOAc in petroleum ether from 0% to 30%), and two main spots were collected. The spot with a lower R$_f$ value was pure ethyl 9-bromo-7-hydroxy-5-oxo-3-(4-(trifluoromethyl)phenyl)-1,2,3,5-tetrahydropyrido[1,2,3-de]quinoxaline-6-carboxylate. The spot with a higher R$_f$ value was a mixture of two compounds: ethyl 9-bromo-7-hydroxy-5-oxo-2-(4-(trifluoromethyl)phenyl)-1,2,3,5-tetrahydropyrido[1,2,3-de]quinoxaline-6-carboxylate and ethyl 8-bromo-7-hydroxy-5-oxo-2-(4-(trifluoromethyl)phenyl)-1,2,3,5-tetrahydropyrido[1,2,3-de]quinoxaline-6-carboxylate.

Step C: 2-(9-cyano-7-hydroxy-5-oxo-3-(4-(trifluoromethyl)phenyl)-1,2,3,5-tetrahydropyrido[1,2,3-de]quinoxaline-6-carboxamido)acetic acid A 10 mL vial was charged with ethyl 9-bromo-7-hydroxy-5-oxo-3-(4-(trifluoromethyl)phenyl)-1,2,3,5-tetrahydropyrido[1,2,3-de]quinoxaline-6-carboxylate (250 mg, 0.503 mmol), tert-butyl 2-aminoacetate hydrochloride (126 mg, 0.754 mmol), DIPEA (0.351 mL, 2.011 mmol) and toluene (5 mL). The mixture was heated to 115° C. and stirred for 3 hr. LCMS showed the starting material was consumed and the desired compound was formed. The reaction mixture was poured into water and acidified to pH 3 by 1M HCl, then extracted with EtOAc (30 mL*3). The combined organic layers were dried over $Na_2SO_4$, filtered and evaporated to dryness to give tert-butyl 2-(9-bromo-7-hydroxy-5-oxo-3-(4-(trifluoromethyl)phenyl)-1,2,3,5-tetrahydropyrido[1,2,3-de]quinoxaline-6-carboxamido)acetate as a solid. $^1$H NMR (CDCl$_3$, 400 MHz): δ 10.37 (t, J=5.1 Hz, 1H), 7.71 (d, J=2.0 Hz, 1H), 7.46 (d, J=8.2 Hz, 2H), 7.10 (d, J=8.4 Hz, 2H), 6.97 (d, J=2.0 Hz, 1H), 6.12 (s, 1H), 4.32-4.21 (m, 1H), 4.15-4.01 (m, 1H), 3.88 (dd, J=4.7, 18.2 Hz, 1H), 3.67-3.60 (m, 1H), 3.57-3.49 (m, 1H), 1.39 (s, 9H).

A microwave tube was charged with zinc cyanide (73.4 mg, 0.625 mmol), tert-butyl 2-(9-bromo-7-hydroxy-5-oxo-3-(4-(trifluoromethyl)phenyl)-1,2,3,5-tetrahydropyrido[1,2,3-de]quinoxaline-6-carboxamido)acetate (140 mg, 0.240 mmol), Pd$_2$(dba)$_3$ (28.6 mg, 0.031 mmol), DPPF (17.33 mg, 0.031 mmol), zinc (40.9 mg, 0.625 mmol) and DMA (5 mL). The tube was purged with N$_2$ and the reaction was kept at 120° C. for 30 min under microwave. LCMS showed the starting material was consumed and the desired compound was formed. The reaction mixture was diluted with EtOAc (20 mL) and filtered; the filtrate was washed with brine (30 mL*3). The organic layer was then evaporated to give tert-butyl 2-(9-cyano-7-hydroxy-5-oxo-3-(4-(trifluoromethyl)phenyl)-1,2,3,5-tetrahydropyrido[1,2,3-de]quinoxaline-6-carboxamido)acetate as a solid. The crude product was used in the next step without further purification.

To a suspension of tert-butyl 2-(9-cyano-7-hydroxy-5-oxo-3-(4-(trifluoromethyl)phenyl)-1,2,3,5-tetrahydropyrido[1,2,3-de]quinoxaline-6-carboxamido)acetate (120 mg, 0.227 mmol) in DCM (5 mL) was added TFA (2 mL, 26.0 mmol). The mixture was stirred at room temperature for 2 hr. Then the solvent was removed under vacuo, and the residue was purified via prep-HPLC (Column: ASB C18 150*25 mm; Mobile phase: 45-75-15% MeCN in water (0.1% HCl); Wavelength: 220 nm) to give Example 92 product 2-(9-cyano-7-hydroxy-5-oxo-3-(4-(trifluoromethyl)phenyl)-1,2,3,5-tetrahydropyrido[1,2,3-de]quinoxaline-6-carboxamido)acetic acid as a solid. $^1$H NMR (DMSO-d$_6$, 400 MHz) δ 10.15-10.33 (m, 1H), 7.77 (s, 1H), 7.65 (d, J=8.0 Hz, 2H), 7.28 (s, 1H), 7.25 (d, J=5.0 Hz, 2H), 6.85 (brs, 1H), 6.19 (brs, 1H), 4.08 (d, J=2.5 Hz, 2H), 3.72-3.57 (m, 2H). LC/MS (m/z): 473 (M+H)$^+$. Human HIF-PHD2 IC$_{50}$ 3.1 nM.

Step D: 2-(9-cyano-7-hydroxy-5-oxo-2-(4-(trifluoromethyl)phenyl)-1,2,3,5-tetrahydropyrido[1,2,3-de]quinoxaline-6-carboxamido)acetic acid and 2-(8-cyano-7-hydroxy-5-oxo-2-(4-(trifluoromethyl)phenyl)-1,2,3,5-tetrahydropyrido[1,2,3-de]quinoxaline-6-carboxamido)acetic acid A 10 mL vial was charged with ethyl 8-bromo-7-hydroxy-5-oxo-2-(4-(trifluoromethyl)phenyl)-1,2,3,5-tetrahydropyrido[1,2,3-de]quinoxaline-6-carboxylate (~40 mg, 0.080 mmol, estimated from NMR), ethyl 9-bromo-7-hydroxy-5-oxo-2-(4-(trifluoromethyl)phenyl)-1,2,3,5-tetrahydropyrido[1,2,3-de]quinoxaline-6-carboxylate (~300 mg, 0.603 mmol, estimated from NMR), tert-butyl 2-aminoacetate hydrochloride (152 mg, 0.905 mmol) and toluene (5 mL). The mixture was heated to 115° C. and stirred for 3 hr. LCMS showed the starting material was consumed and the desired compound was formed. The reaction mixture was poured into water and acidified to pH 3 by 1M HCl, then extracted with EtOAc (30 mL*3). The combined organic layers were dried over Na$_2$SO$_4$, filtered and evaporated to give tert-butyl 2-(8-bromo-7-hydroxy-5-oxo-2-(4-(trifluoromethyl)phenyl)-1,2,3,5-tetrahydropyrido[1,2,3-de]quinoxaline-6-carboxamido)acetate and tert-butyl 2-(9-bromo-7-hydroxy-5-oxo-2-(4-(trifluoromethyl)phenyl)-1,2,3,5-tetrahydropyrido[1,2,3-de]quinoxaline-6-carboxamido)acetate as a solid (mixture).

A microwave tube was charged with dicyanozinc (89 mg, 0.759 mmol), tert-butyl 2-(9-bromo-7-hydroxy-5-oxo-2-(4-(trifluoromethyl)phenyl)-1,2,3,5-tetrahydropyrido[1,2,3-de]quinoxaline-6-carboxamido)acetate (170 mg, 0.292 mmol), tert-butyl 2-(8-bromo-7-hydroxy-5-oxo-2-(4-(trifluoromethyl)phenyl)-1,2,3,5-tetrahydropyrido[1,2,3-de]quinoxaline-6-carboxamido)acetate (15 mg, 0.026 mmol), Pd$_2$(dba)$_3$ (34.8 mg, 0.038 mmol), DPPF (21.04 mg, 0.038 mmol), zinc (49.6 mg, 0.759 mmol) and DMA (5 mL). The tube was purged with N$_2$ and the reaction was heated by microwave at 120° C. for 30 min. LCMS showed the starting material was consumed and the desired compound was formed. The reaction mixture was diluted with EtOAc (20 mL) and filtered; the filtrate was washed with brine (30 mL*3). The organic layer was then evaporated to dryness to give tert-butyl 2-(9-cyano-7-hydroxy-5-oxo-2-(4-(trifluoromethyl)phenyl)-1,2,3,5-tetrahydropyrido[1,2,3-de]quinoxaline-6-carboxamido)acetate and tert-butyl 2-(8-cyano-7-hydroxy-5-oxo-2-(4-(trifluoromethyl)phenyl)-1,2,3,5-tetrahydropyrido[1,2,3-de]quinoxaline-6-carboxamido)acetate as a solid. The crude product was used in the next step without further purification.

To a suspension of tert-butyl 2-(9-cyano-7-hydroxy-5-oxo-2-(4-(trifluoromethyl)phenyl)-1,2,3,5-tetrahydropyrido[1,2,3-de]quinoxaline-6-carboxamido)acetate (150 mg, 0.284 mmol) in DCM (5 mL) was added TFA (2 mL, 26.0 mmol). The mixture was stirred at room temperature for 2 hr. Then the solvent was removed in vacuo, and the residue was purified via prep-HPLC (Column: ASB C18 150*25 mm; Mobile phase: 45-75-15% MeCN in water (0.1% HCl); Wavelength: 220 nm) to give:

Example 93: 2-(9-cyano-7-hydroxy-5-oxo-2-(4-(trifluoromethyl)phenyl)-1,2,3,5-tetrahydropyrido[1,2,3-de]quinoxaline-6-carboxamido)acetic acid as a solid. $^1$H NMR (Example 94) (DMSO-d$_6$, 400 MHz) δ 10.51 (brs, 1H), 8.03 (brs, 1H), 7.80 (d, J=8.0 Hz, 2H), 7.66 (d, J=8.0 Hz, 2H), 7.62 (d, J=8.0 Hz, 1H), 7.12 (d, J=8.0 Hz, 1H), 4.88 (brs, 1H), 4.51 (d, J=10.5 Hz, 1H), 4.14 (d, J=5.5 Hz, 2H), 4.02 (dd, J=13.0, 7.5 Hz, 1H). LC/MS (m/z): 473 (M+H)$^+$. Human HIF-PHD2 IC$_{50}$ 1.0 nM.

Example 94: 2-(8-cyano-7-hydroxy-5-oxo-2-(4-(trifluoromethyl)phenyl)-1,2,3,5-tetrahydropyrido[1,2,3-de]quinoxaline-6-carboxamido)acetic acid as a solid $^1$H NMR (Example 93) (DMSO-d$_6$, 400 MHz) δ 10.34 (t, J=5.3 Hz, 1H), 7.81 (d, J=8.0 Hz, 1H), 7.71 (s, 1H), 7.69 (d, J=8.0 Hz, 2H), 7.49 (s, 1H), 7.30 (s, 1H), 4.77 (d, J=5.0 Hz, 1H), 4.54 (d, J=11.0 Hz, 1H), 4.13 (d, J=5.0 Hz, 2H), 3.88 (dd, J=12.8, 8.3 Hz, 1H). LC/MS (m/z): 473 (M+H)$^+$. Human HIF-PHD2 IC$_{50}$ 0.8 nM.

Example 95

2-(9-Cyano-7-hydroxy-1-methyl-5-oxo-3-(4-(trifluoromethyl)phenyl)-1,2,3,5-tetrahydropyrido[1,2,3-de]quinoxaline-6-carboxamido)acetic acid

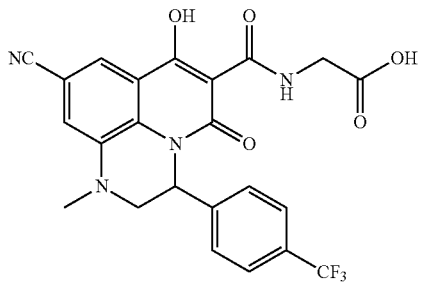

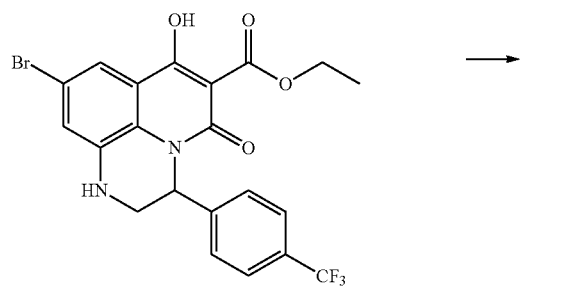

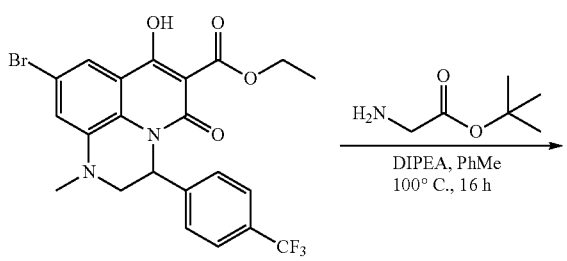

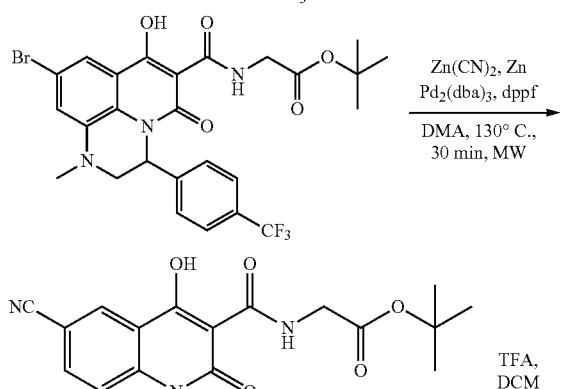

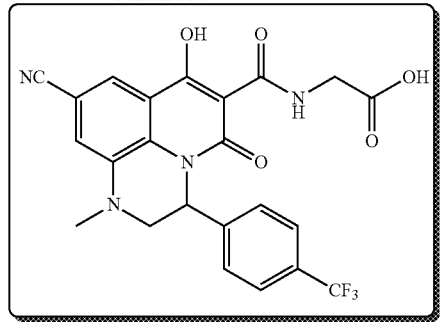

Example 95

Step A: ethyl 9-bromo-7-hydroxy-1-methyl-5-oxo-3-(4-(trifluoromethyl)phenyl)-1,2,3,5-tetrahydropyrido[1,2,3-de]quinoxaline-6-carboxylate A 10 mL vial was charged with ethyl 9-bromo-7-hydroxy-5-oxo-3-(4-(trifluoromethyl)phenyl)-1,2,3,5-tetrahydropyrido[1,2,3-de]quinoxaline-6-carboxylate (200 mg, 0.402 mmol), paraformaldehyde (121 mg, 4.02 mmol), formic acid (0.154 ml, 4.02 mmol) and toluene (2 mL). The mixture was heated to 100° C. and stirred for 4 hr. LCMS showed the starting material was consumed and the desired compound was formed. The mixture was poured into water and basified to pH 8, then extracted with EtOAc (20 mL*3). The organic layers were dired over $Na_2SO_4$, filtered and evaporated to give the product ethyl 9-bromo-7-hydroxy-1-methyl-5-oxo-3-(4-(trifluoromethyl)phenyl)-1,2,3,5-tetrahydropyrido[1,2,3-de]quinoxaline-6-carboxylate as a solid. H NMR ($CDCl_3$, 400 MHz): δ 14.28 (s, 1H), 7.77 (d, J=2.0 Hz, 1H), 7.50 (d, J=8.0 Hz, 2H), 7.19 (d, J=8.5 Hz, 2H), 6.96 (d, J=1.5 Hz, 1H), 6.14 (brs, 1H), 4.56-4.46 (m, 1H), 4.45-4.36 (m, 1H), 3.62 (dd, J=3.5, 12.0 Hz, 1H), 3.47-3.36 (m, 1H), 2.89 (s, 3H), 1.42 (t, J=7.0 Hz, 3H).

Step B: tert-butyl 2-(9-bromo-7-hydroxy-1-methyl-5-oxo-3-(4-(trifluoromethyl)phenyl)-1,2,3,5-tetrahydropyrido[1,2,3-de]quinoxaline-6-carboxamido)acetate A 10 mL vial was charged with ethyl 9-bromo-7-hydroxy-1-methyl-5-oxo-3-(4-(trifluoromethyl)phenyl)-1,2,3,5-tetrahydropyrido[1,2,3-de]quinoxaline-6-carboxylate (110 mg, 0.215 mmol), tert-butyl 2-aminoacetate hydrochloride (54.1 mg, 0.323 mmol), DIPEA (0.150 mL, 0.861 mmol) and toluene (5 mL). The mixture was heated to 115° C. and stirred for 3 hr. LCMS showed the starting material was consumed and the desired compound was formed. The reaction mixture was poured into water and acidified to pH 3 by 1M HCl, then extracted with EtOAc (30 mL*3). The combined organic layers were dried over $Na_2SO_4$, filtered and evaporated to give tert-butyl 2-(9-bromo-7-hydroxy-1-methyl-5-oxo-3-(4-(trifluoromethyl)phenyl)-1,2,3,5-tetrahydropyrido[1,2,3-de]quinoxaline-6-carboxamido)acetate as a solid. $^1$H NMR ($CDCl_3$, 400 MHz): δ 10.47-10.37 (m, 1H), 7.81 (d, J=1.8 Hz, 1H), 7.53 (d, J=8.2 Hz, 2H), 7.18 (d, J=8.2 Hz, 2H), 6.98 (d, J=1.8 Hz, 1H), 6.16 (brs, 1H), 4.21-4.13 (m, 1H), 4.00-3.92 (m, 1H), 3.65 (dd, J=3.5, 11.9 Hz, 1H), 3.44 (d, J=11.7 Hz, 1H), 2.90 (s, 3H), 1.47 (s, 9H).

Step C: tert-butyl 2-(9-cyano-7-hydroxy-1-methyl-5-oxo-3-(4-(trifluoromethyl)phenyl)-1,2,3,5-tetrahydropyrido[1,2,3-de]quinoxaline-6-carboxamido)acetate A microwave tube was charged with dicyanozinc (61.4 mg, 0.523 mmol), tert-butyl 2-(9-bromo-7-hydroxy-1-methyl-5-oxo-3-(4-(trifluoromethyl)phenyl)-1,2,3,5-tetrahydropyrido[1,2,3-de]quinoxaline-6-carboxamido)acetate (120 mg, 0.201 mmol), Pd$_2$(dba)$_3$ (23.95 mg, 0.026 mmol), DPPF (14.50 mg, 0.026 mmol), zinc (34.2 mg, 0.523 mmol) and DMA (5 mL). The tube was purged with N$_2$ and the reaction was kept at 120° C. for 30 min under microwave. LCMS showed the starting material was consumed and the desired compound was formed. The reaction mixture was diluted with EtOAc (20 mL) and filtered; the filtrate was washed with brine (30 mL*3). The organic layer was then evaporated to give tert-butyl 2-(9-cyano-7-hydroxy-1-methyl-5-oxo-3-(4-(trifluoromethyl)phenyl)-1,2,3,5-tetrahydropyrido[1,2,3-de]quinoxaline-6-carboxamido)acetate as a solid. The crude product was used in the next step directly.

Step D: 2-(9-cyano-7-hydroxy-1-methyl-5-oxo-3-(4-(trifluoromethyl)phenyl)-1,2,3,5-tetrahydropyrido[1,2,3-de]quinoxaline-6-carboxamido)acetic acid To a suspension of tert-butyl 2-(9-cyano-7-hydroxy-1-methyl-5-oxo-3-(4-(trifluoromethyl)phenyl)-1,2,3,5-tetrahydropyrido[1,2,3-de]quinoxaline-6-carboxamido)acetate (100 mg, 0.184 mmol) in DCM (5 mL) was added TFA (2 mL, 26.0 mmol). The mixture was stirred at room temperature for 2 hr. Then the solvent was removed in vacuo, and the residue was purified via prep-HPLC (Column: ASB C18 150*25 mm; Mobile phase: 45-75-15% MeCN in water (0.1% HCl); Wavelength: 220 nm) to give 2-(9-cyano-7-hydroxy-1-methyl-5-oxo-3-(4-(trifluoromethyl)phenyl)-1,2,3,5-tetrahydropyrido[1,2,3-de]quinoxaline-6-carboxamido) acetic acid as a solid. $^1$H NMR (DMSO-d$_6$, 400 MHz) δ 10.20 (t, J=5.3 Hz, 1H), 7.87 (s, 1H), 7.65 (d, J=8.0 Hz, 2H), 7.33 (s, 1H), 7.30 (d, J=8.0 Hz, 2H), 6.19 (brs, 1H), 4.17-4.01 (m, 2H), 3.75-3.61 (m, 2H), 2.88 (s, 3H). LC/MS (m/z): 487 (M+H)$^+$. Human HIF-PHD2 IC$_{50}$ 5.5 nM.

Example 96

2-(9-Cyano-7-hydroxy-1-methyl-5-oxo-2-(4-(trifluoromethyl)phenyl)-1,2,3,5-tetrahydropyrido[1,2,3-de]quinoxaline-6-carboxamido)acetic acid

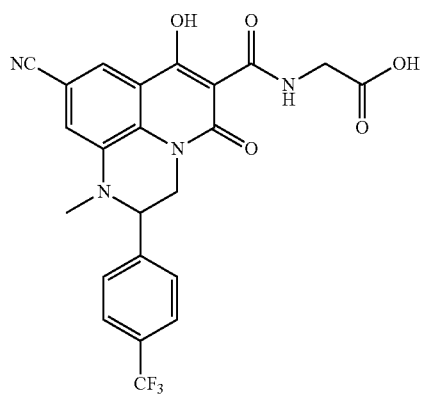

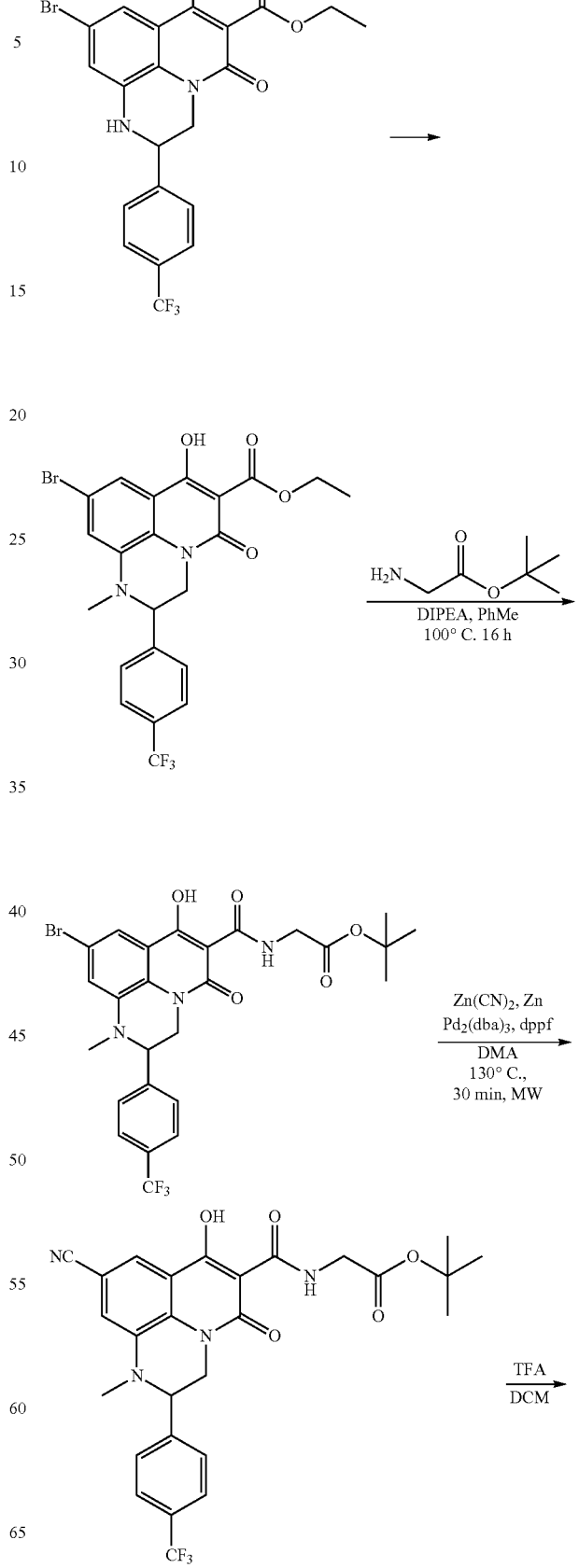

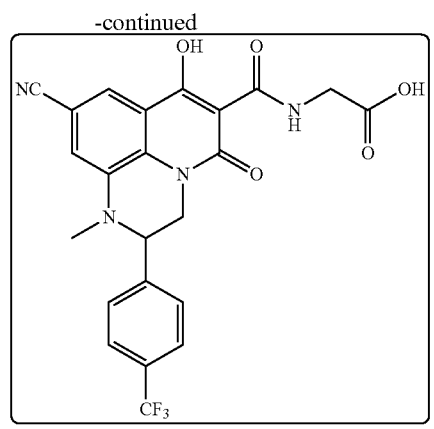

Example 96

Step A: Ethyl 9-bromo-7-hydroxy-1-methyl-5-oxo-2-(4-(trifluoromethyl)phenyl)-1,2,3,5-tetrahydropyrido[1,2,3-de]quinoxaline-6-carboxylate A 10 mL vial was charged with ethyl 9-bromo-7-hydroxy-5-oxo-2-(4-(trifluoromethyl)phenyl)-1,2,3,5-tetrahydropyrido[1,2,3-de]quinoxaline-6-carboxylate (300 mg, 0.603 mmol), paraformaldehyde (181 mg, 6.03 mmol), formic acid (0.231 ml, 6.03 mmol) and toluene (2 mL). The mixture was heated to 100° C. and stirred for 4 hr. LCMS showed the starting material was consumed and the desired compound was formed. The mixture was poured into water and basified to pH 8, then extracted with EtOAc (20 mL*3). The organic layers were dried over $Na_2SO_4$, filtered and evaporated to give the product ethyl 9-bromo-7-hydroxy-1-methyl-5-oxo-2-(4-(trifluoromethyl)phenyl)-1,2,3,5-tetrahydropyrido[1,2,3-de]quinoxaline-6-carboxylatec as a solid. $^1$H NMR (CDCl$_3$, 400 MHz): δ 14.20 (s, 1H), 8.11 (s, 1H), 7.56 (d, J=8.3 Hz, 2H), 7.19 (d, J=8.1 Hz, 2H), 6.93 (d, J=2.0 Hz, 1H), 4.97-4.89 (m, 2H), 4.69-4.63 (m, 2H), 4.46 (d, J=7.1 Hz, 1H), 2.96 (s, 3H), 1.44 (t, J=7.2 Hz, 3H).

Step B: tert-butyl 2-(9-bromo-7-hydroxy-1-methyl-5-oxo-2-(4-(trifluoromethyl)phenyl)-1,2,3,5-tetrahydropyrido[1,2,3-de]quinoxaline-6-carboxamido)acetate A 10 mL vial was charged with ethyl 9-bromo-7-hydroxy-1-methyl-5-oxo-2-(4-(trifluoromethyl)phenyl)-1,2,3,5-tetrahydropyrido[1,2,3-de]quinoxaline-6-carboxylate (70 mg, 0.137 mmol), tert-butyl 2-aminoacetate hydrochloride (34.4 mg, 0.205 mmol), DIPEA (0.096 mL, 0.548 mmol) and toluene (5 mL). The mixture was heated to 115° C. and stirred for 3 hr. LCMS showed the starting material was consumed and the desired compound was formed. The reaction mixture was poured into water and acidified to pH 3 by 1 M HCl, then extracted with EtOAc (30 mL*3). The combined organic layers were dried over $Na_2SO_4$, filtered and evaporated to dryness. The residue was purified via prep-TLC (petroleum ether: EtOAc=2:1) to give tert-butyl 2-(9-bromo-7-hydroxy-1-methyl-5-oxo-2-(4-(trifluoromethyl)phenyl)-1,2,3,5-tetrahydropyrido[1,2,3-de]quinoxaline-6-carboxamido)acetate as a solid. $^1$H NMR (CDCl$_3$, 400 MHz): δ 10.45 (brs, 1H), 7.64 (d, J=2.0 Hz, 1H), 7.50 (d, J=8.1 Hz, 2H), 7.13 (d, J=8.1 Hz, 2H), 6.93 (d, J=2.0 Hz, 1H), 4.65-4.54 (m, 2H), 4.20-4.11 (m, 1H), 4.01 (d, J=5.1 Hz, 2H), 2.88 (s, 3H), 1.41 (s, 9H).

Step C: tert-butyl 2-(9-cyano-7-hydroxy-1-methyl-5-oxo-2-(4-(trifluoromethyl)phenyl)-1,2,3,5-tetrahydropyrido[1,2,3-de]quinoxaline-6-carboxamido)acetate A microwave tube was charged with dicyanozinc (17.92 mg, 0.153 mmol), tert-butyl 2-(9-bromo-7-hydroxy-1-methyl-5-oxo-2-(4-(trifluoromethyl)phenyl)-1,2,3,5-tetrahydropyrido[1,2,3-de]quinoxaline-6-carboxamido)acetate (35 mg, 0.059 mmol), Pd$_2$(dba)$_3$ (6.99 mg, 7.63 μmol), DPPF (4.23 mg, 7.63 μmol), zinc (9.98 mg, 0.153 mmol) and DMA (3 mL). The tube was purged with $N_2$ and the reaction was kept at 120° C. for 30 min under microwave. Then the reaction mixture was diluted with EtOAc (20 mL) and filtered, and the filtrate was washed with brine (30 mL*3), then evaporated to give tert-butyl 2-(9-cyano-7-hydroxy-1-methyl-5-oxo-2-(4-(trifluoromethyl)phenyl)-1,2,3,5-tetrahydropyrido[1,2,3-de]quinoxaline-6-carboxamido)acetate as an oil. The crude product was used in the next step without further purification.

Step D: 2-(9-cyano-7-hydroxy-1-methyl-5-oxo-2-(4-(trifluoromethyl)phenyl)-1,2,3,5-tetrahydropyrido[1,2,3-de]quinoxaline-6-carboxamido)acetic acid To a suspension of tert-butyl 2-(9-cyano-7-hydroxy-1-methyl-5-oxo-2-(4-(trifluoromethyl)phenyl)-1,2,3,5-tetrahydropyrido[1,2,3-de]quinoxaline-6-carboxamido)acetate (30 mg, 0.055 mmol) in DCM (5 mL) was added TFA (2 mL, 26.0 mmol). The mixture was stirred at room temperature for 2 hr. Then the solvent was removed under vacuo, and the residue was purified via prep-HPLC (Column: ASB C18 150*25 mm; Mobile phase: 45-75-15% MeCN in water (0.1% HCl); Wavelength: 220 nm) to give 2-(9-cyano-7-hydroxy-1-methyl-5-oxo-2-(4-(trifluoromethyl)phenyl)-1,2,3,5-tetrahydropyrido[1,2,3-de]quinoxaline-6-carboxamido)acetic acid as a solid. $^1$H NMR (DMSO-d$_6$, 400 MHz) δ 10.23 (brs, 1H), 7.76 (s, 1H), 7.68 (d, J=8.0 Hz, 2H), 7.35 (s, 1H), 7.31 (d, J=8.5 Hz, 2H), 5.15 (brs, 1H), 4.86 (d, J=13.0 Hz, 1H), 4.12-4.00 (m, 3H), 3.04 (s, 3H). LC/MS (m/z): 487 (M+H)$^+$. Human HIF-PHD2 IC$_{50}$ 3.0 nM.

Example 97

2-(8-Cyano-7-hydroxy-5-oxo-2-(4-(trifluoromethyl)phenyl)-3,5-dihydro-2H-[1,4]thiazino[2,3,4-ij]quinoline-6-carboxamido)acetic acid

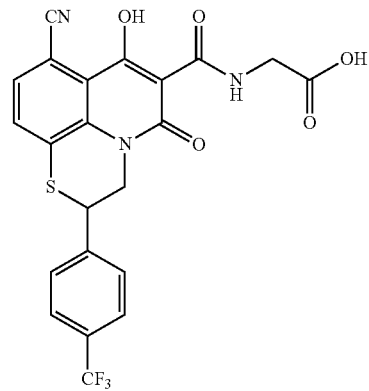

Step A: 2-amino-4-bromobenzenethiol

A 250 mL round bottom flask was charged with 1,4-dibromo-2-nitrobenzene (7 g, 24.92 mmol), $Na_2S \cdot 9H_2O$ (59.9 g, 249 mmol) and water (80 mL). The reaction was heated to 100° C. and stirred for 24 hr. Then the reaction mixture was extracted with EtOAc (50 mL*4) to remove by-product. The aqueous layer was acidified to pH=7 by conc. HCl. The resulting solution was extracted with EtOAc (50 mL*4). The organic layers were combined and dried over $Na_2SO_4$, filtered and evaporated to give the crude product 2-amino-4-bromobenzenethiol, which was used in the next step directly.

Step B: 6-bromo-2-(4-(trifluoromethyl)phenyl)-2H-benzo[b][1,4]thiazin-3(4H)-one A 30 mL vial was charged with 2-amino-4-bromobenzenethiol (1.312 g, 6.43 mmol), ethyl 2-bromo-2-(4-(trifluoromethyl)phenyl)acetate (2 g, 6.43 mmol), DIPEA (3.37 mL, 19.29 mmol) and toluene (20 mL). The mixture was stirred at 110° C. for 20 hr. TLC (Petroleum ether: EtOAc=8:1) showed the product was formed ($R_f$=0.3). The reaction mixture was poured into water and extracted with EtOAc (50 mL*3). The combined organic layers were evaporated to dryness. The residue was purified via silica gel column chromatography (EtOAc in Petroleum ether form 0% to 25%) to give 6-bromo-2-(4-(trifluoromethyl)phenyl)-2H-benzo[b][1,4]thiazin-3(4H)-one as a solid. $^1H$ NMR ($CDCl_3$, 400 MHz): δ 8.56 (brs, 1H), 7.59 (d, J=8.3 Hz, 2H), 7.50 (d, J=8.3 Hz, 2H), 7.21 (d, J=8.0 Hz, 1H), 7.16 (dd, J=8.0 Hz, 1.8Hz, 1H), 7.04 (d, J=1.7 Hz, 1H), 4.74 (s, 1H).

Step C: 6-bromo-2-(4-(trifluoromethyl)phenyl)-3,4-dihydro-2H-benzo[b][1,4]thiazine To a solution of 6-bromo-2-(4-(trifluoromethyl)phenyl)-2H-benzo[b][1,4]thiazin-3(4H)-one (0.5 g, 1.288 mmol) in THF (10 mL) was added $BH_3$-DMS (0.612 mL, 6.44 mmol) slowly at room temperature. The resulting mixture was stirred at room temperature for 16 hr. TLC (petroleum ether: EtOAc=10:1) showed the starting material was consumed. The reaction mixture was then poured into a solution of 1M HCl slowly with stirring. After stirring for 5 min, the solution was basified to pH=12 with 10% NaOH solution. The mixture was extracted with EtOAc (30 mL*3), and the combined organic layers were dried over $Na_2SO_4$, filtered and evaporated. The residue was purified via Combi-Flash (EtOAc in petroleum ether from 0% to 15%) to give 6-bromo-2-(4-(trifluoromethyl)phenyl)-3,4-dihydro-2H-benzo[b][1,4]thiazine as a solid. $^1H$ NMR ($CDCl_3$, 400 MHz): δ 7.62 (d, J=8.2 Hz, 2H), 7.48 (d, J=8.2 Hz, 2H), 6.91 (d, J=8.4 Hz, 1H), 6.79 (dd, J=8.3, 1.9 Hz, 1H), 6.72 (d, J=1.8 Hz, 1H), 4.36 (dd, J=8.2, 2.9 Hz, 1H), 4.25 (brs, 1H), 3.79 (d, J=12.1 Hz, 1H), 3.62 (dd, J=12.0, 8.5 Hz, 1H).

Step D: Ethyl 8-bromo-7-hydroxy-5-oxo-2-(4-(trifluoromethyl)phenyl)-3,5-dihydro-2H-[1,4]thiazino[2,3,4-ij]quinoline-6-carboxylate A 30 mL thumb flask was charged with 6-bromo-2-(4-(trifluoromethyl)phenyl)-3,4-dihydro-2H-benzo[b][1,4]thiazine (120 mg, 0.321 mmol) and triethyl methanetricarboxylate (298 mg, 1.283 mmol). The reaction was stirred at 260° C. for 80 min with the protection of $N_2$. The reaction mixture was then cooled to room temperature and purified via silica gel column chromatography (EtOAc in petroleum ether from 0% to 15%) to give ethyl 8-bromo-7-hydroxy-5-oxo-2-(4-(trifluoromethyl)phenyl)-3,5-dihydro-2H-[1,4]thiazino[2,3,4-ij]quinoline-6-carboxylate as a solid. $^1H$ NMR ($CDCl_3$, 400 MHz): δ 15.18 (s, 1H), 7.65 (d, J=8.0 Hz, 2H), 7.52 (d, J=8.5 Hz, 2H), 7.48 (d, J=8.5 Hz, 1H), 7.31 (d, J=8.5 Hz, 1H), 5.34 (dd, J=14.1, 2.5 Hz, 1H), 4.55-4.46 (m, 2H), 4.45-4.40 (m, 1H), 4.13 (d, J=7.5 Hz, 1H), 1.47 (t, J=7.0 Hz, 3H).

Step E: tert-butyl 2-(8-bromo-7-hydroxy-5-oxo-2-(4-(trifluoromethyl)phenyl)-3,5-dihydro-2H-[1,4]thiazino[2,3,4-ij]quinoline-6-carboxamido)acetate A 10 mL vial was charged with ethyl 8-bromo-7-hydroxy-5-oxo-2-(4-(trifluoromethyl)phenyl)-3,5-dihydro-2H-[1,4]thiazino[2,3,4-ij]quinoline-6-carboxylate (110 mg, 0.214 mmol), tert-butyl 2-aminoacetate hydrochloride (53.8 mg, 0.321 mmol), DIPEA (0.112 mL, 0.642 mmol) and toluene (5 mL). The mixture was heated to 115° C. and stirred for 1 hr. LCMS showed the starting material was consumed and the desired compound was formed. The reaction mixture was poured into water and acidified to pH=3 by 1M HCl, then extracted with EtOAc (30 mL*3). The combined organic layers were dried over $Na_2SO_4$, filtered and evaporated. The residue was purified via Combi-Flash (12 g column, EtOAc in petroleum ether from 0% to 10%) to give tert-butyl 2-(8-bromo-7-hydroxy-5-oxo-2-(4-(trifluoromethyl)phenyl)-3,5-dihydro-2H-[1,4]thiazino[2,3,4-ij]quinoline-6-carboxamido)acetate as a solid. $^1H$ NMR ($CDCl_3$, 400 MHz): δ 10.67 (brs, 1H), 7.66 (d, J=8.1 Hz, 2H), 7.53 (d, J=8.1 Hz, 2H), 7.50 (d, J=8.3 Hz, 1H), 7.31 (d, J=8.3 Hz, 1H), 5.34 (dd, J=13.9, 2.4 Hz, 1H), 4.44 (dd, J=13.9, 2.4 Hz, 1H), 4.24-4.16 (m, 1H), 4.13 (dd, J=12.0, 5.1 Hz, 2H), 1.50 (s, 9H).

Step F: tert-butyl 2-(8-cyano-7-hydroxy-5-oxo-2-(4-(trifluoromethyl)phenyl)-3,5-dihydro-2H-[1,4]thiazino[2,3,4-ij]quinoline-6-carboxamido)acetate A microwave tube was charged with dicyanozinc (25.5 mg, 0.217 mmol), $Pd_2(dba)_3$ (9.93 mg, 10.84 μmol), DPPF (6.01 mg, 10.84 μmol), zinc (14.18 mg, 0.217 mmol) and DMA (3 mL). The tube was purged with $N_2$ and the reaction was kept at 120° C. for 30 min under microwave. LCMS showed the starting material was consumed and the desired compound was formed. Then the reaction mixture was diluted with EtOAc (20 mL) and filtered. The filtrate was washed with brine (30 mL*3), then evaporated to give tert-butyl 2-(8-cyano-7-hydroxy-5-oxo-2-(4-(trifluoromethyl)phenyl)-3,5-dihydro-2H-[1,4]thiazino[2,3,4-ij]quinoline-6-carboxamido)acetate as an oil. The crude product was used in the next step without further purification.

Step G: 2-(8-cyano-7-hydroxy-5-oxo-2-(4-(trifluoromethyl)phenyl)-3,5-dihydro-2H-[1,4]thiazino[2,3,4-ij]quinoline-6-carboxamido)acetic acid To a suspension of tert-butyl 2-(8-cyano-7-hydroxy-5-oxo-2-(4-(trifluoromethyl)phenyl)-3,5-dihydro-2H-[1,4]thiazino[2,3,4-ij]quinoline-6-carboxamido)acetate (40 mg, 0.073 mmol) in DCM (5 mL) was added TFA (2 mL, 26.0 mmol). The mixture was stirred at room temperature for 2 hr. Then the solvent was removed in vacuo, and the residue was purified via prep-HPLC (Column: ASB C18 150*25 mm; Mobile phase: 42-72% MeCN in water (0.1% HCl); Wavelength: 220 nm) to give 2-(8-cyano-7-hydroxy-5-oxo-2-(4-(trifluoromethyl)phenyl)-3,5-dihydro-2H-[1,4]thiazino[2,3, 4-ij]quinoline-6-carboxamido)acetic acid as a solid. $^1$H NMR (DMSO-d$_6$, 400 MHz): δ 10.37 (brs, 1H), 7.84 (d, J=7.8 Hz, 1H), 7.75 (d, J=8.3 Hz, 2H), 7.72 (d, J=7.8 Hz, 1H), 7.63 (d, J=8.1 Hz, 2H), 5.00 (d, J=6.4 Hz, 1H), 4.84 (d, J=12.7 Hz, 1H), 4.56 (dd, J=13.9, 8.1 Hz, 1H), 4.12 (d, J=5.1 Hz, 2H). LC/MS (m/z): 490 (M+H)$^+$. Human HIF-PHD2 IC$_{50}$ 1.5 nM.

Example 98

2-(8-Fluoro-7-hydroxy-5-oxo-3-(4-(trifluoromethyl)phenyl)-3,5-dihydro-2H-[1,4]thiazino[2,3,4-ij]quinoline-6-carboxamido)acetic acid

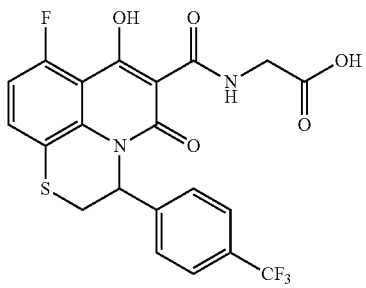 [SMILES: O=C(O)CNC(=O)c1c(O)c2c(F)ccc3c2n(c1=O)C(c1ccc(C(F)(F)F)cc1)CS3]

Step A: 2-amino-4-fluorobenzenethiol

A solution of 1-chloro-4-fluoro-2-nitrobenzene (10 g, 57.0 mmol) and sodium sulfide (17.78 g, 228 mmol) in deionized water (130 mL) was heated to reflux and stirred under nitrogen for 32 h. The resulting solution was then cooled to room temperature, the pH of this solution was adjusted to 6-7 and washed with ethyl acetate 5*50 mL). The organic phase was dried over anhydrous magnesium sulfate, filtered, and evaporated to give 2-amino-4-fluorobenzenethiol as an oil, which was used for next step without further purification.

Step B: 6-fluoro-3-(4-(trifluoromethyl)phenyl)-2H-benzo[b][1,4]thiazine

To a solution of 2-amino-4-fluorobenzenethiol (1 g, 6.98 mmol) in DCM (20 mL) were added K$_2$CO$_3$ (15 mL, 6.35 mmol) in water (15 mL) and tetrabutylammonium hydrogen sulfate (0.022 g, 0.063 mmol), then 2-bromo-1-(4-(trifluoromethyl)phenyl)ethanone (1.696 g, 6.35 mmol) in DCM (5 mL) was added dropwise to the reaction mixture. The resulting mixture was stirred at room temperature for 20 h. LCMS showed the desired compound was formed, then the mixture was extracted with DCM (100 mL*3). The combined organic layers were washed with brine (100 mL*3), dried over Na$_2$SO$_4$, filtered and concentrated in vacuo to give 6-fluoro-3-(4-(trifluoromethyl)phenyl)-2H-benzo[b][1,4]thiazine as an oil, which was used in the next step directly. LC/MS (m/z): 312 (M+H)$^+$.

Step C: 6-fluoro-3-(4-(trifluoromethyl)phenyl)-3,4-dihydro-2H-benzo[b][1,4]thiazine To a solution of 6-fluoro-3-(4-(trifluoromethyl)phenyl)-2H-benzo[b][1,4]thiazine (1.9 g, 3.05 mmol) in DCM (10 mL) and MeOH (10 mL) were added AcOH (0.524 mL, 9.16 mmol) and sodium cyanoborohydride (0.959 g, 15.26 mmol). The resulting mixture was stirred at room temperature for 2 h. The mixture was added to water (50 mL), basified to pH 9 and extracted with ethyl acacate (3*50 mL). The combined organic fractions were washed with brine (saturated, 3*50 mL), dried (Na$_2$SO$_4$), filtered and the solvent was evaporated under reduced pressure. The residue was purified by column chromatography on silica gel Biotage 25M (EtOAc in petroleum ether: 0-5%, R$_f$=0.8) to give 6-fluoro-3-(4-(trifluoromethyl)phenyl)-3,4-dihydro-2H-benzo[b][1,4]thiazine as an oil. $^1$H NMR (CDCl$_3$, 400 MHz): δ 7.66 (d, J=8.2 Hz, 2H), 7.49 (d, J=8.2 Hz, 2H), 7.00 (dd, J=8.6, 6.17 Hz, 1H), 6.43 (td, J=8.5, 2.4 Hz, 1H), 6.32 (dd, J=10.5, 2.5 Hz, 1H), 4.89-4.81 (m, 1H), 4.29 (brs, 1H), 3.09-3.04 (m, 2H).

Step D: ethyl 8-fluoro-7-hydroxy-5-oxo-3-(4-(trifluoromethyl)phenyl)-3,5-dihydro-2H-[1,4]thiazino[2,3,4-ij]quinoline-6-carboxylate A 30 mL thumb flask was charged with 6-fluoro-3-(4-(trifluoromethyl)phenyl)-3,4-dihydro-2H-benzo[b][1,4]thiazine (420 mg, 1.341 mmol) and triethyl methanetricarboxylate (1245 mg, 5.36 mmol). The mixture was stirred at 260° C. for 20 min with the protection of N$_2$. LCMS showed the starting material was consumed and the desired compound was formed. The reaction mixture was purified via combi flash (12g column, EtOAc in petroleum ether from 0% to 15%) to give ethyl 8-fluoro-7-hydroxy-5-oxo-3-(4-(trifluoromethyl)phenyl)-3,5-dihydro-2H-[1,4]thiazino[2,3,4-ij]quinoline-6-carboxylate as a solid. $^1$H NMR (CDCl$_3$, 400 MHz): δ 14.89 (brs, 1H), 7.54 (d, J=8.5 Hz, 2H), 7.49 (dd, J=8.5, 5.5 Hz, 1H), 7.14 (d, J=8.0 Hz, 2H), 6.94 (dd, J=11.3, 8.8 Hz, 1H), 6.82 (brs, 1H), 4.56-4.38 (m, 2H), 3.41 (dd, J=13.8, 3.3 Hz, 1H), 3.21 (dd, J=13.65, 3.0 Hz, 1H), 1.43 (t, J=7.3 Hz, 3H).

Step E: 2-(8-fluoro-7-hydroxy-5-oxo-3-(4-(trifluoromethyl)phenyl)-3,5-dihydro-2H-[1,4]thiazino[2,3,4-ij]quinoline-6-carboxamido)acetate A 10 mL vial was charged with ethyl 8-fluoro-7-hydroxy-5-oxo-3-(4-(trifluoromethyl)phenyl)-3,5-dihydro-2H-[1,4]thiazino[2,3,4-ij]quinoline-6-carboxylate (100 mg, 0.221 mmol), tert-butyl 2-aminoacetate hydrochloride (55.5 mg, 0.331 mmol), DIPEA (0.116 ml, 0.662 mmol) and toluene (5 mL). The mixture was heated to 115° C. and stirred for 1 hr. LCMS showed the starting material was consumed and the desired compound was formed. The reaction mixture was poured into water and acidified to pH 3 by 1M HCl, then extracted with EtOAc (30 mL*3). The combined organic layers were dried over Na$_2$SO$_4$, filtered and evaporated to give crude product tert-butyl 2-(8-fluoro-7-hydroxy-5-oxo-3-(4-(trifluoromethyl)phenyl)-3,5-dihydro-2H-[1,4]thiazino[2,3,4-ij]quinoline-6-carboxamido)acetate as a solid, which was used in the next step directly.

Step F: 2-(8-fluoro-7-hydroxy-5-oxo-3-(4-(trifluoromethyl)phenyl)-3,5-dihydro-2H-[1,4]thiazino[2,3,4-ij]quinoline-6-carboxamido)acetic acid To a suspension of tert-butyl 2-(8-fluoro-7-hydroxy-5-oxo-3-(4-(trifluoromethyl)phenyl)-3,5-dihydro-2H-[1,4]thiazino[2,3,4-ij]quinoline-6-carboxamido)acetate (119 mg, 0.221 mmol) in DCM (5 mL) was added TFA (2 mL, 26.0 mmol). The mixture was stirred at room temperature for 2 hr. Then the solvent was removed in vacuo, and the residue was purified via prep-HPLC (Column: ASB C18 150*25 mm;

Mobile phase: 50-80-15% MeCN in water (0.1% HCl); Wavelength: 220 nm) to give 2-(8-fluoro-7-hydroxy-5-oxo-3-(4-(trifluoromethyl)phenyl)-3,5-dihydro-2H-[1,4]thiazino[2,3,4-ij]quinoline-6-carboxamido)acetic acid as a solid. $^1$H NMR (DMSO-d$_6$, 400 MHz) δ 10.30 (t, J=5.5 Hz, 1H), 7.68-7.59 (m, 3H), 7.28 (d, J=8.2 Hz, 2H), 7.13 (dd, J=11.6, 8.7 Hz, 1H), 6.73 (brs, 1H), 4.05 (dd, J=5.3, 3.3 Hz, 2H), 3.60-3.43 (m, 2H). LC/MS (m/z): 483 (M+H)$^+$. Human HIF-PHD2 IC$_{50}$ 13.7 nM.

Example 99

2-(8-Cyano-7-hydroxy-5-oxo-3-(4-(trifluoromethyl)phenyl)-3,5-dihydro-2H-[1,4]thiazino[2,3,4-ij]quinoline-6-carboxamido)acetic acid

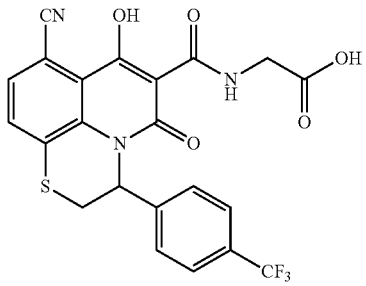 [SMILES: N#Cc1ccc2c3c1c(O)c(C(=O)NCC(=O)O)c(=O)n3C(c1ccc(C(F)(F)F)cc1)CS2]

Step A: 6-bromo-3-(4-(trifluoromethyl)phenyl)-2H-benzo[b][1,4]thiazine

To a solution of 2-amino-4-bromobenzenethiol (1 g, 4.90 mmol) in DCM (20 mL) were added K$_2$CO$_3$ (15 mL, 4.45 mmol) in water (15 mL) and tetrabutylammonium hydrogen sulfate (0.015 g, 0.045 mmol), then 2-bromo-1-(4-(trifluoromethyl)phenyl)ethanone (1.190 g, 4.45 mmol) in DCM (5 mL) was added dropwise to the reaction mixture. The resulting mixture was stirred at room temperature for 20 h. LCMS showed the desired compound was formed, then the mixture was extracted with DCM (100 mL*3). The combined organic layers were washed with brine (100 mL*3), dried over Na$_2$SO$_4$, filtered and concentrated in vacuo to give 6-bromo-3-(4-(trifluoromethyl)phenyl)-2H-benzo[b][1,4]thiazine as an oil, which was used in the next step directly. LC/MS (m/z): 373 (M+H)$^+$.

Step B: 6-bromo-3-(4-(trifluoromethyl)phenyl)-3,4-dihydro-2H-benzo[b][1,4]thiazine To a solution of 6-bromo-3-(4-(trifluoromethyl)phenyl)-2H-benzo[b][1,4]thiazine (1.6 g, 4.30 mmol) in DCM (10 mL) and MeOH (5.00 mL) were added AcOH (0.738 mL, 12.90 mmol) and sodium cyanoborohydride (1.351 g, 21.49 mmol). The reaction was stirred at room temperature for 2 h. The mixture was then added to water (50 mL), basified to pH 9 and extracted with ethyl acetate (3*50 mL). The combined organic fractions were washed with brine (saturated, 3*50 mL), dried (Na$_2$SO$_4$), filtered and the solvent was evaporated under reduced pressure. The residue was purified by column chromatography on silica gel Biotage 25M (EtOAc in petroleum ether: 0-10%, R$_h$=0.87) to give 6-bromo-3-(4-(trifluoromethyl)phenyl)-3,4-dihydro-2H-benzo[b][1,4]thiazine as an oil. $^1$H NMR (CDCl$_3$, 400 MHz): δ 7.65 (d, J=8.0 Hz, 2H), 7.47 (d, J=8.0 Hz, 2H), 6.92 (d, J=8.5 Hz, 1H), 6.80 (dd, J=8.3, 1.8 Hz, 1H), 6.72 (d, J=1.5 Hz, 1H), 4.86-4.76 (m, 1H), 4.24 (s, 1H), 3.09-3.03 (m, 2H).

Step C: Ethyl 8-bromo-7-hydroxy-5-oxo-3-(4-(trifluoromethyl)phenyl)-3,5-dihydro-2H-[1,4]thiazino[2,3,4-ij]quinoline-6-carboxylate A 30 mL thumb flask was charged with 6-bromo-3-(4-(trifluoromethyl)phenyl)-3,4-dihydro-2H-benzo[b][1,4]thiazine (200 mg, 0.534 mmol) and triethyl methanetricarboxylate (496 mg, 2.138 mmol). The mixture was stirred at 260° C. for 70 min with the protection of N$_2$. LCMS showed the starting material was consumed and the desired compound was formed. The reaction mixture was purified via silica gel column chromatography (12g column, EtOAc in petroleum ether from 0% to 60%) to give ethyl 8-bromo-7-hydroxy-5-oxo-3-(4-(trifluoromethyl)phenyl)-3,5-dihydro-2H-[1,4]thiazino[2,3,4-ij]quinoline-6-carboxylate as a solid. $^1$H NMR (CDCl$_3$, 400 MHz): δ 15.31 (brs, 1H), 7.70 (d, J=3.2 Hz, 1H), 7.51 (d, J=7.1 Hz, 2H), 7.10 (d, J=7.3 Hz, 2H), 6.91 (s, 1H), 4.55-4.39 (m, 2H), 4.35-4.26 (m, 1H), 3.42 (d, J=13.7 Hz, 1H), 3.23 (d, J=13.9 Hz, 1H), 1.44-1.39 (m, 3H).

Step D: tert-butyl 2-(8-bromo-7-hydroxy-5-oxo-3-(4-(trifluoromethyl)phenyl)-3,5-dihydro-2H-[1,4]thiazino[2,3,4-ij]quinoline-6-carboxamido)acetate A 10 mL vial was charged with ethyl 8-bromo-7-hydroxy-5-oxo-3-(4-(trifluoromethyl)phenyl)-3,5-dihydro-2H-[1,4]thiazino[2,3,4-ij]quinoline-6-carboxylate (90 mg, 0.175 mmol), tert-butyl 2-aminoacetate hydrochloride (44.0 mg, 0.262 mmol), DIPEA (0.092 mL, 0.525 mmol) and toluene (5 mL). The mixture was heated to 115° C. and stirred for 1 hr. LCMS showed the starting material was consumed and the desired compound was formed. The reaction mixture was poured into water and acidified to pH 3 by 1M HCl, then extracted with EtOAc (30 mL*3). The combined organic layers were dried over Na$_2$SO$_4$, filtered and evaporated to give crude product which was purified prep-TLC (petroleum ether: EtOAc=3:1) to give tert-butyl 2-(8-bromo-7-hydroxy-5-oxo-3-(4-(trifluoromethyl)phenyl)-3,5-dihydro-2H-[1,4]thiazino[2,3,4-ij]quinoline-6-carboxamido)acetate as a solid. LC/MS (m/z): 623 (M+Na)$^+$.

Step E: tert-butyl 2-(8-cyano-7-hydroxy-5-oxo-3-(4-(trifluoromethyl)phenyl)-3,5-dihydro-2H-[1,4]thiazino[2,3,4-ij]quinoline-6-carboxamido)acetate A microwave tube was charged with dicyanozinc (21.90 mg, 0.187 mmol), Pd$_2$(dba)$_3$ (8.54 mg, 9.33 μmol), DPPF (5.17 mg, 9.33 μmol), zinc (12.19 mg, 0.187 mmol) and DMA (3 mL). The tube was purged with N$_2$ and the reaction was kept at 120° C. for 30 min under microwave. LCMS showed the starting material was consumed and the desired compound was formed. Then the reaction mixture was diluted with EtOAc (20 mL) and filtered. The filtrate was washed with brine (30 mL*3), then evaporated to give tert-butyl 2-(8-cyano-7-hydroxy-5-oxo-3-(4-(trifluoromethyl)phenyl)-3,5-dihydro-2H-[1,4]thiazino[2,3,4-ij]quinoline-6-carboxamido)acetate as a yellow oil. The crude product was used in the next step without further purification. LC/MS (m/z): 568 (M+Na)$^+$.

Step F: 2-(8-cyano-7-hydroxy-5-oxo-3-(4-(trifluoromethyl)phenyl)-3,5-dihydro-2H-[1,4]thiazino[2,3,4-ij]quinoline-6-carboxamido)acetic acid To a suspension of tert-butyl 2-(8-cyano-7-hydroxy-5-oxo-3-(4-(trifluoromethyl)phenyl)-3,5-dihydro-2H-[1,4]thiazino[2,3,4-ij]quinoline-6-carboxamido)acetate (39 mg, 0.071 mmol) in DCM (5 mL) was added TFA (2 mL, 26.0 mmol). The mixture was stirred at room temperature for 2 h. Then the solvent was removed under vacuo, and the residue was purified via prep-HPLC (Column: ASB C18 150*25 mm; Mobile phase: 50-80-15% MeCN in water (0.1% HCl); Wavelength: 220 nm) to give 2-(8-cyano-7-hydroxy-5-oxo-3-(4-(trifluoromethyl)phenyl)-3,5-dihydro-2H-[1,4]thiazino[2,3,4-ij]quinoline-6-carboxamido)acetic acid as a solid. $^1$H NMR (DMSO-$d_6$, 400 MHz) δ 10.32 (brs, 1H), 7.77 (d, J=8.0 Hz, 1H), 7.72 (d, J=8.0 Hz, 1H), 7.62 (d, J=8.4 Hz, 2H), 7.29 (d, J=8.2 Hz, 2H), 6.80 (brs, 1H), 4.09 (brs, 2H), 3.72-3.53 (m, 2H). LC/MS (m/z): 490 (M+H)$^+$. Human HIF-PHD2 IC$_{50}$ 5.1 nM.

Example 100

2-(7-Hydroxy-5-oxo-3-(4-(trifluoromethyl)phenyl)-3,5-dihydro-2H-[1,4]thiazino[2,3,4-ij]quinoline-6-carboxamido)acetic acid

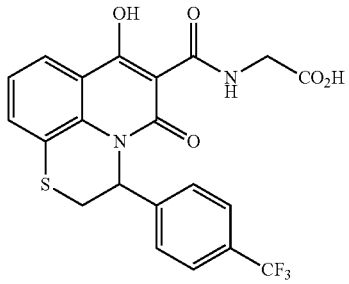 [SMILES: O=C(O)CNC(=O)c1c(O)c2cccc3c2n(c1=O)C(c1ccc(C(F)(F)F)cc1)CS3]

Step A: 3-(4-(trifluoromethyl)phenyl)-2H-benzo[b][1,4]thiazine

To a solution of 2-aminobenzenethiol (1 g, 7.99 mmol) in DCM (20 mL) were added a.q K$_2$CO$_3$ (20 mL, 7.99 mmol) and tetrabutylammonium hydrogen sulfate (0.027 g, 0.080 mmol). A solution of 2-bromo-1-(4-(trifluoromethyl)phenyl)ethanone (2.133 g, 7.99 mmol) in DCM (10 mL) was added dropwise. The reaction was stirred at room temperature for 20 h. LCMS showed that the reaction was complete. The resulting mixture was extracted with DCM (50 mL*3). The combined organic layers were washed with brine (50 mL*3), dried over Na$_2$SO$_4$, filtered and concentrated in vacuo to give 3-(4-(trifluoromethyl)phenyl)-2H-benzo[b][1,4]thiazine as an oil. $^1$H NMR (CDCl$_3$, 400 MHz): δ 7.86 (d, J=8.5 Hz, 2H), 7.69 (d, J=8.0 Hz, 2H), 7.18 (d, J=7.5 Hz, 1H), 7.07 (td, J=1.0 Hz, 8.4 Hz, 1H), 6.80 (t, J=7.5 Hz, 1H), 6.62 (d, J=8.0 Hz, 1H), 3.15 (d, J=12.5 Hz, 1H), 2.82 (d, J=12.5 Hz, 1H).

Step B: 3-(4-(trifluoromethyl)phenyl)-3,4-dihydro-2H-benzo[b][1,4]thiazine

To a solution of 3-(4-(trifluoromethyl)phenyl)-2H-benzo[b][1,4]thiazine (2.98 g, 7.62 mmol) in DCM (15 mL) and MeOH (7.50 mL) were added AcOH (0.5 mL, 8.73 mmol) and sodium cyanoborohydride (2.394 g, 38.1 mmol). The resulting mixture was stirred at room temperature for 2 h. LCMS showed that the reaction was complete. Water (50 mL) was added and the mixture was extracted with ethyl acetate (3*50 mL). The combined organic fractions were washed with aqueous ammonium chloride (saturated, 3*50 mL), dried (Na$_2$SO$_4$), filtered and the solvent was evaporated under reduced pressure. The residue was purified by column chromatography on silica gel Biotage 25S (EtOAc in petroleum ether: 0-10%) to give 3-(4-(trifluoromethyl)phenyl)-3,4-dihydro-2H-benzo[b][1,4]thiazine as an oil. $^1$H NMR (CDCl$_3$, 400 MHz): δ 7.65 (d, J=8.5 Hz, 2H), 7.51 (d, J=8.0 Hz, 2H), 7.08 (dd, J=1.0 Hz, 8.0 Hz, 1H), 6.98 (td, J=1.0 Hz, 8.4 Hz, 1H), 6.71 (t, J=7.3 Hz, 1H), 6.58 (d, J=8.0 Hz, 1H), 4.81 (dd, J=2.5 Hz, 8.0 Hz, 1H), 4.17 (s, 1H), 3.15 (dd, J=8.0 Hz, 12.4 Hz, 1H), 3.05 (dd, J=2.7 Hz, 12.4 Hz, 1H).

Step C: ethyl 7-hydroxy-5-oxo-3-(4-(trifluoromethyl)phenyl)-3,5-dihydro-2H-[1,4]thiazino[2,3,4-ij]quinoline-6-carboxylate A solution of 3-(4-(trifluoromethyl)phenyl)-3,4-dihydro-2H-benzo[b][1,4]thiazine (700 mg, 2.370 mmol) in triethyl methanetricarboxylate (2202 mg, 9.48 mmol) was stirred at 250° C. for 1 h. The resulting mixture was cooled to room temperature and recrystallized with petroleum ether (10 mL) to give ethyl 7-hydroxy-5-oxo-3-(4-(trifluoromethyl)phenyl)-3,5-dihydro-2H-[1,4]thiazino[2,3,4-ij]quinoline-6-carboxylate as a solid. $^1$H NMR (CDCl$_3$, 400 MHz): δ 14.40 (s, 1H), 8.12 (dd, J=1.6 Hz, 8.0 Hz, 1H), 7.56 (dd, J=1.6 Hz, 8.0 Hz, 1H), 7.54 (d, J=8.0 Hz, 2H), 7.23 (t, J=7.8 Hz, 1H), 7.16 (d, J=8.0 Hz, 2H), 6.80 (brs, 1H), 4.41-4.54 (m, 2H), 3.47 (dd, J=3.5 Hz, 13.6 Hz, 1H), 3.22 (dd, J=3.0 Hz, 13.6 Hz, 1H), 1.44 (t, J=7.3 Hz, 3H).

Step D: tert-butyl 2-(7-hydroxy-5-oxo-3-(4-(trifluoromethyl)phenyl)-3,5-dihydro-2H-[1,4]thiazino[2,3,4-ij]quinoline-6-carboxamido)acetate A solution of ethyl 7-hydroxy-5-oxo-3-(4-(trifluoromethyl)phenyl)-3,5-dihydro-2H-[1,4]thiazino[2,3,4-ij]quinoline-6-carboxylate (720 mg, 1.654 mmol), tert-butyl 2-aminoacetate HCl salt (333 mg, 1.984 mmol) and DIPEA (664 µL, 3.80 mmol) in toluene (5 mL) was heated to 120° C. and stirred at 120° C. for 2 h. TLC (petroleum ether: EtOAc=5:1) showed that the reaction was completed. The resulting mixture was concentrated in vacuo and the residue was purified Combi-Flash (EtOAc in DCM: 0-10%) to give tert-butyl 2-(7-hydroxy-5-oxo-3-(4-(trifluoromethyl)phenyl)-3,5-dihydro-2H-[1,4]thiazino[2,3,4-ij]quinoline-6-carboxamido)acetate as a solid. $^1$H NMR (CDCl$_3$, 400 MHz): δ 10.42 (s, 1H), 8.15 (t, J=6.0 Hz, 1H), 7.56 (d, J=7.6 Hz, 2H), 7.56 (d, J=7.6 Hz, 1H), 7.26 (t, J=8.0 Hz, 1H), 7.16 (d, J=8.4 Hz, 2H), 6.81 (s, 1H), 5.17 (dd, J=5.6 Hz, 20.0 Hz, 1H), 4.00 (dd, J=13.2 Hz, 20.4 Hz, 1H), 3.50 (dd, J=3.2 Hz, 15.6 Hz, 1H), 3.24 (dd, J=3.2 Hz, 14.0 Hz, 1H), 1.47 (s, 9H).

Step E: 2-(7-hydroxy-5-oxo-3-(4-(trifluoromethyl)phenyl)-3,5-dihydro-2H-[1,4]thiazino[2,3,4-ij]quinoline-6-carboxamido)acetic acid To a solution of tert-butyl 2-(7-hydroxy-5-oxo-3-(4-(trifluoromethyl)phenyl)-3,5-dihydro-2H-[1,4]thiazino[2,3,4-ij]quinoline-6-carboxamido)acetate (600 mg, 1.153 mmol) in DCM (5 mL) was added 2,2,2-trifluoroacetic acid (1314 mg, 11.53 mmol). The resulting mixture was heated to 50° C. and stirred for 3 h. TLC (petroleum ether: EtOAc=5:1) showed that the reaction was completed. The resulting mixture was concentrated in vacuo to give crude which was re-crystallised from EtOAc (5 mL) and petroleum ether (5 mL) to give 2-(7-hydroxy-5-oxo-3-(4-(trifluoromethyl)phenyl)-3,5-dihydro-2H-[1,4]thiazino[2,3,4-ij]quinoline-6-carboxamido)acetic acid as a solid. $^1$H NMR (DMSO-d$_6$, 400 MHz): δ 10.30 (t, J=5.6 Hz, 1H), 8.02 (d, J=8.0 Hz, 1H), 7.67 (d, J=8.0 Hz, 1H), 7.66 (d, J=8.0 Hz, 2H), 7.33 (d, J=8.0 Hz, 1H), 7.28 (d, J=8.0 Hz, 2H), 6.74 (t, J=4.0 Hz, 1H), 4.02-4.10 (m, 2H), 3.54-3.62 (m, 2H). LC/MS (m/z): 465 (M+H)$^+$. Human HIF-PHD2 IC$_{50}$ 32 nM.

Example 101

2-(7-hydroxy-1,1-dioxido-5-oxo-3-(4-(trifluoromethyl)phenyl)-3,5-dihydro-2H-[1,4]thiazino[2,3,4-ij]quinoline-6-carboxamido)acetic acid

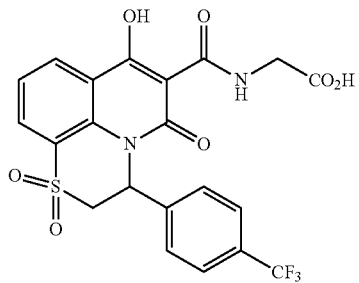 [SMILES: O=C(O)CNC(=O)c1c(O)c2cccc3c2n(c1=O)C(c1ccc(C(F)(F)F)cc1)CS3(=O)=O]

To a solution of Example 100 product (250 mg, 0.538 mmol) in acetonitrile (10 mL) and TFA (3.33 mL) was added H$_2$O$_2$ (2 mL, 22.84 mmol). The resulting mixture was heated to 80° C. and stirred for 1 h. LCMS showed that the reaction was complete. The reaction mixture was evaporated in vacuo. The residue was recrystallised from EtOAc (3 mL) and petroleum ether (5 mL) to give 2-(7-hydroxy-1,1-dioxido-5-oxo-3-(4-(trifluoromethyl)phenyl)-3,5-dihydro-2H-[1,4]thiazino[2,3,4-ij]quinoline-6-carboxamido)acetic acid as a solid. $^1$H NMR (DMSO-d$_6$, 400 MHz): δ 10.14 (t, J=5.6 Hz, 1H), 8.50 (d, J=7.2 Hz, 1H), 8.26 (d, J=7.2 Hz, 1H), 7.63 (d, J=7.2 Hz, 1H), 7.62 (d, J=8.0 Hz, 2H), 7.34 (d, J=8.0 Hz, 2H), 6.91 (t, J=4.0 Hz, 1H), 4.56 (dd, J=3.6 Hz, 15.2 Hz, 1H), 4.42 (dd, J=3.6 Hz, 15.2 Hz, 1H), 4.02-4.13 (m, 2H). LC/MS (m/z): 497 (M+H)$^+$. Human HIF-PHD2 IC$_{50}$ 8.6 nM.

Example 102

2-(9-Cyano-7-hydroxy-5-oxo-3-(4-(trifluoromethyl)phenyl)-3,5-dihydro-2H-[1,4]thiazino[2,3,4-ij]quinoline-6-carboxamido)acetic acid

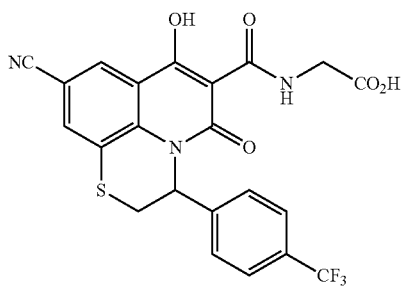 [SMILES: N#Cc1cc2c3c(c1)c(O)c(C(=O)NCC(=O)O)c(=O)n3C(c1ccc(C(F)(F)F)cc1)CS2]

Step A: 7-bromo-3-(4-(trifluoromethyl)phenyl)-3,4-dihydro-2H-benzo[b][1,4]thiazine To a solution of Example 100 Step B product (1.2 g, 4.06 mmol) in DMF (10 mL) was added NBS (0.940 g, 5.28 mmol). The resulting mixture was stirred at room temperature for 16 h. LCMS showed that the reaction was complete. The reaction mixture was diluted with EtOAc (50 mL) and washed with brine (30 mL*3). The organic layer was then dried over Na$_2$SO$_4$, filtered and evaporated to give 7-bromo-3-(4-(trifluoromethyl)phenyl)-3,4-dihydro-2H-benzo[b][1,4]thiazine as an oil. LC/MS (m/z): 373 (M+H)$^+$.

Step B: ethyl 9-bromo-7-hydroxy-5-oxo-3-(4-(trifluoromethyl)phenyl)-3,5-dihydro-2H-[1,4]thiazino[2,3,4-ij]quinoline-6-carboxylate A mixture of 7-bromo-3-(4-(trifluoromethyl)phenyl)-3,4-dihydro-2H-benzo[b][1,4]thiazine (1.6 g, 2.99 mmol) and triethyl methanetricarboxylate (2.78 g, 11.97 mmol) was heated to 250° C. and stirred at 250° C. for 1.5 h. The resulting mixture was cooled to room temperature, then recrystallised from petroleum ether (50 mL) to give ethyl 9-bromo-7-hydroxy-5-oxo-3-(4-(trifluoromethyl)phenyl)-3,5-dihydro-2H-[1,4]thiazino[2,3,4-ij]quinoline-6-carboxylate as a solid. $^1$H NMR (CDCl$_3$, 400 MHz): δ 14.41 (s, 1H), 8.21 (d, J=2.0 Hz, 1H), 7.66 (d, J=2.2 Hz, 1H), 7.54 (d, J=8.2 Hz, 2H), 7.14 (d, J=7.9 Hz, 2H), 6.77 (s, 1H), 4.41-4.54 (m, 2H), 3.46 (dd, J=3.1 Hz, 13.7 Hz, 1H), 3.22 (dd, J=3.2 Hz, 13.8 Hz, 1H), 1.43 (t, J=7.2 Hz, 3H).

Step C: tert-butyl 2-(9-bromo-7-hydroxy-5-oxo-3-(4-(trifluoromethyl)phenyl)-3,5-dihydro-2H-[1,4]thiazino[2,3,4-ij]quinoline-6-carboxamido)acetate A solution of ethyl 9-bromo-7-hydroxy-5-oxo-3-(4-(trifluoromethyl)phenyl)-3,5-dihydro-2H-[1,4]thiazino[2,3,4-ij]quinoline-6-carboxylate (580 mg, 1.071 mmol), tert-butyl 2-aminoacetate HCl salt (216 mg, 1.286 mmol) and DIPEA (0.430 mL, 2.464 mmol) in toluene (5 mL) was heated to 120° C. and stirred for 2 h. TLC (petroleum ether: EtOAc=5:1) showed that the reaction was completed. The resulting mixture was concentrated in vacuo and the residue was purified by silica gel column chromatography (DCM in petroleum ether: 0-70%) to give tert-butyl 2-(9-bromo-7-hydroxy-5-oxo-3-(4-(trifluoromethyl)phenyl)-3,5-dihydro-2H-[1,4]thiazino[2,3,4-ij]quinoline-6-carboxamido)acetate as a solid. $^1$H NMR (CDCl$_3$, 400 MHz): δ 10.35 (brs, 1H), 8.23 (d, J=2.0 Hz, 1H), 7.66 (d, J=2.0 Hz, 1H), 7.56 (d, J=8.0 Hz, 2H), 7.13 (d, J=8.0 Hz, 2H), 6.79 (s, 1H), 4.14-4.20 (m, 1H), 3.95-4.01 (m, 1H), 3.49 (dd, J=3.3 Hz, 13.8 Hz, 1H), 3.24 (dd, J=3.3 Hz, 13.8 Hz, 1H), 1.47 (s, 9H).

Step D: tert-butyl 2-(9-cyano-7-hydroxy-5-oxo-3-(4-(trifluoromethyl)phenyl)-3,5-dihydro-2H-[1,4]thiazino[2,3,4-ij]quinoline-6-carboxamido)acetate To a solution of tert-butyl 2-(9-bromo-7-hydroxy-5-oxo-3-(4-(trifluoromethyl)phenyl)-3,5-dihydro-2H-[1,4]thiazino[2,3,4-ij]quinoline-6-carboxamido)acetate (680 mg, 1.078 mmol) in DMA (5 mL) were added dicyanozinc (253 mg, 2.155 mmol), Pd$_2$(dba)$_3$ (99 mg, 0.108 mmol), dppf (59.7 mg, 0.108 mmol) and zinc (141 mg, 2.155 mmol). The reaction solution was heated with microwave at 130° C. for 30 min. TLC (petroleum ether: EtOAc=5:1) showed that the reaction was complete. The mixture was cooled, water (10 mL) was added and the mixture was extracted with ethyl acacate (3*20 mL). The combined organic fractions were washed with water (3*30 mL), dried (Na$_2$SO$_4$), filtered and the solvent was evaporated under reduced pressure. The residue was purified by silica gel column chromatography (EtOAc in petroleum ether: 0-60%) to give tert-butyl 2-(9-cyano-7-hydroxy-5-oxo-3-(4-(trifluoromethyl)phenyl)-3,5-dihydro-2H-[1,4]thiazino[2,3,4-ij]quinoline-6-carboxamido)acetate as a solid. $^1$H NMR (CDCl$_3$, 400 MHz): δ 10.21 (brs, 1H), 8.43 (d, J=2.0 Hz, 1H), 7.76 (d, J=2.0 Hz, 1H), 7.58 (d, J=8.1 Hz, 2H), 7.13 (d, J=8.1 Hz, 2H), 6.80 (s, 1H), 4.14-4.20 (m, 1H), 3.97-4.02 (m, 1H), 3.48-3.52 (m, 1H), 3.28 (dd, J=3.2 Hz, 13.9 Hz, 1H), 1.48 (s, 9H).

Step E: 2-(9-cyano-7-hydroxy-5-oxo-3-(4-(trifluoromethyl)phenyl)-3,5-dihydro-2H-[1,4]thiazino[2,3,4-ij]quinoline-6-carboxamido)acetic acid To a solution of tert-butyl 2-(9-cyano-7-hydroxy-5-oxo-3-(4-(trifluoromethyl)phenyl)-3,5-dihydro-2H-[1,4]thiazino[2,3,4-ij]quinoline-6-carboxamido)acetate (400 mg, 0.697 mmol) in DCM (5 mL) was added 2,2,2-trifluoroacetic acid (794 mg, 6.97 mmol). The resulting mixture was stirred at 50° C. for 3 h. TLC (petroleum ether: EtOAc=2:1) showed that the reaction was completed. The resulting mixture was concentrated in vacuo and the residue was re-crystallised from EtOAc (5 mL) and petroleum ether (5 mL) to give 2-(9-cyano-7-hydroxy-5-oxo-3-(4-(trifluoromethyl)phenyl)-3,5-dihydro-2H-[1,4]thiazino[2,3,4-ij]quinoline-6-carboxamido)acetic acid as a solid. $^1$H NMR (DMSO-d$_6$, 400 MHz): δ 10.22 (s, 1H), 8.35 (s, 1H), 8.11 (s, 1H), 7.65 (d, J=8.0 Hz, 2H), 7.31 (d, J=8.0 Hz, 2H), 6.75 (s, 1H), 4.02-4.08 (m, 2H), 3.57-3.66 (m, 2H). LC/MS (m/z): 490 (M+H)$^+$. Human HIF-PHD2 IC$_{50}$ 5.8 nM.

Example 103

2-(7-Hydroxy-5-oxo-2-(6-(trifluoromethyl)pyridin-3-yl)-3,5-dihydro-2H-[1,4]thiazino[2,3,4-ij]quinoline-6-carboxamido)acetic acid

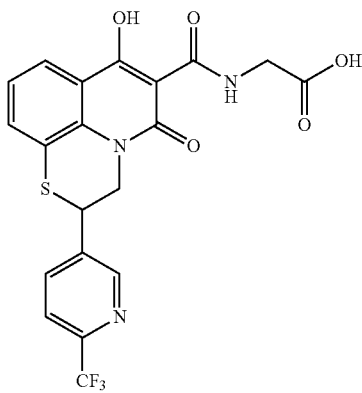

Step A: (2-(tert-butoxy)-2-oxoethyl)zinc(II) bromide

A 250 mL three necked flask was charged with zinc (16.28 g, 249 mmol) in THF (30 mL), the flask was purged with N$_2$, and 1,2-dibromoethane (0.998 g, 5.31 mmol) was added by syringe. The mixture was heated to reflux and maintained at 45° C. for 30 minutes. Then tert-butyl 2-bromoacetate (12.95 g, 66.4 mmol) in THF (70 mL) was added slowly. The resulting mixture was stirred at 60° C. for 1 h. The reaction mixture was used in the next step directly.

Step B: tert-butyl 2-(6-(trifluoromethyl)pyridin-3-yl)acetate

A solution (2-(tert-butoxy)-2-oxoethyl)zinc(II) bromide in THF (100 mL, 66.4 mmol) was added to 5-bromo-2-(trifluoromethyl)pyridine (5 g, 22.12 mmol), dicyclohexyl (2',4',6'-triisopropyl[1,1'-biphenyl]-2-yl)phosphine (1.055 g, 2.212 mmol) and Pd$_2$(dba)$_3$ (1.013 g, 1.106 mmol). The reaction mixture was heated to 60° C. and stirred for 16 h. LCMS showed that the reaction was complete. The reaction was quenched with aqueous NH$_4$Cl and extracted with EtOAc (50 mL*3). The combined organic layers were dried over Na$_2$SO$_4$, filtered and evaporated in vacuo. The residue was purified by silica gel column chromatography (EtOAc in petroleum ether: 0-10%) to give tert-butyl 2-(6-(trifluoromethyl)pyridin-3-yl)acetate as a solid. $^1$H NMR (CDCl$_3$, 400 MHz): δ 8.63 (s, 1H), 7.83 (d, J=8.0 Hz, 1H), 7.67 (d, J=8.0 Hz, 1H), 3.64 (s, 2H), 1.46 (s, 9H).

Step C: tert-butyl 2-bromo-2-(6-(trifluoromethyl)pyridin-3-yl)acetate

To a solution of tert-butyl 2-(6-(trifluoromethyl)pyridin-3-yl)acetate (4.5 g, 17.23 mmol) in CCl$_4$ (40 mL) were added 1-bromopyrrolidine-2,5-dione (9.20 g, 51.7 mmol) and benzoyl peroxide (0.417 g, 1.723 mmol). The reaction mixture was heated to 80° C. and stirred for 16 h. TLC (petroleum ether: EtOAc=20:1) showed that the reaction was complete. The resulting mixture was filtered and evaporated in vacuo and the residue purified by silica gel column chromatography (EtOAc in petroleum ether: 0-5%) to give tert-butyl 2-bromo-2-(6-(trifluoromethyl)pyridin-3-yl)acetate as a solid. $^1$H NMR (CDCl$_3$, 400 MHz): δ 8.80 (d, J=1.3 Hz, 1H), 8.17 (dd, J=1.5 Hz, 8.2 Hz, 1H), 7.73 (d, J=8.2 Hz, 1H), 5.29 (s, 1H), 1.49 (s, 9H).

Step D: 2-(6-(trifluoromethyl)pyridin-3-yl)-2H-benzo[b][1,4]thiazin-3(4H)-one

To a solution of 2-aminobenzenethiol (1.333 g, 10.64 mmol) and tert-butyl 2-bromo-2-(4-(trifluoromethyl)phenyl)acetate (3.8 g, 10.64 mmol) in toluene (30 mL) was added DIPEA (5.58 mL, 31.9 mmol). The reaction mixture was heated to 120° C. and stirred for 60 h. The reaction mixture was evaporated in vacuo. The residue was purified by silica gel column chromatography (EtOAc in petroleum ether: 0-20%) to give 2-(4-(trifluoromethyl)phenyl)-2H-benzo[b][1,4]thiazin-3(4H)-one as a solid. $^1$H NMR (CDCl$_3$, 400 MHz): δ 8.75 (s, 1H), 8.60 (s, 1H), 7.90 (d, J=8.0 Hz, 1H), 7.65 (d, J=8.0 Hz, 1H), 7.35 (d, J=7.5 Hz, 1H), 7.23 (t, J=8.0 Hz, 1H), 7.07 (t, J=7.5 Hz, 1H), 6.9 (d, J=7.5 Hz, 1H), 4.78 (s, 1H).

Step E: 2-(6-(trifluoromethyl)pyridin-3-yl)-3,4-dihydro-2H-benzo[b][1,4]thiazine To a solution of 2-(6-(trifluoromethyl)pyridin-3-yl)-2H-benzo[b][1,4]thiazin-3(4H)-one (400 mg, 1.289 mmol) in THF (15 mL) was added BH$_3$-DMS (1.224 ml, 12.89 mmol) dropwise at room temperature under nitrogen atmosphere. The reaction mixture was stirred at room temperature for 16 h. The reaction was quenched by adding MeOH. The reaction mixture was evaporated in vacuo to give 2-(6-(trifluoromethyl)pyridin-3-yl)-3,4-dihydro-2H-benzo[b][1,4]thiazine as an oil.

Step F: ethyl 7-hydroxy-5-oxo-2-(6-(trifluoromethyl)pyridin-3-yl)-3,5-dihydro-2H-[1,4]thiazino[2,3,4-ij]quinoline-6-carboxylate A mixture of 2-(6-(trifluoromethyl)pyridin-3-yl)-3,4-dihydro-2H-benzo [b][1,4]thiazine (380 mg, 1.218 mmol) and triethyl methanetricarboxylate (1132 mg, 4.87 mmol) was stirred at 250° C. for 1.5 h. The resulting mixture was cooled to room temperature then purified by silica gel column chromatography (EtOAc in DCM: 0-30%) to give ethyl 7-hydroxy-5-oxo-2-(6-(trifluoromethyl)pyridin-3-yl)-3,5-dihydro-2H-[1,4]thiazino[2,3,4-ij]quinoline-6-carboxylate as an oil.

Step G: tert-butyl 2-(7-hydroxy-5-oxo-2-(6-(trifluoromethyl)pyridin-3-yl)-3,5-dihydro-2H-[1,4]thiazino[2,3,4-ij]quinoline-6-carboxamido)acetate A solution of ethyl 7-hydroxy-5-oxo-2-(6-(trifluoromethyl)pyridin-3-yl)-3,5-dihydro-2H-[1,4]thiazino[2,3,4-ij]quinoline-6-carboxylate (200 mg, 0.275 mmol), tert-butyl 2-aminoacetate HCl salt (55.3 mg, 0.330 mmol) and DIPEA (0.110 mL, 0.632 mmol) in toluene (5 mL) was stirred at 120° C. for 2 h. TLC (petroleum ether: EtOAc=2:1) showed that the reaction was complete. The resulting mixture was concentrated in vacuo and the residue was purified by silica gel column chromatography (EtOAc in petroleum ether: 0-30%) to give tert-butyl 2-(7-hydroxy-5-oxo-2-(6-(trifluoromethyl)pyridin-3-yl)-3,5-dihydro-2H-[1,4]thiazino[2,3,4-ij]quinoline-6-carboxamido)acetate as a solid. $^1$H NMR (CDCl$_3$, 400 MHz): δ 10.53 (brs, 1H), 8.80 (s, 1H), 8.06 (dd, J=1.3 Hz, 7.9 Hz, 1H), 7.89 (d, J=7.9 Hz, 1H), 7.71 (d, J=8.2 Hz, 1H), 7.56 (dd, J=1.3 Hz, 7.5 Hz, 1H), 7.24 (t, J=8.0 Hz, 1H), 5.10-5.17 (m, 1H), 4.49-4.58 (m, 2H), 4.08-4.20 (m, 2H), 1.51 (s, 9H).

Step H: 2-(7-hydroxy-5-oxo-2-(6-(trifluoromethyl)pyridin-3-yl)-3,5-dihydro-2H-[1,4]thiazino[2,3,4-ij]quinoline-6-carboxamido)acetic acid To a solution of tert-butyl 2-(7-hydroxy-5-oxo-2-(6-(trifluoromethyl)pyridin-3-yl)-3,5-dihydro-2H-[1,4]thiazino[2,3,4-ij]quinoline-6-carboxamido)acetate (45 mg, 0.086 mmol) in DCM (5 mL) was added 2,2,2-trifluoroacetic acid (98 mg, 0.863 mmol). The resulting mixture was stirred at 30° C. for 3 h. TLC (petroleum ether: EtOAc=2:1) showed that the reaction was complete. The resulting mixture was concentrated in vacuo and the residue was re-crystallised from EtOAc (5 mL) and petroleum ether (5 mL) to give 2-(7-hydroxy-5-oxo-2-(6-(trifluoromethyl)pyridin-3-yl)-3,5-dihydro-2H-[1,4]thiazino[2,3,4-ij]quinoline-6-carboxamido)aceticcacid as a solid. $^1$H NMR (DMSO-d$_6$, 400 MHz): δ 12.95 (brs, 1H), 10.38 (s, 1H), 8.86 (s, 1H), 8.07 (d, J=8.0 Hz, 1H), 7.95 (d, J=8.0 Hz, 1H), 7.94 (d, J=8.0 Hz, 1H), 7.74 (t, J=8.0 Hz, 1H), 7.33 (t, J=8.0 Hz, 1H), 5.06 (s, 1H), 4.10-4.15 (m, 2H), 4.12 (d, J=5.2 Hz, 2H). LC/MS (m/z): 466 (M+H)$^+$. Human HIF-PHD2 IC$_{50}$ 3.4 nM.

Example 104

2-(7-Hydroxy-1,1-dioxido-5-oxo-2-(6-(trifluoromethyl)pyridin-3-yl)-3,5-dihydro-2H-[1,4]thiazino[2,3,4-ij]quinoline-6-carboxamido)acetic acid

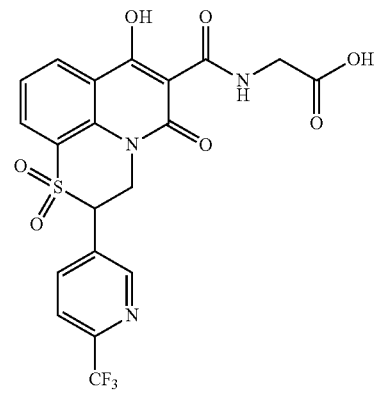 [SMILES: O=C(O)CNC(=O)c1c(O)c2cccc3c2n(c1=O)CC(c1ccc(C(F)(F)F)nc1)S3(=O)=O]

To a solution of Example 103 product (2 mg, 4.30 μmol) in acetonitrile (1 mL) was added H$_2$O$_2$ (0.1 mL, 1.142 mmol). The resulting mixture was stirred at 80° C. for 16 h. LCMS showed that the reaction was complete. The reaction mixture was evaporated in vacuo to give 2-(7-hydroxy-1,1-dioxido-5-oxo-2-(6-(trifluoromethyl)pyridin-3-yl)-3,5-dihydro-2H-[1,4]thiazino[2,3,4-ij]quinoline-6-carboxamido) acetic acid as a solid. $^1$H NMR (DMSO-d$_6$, 400 MHz): δ 10.25 (s, 1H), 8.92 (s, 1H), 8.47 (d, J=6.8 Hz, 1H), 8.40 (s, 1H), 8.28 (s, 1H), 8.09 (d, J=8.0 Hz, 1H), 7.64 (s, 1H), 5.68 (d, J=10.4 Hz, 1H), 5.45-5.49 (m, 1H), 4.76-4.79 (m, 1H), 4.16 (s, 2H). LC/MS (m/z): 498 (M+H)$^+$. Human HIF-PHD2 IC$_{50}$ 6.3 nM.

Example 105

2-(7-Hydroxy-5-oxo-3-(thiazol-5-yl)-3,5-dihydro-2H-[1,4]thiazino[2,3,4-ij]quinoline-6-carboxamido)acetic acid

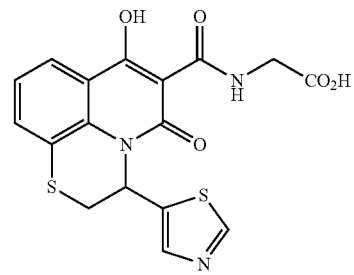 [SMILES: O=C(O)CNC(=O)c1c(O)c2cccc3c2n(c1=O)C(c1cncs1)CS3]

Step A: 3-(thiazol-5-yl)-2H-benzo[b][1,4]thiazine

To a solution of 2-aminobenzenethiol (0.480 g, 3.83 mmol) in DCM (15 mL) were added aq K$_2$CO$_3$ (15 mL, 3.48 mmol) and tetrabutylammonium hydrogen sulfate (0.012 g, 0.035 mmol). Then 2-bromo-1-(thiazol-5-yl)ethanone (HBr salt, 1 g, 3.48 mmol) in DCM (10 mL) was added dropwise to the reaction mixture and the mixture was stirred at room temperature for 20 h. The resulting mixture was extracted with DCM (100 mL*3). The combined organic layers were washed with brine (100 mL*3), dried over Na$_2$SO$_4$, filtered and concentrated in vacuo to give 3-(thiazol-5-yl)-2H-benzo[b][1,4]thiazine as a yellow oil which was used in the next step directly.

Step B: 3-(thiazol-5-yl)-3,4-dihydro-2H-benzo[b][1,4]thiazine

To a solution of 3-(thiazol-5-yl)-2H-benzo[b][1,4]thiazine (1.2 g, 3.10 mmol) in DCM (15 mL) and MeOH (7.50 mL) were added AcOH (0.5 mL, 8.73 mmol) and sodium cyanoborohydride (0.974 g, 15.50 mmol). The resulting mixture was stirred at room temperature for 2 h, then water (50 mL) was added and the mixture was extracted with ethyl acetate (3*50 mL). The combined organic fractions were washed with aqueous ammonium chloride (saturated, 3*50 mL), dried (Na$_2$SO$_4$), filtered and the solvent was evaporated under reduced pressure. The residue was purified by column chromatography on silica gel Biotage 25M (EtOAc in petroleum ether: 0-20%) to give 3-(thiazol-5-yl)-3,4-dihydro-2H-benzo[b][1,4]thiazine as an oil. $^1$H NMR (CDCl$_3$, 400 MHz): δ 8.80 (s, 1H), 7.88 (s, 1H), 7.07 (dd, J=1.3 Hz, 7.7 Hz, 1H), 6.96 (td, J=1.2 Hz, 8.4 Hz, 1H), 6.72 (td, J=1.2 Hz, 8.0 Hz, 1H), 6.54 (dd, J=0.9 Hz, 7.9 Hz, 1H), 5.19 (t, J=5.1 Hz, 1H), 4.30 (brs, 1H), 3.81 (d, J=5.3 Hz, 2H).

Step C: ethyl 7-hydroxy-5-oxo-3-(thiazol-5-yl)-3,5-dihydro-2H-[1,4]thiazino[2,3,4-ij]quinoline-6-carboxylate A mixture of 3-(thiazol-5-yl)-3,4-dihydro-2H-benzo[b][1,4]thiazine (370 mg, 1.500 mmol) and triethyl methanetricarboxylate (1393 mg, 6.00 mmol) was stirred at 250° C. for 1 h. The resulting mixture was cooled to room temperature and purified by Combi-Flash (EtOAc in DCM: 0-20%) to give ethyl 7-hydroxy-5-oxo-3-(thiazol-5-yl)-3,5-dihydro-2H-[1,4]thiazino[2,3,4-ij]quinoline-6-carboxylate as a solid. $^1$H NMR (CDCl$_3$, 400 MHz): δ 14.35 (s, 1H), 8.70 (s, 1H), 8.05 (d, J=8.0 Hz, 1H), 7.83 (s, 1H), 7.57 (d, J=7.5 Hz, 1H), 7.21 (t, J=8.0 Hz, 1H), 7.20 (t, J=2.8 Hz, 1H), 4.44-4.58 (m, 2H), 3.51 (dd, J=3.0 Hz, 13.6 Hz, 1H), 3.22 (dd, J=3.3 Hz, 13.8 Hz, 1H), 1.47 (t, J=7.0 Hz, 3H).

Step D: tert-butyl 2-(7-hydroxy-5-oxo-3-(thiazol-5-yl)-3,5-dihydro-2H-[1,4]thiazino[2,3,4-ij]quinoline-6-carboxamido)acetate A solution of ethyl 7-hydroxy-5-oxo-3-(thiazol-5-yl)-3,5-dihydro-2H-[1,4]thiazino[2,3,4-ij]quinoline-6-carboxylate (120 mg, 0.304 mmol), tert-butyl 2-aminoacetate HCl salt (61.2 mg, 0.365 mmol) and DIPEA (0.122 ml, 0.700 mmol) in toluene (5 mL) was stirred at 120° C. for 2 h. TLC (petroleum ether: EtOAc=2:1) showed that the reaction was complete. The resulting mixture was concentrated in vacuo and the residue was purified silica gel column chromatography (EtOAc in petroleum ether: 0-30%) to give tert-butyl 2-(7-hydroxy-5-oxo-3-(thiazol-5-yl)-3,5-dihydro-2H-[1,4]thiazino[2,3,4-ij]quinoline-6-carboxamido)acetate as a solid. $^1$H NMR (CDCl$_3$, 400 MHz): δ 10.49 (brs, 1H), 8.72 (s, 1H), 8.08 (d, J=7.8 Hz, 1H), 7.84 (s, 1H), 7.57 (d, J=6.8 Hz, 1H), 7.25 (t, J=8.0 Hz, 1H), 7.21 (t, J=3.2 Hz, 1H), 4.20 (dd, J=5.6 Hz, 18.4 Hz, 1H), 4.03 (dd, J=4.8 Hz, 18.4 Hz, 1H), 3.54 (dd, J=3.2 Hz, 13.7 Hz, 1H), 3.23 (dd, J=3.3 Hz, 13.8 Hz, 1H), 1.51 (s, 9H).

Step E: 2-(7-hydroxy-5-oxo-3-(thiazol-5-yl)-3,5-dihydro-2H-[1,4]thiazino[2,3,4-ij]quinoline-6-carboxamido)acetic acid To a solution of tert-butyl 2-(7-hydroxy-5-oxo-3-(thiazol-5-yl)-3,5-dihydro-2H-[1,4]thiazino[2,3,4-ij]quinoline-6-carboxamido)acetate (88 mg, 0.182 mmol) in DCM (5 mL) was added 2,2,2-trifluoroacetic acid (207 mg, 1.819 mmol). The resulting mixture was stirred at 30° C. for 3 h. TLC (petroleum ether: EtOAc=2:1) showed that the reaction was complete. The resulting mixture was concentrated in vacuo and the residue was re-crystallised from EtOAc (5 mL) and petroleum ether (5 mL) to give 2-(7-hydroxy-5-oxo-3-(thiazol-5-yl)-3,5-dihydro-2H-[1,4]thiazino[2,3,4-ij]quinoline-6-carboxamido)acetic acid as a solid. $^1$H NMR (DMSO-d$_6$, 400 MHz): δ 12.93 (s, 1H), 10.33 (t, J=5.6 Hz, 1H), 8.97 (s, 1H), 7.97 (d, J=7.6 Hz, 1H), 7.72 (s, 1H), 7.71 (dd, J=1.6 Hz, 7.6 Hz, 1H), 7.32 (t, J=8.0 Hz, 1H), 7.05 (s, 1H), 4.07-4.17 (m, 2H), 3.51-3.63 (m, 2H). LC/MS (m/z): 404 (M+H)$^+$. Human HIF-PHD2 IC$_{50}$ 5.1 nM.

Example 106

2-(7-Hydroxy-5-oxo-3-(4-(trifluoromethyl)phenyl)-1,2,3,5-tetrahydropyrido[1,2,3-de]quinoxaline-6-carboxamido)acetic acid

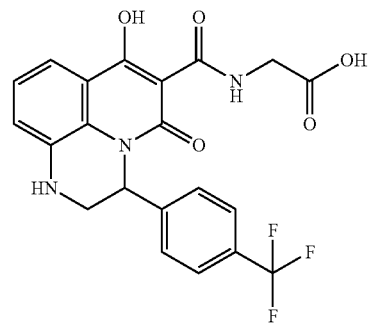 [SMILES: O=C(O)CNC(=O)c1c(O)c2cccc3c2n(c1=O)C(c1ccc(C(F)(F)F)cc1)CN3]

Step A: 2-(4-(trifluoromethyl)phenyl)quinoxaline

A mixture of (4-(trifluoromethyl)phenyl)boronic acid (8.31 g, 43.7 mmol), 2-chloroquinoxaline (6 g, 36.5 mmol), Cs$_2$CO$_3$ (23.75 g, 72.9 mmol), Pd(Ph$_3$P)$_4$ (2.106 g, 1.823 mmol) in N,N-dimethylformamide (100 mL) was stirred at 130° C. for 2.5 h. The reaction mixture was cooled to rt, water (400 mL) was added and the mixture was extracted with ethyl acacate (100 mL*3). The combined organic fractions were washed with brine (100 mL), dried (Na$_2$SO$_4$), filtered and the solvent was evaporated under reduced pressure. The residue was purified by column chromatography on silica eluting with petroleum ether/EtOAc (from 100/0 to 80/20) to give 2-(4-(trifluoromethyl)phenyl)quinoxaline as a solid. $^1$H NMR (CDCl$_3$, 400 MHz): δ 9.37 (s, 1H), 8.35 (d, J=8.0 Hz, 2H), 8.16-8.21 (m, 2H), 7.80-7.86 (m, 4H).

Step B: 2-(4-(trifluoromethyl)phenyl)-1,2,3,4-tetrahydroquinoxaline

To a solution of 2-(4-(trifluoromethyl)phenyl)quinoxaline (2.74 g, 10 mmol) in THF (20 mL) was added BH$_3$-THF (30.0 mL, 30.0 mmol) at room temperature. The mixture was stirred at 23° C. for 15 min. TLC (petroleum ether: EtOAc=2:1) indicated the starting material was consumed. 10 mL of MeOH was added, and the mixture was stirred for 20 min. The mixture was concentrated in vacuum to remove the solvent. This crude product was purified by column chromatography (EtOAc in petroleum ether from 0% to 40%) to give 2-(4-(trifluoromethyl)phenyl)-1,2,3,4-tetrahydroquinoxaline as a solid. $^1$H NMR (CDCl$_3$, 400 MHz): δ 7.63 (d, J=8.1 Hz, 2H), 7.52 (d, J=8.1 Hz, 2H), 6.59-6.69 (m, 4H), 4.58 (d, J=7.3 Hz, 1H), 3.94 (brs, 1H), 3.83 (brs, 1H), 3.48-3.51 (m, 1H), 3.30-3.35 (m, 1H).

Step C: tert-butyl 3-(4-(trifluoromethyl)phenyl)-3,4-dihydroquinoxaline-1(2H)-carboxylate A solution of 2-(4-(trifluoromethyl)phenyl)-1,2,3,4-tetrahydroquinoxaline (2 g, 7.19 mmol), Boc$_2$O (5.01 mL, 21.56 mmol) and DMAP (0.044 g, 0.359 mmol) in DCM was stirred at room temperature overnight. This reaction mixture was concentrated and purified by column chromatography (SiO$_2$, EtOAc in petroleum ether from 0% to 20%) to give the desired product as a pale-yellow solid. $^1$H NMR (CDCl$_3$, 400 MHz): δ 7.60 (d, J=8.3 Hz, 2H), 7.52 (d, J=8.1 Hz, 1H), 7.47 (d, J=8.1 Hz, 2H), 6.99 (t, J=8.0 Hz, 1H), 6.75 (d, J=8.0 Hz, 1H), 6.70 (d, J=7.8 Hz, 1H), 4.72 (d, J=4.3 Hz, 1H), 4.34 (brs, 1H), 3.81-3.92 (m, 2H), 1.33 (s, 9H).

Step D: ethyl 7-hydroxy-5-oxo-3-(4-(trifluoromethyl)phenyl)-1,2,3,5-tetrahydropyrido[1,2,3-de]quinoxaline-6-carboxylate A mixture of tert-butyl 3-(4-(trifluoromethyl)phenyl)-3,4-dihydroquinoxaline-1(2H)-carboxylate (650 mg, 1.718 mmol)) and triethyl methanetricarboxylate (997 mg, 4.29 mmol) was stirred at 210° C. under N$_2$ atmosphere for 20 min. The reaction mixture was cooled to room temperature and purified by prep-TLC (Petroleum ether: EtOAc=1:1) to give ethyl 7-hydroxy-5-oxo-3-(4-(trifluoromethyl)phenyl)-1,2,3,5-tetrahydropyrido[1,2,3-de]quinoxaline-6-carboxylate as a solid. $^1$H NMR (CDCl$_3$, 400 MHz): δ 14.33 (s, 1H), 7.69 (d, J=8.0 Hz, 1H), 7.52 (d, J=8.0 Hz, 2H), 7.22 (d, J=8.0 Hz, 2H), 7.15 (t, J=8.0 Hz, 1H), 6.95 (d, J=7.5 Hz, 1H), 6.21 (brs, 1H), 4.40-4.54 (m, 2H), 3.69 (dd, J=3.6 Hz, 12.0 Hz, 1H), 3.58-3.61 (m, 1H), 1.44 (t, J=7.3 Hz, 3H).

Step E: tert-butyl 2-(7-hydroxy-5-oxo-3-(4-(trifluoromethyl)phenyl)-1,2,3,5-tetrahydropyrido[1,2,3-de]quinoxaline-6-carboxamido)acetate A solution of ethyl 7-hydroxy-5-oxo-3-(4-(trifluoromethyl)phenyl)-1,2,3,5-tetrahydropyrido[1,2,3-de]quinoxaline-6-carboxylate (50 mg, 0.120 mmol), tert-butyl 2-aminoacetate HCl salt (24.04 mg, 0.143 mmol) and DIPEA (0.048 mL, 0.275 mmol) in toluene (1 mL) was stirred at 120° C. for 2 h. TLC (petroleum ether: EtOAc=5:1) showed that the reaction was completed. The resulting mixture was concentrated in vacuo and the residue was purified by silica gel column chromatography (EtOAc in petroleum ether: 0-30%) to give tert-butyl 2-(7-hydroxy-5-oxo-3-(4-(trifluoromethyl)phenyl)-1,2,3,5-tetrahydropyrido[1,2,3-de]quinoxaline-6-carboxamido)acetate as a solid. $^1$H NMR (CDCl$_3$, 400 MHz): δ 10.52 (brs, 1H), 7.71 (d, J=8.0 Hz, 1H), 7.54 (d, J=8.0 Hz, 2H), 7.21 (d, J=8.0 Hz, 2H), 7.18 (t, J=8.0 Hz, 1H), 6.96 (d, J=7.5 Hz, 1H), 6.23 (brs, 1H), 4.18 (dd, J=6.0 Hz, 18.1 Hz, 1H), 3.97 (dd, J=5.0 Hz, 18.1 Hz, 1H), 3.72 (dd, J=3.2 Hz, 11.2 Hz, 1H), 3.62 (d, J=11.2 Hz, 1H), 1.47 (s, 9H).

Step F: 2-(7-hydroxy-5-oxo-3-(4-(trifluoromethyl)phenyl)-1,2,3,5-tetrahydropyrido[1,2,3-de]quinoxaline-6-carboxamido)acetic acid To a solution of tert-butyl 2-(7-hydroxy-5-oxo-3-(4-(trifluoromethyl)phenyl)-1,2,3,5-tetrahydropyrido[1,2,3-de]quinoxaline-6-carboxamido)acetate (63 mg, 0.119 mmol) in DCM (2 mL) was added 2,2,2-trifluoroacetic acid (136 mg, 1.189 mmol). The resulting mixture was stirred at 30° C. for 3 h. TLC (petroleum ether: EtOAc=2:1) showed that the reaction was complete. The resulting mixture was concentrated in vacuo and the residue was re-crystallised from EtOAc (3 mL) and petroleum ether (5 mL) to give 2-(7-hydroxy-5-oxo-3-(4-(trifluoromethyl)phenyl)-1,2,3,5-tetrahydropyrido[1,2,3-de]quinoxaline-6-carboxamido)acetic acid as a solid. $^1$H NMR (DMSO-d$_6$, 400 MHz): δ 10.40 (t, J=5.6 Hz, 1H), 7.64 (d, J=8.4 Hz, 2H), 7.43 (d, J=8.0 Hz, 1H), 7.24 (d, J=8.0 Hz, 2H), 7.15 (t, J=8.0 Hz, 1H), 7.01 (d, J=7.6 Hz, 1H), 6.42 (s, 1H), 6.15 (s, 1H), 4.01-4.11 (m, 2H), 3.55-3.63 (m, 2H). LC/MS (m/z): 448 (M+H)$^+$. Human HIF-PHD2 IC$_{50}$ 27 nM.

Example 107

2-(7-Hydroxy-1-methyl-5-oxo-3-(4-(trifluoromethyl)phenyl)-1,2,3,5-tetrahydropyrido[1,2,3-de]quinoxaline-6-carboxamido)acetic acid

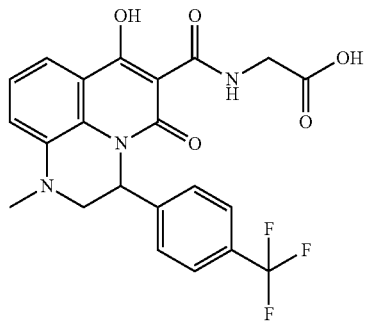 [SMILES: CN1CC(c2ccc(C(F)(F)F)cc2)n2c(=O)c(C(=O)NCC(=O)O)c(O)c3cccc1c32]

Step A: ethyl 7-hydroxy-1-methyl-5-oxo-3-(4-(trifluoromethyl)phenyl)-1,2,3,5 tetrahydropyrido[1,2,3-de]quinoxaline-6-carboxylate A 10 mL vial was charged with Example 106 Step D product (120 mg, 0.287 mmol), formaldehyde (86 mg, 2.87 mmol), formic acid (0.2 mL, 0.287 mmol) and toluene (2 mL). The mixture was stirred at 100° C. for 4 h. LCMS showed the starting material was consumed and the desired compound was formed. The reaction mixture was evaporated in vacuo. The residue was purified by Combi-Flash (EtOAc in petroleum ether: 0-30%) to give ethyl 7-hydroxy-1-methyl-5-oxo-3-(4-(trifluoromethyl)phenyl)-1,2,3,5-tetrahydropyrido[1,2,3-de]quinoxaline-6-carboxylate as a solid. $^1$H NMR (CDCl$_3$, 400 MHz): δ 14.29 (s, 1H), 7.68 (d, J=7.5 Hz, 1H), 7.50 (d, J=8.5 Hz, 2H), 7.21-7.25 (m, 3H), 6.92 (d, J=7.5 Hz, 1H), 6.16 (brs, 1H), 4.40-4.54 (m, 2H), 3.60 (dd, J=3.5 Hz, 11.5 Hz, 1H), 3.42 (dd, J=1.5 Hz, 12.0 Hz, 1H), 2.89 (s, 3H), 1.43 (t, J=7.0 Hz, 3H).

Step B: tert-butyl 2-(7-hydroxy-1-methyl-5-oxo-3-(4-(trifluoromethyl)phenyl)-1,2,3,5-tetrahydropyrido[1,2,3-de]quinoxaline-6-carboxamido)acetate A solution of ethyl 7-hydroxy-1-methyl-5-oxo-3-(4-(trifluoromethyl)phenyl)-1,2,3,5-tetrahydropyrido[1,2,3-de]quinoxaline-6-carboxylate (40 mg, 0.088 mmol), tert-butyl 2-aminoacetate HCl salt (17.68 mg, 0.105 mmol) and DIPEA (0.035 mL, 0.202 mmol) in toluene (1 mL) was stirred at 120° C. for 2 h. TLC (petroleum ether: EtOAc=2:1) showed that the reaction was complete. The resulting mixture was concentrated in vacuo and the residue was purified by silica gel column chromatography (EtOAc in petroleum ether: 0-30%) to give tert-butyl 2-(7-hydroxy-1-methyl-5-oxo-3-(4-(trifluoromethyl)phenyl)-1,2,3,5-tetrahydropyrido [1,2,3-de]quinoxaline-6-carboxamido)acetate as a solid. $^1$H NMR (CDCl$_3$, 400 MHz): δ 10.50 (brs, 1H), 7.71 (d, J=7.5 Hz, 1H), 7.52 (d, J=8.0 Hz, 2H), 7.27 (t, J=8.0 Hz, 1H), 7.21 (d, J=8.0 Hz, 2H), 6.93 (d, J=8.0 Hz, 1H), 6.18 (brs, 1H), 4.17 (dd, J=6.0 Hz, 18.6 Hz, 1H), 3.96 (dd, J=5.0 Hz, 18.1 Hz, 1H), 3.66 (dd, J=3.5 Hz, 12.0 Hz, 1H), 3.44 (d, J=10.5 Hz, 1H), 2.90 (s, 3H), 1.47 (s, 9H).

Step C: 2-(7-hydroxy-1-methyl-5-oxo-3-(4-(trifluoromethyl)phenyl)-1,2,3,5-tetrahydropyrido[1,2,3-de] quinoxaline-6-carboxamido)acetic acid To a solution of tert-butyl 2-(7-hydroxy-1-methyl-5-oxo-3-(4-(trifluoromethyl)phenyl)-1,2,3,5-tetrahydropyrido[1,2,3-de]quinoxaline-6-carboxamido)acetate (31 mg, 0.057 mmol) in DCM (2 mL) was added 2,2,2-trifluoroacetic acid (64.9 mg, 0.569 mmol). The resulting mixture was stirred at 30° C. for 3 h. TLC (petroleum ether: EtOAc=2:1) showed that the reaction was completed. The resulting mixture was concentrated in vacuo and the residue was re-crystallised from EtOAc (1 mL) and petroleum ether (2 mL) to give 2-(7-hydroxy-1-methyl-5-oxo-3-(4-(trifluoromethyl)phenyl)-1,2,3,5-tetrahydropyrido[1,2,3-de]quinoxaline-6-carboxamido)acetic acid as a solid. $^1$H NMR (DMSO-d$_6$, 400 MHz): δ 10.36 (t, J=5.6 Hz, 1H), 7.65 (d, J=8.8 Hz, 2H), 7.54 (d, J=7.6 Hz, 1H), 7.29 (t, J=8.8 Hz, 1H), 7.27 (d, J=8.8 Hz, 2H), 7.05 (d, J=8.0 Hz, 1H), 6.17 (s, 1H), 4.02-4.12 (m, 2H), 3.55-3.66 (m, 2H), 2.83 (s, 3H). LC/MS (m/z): 462 (M+H)$^+$. Human HIF-PHD2 IC$_{50}$ 68 nM.

Example 108

2-(7-Hydroxy-5-oxo-2-(4-(trifluoromethyl)phenyl)-1,2,3,5-tetrahydropyrido[1,2,3-de]quinoxaline-6-carboxamido)acetic acid

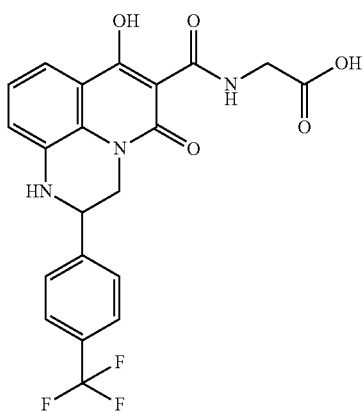 [SMILES: O=C(O)CNC(=O)c1c(O)c2cccc3c2n(c1=O)CC(c1ccc(C(F)(F)F)cc1)N3]

Step A: ethyl 7-hydroxy-5-oxo-2-(4-(trifluoromethyl)phenyl)-1,2,3,5-tetrahydropyrido[1,2,3-de] quinoxaline-6-carboxylate A mixture of Example 106 Step B product (1.391 g, 5 mmol) and triethyl methanetricarboxylate (3.48 g, 15.00 mmol) was stirred at 220-230° C. under N$_2$ atmosphere for 15 min. TLC (petroleum ether: EtOAc=2:1) showed that the starting material was consumed. The reaction mixture was cooled to rt and purified by column chromatography (SiO$_2$, Petroleum ether: EtOAc from 100:0 to 50:50) to give the desired product as a solid.

Step B: tert-butyl 2-(7-hydroxy-5-oxo-2-(4-(trifluoromethyl)phenyl)-1,2,3,5-tetrahydropyrido[1,2,3-de] quinoxaline-6-carboxamido)acetate A solution of ethyl 7-hydroxy-5-oxo-2-(4-(trifluoromethyl)phenyl)-1,2,3,5-tetrahydropyrido[1,2,3-de]quinoxaline-6-carboxylate (500 mg, 1.195 mmol), tert-butyl 2-aminoacetate HCl salt (240 mg, 1.434 mmol) and DIPEA (0.480 mL, 2.75 mmol) in toluene (5 mL) was stirred at 120° C. for 2 h. TLC (petroleum ether: EtOAc=5:1) showed that the reaction was complete. The resulting mixture was concentrated in vacuo and the residue was purified by silica gel column chromatography (EtOAc in petroleum ether: 0-30%) to give tert-butyl 2-(7-hydroxy-5-oxo-2-(4-(trifluoromethyl) phenyl)-1,2,3,5-tetrahydropyrido[1,2,3-de]quinoxaline-6-carboxamido)acetate as a solid. $^1$H NMR (CDCl$_3$, 400 MHz): δ 10.68 (t, J=5.2 Hz, 1H), 7.70 (d, J=8.0 Hz, 2H), 7.64 (dd, J=0.8 Hz, 8.0 Hz, 1H), 7.59 (d, J=8.0 Hz, 2H), 7.14 (d, J=8.0 Hz, 1H), 7.00 (d, J=0.8 Hz, 1H), 4.93 (dd, J=2.8 Hz, 13.2 Hz, 1H), 4.52 (dd, J=6.8 Hz, 10.0 Hz, 1H), 4.40 (brs, 1H), 4.06-4.15 (m, 2H), 3.59 (dd, J=10.0 Hz, 13.6 Hz, 1H), 1.50 (s, 9H).

Step C: 2-(7-hydroxy-5-oxo-2-(4-(trifluoromethyl) phenyl)-1,2,3,5-tetrahydropyrido[1,2,3-de]quinoxaline-6-carboxamido)acetic acid To a solution of tert-butyl 2-(7-hydroxy-5-oxo-2-(4-(trifluoromethyl)phenyl)-1,2,3,5-tetrahydropyrido[1,2,3-de]quinoxaline-6-carboxamido)acetate (350 mg, 0.695 mmol) in DCM (5 mL) was added 2,2,2-trifluoroacetic acid (793 mg, 6.95 mmol). The resulting mixture was stirred at 30° C. for 3 h. TLC (retroleum ether: EtOAc=2:1) showed that the reaction was complete. The resulting mixture was concentrated in vacuo and the residue was re-crystallised from EtOAc (2 mL) and petroleum ether (5 mL) to give 2-(7-hydroxy-5-oxo-2-(4-(trifluoromethyl)phenyl)-1,2,3,5-tetrahydropyrido[1,2,3-de]quinoxaline-6-carboxamido)acetic acid as a solid. $^1$H NMR (DMSO-d$_6$, 400 MHz): δ 10.52 (t, J=5.6 Hz, 1H), 7.79 (d, J=8.4 Hz, 2H), 7.70 (d, J=8.0 Hz, 2H), 7.38 (t, J=7.2 Hz, 1H), 7.11-7.19 (m, 2H), 7.03 (s, 1H), 4.70 (d, J=5.2 Hz, 1H), 4.55 (d, J=11.2 Hz, 1H), 4.11 (d, J=5.2 Hz, 2H), 3.82-3.87 (m, 1H). LC/MS (m/z): 448 (M+H)$^+$. Human HIF-PHD2 IC$_{50}$ 6.5 nM.

Example 109

2-(10-Cyano-7-hydroxy-5-oxo-2-(thiazol-5-yl)-1,2,3,5-tetrahydropyrido[1,2,3-de]quinoxaline-6-carboxamido)acetic acid

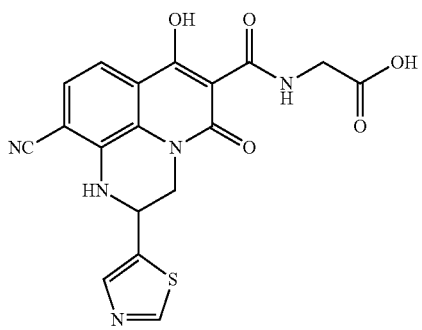 [SMILES: N#Cc1ccc2c(O)c(C(=O)NCC(=O)O)c(=O)n3c2c1NC(c1cncs1)C3]

Step A: 5-(8-bromo-3,4-dihydroquinoxalin-2-yl)thiazole

To a solution of 3-bromobenzene-1,2-diamine (450 mg, 2.406 mmol) in MeOH (10 mL) were added sodium acetate (296 mg, 3.61 mmol) and 2-bromo-1-(thiazol-5-yl)ethanone (HBr salt, 690 mg, 2.406 mmol). The reaction was stirred at room temperature for 20 h. LCMS showed that the reaction was complete. The reaction mixture was filtered and evaporated to give crude 5-(8-bromo-3,4-dihydroquinoxalin-2-yl)thiazole as a solid, which was used in the next step directly.

Step B: 5-(8-bromo-1,2,3,4-tetrahydroquinoxalin-2-yl)thiazole

To a solution of 5-(8-bromo-3,4-dihydroquinoxalin-2-yl)thiazole (1 g, 2.040 mmol) in DCM (15 mL) and MeOH (7.50 mL) were added AcOH (0.5 mL, 8.73 mmol) and sodium cyanoborohydride (0.641 g, 10.20 mmol). The resulting mixture was stirred at room temperature for 2 h. LCMS showed that the reaction was completed. To the mixture was added water (50 mL) and the mixture was extracted with ethyl acacate (3*50 mL). The combined organic fractions were washed with aqueous ammonium chloride (saturated, 3*50 mL), dried ($Na_2SO_4$), filtered and the solvent was evaporated under reduced pressure. The residue was purified by column chromatography on silica gel Biotage 25M (EtOAc in petroleum ether: 0-30%) to give 5-(8-bromo-1,2,3,4-tetrahydroquinoxalin-2-yl)thiazole as an oil. $^1$H NMR (CDCl$_3$, 400 MHz): δ 8.79 (s, 1H), 7.88 (s, 1H), 6.89-6.91 (m, 1H), 6.58-6.60 (m, 1H), 6.53 (d, J=1.1 Hz, 1H), 6.52 (s, 1H), 5.02 (brs, 1H), 4.58 (brs, 1H), 3.61-3.65 (m, 2H).

Step C: ethyl 10-bromo-7-hydroxy-5-oxo-2-(thiazol-5-yl)-1,2,3,5-tetrahydropyrido[1,2,3-de]quinoxaline-6-carboxylate A mixture of 5-(8-bromo-1,2,3,4-tetrahydroquinoxalin-2-yl)thiazole (250 mg, 0.591 mmol) and triethyl methanetricarboxylate (549 mg, 2.363 mmol) was stirred at 230° C. for 15 min. The resulting mixture was cooled to room temperature and purified by silica gel column chromatography (EtOAc in DCM: 0-80%) to give ethyl 10-bromo-7-hydroxy-5-oxo-2-(thiazol-5-yl)-1,2,3,5-tetrahydropyrido[1,2,3-de]quinoxaline-6-carboxylate as a solid.

Step D: tert-butyl 2-(10-bromo-7-hydroxy-5-oxo-2-(thiazol-5-yl)-1,2,3,5-tetrahydropyrido[1,2,3-de]quinoxaline-6-carboxamido)acetate A solution of ethyl 10-bromo-7-hydroxy-5-oxo-2-(thiazol-5-yl)-1,2,3,5-tetrahydropyrido[1,2,3-de]quinoxaline-6-carboxylate (250 mg, 0.573 mmol), tert-butyl 2-aminoacetate HCl salt (115 mg, 0.688 mmol) and DIPEA (0.230 mL, 1.318 mmol) in toluene (5 mL) was stirred at 120° C. for 2 h. TLC (petroleum ether: EtOAc=2:1) showed that the reaction was complete. The resulting mixture was concentrated in vacuo and the residue was purified by silica gel column chromatography (EtOAc in petroleum ether: 0-50%) to give tert-butyl 2-(10-bromo-7-hydroxy-5-oxo-2-(thiazol-5-yl)-1,2,3,5-tetrahydropyrido[1,2,3-de]quinoxaline-6-carboxamido)acetate as a solid. $^1$H NMR (CDCl$_3$, 400 MHz): δ 10.55 (brs, 1H), 8.84 (s, 1H), 7.93 (s, 1H), 7.54 (d, J=8.4 Hz, 1H), 7.39 (d, J=8.8 Hz, 1H), 5.06 (brs, 2H), 4.78 (d, J=12.5 Hz, 1H), 4.31 (t, J=6.6 Hz, 1H), 4.11-4.14 (m, 2H), 1.51 (s, 9H).

Step E: tert-butyl 2-(10-cyano-7-hydroxy-5-oxo-2-(thiazol-5-yl)-1,2,3,5-tetrahydropyrido[1,2,3-de]quinoxaline-6-carboxamido)acetate To a solution of tert-butyl 2-(10-bromo-7-hydroxy-5-oxo-2-(thiazol-5-yl)-3,5-dihydro-2H-[1,4]oxazino[2,3,4-ij]quinoline-6-carboxamido)acetate (70 mg, 0.134 mmol) in DMA (2 mL) were added dicyanozinc (31.5 mg, 0.268 mmol), Pd$_2$(dba)$_3$ (12.27 mg, 0.013 mmol), DPPF (7.43 mg, 0.013 mmol) and zinc (17.52 mg, 0.268 mmol). The reaction solution was heated at 130° C. by microwave for 30 min. TLC (Petroleum ether: EtOAc=1:1) showed that the reaction was complete. The mixture was cooled, water (10 mL) was added and the mixture was extracted with ethyl acetate (3*20 mL). The combined organic fractions were washed with water (3*30 mL), dried ($Na_2SO_4$), filtered and the solvent was evaporated under reduced pressure. The residue was purified by silica gel column chromatography (EtOAc in petroleum ether: 0-60%) to give tert-butyl 2-(10-cyano-7-hydroxy-5-oxo-2-(thiazol-5-yl)-3,5-dihydro-2H-[1,4]oxazino[2,3,4-ij]quinoline-6-carboxamido)acetate as a solid. $^1$H NMR (CDCl$_3$, 400 MHz): δ 10.51 (brs, 1H), 8.86 (s, 1H), 7.94 (s, 1H), 7.64 (d, J=8.4 Hz, 1H), 7.32 (d, J=8.4 Hz, 1H), 5.35 (s, 1H), 5.13 (brs, 1H), 4.77 (d, J=10.5 Hz, 1H), 4.32 (t, J=6.8 Hz, 1H), 4.12-4.18 (m, 2H), 1.51 (s, 9H).

Step F: 2-(10-cyano-7-hydroxy-5-oxo-2-(thiazol-5-yl)-1,2,3,5-tetrahydropyrido[1,2,3-de]quinoxaline-6-carboxamido)acetic acid To a solution of tert-butyl 2-(10-cyano-7-hydroxy-5-oxo-2-(thiazol-5-yl)-1,2,3,5-tetrahydropyrido[1,2,3-de]quinoxaline-6-carboxamido)acetate (30 mg, 0.061 mmol) in DCM (2 mL) was added 2,2,2-trifluoroacetic acid (69.5 mg, 0.610 mmol). The resulting mixture was stirred at 30° C. for 3 h. TLC (petroleum ether: EtOAc=2:1) showed that the reaction was complete. The resulting mixture was concentrated in vacuo and the residue was re-crystallised from EtOAc (1 mL) and petroleum ether (2 mL) to give 2-(10-cyano-7-hydroxy-5-oxo-2-(thiazol-5-yl)-1,2,3,5-tetrahydropyrido[1,2,3-de]quinoxaline-6-carboxamido)acetic acid as a solid. $^1$H NMR (DMSO-d$_6$, 400 MHz): δ 8.92 (s, 1H), 7.77 (s, 1H), 7.55 (s, 1H), 7.42 (s, 1H), 7.23 (s, 1H), 5.31 (s, 1H), 4.65-4.82 (m, 2H), 3.65 (s, 2H). LC/MS (m/z): 412 (M+H)⁺. Human HIF-PHD2 IC$_{50}$ 4.2 nM.

Example 110

2-(7-Hydroxy-5-oxo-2-(thiazol-5-yl)-1,2,3,5-tetrahydropyrido[1,2,3-de]quinoxaline-6-carboxamido)acetic acid

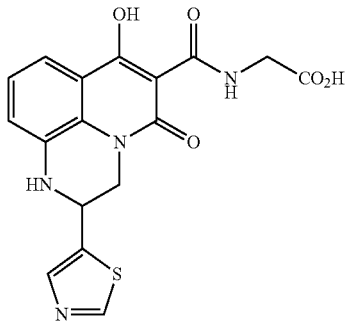 [SMILES: O=C(O)CNC(=O)c1c(O)c2cccc3c2n(c1=O)CC(c1cncs1)N3]

And Example 111

2-(7-Hydroxy-5-oxo-3-(thiazol-5-yl)-1,2,3,5-tetrahydropyrido[1,2,3-de]quinoxaline-6-carboxamido)acetic acid

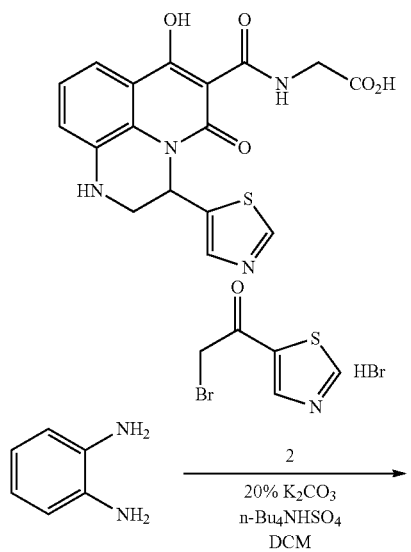

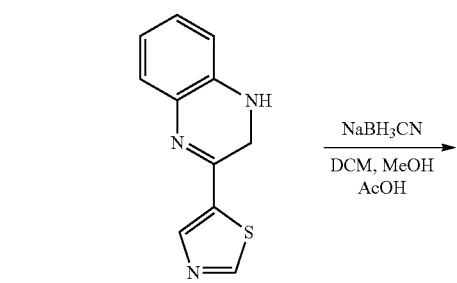

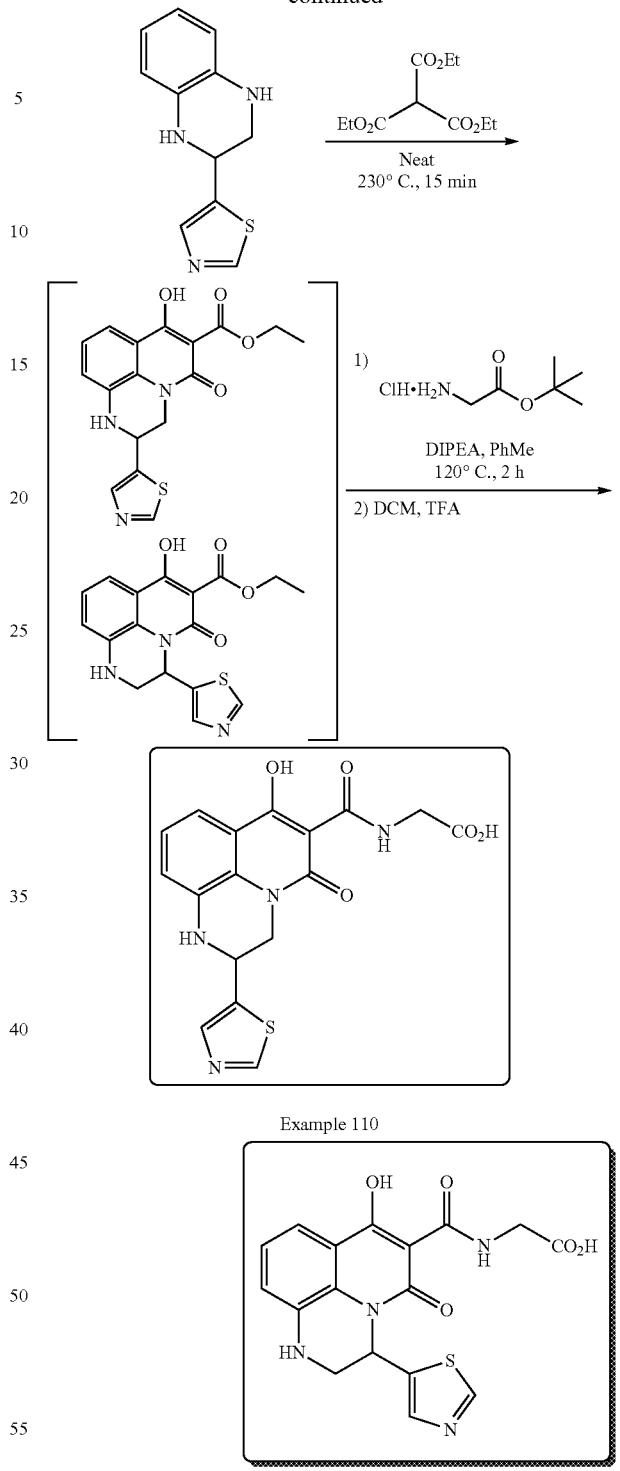

Step A: 5-(3,4-dihydroquinoxalin-2-yl)thiazole

To a solution of benzene-1,2-diamine (0.377 g, 3.48 mmol) in DCM (15 mL) were added K$_2$CO$_3$ (15 mL, 3.48 mmol) and tetrabutylammonium hydrogen sulfate (0.012 g, 0.035 mmol). Then 2-bromo-1-(thiazol-5-yl)ethanone (HBr salt, 1 g, 3.48 mmol) in DCM (10 mL) was added dropwise and the reaction mixture stirred at room temperature for 20 h. The resulting mixture was extracted with DCM (20 mL*3). The combined organic layers were washed with brine (20 mL*3), dried over $Na_2SO_4$, filtered and concentrated in vacuo to give 5-(3,4-dihydroquinoxalin-2-yl)thiazole as an oil which was used for the next step directly.

Step B:
5-(1,2,3,4-tetrahydroquinoxalin-2-yl)thiazole

To a solution of 5-(3,4-dihydroquinoxalin-2-yl)thiazole (4.2 g, 9.75 mmol) in DCM (30 mL) and MeOH (15 mL) were added AcOH (0.5 mL, 8.73 mmol) and sodium cyanoborohydride (3.07 g, 48.8 mmol). The resulting mixture was stirred at room temperature for 2 h. LCMS showed that the reaction was complete. To the mixture was added water (50 mL) and the mixture was extracted with ethyl acetate (3*50 mL). The combined organic fractions were washed with aqueous ammonium chloride (saturated, 3*50 mL), dried ($Na_2SO_4$), filtered and the solvent was evaporated under reduced pressure. The residue was purified by column chromatography on silica gel Biotage 25M (EtOAc in petroleum ether: 0-50%) to give 5-(1,2,3,4-tetrahydroquinoxalin-2-yl)thiazole as an oil. $^1$H NMR ($CDCl_3$, 400 MHz): δ 8.93 (s, 1H), 7.89 (s, 1H), 6.70-6.75 (m, 2H), 6.65 (t, J=4.8 Hz, 1H), 6.55 (d, J=5.2 Hz, 1H), 5.03 (s, 1H), 4.15 (brs, 1H), 3.67 (dd, J=2.4 Hz, 11.2 Hz, 1H), 3.29 (dd, J=3.6 Hz, 11.2 Hz, 2H).

Step C: ethyl 7-hydroxy-5-oxo-2-(thiazol-5-yl)-1,2,3,5-tetrahydropyrido[1,2,3-de]quinoxaline-6-carboxylate and ethyl 7-hydroxy-5-oxo-3-(thiazol-5-yl)-1,2,3,5-tetrahydropyrido[1,2,3-de]quinoxaline-6-carboxylate The solution of 5-(1,2,3,4-tetrahydroquinoxalin-2-yl)thiazole (1 g, 2.76 mmol) in triethyl methanetricarboxylate (2.57 g, 11.05 mmol) was stirred at 210° C. for 5 min. The resulting mixture was cooled to room temperature and purified by silica gel column chromatography (EtOAc in DCM: 0-30%) to give a mixture of (ethyl 7-hydroxy-5-oxo-3-(thiazol-5-yl)-1,2,3,5-tetrahydropyrido[1,2,3-de]quinoxaline-6-carboxylate and ethyl 7-hydroxy-5-oxo-2-(thiazol-5-yl)-1,2,3,5-tetrahydropyrido[1,2,3-de]quinoxaline-6-carboxylate) as a solid.

Step D: 2-(7-hydroxy-5-oxo-2-(thiazol-5-yl)-1,2,3,5-tetrahydropyrido[1,2,3-de]quinoxaline-6-carboxamido)acetic acid and 2-(7-hydroxy-5-oxo-3-(thiazol-5-yl)-1,2,3,5-tetrahydropyrido[1,2,3-de]quinoxaline-6-carboxamido)acetic acid A solution of ethyl 7-hydroxy-5-oxo-3-(thiazol-5-yl)-1,2,3,5-tetrahydropyrido[1,2,3-de]quinoxaline-6-carboxylate (192 mg, 0.537 mmol) and ethyl 7-hydroxy-5-oxo-3-(thiazol-5-yl)-1,2,3,5-tetrahydropyrido[1,2,3-de]quinoxaline-6-carboxylate (192 mg, 0.537 mmol), tert-butyl 2-aminoacetate HCl (108 mg, 0.645 mmol) and DIPEA (0.216 mL, 1.236 mmol) in toluene (5 mL) was stirred at 120° C. for 2 h. TLC (petroleum ether: EtOAc=2:1) showed that the reaction was complete. The resulting mixture was concentrated in vacuo and the residue was purified by silica gel column chromatography (EtOAc in petroleum ether: 0-30%) to give a mixture of (tert-butyl 2-(7-hydroxy-5-oxo-2-(thiazol-5-yl)-1,2,3,5-tetrahydropyrido[1,2,3-de]quinoxaline-6-carboxamido)acetate and ethyl 7-hydroxy-5-oxo-3-(thiazol-5-yl)-1,2,3,5-tetrahydropyrido[1,2,3-de]quinoxaline-6-carboxylate) as a solid.

To a solution of tert-butyl 2-(7-hydroxy-5-oxo-2-(thiazol-5-yl)-1,2,3,5-tetrahydropyrido[1,2,3-de]quinoxaline-6-carboxamido)acetate (120 mg, 0.244 mmol) and tert-butyl 2-(7-hydroxy-5-oxo-3-(thiazol-5-yl)-1,2,3,5-tetrahydropyrido[1,2,3-de]quinoxaline-6-carboxamido)acetate (30 mg, 0.061 mmol) in DCM (2 mL) was added 2,2,2-trifluoroacetic acid (278 mg, 2.441 mmol). The resulting mixture was stirred at 30° C. for 3 h. TLC (petroleum ether: EtOAc=2:1) showed that the reaction was completed. The resulting mixture was concentrated in vacuo and the residue was purified by HPLC (Column: Gemini 150*23.5mm*5 um; Mobile phase: From 26% MeCN in water (0.225% FA) to 56% MeCN in water (0.225% FA); Wavelength: 220 nm) to give a solid. This mixture was separated by SFC (Instrument: MG II; Column: Chiral Pak OJ, 5 μm, Daicel Chemical Industries, Ltd 250×30 mm I.D.; Mobile phase: A: Supercritical $CO_2$, B: MeOH(contained 0.1% $NH_3$ in $H_2O$), A:B=70:30 at 60 ml/min; Column Temp: 38° C.; Wavelength: 220 nm; Nozzle Pressure: 100Bar; Nozzle Temp: 60° C.; Evaporator Temp: 20° C.; Trimmer Temp: 25° C.) to give 2-(7-hydroxy-5-oxo-2-(thiazol-5-yl)-1,2,3,5-tetrahydropyrido[1,2,3-de]quinoxaline-6-carboxamido)acetic acid (Example 110) and 2-(7-hydroxy-5-oxo-3-(thiazol-5-yl)-1,2,3,5-tetrahydropyrido[1,2,3-de]quinoxaline-6-carboxamido)acetic acid (Example 111).

$^1$H NMR (Example 110) (DMSO-$d_6$, 400 MHz): δ 10.58 (s, 1H), 8.93 (s, 1H), 7.87 (s, 1H), 7.42 (d, J=7.2 Hz, 1H), 7.02-7.09 (m, 2H), 6.85 (s, 1H), 5.12 (s, 1H), 4.22-4.31 (m, 2H), 3.91 (s, 2H). LC/MS (m/z): 387 (M+H)$^+$. Human HIF-PHD2 $IC_{50}$ 12 nM.

$^1$H NMR (Example 111) (DMSO-$d_6$, 400 MHz): δ 8.91 (s, 1H), 7.91 (s, 1H), 7.41 (s, 1H), 6.85 (m, 2H), 6.47 (s, 2H), 3.87 (s, 2H), 3.51 (s, 2H). LC/MS (m/z): 387 (M+H)$^+$. Human HIF-PHD2 $IC_{50}$ 15 nM.

Example 112
2-(7-Hydroxy-1-methyl-5-oxo-2-(thiazol-5-yl)-1,2,3,5-tetrahydropyrido[1,2,3-de]quinoxaline-6-carboxamido)acetic acid
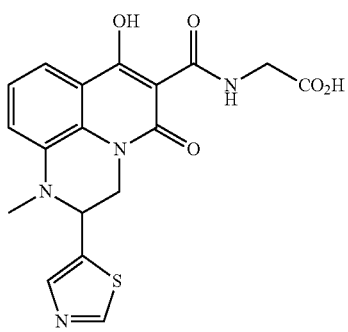 [SMILES: CN1c2cccc3c(O)c(C(=O)NCC(=O)O)c(=O)n(c23)CC1c1cncs1]
And Example 113
2-(7-Hydroxy-1-methyl-5-oxo-3-(thiazol-5-yl)-1,2,3,5-tetrahydropyrido[1,2,3-de]quinoxaline-6-carboxamido)acetic acid
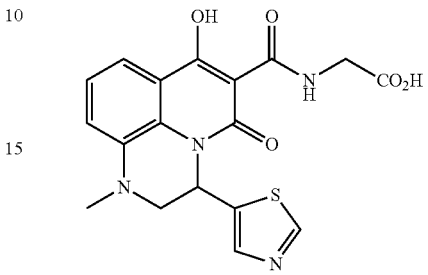
Scheme
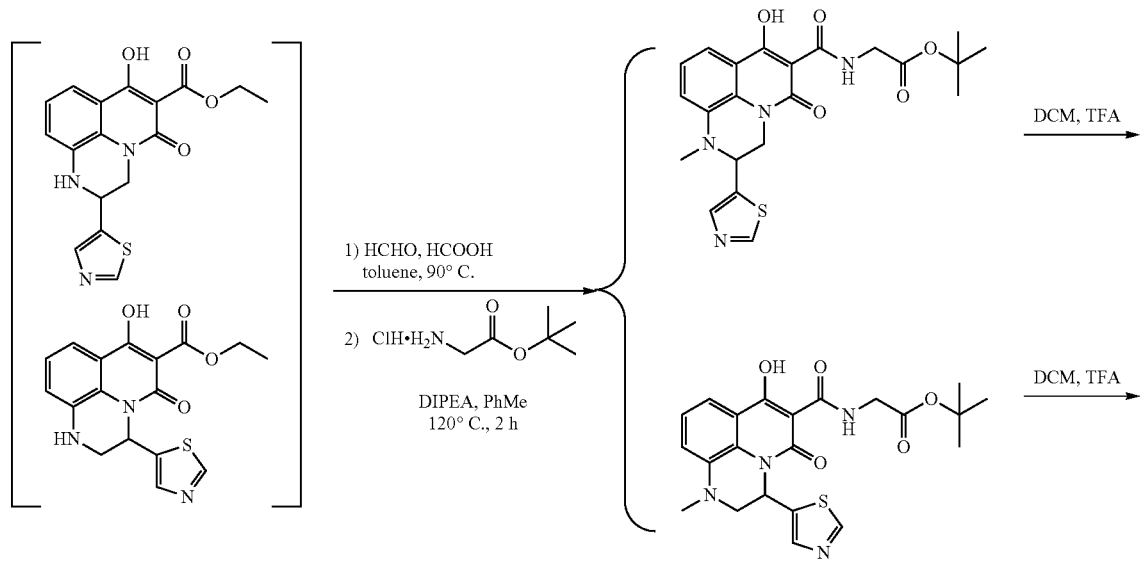
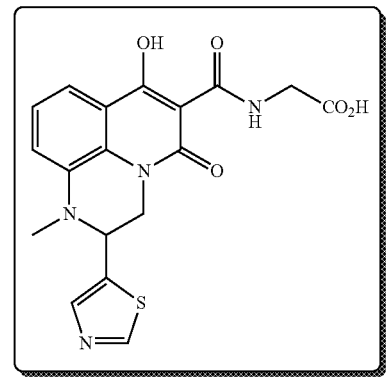
Example 112

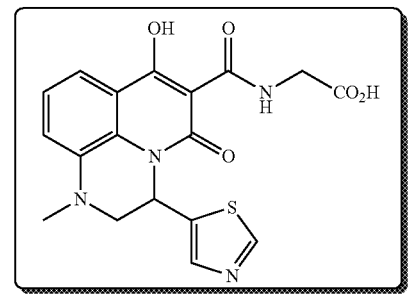

Example 113

Step A: tert-butyl 2-(7-hydroxy-1-methyl-5-oxo-2-(thiazol-5-yl)-1,2,3,5-tetrahydropyrido[1,2,3-de]quinoxaline-6-carboxamido)acetate and tert-butyl 2-(7-hydroxy-1-methyl-5-oxo-3-(thiazol-5-yl)-1,2,3,5-tetrahydropyrido[1,2,3-de]quinoxaline-6-carboxamido)acetate A 10 mL vial was charged with ethyl 7-hydroxy-5-oxo-2-(thiazol-5-yl)-1,2,3,5-tetrahydropyrido[1,2,3-de]quinoxaline-6-carboxylate (105 mg, 0.235 mmol), ethyl 7-hydroxy-5-oxo-3-(thiazol-5-yl)-1,2,3,5-tetrahydropyrido[1,2,3-de]quinoxaline-6-carboxylate (35 mg, 0.078 mmol), formaldehyde (70.6 mg, 2.350 mmol), formic acid (0.1 mL, 0.235 mmol) and toluene (1 mL). The mixture was heated to 100° C. and stirred for 4 hr. LCMS showed the starting material was consumed and the desired compound was formed. The reaction mixture was evaporated in vacuo. The residue was purified by column chromatography on silica gel (EtOAC in petroleum: 0-60%) to give a mixture (ethyl 7-hydroxy-1-methyl-5-oxo-2-(thiazol-5-yl)-1,2,3,5-tetrahydropyrido[1,2,3-de]quinoxaline-6-carboxylate and ethyl 7-hydroxy-1-methyl-5-oxo-3-(thiazol-5-yl)-1,2,3,5-tetrahydropyrido[1,2,3-de]quinoxaline-6-carboxylate) as a solid.

A solution of ethyl 7-hydroxy-1-methyl-5-oxo-3-(thiazol-5-yl)-1,2,3,5-tetrahydropyrido[1,2,3-de]quinoxaline-6-carboxylate (25 mg, 0.067 mmol), ethyl 7-hydroxy-1-methyl-5-oxo-3-(thiazol-5-yl)-1,2,3,5-tetrahydropyrido[1,2,3-de]quinoxaline-6-carboxylate (25 mg, 0.067 mmol), tert-butyl 2-aminoacetate HCl salt (46.0 mg, 0.275 mmol) and DIPEA (0.092 mL, 0.526 mmol) in toluene (5 mL) was stirred at 120° C. for 2 h. TLC (petroleum ether: EtOAc=2:1) showed that the reaction was complete. The resulting mixture was concentrated in vacuo and the residue was purified by prep TLC (petroleum ether: EtOAc=2:1) to give tert-butyl 2-(7-hydroxy-1-methyl-5-oxo-2-(thiazol-5-yl)-1,2,3,5-tetrahydropyrido[1,2,3-de]quinoxaline-6-carboxamido)acetate as a solid and ethyl 7-hydroxy-1-methyl-5-oxo-3-(thiazol-5-yl)-1,2,3,5-tetrahydropyrido[1,2,3-de]quinoxaline-6-carboxylate as a solid. $^1$H NMR (CDCl$_3$, 400 MHz): δ 10.63 (brs, 1H), 8.64 (s, 1H), 7.74 (s, 1H), 7.67 (d, J=8.0 Hz, 1H), 7.23 (t, J=8.0 Hz, 1H), 6.85 (d, J=7.6 Hz, 1H), 5.05 (brs, 1H), 4.99 (d, J=13.4 Hz, 1H), 4.12-4.15 (m, 3H), 2.94 (s, 3H), 1.50 (s, 9H). $^1$H NMR (CDCl$_3$, 400 MHz): δ 10.61 (brs, 1H), 8.69 (s, 1H), 8.12 (s, 1H), 7.65 (d, J=8.0 Hz, 1H), 7.24 (brs, 1H), 6.99 (d, J=8.4 Hz, 1H), 6.59 (s, 1H), 4.19 (dd, J=6.0 Hz, 1H), 3.98-4.02 (m, 2H), 3.61 (d, J=11.6 Hz, 1H), 3.09 (s, 3H), 1.51 (s, 9H).

Step B: 2-(7-hydroxy-1-methyl-5-oxo-2-(thiazol-5-yl)-1,2,3,5-tetrahydropyrido[1,2,3-de]quinoxaline-6-carboxamido)acetic acid (Example 112)

To a solution of tert-butyl 2-(7-hydroxy-1-methyl-5-oxo-2-(thiazol-5-yl)-1,2,3,5-tetrahydropyrido[1,2,3-de]quinoxaline-6-carboxamido)acetate (19 mg, 0.040 mmol) in DCM (2 mL) was added 2,2,2-trifluoroacetic acid (45.1 mg, 0.395 mmol). The resulting mixture was stirred at 30° C. for 3 h. TLC (petroleum ether: EtOAc=2:1) showed that the reaction was complete. The resulting mixture was concentrated in vacuo and the residue was recrystallised from EtOAc (1 mL) and petroleum ether (3 mL) to give 2-(7-hydroxy-1-methyl-5-oxo-2-(thiazol-5-yl)-1,2,3,5-tetrahydropyrido[1,2,3-de]quinoxaline-6-carboxamido)acetic acid as a solid (Example 112). $^1$H NMR (DMSO-d$_6$, 400 MHz): δ 10.44 (s, 1H), 8.84 (s, 1H), 7.84 (s, 1H), 7.47 (d, J=8.0 Hz, 1H), 7.24 (s, 1H), 6.95 (s, 1H), 5.41 (s, 1H), 5.31 (s, 1H), 4.85 (d, J=13.6 Hz, 1H), 3.98-4.05 (m, 2H), 2.80-2.88 (m, 3H). LC/MS (m/z): 401 (M+H)$^+$. Human HIF-PHD2 IC$_{50}$ 29 nM.

2-(7-hydroxy-1-methyl-5-oxo-3-(thiazol-5-yl)-1,2,3,5-tetrahydropyrido[1,2,3-de]quinoxaline-6-carboxamido)acetic acid (Example 113)

To a solution of tert-butyl 2-(7-hydroxy-1-methyl-5-oxo-3-(thiazol-5-yl)-1,2,3,5-tetrahydropyrido[1,2,3-de]quinoxaline-6-carboxamido)acetate (20 mg, 0.020 mmol) in DCM (2 mL) was added 2,2,2-trifluoroacetic acid (22.48 mg, 0.197 mmol). The resulting mixture was stirred at 30° C. for 3 h. TLC (petroleum ether: EtOAc=2:1) showed that the reaction was complete. The resulting mixture was concentrated in vacuo and the residue was recrystallised from EtOAc (1 mL) and petroleum ether (2 mL) to give 2-(7-hydroxy-1-methyl-5-oxo-3-(thiazol-5-yl)-1,2,3,5-tetrahydropyrido[1,2,3-de]quinoxaline-6-carboxamido)acetic acid as a solid (Example 113). $^1$H NMR (DMSO-d$_6$, 400 MHz): δ 8.96 (s, 1H), 7.95 (s, 1H), 7.62-7.66 (m, 1H), 7.13 (s, 1H), 6.97 (s, 1H), 6.52 (s, 1H), 4.00-4.07 (m, 2H), 3.41-3.51 (m, 2H), 3.04 (d, J=8.8 Hz, 3H). LC/MS (m/z): 401 (M+H)$^+$. Human HIF-PHD2 IC$_{50}$ 125 nM.

Example 114

2-(10-Cyano-7-hydroxy-5-oxo-2-(4-(trifluoromethyl)phenyl)-1,2,3,5-tetrahydropyrido[1,2,3-de]quinoxaline-6-carboxamido)acetic acid

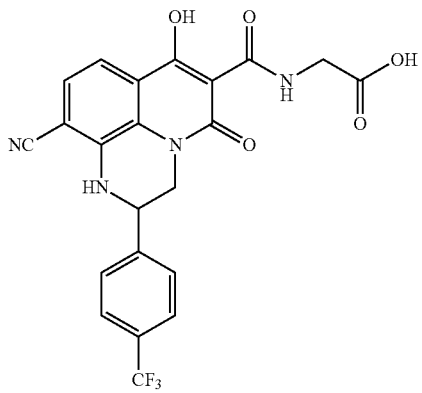 [SMILES: N#Cc1ccc2c(O)c(C(=O)NCC(=O)O)c(=O)n3c2c1NC(c1ccc(C(F)(F)F)cc1)C3]

Step A: 3-bromobenzene-1,2-diamine

To a solution of 3-bromo-2-nitroaniline (5 g, 23.04 mmol) in ethanol (80 mL) was added tin(II) chloride dihydrate (26.0 g, 115 mmol). The reaction was heated to 80° C. and stirred for 2 h. The reaction mixture was cooled to room temperature and the ethanol was evaporated under reduced pressure. The mixture was neutralized with saturated aqueous $NaHCO_3$ and extracted with EtOAc (100 mL*3). The EtOAc extracts were washed with saturated $NaHCO_3$, dried over $Na_2SO_4$, filtered and concentrated to give 3-bromobenzene-1,2-diamine as a solid. $^1$H NMR (CDCl$_3$, 400MHz) δ 6.98 (d, J=8.0 Hz, 1H), 6.65 (d, J=6.8 Hz, 1H), 6.57 (t, J=8.0 Hz, 1H), 3.63 (brs, 2H).

Step B: 5-bromo-3-(4-(trifluoromethyl)phenyl)-1,2-dihydroquinoxaline

To a solution of 3-bromobenzene-1,2-diamine (370 mg, 1.978 mmol) in MeOH (15 mL) was added sodium acetate (162 mg, 1.978 mmol), then 2-bromo-1-(4-(trifluoromethyl)phenyl)ethanone (528 mg, 1.978 mmol) was added dropwise. The reaction mixture was stirred at room temperature overnight. TLC (Petroleum ether: EtOAc=5:1) showed that the reaction was complete. The reaction mixture was diluted by water (20 mL) and extracted by EtOAc (3*20 mL). The organic layers were dried over $Na_2SO_4$ and evaporated under reduced pressure to give 5-bromo-3-(4-(trifluoromethyl)phenyl)-1,2-dihydroquinoxaline as a solid, which was directly used in the next step.

Step C: 8-bromo-2-(4-(trifluoromethyl)phenyl)-1,2,3,4-tetrahydroquinoxaline

To a solution of 5-bromo-3-(4-(trifluoromethyl) phenyl)-1,2-dihydroquinoxaline (483 mg, 1.360 mmol) in THF(20 mL) was added BH$_3$-DMS (1.3 mL, 13.60 mmol) dropwise over 5 mins. The reaction mixture was stirred at room temperature for 1 hr. TLC (petroleum ether: EtOAc=5:1) showed that the starting material was consumed. MeOH (20 mL) was added dropwise to quench the reaction. The solvent was then evaporated to give the crude product, which was further purified by column-chromatography (EtOAc in Petroleum ether=0-10%) to give 8-bromo-2-(4-(trifluoromethyl)phenyl)-1,2,3,4-tetrahydroquinoxaline as a solid. $^1$H NMR (CDCl$_3$, 400 MHz) δ 7.64 (d, J=8.0 Hz, 2H), 7.51 (d, J=8.4 Hz, 2H), 6.89-6.94 (m, 1H), 6.52 (d, J=4.40 Hz, 2H), 4.64 (t, J=4.4 Hz, 1H), 4.53 (brs, 1H), 3.51 (dd, J=10.8, 2.8 Hz, 1H), 3.30 (dd, J=10.8, 7.2 Hz, 1H).

Step D: ethyl 10-bromo-7-hydroxy-5-oxo-2-(4-(trifluoromethyl)phenyl)-1,2,3,5-tetrahydropyrido[1,2,3-de]quinoxaline-6-carboxylate A 10 mL thumb bottle was charged with 8-bromo-2-(4-(trifluoromethyl)phenyl)-1,2,3,4-tetrahydroquinoxaline (450 mg, 1.260 mmol) and triethyl methanetricarboxylate (1.17 g, 5.04 mmol), and the reaction mixture was stirred at 220° C. under nitrogen for 20 mins. TLC (petroleum ether: EtOAc=2:1) showed that the starting material was consumed. After cooling to rt, to the reaction mixture was added petroleum ether (15 mL) with stirring. Yellow solid appeared, then the suspension was filtered. The filter cake was dried in vacuo to give ethyl 10-bromo-7-hydroxy-2-(4-(trifluoromethyl)phenyl)-1,2,3,5-tetrahydropyrido[1,2,3-de]quinoxaline-6-carboxylate as a solid. $^1$H NMR (CDCl$_3$, 400 MHz) δ 14.22 (s, 1H), 7.71 (d, J=8.0 Hz, 2H), 7.57 (d, J=8.0 Hz, 2H), 7.50 (d, J=9.2 Hz, 1H), 7.36 (d, J=9.2 Hz, 1H), 4.89-4.93 (m, 1H), 4.48-4.56 (m, 3H), 3.66 (dd, J=9.2, 13.6 Hz, 1H), 1.47 (t, J=7.2 Hz, 3H).

Step E: tert-butyl 2-(10-bromo-7-hydroxy-5-oxo-2-(4-(trifluoromethyl)phenyl)-1,2,3,5-tetrahydropyrido[1,2,3-de]quinoxaline-6-carboxamido)acetate To a solution of ethyl 10-bromo-7-hydroxy-5-oxo-2-(4-(trifluoromethyl)phenyl)-3,5-dihydro-2H-[1,4]oxazino[2,3,4-ij]quinoline-6-carboxylate (200 mg, 0.401 mmol) and tert-butyl 2-aminoacetate HCl salt (81 mg, 0.482 mmol) in PhCH$_3$ (20 mL) was added DIPEA (0.21 mL, 1.204 mmol). The reaction mixture was stirred and heated to 120° C. for 2 h. TLC (Petroleum ether: EtOAc=3:1) showed that the starting material was consumed. The solvent was evaporated and the residue was further purified by column-chromatography (EtOAc: Petroleum ether=0-20%) to give the tert-butyl 2-(10-bromo-7-hydroxy-5-oxo-2-(4-(trifluoromethyl) phenyl)-3,5-dihydro-2H-[1,4]oxazino[2,3,4-ij]quinoline-6-carboxamido)acetate as a solid. $^1$H NMR (CDCl$_3$, 400 MHz) δ 10.59 (brs, 1H), 7.73(d, J=8.0 Hz, 2H), 7.60 (d, J=8.4 Hz, 2H), 7.52 (d, J=8.8 Hz, 1H), 7.39 (d, J=8.8 Hz, 1H), 4.95 (s, 1H), 4.59 (d, J=7.2 Hz, 1H), 4.07-4.20 (m, 2H), 3.68 (dd, J=12.8, 9.2Hz, 1 H), 1.50 (s, 9H).

Step F: tert-butyl 2-(10-cyano-7-hydroxy-5-oxo-2-(4-(trifluoromethyl)phenyl)-1,2,3,5-tetrahydropyrido[1,2,3-de]quinoxaline-6-carboxamido)acetate To a solution of 2-(10-bromo-7-hydroxy-5-oxo-2-(4-(trifluoromethyl)phenyl)-3,5-dihydro-2H-[1,4]oxazino[2,3,4-ij]quinoline-6-carboxamido)acetate (46.6 mg, 0.088 mmol) in DMA (5 mL) were added dicyanozinc (20.7 mg, 0.176 mmol), Pd$_2$(dba)$_3$ (8.1 mg, 8.80 μmol), DPPF (4.9 mg, 8.80 μmol) and zinc (11.5 mg, 0.176 mmol). The reaction solution was heated at 120° C. with microwave for 30 min. TLC (Petroleum ether: EtOAc=2:1) showed that the reaction was complete. The mixture was cooled, water (20 mL) was added and the mixture was extracted with EtOAc (3*20 mL). The combined organic fractions were washed with water (3*30 mL), dried over $Na_2SO_4$ and filtered. The organic layers were evaporated under reduced pressure. The residue was purified by Combi-Flash (EtOAc in petroleum ether: 0-60%) to give tert-butyl 2-(10-cyano-7-hydroxy-2-(4-(trifluoromethyl)phenyl)-1,2,3,5-tetrahydropyrido[1,2,3-de]quinoxaline-6-carboxamido)acetate as a solid. $^1$H NMR (CDCl$_3$, 400 MHz) δ 10.51 (brs, 1H), 7.74 (d, J=8.0 Hz, 2H), 7.62 (d, J=8.0 Hz, 1H), 7.59 (d, J=8.0 Hz, 2H), 7.32 (d, J=8.4 Hz, 1H), 5.28 (s, 1 H), 4.94 (d, J=12.0Hz, 1 H), 4.67-4.70 (m, 1H), 4.06-4.18 (m, 2H), 3.72 (dd, J=13.6, 9.6 Hz, 1H), 1.50 (s, 9H).

Step G: 2-(10-cyano-7-hydroxy-5-oxo-2-(4-(trifluoromethyl)phenyl)-1,2,3,5-tetrahydropyrido[1,2,3-de]quinoxaline-6-carboxamido)acetic acid To a solution of tert-butyl 2-(10-cyano-7-hydroxy-2-(4-(trifluoromethyl)phenyl)-1,2,3,5-tetrahydropyrido[1,2,3-de]quinoxaline-6-carboxamido)acetate (50 mg, 0.097 mmol) in DCM (5 mL) was added TFA (1 mL). The reaction solution was stirred at room temperature for 3 h. TLC (petroleum ether: EtOAc=2:1) showed that the reaction was complete. The solvent was evaporated under reduced pressure. The crude product was further purified by recrystallation (pure EtOAc) to give 2-(10-cyano-7-hydroxy-2-(4-(trifluoromethyl)phenyl)-1,2,3,5-tetrahydropyrido[1,2,3-de]quinoxaline-6-carboxamido)acetic acid as a solid. $^1$H NMR (DMSO-d$_6$, 400 MHz) δ 10.33 (s, 1H), 7.81 (s, 1H), 7.71 (d, J=6.8 Hz, 2H), 7.53 (d, J=8.0 Hz, 2H), 7.42 (d, J=8.0 Hz, 1H), 7.31 (d, J=8.4 Hz, 1H), 4.97 (s, 1H), 4.40 (dd, J=5.6, 13.2 Hz, 1H), 4.25 (d, J=3.6 Hz, 1H), 4.06 (d, J=4.0 Hz, 2H). LC/MS (m/z): 473 (M+H)$^+$. Human HIF-PHD2 IC$_{50}$ 1.0 nM.

Example 115

2-(10-Fluoro-7-hydroxy-5-oxo-3-(4-(trifluoromethyl)phenyl)-1,2,3,5-tetrahydropyrido[1,2,3-de]quinoxaline-6-carboxamido)acetic acid

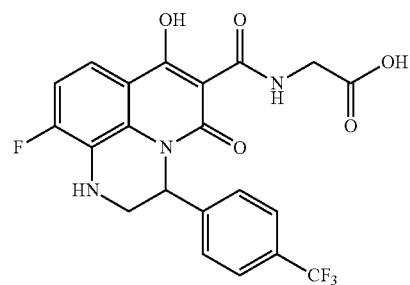 [SMILES: O=C(O)CNC(=O)c1c(O)c2ccc(F)c3c2n(c1=O)C(c1ccc(C(F)(F)F)cc1)CN3]

And Example 116

2-(10-Fluoro-7-hydroxy-5-oxo-2-(4-(trifluoromethyl)phenyl)-1,2,3,5-tetrahydropyrido[1,2,3-de]quinoxaline-6-carboxamido)acetic acid

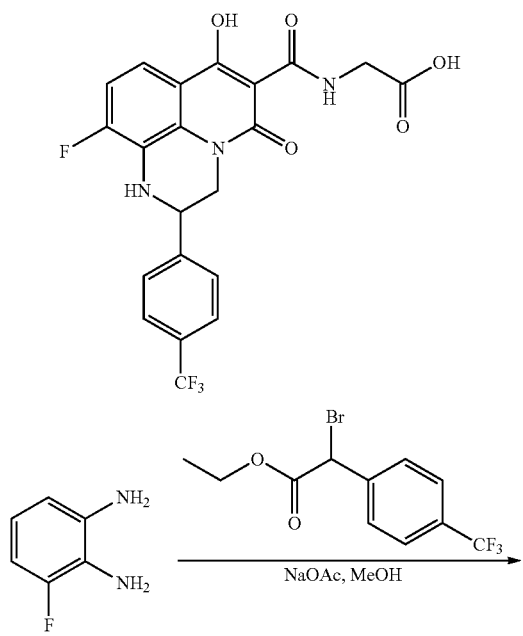

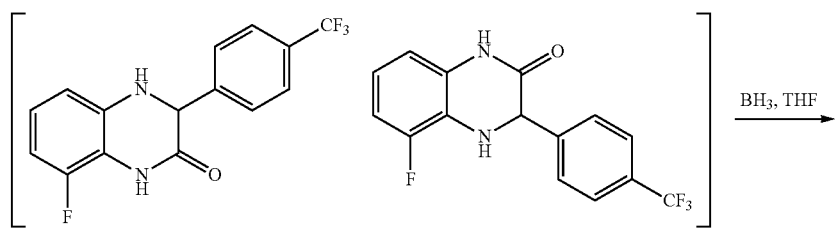

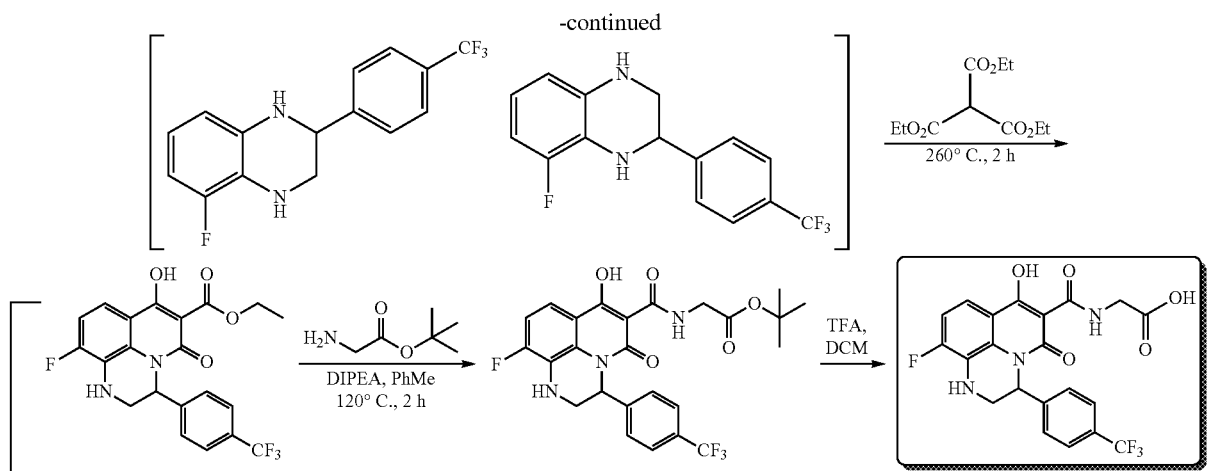

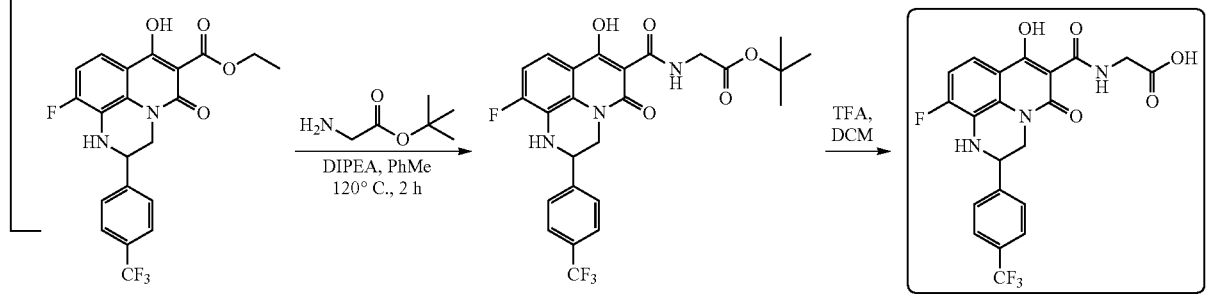

Example 115

Example 116

Step A: 8-fluoro-3-(4-(trifluoromethyl)phenyl)-3,4-dihydroquinoxalin-2(1H)-one and 5-fluoro-3-(4-(trifluoromethyl)phenyl)-3,4-dihydroquinoxalin-2(1H)-one To a solution of 3-fluorobenzene-1,2-diamine (1.0 g, 7.93 mmol) in toluene (30 mL) was added DIPEA (2.77 mL, 15.86 mmol) and then ethyl 2-bromo-2-(4-(trifluoromethyl)phenyl)acetate (2.96 g, 9.51 mmol) was added dropwise over 10 mins. The reaction mixture was stirred at room temperature overnight. TLC (petroleum ether: EtOAc=5:1) showed that the reaction was complete. The solvent was evaporated under reduced pressure and the residue was purified by silica gel column chromatography (EtOAc in petroleum ether, 0-20%) to get the mixture (8-fluoro-3-(4-(trifluoromethyl)phenyl)-3,4-dihydroquinoxalin-2(1H)-one and 5-fluoro-3-(4-(trifluoromethyl)phenyl)-3,4-dihydroquinoxalin-2(1H)-one) as a solid.

Step B: 5-fluoro-2-(4-(trifluoromethyl)phenyl)-1,2,3,4-tetrahydroquinoxaline and 8-fluoro-2-(4-(trifluoromethyl)phenyl)-1,2,3,4-tetrahydroquinoxaline The mixture of 3-(4-bromophenyl)-8-fluoro-3,4-dihydroquinoxalin-2(1H)-one and 5-fluoro-3-(4-(trifluoromethyl)phenyl)-3,4-dihydroquinoxalin-2(1H)-one (2.0 g, 6.45 mmol) was dissolved in THF (30 mL), then BH$_3$-DMS (4.73 mL, 49.8 mmol) was added dropwise. The reaction mixture was stirred at room temperature for 3 h. TLC (Petroleum ether: EtOAc=5:1) showed that the reaction was complete. The solvent was evaporated under reduced pressure. The residue was purified by column chromatography (EtOAc in Petroleum ether=0-20%) to give a mixture (2-(4-bromophenyl)-5-fluoro-1,2,3,4-tetrahydroquinoxaline and 8-fluoro-2-(4-(trifluoromethyl)phenyl)-1,2,3,4-tetrahydroquinoxaline) as a solid.

Step C: ethyl 10-fluoro-7-hydroxy-5-oxo-3-(4-(trifluoromethyl)phenyl)-1,2,3,5-tetrahydropyrido[1,2,3-de]quinoxaline-6-carboxylate and ethyl 10-fluoro-7-hydroxy-5-oxo-2-(4-(trifluoromethyl)phenyl)-1,2,3,5-tetrahydropyrido[1,2,3-de]quinoxaline-6-carboxylate A mixture of (2-(4-bromophenyl)-5-fluoro-1,2,3,4-tetrahydroquinoxaline and 8-fluoro-2-(4-(trifluoromethyl)phenyl)-1,2,3,4-tetrahydroquinoxaline) (200 mg, 0.675 mmol) and triethyl methanetricarboxylate (627 mg, 2.70 mmol) was stirred at 220° C. for 20 mins. TLC (Petroleum ether: EtOAc=2:1) showed that the starting material was consumed. After cooled to rt, to the mixture was added petroleum ether (15 mL) with stirring. The mixture was filtered, and the filter cake was dried in vacuo. The residue was purified by Combi-Flash (EtOAc in petroleum ether: 0-50%) to give 2 products: ethyl 10-fluoro-7-hydroxy-2-(4-(trifluoromethyl)phenyl)-1,2,3,5-tetrahydropyrido[1,2,3-de]quinoxaline-6-carboxylate as a solid. $^1$H NMR (DMSO-d$_6$, 400 MHz) 7.65 (d, J=8.0 Hz, 2 H), 7.44 (dd, J=8.8, 5.6 Hz, 1 H), 7.24 (d, J=8.0 Hz, 2 H), 7.17 (d, J=10.8 Hz, 1 H), 6.30 (brs, 1 H), 6.11 (brs, 1 H), 4.30 (q, J=7.2 Hz, 2 H), 3.62 (d, J=12.4 Hz, 1 H), 3.52 (dd, J=12.4, 3.6 Hz, 1 H), 1.27 (t, J=7.2 Hz, 3 H). And ethyl 10-fluoro-7-hydroxy-5-oxo-2-(4-(trifluoromethyl)phenyl)-1,2,3,5-tetrahydropyrido[1,2,3-de]quinoxaline-6-carboxylate as a yellow solid. $^1$H NMR (DMSO-$d_6$, 400 MHz) 7.76 (d, J=8.0 Hz, 2H), 7.64 (d, J=8.0 Hz, 2H), 7.38 (dd, J=9.2, 5.6 Hz, 1 H), 7.14 (t, J=10.8 Hz, 1 H), 6.85 (s, 1H), 4.75 (brs, 1H), 4.29-4.37(m, 3H), 3.95 (dd, J=13.2, 7.2Hz, 1H), 1.29 (t, J=7.2 Hz, 3H).

Step D: tert-butyl 2-(10-fluoro-7-hydroxy-5-oxo-3-(4-(trifluoromethyl)phenyl)-1,2,3,5-tetrahydropyrido[1,2,3-de]quinoxaline-6-carboxamido)acetate A solution of ethyl 10-fluoro-7-hydroxy-5-oxo-3-(4-(trifluoromethyl)phenyl)-1,2,3,5-tetrahydropyrido[1,2,3-de]quinoxaline-6-carboxylate (100 mg, 0.229 mmol), tert-butyl 2-aminoacetate (HCl salt, 46.1 mg, 0.275 mmol) and DIPEA (0.080 mL, 0.458 mmol) in toluene (20 mL) was heated to120° C. for 2 h. TLC (petroleum ether: EtOAc=2:1) showed that the starting material was consumed. The solvent was evaporated and the residue was purifired by column—chromatography (EtOAc in Petroleum ether=0-20%) to give the tert-butyl 2-(10-fluoro-7-hydroxy-5-oxo-3-(4-(trifluoromethyl)phenyl)-1,2,3,5-tetrahydropyrido[1,2,3-de]quinoxaline-6-carboxamido)acetate as a solid. $^1$H NMR (CDCl$_3$, 400 MHz) 10.41 (brs, 1H), 7.68 (dd, J=9.2, 5.6 Hz, 1H), 7.55 (d, J=8.0 Hz, 2H), 7.21 (d, J=8.0 Hz, 2H), 7.06 (t, J=9.2 Hz, 1H), 6.24 (brs, 1H), 4.30 (brs, 1H), 3.94-4.20 (m, 2H), 3.70 (s, 2 H), 1.47 (s, 9H).

Step E: 2-(10-fluoro-7-hydroxy-5-oxo-3-(4-(trifluoromethyl)phenyl)-1,2,3,5-tetrahydropyrido[1,2,3-de]quinoxaline-6-carboxamido)acetic acid To a solution of tert-butyl 2-(10-fluoro-7-hydroxy-3-(4-(trifluoromethyl)phenyl)-1,2,3,5-tetrahydropyrido[1,2,3-de]quinoxaline-6-carboxamido)acetate (100 mg, 0.197 mmol) in DCM (5 mL) was added TFA (1 mL). The reaction solution was stirred at room temperature for 3 h. TLC (Petroleum ether: EtOAc=2:1) showed that the reaction was complete. The solvent was evaporated under reduced pressure. The residue was crystallized from EtOAc to give 2-(10-fluoro-7-hydroxy-3-(4-(trifluoromethyl)phenyl)-1,2,3,5-tetrahydropyrido[1,2,3-de]quinoxaline-6-carboxamido)acetic acid as a solid (Example 115). $^1$H NMR (DMSO-$d_6$, 400 MHz) δ 10.31 (s, 1H), 7.66 (d, J=8.4 Hz, 2H), 7.48 (dd, J=5.2, 8.4 Hz, 1H), 7.27 (d, J=8.4 Hz, 2H), 7.22(s, 1H), 6.39 (s, 1H), 6.20 (s, 1H), 4.06 (s, 2H), 3.60 (dd, J=7.2, 30.8 Hz, 2H). LC/MS (m/z): 466 (M+H)$^+$. Human HIF-PHD2 IC$_{50}$ 13 nM.

Step F: tert-butyl 2-(10-fluoro-7-hydroxy-5-oxo-2-(4-(trifluoromethyl)phenyl)-1,2,3,5-tetrahydropyrido[1,2,3-de]quinoxaline-6-carboxamido)acetate To a solution of ethyl 10-fluoro-7-hydroxy-5-oxo-2-(4-(trifluoromethyl)phenyl)-1,2,3,5-tetrahydropyrido[1,2,3-de]quinoxaline-6-carboxylate (100 mg, 0.23 mmol) and tert-butyl 2-aminoacetate (HCl salt, 46.1 mg, 0.275 mmol) in toluene (20 mL) was added DIPEA (0.080 mL, 0.458 mmol). The above mixture was heated at 120° C. for 2 h. TLC (petroleum ether: EtOAc=2:1) showed that the starting material was consumed. The solvent was evaporated and the residue was further purifired by silica gel column chromatography (EtOAc in Petroleum ether=0-20%) to give the tert-butyl 2-(10-fluoro-7-hydroxy-5-oxo-2-(4-(trifluoromethyl)phenyl)-1,2,3,5-tetrahydropyrido[1,2,3-de]quinoxaline-6-carboxamido)acetate as a solid. $^1$H NMR (CDCl$_3$, 400 MHz) δ 10.57 (brs, 1H), 7.71 (d, J=8.0 Hz, 2H), 7.59-7.65 (m, 3H), 7.04 (t, J=9.6 Hz, 1H), 4.95 (d, J=12.8 Hz, 1H), 4.48-4.56 (m, 2H), 4.12 (q, J=5.6 Hz, 2H), 3.60 (dd, J=13.6, 9.6 Hz, 1H), 1.50 (s, 9H).

Step G: 2-(10-fluoro-7-hydroxy-5-oxo-2-(4-(trifluoromethyl)phenyl)-1,2,3,5-tetrahydropyrido[1,2,3-de]quinoxaline-6-carboxamido)acetic acid To a solution of tert-butyl 2-(10-fluoro-7-hydroxy-2-(4-(trifluoromethyl)phenyl)-1,2,3,5-tetrahydropyrido[1,2,3-de]quinoxaline-6-carboxamido)acetate (100 mg, 0.197 mmol) in DCM (5 mL) was added TFA (1 mL). The reaction solution was stirred at room temperature for 3 h. TLC (Petroleum ether: EtOAc=2:1) showed that the reaction was complete. The solvent was evaporated under reduced pressure and the residue was crystallized from EtOAc to give 2-(10-fluoro-7-hydroxy-2-(4-(trifluoromethyl)phenyl)-1,2,3,5-tetrahydropyrido[1,2,3-de]quinoxaline-6-carboxamido)acetic acid as a solid (Example 116). $^1$H NMR (DMSO-$d_6$, 400 MHz,) δ 10.41 (s, 1H), 7.77 (d, J=8.0 Hz, 2H), 7.66 (d, J=8.4 Hz, 2H), 7.41 (s, 1H), 7.20(s, 1H), 6.94 (s, 1H), 4.81 (s, 1H), 4.44 (d, J=16.0 Hz, 1H), 4.04 (s, 3H). LC/MS (m/z): 466 (M+H)$^+$. Human HIF-PHD2 IC$_{50}$ 8.8 nM.

Example 117

2-(10-Fluoro-7-hydroxy-1-methyl-5-oxo-3-(4-(trifluoromethyl)phenyl)-1,2,3,5-tetrahydropyrido[1,2,3-de]quinoxaline-6-carboxamido)acetic acid

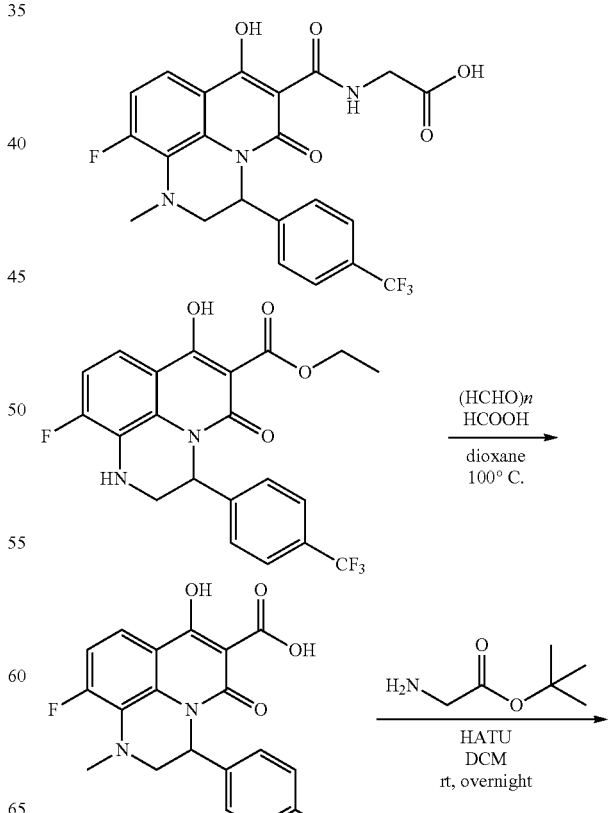

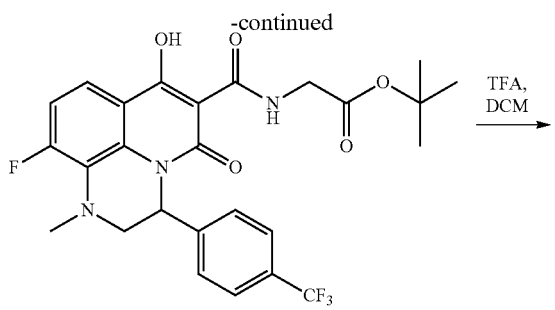

-continued

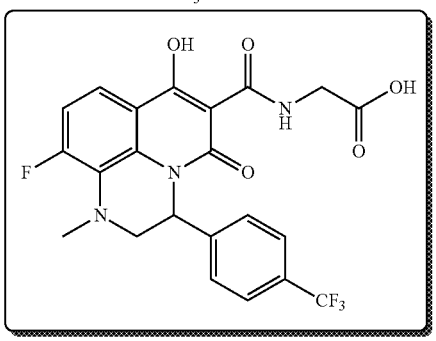

Example 117

Step A: 10-fluoro-7-hydroxy-1-methyl-5-oxo-3-(4-(trifluoromethyl)phenyl)-1,2,3,5-tetrahydropyrido[1,2,3-de]quinoxaline-6-carboxylic acid To a solution of ethyl 10-fluoro-7-hydroxy-5-oxo-3-(4-(trifluoromethyl)phenyl)-1,2,3,5-tetrahydropyrido[1,2,3-de]quinoxaline-6-carboxylate (400 mg, 0.917 mmol) in toluene (10 mL) was added fomic acid (2 mL), and then formaldehyde (275 mg, 9.17 mmol) was added in one portion. The reaction mixture was stirred at 100° C. for 3 h. TLC (EtOAc:Petroleum ether=2:1) showed that the starting material was consumed. The reaction mixture was diluted by water (15 mL) and extracted by EtOAc (3*20 mL). The organic extracts were dried, filtered and concentrated to give the crude product 10-fluoro-7-hydroxy-1-methyl-5-oxo-3-(4-(trifluoromethyl)phenyl)-1,2,3,5-tetrahydropyrido[1,2,3-de]quinoxaline-6-carboxylic acid, which was directly used in the next step. LC/MS (m/z): 423 (M+H)$^+$.

Step B: 2-(10-fluoro-7-hydroxy-1-methyl-5-oxo-3-(4-(trifluoromethyl)phenyl)-1,2,3,5-tetrahydropyrido[1,2,3-de]quinoxaline-6-carboxamido)acetate To a solution of 10-fluoro-7-hydroxy-1-methyl-5-oxo-3-(4-(trifluoromethyl)phenyl)-1,2,3,5-tetrahydropyrido[1,2,3-de]quinoxaline-6-carboxylic acid (125 mg, 0.296 mmol) in DCM (10 mL) were added tert-butyl 2-aminoacetate HCl salt (99.2 mg, 0.59 mmol), DIPEA (0.21 mL, 1.18 mmol), and then HATU (180 mg, 0.47 mmol) was added in one portion. The reaction mixture was stirred at room temperature overnight. LCMS showed that the starting material was consumed. The reaction mixture was diluted with water (15 mL) and extracted with EtOAc (3*20 mL). The organic layer was dried, filtered and concentrated to give crude tert-butyl 2-(10-fluoro-7-hydroxy-1-methyl-5-oxo-3-(4-(trifluoromethyl)phenyl)-1,2,3,5-tetrahydropyrido[1,2,3-de]quinoxaline-6-carboxamido)acetate, which was directly used in the next step.

Step C: 2-(10-fluoro-7-hydroxy-1-methyl-5-oxo-3-(4-(trifluoromethyl)phenyl)-1,2,3,5-tetrahydropyrido[1,2,3-de]quinoxaline-6-carboxamido)acetic acid To a solution of tert-butyl 2-(10-fluoro-7-hydroxy-1-methyl-3-(4-(trifluoromethyl)phenyl)-1,2,3,5-tetrahydropyrido[1,2,3-de]quinoxaline-6-carboxamido)acetate (20 mg, 0.038 mmol) in DCM (5 mL) was added TFA (1 mL). The reaction solution was stirred at room temperature for 3 h. TLC (Petroleum ether: EtOAc=2:1) showed that the reaction was complete. The solvent was evaporated under reduced pressure. Then the crude product was further purified by pre-HPLC (Column: ASB C18 150*25mm; Mobile phase: from 48% MeCN in water (0.1% HCl) to 78% MeCN in water (0.1% HCl)) to give 2-(10-fluoro-7-hydroxy-1-methyl-3-(4-(trifluoromethyl)phenyl)-1,2,3,5-tetrahydropyrido[1,2,3-de]quinoxaline-6-carboxamido)acetic acid as a solid. $^1$H NMR (DMSO-d$_6$, 400 MHz) δ 10.23 (brs, 1H), 7.64 (d, J=8.0 Hz, 3H), 7.26 (d, J=8.0 Hz, 3H), 6.16 (brs, 1H), 4.05 (s, 2H), 3.63-3.69 (m, 2H), 2.79 (d, J=4.0 Hz, 3 H). LC/MS (m/z): 480 (M+H)$^+$. Human HIF-PHD2 IC$_{50}$ 55 nM.

Example 118

2-(9-Fluoro-7-hydroxy-5-oxo-3-(4-(trifluoromethyl)phenyl)-1,2,3,5-tetrahydropyrido[1,2,3-de]quinoxaline-6-carboxamido)acetic acid

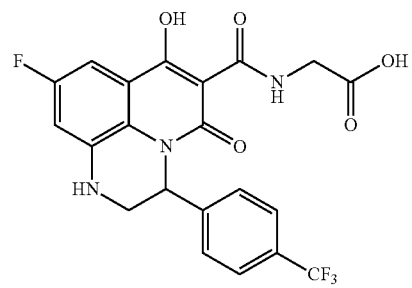 [SMILES: O=C(O)CNC(=O)c1c(O)c2cc(F)cc3c2n(c1=O)C(c1ccc(C(F)(F)F)cc1)CN3]

And Example 119

2-(8-Fluoro-7-hydroxy-5-oxo-2-(4-(trifluoromethyl)phenyl)-1,2,3,5-tetrahydropyrido[1,2,3-de]quinoxaline-6-carboxamido)acetic acid (HCl salt)

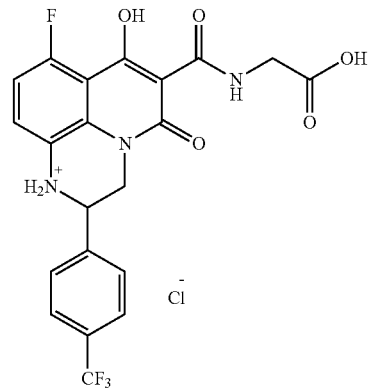

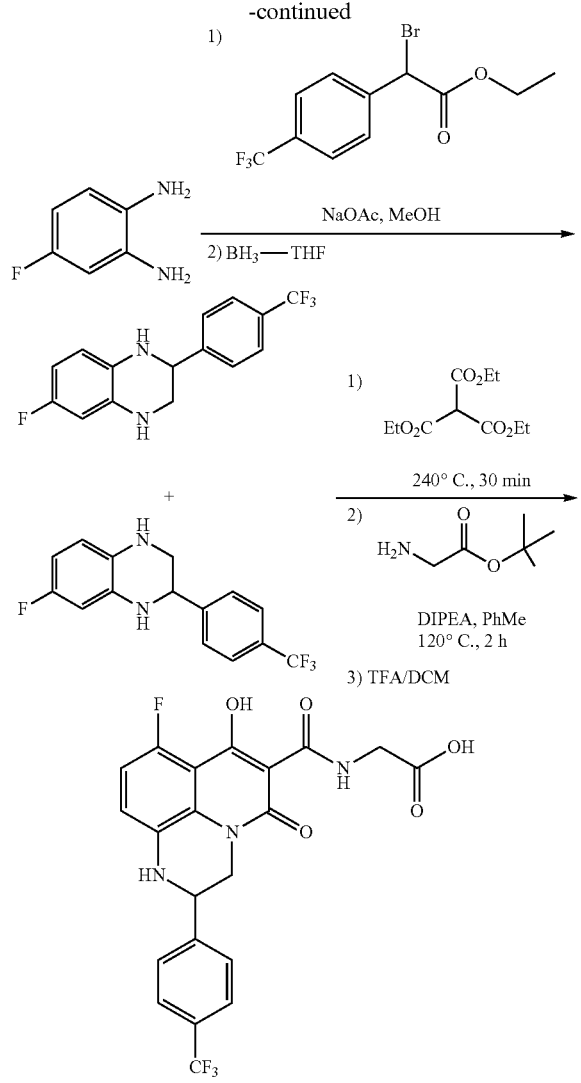

Example 118

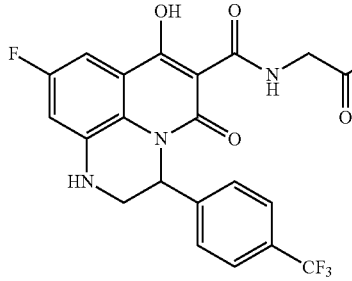

Example 119

Step A: 6-fluoro-2-(4-(trifluoromethyl)phenyl)-1,2,3,4-tetrahydroquinoxaline and 7-fluoro-2-(4-(trifluoromethyl)phenyl)-1,2,3,4-tetrahydroquinoxaline To a solution of 4-fluorobenzene-1,2-diamine (3 g, 23.78 mmol) in MeOH (100 mL) was added NaOAc (5.8 g, 71.4 mmol) and then ethyl 2-bromo-2-(4-(trifluoromethyl)phenyl)acetate (8.88 g, 28.5 mmol) was added dropwise. The reaction solution was stirred at 60° C. overnight. TLC (Petroleum ether: EtOAc=5:1) showed that the reaction was complete. The solvent was evaporated under reduced pressure and the residue was further purified by column chromatography (EtOAc in Petroleum ether=0-20%) to give a mixture of 7-fluoro-3-(4-(trifluoromethyl)phenyl)-3,4-dihydroquinoxalin-2(1H)-one and 6-fluoro-3-(4-(trifluoromethyl)phenyl)-3,4-dihydroquinoxalin-2(1H)-one as a solid.

To a solution of the above mixture of 7-fluoro-3-(4-(trifluoromethyl)phenyl)-3,4-dihydroquinoxalin-2(1H)-one (4.5 g, 14.50 mmol) and 6-fluoro-3-(4-(trifluoromethyl)phenyl)-3,4-dihydroquinoxalin-2(1H)-one (1.5 g, 4.83 mmol) in THF (100 mL) was added $BH_3$-DMS (19.28 mL, 203 mmol) dropwise. The reaction was stirred at room temperature overnight. TLC (petroleum ether: EtOAc=5:1) showed that the reaction was complete. MeOH (20 mL) was added dropwise to quench the reaction, then EtOAc (300 mL) was added. The mixture was washed with sodium bicarbonate (300 mL, 5%), water (300 mL), and brine. The organic layer was evaporated under reduced pressure. The residue was purified by silica gel column chromatography (EtOAc in petroleum ether: 0-30%) to give 6-fluoro-2-(4-(trifluoromethyl)phenyl)-1,2,3,4-tetrahydroquinoxaline as a solid: $^1$H NMR (CDCl$_3$, 400 MHz) δ 7.63 (d, J=8.4 Hz, 2H), 7.51 (d, J=8.4 Hz, 2H), 6.50 (dd, J=8.4, 5.2 Hz, 1H), 6.29-6.34(m, 2H), 4.49 (dd, J=8.0, 2.8 Hz, 1H), 3.48 (dd, J=10.4, 2.8 Hz, 1H), 3.32 (dd, J=11.2, 8.0 Hz, 1H); and 7-fluoro-2-(4-(trifluoromethyl)phenyl)-1,2,3,4-tetrahydroquinoxaline as a yellow pink solid: $^1$H NMR (CDCl$_3$, 400 MHz) δ 7.61 (d, J=8.0 Hz, 2H), 7.47 (d, J=8.8 Hz, 2H), 6.48 (d, J=5.6 Hz, 1H), 6.31-6.35 (m, 2H), 4.56 (dd, J=7.2, 2.8 Hz, 1H), 3.45 (dd, J=11.2, 3.2 Hz, 1H), 3.25 (dd, J=11.2, 7.2 Hz, 1H).

Step B: 2-(8-fluoro-7-hydroxy-5-oxo-2-(4-(trifluoromethyl)phenyl)-1,2,3,5-tetrahydropyrido[1,2,3-de]quinoxaline-6-carboxamido)acetic acid (HCl salt) and 2-(9-fluoro-7-hydroxy-5-oxo-3-(4-(trifluoromethyl)phenyl)-1,2,3,5-tetrahydropyrido[1,2,3-de]quinoxaline-6-carboxamido)acetic acid A mixture of 6-fluoro-2-(4-(trifluoromethyl)phenyl)-1,2,3,4-tetrahydroquinoxaline (300 mg, 1.013 mmol) and triethyl methanetricarboxylate (941 mg, 4.05 mmol) was heated at 220° C. for 20 mins. TLC (petroleum ether: EtOAc=2:1) showed that the starting material was consumed. After cooling to rt, to the reaction mixture was added petroleum ether (15 ml) with stirring. The reacton mixture was filtered, and the filter cake was dried in vacuo to give ethyl 8-fluoro-7-hydroxy-5-oxo-2-(4-(trifluoromethyl)phenyl)-1,2,3,5-tetrahydropyrido[1,2,3-de]quinoxaline-6-carboxylate and ethyl 9-fluoro-7-hydroxy-5-oxo-3-(4-(trifluoromethyl)phenyl)-1,2,3,5-tetrahydropyrido[1,2,3-de]quinoxaline-6-carboxylate. LC/MS (m/z): 437 (M+H)$^+$.

To a mixture of ethyl 9-fluoro-7-hydroxy-5-oxo-3-(4-(trifluoromethyl)phenyl)-1,2,3,5-tetrahydropyrido[1,2,3-de]quinoxaline-6-carboxylate (150 mg, 0.344 mmol), ethyl 8-fluoro-7-hydroxy-5-oxo-2-(4-(trifluoromethyl)phenyl)-1,2,3,5-tetrahydropyrido[1,2,3-de]quinoxaline-6-carboxylate (50 mg, 0.115 mmol) and tert-butyl 2-aminoacetate hydrochloride salt (92 mg, 0.550 mmol) in toluene (20 mL) was added DIPEA (0.160 mL, 0.914 mmol). The mixture was stirred at 120° C. for 2 h. TLC (petroleum ether: EtOAc=2:1) showed that the starting material was consumed. The solvent was evaporated and the residue was further purifired by column chromatography (EtOAc in Petroleum ether=0-20%) to give a mixture of (tert-butyl 2-(9-fluoro-7-hydroxy-5-oxo-3-(4-(trifluoromethyl)phenyl)-1,2,3,5-tetrahydropyrido[1,2,3-de]quinoxaline-6-carboxamido)acetate and tert-butyl 2-(8-fluoro-7-hydroxy-5-oxo-2-(4-(trifluoromethyl)phenyl)-1,2,3,5-tetrahydropyrido[1,2,3-de]quinoxaline-6-carboxamido)acetate) as a light yellow solid. LC/MS (m/z): 522 (M+H)$^+$.

The mixture of tert-butyl 2-(8-fluoro-7-hydroxy-2-(4-(trifluoromethyl)phenyl)-1,2,3,5-tetrahydropyrido[1,2,3-de]quinoxaline-6-carboxamido)acetate and tert-butyl 2-(9-fluoro-7-hydroxy-3-(4-(trifluoromethyl)phenyl)-1,2,3,5-tetrahydropyrido[1,2,3-de]quinoxaline-6-carboxamido)acetate (75 mg, 0.15 mmol) was dissolved in DCM (5 mL), to which TFA (1 mL) was added. The reaction solution was stirred at room temperature for 3 h. TLC (petroleum ether: EtOAc=2:1) showed that the reaction was complete. The solvent was evaporated under reduced pressure. The residue was purified by SFC to give:

Example 118: 2-(9-fluoro-7-hydroxy-3-(4-(trifluoromethyl)phenyl)-1,2,3,5-tetrahydropyrido[1,2,3-de]quinoxaline-6-carboxamido)acetic acid as a solid $^1$H NMR (DMSO-d$_6$, 400 MHz) δ 10.54 (t, J=5.2 Hz, 1H), 7.80 (d, J=8.0 Hz, 2H), 7.70 (d, J=8.0 Hz, 2H), 7.07-7.12 (m, 1H), 6.94-7.03 (m, 1H), 6.90 (s, 1H), 4.63 (d, J=8.0 Hz, 1H), 4.56 (d, J=13.6 Hz, 1H), 4.12 (d, J=5.2 Hz, 2H), 3.78 (dd, J=13.2, 8.4 Hz, 1 H). LC/MS (m/z): 466 (M+H)$^+$. Human HIF-PHD2 IC$_{50}$ 5.7 nM.

Example 119: 2-(8-fluoro-7-hydroxy-2-(4-(trifluoromethyl)phenyl)-1,2,3,5-tetrahydropyrido[1,2,3-de]quinoxaline-6-carboxamido)acetic acid (HCl salt) as a solid. $^1$H NMR (DMSO-d$_6$, 400 MHz) δ 10.40 (brs, 1H), 7.65 (d, J=8.0 Hz, 2H), 7.24 (d, J=8.0 Hz, 2H), 7.07 (dd, J=9.2, 2.8 Hz, 1H), 6.83 (dd, J=10.0, 2.8 Hz, 1H), 6.74 (brs, 1H), 6.17 (brs, 1H), 3.96 (s, 2H), 3.61-3.68 (m, 2H). LC/MS (m/z): 466 (M+H)$^+$. Human HIF-PHD2 IC$_{50}$ 10 nM.

Example 120

2-(9-Fluoro-7-hydroxy-5-oxo-2-(4-(trifluoromethyl)phenyl)-1,2,3,5-tetrahydropyrido[1,2,3-de]quinoxaline-6-carboxamido)acetic acid

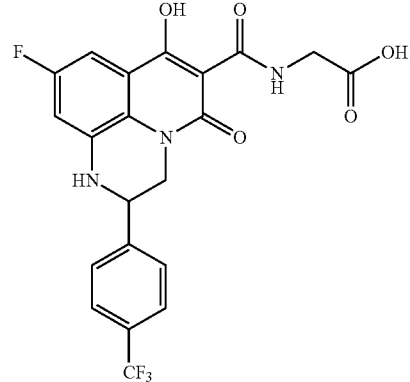

And Example 121

2-(8-Fluoro-7-hydroxy-5-oxo-3-(4-(trifluoromethyl)phenyl)-1,2,3,5-tetrahydropyrido[1,2,3-de]quinoxaline-6-carboxamido)acetic acid (HCl salt)

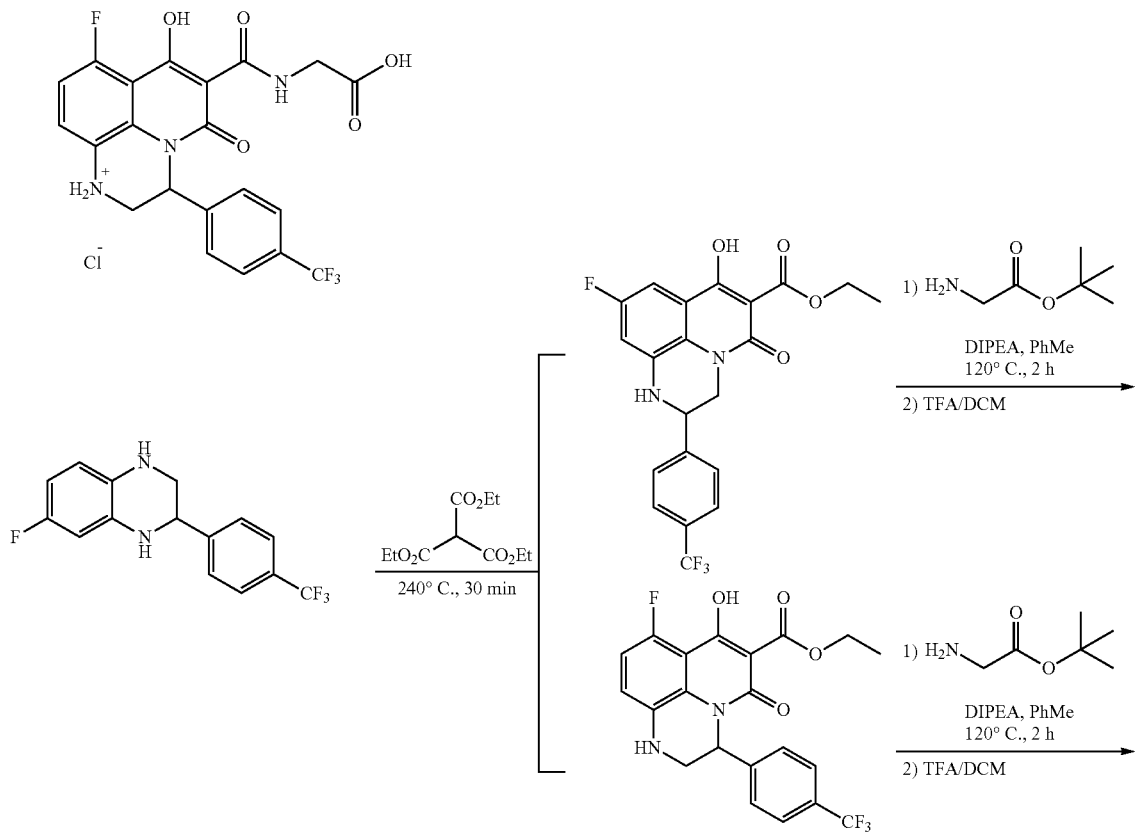

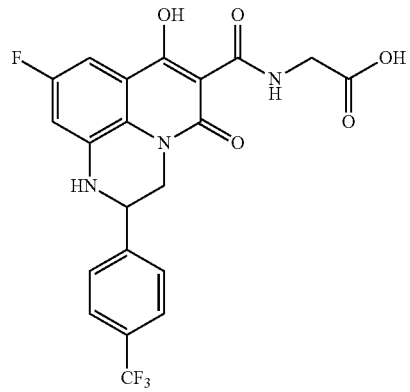

Example 120

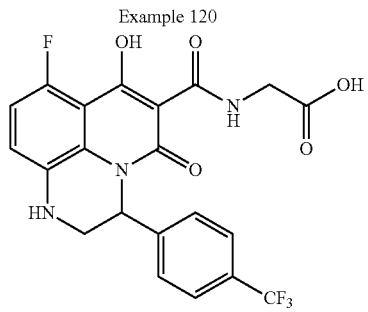

Example 121

Step A: ethyl 9-fluoro-7-hydroxy-5-oxo-2-(4-(trifluoromethyl)phenyl)-1,2,3,5-tetrahydropyrido[1,2,3-de]quinoxaline-6-carboxylate and ethyl 8-fluoro-7-hydroxy-5-oxo-3-(4-(trifluoromethyl)phenyl)-1,2,3,5-tetrahydropyrido[1,2,3-de]quinoxaline-6-carboxylate A mixture of 7-fluoro-2-(4-(trifluoromethyl)phenyl)-1,2,3,4-tetrahydroquinoxaline (300 mg, 1.013 mmol) and triethyl methanetricarboxylate (941 mg, 4.05 mmol) was stirred at 220° C. for 20 mins. TLC (petroleum ether:EtOAc=2:1) showed that the starting material was consumed. After cooled to rt, to the reaction mixture was added petroleum ether(15 mL) with stirring. The mixture was filtered and the filter cake was purified by silica gel column chromatography (EtOAc in petroleum ether: 0-30%) to give the ethyl 9-fluoro-7-hydroxy-2-(4-(trifluoromethyl)phenyl)-1,2,3,5-tetrahydropyrido[1,2,3-de]quinoxaline-6-carboxylate as a yellow solid and ethyl 8-fluoro-7-hydroxy-3-(4-(trifluoromethyl)phenyl)-1,2,3,5-tetrahydropyrido[1,2,3-de]quinoxaline-6-carboxylate as a solid. LC/MS (m/z): 437 (M+H)$^+$.

Step B: 2-(9-fluoro-7-hydroxy-5-oxo-2-(4-(trifluoromethyl)phenyl)-1,2,3,5-tetrahydropyrido[1,2,3-de]quinoxaline-6-carboxamido)acetic acid (Example 120)

A solution of ethyl 9-fluoro-7-hydroxy-5-oxo-2-(4-(trifluoromethyl)phenyl)-1,2,3,5-tetrahydropyrido[1,2,3-de]quinoxaline-6-carboxylate (100 mg, 0.229 mmol), tert-butyl 2-aminoacetate hydrochloride (46.1 mg, 0.275 mmol) and DIPEA (0.080 mL, 0.458 mmol) in toluene (20 mL) was heated to 120° C. for 2 h. TLC (petroleum ether: EtOAc=2:1) showed that the starting material was consumed. The solvent was evaporated to give the crude product which was further purified by silica gel column chromatography (EtOAc in petroleum ether=0-20%) to give the tert-butyl 2-(9-fluoro-7-hydroxy-5-oxo-2-(4-(trifluoromethyl)phenyl)-1,2,3,5-tetrahydropyrido[1,2,3-de]quinoxaline-6-carboxamido)acetate as a solid. $^1$H NMR (CDCl$_3$, 400 MHz) δ 10.65 (brs, 1H), 7.69 (d, J=8.4 Hz, 2H), 7.56 (d, J=8.0 Hz, 2H), 7.28 (dd, J=8.8, 2.4 Hz, 1H), 6.72 (dd, J=2.4, 8.8 Hz, 1H), 4.91 (d, J=13.2 Hz, 1H), 4.53-4.56(m, 2H), 4.05-4.18 (m, 2H), 3.59 (dd, J=9.6, 13.2 Hz, 1H), 1.48 (s, 9H).

To a solution of tert-butyl 2-(9-fluoro-7-hydroxy-2-(4-(trifluoromethyl)phenyl)-1,2,3,5-tetrahydropyrido[1,2,3-de]quinoxaline-6-carboxamido)acetate (40 mg, 0.079 mmol) in DCM (5 mL) was added TFA (1 mL). The reaction mixture was stirred at room temperature for 3 h. TLC (Petroleum ether: EtOAc=2:1) showed that the reaction was complete. The solvent was evaporated under reduced pressure. The residue was crystallized from EtOAc to give 2-(9-fluoro-7-hydroxy-2-(4-(trifluoromethyl)phenyl)-1,2,3,5-tetrahydropyrido[1,2,3-de]quinoxaline-6-carboxamido)acetic acid as a solid. $^1$H NMR (DMSO-d$_6$, 400 MHz) δ 10.52 (s, 1H), 7.81 (d, J=8.0 Hz, 2H), 7.69 (d, J=7.2 Hz, 2H), 7.39 (s, 1H), 7.02 (d, J=7.6 Hz, 1H), 6.93 (d, J=10.0 Hz, 1H), 4.77 (s, 1H), 4.52 (d, J=12.0 Hz, 1H), 4.11 (d, J=4.2 Hz, 2H), 3.91 (dd, J=8.0, 12.8 Hz, 1H). LC/MS (m/z): 466 [M+H]$^+$. Human HIF-PHD2 IC$_{50}$ 4.6 nM.

Step C: 2-(8-fluoro-7-hydroxy-5-oxo-3-(4-(trifluoromethyl)phenyl)-1,2,3,5-tetrahydropyrido[1,2,3-de]quinoxaline-6-carboxamido)acetic acid HCl salt (Example 121)

To a solution of ethyl 8-fluoro-7-hydroxy-5-oxo-3-(4-(trifluoromethyl)phenyl)-1,2,3,5-tetrahydropyrido[1,2,3-de]

quinoxaline-6-carboxylate (80 mg, 0.183 mmol) and tert-butyl 2-aminoacetate HCl salt (36.9 mg, 0.220 mmol) in toluene (20 mL) was added DIPEA (0.064 mL, 0.367 mmol). The mixture was stirred at 120° C. for 2 h. TLC (petroleum ether: EtOAc=2:1) showed that the starting material was consumed. The solvent was evaporated to give the crude product, which was further purified by silica gel column chromatography (EtOAc in Petroleum ether=0-20%) to give the tert-butyl 2-(8-fluoro-7-hydroxy-5-oxo-3-(4-(trifluoromethyl)phenyl)-1,2,3,5-tetrahydropyrido[1,2,3-de]quinoxaline-6-carboxamido)acetate as a solid.

To a solution of tert-butyl 2-(8-fluoro-3-(4-(trifluoromethyl)phenyl)-1,2,3,5-tetrahydropyrido[1,2,3-de]quinoxaline-6-carboxamido)acetate (40 mg, 0.079 mmol) in DCM (5 mL) was added TFA (1 mL). The reaction solution was stirred at room temperature for 3 h. TLC (petroleum ether: EtOAc=2:1) showed that the reaction was complete. The solvent was evaporated under reduced pressure. The residue was crystallized from EtOAc to give 2-(8-fluoro-7-hydroxy-3-(4-(trifluoromethyl)phenyl)-1,2,3,5-tetrahydropyrido[1,2,3-de]quinoxaline-6-carboxamido)acetic acid (HCl salt) as a solid. $^1$H NMR (DMSO-$d_6$, 400 MHz) δ 10.38 (t, J=5.6 Hz, 1H), 7.62 (d, J=8.0 Hz, 2H), 7.22 (d, J=8.0 Hz, 2H), 7.04 (dd, J=8.8, 2.8 Hz, 1H), 6.81 (dd, J=10.0, 2.4 Hz, 1H), 6.80 (brs, 1H), 6.15 (brs, 1H), 4.05 (dd, J=5.2, 2.8 Hz, 2H), 3.56-3.66 (m, 2H). LC/MS (m/z): 466 [M+H]$^+$. Human HIF-PHD2 IC$_{50}$ 9.4 nM.

Example 122

2-(9-Fluoro-7-hydroxy-1-methyl-5-oxo-3-(4-(trifluoromethyl)phenyl)-1,2,3,5-tetrahydropyrido[1,2,3-de]quinoxaline-6-carboxamido)acetic acid (HCl salt)

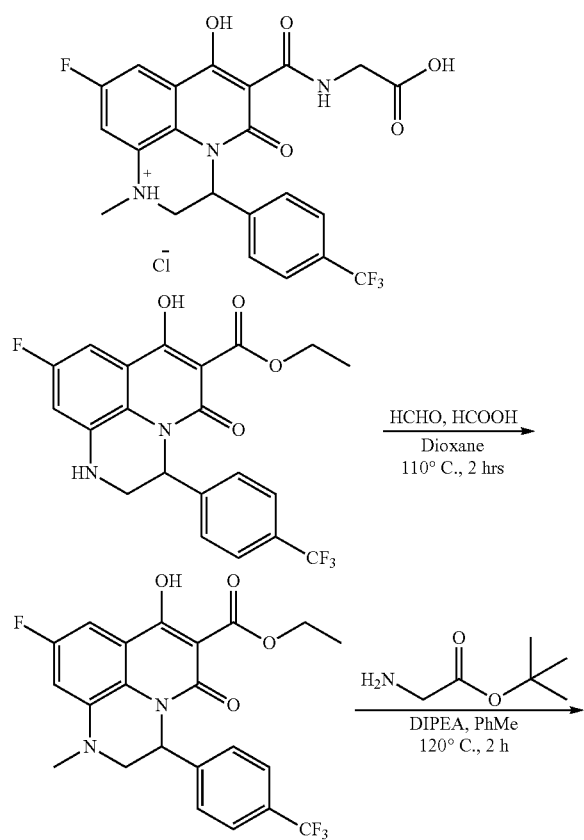

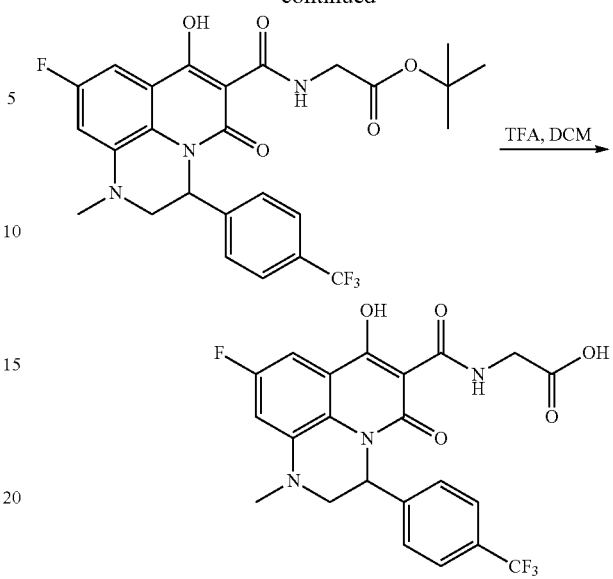

Example 122

Step A: ethyl 9-fluoro-7-hydroxy-1-methyl-5-oxo-3-(4-(trifluoromethyl)phenyl)-1,2,3,5-tetrahydropyrido[1,2,3-de]quinoxaline-6-carboxylate To a solution of ethyl 9-fluoro-7-hydroxy-5-oxo-3-(4-(trifluoromethyl)phenyl)-1,2,3,5-tetrahydropyrido[1,2,3-de]quinoxaline-6-carboxylate (400 mg, 0.917 mmol) in toluene (10 mL) was added fomic acid (2 mL), then formaldehyde (275 mg, 9.17 mmol) was added in one portion. The reaction mixture was stirred at 100° C. for 3 h. TLC (EtOAc: Petroleum ether=2:1) showed that the starting material was consumed. The reaction mixture was diluted with water (15 mL) and extracted with EtOAc (3*20 mL). The organic extracts were dried, filtered and concentrated to give the crude product ethyl 9-fluoro-7-hydroxy-1-methyl-5-oxo-3-(4-(trifluoromethyl)phenyl)-1,2,3,5-tetrahydropyrido[1,2,3-de]quinoxaline-6-carboxylate, which was directly used in the next step. LC/MS (m/z): 451 [M+H]$^+$.

Step B: tert-butyl 2-(9-fluoro-7-hydroxy-1-methyl-5-oxo-3-(4-(trifluoromethyl)phenyl)-1,2,3,5-tetrahydropyrido[1,2,3-de]quinoxaline-6-carboxamido)acetate To a solution of ethyl 9-fluoro-7-hydroxy-1-methyl-5-oxo-3-(4-(trifluoromethyl)phenyl)-1,2,3,5-tetrahydropyrido[1,2,3-de]quinoxaline-6-carboxylate (125 mg, 0.296 mmol) in toluene (10 mL) were added tert-butyl 2-aminoacetate HCl salt (99.2 mg, 0.59 mmol) and DIPEA (0.21 mL, 1.18 mmol). The reaction mixture was stirred at 120° C. for 2 h. LCMS showed that the starting material was consumed. The reaction mixture was diluted with water (15 mL) and extracted by EtOAc (3*20 mL). The organic layer was dried, filtered and concentrated to give crude tert-butyl 2-(9-fluoro-7-hydroxy-1-methyl-5-oxo-3-(4-(trifluoromethyl)phenyl)-1,2,3,5-tetrahydropyrido[1,2,3-de]quinoxaline-6-carboxamido)acetate, which was directly used in the next step.

Step C: 2-(9-fluoro-7-hydroxy-1-methyl-5-oxo-3-(4-(trifluoromethyl)phenyl)-1,2,3,5-tetrahydropyrido[1,2,3-de]quinoxaline-6-carboxamido)acetic acid (HCl salt)

To a solution of tert-butyl 2-(9-fluoro-7-hydroxy-1-methyl-5-oxo-3-(4-(trifluoromethyl)phenyl)-1,2,3,5-tetrahydropyrido[1,2,3-de]quinoxaline-6-carboxamido)acetate (20 mg, 0.038 mmol) in DCM (5 mL) was added TFA (1 mL). The reaction solution was stirred at room temperature for 3 h. TLC (petroleum ether: EtOAc=2:1) showed that the reaction was complete. The solvent was evaporated under reduced pressure. The residue was purified by HPLC (Column: ASB C18 150*25mm; Mobile phase: from 48% MeCN in water (0.1% HCl) to 78% MeCN in water (0.1% HCl)) to give 2-(9-fluoro-7-hydroxy-1-methyl-5-oxo-3-(4-(trifluoromethyl)phenyl)-1,2,3,5-tetrahydropyrido[1,2,3-de]quinoxaline-6-carboxamido)acetic acid (HCl salt) as a solid. $^1$H NMR (DMSO-$d_6$, 400 MHz) δ 10.36 (t, J=5.6 Hz, 1H), 7.65 (d, J=8.0 Hz, 2H), 7.27 (d, J=8.0 Hz, 2H), 7.09-7.19 (m, 1H), 6.94 (d, J=12.0 Hz, 1H), 6.19 (brs, 1 H), 4.06 (d, J=4.0 Hz, 2H), 3.58-3.72 (m, 2H), 2.85 (s, 3H). LC/MS (m/z): 480 [M+H]$^+$. Human HIF-PHD2 IC$_{50}$ 30 nM.

Example 123

2-(9-Fluoro-7-hydroxy-1-methyl-5-oxo-2-(4-(trifluoromethyl)phenyl)-1,2,3,5-tetrahydropyrido[1,2,3-de]quinoxaline-6-carboxamido)acetic acid (HCl salt)

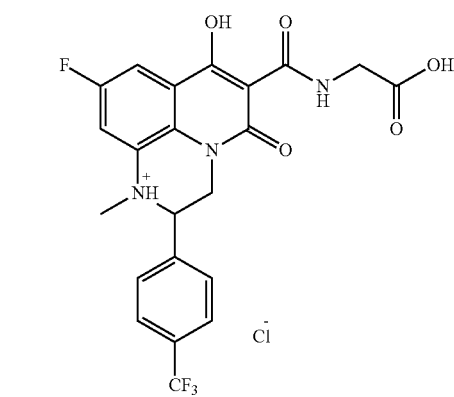

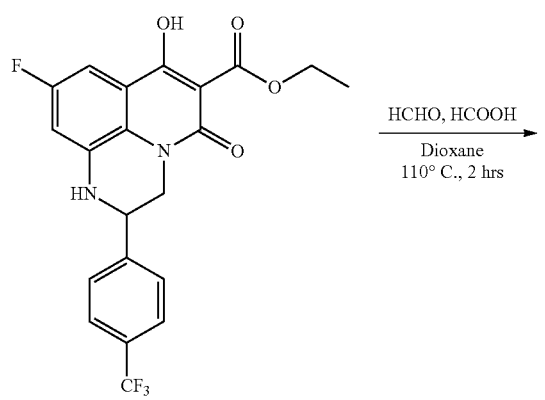

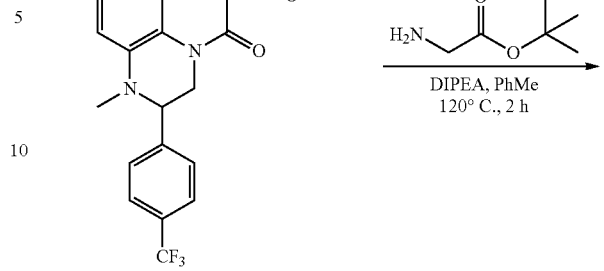

Following similar procedure described in Example 122 and starting with ethyl 9-fluoro-7-hydroxy-5-oxo-2-(4-(trifluoromethyl)phenyl)-1,2,3,5-tetrahydropyrido[1,2,3-de]quinoxaline-6-carboxylate, the title compound was prepared. $^1$H NMR (DMSO-$d_6$, 400 MHz) δ 10.35 (d, J=5.6 Hz, 1H), 7.65 (d, J=8.0 Hz, 2H), 7.28 (d, J=8.0 Hz, 2H), 7.00 (d, J=8.8 Hz, 1H), 6.94 (d, J=11.6 Hz, 1H), 5.10 (brs, 1H), 4.84 (d, J=11.2 Hz, 1H), 3.98-4.05 (m, 3H), 2.99 (s, 3H). LC/MS (m/z): 480 [M+H]$^+$. Human HIF-PHD2 IC$_{50}$ 15 nM.

Example 124

2-(7-Hydroxy-5-oxo-9-(trifluoromethoxy)-2-(4-(trifluoromethyl)phenyl)-3,5-dihydro-2H-[1,4]oxazino[2,3,4-ij]quinoline-6-carboxamido)acetic acid

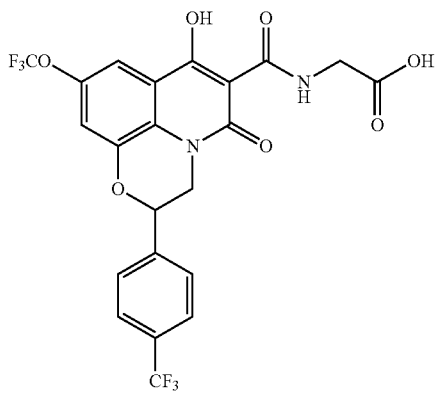 [SMILES: O=C(O)CNC(=O)c1c(O)c2cc(OC(F)(F)F)cc3c2n(c1=O)CC(c1ccc(C(F)(F)F)cc1)O3]

Step A: 2-amino-5-(trifluoromethoxy)phenol

To a solution of 3-(trifluoromethoxy)phenol (1 g, 5.6 mmol) in AcOH (8 mL) was added HNO₃ (1 mL) dropwise at 10-15° C. Then the mixture was stirred at this temperature for 1.5 h. TLC (petroleum ether: EtOAc=2:1) showed the reaction was complete. The mixture was poured into ice water (15 mL), and extracted with EtOAc (10 mL*3). The combined organic layers were dried over Na₂SO₄ and concentrated in vacuum. The residue was purified by column chromatography on SiO₂ (EtOAc in petroleum ether=0~30%) to give 2-nitro-5-(trifluoromethoxy)phenol as an oil. $^1$H NMR (CDCl₃, 400 MHz) δ 10.72 (s, 1H), 8.16 (d, J=9.2 Hz, 1H). 6.98 (s, 1H), 6.82 (d, J=9.6 Hz, 1H).

To a solution of 2-nitro-5-(trifluoromethoxy)phenol (1 g, 4.4 mmol) in EtOAc (10 mL) was added Pd/C (200 mg, 5% wt). The mixture was stirred under H₂ balloon at room temperature for 2 h. The mixture was filtered through the celite, and the filtrate was concentrated under vacuum to give the 2-amino-5-(trifluoromethoxy)phenol as a solid. $^1$H NMR (CDCl₃, 400 MHz) δ 6.72 (d, J=8.0 Hz, 1H), 6.97-6.65 (m, 2H).

Step B: 7-(trifluoromethoxy)-2-(4-(trifluoromethyl)phenyl)-2H-benzo[b][1,4]oxazin-3(4H)-one To a solution of 2-amino-5-(trifluoromethoxy)phenol (1 g, 5.18 mmol) in DCM (20 mL) were added DIPEA (1 mL, 6.35 mmol) and 2-bromo-2-(4-(trifluoromethyl)phenyl)acetyl chloride (1.56 g, 5.18 mmol). The reaction mixture was stirred at room temperature for 20 h. LCMS showed the desired compound was formed. The mixture was extracted with DCM (100 mL*3). The combined organic layers were washed with brine (100 mL*3), dried over Na₂SO₄, filtered and concentrated in vacuo to give 7-(trifluoromethoxy)-2-(4-(trifluoromethyl)phenyl)-2H-benzo[b][1,4]oxazin-3(4H)-one as a solid, which was used in the next step directly. LC/MS (m/z): 378 (M+H)⁺.

Step C: 7-(trifluoromethoxy)-2-(4-(trifluoromethyl)phenyl)-3,4-dihydro-2H-benzo[b][1,4]oxazine To a solution of 7-(trifluoromethoxy)-2-(4-(trifluoromethyl)phenyl)-2H-benzo[b][1,4]oxazin-3(4H)-one (2.00 g, 5.30 mmol) in THF (30 mL) was added BH₃-DMS (2.20 mL, 23.17 mmol) dropwise at room temperature. The mixture was stirred at room temperature for 4 h. TLC (petroleum ether: EtOAc=3:1) indicated the reaction was complete. The mixture was poured into ice water (200 mL), then extracted with EtOAc (100 mL*2). The organic layer was washed with brine, dried over Na₂SO₄ and concentrated in vacuo. The residue was purified by silica gel column chromatography (EtOAc in petroleum ether=0~30%) to give the 7-(trifluoromethoxy)-2-(4-(trifluoromethyl)phenyl)-3,4-dihydro-2H-benzo[b][1,4]oxazine as a solid. $^1$H NMR (CDCl₃, 400 MHz) δ 7.66 (d, J=8.4 Hz, 2H), 7.52 (d, J=8.0 Hz, 2H), 6.81 (s, 1H), 6.71-6.69 (m, 1H), 6.62-6.60 (m, 1H), 5.16-5.13 (m, 1H), 3.56-3.53 (m, 1H), 3.35-3.29 (m, 1H).

Step D: ethyl 7-hydroxy-5-oxo-9-(trifluoromethoxy)-2-(4-(trifluoromethyl)phenyl)-3,5-dihydro-2H-[1,4]oxazino[2,3,4-ij]quinoline-6-carboxylate A mixture of 7-(trifluoromethoxy)-2-(4-(trifluoromethyl)phenyl)-3,4-dihydro-2H-benzo[b][1,4]oxazine (850 mg, 2.34 mmol) and triethyl methanetricarboxylate (2174 mg, 9.36 mmol) was stirred at 250° C. for 1 h. TLC (petroleum ether: EtOAc=4:1) showed the starting material was consumed. The mixture was diluted with petroleum ether (20 mL), and the solid thus formed was collected by filtration, dried under vacuum to give ethyl 7-hydroxy-5-oxo-9-(trifluoromethoxy)-2-(4-(trifluoromethyl)phenyl)-3,5-dihydro-2H-[1,4]oxazino[2,3,4-ij]quinoline-6-carboxylate as a solid. $^1$H NMR (CDCl₃, 400 MHz) δ 14.33 (s, 1H), 7.71 (d, J=8.0 Hz, 2H), 7.64 (s, 1H), 7.58 (d, J=8.0 Hz, 2H), 7.24-7.20 (m, 1H), 5.21-5.18 (m, 1H), 4.95 (d, J=11.6 Hz, 1H), 4.50 (q, J=4.8 Hz, 2H), 3.66-3.60 (m, 1H), 1.45 (t, J=7.2 Hz, 3H).

Step E: tert-butyl 2-(7-hydroxy-5-oxo-9-(trifluoromethoxy)-2-(4-(trifluoromethyl)phenyl)-3,5-dihydro-2H-[1,4]oxazino[2,3,4-ij]quinoline-6-carboxamido)acetate To a suspension of ethyl 7-hydroxy-5-oxo-9-(trifluoromethoxy)-2-(4-(trifluoromethyl)phenyl)-3,5-dihydro-2H-[1,4]oxazino[2,3,4-ij]quinoline-6-carboxylate (500 mg, 0.99 mmol) and 2-(tert-butoxy)-2-oxoethanaminium chloride (250 mg, 1.49 mmol) in toluene (10 mL) was added DIPEA (0.69 mL, 3.97 mmol). The mixture was stirred at 110° C. for 3 h. TLC (petroleum ether: EtOAc=3:1) showed the reaction was complete. The mixture was cooled to room temperature, concentrated in vacuo. The residue was diluted with DCM (100 mL), washed with water, aq HCl (0.5 M) and brine. The organic layer was dried over Na₂SO₄ and concentrated. The residue was purified by silica gel column chromatography (EtOAc in petroleum ether=0~30%) to give the tert-butyl 2-(7-hydroxy-5-oxo-9-(trifluoromethoxy)-2-(4-(trifluoromethyl)phenyl)-3,5-dihydro-2H-[1,4]oxazino[2,3,4-ij]quinoline-6-carboxamido)acetate as a solid. $^1$H NMR (CDCl₃, 400 MHz) δ 10.51 (s, 1H), 7.74 (d, J=8.0 Hz, 2H), 7.68 (s, 1H), 7.62 (d, J=8.4 Hz, 2H), 7.22-7.21 (m, 1H), 5.24-5.22 (m, 1H), 4.99 (d, J=11.2 Hz, 1H), 4.14 (dd, J=9.2 Hz, 5.2 Hz, 2H), 3.70-3.64 (m, 1H), 1.50 (s, 9H).

Step F: 2-(7-hydroxy-5-oxo-9-(trifluoromethoxy)-2-(4-(trifluoromethyl)phenyl)-3,5-dihydro-2H-[1,4]oxazino[2,3,4-ij]quinoline-6-carboxamido)acetic acid To a solution of tert-butyl 2-(7-hydroxy-5-oxo-9-(trifluoromethoxy)-2-(4-(trifluoromethyl)phenyl)-3,5-dihydro-2H-

[1,4]oxazino[2,3,4-ij]quinoline-6-carboxamido)acetate (400 mg, 0.680 mmol) in DCM (15 mL) was added TFA (3 mL, 38.9 mmol). The mixture was stirred at 25° C. for 5 h. TLC (petroleum ether: EtOAc=1:1) showed the reaction was complete. The mixture was concentrated in vacuo to give a crude. After washing with 20 mL of petroleum ether/EtOAc (v/v=10:1), the solid was collected and dried to give the 2-(7-hydroxy-5-oxo-9-(trifluoromethoxy)-2-(4-(trifluoromethyl)phenyl)-3,5-dihydro-2H-[1,4]oxazino[2,3,4-ij]quinoline-6-carboxamido)acetic acid as a solid. $^1$H NMR (DMSO-d$_6$, 400 MHz) δ 12.90 (br. s, 1H), 10.36 (s, 1H), 7.87 (d, J=8.8 Hz, 2H), 7.80 (d, J=8.0 Hz, 2H), 7.59-7.57 (m, 2H), 5.59 (d, J=8.0 Hz, 1H), 4.78 (d, J=12.4 Hz, 1H), 4.15 (d, J=5.2 Hz, 2H), 3.90-3.84 (m, 1H). LC/MS (m/z): 533 [M+H]$^+$. Human HIF-PHD2 IC$_{50}$ 9.6 nM.

Example 125

2-(2-(4-Cyanophenyl)-7-hydroxy-5-oxo-9-(trifluoromethoxy)-3,5-dihydro-2H-[1,4]oxazino[2,3,4-ij]quinoline-6-carboxamido)acetic acid

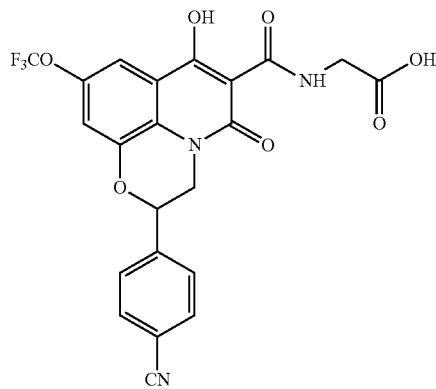

Step A: 2-(4-bromophenyl)-7-(trifluoromethoxy)-2H-benzo[b][1,4]oxazin-3(4H)-one

To a solution of 2-amino-5-(trifluoromethoxy)phenol (2 g, 10.36 mmol) in DCM (30 mL) was added DIPEA (7.23 mL, 41.4 mmol). After stirring at room temperature for 10 min, 2-bromo-2-(4-bromophenyl)acetyl chloride (3.88 g, 12.43 mmol) was added dropwise. The resulting mixture was stirred at room temperature for 6 h. TLC (petroleum ether: EtOAc=4:1) showed the reaction was complete. The mixture was quenched with water. The organic layer was washed with HCl (0.5 M) and brine, dried over Na$_2$SO$_4$ and concentrated in vacuo to give crude 2-(4-bromophenyl)-7-(trifluoromethoxy)-2H-benzo[b][1,4]oxazin-3(4H)-one which was used in the next step without any purification.

Step B: 2-(4-bromophenyl)-7-(trifluoromethoxy)-3,4-dihydro-2H-benzo[b][1,4]oxazine To a solution of 2-(4-bromophenyl)-7-(trifluoromethoxy)-2H-benzo[b][1,4]oxazin-3(4H)-one (4 g, 10.31 mmol) in THF (100 mL) was added BH$_3$-DMS (4.89 mL, 51.5 mmol) dropwise at room temperature. The mixture was stirred at this temperature for 4 h. TLC (petroleum ether: EtOAc=3:1) indicated the reaction was complete. The mixture was poured into ice water (200 mL), then extracted with EtOAc (100 mL*2). The organic layer was washed with brine, dried over Na$_2$SO$_4$ and concentrated in vacuum. The residue was purified by column chromatography on SiO$_2$ (EtOAc in petroleum ether=0-30%) to give the 2-(4-bromophenyl)-7-(trifluoromethoxy)-3,4-dihydro-2H-benzo[b][1,4]oxazine as a solid. $^1$H NMR (CDCl$_3$, 400 MHz) δ 7.54 (d, J=8.0 Hz, 2H), 7.28 (d, J=8.4 Hz, 2H), 6.82 (s, 1H), 6.71-6.69 (m, 1H), 6.62-6.60 (m, 1H), 5.06-5.04 (m, 1H), 3.52-3.49 (m, 1H), 3.33-3.28 (m, 1H).

Step C: ethyl 2-(4-bromophenyl)-7-hydroxy-5-oxo-9-(trifluoromethoxy)-3,5-dihydro-2H-[1,4]oxazino[2,3,4-ij]quinoline-6-carboxylate A mixture of 2-(4-bromophenyl)-7-(trifluoromethoxy)-3,4-dihydro-2H-benzo[b][1,4]oxazine (2.5 g, 6.68 mmol) and triethyl methanetricarboxylate (6.21 g, 26.7 mmol) was stirred at 250° C. for 1 h. TLC (petroleum ether: EtOAc=3:1) showed the starting material was consumed. The mixture was diluted with petroleum ether (20 mL). The solid was collected by filtration and dried under vacuum to give ethyl 2-(4-bromophenyl)-7-hydroxy-5-oxo-9-(trifluoromethoxy)-3,5-dihydro-2H-[1,4]oxazino[2,3,4-ij]quinoline-6-carboxylate as a solid. $^1$H NMR (CDCl$_3$, 400 MHz) δ 14.33 (s, 1H), 7.64 (s, 1H), 7.59 (d, J=8.4 Hz, 2H), 7.33 (d, J=8.0 Hz, 2H), 7.26-7.19 (m, 1H), 5.11-5.10 (m, 1H), 4.89 (d, J=11.6 Hz, 1H), 4.51 (q, J=4.8 Hz, 2H), 3.65-3.59 (m, 1H), 1.48 (t, J=7.2 Hz, 3H).

Step D: tert-butyl 2-(2-(4-bromophenyl)-7-hydroxy-5-oxo-9-(trifluoromethoxy)-3,5-dihydro-2H-[1,4]oxazino[2,3,4-ij]quinoline-6-carboxamido)acetate To a suspension of ethyl 2-(4-bromophenyl)-7-hydroxy-5-oxo-9-(trifluoromethoxy)-3,5-dihydro-2H-[1,4]oxazino[2,3,4-ij]quinoline-6-carboxylate (1.7 g, 3.31 mmol) and 2-(tert-butoxy)-2-oxoethanaminium chloride (0.83 g, 4.96 mmol) in toluene (10 mL) was added DIPEA (2.31 mL, 13.22 mmol). The mixture was stirred at 110° C. for 3 h. TLC (petroleum ether: EtOAc=2:1) showed the reaction was complete. The mixture was cooled to room temperature and concentrated in vacuo. The residue was diluted with DCM (100 mL), washed with water, HCl (0.5 M) and brine. The organic layer was dried over Na$_2$SO$_4$ and concentrated to give tert-butyl 2-(2-(4-bromophenyl)-7-hydroxy-5-oxo-9-(trifluoromethoxy)-3,5-dihydro-2H-[1,4]oxazino[2,3,4-ij]quinoline-6-carboxamido)acetate as a solid which was used in the next step without any purification. $^1$H NMR (CDCl$_3$, 400 MHz) δ 10.52 (s, 1H), 7.66 (s, 1H), 7.60 (d, J=8.4 Hz, 2H), 7.35 (d, J=8.4 Hz, 2H), 7.19-7.16 (m, 1H), 5.14-5.11 (m, 1H), 4.93 (d, J=11.2 Hz, 1H), 4.13 (dd, J=9.2 Hz, 5.2 Hz, 2H), 3.68-3.62 (m, 1H), 1.50 (s, 9H).

Step E: tert-butyl 2-(2-(4-cyanophenyl)-7-hydroxy-5-oxo-9-(trifluoromethoxy)-3,5-dihydro-2H-[1,4]oxazino[2,3,4-ij]quinoline-6-carboxamido)acetate A mixture of tert-butyl 2-(2-(4-bromophenyl)-7-hydroxy-5-oxo-9-(trifluoromethoxy)-3,5-dihydro-2H-[1,4]oxazino[2,3,4-ij]quinoline-6-carboxamido)acetate (180 mg, 0.300 mmol), Pd$_2$(dba)$_3$ (35.8 mg, 0.039 mmol), DPPF (21.64 mg, 0.039 mmol), zinc (49.1 mg, 0.751 mmol), and dicyanozinc (88 mg, 0.751 mmol) in DMA (3 mL) was heated with microwave at 120° C. for 30 mins. TLC (petroleum ether: EtOAc=3:1) showed the reacrion was complete. The mixture was diluted with EtOAc (20 mL) and washed with brine. The organic layer was dried over Na$_2$SO$_4$ and concentrated in vacuo. The residue was purified by column chromatography on SiO$_2$ (EtOAc in petroleum ether=0~30%) to give the tert-butyl 2-(2-(4-cyanophenyl)-7-hydroxy-5-oxo-9-(trifluoromethoxy)-3,5-dihydro-2H-[1,4]oxazino[2,3,4-ij]quinoline-6-carboxamido)acetate as a solid. $^1$H NMR (CDCl$_3$, 400 MHz) δ 10.49 (s, 1H), 7.78 (d, J=8.0 Hz, 2H), 7.69 (s, 1H), 7.62(d, J=8.4 Hz, 2H), 7.25-7.22 (m, 1H), 5.25-5.22 (m, 1H), 4.99 (d, J=11.2 Hz, 1H), 4.13 (dd, J=9.2 Hz, 5.2 Hz, 2H), 3.69-3.63 (m, 1H), 1.51 (s, 9H).

Step F: 2-(2-(4-cyanophenyl)-7-hydroxy-5-oxo-9-(trifluoromethoxy)-3,5-dihydro-2H-[1,4]oxazino[2,3,4-ij]quinoline-6-carboxamido)acetic acid To a solution of tert-butyl 2-(2-(4-cyanophenyl)-7-hydroxy-5-oxo-9-(trifluoromethoxy)-3,5-dihydro-2H-[1,4]oxazino[2,3,4-ij]quinoline-6-carboxamido)acetate (90 mg, 0.165 mmol) in DCM (8 mL) was added TFA (1.5 mL, 19.47 mmol). The mixture was stirred at 25° C. for 5 h. TLC (petroleum ether: EtOAc=2:1) showed the reaction was complete. The mixture was concentrated in vacuo to give a crude which was washed with 20 mL petroleum ether: EtOAc (v/v=10:1) to afford 2-(2-(4-cyanophenyl)-7-hydroxy-5-oxo-9-(trifluoromethoxy)-3,5-dihydro-2H-[1,4]oxazino[2,3,4-ij]quinoline-6-carboxamido)acetic acid as a solid. $^1$H NMR (DMSO-d$_6$, 400 MHz) δ 10.39 (s, 1H), 7.97 (d, J=8.0 Hz, 2H), 7.77 (d, J=7.2 Hz, 2H), 7.59-7.57 (m, 2H), 5.58-5.54 (m, 1H), 4.76 (d, J=11.6 Hz, 1H), 4.12 (d, J=5.2 Hz, 2H), 3.87-3.84 (m, 1H). LC/MS (m/z): 490 [M+H]$^+$. Human HIF-PHD2 IC__2.0 nM.

Example 126

2-(7-Hydroxy-5-oxo-2-(6-(trifluoromethyl)pyridin-3-yl)-1,2,3,5-tetrahydropyrido[1,2,3-de]quinoxaline-6-carboxamido)acetic acid (TFA salt)

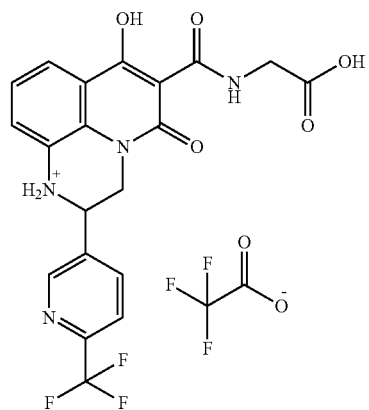

And Example 127

2-(7-Hydroxy-5-oxo-3-(6-(trifluoromethyl)pyridin-3-yl)-1,2,3,5-tetrahydropyrido[1,2,3-de]quinoxaline-6-carboxamido)acetic acid (TFA salt)

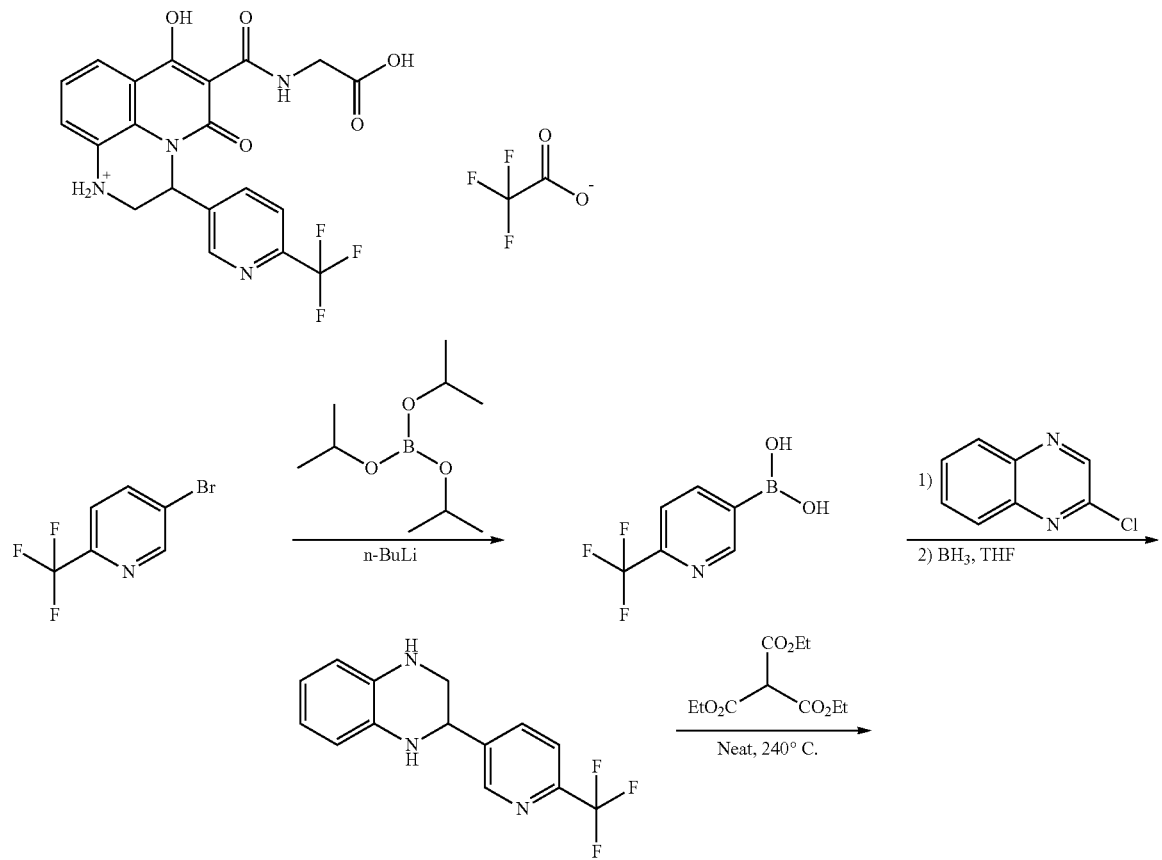

225
-continued
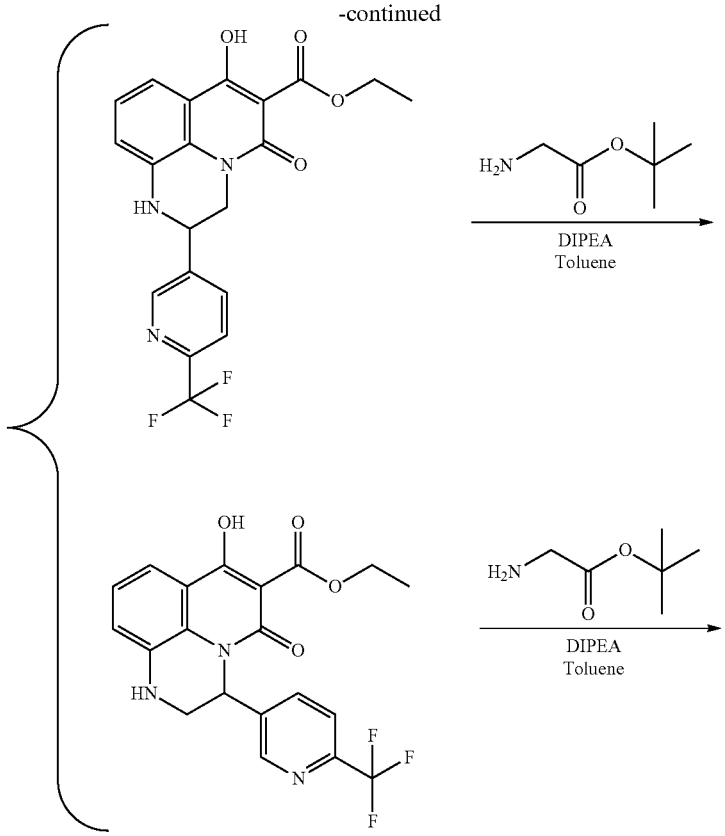
226
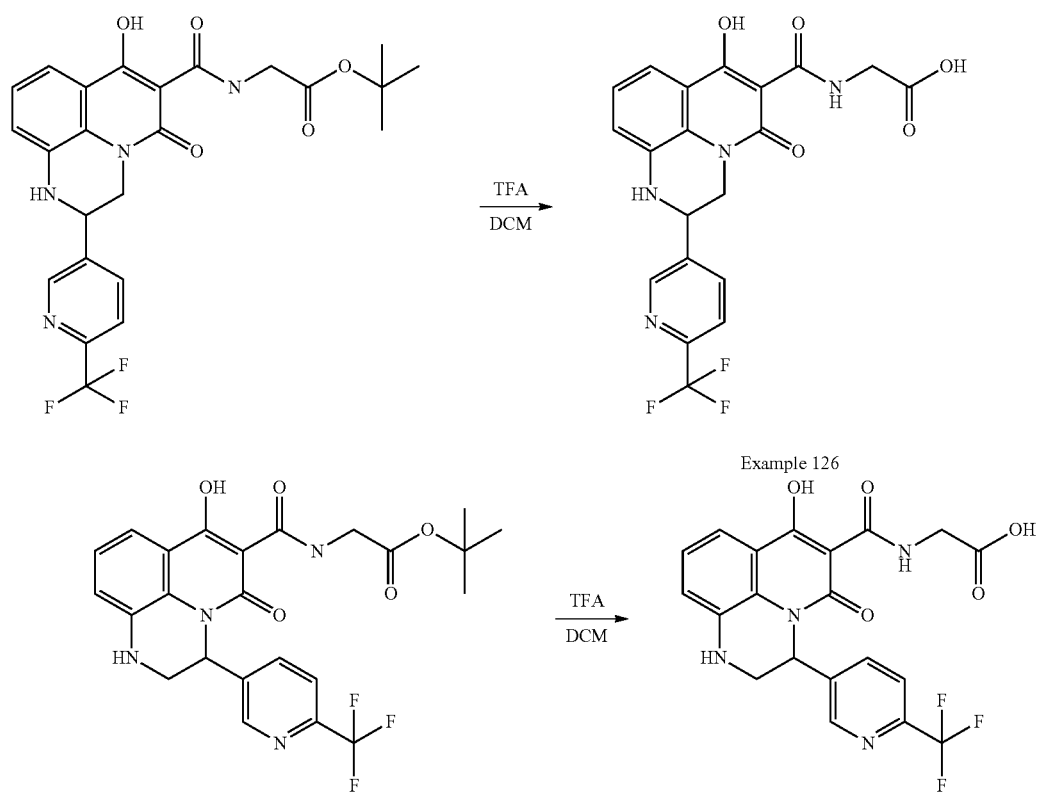
Example 126
Example 127

Step A: (6-(trifluoromethyl)pyridin-3-yl)boronic acid

To a solution of 5-bromo-2-(trifluoromethyl)pyridine (10 g, 44.2 mmol) and triisopropyl borate (9.97 g, 53 mmol) in THF (80 mL) at −78° C. under nitrogen was added butyl-lithium (19.60 mL, 49 mmol) dropwise. The mixture was stirred at −78° C. for 3.5 h before warming up gradually to −10° C. Then the reaction was quenched with water (80 mL). The organic solvent was removed in vacuo. The resulting aqueous phase was adjusted to pH=10 with aq solution of NaOH (1 M), washed with MTBE (1*80 mL) and acidified to pH=5 with aq of HCl (0.5 M). The solution was extracted with EtOAc (150 mL*2) and concentrated in vacuo to give (6-(trifluoromethyl)pyridin-3-yl)boronic acid as a solid.

Step B: 2-(6-(trifluoromethyl)pyridin-3-yl)-1,2,3,4-tetrahydroquinoxaline

To a solution of 2-chloroquinoxaline (2 g, 12.15 mmol), (6-(trifluoromethyl)pyridin-3-yl)boronic acid (2.436 g, 12.76 mmol) and $K_2CO_3$ (3.36 g, 24.30 mmol) in dioxane (24 mL) and water (8 mL) was added $Pd(Ph_3P)_4$ (0.702 g, 0.608 mmol) under nitrogen. The mixture was stirred at 90° C. under nitrogen for 4 h. TLC (petroleum ether: EtOAc=3:1) showed the reaction was complete. The mixture was cooled to room temperature, diluted with EtOAc (100 mL), and washed with water and brine. The organic layer was dried over $Na_2SO_4$, concentrated in vauo. The residue was purified by silica gel column chromatgraphy (EtOAc in petroleum ether=0~10%) to give the 2-(6-(trifluoromethyl)pyridin-3-yl)quinoxaline as a solid. $^1$H NMR (CDCl$_3$, 400 MHz) δ 9.53 (s, 1H), 9.38 (s, 1H), 8.72 (d, J=7.6 Hz, 1H), 8.21-8.19 (m, 2H), 7.90-7.83 (m, 3H).

To a solution of 2-(6-(trifluoromethyl)pyridin-3-yl)quinoxaline (2.5 g, 9.08 mmol) in THF (40 mL) was added $BH_3$-THF (21 mL, 21.00 mmol) at room temperature. The mixture was stirred at 23° C. for 15 mins. TLC (petroleum ether: EtOAc=2:1) indicated the starting material was consumed. MeOH (30 mL) was added, and the mixture was stirred for another 20 mins. The mixture was concentrated in vacuo. DCM (30 mL) was added, and the solution was washed with brine. The organic layer was concentrated in vacuo. The residue was purified by silica gel column chromatography (EtOAc in petroleum ether=0~20%) to give 2-(6-(trifluoromethyl)pyridin-3-yl)-1,2,3,4-tetrahydroquinoxaline as an oil. $^1$H NMR (CDCl$_3$, 400 MHz) δ 8.73 (s, 1H), 7.92-7.86 (m, 1H), 7.68 (d, J=8.4 Hz, 1H), 6.72-6.65 (m, 2H), 6.65-6.57 (m, 2H), 4.66 (dd, J=2.8, 6.8 Hz, 1H), 3.96 (br. s., 1H), 3.86 (br. s., 1H), 3.53 (dd, J=3.2, 11.2 Hz, 1H), 3.33 (dd, J=7.2, 11.2 Hz, 1H).

Step C: ethyl 7-hydroxy-5-oxo-2-(6-(trifluoromethyl)pyridin-3-yl)-1,2,3,5-tetrahydropyrido[1,2,3-de]quinoxaline-6-carboxylate and ethyl 7-hydroxy-5-oxo-3-(6-(trifluoromethyl)pyridin-3-yl)-1,2,3,5-tetrahydropyrido[1,2,3-de]quinoxaline-6-carboxylate A mixture of 2-(6-(trifluoromethyl)pyridin-3-yl)-1,2,3,4-tetrahydroquinoxaline (500 mg, 1.790 mmol) and triethyl methanetricarboxylate (1663 mg, 7.16 mmol) was stirred at 240° C. for 40 min. TLC (petroleum ether: EtOAc=2:1) showed the starting material was consumed. The mixture was diluted with DCM (20 mL), concentrated and purified by silica gel column chromatography (EtOAc in petroleum ether=0~50%) to give ethyl 7-hydroxy-5-oxo-2-(6-(trifluoromethyl)pyridin-3-yl)-1,2,3,5-tetrahydropyrido[1,2,3-de]quinoxaline-6-carboxylate as a solid $^1$H NMR (CDCl$_3$, 400 MHz) δ 14.21 (s, 1H), 8.78 (s, 1H), 7.92 (d, J=8.0 Hz, 1H), 7.73 (d, J=8.0 Hz, 1H), 7.64 (d, J=8.0 Hz, 1H), 7.11 (t, J=8.0 Hz, 1H), 6.99 (d, J=8.0 Hz, 1H), 4.86 (d, J=13.4 Hz, 1H), 4.59 (dd, J=2.8, 9.2 Hz, 1H), 4.52-4.43 (m, 2H), 4.41 (s, 1H), 3.66 (dd, J=9.2, 13.2 Hz, 1H), 1.25 (t, J=7.6 Hz, 3H); and ethyl 7-hydroxy-5-oxo-3-(6-(trifluoromethyl)pyridin-3-yl)-1,2,3,5-tetrahydropyrido[1,2,3-de]quinoxaline-6-carboxylate as a solid. $^1$H NMR (CDCl$_3$, 400 MHz) δ 14.32 (s, 1H), 8.61 (s, 1H), 7.67 (d, J=8.0 Hz, 1H), 7.57-7.52 (m, 2H), 7.11 (t, J=8.0 Hz, 1H), 6.96 (d, J=7.6 Hz, 1H), 6.21 (s, 1H), 4.52-4.38 (m, 2H), 4.16 (s, 1H), 3.71 (dd, J=12.0, 3.4 Hz, 1H), 3.55 (d, J=11.2 Hz, 1H), 1.42 (t, J=7.2 Hz, 3H).

Step D: tert-butyl 2-(7-hydroxy-5-oxo-2-(6-(trifluoromethyl)pyridin-3-yl)-1,2,3,5-tetrahydropyrido[1,2,3-de]quinoxaline-6-carboxamido)acetate To a solution of ethyl 7-hydroxy-5-oxo-2-(6-(trifluoromethyl)pyridin-3-yl)-1,2,3,5-tetrahydropyrido[1,2,3-de]quinoxaline-6-carboxylate (300 mg, 0.715 mmol) and 2-(tert-butoxy)-2-oxoethanaminium chloride (180 mg, 1.073 mmol) in toluene (8 mL) was added DIPEA (0.500 mL, 2.86 mmol). The mixture was stirred at 100° C. for 3 h. TLC (petroleum ether: EtOAc=2:1) showed the reaction was complete. The mixture was cooled to room temperature and concentrated in vacuo. The residue was diluted with DCM (20 mL), washed with water and brine. The organic layer was dried over $Na_2SO_4$, and concentrated in vacuo. The residue was purified by silica gel column chromatography (EtOAc in petroleum ether=10%-40%) to give tert-butyl 2-(7-hydroxy-5-oxo-2-(6-(trifluoromethyl)pyridin-3-yl)-1,2,3,5-tetrahydropyrido[1,2,3-de]quinoxaline-6-carboxamido)acetate as a solid. $^1$H NMR (CDCl$_3$, 400 MHz) δ 10.59 (br.s., 1H), 8.82 (s, 1H), 7.96 (d, J=6.8 Hz, 1H), 7.75 (d, J=8.0 Hz, 1H), 7.63 (d, J=7.8 Hz, 1H), 7.14 (t, J=7.8 Hz, 1H), 6.98 (d, J=7.6 Hz, 1H), 4.90 (d, J=12.7 Hz, 1H), 4.59 (d. J=7.2 Hz 1H), 4.48 (br.s., 1H), 4.12-4.03 (m, 2H), 3.66 (dd, J=9.6, 13.2 Hz, 1H), 1.46 (s, 9H).

Step E: 2-(7-hydroxy-5-oxo-2-(6-(trifluoromethyl)pyridin-3-yl)-1,2,3,5-tetrahydropyrido[1,2,3-de]quinoxaline-6-carboxamido)acetic acid (TFA salt)

To a solution of tert-butyl 2-(7-hydroxy-5-oxo-2-(6-(trifluoromethyl)pyridin-3-yl)-1,2,3,5-tetrahydropyrido[1,2,3-de]quinoxaline-6-carboxamido)acetate (100 mg, 0.198 mmol) in DCM (8 mL) was added TFA (1 mL, 12.98 mmol). The mixture was stirred at 25° C. for 5 h. TLC (DCM: MeOH=10:1) showed the reaction was complete. The mixture was concentrated in vacuo. The residue was triturated with 20 mL of petroleum ether/EtOAc (v/v 10:1) to afford Example 126 product, 2-(7-hydroxy-5-oxo-2-(6-(trifluoromethyl)pyridin-3-yl)-1,2,3,5-tetrahydropyrido[1,2,3-de]quinoxaline-6-carboxamido)acetic acid (TFA salt) as a solid. $^1$H NMR (DMSO-d$_6$, 400 MHz) δ 10.46 (s, 1H), 8.85 (s, 1H), 8.10 (d, J=7.6 Hz, 1H), 7.93 (d, J=8.0 Hz, 1H), 7.36 (d, J=7.6 Hz, 1H), 7.13-7.03 (m, 3H), 4.74 (d, J=6.4 Hz, 1H), 4.55 (d, J=12.8 Hz, 1H), 3.99 (d, J=3.2 Hz, 2H), 3.93-3.88 (m, 1H). LC/MS (m/z): 449 [M+H]$^+$. Human HIF-PHD2 IC$_{50}$ 5.4 nM.

Step F: tert-butyl 2-(7-hydroxy-5-oxo-3-(6-(trifluoromethyl)pyridin-3-yl)-1,2,3,5-tetrahydropyrido[1,2,3-de]quinoxaline-6-carboxamido)acetate To a suspension of ethyl 7-hydroxy-5-oxo-3-(6-(trifluoromethyl)pyridin-3-yl)-1,2,3,5-tetrahydropyrido[1,2,3-de]

quinoxaline-6-carboxylate (200 mg, 0.477 mmol) and 2-(tert-butoxy)-2-oxoethanaminium chloride (120 mg, 0.715 mmol) in toluene (5 mL) was added DIPEA (0.333 mL, 1.908 mmol). The mixture was stirred at 100° C. for 3 h. TLC (petroleum ether: EtOAc=4:1) showed the reaction was complete. The mixture was cooled to room temperature and concentrated in vacuo. The residue was diluted with DCM (20 mL), and washed with water and brine. The organic layer was dried over $Na_2SO_4$ and concentrated. The residue was purified by silica gel column chromatography (EtOAc in petroleum ether=10%-40%) to give tert-butyl 2-(7-hydroxy-5-oxo-3-(6-(trifluoromethyl)pyridin-3-yl)-1,2,3,5-tetrahydropyrido[1,2,3-de]quinoxaline-6-carboxamido)acetate as a solid. $^1$H NMR ($CDCl_3$, 400 MHz) δ 10.43 (brs, 1H), 8.64 (brs, 1H), 7.69 (d, J=8.0 Hz, 1H), 7.59-7.42 (m, 2H), 7.17 (t, J=7.6 Hz, 1H), 6.96 (d, J=7.6 Hz, 1H), 6.24 (br.s., 1H), 4.18-4.17 (m, 1H), 4.13 (d, J=5.8 Hz, 1H), 4.01-3.92 (m, 1H), 3.77-3.69 (m, 1H), 3.58 (d, J=11.6 Hz, 1H), 1.46 (s, 9H).

Step G: 2-(7-hydroxy-5-oxo-3-(6-(trifluoromethyl)pyridin-3-yl)-1,2,3,5-tetrahydropyrido[1,2,3-de]quinoxaline-6-carboxamido)acetic acid (TFAsalt)

To a solution of tert-butyl 2-(7-hydroxy-5-oxo-3-(6-(trifluoromethyl)pyridin-3-yl)-1,2,3,5-tetrahydropyrido[1,2,3-de]quinoxaline-6-carboxamido)acetate (80 mg, 0.16 mmol) in DCM (5 mL) was added TFA (1 mL, 12.98 mmol). The mixture was stirred at 25° C. for 5 h. TLC (DCM: MeOH=10:1) showed the reaction was complete. The mixture was concentrated in vacuo. The residue was trituated with 20 mL of petroleum ether/EtOAc (v/v 10:1) to afford Example 127 product, 2-(7-hydroxy-5-oxo-3-(6-(trifluoromethyl)pyridin-3-yl)-1,2,3,5-tetrahydropyrido[1,2,3-de]quinoxaline-6-carboxamido)acetic acid (TFA salt) as a solid. $^1$H NMR (DMSO-$d_6$, 400 MHz) δ 10.31 (s, 1H), 8.62 (s, 1H), 7.76 (d, J=8.0 Hz, 1H), 7.54 (d, J=7.6 Hz, 1H), 7.42 (d, J=8.0 Hz, 1H), 7.15 (t, J=7.6 Hz, 1H), 7.02 (d, J=7.6 Hz, 1H), 6.45 (s, 1H), 6.18 (s, 1H), 4.02-3.98 (m, 2H), 3.59-3.54 (m, 2H). LC/MS (m/z): 449 [M+H]$^+$. Human HIF-PHD2 $IC_{50}$ 3.6 nM.

Example 128

2-(7-Hydroxy-1-methyl-5-oxo-3-(6-(trifluoromethyl)pyridin-3-yl)-1,2,3,5-tetrahydropyrido[1,2,3-de]quinoxaline-6-carboxamido)acetic acid

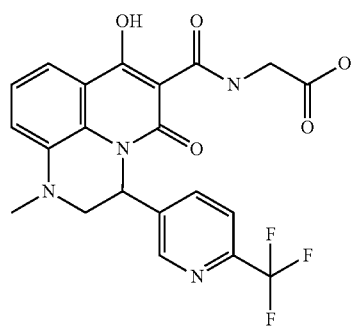

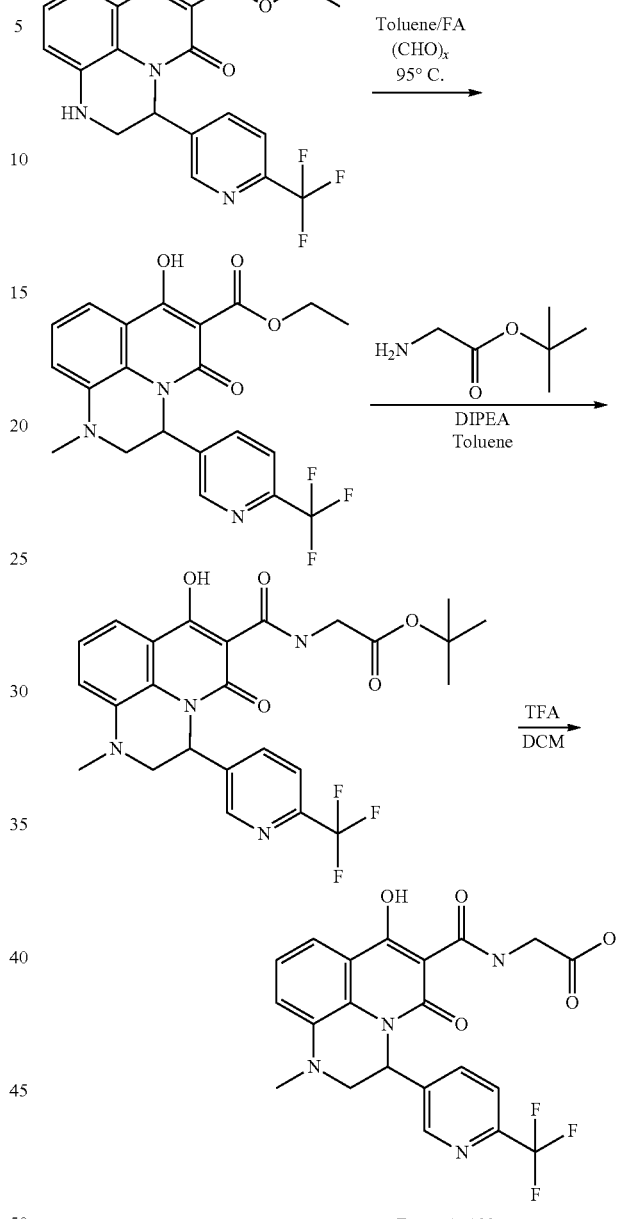

Example 128

Step A: ethyl 7-hydroxy-1-methyl-5-oxo-3-(6-(trifluoromethyl)pyridin-3-yl)-1,2,3,5-tetrahydropyrido[1,2,3-de]quinoxaline-6-carboxylate To a solution of ethyl 7-hydroxy-5-oxo-3-(6-(trifluoromethyl)pyridin-3-yl)-1,2,3,5-tetrahydropyrido[1,2,3-de]quinoxaline-6-carboxylate (250 mg, 0.596 mmol) in toluene (5 mL) were added formic acid (0.513 mL, 11.92 mmol) and paraformaldehyde (537 mg, 5.96 mmol). The mixture was stirred at 100° C. for 5 h. TLC (petroleum ether: EtOAc=4:1) indicated the starting material was consumed. The mixture was concentrated in vacuo and the residue was purified by silica gel column chromatography (EtOAc in petroleum ether=20%-50%) to give ethyl 7-hydroxy-1-methyl-5-oxo- 3-(6-(trifluoromethyl)pyridin-3-yl)-1,2,3,5-tetrahydropyrido[1,2,3-de]quinoxaline-6-carboxylate as a solid. $^1$H NMR (CDCl$_3$, 400 MHz) δ 14.32 (s, 1H), 8.63 (s, 1H), 7.70 (d, J=8.0 Hz, 1H), 7.60-7.51 (m, 2H), 7.26-7.22 (m, 1H), 6.96 (d, J=8.0 Hz, 1H), 6.19 (br.s., 1H), 4.56-4.37 (m, 2H), 3.63 (dd, J=3.2, 11.8 Hz, 1H), 3.39 (d, J=12.0 Hz, 1H), 2.91 (s, 3H), 1.43 (t, J=7.2 Hz, 3H).

Step B: tert-butyl 2-(7-hydroxy-1-methyl-5-oxo-3-(6-(trifluoromethyl)pyridin-3-yl)-1,2,3,5-tetrahydropyrido[1,2,3-de]quinoxaline-6-carboxamido)acetate To a suspension of ethyl 7-hydroxy-1-methyl-5-oxo-3-(6-(trifluoromethyl)pyridin-3-yl)-1,2,3,5-tetrahydropyrido[1,2,3-de]quinoxaline-6-carboxylate (170 mg, 0.392 mmol) and 2-(tert-butoxy)-2-oxoethanaminium chloride (99 mg, 0.588 mmol) in toluene (5 mL) was added DIPEA (0.274 mL, 1.569 mmol). The mixture was stirred at 100° C. for 3 h. TLC (petroleum ether: EtOAc=3:1) showed the reaction was complete. The mixture was cooled to room temperature and concentrated in vacuo. The residue was purified by silica gel column chromatography (EtOAc in petroleum ether=10-40%) to give tert-butyl 2-(7-hydroxy-1-methyl-5-oxo-3-(6-(trifluoromethyl)pyridin-3-yl)-1,2,3,5-tetrahydropyrido[1,2,3-de]quinoxaline-6-carboxamido)acetate as a solid. $^1$H NMR (CDCl$_3$, 400 MHz) δ 10.42 (br.s., 1H), 8.66 (s, 1H), 7.72 (d, J=8.0 Hz, 1H), 7.56-7.54 (m, 2H), 7.30-7.27 (m, 1H), 6.97 (d, J=7.6 Hz, 1H), 6.22 (br.s., 1H), 4.20-3.96 (m, 2H), 3.70-3.63 (m, 1H), 3.42 (dd, J=1.6, 12.0 Hz, 1H), 2.93 (s, 3H), 1.48 (s, 9H).

Step C: 2-(7-hydroxy-1-methyl-5-oxo-3-(6-(trifluoromethyl)pyridin-3-yl)-1,2,3,5-tetrahydropyrido[1,2,3-de]quinoxaline-6-carboxamido)acetic acid To a solution of tert-butyl 2-(7-hydroxy-1-methyl-5-oxo-3-(6-(trifluoromethyl)pyridin-3-yl)-1,2,3,5-tetrahydropyrido[1,2,3-de]quinoxaline-6-carboxamido)acetate (120 mg, 0.23 mmol) in DCM (10 mL) was added TFA (1 mL, 12.98 mmol). The mixture was stirred at 25° C. for 5 h. TLC (DCM: MeOH=10:1) showed the reaction was complete. The mixture was concentrated in vacuo and the residue was purified by HPLC (Column: Gemini 150*23.5mm*10 um, Mobile phase: from 25% MeCN in water (0.225% FA) to 55% MeCN in water (0.225% FA)) to give the 2-(7-hydroxy-1-methyl-5-oxo-3-(6-(trifluoromethyl)pyridin-3-yl)-1,2,3,5-tetrahydropyrido[1,2,3-de]quinoxaline-6-carboxamido)acetic acid as a solid. $^1$H NMR (DMSO-d$_6$, 400 MHz) δ 10.30 (t, J=6.4 Hz, 1H), 8.69 (s, 1H), 7.79 (d, J=8.0 Hz, 1H), 7.61 (d, J=8.0 Hz, 1H), 7.56 (d, J=7.2 Hz, 1H), 7.31 (t, J=8.0 Hz, 1H), 7.09 (d, J=8.0 Hz, 1H), 6.23 (s, 1H), 4.08-4.05 (m, 2H), 3.68 (d, J=12.4 Hz, 1H), 3.61-3.58 (m, 1H), 2.85 (s, 3H). LC/MS (m/z): 463 [M+H]$^+$. Human HIF-PHD2 IC$_{50}$ 6.9 nM.

Example 129

2-(6-Hydroxy-4-oxo-2-phenyl-2,4-dihydro-1H-pyrrolo[3,2,1-ij]quinoline-5-carboxamido)acetic acid

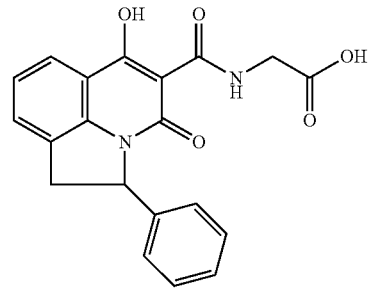 [SMILES: O=C(O)CNC(=O)c1c(O)c2cccc3c2n(c1=O)C(c1ccccc1)C3]

Step A: 2-phenylindoline

A mixture of 2-phenyl-1H-indole (1.0 g, 5.17 mmol) and acetic acid (20 ml) was treated with sodium cyanoborohydride (3.25 g, 51.7 mmol) and the mixture stirred at rt for 8 h. The mixture was diluted with water and the mixture neutralized with NaOH pellets. The mixture was extracted with DCM and the organic layer dried (MgSO$_4$) and concentrated to afford an oil. Purification on the CombiFlash companion eluting with 0 to 50% EtOAc/Hexane afforded a racemic mixture of the title compound.

Step B: ethyl 6-hydroxy-4-oxo-2-phenyl-2,4-dihydro-1H-pyrrolo[3,2,1-ij]quinoline-5-carboxylate A neat mixture of the product from step A (300 mg, 1.536 mmol) and triethyl methanetricarboxylate (1427 mg, 6.15 mmol) was heated at 200° C. for a total of 8 h. The mixture was cooled to rt followed by trituration from ether/hexane to afford the title compound (racemic). LC/MS (m/z): 358 (M+Na)$^+$.

Step C: tert-butyl 2-(6-hydroxy-4-oxo-2-phenyl-2,4-dihydro-1H-pyrrolo[3,2,1-ij]quinoline-5-carboxamido)acetate A suspension of Step B product (0.260 g, 0.775 mmol) and tert-butyl 2-aminoacetate (0.131 ml, 0.930 mmol) in DME (3.0 ml) was stirred at 80° C. for 8 h. The mixture was cooled and concentrated. Triturated of the residue with ether/hexane followed by filtration afforded the racemic title compound. LC/MS (m/z): 443 (M+Na)$^+$.

Step D: 2-(6-Hydroxy-4-oxo-2-phenyl-2,4-dihydro-1H-pyrrolo[3,2,1-ij]quinoline-5-carboxamido)acetic acid A solution of Step C product in DCM (4 ml) was treated with 20% TFA and the mixture stirred at rt overnight. The solvent was evaporated and triuration with ether/hexane followed by filtration afforded the title compound as a racemic mixture. LC/MS (m/z): 387 (M+H)$^+$. Human HIF-PHD2 IC$_{50}$: 74 nM.

Example 130

2-(1-Hydroxy-3-oxo-5-phenyl-3,5,6,7-tetrahydropyrido[3,2,1-ij]quinoline-2-carboxamido)acetic acid

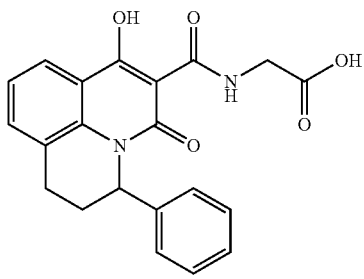 [SMILES: O=C(O)CNC(=O)c1c(O)c2cccc3c2n(c1=O)C(c1ccccc1)CC3]

Step A: 2-(4-chlorophenyl)-1,2-dihydroquinoline and 2-(4-chlorophenyl)quinoline To a THF solution of (4-chlorophenyl) magnesium chloride (15.48 ml, 15.48 mmol) at 0° C. was added dropwise a solution of Quinoline (1.835 ml, 15.48 mmol) in THF. The resulting homogenous brown solution was then stirred at rt for 3 h. The mixture was then heated at 55° C. for 5 h. After cooling to rt the mixture was poured into sat. NH4Cl and extrracted with DCM. The organic layer was dried with MgSO$_4$ and concentrated in vacuo to afford an oil. Purification on the CombiFlash Companion eluting with 0 to 10% EtOAc/Hexane afforded a mixture of the 2 title products in the ratio 6:4. LC/MS (m/z): 242 (M+H)$^+$ and 240 (M+H)$^+$.

Step B: 2-phenyl-1,2,3,4-tetrahydroquinoline

A solution of the mixture from Step A (1.1 g, 4.55 mmol) in ethanol (18 ml) was heated at 90° C. and sodium (1.883 g, 82 mmol) added over a period of 2 h. The reaction was monitored by TLC. After 3 h there was complete conversion and the mixture was cooled to rt and poured into water. Extraction with EtOAc (×3) followed by concentration of the solvent afforded the racemic title compound. LC/MS (m/z): 210 (M+H)$^+$.

Step C: ethyl 1-hydroxy-3-oxo-5-phenyl-3,5,6,7-tetrahydropyrido[3,2,1-ij]quinoline-2-carboxylate A neat mixture of Step B product (243 mg, 1.161 mmol) and triethyl methanetricarboxylate (404 mg, 1.742 mmol) was heated at 200° C. for 45 mins. The yellow oil was cooled to rt and trituration from ether/hexane followed by filtration afforded the title compound as a racemate. LC/MS (m/z): 350.2 (M+H)$^+$.

Step D: tert-Butyl 2-(1-hydroxy-3-oxo-5-phenyl-3,5,6,7-tetrahydropyrido[3,2,1-ij]quinoline-2-carboxamido)acetate A solution of Step C product (150 mg, 0.429 mmol) in DME (4.0 ml) was treated with tert-butyl 2-aminoacetate (0.070 ml, 0.515 mmol) and the mixture stirred at 82° C. for 15 h. The solvent was evaporated and trituration and filtration from ether/ hexane afforded the desired product (racemic). LC/MS (m/z): 457 (M+H)$^+$.

Step E: R or S-tert-Butyl 2-(1-hydroxy-3-oxo-5-phenyl-3,5,6,7-tetrahydropyrido[3,2,1-ij]quinoline-2-carboxamido)acetate.

Chiral separation of the racemic mixture from step D on an OD column eluting with 5% IPA/Heptane afforded enantiomer 1 and enantiomer 2.

Step F: R or S-2-(1-hydroxy-3-oxo-5-phenyl-3,5,6,7-tetrahydropyrido[3,2,1-ij]quinoline-2-carboxamido)acetic acid A solution of enantiomer 2 (slower enantiomer) from Step E in DCM (2 ml) was treated with 20% TFA and the mixture stirred at rt overnight. The solvent was evaporated and triuration with ether/hexane followed by filtration afforded the title compound. $^1$H NMR (500 MHz, (CD$_3$)$_2$S0) δ 12.85 (b, 1H), 10.42 (t, 1H), 8.01 (d, J=7.7 Hz, 1H), 7.57 (d, J=7.1, 1H), 7.38-7.19 (m, 4H), 6.94 (d, J=7.6 Hz, 2H), 6.16 (s, 1H), 4.06-4.04 (m, 2H), 3.35 (m, 1H), 2.81 (d, J=15.6 Hz, 1H), 2.45 (m, 1H), 2.36 (d, J=13.5 Hz, 1H), 2.23-2.16 (m, 1H). LC/MS (m/z): 379.6 (M+H)$^+$. Human HIF-PHD2 IC$_{50}$: 18 nM.

Example 131

2-(5-(4-Chlorobenzyl)-1-hydroxy-3-oxo-3,5,6,7-tetrahydropyrido[3,2,1-ij]quinoline-2-carboxamido) acetic acid

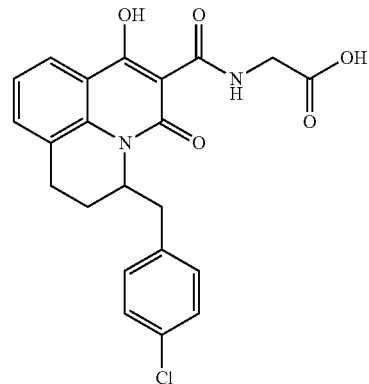 [SMILES: O=C(O)CNC(=O)c1c(O)c2cccc3c2n(c1=O)C(Cc1ccc(Cl)cc1)CC3]

Step A: 2-(4-chlorobenzyl)-1,2,3,4-tetrahydroquinoline

To a THF solution of (4-chlorobenzyl) magnesium chloride (34.1 ml, 8.52 mmol) at 0° C. was added dropwise a solution of quinoline (0.917 ml, 7.74 mmol) in THF (10 ml). The resulting homogenous brown solution was then stirred at 55° C. for 3 h. After cooling to rt, the mixture was poured into sat. NH$_4$Cl and extracted with DCM. The organic layer was dried (MgSO$_4$) and concentrated in the vacuo to afford an oil. Purification on the CombiFlash Companion eluting with 0 to 10% EtOAc/hexane afforded the desired product as a racemic mixture. LC/MS (m/z): 258 (M+H)$^+$.

Step B: ethyl 5-(4-chlorobenzyl)-1-hydroxy-3-oxo-3,5,6,7-tetrahydropyrido[3,2,1-ij]quinoline-2-carboxylate A neat mixture of Step A product (255 mg, 0.989 mmol) and triethyl methanetricarboxylate (345 mg, 1.484 mmol) was heated at 200° C. for 30 mins and then cooled to rt.

Trituration from ether/hexane followed by filtration afforded the desired product as a racemic mixture. LC/MS (m/z): 398 (M+H)⁺.

Step C: 2-(5-(4-chlorobenzyl)-1-hydroxy-3-oxo-3,5,6,7-tetrahydropyrido[3,2,1-ij]quinoline-2-carboxamido)acetic acid A solution of Step B product (250. mg, 0.628 mmol) in DME (4.0 ml) was treated with tert-butyl 2-aminoacetate (0.103 ml, 0.754 mmol) and the mixture stirred at 82° C. for 3 h. The solvent was evaporated and the crude mixture was purified on the CombiFlash Companion eluting with 0 to 20% EtOAc/Hexane to afford the t-butyl ester of the title compound. $^1$H NMR (500 MHz, CDCl$_3$) δ 10.80 (t, 1H), 8.10 (d, J=8.0 Hz, 1H), 7.32 (d, J=8.5, 2H), 7.28 (d, J=6.4 Hz, 1H), 7.17 (t, J=7.6 Hz, 1H), 7.10 (d, J=8.3 Hz, 2H), 4.55-4.54 (d,t, 1H), 4.16 (d, J=5.5 Hz, 2H), 3.92-3.85 (m, 1H), 3.27-3.22 (m, 1H), 3.06-3.02 (dd, 1H), 2.83-2.78 (dd, 1H) 2.03-2.00 (m, 2H), 1.60 (b, 1H) 1.57 (s, 9H). Hydrolysis the t-butyl ester with 20% TFA/DCM followed by trituration from ether/hexane afforded the title compound as a racemic mixture. LC/MS (m/z): 427.5 (M+H)⁺. Human HIF-PHD2 IC$_{50}$: 15 nM.

Example 132

2-(7-Hydroxy-5-oxo-3,5-dihydro-2H-[1,4]oxazino[2,3,4-ij]quinoline-6-carboxamido)acetic acid

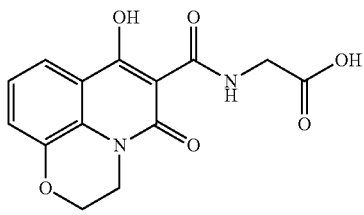 [SMILES: O=C(O)CNC(=O)c1c(O)c2cccc3c2n(c1=O)CCO3]

Step A: ethyl 7-hydroxy-5-oxo-3,5-dihydro-2H-[1,4]oxazino[2,3,4-ij]quinoline-6-carboxylate A neat mixture of 3,4-dihydro-2H-benzo[b][1,4]oxazine (200 mg, 1.480 mmol) and triethyl methanetricarboxylate (687 mg, 2.96 mmol) was heated at 100° C. then slowly to 200° C. After 30 mins the mixture was cooled to rt. The yellow oil was triturated with ether followed by filtration to afford the title compound. $^1$H NMR (500 MHz, CDCl$_3$) δ 7.76 (d, J=8.0, 1.3 Hz, 1H), 7.21 (d, J=6.7 Hz, 1H), 7.16 (t, J=8.0 Hz, 1H), 4.52 (q, J=7.1, 2H), 4.36 (t, J=4.3 Hz, 2H), 4.23 (t, J=4.2, 2H), 2.65 (b, 1H), 1.49 (t, J=7.1 Hz, 3H).

Step B: tert-butyl 2-(7-hydroxy-5-oxo-3,5-dihydro-2H-[1,4]oxazino[2,3,4-ij]quinoline-6-carboxamido)acetate A solution of Step A product (200 mg, 0.727 mmol) in DME (5.0 ml) was treated with tert-butyl 2-aminoacetate (0.119 ml, 0.872 mmol) and the mixture stirred at 82° C. for 15 h. The solvent was evaporated and trituration from ether followed by filtration provided the desired product. LC/MS (m/z): 383 (M+Na)⁺.

Step C: 2-(7-Hydroxy-5-oxo-3,5-dihydro-2H-[1,4]oxazino[2,3,4-ij]quinoline-6-carboxamido)acetic acid Hydrolysis of Step B product (100 mg, 0.277 mmol) with 20% TFA/hexane afforded the title product. $^1$H NMR (500 MHz, (CD$_3$)$_2$SO) δ 12.95 (b, 1H), 10.47 (b, 1H), 7.63 (m, 1H), 7.260 (m, 1H), 7.23 (m, 1H), 4.39 (t, J=4.3 Hz, 2H), 4.13 (m, 4H), 3.52 (b, 1H). Human HIF-PHD2 IC$_{50}$: 21 nM.

Example 133

2-(3-(4-Bromophenyl)-7-hydroxy-5-oxo-3,5-dihydro-2H-[1,4]oxazino[2,3,4-ij]quinoline-6-carboxamido)acetic acid

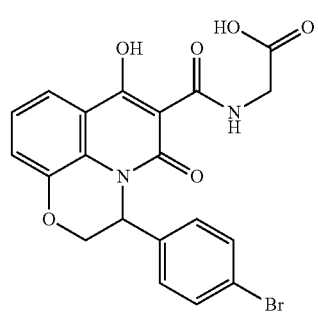 [SMILES: O=C(O)CNC(=O)c1c(O)c2cccc3c2n(c1=O)C(c1ccc(Br)cc1)CO3]

A solution of Intermediate 4 (45 mg, 0.087 mmol) in DCM (4 ml) was treated with 20% TFA and the mixture stirred at rt overnight. The solvent was concentrated and the residue was triturated with ether/hexane followed by filtration to afford the title compound as a racemic mixture. LC/MS (m/z): 461 (M+2)⁺. Human HIF-PHD2 IC$_{50}$: 17 nM.

Example 134

N-[(7-Hydroxy-10-{4-[(methylsulfonyl)amino]phenyl}-5-oxo-3-[4-(trifluoromethyl)phenyl]-2,3-dihydro-5H-[1,4]oxazino[2,3,4-ij]quinolin-6-yl)carbonyl]glycine

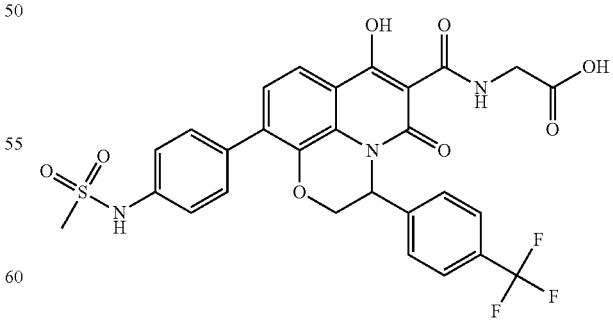

To a solution of (4-(methylsulfon-amido)phenyl)boronic acid (14 mg, 0.051 mmol), tert-butyl 2-(10-bromo-7-hydroxy-5-oxo-3-(4-(trifluoromethyl)phenyl)-3,5-dihydro-2H-[1,4]oxazino[2,3,4-ij]quinoline-6-carboxamido)acetate (Intermediate 1, 15 mg, 0.026 mmol), and potassium carbonate (17.77 mg, 0.129 mmol) in methanol (5 ml), was added Silicyclo-DPPPd (5.14 μmol). The reaction was refluxed for 16 hr. The reaction mixture was filtered and the filtrate was purified by MS directed prep. HPLC to give the desired product N-[(7-hydroxy-10-{4-[(methylsulfonyl)amino]phenyl}-5-oxo-3-[4-(trifluoromethyl)phenyl]-2,3-dihydro-5H-[1,4]oxazino[2,3,4-ij]quinolin-6-yl)carbonyl]glycine. LC/MS (m/z): 618 (M+H)+. Human HIF-PHD2 IC$_{50}$: 38 nM.

Examples 135-140 in Table 10 were prepared following the similar procedures described in Example 134 and using Intermediate 1 and appropriate starting materials.

TABLE 10

| Example | Name | Structure | MS m/z (M + 1)+ and human HIF-PHD2 IC$_{50}$ |
|---|---|---|---|
| Example 135 | N-({7-hydroxy-10-(5-methoxypyridin-3-yl)-5-oxo-3-[4-(trifluoromethyl)phenyl]-2,3-dihydro-5H-[1,4]oxazino[2,3,4-ij]quinolin-6-yl}carbonyl)glycine | 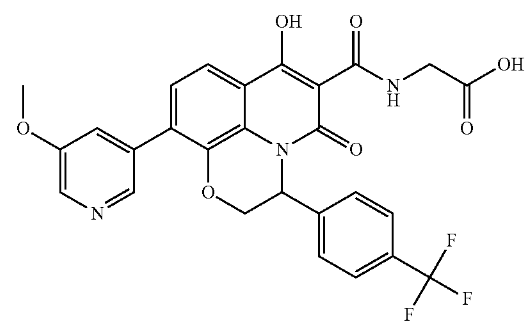 [SMILES: COc1cncc(-c2ccc3c(O)c(C(=O)NCC(=O)O)c(=O)n4c3c2OCC4c2ccc(C(F)(F)F)cc2)c1] | (M + 1)+ 556 IC$_{50}$ 15 nM |
| Example 136 | N-({7-hydroxy-5-oxo-10-pyridin-2-yl-3-[4-(trifluoromethyl)phenyl]-2,3-dihydro-5H-[1,4]oxazino[2,3,4-ij]quinolin-6-yl}carbonyl)glycine | 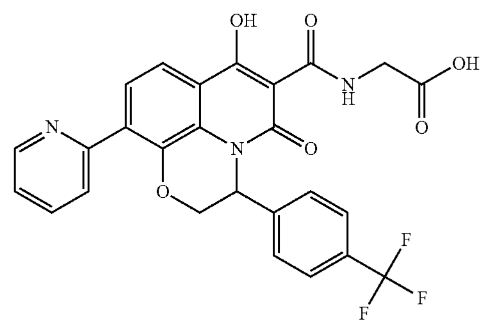 [SMILES: O=C(O)CNC(=O)c1c(O)c2ccc(-c3ccccn3)c3c2n(c1=O)C(c1ccc(C(F)(F)F)cc1)CO3] | (M + 1)+ 526 IC$_{50}$ 19 nM |
| Example 137 | N-({7-hydroxy-10-(2-methoxypyrimidin-5-yl)-5-oxo-3-[4-(trifluoromethyl)phenyl]-2,3-dihydro-5H-[1,4]oxazino[2,3,4-ij]quinolin-6-yl}carbonyl)glycine | 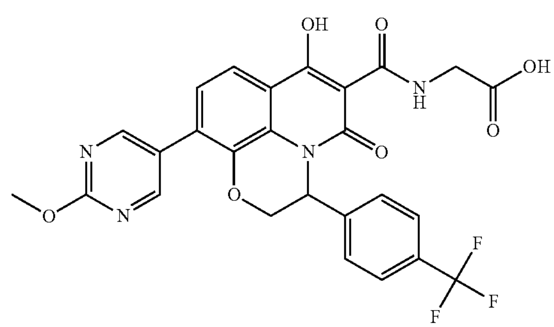 [SMILES: COc1ncc(-c2ccc3c(O)c(C(=O)NCC(=O)O)c(=O)n4c3c2OCC4c2ccc(C(F)(F)F)cc2)cn1] | (M + 1)+ 557 IC$_{50}$ 14 nM |
| Example 138 | N-({7-hydroxy-5-oxo-10-pyrimidin-5-yl-3-[4-(trifluoromethyl)phenyl]-2,3-dihydro-5H-[1,4]oxazino[2,3,4-ij]quinolin-6-yl}carbonyl)glycine | 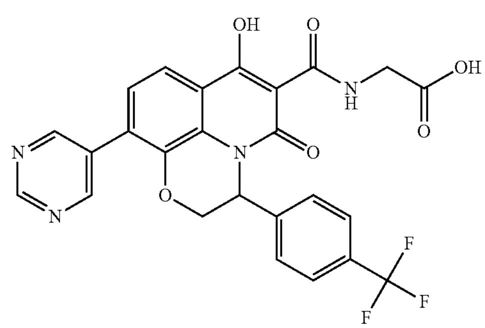 [SMILES: O=C(O)CNC(=O)c1c(O)c2ccc(-c3cncnc3)c3c2n(c1=O)C(c1ccc(C(F)(F)F)cc1)CO3] | (M + 1)+ 527 IC$_{50}$ 12 nM |

TABLE 10-continued

| Example | Name | Structure | MS m/z (M + 1)+ and human HIF-PHD2 IC$_{50}$ |
|---|---|---|---|
| Example 139 | N-({10-(3-carbamoylphenyl)-7-hydroxy-5-oxo-3-[4-(trifluoromethyl)phenyl]-2,3-dihydro-5H-[1,4]oxazino[2,3,4-ij]quinolin-6-yl}carbonyl)glycine | 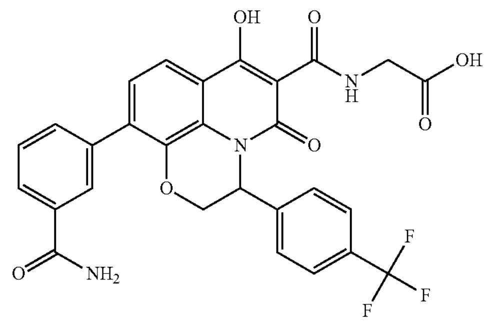 [SMILES: NC(=O)c1cccc(-c2ccc3c(O)c(C(=O)NCC(=O)O)c(=O)n4c3c2OCC4c2ccc(C(F)(F)F)cc2)c1] | (M + 1)+ 568 IC$_{50}$ 14 nM |
| Example 140 | 2-(7-hydroxy-5-oxo-10-(1H-pyrazol-5-yl)-3-(4-(trifluoromethyl)phenyl)-3,5-dihydro-2H-[1,4]oxazino[2,3,4-ij]quinoline-6-carboxamido)acetic acid | 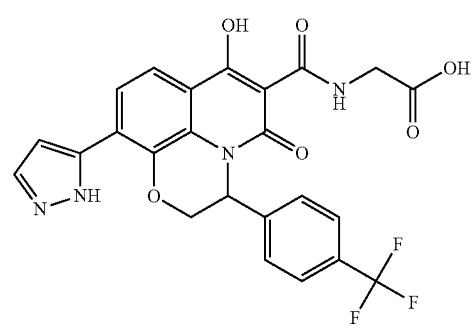 [SMILES: O=C(O)CNC(=O)c1c(O)c2ccc(-c3ccn[nH]3)c3c2n(c1=O)C(c1ccc(C(F)(F)F)cc1)CO3] | (M + 1)+ 515 IC$_{50}$ 11 nM |

Example 141

N-{[3-(4'-Carbamoylbiphenyl-4-yl)-7-hydroxy-5-oxo-2,3-dihydro-5H-[1,4]oxazino[2,3,4-ij]quinolin-6-yl]carbonyl}glycine

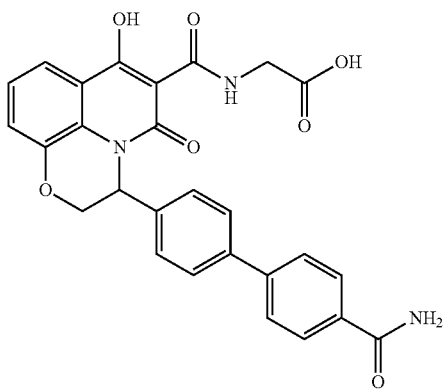 [SMILES: NC(=O)c1ccc(-c2ccc(C3COc4cccc5c(O)c(C(=O)NCC(=O)O)c(=O)n3c45)cc2)cc1]

To a solution of (4-carbamoylphenyl)boronic acid (19.20 mg, 0.116 mmol), teat-butyl 2-(3-(4-bromophenyl)-7-hydroxy-5-oxo-3,5-dihydro-2H-[1,4]oxazino[2,3,4-ij]quinoline-6-carboxamido)acetate (Intermediate 4, 60 mg, 0.116 mmol), potassium carbonate (80 mg, 0.582 mmol) in methanol (5 ml), was added Silicyclo-DPPPd (0.023 mmol). The reaction was refluxed for 16 hr. The reaction mixture was filtered and the filtrate was purifed by MS-directed prep. HPLC to give N-{[3-(4'-carbamoylbiphenyl-4-yl)-7-hydroxy-5-oxo-2,3-dihydro-5H-[1,4]oxazino[2,3,4-ij]quinolin-6-yl]carbonyl}glycine. LC/MS (m/z): 500 (M+H)$^+$. Human HIF-PHD2 IC$_{50}$: 6.1 nM.

Examples 142-152 in Table 11 were prepared following the similar procedures described in Example 141 and using Intermediate 4 and appropriate starting materials.

TABLE 11

| Example Name | Structure | MS m/z (M + 1)$^+$ and human HIF-PHD2 IC$_{50}$ |
|---|---|---|
| Example 142 N-{[3-(3'-chlorobiphenyl-4-yl)-7-hydroxy-5-oxo-2,3-dihydro-5H-[1,4]oxazino[2,3,4-ij]quinolin-6-yl]carbonyl}glycine | 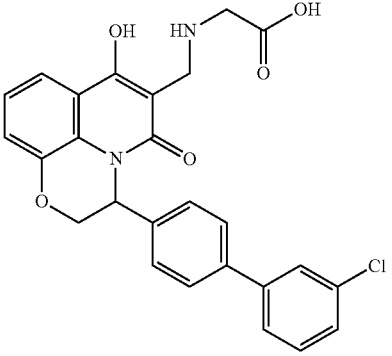 [SMILES: O=C(O)CNCc1c(O)c2cccc3c2n(c1=O)C(c1ccc(-c2cccc(Cl)c2)cc1)CO3] | (M + 1)$^+$ 491 IC$_{50}$ 19 nM |
| Example 143 N-[(7-hydroxy-5-oxo-3-{4-[6-(trifluoromethyl)pyridin-3-yl]phenyl}-2,3-dihydro-5H-[1,4]oxazino[2,3,4-ij]quinolin-6-yl)carbonyl]glycine | 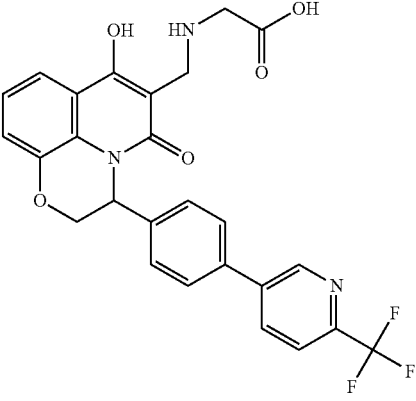 [SMILES: O=C(O)CNCc1c(O)c2cccc3c2n(c1=O)C(c1ccc(-c2ccc(C(F)(F)F)nc2)cc1)CO3] | (M + 1)$^+$ 526 IC$_{50}$ 4.7 nM |

TABLE 11-continued

| Example | Name | Structure | MS m/z (M + 1)+ and human HIF-PHD2 IC50 |
|---|---|---|---|
| Example 144 | N-{[7-hydroxy-3-(4'-methylbiphenyl-4-yl)-5-oxo-2,3-dihydro-5H-[1,4]oxazino[2,3,4-ij]quinolin-6-yl]carbonyl}glycine | 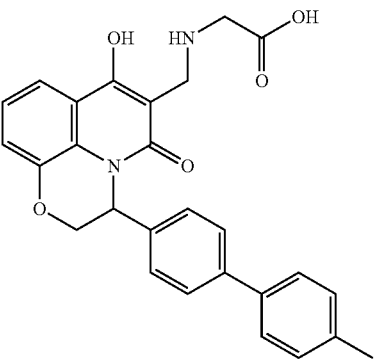 | (M + 1)+ 471 IC50 10 nM |
| Example 145 | N-{[7-hydroxy-3-(4'-methoxybiphenyl-4-yl)-5-oxo-2,3-dihydro-5H-[1,4]oxazino[2,3,4-ij]quinolin-6-yl]carbonyl}glycine | 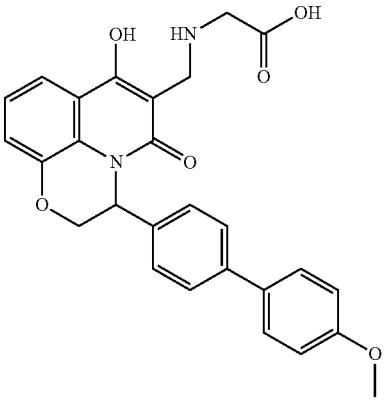 | (M + 1)+ 487 IC50 6.7 nM |
| Example 146 | N-{[3-(4'-cyanobiphenyl-4-yl)-7-hydroxy-5-oxo-2,3-dihydro-5H-[1,4]oxazino[2,3,4-ij]quinolin-6-yl]carbonyl}glycine | 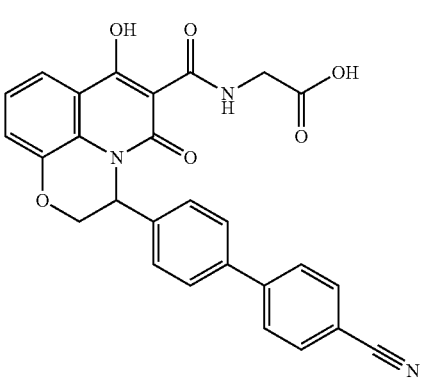 [SMILES: N#Cc1ccc(-c2ccc(C3COc4cccc5c(O)c(C(=O)NCC(=O)O)c(=O)n3c45)cc2)cc1] | (M + 1)+ 482 IC50 6.1 nM |
| Example 147 | N-({7-hydroxy-3-[4-(2-methoxypyridin-3-yl)phenyl]-5-oxo-2,3-dihydro-5H-[1,4]oxazino[2,3,4-ij]quinolin-6-yl}carbonyl)glycine | 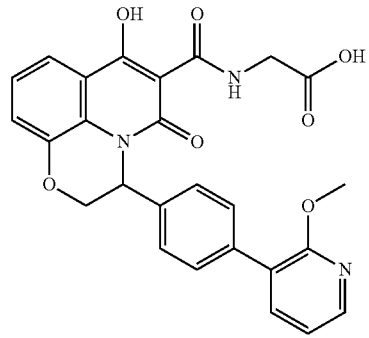 [SMILES: COc1ncccc1-c1ccc(C2COc3cccc4c(O)c(C(=O)NCC(=O)O)c(=O)n2c34)cc1] | (M + 1)+ 488 IC50 18 nM |

TABLE 11-continued

| Example | Name | Structure | MS m/z (M + 1)+ and human HIF-PHD2 IC$_{50}$ |
|---|---|---|---|
| Example 148 | N-{[7-hydroxy-5-oxo-3-(4-pyridin-4-ylphenyl)-2,3-dihydro-5H-[1,4]oxazino[2,3,4-ij]quinolin-6-yl]carbonyl}glycine | 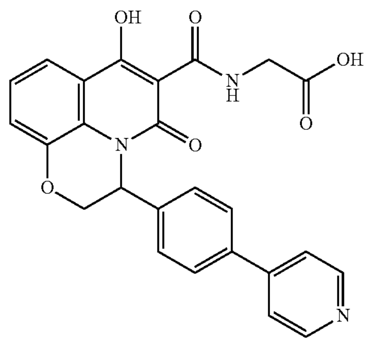 [SMILES: O=C(O)CNC(=O)c1c(O)c2cccc3c2n(c1=O)C(c1ccc(-c2ccncc2)cc1)CO3] | (M + 1)+ 458 IC$_{50}$ 5.7 nM |
| Example 149 | N-({3-[4-(6-aminopyridin-3-yl)phenyl]-7-hydroxy-5-oxo-2,3-dihydro-5H-[1,4]oxazino[2,3,4-ij]quinolin-6-yl}carbonyl)glycine | 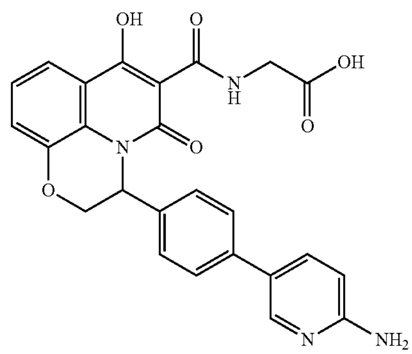 [SMILES: Nc1ccc(-c2ccc(C3COc4cccc5c(O)c(C(=O)NCC(=O)O)c(=O)n3c45)cc2)cn1] | (M + 1)+ 473 IC$_{50}$ 13 nM |
| Example 150 | N-{[3-(3'-cyanobiphenyl-4-yl)-7-hydroxy-5-oxo-2,3-dihydro-5H-[1,4]oxazino[2,3,4-ij]quinolin-6-yl]carbonyl}glycine | 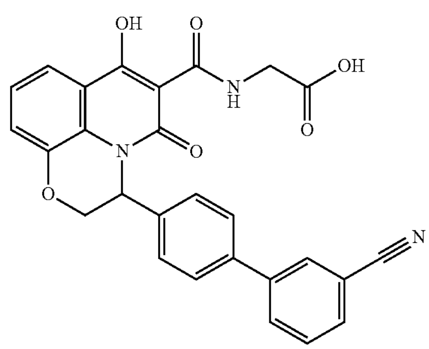 [SMILES: N#Cc1cccc(-c2ccc(C3COc4cccc5c(O)c(C(=O)NCC(=O)O)c(=O)n3c45)cc2)c1] | (M + 1)+ 482 IC$_{50}$ 13 nM |
| Example 151 | N-{[7-hydroxy-5-oxo-3-(4-pyridin-3-ylphenyl)-2,3-dihydro-5H-[1,4]oxazino[2,3,4-ij]quinolin-6-yl]carbonyl}glycine | 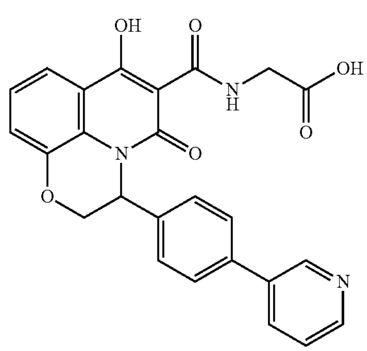 [SMILES: O=C(O)CNC(=O)c1c(O)c2cccc3c2n(c1=O)C(c1ccc(-c2cccnc2)cc1)CO3] | (M + 1)+ 458 IC$_{50}$ 9.2 nM |

TABLE 11-continued

| Example | Name | Structure | MS m/z (M + 1)+ and human HIF-PHD2 IC50 |
|---|---|---|---|
| Example 152 | 2-(3-(4-(1H-pyrazol-5-yl)phenyl)-7-hydroxy-5-oxo-3,5-dihydro-2H-[1,4]oxazino[2,3,4-ij]quinoline-6-carboxamido)acetic acid | 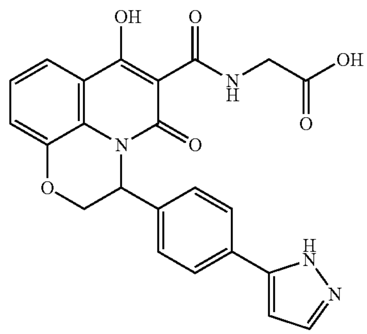 [SMILES: O=C(O)CNC(=O)c1c(O)c2cccc3c2n(c1=O)C(c1ccc(-c2ccn[nH]2)cc1)CO3] | (M + 1)+ 447<br>IC50 11 nM |

Example 153

N-[(7-Hydroxy-5-oxo-10-pyridin-3-yl-2,3-dihydro-5H-[1,4]oxazino[2,3,4-ij]quinolin-6-yl)carbonyl]glycine

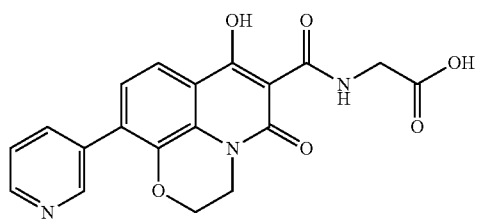 [SMILES: O=C(O)CNC(=O)c1c(O)c2ccc(-c3cccnc3)c3c2n(c1=O)CCO3]

To a solution of pyridin-3-ylboronic acid (7 mg, 0.068 mmol), tert-butyl 2-(10-bromo-7-hydroxy-5-oxo-3,5-dihydro-2H-[1,4]oxazino[2,3,4-ij]quinoline-6-carboxamido)acetate (Intermediate 5, 15 mg, 0.034 mmol), and potassium carbonate (23.60 mg, 0.171 mmol) in methanol (2 ml), was added Silicyclo-DPPPd (6.83 μmol). The reaction was refluxed for 15 hr.

The reaction mixture was filtered and the filtrate was purifed by HPLC to give N-[(7-hydroxy-5-oxo-10-pyridin-3-yl-2,3-dihydro-5H-[1,4]oxazino[2,3,4-ij]quinolin-6-yl)carbonyl]glycine acid. LC/MS (m/z): 382 (M+H)+. Human HIF-PHD2 IC50: 3.6 nM.

Examples 154-156 in Table 12 were prepared following the similar procedures described in Example 153 and using Intermediate 5 and appropriate starting materials.

TABLE 12

| Example | Name | Structure | MS m/z (M + 1)+ and human HIF-PHD2 IC50 |
|---|---|---|---|
| Example 154 | N-{[7-hydroxy-10-(6-methoxypyridin-3-yl)-5-oxo-2,3-dihydro-5H-[1,4]oxazino[2,3,4-ij]quinolin-6-yl]carbonyl}glycine | 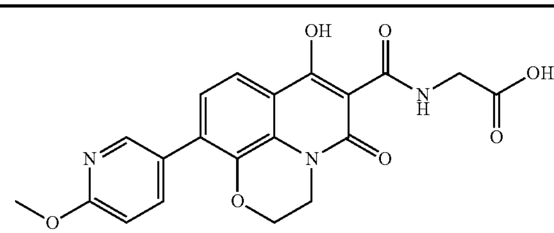 | (M + 1)+ 412<br>IC50 3.7 nM |
| Example 155 | N-{[10-(3,5-dimethylisoxazol-4-yl)-7-hydroxy-5-oxo-2,3-dihydro-5H-[1,4]oxazino[2,3,4-ij]quinolin-6-yl]carbonyl}glycine | 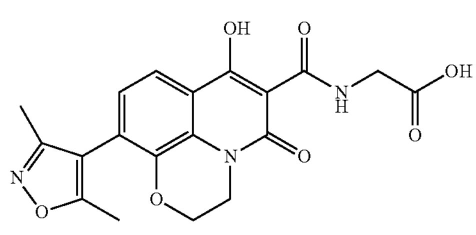 [SMILES: Cc1noc(C)c1-c1ccc2c(O)c(C(=O)NCC(=O)O)c(=O)n3c2c1OCC3] | (M + 1)+ 400<br>IC50 3.3 nM |

TABLE 12-continued

| Example Name | Structure | MS m/z (M + 1)+ and human HIF-PHD2 IC50 |
|---|---|---|
| Example 156 | N-{[10-(6-aminopyridin-3-yl)-7-hydroxy-5-oxo-2,3-dihydro-5H-[1,4]oxazino[2,3,4-ij]quinolin-6-yl]carbonyl}glycine | (M + 1)+ 397<br>IC50 8.1 nM |

Examples 157

2-(7-Hydroxy-5-oxo-3-(4-chlorophenyl)-3,5-dihydro-2H-[1,4]oxazino[2,3,4-ij]quinoline-6-carboxamido)acetic acid

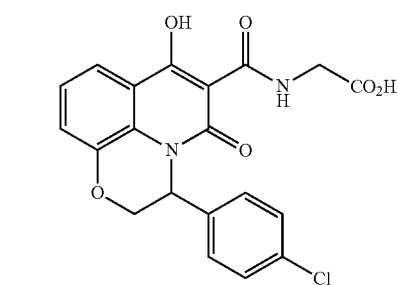

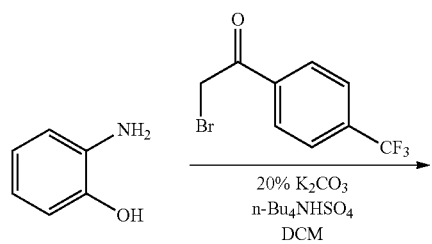

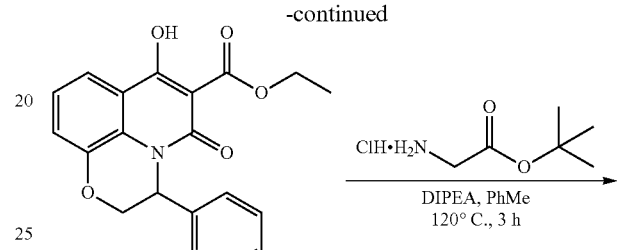

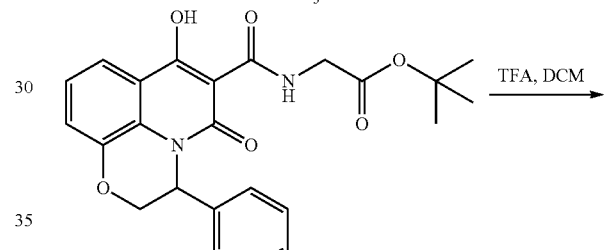

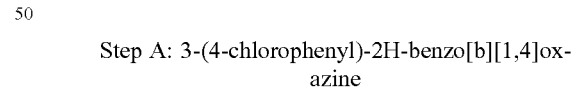

Step A: 3-(4-chlorophenyl)-2H-benzo[b][1,4]oxazine

To a solution of 2-aminophenol (561 mg, 5.14 mmol) in DCM (8 mL) were added 20% aq K$_2$CO$_3$ (3.55g, 5.14 mmol) and n-Bu$_4$NHSO$_4$ (116 mg, 0.343 mmol). Then 2-bromo-1-(4-chloro phenyl)ethanone (800 mg, 3.43 mmol) in DCM (3 mL) was added dropwise to the above reaction mixture. The reaction was stirred at room temperature overnight. Then the mixture was extracted with DCM (500 mL*3). The combined organic layers were washed with brine (500 mL*3), dried over Na$_2$SO$_4$, filtered and concentrated in vacuo. The residue was purified by silica chromatography (eluting with 5-30% EtOAc in hexanes) to give 3-(4-chlorophenyl)-2H-benzo[b][1,4]oxazine as a solid. LC/MS (m/z): 244 (M+H)+.

Step B: 3-(4-chlorophenyl)-3,4-dihydro-2H-benzo[b][1,4]oxazine

To a solution of Step A product (580 mg, 2.38 mmol) in MeOH (24 mL) was added NaBH$_4$ (450 mg, 11.9 mmol) portionwise. The resulting solution was stirred at room temperature for 2 h. LCMS showed that the reaction was completed. The resulting mixture was concentrated and the residue was partoned between EtOAc (50 mL) and water (30 mL). The layers were separated and the aqueous layer was extracted with EtOAc (30 mL*2). The combined organic layers were washed with brine (50 mL*2), dried over Na$_2$SO$_4$, filtered and concentrated in vacuo to give the crude product which was used in the next step without further purificaton. LC/MS (m/z): 246 (M+H)$^+$.

Step C: ethyl 7-hydroxy-5-oxo-3-(4-chlorophenyl)-3,5-dihydro-2H-[1,4]oxazino[2,3,4-ij]quinoline-6-carboxylate Step B product (575 mg, 2.34 mmol) was mixed with triethyl methanetricarboxylate (2.17 g, 9.36 mmol). Then the mixture was stirred at 200° C. for 4 h under nitrogen. After cooling to room temperature, the mixture was purified by silica column eluting with 0-5% MeOH in DCM to give ethyl 7-hydroxy-5-oxo-3-(4-chlorophenyl)-3,5-dihydro-2H-[1,4]oxazino[2,3,4-ij]quinoline-6-carboxylate as a solid. LC/MS (m/z): 386 (M+H)$^+$.

Step D: tert-butyl 2-(7-hydroxy-5-oxo-3-(4-chlorophenyl)-3,5-dihydro-2H-[1,4]oxazino[2,3,4-ij]quinoline-6-carboxamido)acetate To a solution of Step C product (585 mg, 1.516 mmol) and tert-butyl 2-aminoacetate (298 mg, 2.27 mmol) in toluene (3.8 mL) was added DIPEA (0.397 mL, 2.275 mmol). The resulting mixture was stirred at 120° C. for 3 hours under nitrogen. TLC (petroleum ether: EtOAc=5:1) showed that the reaction was completed. The reaction mixture was cooled to rt and concentrated under reduced pressure. The residue was purified by silica column eluting with 1-50% EtOAc in hexanes to afford tert-butyl 2-(7-hydroxy-5-oxo-3-(4-chlorophenyl)-3,5-dihydro-2H-[1,4]oxazino[2,3,4ij]quinoline-6-carboxamido)acetate as an off-white solid. LC/MS (m/z): 471 (M+H)$^+$.

Step E: 2-(7-hydroxy-5-oxo-3-(4-chlorophenyl)-3,5-dihydro-2H-[1,4]oxazino[2,3,4-ij]quinoline-6-carboxamido)acetic acid To a solution of Step D product (350 mg, 0.743 mmol) in DCM (2.48 mL) was added TFA (0.573 mL, 7.43 mmol). The resulting mixture was stirred at rt for 3 hours. LCMS showed that the reaction was completed. The reaction mixture was concentrated and the TFA azeotroped off with acetonitrile (×3). The resulting solid was triturated with hexanes (×2) to afford the title compound as a solid. $^1$H NMR (DMSO-d$_6$, 500 MHz): δ 12.93 (brs, 1H), 10.32 (t, 1H), 7.78 (d, 1H), 7.38 (m, 4H), 7.36 (dd, 1H), 7.12 (d, 1H), 6.15 (s, 1H), 4.68 (d, 1H), 4.45 (dd, 1H), 4.08 (m, 2H). LC/MS (m/z): 415 (M+H)$^+$. Human HIF-PHD2 IC$_{50}$: 25 nM.

Examples 158-177 in Table 13 were prepared following the similar procedures described in Example 157 and using appropriate starting materials (aminophenol and bromoketone of Step A).

TABLE 13

| Example Name | Structure | MS m/z (M + 1)$^+$ and human HIF-PHD2 IC$_{50}$ |
|---|---|---|
| Example 158 | 2-(9-fluoro-7-hydroxy-5-oxo-3-(4-(trifluoromethyl)phenyl)-3,5-dihydro-2H-[1,4]oxazino[2,3,4-ij]quinoline-6-carboxamido)acetic acid | (M + 1)$^+$ 467 IC$_{50}$ 16 nM |
| Example 159 | 2-(9-bromo-7-hydroxy-5-oxo-3-(4-(trifluoromethyl)phenyl)-3,5-dihydro-2H-[1,4]oxazino[2,3,4-ij]quinoline-6-carboxamido)acetic acid | (M + 1)$^+$ 527 IC$_{50}$ 47 nM |

TABLE 13-continued

| Example | Name | Structure | MS m/z (M + 1)+ and human HIF-PHD2 IC$_{50}$ |
|---|---|---|---|
| Example 2-160 | 2-(7-hydroxy-5-oxo-3-(6-(trifluoromethyl)pyridin-3-yl)-3,5-dihydro-2H-[1,4]oxazino[2,3,4-ij]quinoline-6-carboxamido)acetic acid | | (M + 1)+ 450 IC$_{50}$ 6.1 nM |
| Example 2-161 | 2-(10-bromo-7-hydroxy-5-oxo-3-(4-(trifluoromethyl)phenyl)-3,5-dihydro-2H-[1,4]oxazino[2,3,4-ij]quinoline-6-carboxamido)acetic acid | | (M + 1)+ 527 IC$_{50}$ 16 nM |
| Example 2-162 | 2-(8-fluoro-7-hydroxy-5-oxo-3-(4-(trifluoromethyl)phenyl)-3,5-dihydro-2H-[1,4]oxazino[2,3,4-ij]quinoline-6-carboxamido)acetic acid | | (M + 1)+ 467 IC$_{50}$ 15 nM |
| Example 2-163 | 2-(7-hydroxy-3-(4-methoxyphenyl)-5-oxo-3,5-dihydro-2H-[1,4]oxazino[2,3,4-ij]quinoline-6-carboxamido)acetic acid | | (M + 1)+ 411 IC$_{50}$ 27 nM |

TABLE 13-continued

| Example | Name | Structure | MS m/z (M + 1)+ and human HIF-PHD2 IC$_{50}$ |
|---|---|---|---|
| Example 164 | 2-(10-fluoro-7-hydroxy-5-oxo-3-(4-(trifluoroMethyl)phenyl)-3,5-dihydro-2H-[1,4]oxazino[2,3,4-ij]quinoline-6-carboxamido)acetic acid | 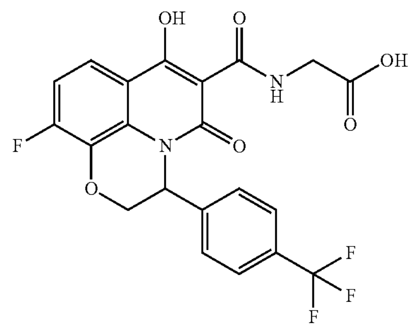 [SMILES: O=C(O)CNC(=O)c1c(O)c2ccc(F)c3c2n(c1=O)C(c1ccc(C(F)(F)F)cc1)CO3] | (M + 1)+ 467 IC$_{50}$ 16 nM |
| Example 165 | 2-(10-chloro-7-hydroxy-5-oxo-3-(4-(trifluoromethyl)phenyl)-3,5-dihydro-2H-[1,4]oxazino[2,3,4-ij]quinoline-6-carboxamido)acetic acid | 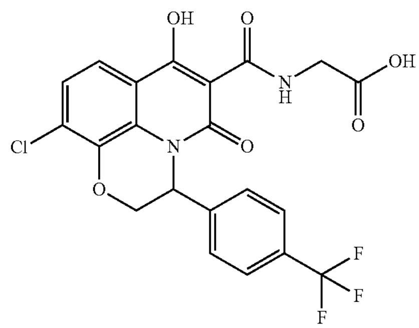 [SMILES: O=C(O)CNC(=O)c1c(O)c2ccc(Cl)c3c2n(c1=O)C(c1ccc(C(F)(F)F)cc1)CO3] | (M + 1)+ 483 IC$_{50}$ 19 nM |
| Example 166 | 2-(9-chloro-7-hydroxy-5-oxo-3-(4-(trifluoromethyl)phenyl)-3,5-dihydro-2H-[1,4]oxazino[2,3,4-ij]quinoline-6-carboxamido)acetic acid | 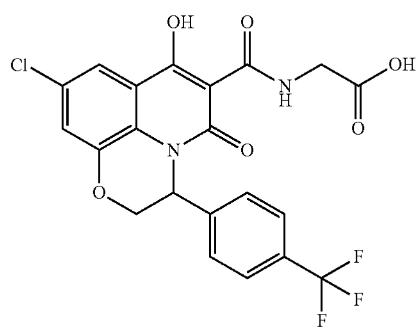 [SMILES: O=C(O)CNC(=O)c1c(O)c2cc(Cl)cc3c2n(c1=O)C(c1ccc(C(F)(F)F)cc1)CO3] | (M + 1)+ 483 IC$_{50}$ 16 nM |
| Example 167 | droxy-5-oxo-3-(3-(trifluoromethyl)phenyl)-3,5-dihydro-2H-[1,4]oxazino[2,3,4-ij]quinoline-6-carboxamido)acetic acid | 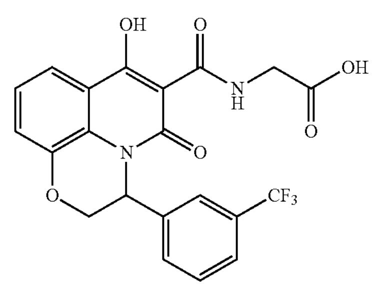 [SMILES: O=C(O)CNC(=O)c1c(O)c2cccc3c2n(c1=O)C(c1cccc(C(F)(F)F)c1)CO3] | (M + 1)+ 449 IC$_{50}$ 74 nM |
| Example 168 | 2-(7-hydroxy-5-oxo-3-(thiazol-2-yl)-3,5-dihydro-2H-[1,4]oxazino[2,3,4-ij]quinoline-6-carboxamido)acetic acid | 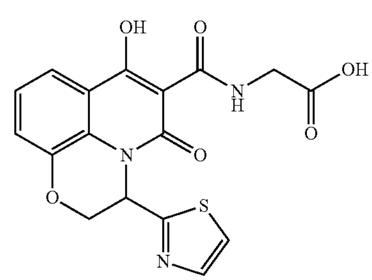 [SMILES: O=C(O)CNC(=O)c1c(O)c2cccc3c2n(c1=O)C(c1nccs1)CO3] | (M + 1)+ 388 IC$_{50}$ 19 nM |

TABLE 13-continued

| Example | Name | Structure | MS m/z (M + 1)+ and human HIF-PHD2 IC$_{50}$ |
|---|---|---|---|
| Example 169 | 2-(8-bromo-7-hydroxy-5-oxo-3-(4-(trifluoromethyl)phenyl)-3,5-dihydro-2H-[1,4]oxazino[2,3,4-ij]quinoline-6-carboxamido)acetic acid | 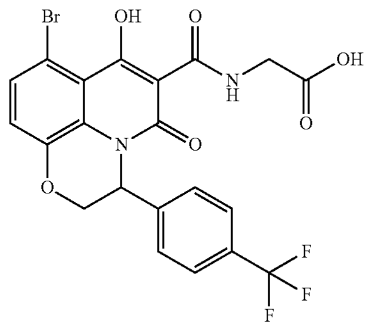 [SMILES: O=C(O)CNC(=O)c1c(O)c2c(Br)ccc3c2n(c1=O)C(c1ccc(C(F)(F)F)cc1)CO3] | (M + 1)+ 527<br>IC$_{50}$ 16 nM |
| Example 170 | 2-(10-bromo-7-hydroxy-5-oxo-3-(thiazol-4-yl)-3,5-dihydro-2H-[1,4]oxazino[2,3,4-ij]quinoline-6-carboxamido)acetic acid | 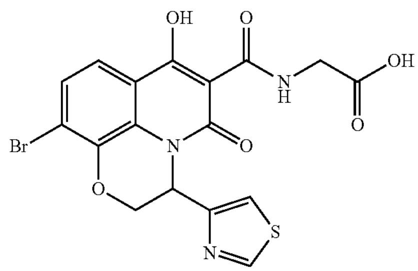 [SMILES: O=C(O)CNC(=O)c1c(O)c2ccc(Br)c3c2n(c1=O)C(c1cscn1)CO3] | (M + 1)+ 466<br>IC$_{50}$ 5.0 nM |
| Example 171 | 2-(7-hydroxy-5-oxo-3-(2-(trifluoromethyl)thiazol-5-yl)-3,5-dihydro-2H-[1,4]oxazino[2,3,4-ij]quinoline-6-carboxamido)acetic acid | 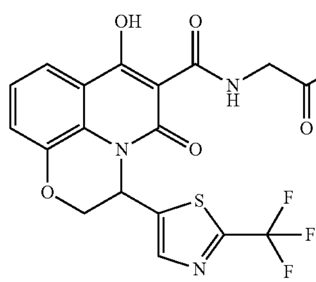 | (M + 1)+ 456<br>IC$_{50}$ 5.4 nM |
| Example 172 | 2-(8-fluoro-7-hydroxy-5-oxo-3-(thiazol-5-yl)-3,5-dihydro-2H-[1,4]oxazino[2,3,4-ij]quinoline-6-carboxamido)acetic acid | 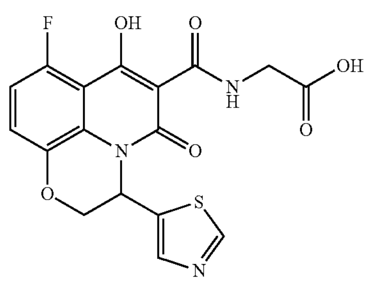 | (M + 1)+ 406<br>IC$_{50}$ 7.3 nM |
| Example 173 | 2-(7-hydroxy-3-(oxazol-5-yl)-5-oxo-3,5-dihydro-2H-[1,4]oxazino[2,3,4-ij]quinoline-6-carboxamido)acetic acid | 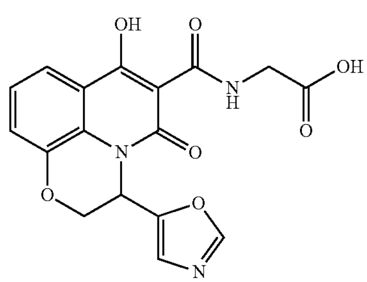 [SMILES: O=C(O)CNC(=O)c1c(O)c2cccc3c2n(c1=O)C(c1cnco1)CO3] | (M + 1)+ 372<br>IC$_{50}$ 14 nM |

TABLE 13-continued

| Example | Name | Structure | MS m/z (M + 1)+ and human HIF-PHD2 IC$_{50}$ |
|---|---|---|---|
| Example 174 | 2-(10-fluoro-7-hydroxy-5-oxo-3-(thiazol-5-yl)-3,5-dihydro-2H-[1,4]oxazino[2,3,4-ij]quinoline-6-carboxamido)acetic acid | 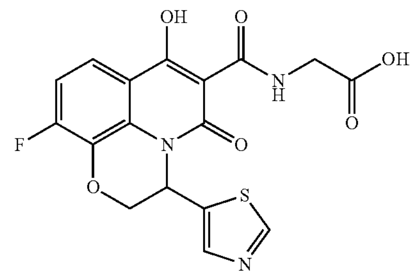 [SMILES: O=C(O)CNC(=O)c1c(O)c2ccc(F)c3c2n(c1=O)C(c1cncs1)CO3] | (M + 1)+ 406 IC$_{50}$ 3.8 nM |
| Example 175 | 2-(8,10-difluoro-7-hydroxy-5-oxo-3-(thiazol-5-yl)-3,5-dihydro-2H-[1,4]oxazino[2,3,4-ij]quinoline-6-carboxamido)acetic acid | 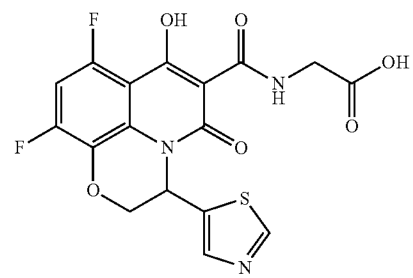 [SMILES: O=C(O)CNC(=O)c1c(O)c2c(F)cc(F)c3c2n(c1=O)C(c1cncs1)CO3] | (M + 1)+ 424 IC$_{50}$ 2.8 nM |
| Example 176 | 2-(8-bromo-7-hydroxy-5-oxo-3-(thiazol-5-yl)-3,5-dihydro-2H-[1,4]oxazino[2,3,4-ij]quinoline-6-carboxamido)acetic acid | 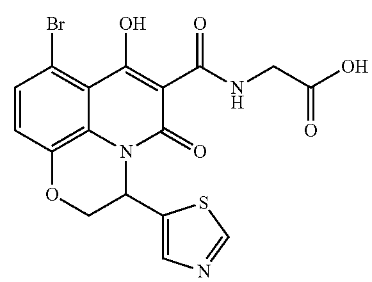 [SMILES: O=C(O)CNC(=O)c1c(O)c2c(Br)ccc3c2n(c1=O)C(c1cncs1)CO3] | (M + 1)+ 466 IC$_{50}$ 7.7 nM |
| Example 177 | 2-(10-bromo-7-hydroxy-5-oxo-3-(thiazol-5-yl)-3,5-dihydro-2H-[1,4]oxazino[2,3,4-ij]quinoline-6-carboxamido)acetic acid | 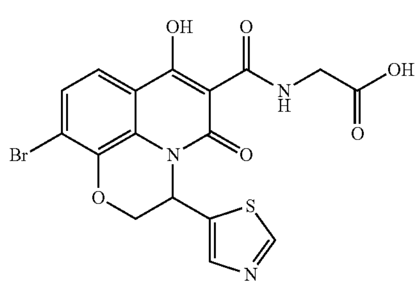 [SMILES: O=C(O)CNC(=O)c1c(O)c2ccc(Br)c3c2n(c1=O)C(c1cncs1)CO3] | (M + 1)+ 466 IC$_{50}$ 5.4 nM |

Examples 178

Ammonium 2-(10-cyano-7-hydroxy-5-oxo-3-(4-(trifluoromethyl)phenyl)-3,5-dihydro-2H-[1,4]oxazino[2,3,4-ij]quinoline-6-carboxamido)acetate

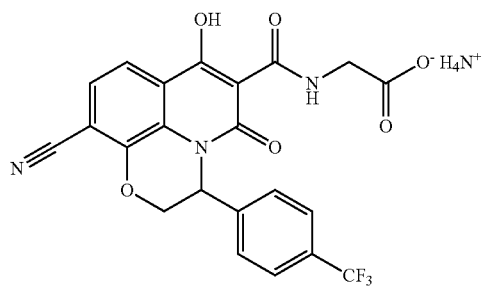

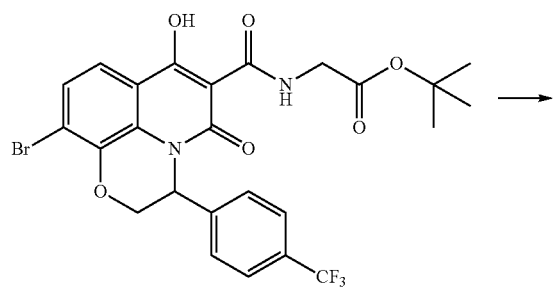

Intermediate 1

Step A: tert-butyl 2-(10-cyano-7-hydroxy-5-oxo-3-(4-(trifluoromethyl)phenyl)-3,5-dihydro-2H-[1,4]oxazino[2,3,4-ij]quinoline-6-carboxamido)acetate A flask was charged with Intermediate 1 (50 mg, 0.086 mmol), dicyanozinc (10.06 mg, 0.086 mmol), DMF (1 mL) and water (0.01 mL), to which were added $Pd_2(dba)_3$ (78 mg, 0.086 mmol) and DPPF (47.5 mg, 0.086 mmol). The mixture was evacuated and backfilled with $N_2$ (3 times), then bubbled with $N_2$ gas for 10 min. The reaction mixture was heated at 100° C. over night. The mixture was cooled, diluted with dichloromethane and washed with water. The organic layer was dried over $MgSO_4$, filtered and concentrated under reduced pressure. The residue was purified by column chromatography on silica gel eluting with EtOAc/hexanes (20% to 100%) to give tert-butyl 2-(10-cyano-7-hydroxy-5-oxo-3-(4-(trifluoromethyl)phenyl)-3,5-dihydro-2H-[1,4]oxazino[2,3,4-ij]quinoline-6-carboxamido)acetate. LC/MS (m/z): 474 (M-$^t$Bu+H)$^+$.

Step B: ammonium 2-(10-cyano-7-hydroxy-5-oxo-3-(4-(trifluoromethyl)phenyl)-3,5-dihydro-2H-[1,4]oxazino[2,3,4-ij]quinoline-6-carboxamido)acetate TFA (20.37 µL, 0.26 mmol) was added to a solution of Step A product (14 mg, 0.026 mmol) in dichloromethane (1 mL) and the reaction was stirred at rt for 8 h. TLC showed that the reaction was completed and the resulting mixture was concentrated in vacuo. The residue was purified by HPLC (C-18). The product containing fractions were collected and freezed/lyophlized overnight. Then 2N $NH_3$ in methanol (2 mL) was added and the mixture was stirred at rt for 2 h. The solution was concentrated and lyophilized with acetonitrile and water overnight to give the title compound as a solid. $^1$H NMR (CD$_3$OD, 500 MHz): δ 7.92 (d, 1H), 7.63 (d, 2H), 7.58 (d, 1H), 7.31 (d, 2H), 6.21 (s, 1H), 4.43 (m, 2H), 4.03 (m, 2H). LC/MS (m/z): 474 (M+H)$^+$. Human HIF-PHD2 IC$_{50}$: 5.4 nM.

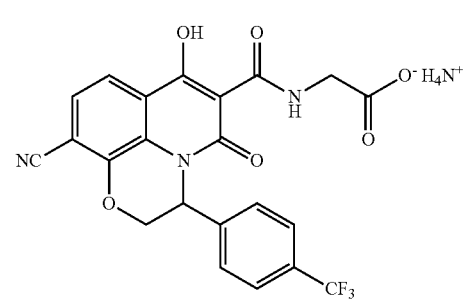

Examples 179-181 in Table 14 were prepared following the similar procedures described in Example 178 and using appropriate intermediates indicated in the table.

TABLE 14

| Example Name | Structure | MS m/z (M + 1)+ and human HIF-PHD2 IC$_{50}$ |
|---|---|---|
| Example 179 | ammonium 2-(9-cyano-7-hydroxy-5-oxo-3-(4-(trifluoromethyl)phenyl)-3,5-dihydro-2H-[1,4]oxazino[2,3,4-ij]quinoline-6-carboxamido)acetate 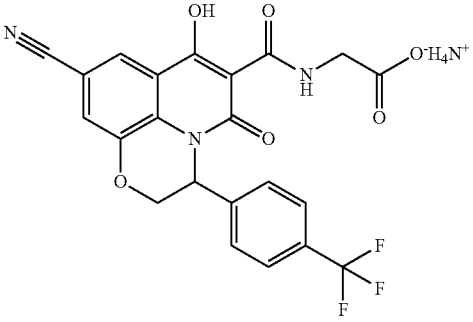<br>Prepared from Intermediate 2 | (M + 1)+ 474<br>IC$_{50}$ 4.6 nM |
| Example 180 | ammonium 2-(8-cyano-7-hydroxy-5-oxo-3-(4-(trifluoromethyl)phenyl)-3,5-dihydro-2H-[1,4]oxazino[2,3,4-ij]quinoline-6-carboxamido)acetate 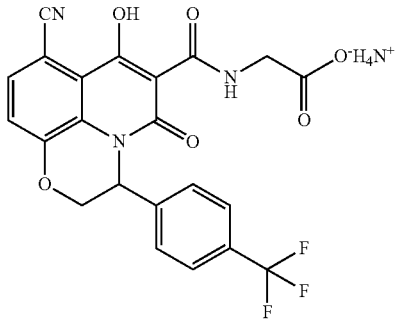<br>Prepared from Intermediate 3 | (M + 1)+ 474<br>IC$_{50}$ 2.9 nM |
| Example 181 | ammonium 2-(3-(4-cyanophenyl)-7-hydroxy-5-oxo-3,5-dihydro-2H-[1,4]oxazino[2,3,4-ij]quinoline-6-carboxamido)acetate 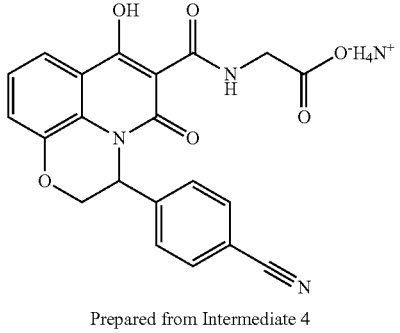<br>Prepared from Intermediate 4 | (M + 1)+ 406<br>IC$_{50}$ 10 nM |

TABLE 14-continued

| Example | Name | Structure | MS m/z (M + 1)+ and human HIF-PHD2 IC$_{50}$ |
|---|---|---|---|
| Example 182 | ammonium 2-(10-cyano-7-hydroxy-5-oxo-3-(thiazol-5-yl)-3,5-dihydro-2H-[1,4]oxazino[2,3,4-ij]quinoline-6-carboxamido)acetate | 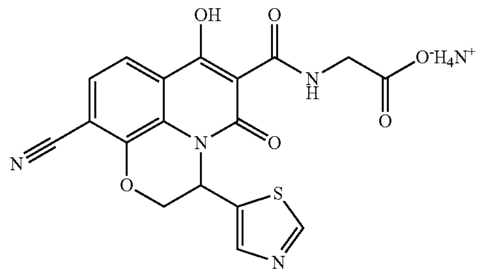 | (M + 1)+ 413<br>IC$_{50}$ 1.4 nM |

Prepared from Intermediate 6

Examples 183

Ammonium 2-(7-hydroxy-3-(4-(methylsulfonyl)phenyl)-5-oxo-3,5-dihydro-2H-[1,4]oxazino[2,3,4-ij]quinoline-6-carboxamido)acetate

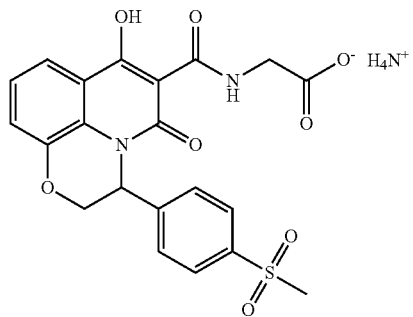

Intermediate 4

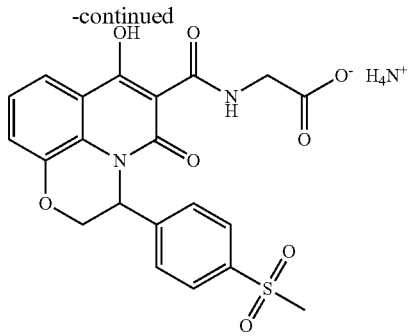

Step A: tert-butyl 2-(7-hydroxy-3-(4-(methylsulfonyl)phenyl)-5-oxo-3,5-dihydro-2H-[1,4]oxazino[2,3,4-ij]quinoline-6-carboxamido)acetate To a solution of Intermediate 4 (100 mg, 0.194 mmol) in DMSO was added sodium methanesulfinate (39.6 mg, 0.388 mmol) and copper(I) iodide (73.9 mg, 0.388 mmol). After degassing with $N_2$, the reaction was heated at 120° C. for 60 h. The reaction mixture was cooled to rt and diluted with 60 ml ether and 100 ml water. The suspension was passed through a pad of Celite. Organic layer was collected from filtrate and washed with $H_2O$. The organic layer was dried over $MgSO_4$, filtered and concentrated under reduced pressure. The residue was purified by column chromatography on silica gel eluting with EtOAc/hexanes (10% to 100%) to give tert-butyl 2-(7-hydroxy-3-(4-(methylsulfonyl)phenyl)-5-oxo-3,5-dihydro-2H-[1,4]oxazino[2,3,4-ij]quinoline-6-carboxamido)acetate. LC/MS (m/z): 516.9 (M+H)+.

Step B: ammonium 2-(7-hydroxy-3-(4-(methylsulfonyl)phenyl)-5-oxo-3,5-dihydro-2H-[1,4]oxazino[2,3,4-ij]quinoline-6-carboxamido)acetate TFA (75 µL, 0.97 mmol) was added to a solution of Step A product (50 mg, 0.097 mmol) in dichloromethane (1 mL) and the reaction was stirred at rt for 8 h. TLC showed that the reaction was completed and the resulting mixture was concentrated in vacuo. The residue was freezed/lyophlized overnight. Then 2N $NH_3$ in methanol (2 mL) was added and the mixture was stirred at rt for 3 h. The solution was concentrated and lyophlized with acetonitrile and water overnight to give the title compound as a solid. $^1H$ NMR (DMSO-$d_6$, 500 MHz): δ 10.35 (brs, 1H), 7.90 (d, 1H), 7.71 (dd, 1H), 7.42 (d, 2H), 7.22 (d, 1H), 7.02 (d, 2H), 6.02 (s, 1H), 4.63 (dd, 1H), 4.41 (dd, 1H), 3.97 (m, 2H). LC/MS (m/z): 460.8 (M+H)+. Human HIF-PHD2 IC$_{50}$: 15 nM.

Examples 184 in Table 15 was prepared following the similar procedures described in Example 183 and using the intermediate indicated in the table.

TABLE 15

| Example Name | Structure | MS m/z (M + 1)+ and human HIF-PHD2 IC50 |
|---|---|---|
| Example 184 | ammonium 2-(7-hydroxy-9-(methylsulfonyl)-5-oxo-3-(4-(trifluoromethyl)phenyl)-3,5-dihydro-2H-[1,4]oxazino[2,3,4-ij]quinoline-6-carboxamido)acetate | (M + 1)+ 527 IC50 19 nM |

Prepared from Intermediate 2

Example 185

2-(7-Hydroxy-5-oxo-9-(1H-pyrazol-5-yl)-3-(4-(trifluoromethyl)phenyl)-3,5-dihydro-2H-[1,4]oxazino[2,3,4-ij]quinoline-6-carboxamido)acetic acid

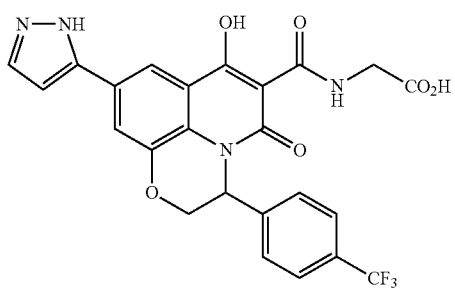 [SMILES: O=C(O)CNC(=O)c1c(O)c2cc(-c3ccn[nH]3)cc3c2n(c1=O)C(c1ccc(C(F)(F)F)cc1)CO3]

A microwave vial was charged with Intermediate 2 (50 mg, 0.086 mmol), (1H-pyrazol-5-yl)boronic acid (14.39 mg, 0.129 mmol) and $Na_2CO_3$ (0.129 mL, 0.257 mmol). This mixture was evacuated and backfilled with $N_2$ (3 times). DMF (1 mL) was added and the mixture was heated via microwave at 100° C. for 30 min. The mixture was cooled, diluted with ethyl acetate (5 mL), and washed with satuated aqueous ammonium chloride and brine. The organic layer was dried over $MgSO_4$, filtered and concentrated in vacuo. The residue was purified by column chromatography on silica gel eluting with EtOAc/hexane (10-50%) to give tert-butyl 2-(7-hydroxy-5-oxo-9-(1H-pyrazol-5-yl)-3-(4-(trifluoromethyl)phenyl)-3,5-dihydro-2H-[1,4]oxazino[2,3,4-ij]quinoline-6-carboxamido)acetate. To this $^t$Bu ester in 1 ml DCM was added 1 ml TFA. The reaction was stirred at rt for overnight. The reaction mixture was concentrated and the TFA azeotroped off with acetonitrile (×3). The resulting solid was triturated with hexanes (×2) to afford the title compound as a solid. LC/MS (m/z): 515 (M+H)+. Human HIF-PHD2 IC50: 12 nM.

Example 186

2-(7-Hydroxy-10-methyl-5-oxo-3-(thiazol-4-yl)-3,5-dihydro-2H-[1,4]oxazino[2,3,4-ij]quinoline-6-carboxamido)acetic acid

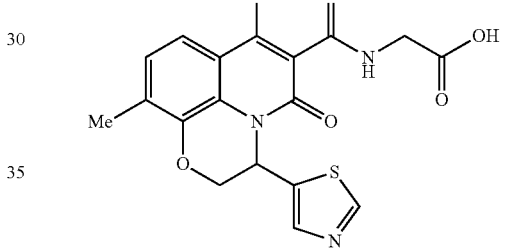

Step A: tert-butyl 2-(7-hydroxy-10-methyl-5-oxo-3-(thiazol-4-yl)-3,5-dihydro-2H-[1,4]oxazino[2,3,4-ij]quinoline-6-carboxamido)acetate Intermediate 7 (64 mg, 0.123 mmol), potassium carbonate (50.8 mg, 0.368 mmol), 2,4,6-trimethyl-1,3,5,2,4,6-trioxatriborinane (0.026 ml, 0.184 mmol) and anhydrous DMF (1 ml) were added to a flask. Nitrogen was bubbled through the DMF solution. Then the reaction was microwaved at 110° C. for 1 h. The reaction was cooled to rt and diluted EtOAc and sat. $NH_4Cl$. The organic layer was dried over $MgSO_4$, filtered and concentrated under reduced pressure. The residue was purified by prep TLC(EtOAc/hexanes: v/v 1:1) to afford tert-butyl 2-(7-hydroxy-10-methyl-5-oxo-3-(thiazol-4-yl)-3,5-dihydro-2H-[1,4]oxazino[2,3,4-ij]quinoline-6-carboxamido)acetate. LC/MS (m/z): 458 (M+H)+.

Step B: 2-(7-hydroxy-10-methyl-5-oxo-3-(thiazol-4-yl)-3,5-dihydro-2H-[1,4]oxazino[2,3,4-ij]quinoline-6-carboxamido)acetic acid TFA (0.5 ml, 6.49 mmol) was added to a solution of Step A product (35 mg, 0.077 mmol) in DCM (1 ml) and the reaction was stirred at rt overnight. LC/MS analysis at this point demonstrated complete consumption of the starting material. The mixture was concentrated under reduced pressure. The residue was lyophlized to afford the title compound. $^1$H NMR (DMSO-d$_6$, 500 MHz): δ 10.38 (brs, 1H), 9.01 (s, 1H), 7.62 (d, 1H), 7.23 (s, 1H), 7.18 (d, 1H), 6.15 (s, 1H), 4.93 (d, 1H), 4.40 (d, 1H), 4.03 (m, 2H), 2.23 (s, 3H). LC/MS (m/z): 402 (M+H)$^-$. Human HIF-PHD2 IC$_{50}$: 12 nM.

Example 187

2-(10-Cyclopropyl-7-hydroxy-5-oxo-3-(thiazol-4-yl)-3,5-dihydro-2H-[1,4]oxazino[2,3,4-ij]quinoline-6-carboxamido)acetic acid

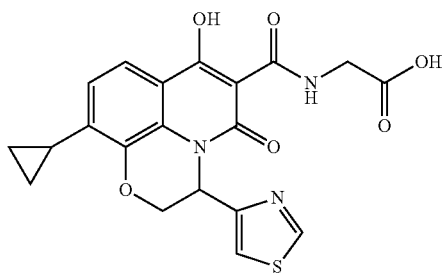 [SMILES: O=C(O)CNC(=O)c1c(O)c2ccc(C3CC3)c3c2n(c1=O)C(c1cscn1)CO3]

Step A: tert-butyl 2-(10-cyclopropyl-7-hydroxy-5-oxo-3-(thiazol-4-yl)-3,5-dihydro-2H-[1,4]oxazino[2,3,4-ij]quinoline-6-carboxamido)acetate A microwave vial was charged with Intermediate 7 (60 mg, 0.115 mmol), PdCl$_2$(dppf)-CH$_2$Cl$_2$ adduct (18.8 mg, 0.023 mmol), 2-cyclopropyl-4,4,5,5-tetramethyl-1,3,2-dioxaborolane (29.0 mg, 0.172 mmol) and Na$_2$CO$_3$ (0.172 mL, 0.345 mmol). This mixture was evacuated and backfilled with N$_2$ (3 times). DMF (1 mL) was added and the reaction mixture was heated via microwave at 100° C. for 30 min. The mixture was cooled, diluted with ethyl acetate (10 mL), washed with satuated aqueous ammonium chloride and brine. The solvent was evaporated under reduced pressure and the residue was purified by reverse phase preparative HPLC to give tert-butyl 2-(10-cyclopropyl-7-hydroxy-5-oxo-3-(thiazol-4-yl)-3,5-dihydro-2H-[1,4]oxazino[2,3,4-ij]quinoline-6-carboxamido)acetate as a solid.

Step B: 2-(10-cyclopropyl-7-hydroxy-5-oxo-3-(thiazol-4-yl)-3,5-dihydro-2H-[1,4]oxazino[2,3,4-ij]quinoline-6-carboxamido)acetic acid TFA (0.5 mL, 6.49 mmol) was added to a solution of Step A product (35 mg, 0.072 mmol) in DCM (1 mL) and the reaction was stirred at rt overnight. LC/MS analysis at this point demonstrated complete consumption of the starting material. The mixture was concentrated under reduced pressure. Ther residue was lyophilized to afford the title compound. $^1$H NMR (DMSO-d$_6$, 500 MHz): δ 10.34 (brs, 1H), 9.03 (s, 1H), 7.61 (d, 1H), 7.56 (d, 1H), 7.22 (s, 1H), 6.18 (s, 1H), 4.98 (d, 1H), 4.40 (d, 1H), 4.05 (m, 2H), 1.05 (m, 2H), 0.82-0.75 (m, 3H)

Biological Assays

The exemplified compounds of the present invention have been found to inhibit the hydroxylation of a HIF peptide by PHD2 and exhibit IC$_5$O values ranging between 0.1 nanomolar to 10 micromolar. Select examples of assays that may be used to detect favorable activity are disclosed in the following publications: Oehme, F., et al., *Anal. Biochem.* 330:74-80 (2004); Hirsilä, M, et al., *J. Bio. Chem.* 278 (33): 30772-30780 (2005); Hyunju, C., et al., *Biochem. Biophys. Res. Comm.* 330 275-280 (2005); and Hewitson, K. S., et al., *Methods in Enzymology*, (Oxygen Biology and Hypoxia); Elsevier Publisher (2007), pg. 25-42 (ISSN: 0076-6879).

The biological activity of the present compounds may be evaluated using assays described herein below:

To each well of a 384-well plate, 1 μL of test compounds in DMSO (final concentration ranging from 0.3 nM to 10 uM) were added into 20 μl of assay buffer (50 mM Tris pH 7.4/0.01% Tween-20/0.1 mg/ml bovine serum albumin/10 μM ferrous sulfate/1 mM sodium ascorbate/20 μg/ml catalase) containing 0.15 μg/ml FLAG-tagged full length PHD2 expressed in and purified from baculovirus-infected Sf9 cells. After a 5 min preincubation at room temperature, the enzymatic reactions were initiated by the addition of 4 μL of substrates {final concentrations of 0.2 μM 2-oxoglutarate and 0.5 μM HIF-1α peptide biotinyl-DLDLEMLAPYIP-MDDDFQL (SEQ ID NO:1)}. After incubation for 45 minutes at room temperature, the reactions were terminated by the addition of a 25 μL quench/detection mix to a final concentration of 1 mM ortho-phenanthroline, 0.1 mM EDTA, 0.5 nM anti-(His)6 LANCE reagent (Perkin-Elmer Life Sciences), 100 nM AF647-labeled streptavidin (Invitrogen), and 2 μg/ml (His)6-VHL complex {S. Tan Protein Expr. Purif. 21, 224-234 (2001)} and the signals were developed for 30 minutes at room temperature. The ratio of time resolved fluorescence signals at 665 and 620 nm was determined, and percent inhibition was calculated relative to the high control samples (DMSO treated) run in parallel, after background substraction.

Inhibition of the catalytic activity of HIF-PHD1 and HIF-PHD3 can be determined similarly, except for HIF-PHD3, final concentrations of 4 μM 2-oxoglutarate is used during the reaction.

What is claimed is:

1. A compound of formula I or a pharmaceutically acceptable salt thereof:

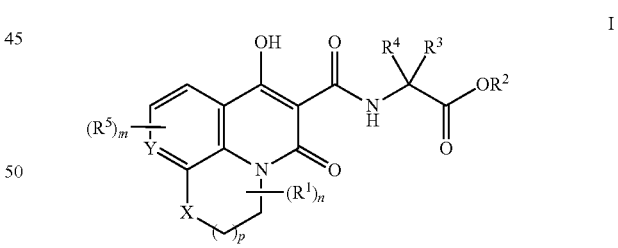

wherein:

Y is CH or N;

X is O, CH$_2$, S, S(O), S(O)$_2$, NH or N-Me;

m is 0, 1, 2 or 3;

n is 0, 1 or 2;

p is 0 or 1;

R$^1$ is independently selected from aryl, heterocyclyl, -Me-aryl, and -Me-heterocyclyl, said aryl and heterocyclyl are optionally substituted with 1, 2, or 3 substituents independently selected from: halogen, CF$_3$, phenyl, CN, S(O)$_2$R$^b$, and heterocyclyl, wherein said phenyl and heterocyclyl are optionally substituted with 1, 2, or 3 substituents independently selected from: $CF_3$, halogen, $C(O)N(R^b)_2$, $N(R^b)_2$, $C_{1-4}$ alkyl, $O(C_{1-4})$ alkyl, and CN;

$R^2$ is hydrogen or methyl;

$R^3$ and $R^4$ are each independently selected from hydrogen, hydroxyl, and $C_{1-4}$ alkyl, said alkyl optionally substituted with OH;

$R^5$ is independently selected from OH, halogen, $CF_3$, $OCF_3$, CN, $C_{1-4}$ alkyl, $O(C_{1-4})$alkyl, $S(O)_2R^b$, $C_{3-6}$ cycloalkyl, phenyl, and heterocyclyl, said cycloalkyl and heterocyclyl are optionally substituted with 1, 2, or 3 substituents independently selected from: OH, $C_{1-4}$ alkyl, $O(C_{1-4})$alkyl, $S(O)_2R^b$, $C(O)N(R^b)_2$, and $N(R^b)_2$; and $R^b$ is independently hydrogen or $C_{1-4}$ alkyl.

2. A compound according to claim 1 of formula II or a pharmaceutically acceptable salt thereof:

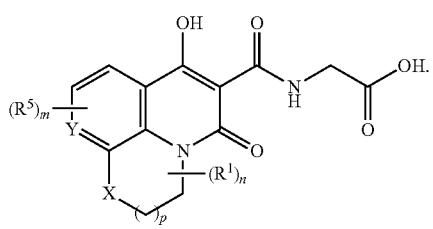

II wherein:

Y is CH or N;

X is O, $CH_2$, S, S(O), $S(O)_2$, NH or N-Me;

m is 0, 1 or 2;

n is 0 or 1;

p is 0 or 1;

$R^1$ is independently selected from phenyl, -Me-phenyl, thiazolyl, -Me-thiazolyl, pyridinyl and oxazolyl, all of which are optionally substituted with 1 or 2 substituents independently selected from: Br, F, Cl, $CF_3$, phenyl, CN, $S(O)_2R^b$, pyrazolyl, and pyridinyl, wherein said phenyl, pyrazolyl and pyridinyl are optionally substituted with 1 or 2 substituents independently selected from: $CF_3$, Cl, $C(O)N(R^b)_2$, $N(R^b)_2$, $C_{1-4}$ alkyl, $O(C_{1-4})$alkyl, and CN;

$R^5$ is independently selected from OH, Br, F, Cl, $CF_3$, $OCF_3$, CN, $C_{1-4}$ alkyl, $O(C_{1-4})$alkyl, $S(O)_2R^b$, cyclopropyl, phenyl, isoxazolyl, pyrazolyl, pyrimidinyl and pyridinyl, said cyclopropy, phenyl, isoxazolyl, pyrazolyl, pyrimidinyl and pyridinyl are optionally substituted with 1 or 2 substituents independently selected from: OH, $C_{1-4}$ alkyl, $O(C_{1-4})$alkyl, $S(O)_2R^b$, $C(O)N(R^b)_2$, and $N(R^b)_2$; and $R^b$ is independently hydrogen or $C_{1-4}$ alkyl.

3. A compound which is:

2-(7-Hydroxy-5-oxo-3-(4-(trifluoromethyl)phenyl)-3,5-dihydro-2H-[1,4]oxazino[2,3,4-ij]quinoline-6-carboxamido)acetic acid;

2-(7-Hydroxy-5-oxo-3-(4-(trifluoromethyl)phenyl)-3,5-dihydro-2H-[1,4]oxazino[2,3,4-ij]quinoline-6-carboxamido)acetic acid;

2-(7-Hydroxy-5-oxo-3-(4-(trifluoromethyl)benzyl)-3,5-dihydro-2H-[1,4]oxazino[2,3,4-ij]quinoline-6-carboxamido)acetic acid;

2-(9-Cyano-7-hydroxy-5-oxo-3-(4-(trifluoromethyl)benzyl)-3,5-dihydro-2H-[1,4]oxazino[2,3,4-ij]quinoline-6-carboxamido)acetic acid;

2-(9-Bromo-7-hydroxy-5-oxo-3-(4-(trifluoromethyl)benzyl)-3,5-dihydro-2H-[1,4]oxazino[2,3,4-ij]quinoline-6-carboxamido)acetic acid;

2-(7-Hydroxy-9-(methylsulfonyl)-5-oxo-3-(4-(trifluoromethyl)benzyl)-3,5-dihydro-2H-[1,4]oxazino[2,3,4-ij]quinoline-6-carboxamido)acetic acid;

2-(7-hydroxy-9-methyl-5-oxo-3-(4-(trifluoromethyl)benzyl)-3,5-dihydro-2H-[1,4]oxazino[2,3,4-ij]quinoline-6-carboxamido)acetic acid;

2-(9-(1,2-Dihydroxypropan-2-yl)-7-hydroxy-5-oxo-3-(4-(trifluoromethyl)benzyl)-3,5-dihydro-2H-[1,4]oxazino[2,3,4-ij]quinoline-6-carboxamido)acetic acid;

2-(1-Hydroxy-3-oxo-6-(4-(trifluoromethyl)phenyl)-3,5,6,7-tetrahydropyrido[3,2,1-ij]quinoline-2-carboxamido) acetic acid;

2-(7-Hydroxy-5-oxo-2-(4-(trifluoromethyl)phenyl)-3,5-dihydro-2H-[1,4]oxazino[2,3,4-ij]quinoline-6-carboxamido)acetic acid;

2-(8-Bromo-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(7-Hydroxy-8-(methylsulfonyl)-5-oxo-2-(4-(trifluoromethyl)phenyl)-3,5-dihydro-2H-[1,4]oxazino[2,3,4-ij]quinoline-6-carboxamido)acetic acid;

2-(8-Cyano-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(9-Cyano-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(9-Bromo-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(7-Hydroxy-9-(methylsulfonyl)-5-oxo-2-(4-(trifluoromethyl)phenyl)-3,5-dihydro-2H-[1,4]oxazino[2,3,4-ij]quinoline-6-carboxamido)acetic acid;

2-(7-Hydroxy-9-methyl-5-oxo-2-(4-(trifluoromethyl)phenyl)-3,5-dihydro-2H-[1,4]oxazino[2,3,4-ij]quinoline-6-carboxamido)acetic acid;

2-(10-Cyano-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(10-Bromo-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(7-Hydroxy-10-(methylsulfonyl)-5-oxo-2-(4-(trifluoromethyl)phenyl)-3,5-dihydro-2H-[1,4]oxazino[2,3,4-ij]quinoline-6-carboxamido)acetic acid;

2-(7-Hydroxy-10-methyl-5-oxo-2-(4-(trifluoromethyl)phenyl)-3,5-dihydro-2H-[1,4]oxazino[2,3,4-ij]quinoline-6-carboxamido)acetic acid;

2-(8-bromo-7-hydroxy-5-oxo-3-(4-(trifluoromethyl)benzyl)-3,5-dihydro-2H-[1,4]oxazino[2,3,4-ij]quinoline-6-carboxamido)acetic acid;

2-(10-Bromo-7-hydroxy-5-oxo-3-(4-(trifluoromethyl)benzyl)-3,5-dihydro-2H-[1,4]oxazino[2,3,4-ij]quinoline-6-carboxamido)acetic acid;

2-(7-Hydroxy-8-(methylsulfonyl)-5-oxo-3-(4-(trifluoromethyl)benzyl)-3,5-dihydro-2H-[1,4]oxazino[2,3,4-ij]quinoline-6-carboxamido)acetic acid;

2-(8-Cyano-7-hydroxy-5-oxo-3-(4-(trifluoromethyl)benzyl)-3,5-dihydro-2H-[1,4]oxazino[2,3,4-ij]quinoline-6-carboxamido)acetic acid;

2-(7-Hydroxy-8-methyl-5-oxo-3-(4-(trifluoromethyl)benzyl)-3,5-dihydro-2H-[1,4]oxazino[2,3,4-ij]quinoline-6-carboxamido)acetic acid;

2-(7-Hydroxy-10-(methylsulfonyl)-5-oxo-3-(4-(trifluoromethyl)benzyl)-3,5-dihydro-2H-[1,4]oxazino[2,3,4-ij]quinoline-6-carboxamido)acetic acid;

2-(10-Cyano-7-hydroxy-5-oxo-3-(4-(trifluoromethyl)benzyl)-3,5-dihydro-2H-[1,4]oxazino[2,3,4-ij]quinoline-6-carboxamido)acetic acid;

2-(7-Hydroxy-10-methyl-5-oxo-3-(4-(trifluoromethyl)benzyl)-3,5-dihydro-2H-[1,4]oxazino[2,3,4-ij]quinoline-6-carboxamido)acetic acid;

2-(9-acetyl-7-hydroxy-5-oxo-3-(4-(trifluoromethyl)benzyl)-3,5-dihydro-2H-[1,4]oxazino[2,3,4-ij]quinoline-6-carboxamido)acetic acid;

2-(7-Hydroxy-9-(1-hydroxyethyl)-5-oxo-3-(4-(trifluoromethyl)benzyl)-3,5-dihydro-2H-[1,4]oxazino[2,3,4-ij]quinoline-6-carboxamido)acetic acid;

2-(7-Hydroxy-9-(2-hydroxypropan-2-yl)-5-oxo-3-(4-(trifluoromethyl)benzyl)-3,5-dihydro-2H-[1,4]oxazino[2,3,4-ij]quinoline-6-carboxamido)acetic acid;

2-(10-cyano-7-hydroxy-5-oxo-3,5-dihydro-2H-[1,4]oxazino[2,3,4-ij]quinoline-6-carboxamido)acetic acid;

2-(7-Hydroxy-10-(methylsulfonyl)-5-oxo-3,5-dihydro-2H-[1,4]oxazino[2,3,4-ij]quinoline-6-carboxamido)acetic acid;

2-(7-Hydroxy-10-methyl-5-oxo-3,5-dihydro-2H-[1,4]oxazino[2,3,4-ij]quinoline-6-carboxamido)acetic acid;

2-(7-hydroxy-5-oxo-10-phenyl-3,5-dihydro-2H-[1,4]oxazino[2,3,4-ij]quinoline-6-carboxamido)acetic acid;

2-(9-Cyano-7-hydroxy-5-oxo-3,5-dihydro-2H-[1,4]oxazino[2,3,4-ij]quinoline-6-carboxamido)acetic acid;

2-(7-hydroxy-9-(methylsulfonyl)-5-oxo-3,5-dihydro-2H-[1,4]oxazino[2,3,4-ij]quinoline-6-carboxamido)acetic acid;

2-(7-hydroxy-9-methyl-5-oxo-3,5-dihydro-2H-[1,4]oxazino[2,3,4-ij]quinoline-6-carboxamido)acetic acid;

2-(8-Cyano-1-hydroxy-3-oxo-3,5,6,7-tetrahydropyrido[3,2,1-ij]quinoline-2-carboxamido)acetic acid;

2-(1-Hydroxy-8-(methylsulfonyl)-3-oxo-3,5,6,7-tetrahydropyrido[3,2,1-ij]quinoline-2-carboxamido)acetic acid;

2-(1-Hydroxy-8-methyl-3-oxo-3,5,6,7-tetrahydropyrido[3,2,1-ij]quinoline-2-carboxamido)acetic acid;

2-(9-Bromo-1-hydroxy-3-oxo-3,5,6,7-tetrahydropyrido[3,2,1-ij]quinoline-2-carboxamido)acetic acid;

2-(9-Cyano-1-hydroxy-3-oxo-3,5,6,7-tetrahydropyrido[3,2,1-ij]quinoline-2-carboxamido)acetic acid;

2-(1-Hydroxy-9-(methylsulfonyl)-3-oxo-3,5,6,7-tetrahydropyrido[3,2,1-ij]quinoline-2-carboxamido)acetic acid;

2-(1-Hydroxy-3-oxo-6-(thiazol-5-yl)-3,5,6,7-tetrahydropyrido[3,2,1-ij]quinoline-2-carboxamido)acetic acid
2-(7-Hydroxy-5-oxo-2-(4-(trifluoromethyl)phenyl)-3,5-dihydro-2H-[1,4]oxazino[2,3,4-ij][1,7]naphthyridine-6-carboxamido)acetic acid;

2-(9-Cyano-2-(4-cyanophenyl)-7-hydroxy-5-oxo-3,5-dihydro-2H-[1,4]oxazino [2,3,4-ij]quinoline-6-carboxamido)acetic acid;

2-(9-Bromo-2-(4-bromophenyl)-7-hydroxy-5-oxo-3,5-dihydro-2H-[1,4]oxazino[2,3,4-ij]quinoline-6-carboxamido)acetic acid;

2-(8-Cyano-2-(4-cyanophenyl)-7-hydroxy-5-oxo-3,5-dihydro-2H-[1,4]oxazino [2,3,4-ij]quinoline-6-carboxamido)acetic acid;

2-(8-Bromo-2-(4-bromophenyl)-7-hydroxy-5-oxo-3,5-dihydro-2H-[1,4]oxazino[2,3,4-ij]quinoline-6-carboxamido)acetic acid;

2-(10-Cyano-2-(4-cyanophenyl)-7-hydroxy-5-oxo-3,5-dihydro-2H-[1,4]oxazino[2,3,4-ij]quinoline-6-carboxamido)acetic acid;

2-(10-Bromo-2-(4-bromophenyl)-7-hydroxy-5-oxo-3,5-dihydro-2H-[1,4]oxazino [2,3,4-ij]quinoline-6-carboxamido)acetic acid;

2-(7-Hydroxy-5-oxo-2-(4-(trifluoromethyl)phenyl)-3,5-dihydro-2H-[1,4]thiazino[2,3,4-ij]quinoline-6-carboxamido)acetic acid;

2-(7-Hydroxy-1-oxido-5-oxo-2-(4-(trifluoromethyl)phenyl)-3,5-dihydro-2H-[1,4]thiazino[2,3,4-ij]quinoline-6-carboxamido)acetic acid;

2-(7-Hydroxy-1,1-dioxido-5-oxo-2-(4-(trifluoromethyl)phenyl)-3,5-dihydro-2H-[1,4]thiazino[2,3,4-ij]quinoline-6-carboxamido)acetic acid;;

2-(7-hydroxy-1-oxido-5-oxo-2-(4-(trifluoromethyl)phenyl)-3,5-dihydro-2H-[1,4]thiazino[2,3,4-ij]quinoline-6-carboxamido)acetic acid;

2-(9-Cyano-1-hydroxy-3-oxo-6-(4-(trifluoromethyl)phenyl)-3,5,6,7-tetrahydropyrido[3,2,1-ij]quinoline-2-carboxamido)acetic acid;

2-(7-Hydroxy-8-methyl-5-oxo-2-(4-(trifluoromethyl)phenyl)-3,5-dihydro-2H-[1,4]oxazino[2,3,4-ij]quinoline-6-carboxamido)acetic acid;

2-(7-Hydroxy-5-oxo-2-(4-(trifluoromethyl)phenyl)-1,2,3,5-tetrahydropyrido[1,2,3-de]quinoxaline-6-carboxamido)acetic acid;

2-(7-Hydroxy-1-methyl-5-oxo-2-(4-(trifluoromethyl)phenyl)-1,2,3,5-tetrahydropyrido[1,2,3-de]quinoxaline-6-carboxamido)acetic acid;

2-(9-Fluoro-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(10-Fluoro-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(8-Fluoro-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(8-fluoro-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(8-Chloro-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(8-chloro-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(10-Chloro-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(10-chloro-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(9-Chloro-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(9-chloro-7-hydroxy-5-oxo-2-(4-(trifluoromethyl)phenyl)-3,5-dihydro-2H-[1,4]oxazino[2,3,4-ij]quinoline-6-carboxamido)acetic acid;

2-(7-Hydroxy-2-(4-(methylsulfonyl)phenyl)-5-oxo-10-(trifluoromethyl)-3,5-dihydro-2H-[1,4]oxazino[2,3,4-ij]quinoline-6-carboxamido)acetic acid;

2-(2-(4-cyanophenyl)-7-hydroxy-5-oxo-10-(trifluoromethyl)-3,5-dihydro-2H-[1,4]oxazino[2,3,4-ij]quinoline-6-carboxamido)acetic acid;

2-(2-(4-cyanophenyl)-7-hydroxy-10-(trifluoromethyl)-3,5-dihydro-2H-[1,4]oxazino[2,3,4-ij]quinoline-6-carboxamido)acetic acid;
2-(7-hydroxy-8-methoxy-5-oxo-2-(4-(trifluoromethyl)phenyl)-3,5-dihydro-2H-[1,4]oxazino[2,3,4-ij]quinoline-6-carboxamido)acetic acid;
2-(7,8-dihydroxy-5-oxo-2-(4-(trifluoromethyl)phenyl)-3,5-dihydro-2H-[1,4]oxazino[2,3,4-ij]quinoline-6-carboxamido)acetic acid;
2-(7-Hydroxy-9-methoxy-5-oxo-2-(4-(trifluoromethyl)phenyl)-3,5-dihydro-2H-[1,4]oxazino[2,3,4-ij]quinoline-6-carboxamido)acetic acid;
2-(7,9-Dihydroxy-5-oxo-2-(4-(trifluoromethyl)phenyl)-3,5-dihydro-2H-[1,4]oxazino[2,3,4-ij]quinoline-6-carboxamido)acetic acid;
2-(1-Hydroxy-3-oxo-6-(6-(trifluoromethyl)pyridin-3-yl)-3,5,6,7-tetrahydropyrido[3,2,1-ij]quinoline-2-carboxamido)acetic acid;
2-(9-cyano-1-hydroxy-3-oxo-6-(6-(trifluoromethyl)pyridin-3-yl)-3,5,6,7-tetrahydropyrido[3,2,1-ij]quinoline-2-carboxamido)acetic acid;
2-(1-hydroxy-9-(methylsulfonyl)-3-oxo-6-(6-(trifluoromethyl)pyridin-3-yl)-3,5,6,7-tetrahydropyrido[3,2,1-ij]quinoline-2-carboxamido)acetic acid;
2-(7-Hydroxy-5-oxo-8-(trifluoromethoxy)-2-(4-(trifluoromethyl)phenyl)-3,5-dihydro-2H-[1,4]oxazino[2,3,4-ij]quinoline-6-carboxamido)acetic acid;
2-(7-hydroxy-5-oxo-8-(trifluoromethoxy)-2-(4-(trifluoromethyl)phenyl)-3,5-dihydro-2H-[1,4]oxazino[2,3,4-ij]quinoline-6-carboxamido)acetic acid;
2-(2-(4-Cyanophenyl)-7-hydroxy-5-oxo-8-(trifluoromethoxy)-3,5-dihydro-2H-[1,4]oxazino[2,3,4-ij]quinoline-6-carboxamido)acetic acid;
2-(2-(4-cyanophenyl)-7-hydroxy-5-oxo-8-(trifluoromethoxy)-3,5-dihydro-2H-[1,4]oxazino[2,3,4-ij]quinoline-6-carboxamido)acetic acid;
2-(9-Cyano-7-hydroxy-5-oxo-2-(4-(trifluoromethyl)phenyl)-3,5-dihydro-2H-[1,4]thiazino[2,3,4-ij]quinoline-6-carboxamido)acetic acid;
2-(9-Cyano-7-hydroxy-1-oxido-5-oxo-2-(4-(trifluoromethyl)phenyl)-3,5-dihydro-2H-[1,4]thiazino[2,3,4-ij]quinoline-6-carboxamido)acetic acid;
2-(9-Cyano-7-hydroxy-5-oxo-3-(4-(trifluoromethyl)phenyl)-1,2,3,5-tetrahydropyrido[1,2,3-de]quinoxaline-6-carboxamido)acetic acid;
2-(9-Cyano-7-hydroxy-5-oxo-2-(4-(trifluoromethyl)phenyl)-1,2,3,5-tetrahydropyrido[1,2,3-de]quinoxaline-6-carboxamido)acetic acid;
2-(8-Cyano-7-hydroxy-5-oxo-2-(4-(trifluoromethyl)phenyl)-1,2,3,5-tetrahydropyrido[1,2,3-de]quinoxaline-6-carboxamido)acetic acid;
2-(9-Cyano-7-hydroxy-1-methyl-5-oxo-3-(4-(trifluoromethyl)phenyl)-1,2,3,5-tetrahydropyrido[1,2,3-de]quinoxaline-6-carboxamido)acetic acid;
2-(9-Cyano-7-hydroxy-1-methyl-5-oxo-2-(4-(trifluoromethyl)phenyl)-1,2,3,5-tetrahydropyrido[1,2,3-de]quinoxaline-6-carboxamido)acetic acid;
2-(8-Cyano-7-hydroxy-5-oxo-2-(4-(trifluoromethyl)phenyl)-3,5-dihydro-2H-[1,4]thiazino[2,3,4-ij]quinoline-6-carboxamido)acetic acid;
2-(8-Fluoro-7-hydroxy-5-oxo-3-(4-(trifluoromethyl)phenyl)-3,5-dihydro-2H-[1,4]thiazino[2,3,4-ij]quinoline-6-carboxamido)acetic acid;
2-(8-Cyano-7-hydroxy-5-oxo-3-(4-(trifluoromethyl)phenyl)-3,5-dihydro-2H-[1,4]thiazino[2,3,4-ij]quinoline-6-carboxamido)acetic acid;
2-(7-Hydroxy-5-oxo-3-(4-(trifluoromethyl)phenyl)-3,5-dihydro-2H-[1,4]thiazino[2,3,4-ij]quinoline-6-carboxamido)acetic acid;
2-(7-hydroxy-1,1-dioxido-5-oxo-3-(4-(trifluoromethyl)phenyl)-3,5-dihydro-2H-[1,4]thiazino[2,3,4-ij]quinoline-6-carboxamido)acetic acid;
2-(9-Cyano-7-hydroxy-5-oxo-3-(4-(trifluoromethyl)phenyl)-3,5-dihydro-2H-[1,4]thiazino[2,3,4-ij]quinoline-6-carboxamido)acetic acid;
2-(7-Hydroxy-5-oxo-2-(6-(trifluoromethyl)pyridin-3-yl)-3,5-dihydro-2H-[1,4]thiazino[2,3,4-ij]quinoline-6-carboxamido)acetic acid;
2-(7-Hydroxy-1,1-dioxido-5-oxo-2-(6-(trifluoromethyl)pyridin-3-yl)-3,5-dihydro-2H-[1,4]thiazino[2,3,4-ij]quinoline-6-carboxamido)acetic acid;
2-(7-Hydroxy-5-oxo-3-(thiazol-5-yl)-3,5-dihydro-2H-[1,4]thiazino[2,3,4-ij]quinoline-6-carboxamido)acetic acid;
2-(7-Hydroxy-5-oxo-3-(4-(trifluoromethyl)phenyl)-1,2,3,5-tetrahydropyrido[1,2,3-de]quinoxaline-6-carboxamido)acetic acid;
2-(7-Hydroxy-1-methyl-5-oxo-3-(4-(trifluoromethyl)phenyl)-1,2,3,5-tetrahydropyrido[1,2,3-de]quinoxaline-6-carboxamido)acetic acid;
2-(7-Hydroxy-5-oxo-2-(4-(trifluoromethyl)phenyl)-1,2,3,5-tetrahydropyrido[1,2,3-de]quinoxaline-6-carboxamido)acetic acid;
2-(10-Cyano-7-hydroxy-5-oxo-2-(thiazol-5-yl)-1,2,3,5-tetrahydropyrido[1,2,3-de]quinoxaline-6-carboxamido)acetic acid;
2-(7-Hydroxy-5-oxo-2-(thiazol-5-yl)-1,2,3,5-tetrahydropyrido[1,2,3-de]quinoxaline-6-carboxamido)acetic acid;
2-(7-Hydroxy-5-oxo-3-(thiazol-5-yl)-1,2,3,5-tetrahydropyrido[1,2,3-de]quinoxaline-6-carboxamido)acetic acid;
2-(7-Hydroxy-1-methyl-5-oxo-2-(thiazol-5-yl)-1,2,3,5-tetrahydropyrido[1,2,3-de]quinoxaline-6-carboxamido)acetic acid;
2-(7-Hydroxy-1-methyl-5-oxo-3-(thiazol-5-yl)-1,2,3,5-tetrahydropyrido[1,2,3-de]quinoxaline-6-carboxamido)acetic acid;
2-(10-Cyano-7-hydroxy-5-oxo-2-(4-(trifluoromethyl)phenyl)-1,2,3,5-tetrahydropyrido[1,2,3-de]quinoxaline-6-carboxamido)acetic acid;
2-(10-Fluoro-7-hydroxy-5-oxo-3-(4-(trifluoromethyl)phenyl)-1,2,3,5-tetrahydropyrido[1,2,3-de]quinoxaline-6-carboxamido)acetic acid;
2-(10-Fluoro-7-hydroxy-5-oxo-2-(4-(trifluoromethyl)phenyl)-1,2,3,5-tetrahydropyrido[1,2,3-de]quinoxaline-6-carboxamido)acetic acid;
2-(10-Fluoro-7-hydroxy-1-methyl-5-oxo-3-(4-(trifluoromethyl)phenyl)-1,2,3,5-tetrahydropyrido[1,2,3-de]quinoxaline-6-carboxamido)acetic acid;
2-(9-Fluoro-7-hydroxy-5-oxo-3-(4-(trifluoromethyl)phenyl)-1,2,3,5-tetrahydropyrido[1,2,3-de]quinoxaline-6-carboxamido)acetic acid;
2-(8-Fluoro-7-hydroxy-5-oxo-2-(4-(trifluoromethyl)phenyl)-1,2,3,5-tetrahydropyrido[1,2,3-de]quinoxaline-6-carboxamido)acetic acid;
2-(9-Fluoro-7-hydroxy-5-oxo-2-(4-(trifluoromethyl)phenyl)-1,2,3,5-tetrahydropyrido[1,2,3-de]quinoxaline-6-carboxamido)acetic acid;
2-(8-Fluoro-7-hydroxy-5-oxo-3-(4-(trifluoromethyl)phenyl)-1,2,3,5-tetrahydropyrido[1,2,3-de]quinoxaline-6-carboxamido)acetic acid;

2-(9-Fluoro-7-hydroxy-1-methyl-5-oxo-3-(4-(trifluoromethyl)phenyl)-1,2,3,5-tetrahydropyrido[1,2,3-de]quinoxaline-6-carboxamido)acetic acid;

2-(9-Fluoro-7-hydroxy-1-methyl-5-oxo-2-(4-(trifluoromethyl)phenyl)-1,2,3,5-tetrahydropyrido[1,2,3-de]quinoxaline-6-carboxamido)acetic acid;

2-(7-Hydroxy-5-oxo-9-(trifluoromethoxy)-2-(4-(trifluoromethyl)phenyl)-3,5-dihydro-2H-[1,4]oxazino[2,3,4-ij]quinoline-6-carboxamido)acetic acid;

2-(2-(4-Cyanophenyl)-7-hydroxy-5-oxo-9-(trifluoromethoxy)-3,5-dihydro-2H-[1,4]oxazino[2,3,4-ij]quinoline-6-carboxamido)acetic acid;

2-(7-Hydroxy-5-oxo-2-(6-(trifluoromethyl)pyridin-3-yl)-1,2,3,5-tetrahydropyrido[1,2,3-de]quinoxaline-6-carboxamido)acetic acid;

2-(7-Hydroxy-5-oxo-3-(6-(trifluoromethyl)pyridin-3-yl)-1,2,3,5-tetrahydropyrido[1,2,3-de]quinoxaline-6-carboxamido)acetic acid;

2-(7-Hydroxy-1-methyl-5-oxo-3-(6-(trifluoromethyl)pyridin-3-yl)-1,2,3,5-tetrahydropyrido[1,2,3-de]quinoxaline-6-carboxamido)acetic acid;

2-(6-Hydroxy-4-oxo-2-phenyl-2,4-dihydro-1H-pyrrolo[3,2,1-ij]quinoline-5-carboxamido)acetic acid;

2-(1-Hydroxy-3-oxo-5-phenyl-3,5,6,7-tetrahydropyrido[3,2,1-ij]quinoline-2-carboxamido)acetic acid;

2-(5-(4-Chlorobenzyl)-1-hydroxy-3-oxo-3,5,6,7-tetrahydropyrido[3,2,1-ij]quinoline-2-carboxamido)acetic acid;

2-(7-Hydroxy-5-oxo-3,5-dihydro-2H-[1,4]oxazino[2,3,4-ij]quinoline-6-carboxamido)acetic acid;

2-(3-(4-Bromophenyl)-7-hydroxy-5-oxo-3,5-dihydro-2H-[1,4]oxazino[2,3,4-ij]quinoline-6-carboxamido)acetic acid;

N-[(7-Hydroxy-10-{4-[(methylsulfonyl)amino]phenyl}-5-oxo-3-[4-(trifluoromethyl)phenyl]-2,3-dihydro-5H-[1,4]oxazino[2,3,4-ij]quinolin-6-yl)carbonyl]glycine;

N-({7-hydroxy-10-(5-methoxypyridin-3-yl)-5-oxo-3-[4-(trifluoromethyl)phenyl]-2,3-dihydro-5H-[1,4]oxazino[2,3,4-ij]quinolin-6-yl}carbonyl)glycine;

N-({7-hydroxy-5-oxo-10-pyridin-2-yl-3-[4-(trifluoromethyl)phenyl]-2,3-dihydro-5H-[1,4]oxazino[2,3,4-ij]quinolin-6-yl}carbonyl)glycine;

N-({7-hydroxy-10-(2-methoxypyrimidin-5-yl)-5-oxo-3-[4-(trifluoromethyl)phenyl]-2,3-dihydro-5H-[1,4]oxazino[2,3,4-ij]quinolin-6-yl}carbonyl)glycine;

N-({10-(3-carbamoylphenyl)-7-hydroxy-5-oxo-3-[4-(trifluoromethyl)phenyl]-2,3-dihydro-5H-[1,4]oxazino[2,3,4-ij]quinolin-6-yl}carbonyl)glycine;

2-(7-hydroxy-5-oxo-10-(1H-pyrazol-5-yl)-3-(4-(trifluoromethyl)phenyl)-3,5-dihydro-2H-[1,4]oxazino[2,3,4-ij]quinoline-6-carboxamido)acetic acid;

N-{[3-(4'-Carbamoylbiphenyl-4-yl)-7-hydroxy-5-oxo-2,3-dihydro-5H-[1,4]oxazino[2,3,4-ij]quinolin-6-yl]carbonyl}glycine;

N-{[3-(3'-chlorobiphenyl-4-yl)-7-hydroxy-5-oxo-2,3-dihydro-5H-[1,4]oxazino[2,3,4-ij]quinolin-6-yl]carbonyl}glycine;

N-[(7-hydroxy-5-oxo-3-{4-[6-(trifluoromethyl)pyridin-3-yl]phenyl}-2,3-dihydro-5H-[1,4]oxazino[2,3,4-ij]quinolin-6-yl)carbonyl]glycine;

N-{[7-hydroxy-3-(4'-methylbiphenyl-4-yl)-5-oxo-2,3-dihydro-5H-[1,4]oxazino[2,3,4-ij]quinolin-6-yl]carbonyl}glycine;

N-{[7-hydroxy-3-(4'-methoxybiphenyl-4-yl)-5-oxo-2,3-dihydro-5H-[1,4]oxazino[2,3,4-ij]quinolin-6-yl]carbonyl}glycine;

N-{[3-(4'-cyanobiphenyl-4-yl)-7-hydroxy-5-oxo-2,3-dihydro-5H-[1,4]oxazino[2,3,4-ij]quinolin-6-yl]carbonyl}glycine;

N-({7-hydroxy-3-[4-(2-methoxypyridin-3-yl)phenyl]-5-oxo-2,3-dihydro-5H-[1,4]oxazino[2,3,4-ij]quinolin-6-yl}carbonyl)glycine;

N-{[7-hydroxy-5-oxo-3-(4-pyridin-4-ylphenyl)-2,3-dihydro-5H-[1,4]oxazino[2,3,4-ij]quinolin-6-yl]carbonyl}glycine;

N-({3-[4-(6-aminopyridin-3-yl)phenyl]-7-hydroxy-5-oxo-2,3-dihydro-5H-[1,4]oxazino[2,3,4-ij]quinolin-6-yl}carbonyl)glycine;

N-{[3-(3'-cyanobiphenyl-4-yl)-7-hydroxy-5-oxo-2,3-dihydro-5H-[1,4]oxazino[2,3,4-ij]quinolin-6-yl]carbonyl}glycine;

N-{[7-hydroxy-5-oxo-3-(4-pyridin-3-ylphenyl)-2,3-dihydro-5H-[1,4]oxazino[2,3,4-ij]quinolin-6-yl]carbonyl}glycine;

2-(3-(4-(1H-pyrazol-5-yl)phenyl)-7-hydroxy-5-oxo-3,5-dihydro-2H-[1,4]oxazino[2,3,4-ij]quinoline-6-carboxamido)acetic acid;

N-[(7-Hydroxy-5-oxo-10-pyridin-3-yl-2,3-dihydro-5H-[1,4]oxazino[2,3,4-ij]quinolin-6-yl)carbonyl]glycine;

N-{[7-hydroxy-10-(6-methoxypyridin-3-yl)-5-oxo-2,3-dihydro-5H-[1,4]oxazino[2,3,4-ij]quinolin-6-yl]carbonyl}glycine;

N-{[10-(3,5-dimethylisoxazol-4-yl)-7-hydroxy-5-oxo-2,3-dihydro-5H-[1,4]oxazino[2,3,4-ij]quinolin-6-yl]carbonyl}glycine;

N-{[10-(6-aminopyridin-3-yl)-7-hydroxy-5-oxo-2,3-dihydro-5H-[1,4]oxazino[2,3,4-ij]quinolin-6-yl]carbonyl}glycine;

2-(7-Hydroxy-5-oxo-3-(4-chlorophenyl)-3,5-dihydro-2H-[1,4]oxazino[2,3,4-ij]quinoline-6-carboxamido)acetic acid;

2-(9-fluoro-7-hydroxy-5-oxo-3-(4-(trifluoromethyl)phenyl)-3,5-dihydro-2H-[1,4]oxazino[2,3,4-ij]quinoline-6-carboxamido)acetic acid;

2-(9-bromo-7-hydroxy-5-oxo-3-(4-(trifluoromethyl)phenyl)-3,5-dihydro-2H-[1,4]oxazino[2,3,4-ij]quinoline-6-carboxamido)acetic acid;

2-(7-hydroxy-5-oxo-3-(6-(trifluoromethyl)pyridin-3-yl)-3,5-dihydro-2H-[1,4]oxazino[2,3,4-ij]quinoline-6-carboxamido)acetic acid;

2-(10-bromo-7-hydroxy-5-oxo-3-(4-(trifluoromethyl)phenyl)-3,5-dihydro-2H-[1,4]oxazino[2,3,4-ij]quinoline-6-carboxamido)acetic acid;

2-(8-fluoro-7-hydroxy-5-oxo-3-(4-(trifluoromethyl)phenyl)-3,5-dihydro-2H-[1,4]oxazino[2,3,4-ij]quinoline-6-carboxamido)acetic acid;

2-(7-hydroxy-3-(4-methoxyphenyl)-5-oxo-3,5-dihydro-2H-[1,4]oxazino[2,3,4-ij]quinoline-6-carboxamido)acetic acid;

2-(10-fluoro-7-hydroxy-5-oxo-3-(4-(trifluoromethyl)phenyl)-3,5-dihydro-2H-[1,4]oxazino[2,3,4-ij]quinoline-6-carboxamido)acetic acid;

2-(10-chloro-7-hydroxy-5-oxo-3-(4-(trifluoromethyl)phenyl)-3,5-dihydro-2H-[1,4]oxazino[2,3,4-ij]quinoline-6-carboxamido)acetic acid;

2-(9-chloro-7-hydroxy-5-oxo-3-(4-(trifluoromethyl)phenyl)-3,5-dihydro-2H-[1,4]oxazino[2,3,4-ij]quinoline-6-carboxamido)acetic acid;

droxy-5-oxo-3-(3-(trifluoromethyl)phenyl)-3,5-dihydro-2H-[1,4]oxazino[2,3,4-ij]quinoline-6-carboxamido)acetic acid;

2-(7-hydroxy-5-oxo-3-(thiazol-2-yl)-3,5-dihydro-2H-[1,4]oxazino[2,3,4-ij]quinoline-6-carboxamido)acetic acid;

2-(8-bromo-7-hydroxy-5-oxo-3-(4-(trifluoromethyl)phenyl)-3,5-dihydro-2H-[1,4]oxazino[2,3,4-ij]quinoline-6-carboxamido)acetic acid;

2-(10-bromo-7-hydroxy-5-oxo-3-(thiazol-4-yl)-3,5-dihydro-2H-[1,4]oxazino[2,3,4-ij]quinoline-6-carboxamido)acetic acid;

2-(7-hydroxy-5-oxo-3-(2-(trifluoromethyl)thiazol-5-yl)-3,5-dihydro-2H-[1,4]oxazino[2,3,4-ij]quinoline-6-carboxamido)acetic acid;

2-(8-fluoro-7-hydroxy-5-oxo-3-(thiazol-5-yl)-3,5-dihydro-2H-[1,4]oxazino[2,3,4-ij]quinoline-6-carboxamido)acetic acid;

2-(7-hydroxy-3-(oxazol-5-yl)-5-oxo-3,5-dihydro-2H-[1,4]oxazino[2,3,4-ij]quinoline-6-carboxamido)acetic acid;

2-(10-fluoro-7-hydroxy-5-oxo-3-(thiazol-5-yl)-3,5-dihydro-2H-[1,4]oxazino[2,3,4-ij]quinoline-6-carboxamido)acetic acid;

2-(8,10-difluoro-7-hydroxy-5-oxo-3-(thiazol-5-yl)-3,5-dihydro-2H-[1,4]oxazino[2,3,4-ij]quinoline-6-carboxamido)acetic acid;

2-(8-bromo-7-hydroxy-5-oxo-3-(thiazol-5-yl)-3,5-dihydro-2H-[1,4]oxazino[2,3,4-ij]quinoline-6-carboxamido)acetic acid;

2-(10-bromo-7-hydroxy-5-oxo-3-(thiazol-5-yl)-3,5-dihydro-2H-[1,4]oxazino[2,3,4-ij]quinoline-6-carboxamido)acetic acid;

ammonium 2-(9-cyano-7-hydroxy-5-oxo-3-(4-(trifluoromethyl)phenyl)-3,5-dihydro-2H-[1,4]oxazino[2,3,4-ij]quinoline-6-carboxamido)acetate;

ammonium 2-(8-cyano-7-hydroxy-5-oxo-3-(4-(trifluoromethyl)phenyl)-3,5-dihydro-2H-[1,4]oxazino[2,3,4-ij]quinoline-6-carboxamido)acetate;

ammonium 2-(3-(4-cyanophenyl)-7-hydroxy-5-oxo-3,5-dihydro-2H-[1,4]oxazino[2,3,4-ij]quinoline-6-carboxamido)acetate;

ammonium 2-(10-cyano-7-hydroxy-5-oxo-3-(thiazol-5-yl)-3,5-dihydro-2H-[1,4]oxazino[2,3,4-ij]quinoline-6-carboxamido)acetate;

ammonium 2-(7-hydroxy-9-(methylsulfonyl)-5-oxo-3-(4-(trifluoromethyl)phenyl)-3,5-dihydro-2H-[1,4]oxazino[2,3,4-ij]quinoline-6-carboxamido)acetate;

2-(7-Hydroxy-5-oxo-9-(1H-pyrazol-5-yl)-3-(4-(trifluoromethyl)phenyl)-3,5-dihydro-2H-[1,4]oxazino[2,3,4-ij]quinoline-6-carboxamido)acetic acid;

2-(7-Hydroxy-10-methyl-5-oxo-3-(thiazol-4-yl)-3,5-dihydro-2H-[1,4]oxazino[2,3,4-ij]quinoline-6-carboxamido)acetic acid; or 2-(10-Cyclopropyl-7-hydroxy-5-oxo-3-(thiazol-4-yl)-3,5-dihydro-2H-[1,4]oxazino[2,3,4-ij]quinoline-6-carboxamido)acetic acid;

or a pharmaceutically acceptable salt thereof.

4. A compound of formula 1 or a pharmaceutically acceptable salt thereof according to claim 1, for use as a medicament.

5. A compound of formula 1 or a pharmaceutically acceptable salt thereof according to claim 1, for the treatment of conditions mediated by HIF prolyl hydroxylase.

6. A pharmaceutical composition comprising a compound of formula 1 or a pharmaceutically acceptable salt thereof, and pharmaceutically acceptable carrier.

* * * * *